(12) United States Patent
Kasai et al.

(10) Patent No.: US 9,365,540 B2
(45) Date of Patent: Jun. 14, 2016

(54) BENZIMIDAZOLE DERIVATIVES AS MCH RECEPTOR ANTAGONISTS

(71) Applicant: Takeda Pharmaceutical Company Limited, Osaka (JP)

(72) Inventors: Shizuo Kasai, Kanagawa (JP); Hideyuki Igawa, Kanagawa (JP); Masashi Takahashi, Kanagawa (JP); Tsuyoshi Maekawa, Kanagawa (JP); Keiko Kakegawa, Kanagawa (JP); Asato Kina, Kanagawa (JP); Jumpei Aida, Kanagawa (JP); Uttam Khamrai, West Bengal (IN); Mrinalkanti Kundu, West Bengal (IN)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/371,824

(22) PCT Filed: Jan. 11, 2013

(86) PCT No.: PCT/JP2013/051017
§ 371 (c)(1),
(2) Date: Jul. 11, 2014

(87) PCT Pub. No.: WO2013/105676
PCT Pub. Date: Jul. 18, 2013

(65) Prior Publication Data
US 2015/0018363 A1 Jan. 15, 2015

Related U.S. Application Data

(60) Provisional application No. 61/585,877, filed on Jan. 12, 2012.

(51) Int. Cl.
| C07D 471/04 | (2006.01) |
| C07D 409/14 | (2006.01) |
| C07D 405/14 | (2006.01) |
| C07D 403/14 | (2006.01) |
| C07D 413/14 | (2006.01) |
| C07D 401/14 | (2006.01) |
| C07D 401/04 | (2006.01) |
| C07D 417/14 | (2006.01) |

(52) U.S. Cl.
CPC ............ *C07D 401/04* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01)

(58) Field of Classification Search
CPC .. C07D 471/04; C07D 409/14; C07D 405/14; C07D 403/14; C07D 413/14; C07D 401/14; C07D 401/04; C07D 417/14

USPC ............ 514/252.04, 300, 338, 274, 256, 269, 514/333; 546/269.7, 273.4, 256, 121, 546/271.4; 544/333, 319, 238, 310
See application file for complete search history.

(56) References Cited

U.S. PATENT DOCUMENTS

| 2004/0077628 | A1 | 4/2004 | Ishihara et al. |
| 2005/0176775 | A1* | 8/2005 | Devadas et al. ............... 514/340 |
| 2007/0088033 | A1* | 4/2007 | Devadas et al. ............... 514/241 |
| 2008/0200494 | A1* | 8/2008 | Kishino et al. ................ 514/300 |
| 2009/0011994 | A1* | 1/2009 | Stein et al. ...................... 514/12 |
| 2009/0264426 | A1* | 10/2009 | Sakuraba et al. ........... 514/235.2 |
| 2009/0275590 | A1* | 11/2009 | Guzzo et al. ............. 514/252.04 |
| 2010/0069362 | A1 | 3/2010 | Murata |
| 2010/0331339 | A9* | 12/2010 | Guzzo et al. ............. 514/252.04 |
| 2012/0157460 | A1* | 6/2012 | Surman et al. ................ 514/250 |
| 2015/0018373 | A1* | 1/2015 | Igawa et al. ................. 514/255.05 |
| 2015/0087672 | A1* | 3/2015 | Kasai et al. .................... 514/302 |
| 2015/0111894 | A1* | 4/2015 | Kasai et al. .................... 514/248 |

FOREIGN PATENT DOCUMENTS

| EP | 1 939 194 | 7/2008 |
| WO | 2004/087677 | 10/2004 |

(Continued)

OTHER PUBLICATIONS

Lu; Bioorganic and Medicinal Chemistry Letters, 2011, 21, 5310-5314.*
MacNeil; Frontiers in Endocrinology, 2013, vol. 4, article 49, pp. 1-14.*

(Continued)

*Primary Examiner* — Janet L Andres
*Assistant Examiner* — Daniel Carcanague
(74) *Attorney, Agent, or Firm* — Wenderoth, Lind & Ponack, L.L.P.

(57) ABSTRACT

The present invention provides an aromatic ring compound having a melanin-concentrating hormone receptor antagonistic action and useful as an agent for the prophylaxis or treatment of obesity and the like. The present invention relates to a compound represented by the formula

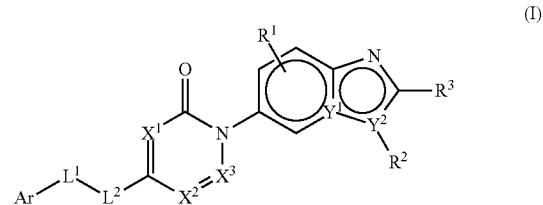

wherein each symbol as defined in the specification, or a salt thereof.

14 Claims, No Drawings

(56) References Cited

FOREIGN PATENT DOCUMENTS

| WO | 2005/018557 |  | 3/2005 |
|----|----|----|----|
| WO | 2007-029847 |  | 3/2007 |
| WO | 2008/022979 |  | 2/2008 |
| WO | WO 2009/137270 | * | 11/2009 |
| WO | 2010/141545 |  | 12/2010 |
| WO | 2011/127643 |  | 10/2011 |
| WO | 2011/130086 |  | 10/2011 |

OTHER PUBLICATIONS

Mendez-Andino; Drug Discovery Today, 2007, 12, 972-979.*
International Search Report issued Apr. 4, 2013 in International (PCT) Application No. PCT/JP2013/051017, along with the Written Opinion.
M. D. Surman et al., "5-(Pyridinon-1-yl)indazoles and 5-(furopyridinon-5-yl)indazoles as MCH-1 Antagonists", Bioorganic & Medicinal Chemistry Letters, vol. 20, No. 23, pp. 7015-7019, 2010.

* cited by examiner

BENZIMIDAZOLE DERIVATIVES AS MCH RECEPTOR ANTAGONISTS

TECHNICAL FIELD

The present invention relates to an aromatic ring compound having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food intake amount and a lighter body weight as compared to normal mouse (Nature, vol. 396, page 670, 1998). Furthermore, MCH receptor-1-deficient mice have been reported to show a lean phenotype (Proc. Natl. Acad. Sci. USA, vol. 99, page 3240, 2002). Therefrom MCH receptor (particularly MCH receptor 1) antagonists are expected to be superior appetite suppressants or anti-obesity agents.

As compounds having a MCH receptor antagonistic action, the following compounds are known.

1) WO2007/029847 (patent document 1) discloses a pyridone derivative represented by the formula:

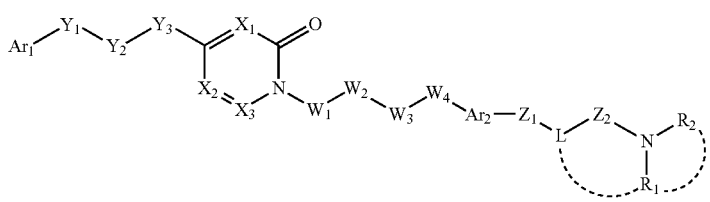

wherein $R_1$ and $R_2$ are the same or different and each is a hydrogen atom, a lower alkyl group optionally having substituent(s) or a lower cycloalkyl group optionally having substituent(s), or $R_1$ and $R_2$ form, together with the nitrogen atom bonded thereto, an aliphatic nitrogen-containing heterocycle optionally having substituent(s), $X_1$, $X_2$ and $X_3$ are the same or different and each is a methine group optionally having substituent(s) or a nitrogen atom, provided that $X_1$, $X_2$ and $X_3$ are not simultaneously nitrogen atoms, $Y_1$ is a single bond, —O—, —NR—, —S—, —SO— or —SO$_2$—, $Y_2$ is a lower alkylene group optionally having substituent(s), a lower alkenylene group optionally having substituent(s) or a lower cycloalkylene group optionally having substituent(s), $Y_3$ is a single bond, —O—, —NR—, —S—, —SO— or —SO$_2$—, each R is independently a hydrogen atom or a lower alkyl group optionally having substituent(s), $W_1$, $W_2$, $W_3$ and $W_4$ are the same or different and each is a single bond, a methylene group optionally having substituent(s) or —O—, provided that continuous two or more of $W_1$, $W_2$, $W_3$ and $W_4$ are not simultaneously —O—, L is a single bond, a methylene group optionally having substituent(s) or an ethylene group optionally having substituent(s), and L optionally forms, together with $Z_2$, $R_1$ and the nitrogen atom bonded to $R_2$, an aliphatic nitrogen-containing heterocycle optionally having substituent(s), $Z_1$ and $Z_2$ are the same or different, and each is a single bond, a $C_{1-4}$ alkylene group optionally having substituent(s) or —O—, $Ar_1$ is an aromatic carbocyclic group optionally having substituent(s) or an aromatic heterocyclic group optionally having substituent(s), and $Ar_2$ is a divalent and bicyclic aromatic carbocyclic group optionally having substituent(s) or a divalent and bicyclic aromatic heterocyclic group optionally having substituent(s), or a pharmaceutically acceptable salt thereof.

2) WO01/82925 (patent document 2) discloses a compound represented by the formula:

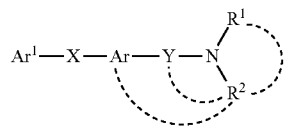

wherein $Ar^1$ is a cyclic group optionally having substituent(s);

X and Y are the same or different and each is a spacer with a main chain having an atom number of 1 to 6;

(I)

Ar is a condensed polycyclic aromatic ring optionally having substituent(s);

$R^1$ and $R^2$ are the same or different and each is a hydrogen atom or a hydrocarbon group optionally having substituent(s), $R^1$ and $R^2$ may form, together with the adjacent nitrogen atom, a nitrogen-containing heterocycle optionally having substituent(s), $R^2$ may form, together with the adjacent nitrogen atom and Y, a nitrogen-containing heterocycle optionally having substituent(s), or $R^2$ may form, together with the adjacent nitrogen atom, Y and Ar, a nitrogen-containing fused ring optionally having substituent(s), or a salt thereof.

3) WO2006/118320 (patent document 3) discloses a compound represented by the formula:

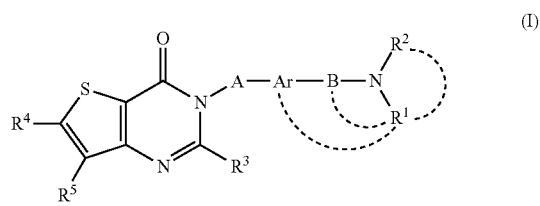

(I)

3 wherein

Ar is an optionally substituted ring;

A is a spacer with a main chain having an atom number of 1 to 4;

B is a bond, a $C_{1-10}$ alkylene group or an oxygen atom;

$R^3$ and $R^5$ are each independently a hydrogen atom or a substituent;

$R^4$ is an optionally substituted cyclic group or an optionally substituted $C_{1-10}$ alkyl group;

$R^1$ and $R^2$ are each independently a hydrogen atom or a substituent, $R^1$ is bonded to $R^2$ or B to form an optionally substituted nitrogen-containing heterocycle, or $R^1$ is bonded to Ar to form an optionally substituted nitrogen-containing fused heterocycle, or a salt thereof.

4) WO2011/130086 (patent, document 5) and WO2011/127643 (patent document 6) disclose a compound represented by the formula:

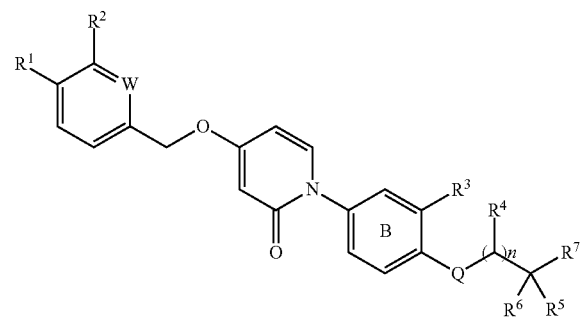

wherein $R^1$ and $R^2$ are each independently selected from the group consisting of halogen, hydrogen, —OH, $C_1$-$C_6$ alkyl, —$OC_1$-$C_6$ alkyl, —O-halogen-substituted $C_1$-$C_6$ alkyl and halogen-substituted $C_1$-$C_6$ alkyl;

W is —N— or —CH—;

Q is —O—, —NH— or —C—, or forms heteroaryl together with $R^4$, aromatic ring B and $R^3$;

$R^3$ is halogen, hydrogen, —$OC_1$-$C_6$ alkyl, $C_1$-$C_6$ alkyl, —O-halogen substituted $C_1$-$C_6$ alkyl, halogen-substituted $C_1$-$C_6$ alkyl, cyano, $SO_2C_1$-$C_6$ alkyl or forms a heteroaryl ring together with aromatic ring B, Q and $R^4$;

$R^4$ is hydrogen, oxo, $C_1$-$C_6$ alkyl, halogen-substituted $C_1$-$C_6$ alkyl or forms heteroaryl together with aromatic ring B, $R^3$ and Q, or forms $C_3$-$C_6$ cycloalkyl together with $R^5$;

$R^5$, $R^6$ and $R^7$ are each independently selected from the group consisting of hydrogen, $C_1$-$C_6$ alkyl, halogen-substituted $C_1$-$C_6$ alkyl, $C_3$-$C_6$ cycloalkyl, halogen-substituted $C_3$-$C_6$ cycloalkyl, $C_1$-$C_6$ alkyl $C_3$-$C_6$ cycloalkyl, —OH, $C_1$-$C_6$ alkyl-OH and —$OC_1$-$C_6$ alkyl, or $R^5$ forms oxo group or $C_3$-$C_6$ cycloalkyl together with $R^6$, or $R^5$ forms $C_3$-$C_6$ cycloalkyl together with $R^4$, and at least one of $R^5$, $R^6$ and $R^7$ is not hydrogen, and n is 1-3, or a pharmaceutically acceptable salt thereof.

On the other hand, as a p38 MAP kinase modulator, the following compound is known.

4

5) WO2005/018557 (patent document 4) discloses a compound represented by the formula:

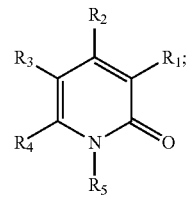

wherein $R_1$ is H, halogen or the like, $R_2$ is optionally substituted arylalkoxy, optionally substituted heteroarylalkyl or the like, $R_3$ is H, halogen or the like, $R_4$ is H or optionally substituted alkyl, and $R_5$ is aryl optionally substituted by substituent(s) such as $C_3$-$C_7$ cycloalkyl, alkoxyalkyl and the like, and the like or a pharmaceutically acceptable salt thereof.

CITATION LIST patent document 1: WO2007/029847
patent document 2: WO01/82925
patent document 3: WO2006/118320
patent document 4: WO2005/018557
patent document 5: WO2011/130086
patent document 6: WO2011/127643

SUMMARY OF THE INVENTION

The development of a compound having an MCH receptor antagonistic action and low toxicity, which is useful as an agent for the prophylaxis or treatment of obesity and the like is desired.

The present inventors have conducted intensive studies of a compound having an MCH receptor antagonistic action and low toxicity [particularly, cardiotoxicity (e.g., human ether-a-go-go related gene (hERG) inhibitory activity), phospholipidosis (PLsis) inducing potential and the like, which sometimes pose problems in drug discovery], and found that compound (I) explained in the following has a superior MCH receptor antagonistic action and shows low toxicity such as cardiotoxicity (e.g., hERG inhibitory activity), PLsis inducing potential and the like as compared to conventional MCH receptor antagonists, which resulted in the completion of the present invention.

Accordingly, the present invention relates to

[1] a compound represented by the formula:

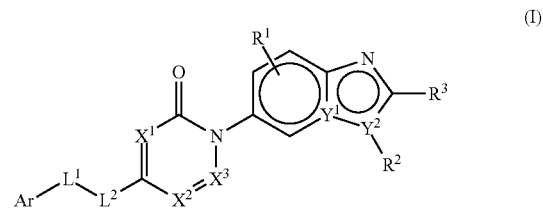

wherein

Ar is an optionally substituted aromatic ring group;

$X^1$ is $CR^4$ or N;

$X^2$ and $X^3$ are each independently CH or N;

one of $Y^1$ and $Y^2$ is C, and the other is N;

$L^1$ is O, $S(O)_{m1}$, $NR^{5A}$ or $CR^{5B}R^{5C}$;

$L^2$ is O, $S(O)_{m2}$, $NR^{6A}$ or $CR^{6B}R^{6C}$;

wherein at least one of $L^1$ and $L^2$ is $CR^{5B}R^{5C}$ or $CR^{6B}R^{6C}$;

$R^1$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group;

$R^2$ is a halogen atom, an optionally substituted $C_{1-6}$ alkyl group or an optionally substituted cyclic group;

$R^3$ is (1) a hydrogen atom, (2) a halogen atom, (3) a cyano group, (4) a $C_{1-6}$ alkyl group optionally substituted by 1 to 3 substituents selected from a halogen atom, a cyano group, an optionally substituted $C_{1-6}$ alkoxy group, an optionally substituted $C_{3-10}$ cycloalkyl group, an optionally substituted aromatic ring group, —CO—$R^{7A}$ and —S(O)$_{n1}$—$R^{7B}$, (5) a $C_{1-6}$ alkoxy group optionally substituted by 1 to 3 substituents selected from a halogen atom, a cyano group, an optionally substituted $C_{1-6}$ alkoxy group, an optionally substituted $C_{3-10}$ cycloalkyl group, an optionally substituted aromatic ring group, —CO—$R^{8A}$ and —S(O)$_{n2}$—$R^{8B}$, (6) an optionally substituted $C_{2-6}$ alkenyl group, (7) an optionally substituted cyclic group, or (8) —CO—$R^9$;

$R^4$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group;

$R^{5A}$ and $R^{6A}$ are each independently a hydrogen atom or an optionally substituted hydrocarbon group;

$R^{5B}$, $R^{5C}$, $R^{6B}$ and $R^{6C}$ are each independently a hydrogen atom or a substituent;

wherein $R^{5B}$ and $R^{6B}$ optionally form an optionally substituted ring together with the adjacent carbon atoms, or $R^{5B}$ and the substituent of Ar are optionally joined to form an optionally substituted ring;

$R^{7A}$, $R^{7B}$, $R^{8A}$, $R^{8B}$ and $R^9$ are each independently an optionally substituted $C_{1-6}$ alkyl group, an optionally substituted $C_{3-10}$ cycloalkyl group or an optionally substituted amino group; and m1, m2, n1 and n2 are each independently an integer of 0 to 2, or a salt thereof (hereinafter sometimes to be abbreviated as "compound (I)");

[2] the compound of the aforementioned [1], wherein $X^1$, $X^2$ and $X^3$ are CH, or a salt thereof;

[3] the compound of the aforementioned [1] or [2], wherein $L^1$ is CH$_2$; and $L^2$ is O, or a salt thereof;

[4] the compound of any one of the aforementioned [1] to [3], wherein $R^1$ is a hydrogen atom, or a salt thereof;

[5] the compound of the aforementioned [1] to [4], wherein Ar is a phenyl group optionally substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms,
or a salt thereof;

[6] the compound of any one of the aforementioned [1] to [4], wherein Ar is a thienyl group or a thiazolyl group, each of which is optionally substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms,
or a salt thereof;

[7] the compound of any one of the aforementioned [1] to [6], wherein $Y^1$ is C, and $Y^2$ is N, or a salt thereof;

[8] the compound of any one of the aforementioned [1] to [7], wherein $R^2$ is a $C_{1-6}$ alkyl group, or a salt thereof;

[9] the compound of any one of the aforementioned [1] to [8], wherein $R^3$ is
(1) a $C_{1-6}$ alkyl group optionally substituted by 1 to 3 substituents selected from
  (a) a halogen atom,
  (b) a cyano group, and
  (c) a $C_{1-6}$ alkoxy group optionally substituted by 1 to 3 halogen atoms, or
(2) a $C_{3-10}$ cycloalkyl group optionally substituted by 1 to 3 substituents selected from
  (a) a halogen atom,
  (b) a cyano group,
  (c) a $C_{1-6}$ alkyl group optionally substituted by 1 to 3 substituents selected from a halogen atom and a hydroxy group,
  (d) a carbamoyl group,
  (e) a $C_{1-6}$ alkoxy group,
  (f) an oxo group,
  (g) a hydroxy group,
  (h) a $C_{1-6}$ alkoxy-carbonyl group, and
  (i) a carboxy group,
or a salt thereof;

[10] the compound of any one of the aforementioned [1] to [9], wherein $R^3$ is a $C_{1-6}$ alkyl group or a $C_{3-6}$ cycloalkyl, or a salt thereof;

[11] the compound of the aforementioned [1], wherein Ar is a phenyl group optionally substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms;
$X^1$, $X^2$ and $X^3$ are CH;
$Y^1$ is C,
$Y^2$ is N;
$L^1$ is CH$_2$;
$L^2$ is O;
$R^1$ is a hydrogen atom;
$R^2$ is a $C_{1-6}$ alkyl group; and
$R^3$ is a $C_{1-6}$ alkyl group or a $C_{3-6}$ cycloalkyl group, or a salt thereof;

[12] 1-(2-cyclopropyl-1-methyl-1H-benzimidazol-6-yl)-4-((4-fluorobenzyl)oxy)pyridin-2(1H)-one or a salt thereof;

[13] 1-(2-ethyl-1-methyl-1H-benzimidazol-6-yl)-4-((4-fluorobenzyl)oxy)pyridin-2(1H)-one or a salt thereof;

[14] 1-(2-cyclopropyl-1-methyl-1H-benzimidazol-6-yl)-4-((3,4-difluorobenzyl)oxy)pyridin-2(1H)-one or a salt thereof;

[15] 1-(1,2-dimethyl-1H-benzimidazol-6-yl)-4-((4-fluorobenzyl)oxy)pyridin-2(1H)-one or a salt thereof;

[1A] a prodrug of the compound of any one of the aforementioned [1] to [15] or a salt thereof;

[16] a medicament comprising the compound of any one of the above-mentioned [1] to [15] or a salt thereof;

[16A] a medicament comprising the compound of any one of the aforementioned [1] to [15] or a salt thereof or a prodrug thereof;

[17] the medicament of the above-mentioned [16] or [16A], which is a melanin-concentrating hormone receptor antagonist;

[18] the medicament of the above-mentioned [16] or [16A], which is an anorexigenic agent;

[19] the medicament of the above-mentioned [16] or [16A], which is a prophylactic or therapeutic agent for obesity;

[20] a method of preventing or treating obesity in a mammal, comprising administering an effective amount of the compound of any one of the aforementioned [1] to [15] or a salt thereof to the mammal;

[20A] a method of preventing or treating obesity in a mammal, comprising administering an effective amount of the compound of any one of the aforementioned [1] to [15] or a salt thereof or a prodrug thereof to the mammal;

[21] a method of antagonizing a melanin-concentrating hormone receptor (MCHR) in a mammal, comprising administering an effective amount of the compound of any one of the aforementioned [1] to [15] or a salt thereof to the mammal;

[21A] a method of antagonizing a melanin-concentrating hormone receptor (MCHR) in a mammal, comprising administering an effective amount of the compound of any one of the aforementioned [1] to [15] or a salt thereof or a prodrug thereof to the mammal;

[22] a method of suppressing food intake in a mammal, comprising administering an effective amount of the compound of any one of the aforementioned [1] to [15] or a salt thereof to the mammal;

[22A] a method of suppressing food intake in a mammal, comprising administering an effective amount of the compound of any one of the aforementioned [1] to [15] or a salt thereof or a prodrug thereof to the mammal;

[23] use of the compound of any one of the aforementioned [1] to [15] or a salt thereof for the production of a prophylactic or therapeutic agent for obesity;

[23A] use of the compound of any one of the aforementioned [1] to [15] or a salt thereof or a prodrug thereof for the production of a prophylactic or therapeutic agent for obesity;

[24] use of the compound of any one of the aforementioned [1] to [15] or a salt thereof for the production of an anorexigenic agent;

[24A] use of the compound of any one of the aforementioned [1] to [15] or a salt thereof or a prodrug thereof for the production of an anorexigenic agent;

[25] the compound of any one of the aforementioned [1] to [15] or a salt thereof for use in the prophylaxis or treatment of obesity;

[25A] the compound of any one of the aforementioned [1] to [15] or a salt thereof or a prodrug thereof for use in the prophylaxis or treatment of obesity;

[26] the compound of any one of the aforementioned [1] to [15] or a salt thereof for use in the suppression of food intake;

[26A] the compound of any one of the aforementioned [1] to [15] or a salt thereof or a prodrug thereof for use in the suppression of food intake;

and the like.

Compound (I) has a high MCH receptor antagonistic action, and low toxicity such as cardiotoxicity (e.g., hERG inhibitory activity), PLsis inducing potential and the like, as compared to conventional MCH receptor antagonists. Therefore, compound (I) is highly useful as an agent for the prophylaxis or treatment of obesity and the like.

DETAILED DESCRIPTION OF THE INVENTION

The definitions of the symbols and terms used in the present invention are described in detail in the following.

In the present specification, the "halogen atom" means, unless otherwise specified, a fluorine atom, a chlorine atom, a bromine atom or an iodine atom.

In the present specification, the "$C_{1-6}$ alkyl group" means, unless otherwise specified, methyl, ethyl, propyl, isopropyl, n-butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 1,2,2-trimethylpropyl, 3,3-dimethylbutyl, 2-ethylbutyl and the like.

In the present specification, the "$C_{1-6}$ alkyl group" of the "optionally substituted $C_{1-6}$ alkyl group" optionally has 1 to 5 (preferably, 1 to 3) substituents at substitutable position(s). Examples of such substituent include the following substituent group A. When two or more substituents are present, the respective substituents may be the same or different.

Substituent group A:
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group (e.g., methylcarbonyl, ethylcarbonyl) optionally substituted by 1 to 3 halogen atoms,
  (c) a $C_{1-6}$ alkoxy-carbonyl group (e.g., methoxycarbonyl, ethoxycarbonyl) optionally substituted by 1 to 3 halogen atoms,
  (d) a carbamoyl group optionally mono- or di-substituted by $C_{1-6}$ alkyl group(s) optionally substituted by 1 to 3 halogen atoms (e.g., methylcarbamoyl, ethylcarbamoyl), and
  (e) a formyl group;
(6) a $C_{1-6}$ alkyl-carbonyl group (e.g., methylcarbonyl, ethylcarbonyl) optionally substituted by 1 to 3 halogen atoms;
(7) a $C_{1-6}$ alkoxy-carbonyl group optionally substituted by 1 to 3 substituents selected from
  (a) a halogen atom, and
  (b) a $C_{1-6}$ alkoxy group;
(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from
 (a) a halogen atom,
 (b) a carboxy group,
 (c) a $C_{1-6}$ alkoxy group,
 (d) a $C_{1-6}$ alkoxy-carbonyl group,
 (e) an amino group optionally mono- or di-substituted by substituent(s) selected from a $C_{1-6}$ alkyl group and a $C_{1-6}$ alkoxy-carbonyl group,
 (f) a $C_{6-14}$ aryl group (e.g., phenyl),
 (g) a $C_{3-10}$ cycloalkyl group (e.g., cyclopropyl, cyclobutyl),
 (h) an aromatic heterocyclic group (e.g., thienyl, furyl), and
 (i) a hydroxy group;
(15) a $C_{2-6}$ alkenyloxy group (e.g., ethenyloxy) optionally substituted by 1 to 3 halogen atoms;
(16) a $C_{6-14}$ aryloxy group (e.g., phenyloxy, naphthyloxy);
(17) a $C_{1-6}$ alkyl-carbonyloxy group (e.g., acetyloxy, tert-butylcarbonyloxy);
(18) a $C_{6-14}$ aryl-carbonyl group (e.g., benzoyl) optionally substituted by 1 to 3 substituents selected from
 (a) a halogen atom, and
 (b) a $C_{1-6}$ alkyl group optionally substituted by 1 to 3 halogen atoms;
(19) a nonaromatic heterocyclylcarbonyl group (e.g., pyrrolidinylcarbonyl, morpholinylcarbonyl, 1,1-dioxidothiomorpholinylcarbonyl) optionally substituted by 1 to 3 $C_{1-6}$ alkyl groups optionally substituted by 1 to 3 halogen atoms;
(20) a mercapto group;
(21) a $C_{1-6}$ alkylthio group (e.g., methylthio, ethylthio) optionally substituted by 1 to 3 halogen atoms;
(22) a $C_{7-12}$ aralkylthio group (e.g., benzylthio);
(23) a $C_{6-14}$ arylthio group (e.g., phenylthio, naphthylthio);
(24) a cyano group;
(25) a nitro group;
(26) a halogen atom;
(27) a $C_{1-3}$ alkylenedioxy group optionally substituted by 1 to 3 halogen atoms;
(28) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms; and
(29) a hydroxyimino group optionally substituted by a $C_{1-6}$ alkyl group optionally substituted by 1 to 3 $C_{6-14}$ aryl groups (e.g., phenyl).

In the present specification, the "$C_{1-6}$ alkoxy group" means, unless otherwise specified, methoxy, ethoxy, propoxy, isopropoxy, butoxy, isobutoxy, sec-butoxy, tert-butoxy and the like.

In the present specification, the "$C_{1-6}$ alkoxy group" of the "optionally substituted $C_{1-6}$ alkoxy group" optionally has 1 to 5 (preferably, 1 to 3) substituents at substitutable position(s). Examples of such substituent include the above-mentioned substituent group A. When two or more substituents are present, the respective substituents may be the same or different.

In the present specification, the "$C_{2-6}$ alkenyl group" means, unless otherwise specified, vinyl, allyl, isopropenyl, butenyl, pentenyl, hexenyl and the like.

In the present specification, the "$C_{2-6}$ alkenyl group" of the "optionally substituted $C_{2-6}$ alkenyl group" optionally has 1 to 5 (preferably, 1 to 3) substituents at substitutable position(s). Examples of such, substituent include the above-mentioned substituent group A. When two or more substituents are present, the respective substituents may be the same or different.

In the present specification, the "$C_{2-6}$ alkynyl group" means, unless otherwise specified, ethynyl, propargyl, butynyl, pentynyl, hexynyl and the like.

In the present specification, the "$C_{2-6}$ alkynyl group" of the "optionally substituted $C_{2-6}$ alkynyl group" optionally has 1 to 5 (preferably, 1 to 3) substituents at substitutable position(s). Examples of such substituent include the above-mentioned substituent group A. When two or more substituents are present, the respective substituents may be the same or different.

In the present specification, the "$C_{3-10}$ cycloalkyl group" means, unless otherwise specified, cyclopropyl, cyclobutyl, cyclopentyl, cyclohexyl, cycloheptyl, cyclooctyl, adamantyl and the like.

In the present specification, the "$C_{2-10}$ cycloalkyl group" of the "optionally substituted $C_{2-10}$ cycloalkyl group" optionally has 1 to 5 (preferably, 1 to 3) substituents at substitutable position(s). Examples of such substituent include the following substituent group B. When two or more substituents are present, the respective substituents may be the same or different.

Substituent group B:
(1) substituent group A;
(2) a $C_{1-6}$ alkyl group optionally substituted by 1 to 5 (preferably 1 to 3) substituents selected from
 (a) a halogen atom,
 (b) a carboxy group,
 (c) a hydroxy group,
 (d) a $C_{1-6}$ alkoxy-carbonyl group,
 (e) a $C_{1-6}$ alkoxy group,
 (f) an amino group optionally mono- or di-substituted by $C_{1-6}$ alkyl group(s), and
 (g) a $C_{3-10}$ cycloalkyloxy group (preferably, cyclopropyloxy);
(3) a $C_{2-6}$ alkenyl group (e.g., ethenyl) optionally substituted by 1 to 3 substituents selected from
 (a) a halogen atom,
 (b) a carboxy group,
 (c) a hydroxy group,
 (d) a $C_{1-6}$ alkoxy-carbonyl group,
 (e) a $C_{1-6}$ alkoxy group,
 (f) an amino group optionally mono- or di-substituted by $C_{1-6}$ alkyl group(s), and
 (g) a $C_{3-10}$ cycloalkyl group (e.g., cyclopropyl);
(4) a $C_{2-6}$ alkynyl group (e.g., ethynyl) optionally substituted by 1 to 3 $C_{3-10}$ cycloalkyl groups (e.g., cyclopropyl, cyclobutyl);
(5) a $C_{7-13}$ aralkyl group (e.g., benzyl) optionally substituted by 1 to 3 substituents selected from
 (a) a $C_{1-6}$ alkyl group optionally substituted by 1 to 3 halogen atoms,
 (b) a hydroxy group,
 (c) a $C_{1-6}$ alkoxy group, and
 (d) a halogen atom; and (6) an oxo group.

In the present specification, the "cyclic group" means, unless otherwise specified, aromatic hydrocarbon group, nonaromatic cyclic hydrocarbon group, aromatic heterocyclic group, nonaromatic heterocyclic group and the like.

In the present specification, the "aromatic ring group" means an aromatic hydrocarbon group or an aromatic heterocyclic group.

In the present specification, examples of the "aromatic hydrocarbon group" include a $C_{6-14}$ aryl group. Examples of the $C_{6-14}$ aryl group include phenyl, naphthyl, anthracenyl, phenanthrenyl, acenaphthyl and the like.

In the present specification, examples of the "nonaromatic cyclic hydrocarbon group" include a $C_{3-10}$ cycloalkyl group, a $C_{3-10}$ cycloalkenyl group, a $C_{4-10}$ cycloalkadienyl group and the like, each of which is optionally fused with a benzene ring.

In the present specification, examples of the $C_{3-10}$ cycloalyl group include cyclopropyl, cyclobutyl, cyclopentyl, cyclohexyl, cycloheptyl, cyclooctyl and the like.

In the present specification, examples of the $C_{3-10}$ cycloalkenyl group include 2-cyclopenten-1-yl, 3-cyclopenten-1-yl, 2-cyclohexen-1-yl, 3-cyclohexen-1-yl and the like.

In the present specification, examples of the $C_{4-10}$ cycloalkadienyl group include 2,4-cyclopentadien-1-yl, 2,4-cyclohexadien-1-yl, 2,5-cyclohexadien-1-yl and the like.

Each of the above-mentioned $C_{3-10}$ cycloalkyl group, $C_{3-10}$ cycloalkenyl group, and $C_{4-10}$ cycloalkadienyl group is optionally fused with a benzene ring. Examples of the fused ring group include indanyl, dihydronaphthyl, tetrahydronaphthyl, fluorenyl and the like.

In the present specification, examples of the "aromatic heterocyclic group" include a 5- to 10-membered monocycle or bicyclic aromatic heterocyclic group, containing, as a ring-constituting atom besides carbon atom, 1 to 4 hetero atoms selected from an oxygen atom, a sulfur atom and a nitrogen atom.

Preferable examples of the "aromatic heterocyclic group" include 5- or 6-membered monocyclic aromatic heterocyclic groups such as furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-3-yl, 1,2,4-oxadiazol-5-yl, 1,3,4-oxadiazol-2-yl), thiadiazolyl (e.g., 1,3,4-thiadiazol-2-yl, 1,2,4-thiadiazol-3-yl, 1,2,4-thiadiazol-5-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,2,4-triazin-5-yl, 1,2,4-triazin-6-yl) and the like;

8- to 10-membered bicyclic aromatic heterocyclic groups such as quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuryl (e.g., 2-benzofuryl, 3-benzofuryl), benzothienyl (e.g., 2-benzothienyl, 3-benzothienyl, 5-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridinyl (e.g., 1H-imidazo[4,5-b]pyridin-2-yl, 1H-imidazo[4,5-c]pyridin-2-yl, 2H-imidazo[1,2-a]pyridin-3-yl), imidazopyrazinyl (e.g., 1H-imidazo[4,5-b]pyrazin-2-yl), pyrazolopyridinyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like; and the like.

Examples of the "nonaromatic heterocyclic group" include a 5- to 12-membered monocycle or bicyclic nonaromatic heterocyclic group containing, besides carbon atom, 1 to 4 hetero atoms selected from an oxygen atom, a sulfur atom and a nitrogen atom.

Preferable examples of the "nonaromatic heterocyclic group" include a 4- to 7-membered monocyclic nonaromatic heterocyclic group such as tetrahydrofuranyl (e.g., tetrahydrofuran-2-yl, tetrahydrofuran-3-yl), dihydrooxazolyl (e.g., 4,5-dihydro-1,3-oxazol-2-yl), oxetanyl (e.g., oxetan-3-yl), pyrrolidinyl (e.g., 1-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), piperazinyl (e.g., 1-piperazinyl, 2-piperazinyl, 3-piperazinyl), hexamethyleniminyl (e.g., hexamethylenimin-1-yl), oxazolidinyl (e.g., oxazolidin-2-yl), thiazolidinyl (e.g., thiazolidin-2-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 4-pyranyl), tetrahydropyranyl (e.g., 4-tetrahydropyranyl), thiopyranyl (e.g., 4-thiopyranyl), tetrahydrothiopyranyl (e.g., 4-tetrahydrothiopyranyl), pyrazolidinyl (e.g., pyrazolidin-1-yl), tetrahydropyrimidinyl and the like;

a 8- to 12-membered bicyclic nonaromatic heterocyclic group such as dihydroindolyl (e.g., 2,3-dihydro-1H-indol-1-yl), dihydroisoindolyl (e.g., 1,3-dihydro-2H-isoindol-2-yl), dihydrobenzodioxinyl (e.g., 2,3-dihydro-1,4-benzodioxinyl), dihydrobenzodioxepinyl (e.g., 3,4-dihydro-2H-1,5-benzodioxepinyl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), chromenyl (e.g., 4H-chromen-2-yl, 2H-chromen-3-yl), dihydroquinolinyl (e.g., 1,2-dihydroquinolin-4-yl), tetrahydroquinolinyl (e.g., 1,2,3,4-tetrahydroquinolin-4-yl), dihydroisoquinolinyl (e.g., 1,2-dihydroisoquinolin-4-yl), tetrahydroisoquinolinyl (e.g., 1,2,3,4-tetrahydroisoquinolin-4-yl), dihydrophthalazinyl (e.g., 1,4-dihydrophthalazin-4-yl), benzazepanyl and the like; and the like.

In the present specification, the "cyclic group" of the "optionally substituted cyclic group" optionally has 1 to 5 (preferably, 1 to 3) substituents at substitutable position(s). Examples of such substituent include the above-mentioned substituent group B. When two or more substituents are present, the respective substituents may be the same or different.

In the present specification, examples of the "optionally substituted ring" include rings corresponding to the aforementioned "optionally substituted cyclic group".

In the present specification, the "aromatic ring group" of the "optionally substituted aromatic ring group" optionally has 1 to 5 (preferably, 1 to 3) substituents at substitutable position(s). Examples of such substituent include (1) to (5) of the above-mentioned substituent group B. When two or more substituents are present, the respective substituents may be the same or different.

In the present specification, the "hydrocarbon group" means, unless otherwise specified, a $C_{1-6}$ alkyl group, a $C_{2-6}$ alkenyl group, a $C_{2-6}$ alkynyl group, a $C_{7-13}$ aralkyl group, an aromatic hydrocarbon group, a nonaromatic cyclic hydrocarbon group and the like.

In the present specification, the "hydrocarbon group" of the "optionally substituted hydrocarbon group" optionally has 1 to 7 (preferably, 1 to 3) substituents at substitutable position(s). When two or more substituents are present, the respective substituents may be the same or different. When the aforementioned "hydrocarbon group" is a $C_{1-6}$ alkyl group, a $C_{2-6}$ alkenyl group, $C_{2-6}$ alkynyl group and the like, examples of the substituents include the above-mentioned substituent group A. When the aforementioned "hydrocarbon group" is a $C_{7-13}$ aralkyl group, an aromatic hydrocarbon group, a nonaromatic cyclic hydrocarbon group and the like, examples of the substituents include the above-mentioned substituent group B.

In the present specification, the "heterocyclic group" means an aromatic heterocyclic group or a nonaromatic heterocyclic group.

In the present specification, the "heterocyclic group" of the "optionally substituted heterocyclic group" optionally has 1 to 5 (preferably, 1 to 3) substituents at substitutable position(s). Examples of such substituent include the above-mentioned substituent group B. When two or more substituents are present, the respective substituents may be the same or different.

In the present specification, the "hydroxy group" of the "optionally substituted hydroxy group" optionally has one substituent. Examples of such substituent include a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

In the present specification, the "mercapto group" of the "optionally substituted mercapto group" optionally has one substituent. Examples of such substituent include a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, a heterocyclic group and the like, each of which is optionally substituted.

In the present specification, the "amino group" of the "optionally substituted amino group" optionally has 1 or 2 substituents at substitutable position(s). Examples of such substituent include a $C_{1-6}$ alkyl group, a $C_{2-6}$ alkenyl group, a $C_{3-10}$ cycloalkyl group, a $C_{3-10}$ cycloalkenyl group, a $C_6$-14 aryl group, a $C_{7-13}$ aralkyl group, a $C_{8-13}$ arylalkenyl group and a heterocyclic group; the below-mentioned acyl group and the like, each of which is optionally substituted. When two of the substituents are present, the respective substituents may be the same or different.

In the present specification, the "acyl group" is, for example, a group represented by the formula: —COR$^A$, —CO—OR$^A$, —SO$_3$R$^A$, —S(O)$_2$R$^A$, —SOR$^A$, —CO—NR$^{A'}$R$^{B'}$, —CS—NR$^{A'}$R$^{B'}$, —S(O)$_2$NR$^{A'}$R$^{B'}$ wherein R$^A$ is a hydrogen atom, an optionally substituted hydrocarbon group, or an optionally substituted heterocyclic group, R$^{A'}$ and R$^{B'}$ are the same or different and each is a hydrogen atom, an optionally substituted hydrocarbon group, or an optionally substituted heterocyclic group, or R$^{A'}$ and R$^{B'}$ optionally form, together with the adjacent nitrogen atom, an optionally substituted nitrogen-containing heterocycle, and the like.

Examples of the "nitrogen-containing heterocycle" of the "optionally substituted nitrogen-containing heterocycle" formed by R$^{A'}$ and R$^{B'}$ together with the adjacent nitrogen atom include a 5- to 7-membered nitrogen-containing heterocycle containing at least one nitrogen atom as a ring-constituting atom besides carbon atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 or 2) substituents at substitutable position(s). Examples of such substituent include the above-mentioned substituent group B. When the number of the substituents is two or more, the respective substituents may be the same or different.

Preferable examples of the "acyl group" include
(1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;
(7) a carbamoyl group optionally mono- or di-substituted by substituent(s) selected from
   (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
   (b) an amino group optionally mono- or di-substituted by a $C_{1-6}$ alkoxy-carbonyl group;
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ arylsulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a nonaromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

In the above-mentioned formula (I), preferable groups are as described below.

Ar is an optionally substituted aromatic ring group.

Examples of Ar include an optionally substituted $C_{6-14}$ aryl group, an optionally substituted 5- or 6-membered aromatic heterocyclic group (preferably, a 5- or 6-membered aromatic heterocyclic group containing, besides carbon atom, 1 to 4 hetero atoms selected from an oxygen atom, a sulfur atom and a nitrogen atom) and the like.

Ar is preferably
a $C_{6-14}$ aryl group (e.g., phenyl) optionally substituted by 1 to 3 substituents selected from substituent group B, (1)-(5), or a 5- or 6-membered aromatic heterocyclic group (preferably, a 5- or 6-membered aromatic heterocyclic group containing, besides carbon atom, 1 to 4 hetero atoms selected from an oxygen atom, a sulfur atom and a nitrogen atom, for example, pyridyl, thienyl, thiazolyl, pyrazolyl, pyrimidinyl, furyl) optionally substituted by 1 to 3 substituents selected from substituent group B, (1)-(5).

Ar is more preferably a $C_{6-14}$ aryl group or a 5- or 6-membered aromatic heterocyclic group, each of which is optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms.

Ar is more preferably a phenyl group, a pyridyl group (e.g., pyridin-2-yl, pyridin-3-yl, pyridin-4-yl), a thienyl group (e.g., thiophen-2-yl, thiophen-3-yl), a thiazolyl group (e.g., thiazol-2-yl, thiazol-5-yl), a pyrazolyl group (e.g., pyrazol-3-yl), a pyrimidinyl group (e.g., pyrimidin-5-yl) or a furyl group (e.g., furan-2-yl), each of which is optionally substituted by 1 to 3 substituents selected from
  (a) a halogen atom (e.g., a fluorine atom, a chlorine atom),
  (b) a cyano group,
  (c) a $C_{1-6}$ alkyl group optionally substituted by 1 to 3 halogen atoms (e.g., trifluoromethyl group), and
  (d) a $C_{1-6}$ alkoxy group optionally substituted by 1 to 3 halogen atoms.

Ar is more preferably a phenyl group, a thienyl group (e.g., thiophen-2-yl, thiophen-3-yl) or a furyl group (e.g., furan-2-yl), each of which is optionally substituted by 1 to 3 substituents selected from
  (a) a halogen atom (e.g., fluorine atom, chlorine atom),
  (b) a cyano group,
  (c) a $C_{1-6}$ alkyl group optionally substituted by 1 to 3 halogen atoms (e.g., trifluoromethyl group), and
  (d) a $C_{1-6}$ alkoxy group optionally substituted by 1 to 3 halogen atoms.

Ar is further preferably a phenyl group optionally substituted by 1 to 3 substituents selected from
  (a) a halogen atom (e.g., a fluorine atom, a chlorine atom),
  (b) a $C_{1-6}$ alkyl group optionally substituted by 1 to 3 halogen atoms (e.g., trifluoromethyl group), and
  (c) a $C_{1-6}$ alkoxy group optionally substituted by 1 to 3 halogen atoms.

Ar is particularly preferably a phenyl group optionally substituted by halogen atom(s) (e.g., a fluorine atom, a chlorine atom).

In another embodiment, Ar is preferably a thienyl group or a thiazolyl group, each of which is optionally substituted by 1 to 3 substituents selected from
  (a) a halogen atom (e.g., a fluorine atom, a chlorine atom),
  (b) a $C_{1-6}$ alkyl group optionally substituted by 1 to 3 halogen atoms (e.g., trifluoromethyl group), and
  (c) a $C_{1-6}$ alkoxy group optionally substituted by 1 to 3 halogen atoms.

Ar is particularly preferably a thienyl group or a thiazolyl group, each of which is optionally substituted by $C_{1-6}$ alkyl group(s) optionally substituted by 1 to 3 halogen atoms (e.g., trifluoromethyl group).

In another embodiment, particularly preferable examples of Ar include phenyl, 4-fluorophenyl, 4-chlorophenyl, 4-methylphenyl, 4-(trifluoromethyl)phenyl, 4-methoxyphenyl, 4-(trifluoromethoxy)phenyl, 4-cyanophenyl, 2-fluorophenyl, 3-fluorophenyl, 2,4-difluorophenyl, 3,4-difluorophenyl, 3,5-difluorophenyl, 4-chloro-3-fluorophenyl, thiophen-2-yl, thiophen-3-yl, 5-chlorothiophen-2-yl, 5-fluorothiophen-2-yl, 5-trifluoromethylthiophen-2-yl, 5-chlorothiophen-3-yl, 5-fluorothiophen-3-yl, 5-trifluoromethylthiophen-3-yl, 4,5-difluorothiophen-2-yl, 4-chloro-5-fluorothiophen-2-yl, 5-chloro-4-fluorothiophen-2-yl, furan-2-yl, 5-chlorofuran-2-yl, 5-trifluoromethylfuran-2-yl and the like.

$L^1$ is O, $S(O)_{m1}$, $NR^{5A}$ or $CR^{5B}R^{5C}$; and
$L^2$ is O, $S(O)_{m2}$, $NR^{6A}$ or $CR^{6B}R^{6C}$.

Here, at least one of $L^1$ and $L^2$ is $CR^{5B}R^{5C}$ or $CR^{6B}R^{6C}$ $R^{5A}$ and $R^{6A}$ are each independently a hydrogen atom or an optionally substituted hydrocarbon group;

$R^{5B}$, $R_{5C}$, $R^{6B}$ and $R^{6C}$ are each independently a hydrogen atom or a substituent;

wherein $R^{5B}$ and $R^{6B}$ optionally form, together with the adjacent carbon atoms, an optionally substituted ring, or $R^{5B}$ and the substituent of Ar are optionally joined to form an optionally substituted ring; and m1 and m2 are each independently an integer of 0 to 2.

Examples of the optionally substituted hydrocarbon group for $R^{5A}$ or $R^{6A}$ include a $C_{1-6}$ alkyl group optionally substituted by 1 to 3 halogen atoms and the like.

$R^{5A}$ and $R^{6A}$ are each preferably a hydrogen atom.

Examples of the substituent for $R^{5B}$, $R^{5C}$, $R^{6B}$ or $R^{6C}$ include a halogen atom, a cyano group, a nitro group, an optionally substituted hydrocarbon group, an optionally substituted heterocyclic group, an optionally substituted hydroxy group, an optionally substituted mercapto group, an optionally substituted amino group, an acyl group and the like.

$R^{5B}$, $R^{5C}$, $R^{6B}$ and $R^{6C}$ are each preferably independently a halogen atom, a cyano group, a nitro group, a hydroxy group, or a $C_{1-6}$ alkyl group optionally substituted by 1 to 3 halogen atoms.

$R^{5B}$, $R^{5C}$, $R^{6B}$ and $R^{6C}$ are more preferably each independently a hydrogen atom or a $C_{1-6}$ alkyl group.

Examples of the optionally substituted ring formed by $R^{5B}$ and $R^{6B}$ together with the adjacent carbon atoms include optionally substituted $C_{3-6}$ cycloalkane (e.g., cyclopropane) and the like. Examples of the substituent that $C_{3-6}$ cycloalkane optionally has include a halogen atom, a cyano group, a nitro group, a hydroxy group, a $C_{1-6}$ alkyl group and the like. The optionally substituted ring formed by $R^{5B}$ and $R^{6B}$ together with the adjacent carbon atoms is preferably cyclopropane.

Examples of the optionally substituted ring formed by $R^{5B}$ and the substituent of Ar in combination include optionally substituted $C_{5-7}$ cycloalkane (e.g., cyclopentane, cyclohexane) and the like. Examples of the substituent that $C_{5-7}$ cycloalkane optionally has include a halogen atom, a cyano group, a nitro group, a hydroxy group, a $C_{1-6}$ alkyl group and the like.

As Ar-$L^1$-$L^2$- when $R^{5B}$ and the substituent of Ar are joined to form an optionally substituted ring, a group represented by the formula

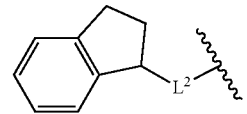

can be mentioned.

Preferable combinations of Ar-$L^1$-$L^2$- are, for example,
Ar—$CR^{5B}R^{5C}$—O—
Ar—O—$CR^{6B}R^{6C}$—,
Ar—$CR^{5B}R^{5C}$—$CR^{6B}R^{6C}$—,
Ar—$CH_2$—$NR^{6A}$—
and the like, more preferably
Ar—$CH_2$—O—,
Ar—O—$CH_2$—, Ar—CH(CH$_3$)—O—,
Ar—CH$_2$—NH—,
Ar—CH$_2$—N(CH$_3$)—,

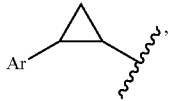

Ar—CH$_2$—CH$_2$—,

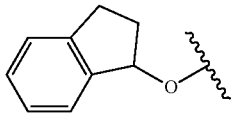

and the like.

Further preferably,

L$^1$ is CR$^{5B}$R$^{5C}$,

L$^2$ is O,

R$^{5B}$ and R$^{5C}$ are each independently a hydrogen atom or a C$_{1-6}$ alkyl group, R$^{5B}$ and the substituent of Ar are optionally joined to form a cyclopentane ring.

Particularly preferably, L$^1$ is CH$_2$, and L$^2$ is O.

X$^1$ is CR$^4$ or N, and X$^2$ and X$^3$ are each independently CH or N, wherein R$^4$ is a hydrogen atom, a halogen atom, an optionally substituted C$_{1-6}$ alkyl group, an optionally substituted C$_{3-10}$ cycloalkyl group, or an optionally substituted C$_{1-6}$ alkoxy group.

R$^4$ is preferably (a) a hydrogen atom, (b) a halogen atom, (c) a C$_{1-6}$ alkyl group optionally substituted by 1 to 3 substituents selected from substituent group A, (d) a C$_{3-10}$ cycloalkyl group optionally substituted by 1 to 3 substituents selected from substituent group B, or (e) a C$_{1-6}$ alkoxy group optionally substituted by 1 to 3 substituents selected from substituent group A.

R$^4$ is more preferably a hydrogen atom, a halogen atom, a C$_{1-6}$ alkyl group, a C$_{3-10}$ cycloalkyl group or a C$_{1-6}$ alkoxy group.

R$^4$ is more preferably a hydrogen atom.

Preferable combinations of X$^1$, X$^2$ and X$^3$ are

X$^1$, X$^2$ and X$^3$ are CH,

X$^2$ and X$^3$ are CH, and X$^1$ is N,

X$^1$ and X$^3$ are CH, and X$^2$ is N, and

X$^1$ and X$^2$ are CH, and X$^3$ is N.

More preferably, X$^1$, X$^2$ and X$^3$ are CH.

R$^1$ is a hydrogen atom, a halogen atom, an optionally substituted C$_{1-6}$ alkyl group, an optionally substituted C$_{3-10}$ cycloalkyl group, or an optionally substituted C$_{1-6}$ alkoxy group.

R$^1$ is preferably (a) a hydrogen atom, (b) a halogen atom, (c) a C$_{1-6}$ alkyl group optionally substituted by 1 to 3 substituents selected from substituent group A, (d) a C$_{3-113}$ cycloalkyl group optionally substituted by 1 to 3 substituents selected from substituent group B, or (e) a C$_{1-6}$ alkoxy group optionally substituted by 1 to 3 substituents selected from substituent group A.

R$^1$ is more preferably a hydrogen atom, a halogen atom, a C$_{1-6}$ alkyl group or a C$_{1-6}$ alkoxy group.

R$^1$ is more preferably a hydrogen atom.

R$^2$ is a halogen atom, an optionally substituted C$_{1-6}$ alkyl group, or an optionally substituted cyclic group.

Examples of the "cyclic group" of the "optionally substituted cyclic group" for R$^2$ include a C$_{3-10}$ cycloalkyl group, a C$_{6-14}$ aryl group, a heterocyclic group and the like. As the heterocyclic group, a 4- to 6-membered heterocyclic group containing, besides carbon atom, 1 to 4 hetero atoms selected from an oxygen atom, a sulfur atom and a nitrogen atom and the like can be mentioned.

R$^2$ is preferably (a) a halogen atom, (b) a C$_{1-6}$ alkyl group optionally substituted by 1 to 3 substituents selected from substituent group A, (c) a C$_{3-10}$ cycloalkyl group optionally substituted by 1 to 3 substituents selected from substituent group B, or (d) a C$_{6-14}$ aryl group optionally substituted by 1 to 3 substituents selected from substituent group B, (1)-(5).

R$^2$ is more preferably a C$_{1-6}$ alkyl group optionally substituted by 1 to 3 substituents selected from a halogen atom, a hydroxy group and a C$_{1-6}$ alkoxy group.

R$^2$ is more preferably a C$_{1-6}$ alkyl group optionally substituted by 1 to 3 substituents selected from a hydroxy group and a C$_{1-6}$ alkoxy group.

R$^2$ is particularly preferably a C$_{1-6}$ alkyl group.

R$^2$ is particularly preferably methyl.

R$^3$ is (a) a hydrogen atom, (b) a halogen atom, (c) a cyano group, (d) a C$_{1-6}$ alkyl group optionally substituted by 1 to 3 substituents selected from a halogen atom, a cyano group, an optionally substituted C$_{1-6}$ alkoxy group, an optionally substituted C$_{3-10}$ cycloalkyl group, an optionally substituted aromatic ring group, —CO—R$^{7A}$, and —S(O)$_{n1}$—R$^{7B}$, (e) a C$_{1-6}$ alkoxy group optionally substituted by 1 to 3 substituents selected from a halogen atom, a cyano group, an optionally substituted C$_{1-6}$ alkoxy group, an optionally substituted C$_{3-10}$ cycloalkyl group, an optionally substituted aromatic ring group, —CO—R$^{8A}$, and —S(O)$_{n2}$—R$^{8B}$, (f) an optionally substituted C$_{2-6}$ alkenyl group, (g) an optionally substituted cyclic group, or (h) —CO—R$^9$.

Here, R$^{7A}$, R$^{7B}$, R$^{8A}$, R$^{8B}$ and R$^9$ are each independently an optionally substituted C$_{1-6}$ alkyl group, an optionally substituted C$_{3-10}$ cycloalkyl group, or an optionally substituted amino group, and n1 and n2 are each independently an integer of 0 to 2.

R$^{7A}$, R$^{7B}$, R$^{8A}$, R$^{8B}$ and R$^9$ are each preferably independently (a) a C$_{1-6}$ alkyl group optionally substituted by 1 to 3 substituents selected from substituent group A, (b) a C$_{3-10}$ cycloalkyl group optionally substituted by 1 to 3 substituents selected from substituent group B, or (c) an amino group optionally substituted by 1 or 2 substituents selected from substituent group B, (1)-(5).

R$^{7A}$, R$^{7B}$, R$^{8A}$, R$^{8B}$ and R$^9$ are each independently more preferably a C$_{1-6}$ alkyl group, a C$_{3-10}$ cycloalkyl group, a (C$_{1-6}$ alkyl)amino group, a di(C$_{1-6}$ alkyl)amino group or a (hydroxy-C$_{1-6}$ alkyl)amino group.

Examples of the "cyclic group" of the "optionally substituted cyclic group" for $R^3$ include a $C_{3-10}$ cycloalkyl group, a $C_{6-14}$ aryl group, a heterocyclic group and the like. As the heterocyclic group, a 4- to 6-membered heterocyclic group containing, besides carbon atom, 1 to 4 hetero atoms selected from an oxygen atom, a sulfur atom and a nitrogen atom and the like.

$R^3$ is preferably
(a) a hydrogen atom,
(b) a halogen atom,
(c) a cyano group,
(d) a $C_{1-6}$ alkyl group optionally substituted by 1 to 3 substituents selected from a halogen atom, a cyano group, a $C_{1-6}$ alkoxy group optionally substituted by 1 to 3 substituents selected from substituent group A, a $C_{3-10}$ cycloalkyl group optionally substituted by 1 to 3 substituents selected from substituent group B, an aromatic ring group optionally substituted by 1 to 3 substituents selected from substituent group B, (1)-(5), —CO—$R^{7A}$, and —S(O)$_{n1}$—$R^{7H}$,
(e) a $C_{1-6}$ alkoxy group optionally substituted by 1 to 3 substituents selected from a halogen atom, a cyano group, a $C_{1-6}$ alkoxy group optionally substituted by 1 to 3 substituents selected from substituent group A, a $C_{3-10}$ cycloalkyl group optionally substituted by 1 to 3 substituents selected from substituent group B, an aromatic ring group optionally substituted by 1 to 3 substituents selected from substituent group B, (1)-(5), —CO—$R^{8A}$, and —S(O)$_{n2}$—$R^{8B}$,
(f) a $C_{2-6}$ alkenyl group optionally substituted by 1 to 3 substituents selected from substituent group A,
(g) a $C_{3-10}$ cycloalkyl group optionally substituted by 1 to 3 substituents selected from substituent group B,
(h) a heterocyclic group (preferably, a 4- to 6-membered heterocyclic group containing, besides carbon atom, 1 to 4 hetero atoms selected from an oxygen atom, a sulfur atom and a nitrogen atom, for example, tetrahydrofuranyl, dihydrooxazolyl, oxazolyl, isoxazolyl, pyrazolyl, oxadiazolyl, oxetanyl, thiazolyl) optionally substituted by 1 to 3 substituents selected from substituent group B, or
(i) —CO—$R^9$.

$R^3$ is more preferably
(1) a hydrogen atom,
(2) a cyano group,
(3) a $C_{1-6}$ alkyl group optionally substituted by 1 to 3 substituents selected from
 (a) a halogen atom (e.g., a fluorine atom, a chlorine atom),
 (b) a cyano group,
 (c) a $C_{1-6}$ alkoxy group optionally substituted by 1 to 3 halogen atoms, and
 (d) a $C_{3-10}$ cycloalkyl group (e.g., cyclopropyl),
(4) a $C_{3-10}$ cycloalkyl group (e.g., cyclopropyl, cyclobutyl, cyclopentyl) optionally substituted by 1 to 3 substituents selected from
 (a) a halogen atom (e.g., a fluorine atom),
 (b) a cyano group,
 (c) a $C_{1-6}$ alkyl group optionally substituted by 1 to 3 substituents selected from a halogen atom and a hydroxy group,
 (d) a carbamoyl group,
 (e) a $C_{1-6}$ alkoxy group,
 (f) an oxo group,
 (g) a hydroxy group,
 (h) a $C_{1-6}$ alkoxy-carbonyl group, and
 (i) a carboxy group,
(5) a tetrahydrofuranyl group (e.g., tetrahydrofuran-2-yl, tetrahydrofuran-3-yl), a dihydrooxazolyl group (e.g., 4,5-dihydro-1,3-oxazol-2-yl), an oxazolyl group (e.g., 1,3-oxazol-5-yl, 1,3-oxazol-4-yl), an isoxazolyl group (e.g., 1,2-oxazol-5-yl, 1,2-oxazol-3-yl), a pyrazolyl group (e.g., 1H-pyrazol-3-yl), an oxadiazolyl group (e.g., 1,3,4-oxadiazol-2-yl), an oxetanyl group (e.g., oxetan-3-yl) or a thiazolyl group (e.g., thiazol-5-yl), each of which is optionally substituted by 1 to 3 substituents selected from a $C_{1-6}$ alkyl group and a $C_{3-10}$ cycloalkyl group, or
(6) —CO—$R^9$
wherein $R^9$ is a $C_{1-6}$ alkyl group, a $C_{3-10}$ cycloalkyl group (e.g., cyclopropyl), a ($C_{1-6}$ alkyl)amino group, a di($C_{1-6}$ alkyl)amino group or a (hydroxy-$C_{1-6}$ alkyl)amino group).

$R^3$ is more preferably
(1) a $C_{1-6}$ alkyl group optionally substituted by 1 to 3 substituents selected from
 (a) a halogen atom,
 (b) a cyano group, and
 (c) a $C_{1-6}$ alkoxy group optionally substituted by 1 to 3 halogen atoms, or
(2) a $C_{3-10}$ cycloalkyl group optionally substituted by 1 to 3 substituents selected from
 (a) a halogen atom,
 (b) a cyano group,
 (c) a $C_{1-6}$ alkyl group optionally substituted by 1 to 3 substituents selected from a halogen atom and a hydroxy group,
 (d) a carbamoyl group,
 (e) a $C_{1-6}$ alkoxy group,
 (f) an oxo group,
 (g) a hydroxy group,
 (h) a $C_{1-6}$ alkoxy-carbonyl group, and
 (i) a carboxy group.

$R^3$ is more preferably a $C_{3-10}$ cycloalkyl group (e.g., cyclopropyl, cyclobutyl, cyclopentyl) optionally substituted by 1 to 3 substituents selected from
 (a) a halogen atom (e.g., a fluorine atom),
 (b) a cyano group,
 (c) a $C_{1-6}$ alkyl group optionally substituted by 1 to 3 substituents selected from a halogen atom and a hydroxy group,
 (d) a carbamoyl group,
 (e) a $C_{1-6}$ alkoxy group,
 (f) an oxo group,
 (g) a hydroxy group,
 (h) a $C_{1-6}$ alkoxy-carbonyl group, and
 (i) a carboxy group.

$R^3$ is particularly preferably cyclopropyl optionally substituted by 1 to 3 substituents selected from
 (a) a halogen atom (e.g., a fluorine atom),
 (b) a cyano group, and
 (c) a $C_{1-6}$ alkyl group optionally substituted by 1 to 3 substituents selected from a halogen atom and a hydroxy group.

In another embodiment, preferable examples of $R^3$ include a $C_{1-6}$ alkyl group or a $C_{3-10}$ cycloalkyl group.

A group represented by the formula

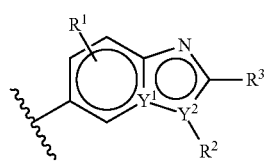

is a group represented by

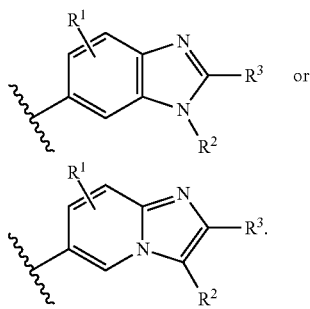

A preferable example of the group represented by the formula

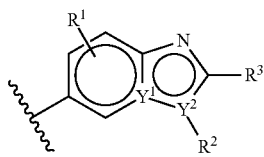

is a group represented by

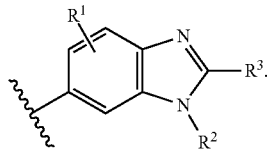

Preferable examples of compound (I) include the following compounds (I-1), (I-A), (I-B), (I-C) and (I-D).
[Compound (I-1)]
Compound (I) wherein
Ar is a phenyl group, a pyridyl group (e.g., pyridin-2-yl, pyridin-3-yl, pyridin-4-yl), a thienyl group (e.g., thiophen-2-yl, thiophen-3-yl), a thiazolyl group (e.g., thiazol-2-yl, thiazol-4-yl, thiazol-5-yl), a pyrazolyl group (e.g., pyrazol-3-yl), a pyrimidinyl group (e.g., pyrimidin-2-yl, pyrimidin-5-yl), a furanyl group (e.g., furan-2-yl, furan-3-yl), a thiadiazolyl group (e.g., 1,2,4-thiadiazol-3-yl), a pyrazinyl group (e.g., pyrazin-2-yl), a benzothienyl group (e.g., benzothiophen-5-yl) or a dihydrobenzofuranyl group (e.g., 2,3-dihydro-1-benzofuran-5-yl), each of which is optionally substituted by 1 to 3 substituents selected from
(a) a halogen atom (e.g., fluorine atom, chlorine atom, bromine atom),
(b) a cyano group,
(c) a $C_{1-6}$ alkyl group optionally substituted by 1 to 5 (preferably 1 to 3) halogen atoms (e.g., fluoromethyl, difluoromethyl, trifluoromethyl, pentafluoroethyl),
(d) a $C_{1-6}$ alkoxy group optionally substituted by 1 to 3 halogen atoms,
(e) a $C_{1-6}$ alkylsulfonyl group,
(f) a $C_{1-3}$ alkylenedioxy group optionally substituted by 1 to 3 halogen atoms (e.g., difluoromethylenedioxy), and
(g) a $C_{3-10}$ cycloalkyl group (e.g., cyclopropyl);
$X^1$, $X^2$ and $X^3$ are CH,
$X^2$ and $X^3$ are CH, and $X^1$ is N,
$X^1$ and $X^3$ are CH, and $X^2$ is N, or
$X^1$ and $X^2$ are CH, and $X^3$ is N;
$Y^1$ is N, and $Y^2$ is C, or
$Y^1$ is C, and $Y^2$ is N;
$L^1$ is O or $CR^{5B}R^{5C}$;
$L^2$ is O, $NR^{6A}$ or $CR^{6B}R^{6C}$;
wherein at least one of $L^1$ and $L^2$ is $CR^{5B}R^{5C}$ or $CR^{6B}R^{6C}$;
$R^{6A}$ is a hydrogen atom or a $C_{1-6}$ alkyl group;
$R^{5B}$, $R^{5C}$, $R^{6B}$ and $R^{6C}$ are each independently a hydrogen atom or a $C_{1-6}$ alkyl group;
wherein $R^{5B}$ and $R^{6B}$ optionally form, together with the adjacent carbon atoms, a cyclopropane ring, or $R^{5B}$ and the substituent of Ar are optionally joined to form a cyclopentane ring;
$R^1$ is a hydrogen atom, a halogen atom, a $C_{1-6}$ alkyl group or a $C_{1-6}$ alkoxy group;
$R^2$ is a $C_{1-6}$ alkyl group optionally substituted by 1 to 3 substituents selected from a halogen atom, a hydroxy group and
a $C_{1-6}$ alkoxy group;
$R^3$ is
(1) a hydrogen atom,
(2) a cyano group,
(3) a $C_{1-6}$ alkyl group optionally substituted by 1 to 3 substituents selected from
(a) a halogen atom (e.g., a fluorine atom, a chlorine atom),
(b) a cyano group,
(c) a $C_{1-6}$ alkoxy group optionally substituted by 1 to 3 halogen atoms, and
(d) a $C_{3-10}$ cycloalkyl group (e.g., cyclopropyl),
(4) a $C_{3-10}$ cycloalkyl group (e.g., cyclopropyl, cyclobutyl, cyclopentyl) optionally substituted by 1 to 3 substituents selected from
(a) a halogen atom (e.g., a fluorine atom),
(b) a cyano group,
(c) a $C_{1-6}$ alkyl group optionally substituted by 1 to 3 substituents selected from a halogen atom and a hydroxy group,
(d) a carbamoyl group,
(e) a $C_{1-6}$ alkoxy group,
(f) an oxo group,
(g) a hydroxy group,
(h) a $C_{1-6}$ alkoxy-carbonyl group, and
(i) a carboxy group,
(5) a tetrahydrofuranyl group (e.g., tetrahydrofuran-2-yl, tetrahydrofuran-3-yl), a dihydrooxazolyl group (e.g., 4,5-dihydro-1,3-oxazol-2-yl), an oxazolyl group (e.g., 1,3-oxazol-5-yl, 1,3-oxazol-4-yl), an isoxazolyl group (e.g., 1,2-oxazol-5-yl, 1,2-oxazol-3-yl), a pyrazolyl group (e.g., pyrazol-3-yl), an oxadiazolyl group (e.g., 1,3,4-oxadiazol-2-yl), an oxetanyl group (e.g., oxetan-3-yl) or a thiazolyl group (e.g., thiazol-5-yl), each of which is optionally substituted by 1 to 3 substituents selected from a $C_{1-6}$ alkyl group and a $C_{3-10}$ cycloalkyl group, or
(6) —CO—$R^9$
wherein $R^9$ is a $C_{1-6}$ alkyl group, a $C_{3-10}$ cycloalkyl group (e.g., cyclopropyl), a ($C_{1-6}$ alkyl) amino group, a di($C_{1-6}$ alkyl) amino group or a (hydroxy-$C_{1-6}$ alkyl)amino group, or a salt thereof.
[Compound (I-A)]
Compound (I) wherein
Ar is a phenyl group, a pyridyl group (e.g., pyridin-2-yl, pyridin-3-yl, pyridin-4-yl), a thienyl group (e.g., thiophen-2-yl, thiophen-3-yl), a thiazolyl group (e.g., thiazol-2-yl, thiazol-5-yl), a pyrazolyl group (e.g., pyrazol-3-yl), a pyrimidinyl group (e.g., pyrimidin-5-yl) or a furanyl group (e.g., furan-2-yl), each of which is optionally substituted by 1 to 3 substituents selected from (a) a halogen atom (e.g., a fluorine atom, a chlorine atom),
(b) a cyano group,
(c) a $C_{1-6}$ alkyl group optionally substituted by 1 to 3 halogen atoms (e.g., trifluoromethyl), and
(d) a $C_{1-6}$ alkoxy group optionally substituted by 1 to 3 halogen atoms;

$X^1$, $X^2$ and $X^3$ are CH,
$X^2$ and $X^3$ are CH, and $X^1$ is N,
$X^1$ and $X^3$ are CH, and $X^2$ is N, or
$X^1$ and $X^2$ are CH, and $X^3$ is N;
$Y^1$ is N, and $Y^2$ is C, or
$Y^1$ is C, and $Y^2$ is N;
$L^1$ is $CR^{5B}R^{5C}$;
$L^2$ is O;
$R^{5B}$ and $R^{5C}$ are each independently a hydrogen atom or a $C_{1-6}$ alkyl group;
$R^{5B}$ and the substituent of Ar are optionally joined to form a cyclopentane ring;
$R^1$ is a hydrogen atom, a halogen atom, a $C_{1-6}$ alkyl group or a $C_{1-6}$ alkoxy group;
$R^2$ is a $C_{1-6}$ alkyl group optionally substituted by 1 to 3 substituents selected from a halogen atom, a hydroxy group and a $C_{1-6}$ alkoxy group;
$R^3$ is
(1) a hydrogen atom,
(2) a cyano group,
(3) a $C_{1-6}$ alkyl group optionally substituted by 1 to 3 substituents selected from
(a) a halogen atom (e.g., a fluorine atom, a chlorine atom),
(b) a cyano group,
(c) a $C_{1-6}$ alkoxy group optionally substituted by 1 to 3 halogen atoms, and
(d) a $C_{3-10}$ cycloalkyl group (e.g., cyclopropyl),
(4) a $C_{3-10}$ cycloalkyl group (e.g., cyclopropyl, cyclobutyl, cyclopentyl) optionally substituted by 1 to 3 substituents selected from
(a) a halogen atom (e.g., a fluorine atom),
(b) a cyano group,
(c) a $C_{1-6}$ alkyl group optionally substituted by 1 to 3 substituents selected from a halogen atom and a hydroxy group,
(d) a carbamoyl group,
(e) a $C_{1-6}$ alkoxy group,
(f) an oxo group,
(g) a hydroxy group,
(h) a $C_{1-6}$ alkoxy-carbonyl group, and
(i) a carboxy group,
(5) a tetrahydrofuranyl group (e.g., tetrahydrofuran-2-yl, tetrahydrofuran-3-yl), a dihydrooxazolyl group (e.g., 4,5-dihydro-1,3-oxazol-2-yl), an oxazolyl group (e.g., 1,3-oxazol-5-yl, 1,3-oxazol-4-yl), an isoxazolyl group (e.g., 1,2-oxazol-5-yl, 1,2-oxazol-3-yl), a pyrazolyl group (e.g., pyrazol-3-yl), an oxadiazolyl group (e.g., 1,3,4-oxadiazol-2-yl), an oxetanyl group (e.g., oxetan-3-yl) or a thiazolyl group (e.g., thiazol-5-yl), each of which is optionally substituted by 1 to 3 substituents selected from a $C_{1-6}$ alkyl group and a $C_{3-10}$ cycloalkyl group, or
(6) —CO—$R^9$
wherein $R^9$ is a $C_{1-6}$ alkyl group, a $C_{3-10}$ cycloalkyl group (e.g., cyclopropyl), a ($C_{1-6}$ alkyl)amino group, a di($C_{1-6}$ alkyl)amino group or a (hydroxy-$C_{1-6}$ alkyl)amino group, or a salt thereof.

[Compound (I-B)]
Compound (I) wherein
Ar is a phenyl group optionally substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms;
$X^1$, $X^2$ and $X^3$ are CH;
$Y^1$ is C,
$Y^2$ is N;
$L^1$ is $CH_2$;
$L^2$ is O;
$R^1$ is a hydrogen atom;
$R^2$ is a $C_{1-6}$ alkyl group; and
$R^3$ is a $C_{1-6}$ alkyl group or a $C_{3-6}$ cycloalkyl group, or a salt thereof.

[Compound (I-C)]
Compound (I) wherein
Ar is a thienyl group or a thiazolyl group, each of which is optionally substituted by 1 to 3 substituents selected from
(1) a halogen atom,
(2) a $C_{1-6}$ alkyl group optionally substituted by 1 to 3 halogen atoms, and
(3) a $C_{1-6}$ alkoxy group optionally substituted by 1 to 3 halogen atoms;
$X^1$, $X^2$ and $X^3$ are CH;
$Y^1$ is C,
$Y^2$ is N;
$L^1$ is $CH_2$;
$L^2$ is O;
$R^1$ is a hydrogen atom;
$R^2$ is a $C_{1-6}$ alkyl group; and
$R^3$ is a $C_{1-6}$ alkyl group or a $C_{3-6}$ cycloalkyl group, or a salt thereof.

[Compound (I-D)]
1-(2-Cyclopropyl-1-methyl-1H-benzimidazol-6-yl)-4-((4-fluorobenzyl)oxy)pyridin-2(1H)-one or a salt thereof (Example 2)
1-(2-Ethyl-1-methyl-1H-benzimidazol-6-yl)-4-((4-fluorobenzyl)oxy)pyridin-2(1H)-one or a salt thereof (Example 63)
1-(2-Cyclopropyl-1-methyl-1H-benzimidazol-6-yl)-4-((3,4-difluorobenzyl)oxy)pyridin-2(1H)-one or a salt thereof (Example 115)
1-(1,2-Dimethyl-1H-benzimidazol-6-yl)-4-((4-fluorobenzyl)oxy)pyridin-2(1H)-one or a salt thereof (Example 254)

More preferable examples of compound (I) include those described in the following Examples and salts thereof.

When compound (I) is in the form of a salt, concrete examples thereof include pharmaceutically acceptable salts, for example, salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be any of an anhydrate or a hydrate.

In addition, compound (I) may be any of non-solvate and solvate.

Moreover, compound (I) may be labeled with an isotope (e.g., $^3H$, $^{11}C$, $^{14}C$, $^{18}F$, $^{35}S$, $^{125}I$)

Compound (I) labeled with or substituted by an isotope can be used, for example, as a tracer used for Positron Emission Tomography (PET) (PET tracer), and is useful in the field of medical diagnosis and the like.

Furthermore, compound (I) may also be a deuterium exchange compound wherein $^1H$ is converted to $^2H(D)$.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [α-methoxy-α-(trifluoromethyl)phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

A prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);

a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

The production methods of compound (I) are explained in the following.

Compound (I) can be produced by, for example, a method shown below or a method analogous thereto, though not limited thereto.

In each of the following schemes, each starting compound may form a salt as long as it does not inhibit the reaction and, as the salt, those exemplified as the salt of the compound represented by the aforementioned formula (I) is used.

In each of the following schemes, as the starting compound, unless specific production method is stated, a commercially available one is easily available, or can be produced by a method known per se or a method analogous thereto.

A solvent to be used for the reaction of each of the following schemes is not particularly limited as long as it does not inhibit the reaction and dissolves the starting material to some extent. Examples thereof include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, dioxane, 1,2-dimethoxyethane and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; water and the like. These solvents may be mixed and used at an appropriate ratio. The reaction temperature is not higher than the boiling points of the aforementioned solvents, and is generally −100° C. to 250° C. In some cases, pressure-resistant reaction conditions and the like may be employed, and the reaction may be performed at a temperature not lower than the boiling point of the solvent. The reaction time is generally 0.5 hr to 100 hr.

In each of the following reactions, the "room temperature" means 15° C. to 30° C.

Compound (I) can be produced, for example, by the reaction of compound (2) and compound (3) shown in the following production method 1-1.

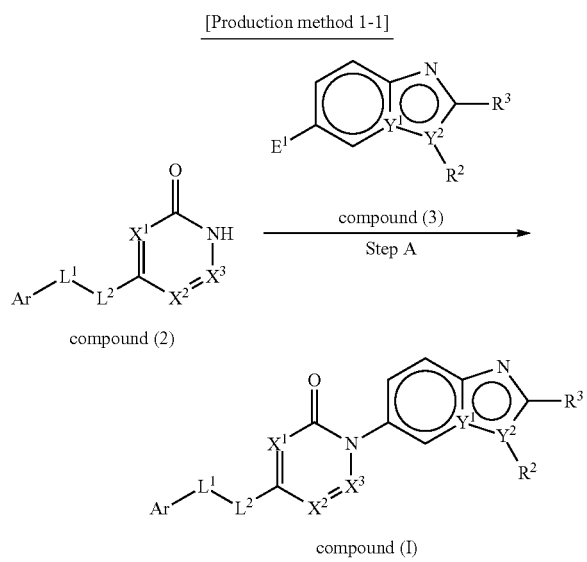

[Production method 1-1]

wherein each symbol is as defined above, $E^1$ is a leaving group (e.g., a halogen atom such as chlorine, bromine, iodine and the like, substituted sulfonic acid ester such as methanesulfonic acid ester, p-toluenesulfonic acid ester and the like, boronic acid etc.).

<Step A>

That is, in production method 1-1, compound (I) is obtained using about 1.0 to 10.0 mol, preferably about 1.0 to 5.0 mol, of compound (3), about 1.0 to 10.0 mol, preferably about 1.0 to 5.0 mol, of a base, and about 0.000001 to 5 mol, preferably about 0.0001 mol to 2 mol, of a metal catalyst, per 1 mol of compound (2).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

Examples of the metal catalyst include copper and a salt thereof (e.g., copper(II) acetate, copper(II) iodide and the like), palladium complexes (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper and a salt thereof are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally from room temperature to 250° C., preferably 50° C. to 200° C.

In addition, this reaction may be performed using a ligand. As the ligand, organic amine compounds such as N,N'-dimethylethylenediamine, N,N'-dimethyl-cyclohexane-1,2-diamine, 2,2-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned. The amount of the ligand to be used is generally about 1.0 to 10.0 mol, preferably about 1.0 to 5.0 mol, relative to the metal catalyst.

The obtained compound (I) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2) can be produced by the method described in the following production method or a method analogous thereto, or a commercially available reagent can be used, or can be produced by a method known per se.

Compound (3) can be produced by the method described in the following production method or a method analogous thereto.

Compound (Ib), which is compound (I) wherein $R^3$ is a group having a hydroxyl group or a cyano group can be produced from, for example, compound (Ia) shown in the following production method 1-2.

[Production method 1-2]

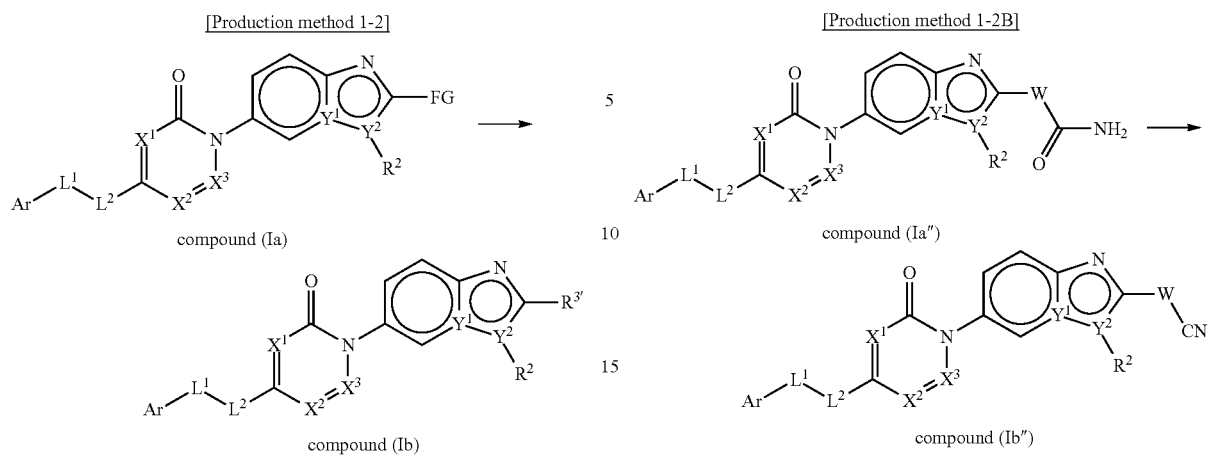

compound (Ia)

compound (Ib)

wherein FG is a group containing a functional group convertible to a hydroxyl group or a cyano group, R$^{3'}$ is the aforementioned R$^3$ having a hydroxyl group or a cyano group, and other symbols are each as defined above.

That is, in production method 1-2, a functional group of a group represented by FG in compound (Ia) is converted to a hydroxyl group or a cyano group to give compound (Ib).

As a production method of compound (Ib') wherein R$^{3'}$ is a group having a hydroxyl group, for example, the reaction shown in the following production method 1-2A can be recited.

[Production method 1-2A]

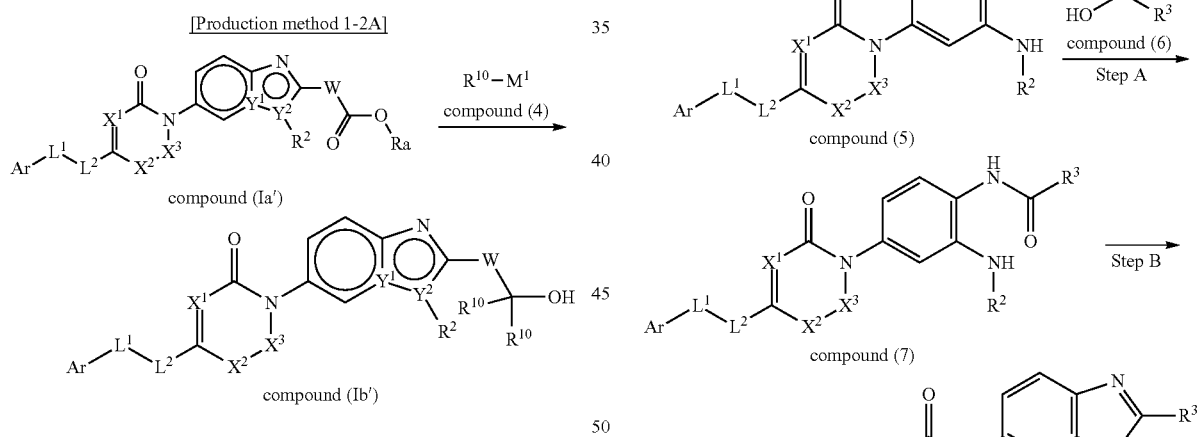

compound (Ia')

compound (Ib')

wherein Ra is a $C_{1-6}$ alkyl group, W is a $C_{1-4}$ alkylene group (—CH$_2$—, —(CH$_2$)$_2$—, —(CH$_2$)$_3$— and the like) or a $C_{3-6}$ cycloalkylene group (cyclopropylene, cyclobutylene, cyclohexylene and the like), R$^{10}$ is an optionally substituted $C_{1-6}$ alkyl group or an optionally substituted $C_{3-10}$ cycloalkyl group, M$^1$ is a metal or metal halide (e.g., lithium, magnesium bromide, copper, zinc and the like), and other symbols are each as defined above.

That is, in production method 1-2A, compound (Ia') is subjected to an alkylation reaction known per se to give the object compound (Ib').

As a production method of compound (Ib") wherein R$^{3'}$ is a group having a cyano group, for example, the reaction shown in the following production method 1-2B can be mentioned.

[Production method 1-2B]

compound (Ia")

compound (Ib")

wherein each symbol is as defined above.

That is, in production method 1-2B, compound (Ia") is subjected to a method known per se to give the object compound (Ib").

Compound (Ic) which is compound (I) wherein Y$^1$ is C and Y$^2$ is N can also be produced by, as a different method, for example, a condensation reaction of compound (5) and compound (6), followed by a dehydration reaction shown in the following production method 1-3.

[Production method 1-3]

compound (5)

compound (7)

compound (Ic)

wherein each symbol is as defined above.
<Step A>

In step A, compound (7) is obtained using about 1.0 to 5.0 mol, preferably about 1.0 to 2.0 mol, of compound (6), about 1.0 to 10.0 mol, preferably about 1.0 to 5.0 mol, of a base, and about 1.0 to 10.0 mol, preferably about 1.0 to 5.0 mol, of an amidation reagent, per 1 mol of compound (5).

Examples of the amidation reagent include 1-ethyl-3-(dimethylaminopropyl)carbodiimide hydrochloride, O-(benzotriazol-1-yl)-N,N,N',N'-tetramethyluronium hexafluorophosphate (HATU) and the like.

As the base, organic amines such as pyridine, triethylamine, N,N-dimethylaminopyridine, diisopropylethylamine, 1,8-diazabicyclo[5.4.0]undec-7-ene and the like can be mentioned. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 0.5 hr to 1 week, preferably 3 hr to 24 hr. The reaction temperature is generally −20° C. to 100° C., preferably 0° C. to 80° C.

The obtained compound (7) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (5) can be produced by the method described in the following production method or a method analogous thereto.

Compound (6) may be a commercially available reagent, or can be produced by a method known per se.

<Step B>

In step B, compound (7) is cyclized in the presence of an acid to give compound (Ic). The amount of the acid to be used is about 0.01 to 100 mol, preferably about 0.1 to 50 mol, relative to compound (7).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide and the like. These acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably from room temperature to 100° C.

The obtained compound (Ic) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Ic') which is compound (Ic) wherein $R^3$ is a group having a carboxy group can also be produced by, as a different method, for example, a reaction of compound (5) and compound (8), followed by a dehydration reaction shown in the following production method 1-4.

[Production method 1-4]

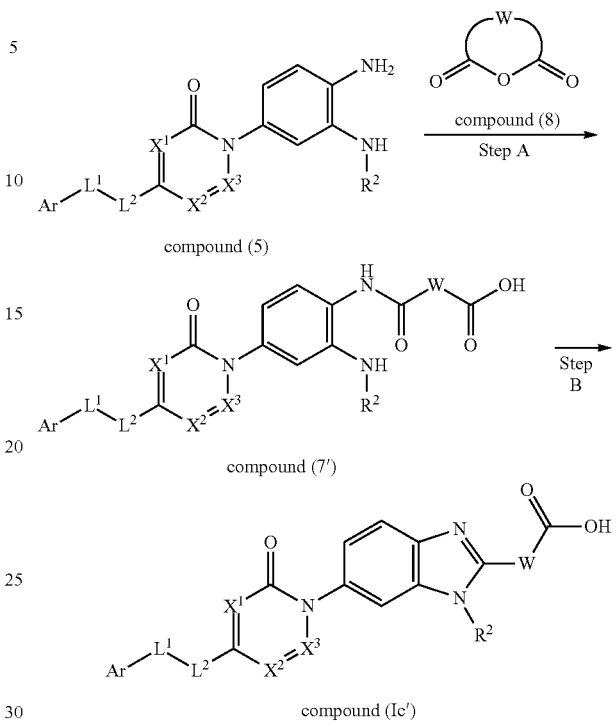

wherein each symbol is as defined above.

<Step A>

In step A, compound (7') is obtained using about 1.0 to 10.0 mol, preferably about 1.0 to 3.0 mol, of compound (8), and about 1.0 to 10.0 mol, preferably about 1.0 to 5.0 mol, of a base, per 1 mol of compound (5).

Examples of the base include inorganic salts such as potassium carbonate, sodium carbonate, cesium carbonate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably from room temperature to 100° C.

The obtained compound (7') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (8) may be a commercially available reagent, or can be produced by a method known per se.

<Step B>

In step B, compound (Ic') is produced from compound (7') by the above-mentioned production method 1-3, step B or a method analogous thereto.

Compound (Id) and compound (Id') which are compound (I) wherein $L^1$ is $CR^{5B}R^{5C}$ and $L^2$ is O, $S(O)_{m2}$ or $NR^{6A}$ can also be produced by, as a different method, for example, a reaction of compound (9) and compound (10), followed by an oxidation reaction as necessary shown in the following production method 1-5.

[Production method 1-5]

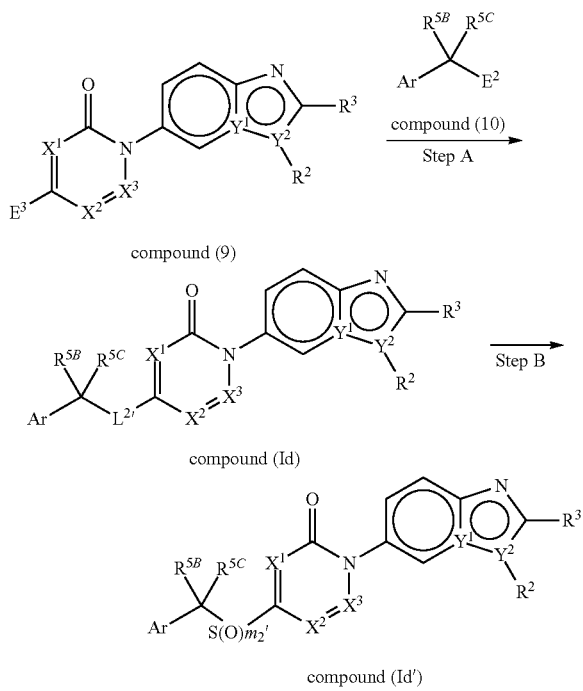

wherein $E^2$ is a leaving group (e.g., a halogen atom such as chlorine, bromine, iodine and the like, substituted sulfonic acid ester such as methanesulfonic acid ester, p-toluenesulfonic acid ester and the like), a hydroxyl group, $NR^{6A}H$ or SH, $E^3$ is a leaving group (e.g., a halogen atom such as chlorine, bromine, iodine and the like, substituted sulfonic acid ester such as methanesulfonic acid ester, p-toluenesulfonic acid ester and the like) or a hydroxyl group, $L^{2'}$ is O, S or $NR^{6A}$, m2' is an integer of 1 or 2, and other symbols are each as defined above.

<Step A>

When $E^2$ is a leaving group and $E^3$ is a hydroxyl group, or $E^3$ is a leaving group and $E^2$ is a hydroxyl group, $NR^{6A}H$ or SH, compound (Id) can be produced using about 1.0 to 10.0 mol, preferably about 1.0 to 3.0 mol of compound (10) and about 1.0 to 10.0 mol, preferably about 1.0 to 5.0 mol, of a base, per 1 mol of compound (9).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, diisopropylethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like; water and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C. This reaction may be performed in a microwave reactor, for which the reaction time is generally 5 min to 24 hr, preferably 30 min to 2 hr. The reaction temperature is generally from room temperature to 250° C., preferably 50° C. to 200° C.

The obtained compound (Id) can be used directly as a reaction mixture, or as a crude product, for the next reaction. It can also be isolated from the reaction mixture according to a conventional method, and can be easily purified by a separation means such as washing, recrystallization, distillation, chromatography and the like.

When both of $E^2$ and $E^3$ are hydroxyl groups, compound (Id) can be produced using the "Mitsunobu reaction" [for example, Synthesis, 1-27, (1981)].

The "Mitsunobu reaction" can be performed, for example, using about 0.5 to 10 mol, preferably about 1 to 2 mol of compound (10), about 1 to 20 mol, preferably about 1 to 5 mol of azodicarbonamide or azodicarboxylate, and about 1 to 20 mol, preferably about 1 to 5 mol, of trialkylphosphine or triarylphosphine, per 1 mol of compound (9).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

Examples of the "azodicarbonamide or azodicarboxylate" include diisopropyl azodicarboxylate, diethyl azodicarboxylate, di-2-methoxyethyl azodicarboxylate, 1,1'-(azodicarbonyl)dipiperidine and the like.

Examples of the "trialkylphosphine or triarylphosphine" include triphenylphosphine, tributylphosphine and the like.

The reaction time is generally 30 min to 1 week, preferably 3 hr to 24 hr. The reaction temperature is generally −20° C. to 100° C., preferably 0° C. to 80° C.

The obtained compound (Id) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (9) can be produced by the method described in the following production method or a method analogous thereto. Compound (10) may be a commercially available reagent, or can be produced by a method known per se.

<Step B>

When $L^{2'}$ is S, in step B, compound (Id') is obtained by reacting 1 mol of compound (Id) with about 1.0 to 30.0 mol, preferably about 1.0 to 5.0 mol, of an oxidizing agent.

As the oxidizing agent, peracids such as hydrogen peroxide, Oxone (registered trademark), peracetic acid, perbenzoic acid, m-chloroperbenzoic acid and the like, oxoacids such as hypochlorous acid, periodic acid and the like and a salt thereof, metal oxoacid such as chromic acid and the like and a salt thereof and other oxidizing agents can be mentioned.

This reaction is preferably performed using a solvent inert to the reaction. The solvent is not particularly limited as long as the reaction proceeds. Examples thereof include alcohols such as methanol, ethanol, propanol, 1,1-dimethylethanol and the like; aromatic hydrocarbons such as benzene, toluene and the like; amides such as N,N-dimethylformamide, N,N-dimethylacetamide and the like; nitriles such as acetonitrile, propionitrile and the like; sulfoxides such as dimethyl sulfoxide and the like; organic acids such as acetic acid, trifluoroacetic acid and the like; water or a mixed solvent thereof and the like.

The reaction time is generally 1 hr to 60 hr, preferably 1 hr to 24 hr. The reaction temperature is generally −50° C. to 150° C., preferably 0° C. to 100° C.

The obtained compound (Id') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Ie) and compound (Ie') which are compound (I) wherein $L^1$ is O, $S(O)_{m1}$ or $NR^{5A}$, and $L^2$ is $CR^{6B}R^{6C}$ can also be produced by, as a different method, for example, a reaction of compound (11) and compound (12), followed by an oxidation reaction as necessary shown in the following production method 1-6.

[Production method 1-6]

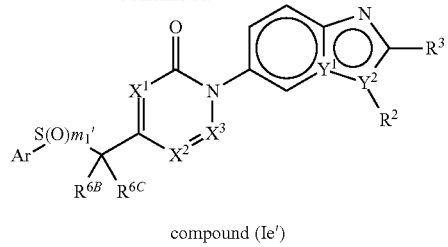

compound (12)

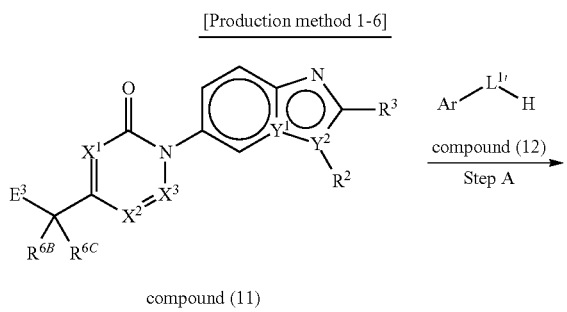

compound (11)

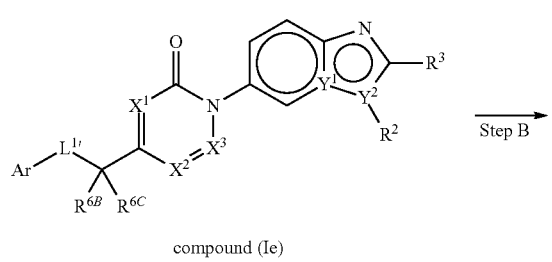

compound (Ie)

compound (Ie')

wherein $L^{1'}$ is O, S or $NR^{5A}$, m1' is an integer of 1 or 2, and other symbols are each as defined above.

<Step A>

When $E^3$ is a hydroxyl group and $L^{1'}$ is an oxygen atom, compound (Ie) can be produced from compound (11) by the "Mitsunobu reaction" shown in the above-mentioned production method 1-5, step B, or a method analogous thereto.

When $E^3$ is a leaving group, compound (Ie) can be produced using about 1.0 to 10.0 mol, preferably about 1.0 to 3.0 mol of compound (12), and about 1.0 to 10.0 mol, preferably about 1.0 to 5.0 mol of a base, per 1 mol of compound (11).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (Ie) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (11) can be produced by the method described in the following production method or a method analogous thereto.

Compound (12) may be a commercially available reagent, or can be produced by a method known per se.

<Step B>

When $L^{1'}$ is S, in step B, compound (Ie') is produced by reacting about 1.0 to 30.0 mol, preferably about 1.0 to 5.0 mol, of a base, per 1 mol of compound (Ie).

Examples of the oxidizing agent include peracids such as hydrogen peroxide, Oxone (registered trademark), peracetic acid, perbenzoic acid, m-chloroperbenzoic acid and the like, oxoacids such as hypochlorous acid, periodic acid and the like and a salt thereof, metal oxoacid such as chromic acid and the like and a salt thereof, and other oxidizing agent.

This reaction is preferably performed using a solvent inert to the reaction. The solvent is not particularly limited as long as the reaction proceeds. Examples thereof include alcohols such as methanol, ethanol, propanol, 1,1-dimethylethanol and the like; aromatic hydrocarbons such as benzene, toluene and the like; amides such as N,N-dimethylformamide, N,N-dimethylacetamide and the like; nitriles such as acetonitrile, propionitrile and the like; sulfoxides such as dimethyl sulfoxide and the like; organic acids such as acetic acid, trifluoroacetic acid and the like; water or a mixed solvent thereof and the like.

The reaction time is generally 1 hr to 60 hr, preferably 1 hr to 24 hr. The reaction temperature is generally −50° C. to 150° C., preferably 0° C. to 100° C.

The obtained compound (Ie') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Ig) and compound (Ih) which are compound (I) wherein $X^1$ is C—$R^4$ can also be produced by, as a different method, for example, halogenation of compound (If) wherein $X^1$ is CH, followed by a coupling reaction shown in the following production method 1-7.

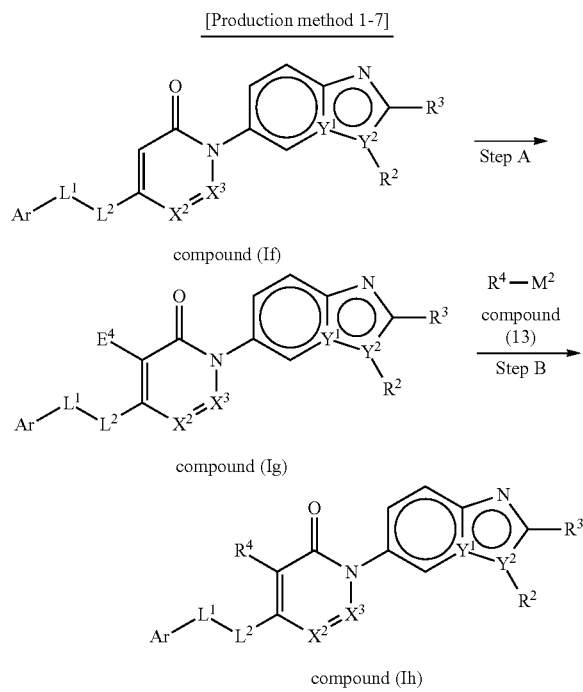

[Production method 1-7]

wherein $E^4$ is a halogen atom such as chlorine, bromine, iodine and the like, $M^2$ is a metal (e.g., boronic acid, borate, alkyltin, zinc, magnesium halide and the like), and other symbols are each as defined above.

<Step A>

In step A, compound (Ig) is obtained by halogenation using about 1.0 to 5.0 mol, preferably about 1.0 to 2.0 mol, of a halogenating reagent, per 1 mol of compound (If).

As the halogenating reagent, chlorine, bromine, iodine, N-chlorosuccinimide, N-bromosuccinimide, and N-iodosuccinimide can be mentioned.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 1 hr to 60 hr, preferably 1 hr to 24 hr. The reaction temperature is generally −50° C. to 150° C., preferably 0° C. to 100° C. This reaction may be performed in a microwave reactor, for which the reaction time is generally 5 min to 24 hr, preferably 30 min to 2 hr. The reaction temperature is generally from room temperature to 250° C., preferably 50° C. to 200° C.

The obtained compound (Ig) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (If) can be produced by the method described in the above-mentioned production method 1-1 or a method analogous thereto.

<Step B>

In step B, compound (Ih) can be produced using about 1.0 to 10.0 mol, preferably about 1.0 to 5.0 mol, of compound (13), and about 0.000001 mol to 5 mol, preferably 0.0001 mol to 1 mol, of a metal catalyst, per 1 mol of compound (Ig).

Examples of the metal catalyst include palladium compounds (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), copper compounds (e.g., copper powder, copper(I) chloride, copper(I) iodide, copper(I) acetate and the like), nickel compounds (e.g., tetrakis(triphenylphosphine)nickel and the like), rhodium compounds (e.g., tris(triphenylphosphine)rhodium chloride and the like), platinum compound and the like.

This reaction may be performed using a base and a ligand. Examples of the base include metal alkoxides such as potassium phenoxide, sodium tert-butoxide and the like; inorganic salts such as potassium carbonate, sodium carbonate, cesium carbonate, potassium phosphate and the like; and the like. As the ligand, organic phosphorus compounds such as triphenylphosphine, tri-tert-butylphosphine, tricyclohexylphosphine, BINAP (2,2'-bis(diphenylphosphino)-1,1'-binaphthyl) and the like; organic amine compounds such as N,N'-dimethyl-cyclohexane-1,2-diamine, 2,2-bipyridyl and the like; and the like can be mentioned.

When a metal catalyst unstable to oxygen is used in this reaction, the reaction is preferably performed in an inactive gas (e.g., argon, nitrogen and the like) atmosphere.

The reaction time is generally 15 min to 60 hr, preferably 30 min to 20 hr. The reaction temperature is generally −50° C. to 150° C., preferably −10° C. to 120° C.

The obtained compound (Ih) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (13) may be a commercially available reagent, or can be produced by a method known per se.

Compound (Ii) which is compound (I) wherein $L^1$ and $L^2$ are $CR^{5B}R^{5C}$ and $CR^{6B}R^{6C}$, respectively, and compound (Ij)

which is compound (I) wherein $R^{5B}$ and $R^{6B}$ form, together with the adjacent carbon atoms, a cyclopropane ring can be produced, for example, by the method shown in the following production method 1-8. That is, compound (Ii') is obtained by a reaction of compound (14) and compound (15), compound (Ii) can be produced by the subsequent reduction reaction, and compound (Ij) can be further produced by a coupling reaction of compound (16).

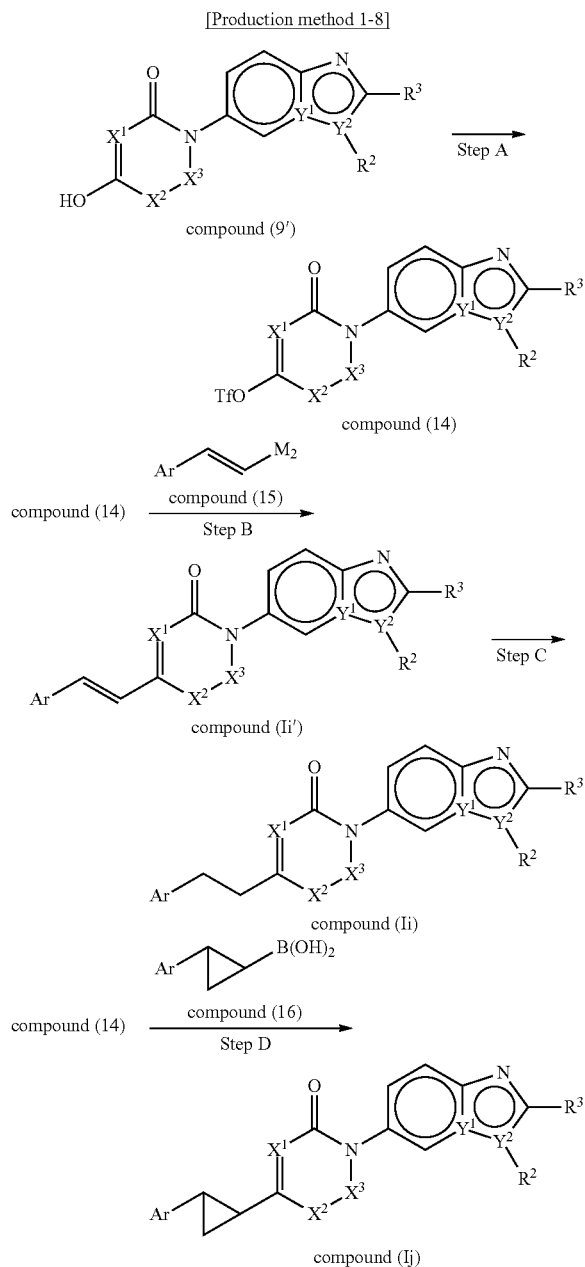

wherein each symbol is as defined above.

<Step A>

In step A, compound (9') is subjected to a method known per se to give the object compound (14).

Compound (9') can be produced by the method described in the following production method or a method analogous thereto.

<Step B>

In step B, compound (Ii') is synthesized from compound (14) by the method described in the above-mentioned production method 1-7, step B, or a method analogous thereto.

Compound (15) may be a commercially available reagent, or can be produced by a method known per se.

<Step C>

In step C, 1 mol of compound (Ii') is reduced with about 0.01 to 5.0 mol, preferably about 0.01 to 2.0 mol, of a metal catalyst under a hydrogen atmosphere to give compound (Ii).

Examples of the metal catalyst include palladium-carbon, palladium hydroxide-carbon, platinum oxide, platinum and the like.

This reaction is preferably performed using a solvent inert to the reaction. Such solvent is not particularly limited as long as the reaction proceeds and, for example, alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water and the like or a mixed solvent thereof and the like are preferable.

The reaction time is generally 1 hr to 60 hr, preferably 5 hr to 48 hr. The reaction temperature is generally −50° C. to 150° C., preferably 0° C. to 100° C. The pressure is about 1 to 10 atm, preferably about 1 to 5 atm.

The obtained compound (Ii) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step D>

In step D, compound (Ij) is synthesized from compound (14) by the method described in the above-mentioned production method 1-7, step B, or a method analogous thereto.

Compound (16) may be a commercially available reagent, or can be produced by a method known per se.

Compound (5) can be produced by a coupling reaction of compound (2) and compound (17) to give compound (18), followed by reduction of nitro group or deprotection of amino group according to the following production method 2-1.

[Production method 2-1]

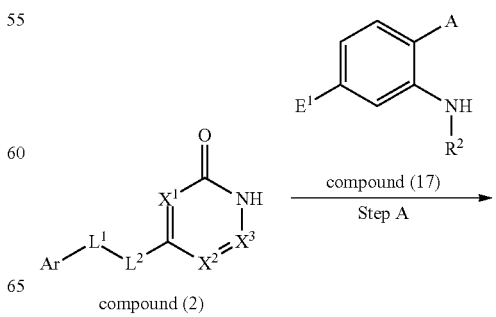

-continued

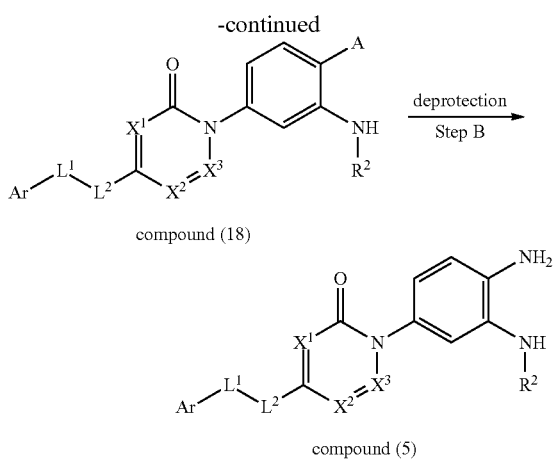

compound (18)

compound (5)

wherein A is a nitro group or an amino group optionally having a protecting group, and other symbols are each as defined above.

<Step A>

In step A, compound (2) and compound (17) are reacted by the method described in the above-mentioned production method 1-1, step A, or a method analogous thereto to give compound (18).

Compound (17) may be a commercially available reagent, or can be produced by a method known per se.

<Step B>

When A is a protected amino group, deprotection is performed by a method known per se to give compound (5).

When A is a nitro group, compound (5) can be produced by reduction using about 0.01 to 5.0 mol, preferably about 0.01 to 2.0 mol, of a metal catalyst per 1 mol of compound (18) under a hydrogen atmosphere.

Examples of the metal catalyst include palladium-carbon, palladium hydroxide-carbon, platinum oxide, platinum and the like.

This reaction is preferably performed using a solvent inert to the reaction. Such solvent is not particularly limited as long as the reaction proceeds and, for example, alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water and the like or a mixed solvent thereof and the like are preferable.

The reaction time is generally 1 hr to 60 hr, preferably 5 hr to 48 hr. The reaction temperature is generally −50° C. to 150° C., preferably 0° C. to 100° C. The pressure is about 1 to 10 atm, preferably about 1 to 5 atm.

The obtained compound (5) can be used directly as a reaction mixture, or as a crude product, for the next reaction. It can also be isolated from the reaction mixture according to a conventional method, and can be easily purified by a separation means such as washing, recrystallization, distillation, chromatography and the like.

When A is a nitro group, compound (5) can also be produced by, as a different method, reduction using about 5.0 to 20.0 mol, preferably about 5.0 to 10.0 mol, of a reducing metal per 1 mol of compound (18).

As the reducing metal, reduced iron, tin, zinc and the like can be mentioned. To promote the reaction, acetic acid, hydrochloric acid or ammonium chloride, calcium chloride and the like can be added.

This reaction is preferably performed using a solvent inert to the reaction. Such solvent is not particularly limited as long as the reaction proceeds and, for example, alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, ketones such as acetone, methyl ethyl ketone and the like, sulfoxides such as dimethyl sulfoxide and the like, aqueous ammonia solution, water and the like or a mixed solvent thereof and the like are preferable.

The reaction time is generally 1 hr to 60 hr, preferably 5 hr to 48 hr. The reaction temperature is generally −50° C. to 150° C., preferably 0° C. to 100° C.

The obtained compound (5) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2') and compound (2''), which are compounds (2), starting material compound in production methods 1-1 and 2-1, wherein $L^1$ is $CR^{5B}R^{5C}$ and $L^2$ is O, $S(O)_{m2}$ or $NR^{6A}$ can also be synthesized by the following production method 2-2.

[Production method 2-2]

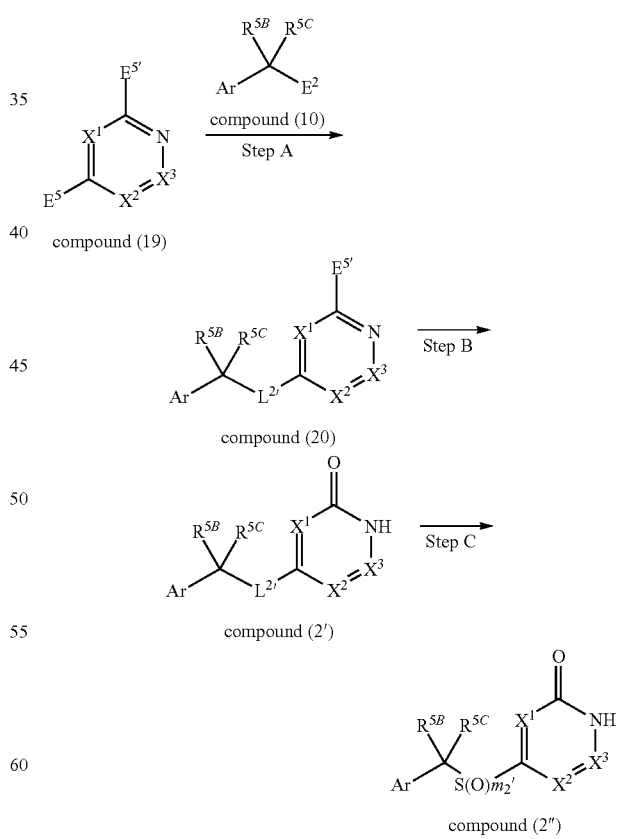

wherein $E^5$ and $E^{5'}$ are each a halogen atom (e.g., a halogen atom such as chlorine, bromine, iodine and the like) or a hydroxyl group, and other symbols are each as defined above.

<Step A>

When $E^5$ is a hydroxyl group, and $E^2$ is a leaving group, or $E^5$ is a halogen atom, and $E^2$ is SH, $NR^{64}H$ or hydroxyl group, in step A, compound (20) is produced using about 1.0 to 10.0 mol, preferably about 1.0 to 3.0 mol, of compound (10) and about 1.0 to 10.0 mol, preferably about 1.0 to 5.0 mol, of a base, per 1 mol of compound (19).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (20) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (19) and compound (10) may be commercially available reagents, or can be produced by a method known per se.

When both of $E^5$ and $E^2$ are hydroxyl groups, compound (20) can be produced from compound (19) according to "Mitsunobu reaction" shown in the above-mentioned production method 1-5, step A, or a method analogous thereto.

<Step B>

In compound (20), when $E^{5'}$ is a hydroxyl group, compound (21) is compound (2').

When $E^{5'}$ is a halogen atom, in step B, compound (2') is produced by hydrolysis in the presence of about 1 to 20 mol, preferably about 1 to 5 mol, of a base per 1 mol of compound (21).

Examples of the base include inorganic salts such as potassium hydroxide, sodium hydroxide, sodium carbonate, potassium carbonate and the like. Two or more kinds of these bases may be mixed and used at an appropriate ratio.

This reaction is preferably performed in water. Where necessary, ethers such as tetrahydrofuran, 1,4-dioxane, diethyl ether and the like; ketones such as acetone, 2-butanone and the like may be mixed and used at an appropriate ratio.

The reaction time is generally 15 min to 60 hr, preferably 15 min to 24 hr. The reaction temperature is generally 0° C. to 200° C., preferably from room temperature to 150° C.

The obtained compound (2') can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In step C, compound (2') is reacted by the method of production method 1-6, step B, or a method analogous thereto to give compound (2'').

Compound (9), which is a starting compound in production method 1-5, can be produced by deprotection of compound (Ik) which is compound (I), wherein Ar is a phenyl group, $L^1$ is $CH_2$, and $L^2$ is an oxygen atom, followed by halogenation or sulfonation shown in the following production method 2-3.

[Production method 2-3]

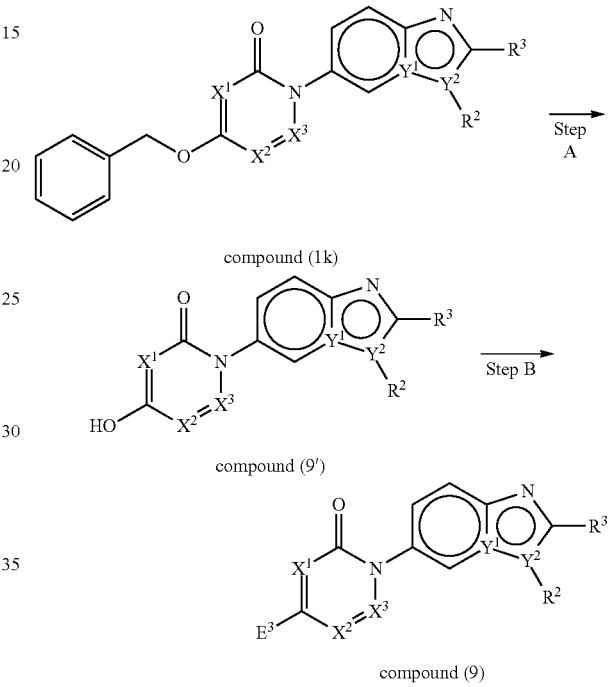

compound (1k)

compound (9')

compound (9)

wherein each symbol is as defined above.

<Step A>

In step A, compound (9') can be obtained by reduction using about 0.01 to 5.0 mol, preferably about 0.01 to 2.0 mol, of a metal catalyst per 1 mol of compound (Ik) under a hydrogen atmosphere.

Examples of the metal catalyst include palladium-carbon, palladium hydroxide-carbon, platinum oxide, platinum and the like can be mentioned.

This reaction is preferably performed using a solvent inert to the reaction. Such solvent is not particularly limited as long as the reaction proceeds and, for example, alcohols such as methanol, ethanol, propanol and the like, aromatic hydrocarbons such as benzene, toluene and the like, saturated hydrocarbons such as cyclohexane, hexane and the like, ethers such as tetrahydrofuran, dioxane, 1,2-dimethoxyethane and the like, amides such as N,N-dimethylformamide, N,N-dimethylacetamide and the like, sulfoxides such as dimethyl sulfoxide and the like, water and the like or a mixed solvent thereof and the like are preferable.

The reaction time is generally 1 hr to 60 hr, preferably 5 hr to 48 hr. The reaction temperature is generally −50° C. to 150° C., preferably 0 to 100° C. The pressure is about 1 to 10 atm, preferably about 1 to 5 atm.

The obtained compound (9') can be used directly as a reaction mixture, or as a crude product, for the next reaction.

It can also be isolated from the reaction mixture according to a conventional method, and can be easily purified by a separation means such as washing, recrystallization, distillation, chromatography and the like.

Step A can also be performed, as a different method, in the presence of an acid. That is, compound (9') is obtained using about 0.01 to 100 mol, preferably about 0.1 to 50 mol, of an acid per 1 mol of compound (Ik).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide and the like. These acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably from room temperature to 100° C.

The obtained compound (9') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Ik) can be produced by the method described in the above-mentioned production method 1-1 or a method analogous thereto.

<Step B>

When $E^3$ is a hydroxyl group, compound (9') is compound (9).

When $E^3$ is a halogen, compound (9) can be produced using about 1.0 to 20.0 mol, preferably 1.0 to 5.0 mol, of a halogenating agent per 1 mol of compound (9').

As the halogenating agent, for example, phosphorus oxybromide, phosphorus tribromide, phosphorus oxychloride, thionyl chloride, sulfuryl chloride and the like can be mentioned.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (9) can be used directly as a reaction mixture, or as a crude product, for the next reaction. It can also be isolated from the reaction mixture according to a conventional method, and can be easily purified by a separation means such as washing, recrystallization, distillation, chromatography and the like.

When $E^3$ is a sulfonic acid ester, compound (9) can be produced using about 1.0 to 20.0 mol, preferably 1.0 to 5.0 mol, of sulfonyl chloride and 1.0 to 20.0 mol, preferably 1.0 to 5.0 mol, of a base, per 1 mol of compound (9').

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, water and the like. Two or more kinds of these solvents may be mixed and used at an appropriate ratio.

The reaction time is generally 15 min to 60 hr, preferably 15 min to 3 hr. The reaction temperature is generally −20° C. to 200° C., preferably 0° C. to 100° C.

The obtained compound (9) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (11) which is a starting compound in production method 1-6 can be produced by reacting compound (21) and compound (3) to give compound (22), followed by a method known per se shown in the following production method 2-4.

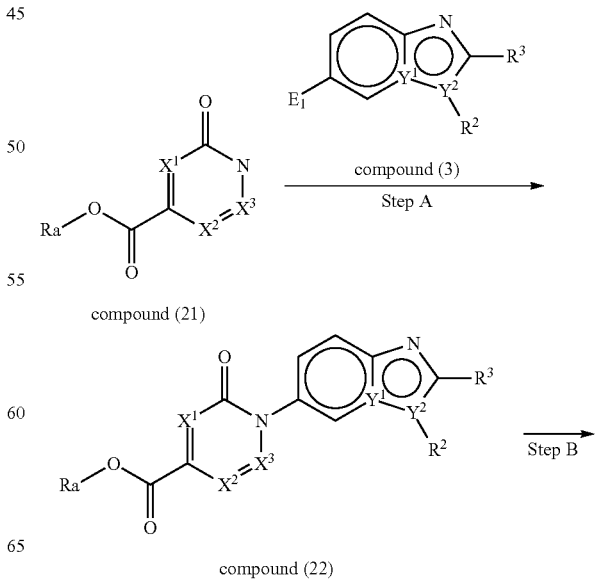

[Production method 2-4]

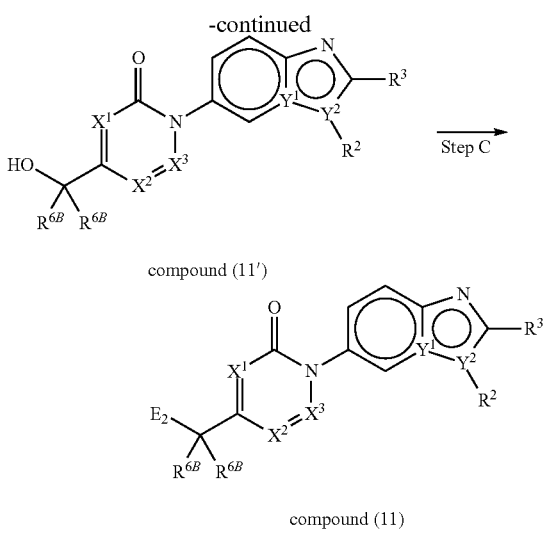

compound (11')

compound (11)

wherein each symbol is as defined above.
<Step A>

In step A, compound (21) and compound (3) are reacted by the method of the above-mentioned production method 1-1, step A, or a method analogous thereto to give compound (22).
<Step B>

In step B, compound (11'), which is compound (11) wherein $E^2$ is a hydroxyl group, is produced from compound (22) by a method known per se.
<Step C>

In step C, compound (11) is produced from compound (11') by a method known per se.

As step B of production method 2-4, for example, the following reaction can be shown.

[Production method 2-4A]

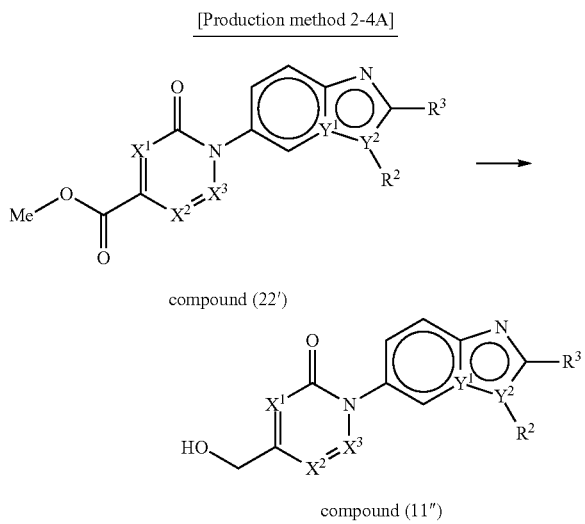

compound (22')

compound (11″)

wherein each symbol is as defined above.

That is, in production method 2-4A, compound (11″) can be obtained by reaction with about 0.5 to 10.0 mol, preferably about 1.0 to 5.0 mol, of a reducing agent per 1 mol of compound (22').

Examples of the reducing agent include diisopropylaluminum hydride, lithium aluminum hydride, lithium borohydride, sodium borohydride and the like can be mentioned.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; and the like. Two or more kinds of these solvents may be mixed and used at an appropriate ratio.

The reaction time is generally 30 min to 48 hr, preferably 3 hr to 24 hr. The reaction temperature is generally −80° C. to 100° C., preferably −80° C. to 80° C.

The obtained compound (11″) can be used directly as a reaction mixture, or as a crude product, for the next reaction. It can also be isolated from the reaction mixture according to a conventional method, and can be easily purified by a separation means such as washing, recrystallization, distillation, chromatography and the like.

As step C of production method 2-4, for example, the following reaction can be shown.

[Production method 2-4B]

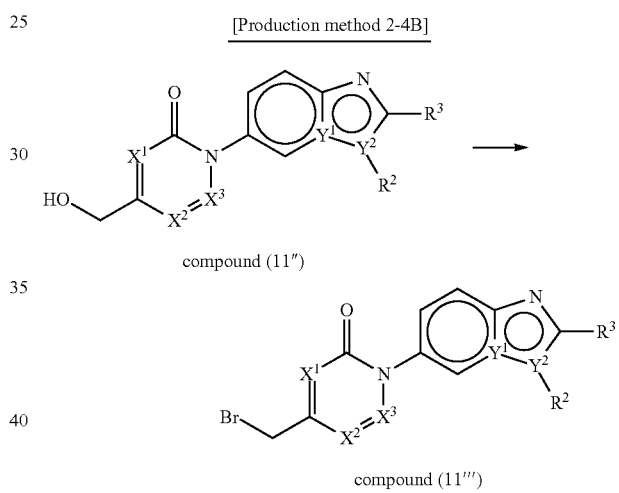

compound (11″)

compound (11‴)

wherein each symbol is as defined above.

That is, in production method 2-4B, compound (11″) is brominated by a method known per se to give compound (11‴).

Compound (3'), which is compound (3), a starting compound in production methods 1-1 and 2-4, wherein $Y^1$ is N, and $Y^2$ is C, can be produced by a reaction of compound (23) and compound (24) or alkylation of compound (25) followed by cyclization reaction.

[Production method 3-1]

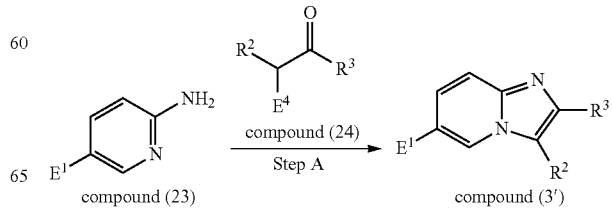

compound (23)        compound (3')

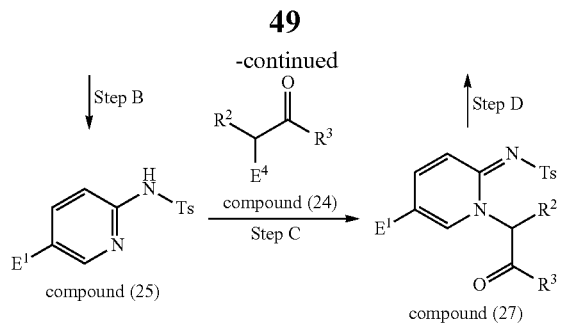

wherein Ts is a p-toluenesulfonyl group, and other symbols are each as defined above.

<Step A>

In step A, compound (3') is obtained by reaction using about 1.0 to 10.0 mol, preferably about 1.0 to 5.0 mol, of compound (24) per 1 mol of compound (23).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; alcohols such as methanol, ethanol, propanol and the like; and the like. Two or more kinds of these solvents may be mixed and used at an appropriate ratio.

The reaction time is generally 30 min to 48 hr, preferably 1 hr to 24 hr. The reaction temperature is generally from room temperature to 200° C., preferably 80° C. to 150° C.

The obtained compound (3') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (24) may be a commercially available reagent, or can be produced by a method known per se.

<Step B>

In step B, compound (25) is obtained by reaction using about 0.9 to 1.5 mol, preferably about 1 to 1.2 mol, of p-toluenesulfonyl chloride per 1 mol of compound (23).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; and the like. Two or more kinds of these solvents may be mixed and used at an appropriate ratio.

The reaction time is generally 1 hr to 48 hr, preferably 1 hr to 24 hr. The reaction temperature is generally 0° C. to 150° C., preferably 0° C. to 80° C.

The obtained compound (25) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In step C, compound (27) can be produced using about 1.0 to 10.0 mol, preferably about 1.0 to 3.0 mol of compound (24), and about 1.0 to 10.0 mol, preferably about 1.0 to 5.0 mol, of a base, per 1 mol of compound (25).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, diisopropylethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like; water and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C. This reaction may be performed in a microwave reactor, for which the reaction time is generally 5 min to 24 hr, preferably 30 min to 2 hr. The reaction temperature is generally from room temperature to 250° C., preferably 50° C. to 200° C.

The obtained compound (27) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step D>

In step D, compound (3') is obtained by reaction using about 1 to 10 mol, preferably about 1 to 5 mol, of acid anhydride per 1 mol of compound (27).

As the acid anhydride, acetic anhydride, trifluoroacetic anhydride and the like can be mentioned.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; and the like. Two or more kinds of these solvents may be mixed and used at an appropriate ratio.

The reaction time is generally 1 hr to 48 hr, preferably 1 hr to 24 hr. The reaction temperature is generally from room temperature to 120° C., preferably 50° C. to 100° C.

The obtained compound (3') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (3"), which is a starting compound (3) in production methods 1-1 and 2-4 wherein $Y^1$ is C and $Y^2$ is N, can be produced from compound (30) via compound (31) and compound (33) or from compound (30) via compound (34) and compound (36), according to the following production method 3-2.

[Production method 3-2]

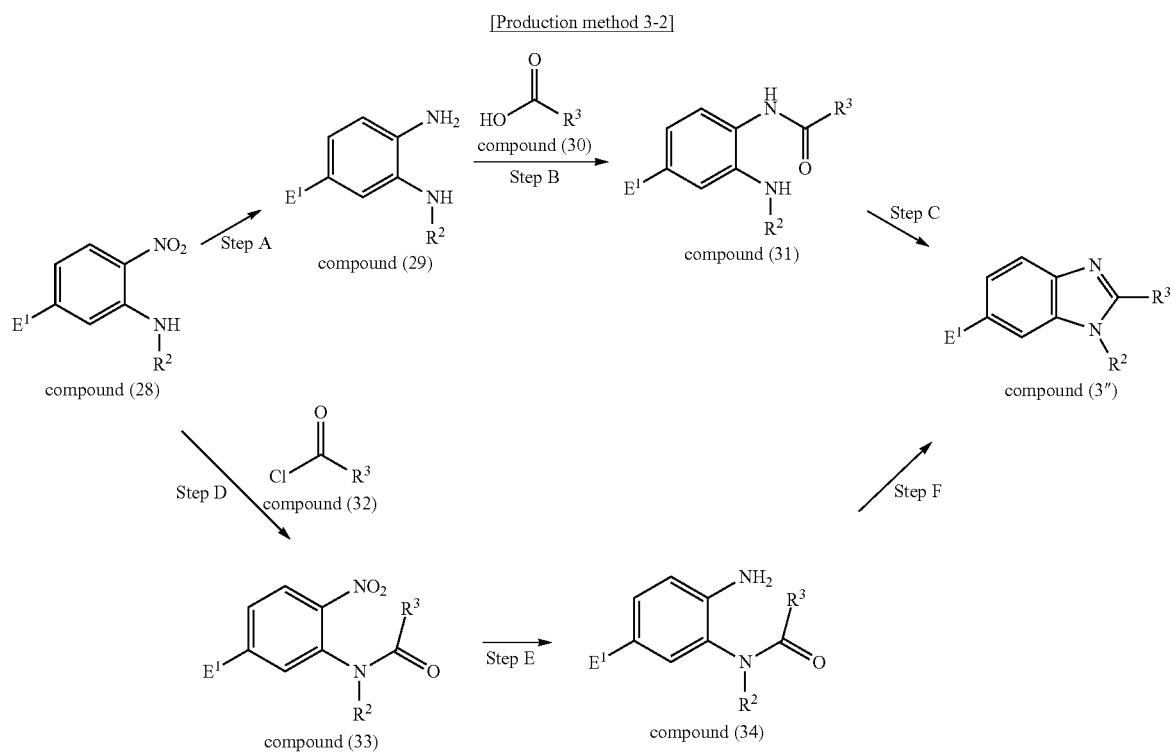

wherein each symbol is as defined above.
<Step A>
In step A, compound (29) is produced by reducing the nitro group of compound (28) by the method shown in the above-mentioned production method 2-1, step B, or a method analogous thereto.
<Step B>
In step B, compound (31) is produced by an amidation reaction of compound (29) and compound (30) by the method shown in the above-mentioned production method 1-3, step A, or a method analogous thereto.

Compound (30) may be a commercially available reagent, or can be produced by a method known per se.
<Step C>
In step C, compound (3″) is produced from compound (31) by the method shown in the above-mentioned production method 1-3, step B, or a method analogous thereto.
<Step D>
In step D, compound (33) is produced using about 1.0 to 10.0 mol, preferably about 1.0 to 3.0 mol, of compound (32) and about 1.0 to 10.0 mol, preferably about 1.0 to 5.0 mol of a base, per 1 mol of compound (28).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (33) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (32) may be a commercially available reagent, or can be produced by a method known per se.
<Step E>
In step E, compound (34) is produced by reducing compound (33) by the method shown in the above-mentioned production method 2-1, step B, or a method analogous thereto.
<Step F>
In step F, compound (3″) is produced from compound (34) by the method of the above-mentioned production method 1-3, step B, or a method analogous thereto.

Compound (3′″), which is a starting compound (3) in production methods 1-1 and 2-4 wherein $R^3$ is —CO—$R^9$, can be produced by a reaction of compound (29) and compound (35), followed by a reaction with a carbon nucleophilic agent or a nitrogen nucleophilic agent.

[Production method 3-3]

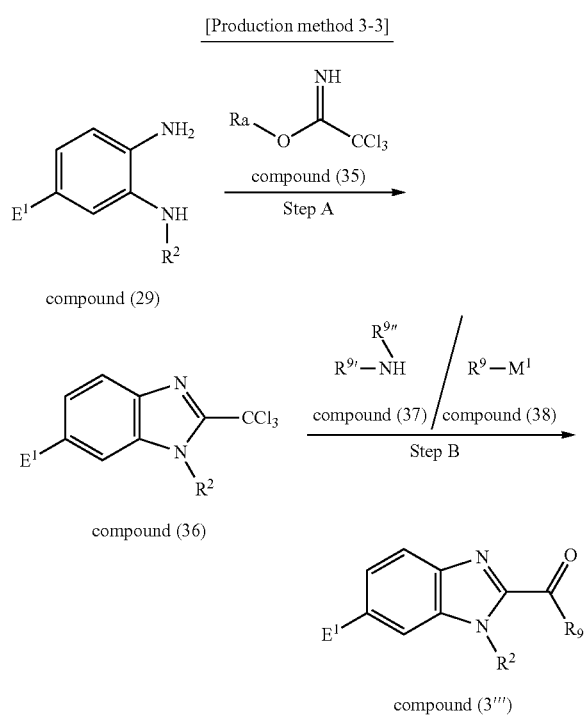

compound (29)

compound (36)

compound (3''')

wherein $R^{9'}$ is a $C_{1-6}$ alkyl group or a $C_{3-10}$ cycloalkyl group, $R^{9''}$ is a hydrogen atom, a $C_{1-6}$ alkyl group or a $C_{3-10}$ cycloalkyl group, and other symbols are each as defined above.

<Step A>

In step A, 1 mol of compound (29) is reacted with about 1 to 10 mol, preferably about 1 to 5 mol, of compound (35) in the presence of acid to give compound (36). The amount of the acid to be used is about 0.01 to 100 mol, preferably about 0.1 to 50 mol, per 1 mol of compound (29).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide and the like. These acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably 0° C. to 100° C.

The obtained compound (36) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (35) may be a commercially available reagent, or can be produced by a method known per se.

<Step B>

In step B, compound (3''') is obtained by reaction using about 1 to 10 mol, preferably about 1 to 5 mol, of compound (37) or compound (38) per 1 mol of compound (36).

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (3''') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (37) and compound (38) may be commercially available reagents, or can be produced by a method known per se.

Compound (3''''), which is a starting compound (3) in production methods 1-1 and 2-4 wherein $R^3$ is a $C_{1-6}$ alkoxy group, can be produced by a reaction of compound (29) and compound (39), or an alkylation reaction of compound (40), according to the following production method 3-4.

[Production method 3-4]

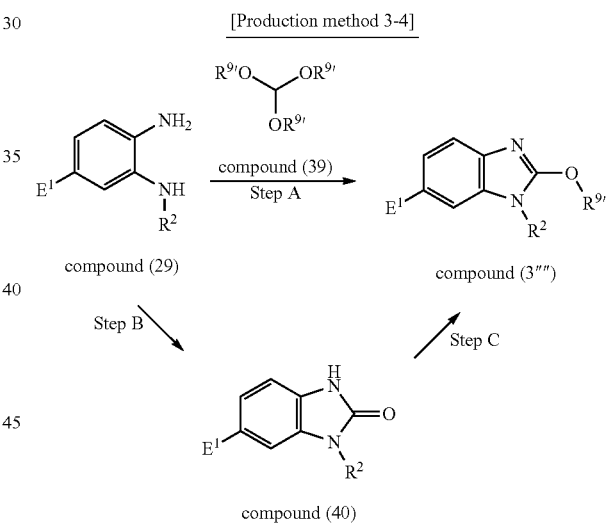

compound (29)

compound (3'''')

compound (40)

wherein each symbol is as defined above.

<Step A>

In step A, compound (3'''') is obtained by reaction using about 1 to 10 mol, preferably about 1 to 5 mol, of compound (39) per 1 mol of compound (29) in the presence of acid. The amount of the acid to be used is about 0.01 to 100 mol, preferably about 0.1 to 50 mol, per 1 mol of compound (29).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide and the like. These acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably 0° C. to 100° C.

The obtained compound (3"") can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (39) may be a commercially available reagent, or can be produced by a method known per se.

<Step B>

In step B, 1 mol of compound (29) is reacted in the presence of about 1 to 5 mol, preferably about 1 to 2 mol of a carbonylation reagent and 1 to 5 mol, preferably about 1 to 2 mol of a base to give compound (40).

As the carbonylation reagent, N,N'-carbonyldiimidazole, triphosgene, methyl chlorocarbonate, ethyl chlorocarbonate and the like can be mentioned.

Examples of the base include organic amines such as triethylamine, pyridine, diisopropylethylamine, 1,8-diazabicyclo[5.4.0]undec-7-ene and the like; inorganic salts such as potassium carbonate, sodium carbonate and the like; and the like. Two or more kinds of these bases may be mixed and used at an appropriate ratio.

This reaction is preferably performed using a solvent inert to the reaction. The solvent is not particularly limited as long as the reaction proceeds. Examples thereof include halogenated hydrocarbons such as dichloromethane, chloroform, carbon tetrachloride and the like; amides such as N,N-dimethylformamide, N,N-dimethylacetamide and the like; ethers such as diethyl ether, 1,4-dioxane, tetrahydrofuran and the like; and the like. Two or more kinds of these solvents may be used in a mixture in an appropriate ratio.

The reaction time is generally 15 min to 24 hr, preferably 30 min to 5 hr. The reaction temperature is generally –50° C. to 100° C., preferably 0° C. to 50° C.

The obtained compound (40) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In step C, compound (40) is subjected to alkylation by a method known per se to give compound (3"").

In each reaction of the aforementioned schemes, when a starting compound has hydroxy, amino (including —NH—, —NH$_2$), carboxy, carbonyl or mercapto as a substituent, a protecting group generally used in the peptide chemistry and the like may be introduced into these groups. By removing the protecting group as necessary after the reaction, the objective compound can be obtained.

Examples of the hydroxyl-protecting group include $C_{1-6}$ alkyl (e.g., methyl, ethyl, propyl, isopropyl, butyl, tert-butyl), phenyl, trityl, $C_{7-10}$ aralkyl (e.g., benzyl), formyl, $C_{1-6}$ alkyl-carbonyl (e.g., acetyl, propionyl), benzoyl, $C_{7-10}$ aralkyl-carbonyl (e.g., benzylcarbonyl), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkyl (e.g., methyl, ethyl, propyl), $C_{1-6}$ alkoxy (e.g., methoxy, ethoxy, propoxy), nitro and the like.

Examples of the amino-protecting group include formyl, $C_{1-6}$ alkyl-carbonyl (e.g., acetyl, propionyl), $C_{1-6}$ alkoxy-carbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), $C_{7-10}$ aralkyl (e.g., benzyl, 4-methoxybenzyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carboxy-protecting group include $C_{1-6}$ alkyl (e.g., methyl, ethyl, propyl, isopropyl, butyl, tert-butyl), $C_{7-11}$ aralkyl (e.g., benzyl), phenyl, trityl, silyl (e.g., trimethylsilyl, triethylsilyl, dimethylphenylsilyl, tert-butyldimethylsilyl, tert-butyldiethylsilyl, tert-butyldiphenylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carbonyl-protecting group include cyclic acetal (e.g., 1,3-dioxane), acyclic acetal (e.g., di-$C_{1-6}$ alkyl acetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The above-mentioned protecting groups can be removed by a method known per se, for example, the method described in Protective Groups in Organic Synthesis, John Wiley & Sons, Inc. (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like are used.

Inasmuch as compound (I) and a prodrug thereof (hereinafter abbreviated as the compound of the present invention) has a superior MCH receptor (particularly, MCH receptor 1) antagonistic action, it is useful as an agent for the prophylaxis or treatment of diseases caused by MCH.

In addition, the compound of the present invention also shows low toxicity (e.g., cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is superior in oral absorbability.

Furthermore, the compound of the present invention is superior in brain transfer function.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of depigmentation due to chloasma, ephelides, sunburn and the like; and further, hyperpigmentation or hypopigmentation for cosmetic purposes.

The compound of the present invention is used as it is or as a pharmaceutical composition formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonicity agent, buffer and soothing agent for liquid preparations and the like can be mentioned. Where necessary, additives such as preservatives, antioxidizing agents, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonicity agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-hydroxybenzoates, chlorobutanol, benzyl alcohol, phenethyl alcohol, dehydroacetic acid and sorbic acid.

Examples of the antioxidizing agent include sulfite and ascorbic acid.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartame and stevia.

Examples of the adsorbent include porous starch, calcium silicate (trade name: Florite RE), magnesium aluminometasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylene lauryl ether.

Examples of the dosage form of the aforementioned pharmaceutical composition include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucosal patch film), injection (e.g., subcutaneous injection, intravenous injection, intramuscular injection, intraperitoneal injection, drip infusion), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound of the present invention in the pharmaceutical composition is, for example, about 0.1 to 100 wt % of the entire pharmaceutical composition.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a pharmaceutically active ingredient (hereinafter sometimes to be referred to as "concomitant drug") that does not adversely influence the compound of the present invention. Examples of such concomitant drug include "therapeutic agent for diabetes", "therapeutic agent for diabetic complications", "anti-obesity agent", "therapeutic agent for hypertension", "therapeutic agent for hyperlipidemia", "antiarteriosclerotic agent", "antithrombotic agent", "diuretic agent", "therapeutic agent for arthritis", "antianxiety agent", "antidepressant", "psychoneurotic agent", "sleep-inducing agent" and the like. These concomitant drugs may be low-molecular-weight compounds, or high-molecular-weight proteins, polypeptides, antibodies, vaccines or the like.

Examples of the above-mentioned "therapeutic agent for diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic agent for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFK inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic agent for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic agent for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compound described in WO97/10224, for example, N-[[(3R, 5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic agent" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic agent" include heparin (e.g., heparin sodium, heparin calcium, enoxaparin sodium, dalteparin sodium), warfarin (e.g., warfarin potassium), anti-thrombin drugs (e.g., argatroban, dabigatran), FXa inhibitors (e.g., rivaroxaban, apixaban, edoxaban, YM150, the compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic agent for arthritis" include ibuprofen and the like.

Examples of the above-mentioned "antianxiety agent" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, setiptiline), selective serotonin uptake inhibitors (e.g., fluoxetine, fluvoxamine, paroxetine, sertraline, escitalopram), serotonin-noradrenaline uptake inhibitors (e.g., milnacipran, duloxetine, venlafaxine), trazodone, mirtazapine, moclobemide and the like.

Examples of the above-mentioned "psychoneurotic agent" include typical antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing agent" include Ramelteon, GABAergic hypnotics (e.g., brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:

1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is explained in more detail in the following by referring to Examples and Preparation Examples, which are not to be construed as limitative.

In the following Examples, % means weight % unless otherwise indicated. In addition, the room temperature means 10-30° C.

In case of a mixed solvent, the numerical value indicated in the parenthesis is a volume mixing ratio of each solvent. In addition, % of a solution means the number of grams in 100 ml of the solution.

NH silica gel means aminopropylsilane-bonded silica gel, and C18 means octadodecyl-bonded silica gel. Unless otherwise noted, C18 column was used in both HPLC and LC/MS.

The abbreviations used in the present specification mean the following.
s: singlet
d: doublet
t: triplet
q: quartet
dd: double doublet
dt: double triplet
m: multiplet
br: broad
J: coupling constant
$CDCl_3$: deuterated chloroform
$CD_3OD$: deuterated methanol
$DMSO-d_6$: dimethyl sulfoxide-$d_6$
$^1H$ NMR: proton nuclear magnetic resonance
MS(ESI): mass spectrometry (electrospray ionization)
MeOH: methanol
EtOH: ethanol
EtOAc: ethyl acetate
$CH_3CN$: acetonitrile
DMSO: dimethyl sulfoxide
n-Hex: n-hexane
IPA: isopropanol
IPE: diisopropyl ether
$Et_2O$: diethyl ether
THF: tetrahydrofuran
DCM: dichloromethane
DME: 1,2-dimethoxyethane
DMA: N,N-dimethylacetamide
DMF: N,N-dimethylformamide
$NaHCO_3$: sodium hydrogen carbonate
$Na_2SO_4$: sodium sulfate
$MgSO_4$: magnesium sulfate
$CaCl_2$: calcium chloride
TBAF: tetrabutylammonium fluoride
$NaBH_4$: sodium borohydride
$NH_3$: ammonia
HATU: O-(7-azabenzotriazol-1-yl)-N,N,N',N'-tetramethyluronium hexafluorophosphate
$NH_4Cl$: ammonium chloride
$POCl_3$: phosphorus oxychloride
BAST: bis(2-methoxyethyl)aminosulfur trifluoride
DAST: N,N-diethylaminosulfur trifluoride
NFSI: N-fluorobenzenesulfonimide
TFA: trifluoroacetic acid.

AcOH: acetic acid
Pd/C: palladium on carbon
MS-4A: molecular sieves-4A
Ar: argon
$H_2$: hydrogen
$N_2$: nitrogen
$CO_2$: carbon dioxide
HPLC: high performance liquid chromatography
SFC: supercritical fluid chromatography In the NMR spectrum, the chemical shift is expressed in δ value (ppm) and the coupling constant is expressed in Hz.

Mass spectrum was measured by LC/MS. ESI (Electron-Spary Ionization) or APCI (Atomospheric Pressure Chemical Ionization) was used as an ionization method. Data was described as a measured value (found). In case of salt, generally molecular ion peak of free acid/base is detected.

Example 1

1-(2-Cyclopropyl-3-methylimidazo[1,2-a]pyridin-6-yl)-4-((4-fluorobenzyl)oxy)pyridin-2(1H)-one A)
N-(5-Iodopyridin-2-yl)-4-methylbenzenesulfonamide A mixture of 5-iodopyridin-2-amine (25.5 g), 4-methylbenzene-1-sulfonyl chloride (23.2 g) and pyridine (250 ml) was heated at 100° C. overnight. The mixture was poured into water (1.2 L) with stirring, and the resulting precipitate was collected by filtration. The solid was washed with water and $Et_2O$ successively, and dried in vacuo to give the title compound (37.4 g) as a white solid.
MS (ESI+): [M+H]+ 374.9.

B) N-(1-(1-Cyclopropyl-1-oxopropan-2-yl)-5-iodopyridin-2(1H)-ylidene)-4-methylbenzenesulfonamide To a solution of N-(5-iodopyridin-2-yl)-4-methylbenzenesulfonamide (33.1 g) in DMF (400 ml) was added NaH (40% oil dispersion, 3.89 g) at 0° C., and the mixture was stirred at room temperature for 30 min. Then 2-bromo-1-cyclopropylpropan-1-one (23.5 g) was added, and the resulting mixture was stirred at room temperature overnight. The mixture was poured into water, and extracted with EtOAc. The extract was washed with brine, dried over $MgSO_4$, and concentrated. The resulting solid was suspended in IPE, stirred for 1 h, and collected by filtration. The crude product was dissolved in EtOAc (1100 ml) at 70° C., and hexane (400 ml) was added while the temperature was maintained at 60° C. Seed crystal was added, and the mixture was stirred at the same temperature for 1 h. Additional hexane (400 ml) was added at 60° C., and the mixture was allowed to cool to room temperature overnight. The precipitate was collected by filtration, washed with hexane/EtOAc (1/1) 3 times, and dried to give the title compound (30.5 g) as a white solid.
MS (ESI+): [M+H]+ 470.9.

C) 2-Cyclopropyl-6-iodo-3-methylimidazo[1,2-a]pyridine

To a solution of N-(1-(1-cyclopropyl-1-oxopropan-2-yl)-5-iodopyridin-2(1H)-ylidene)-4-methylbenzene sulfonamide (30.5 g) in THF (300 ml) was added trifluoroacetic anhydride (18.3 ml) dropwise. After 3 h, the resulting precipitate was collected by filtration, and washed with ether to give p-toluenesulfonic acid salt of the title compound as a white solid. The solid obtained was dissolved in a mixture of 1 M NaOH, EtOAc and THF. Then the organic layer was washed with brine, dried over MgSO$_4$ and concentrated. The resulting solid was triturated with IPE, and collected to give the title compound (17.7 g) as a pale yellow solid.

MS (ESI+): [M+H]+ 299.0.

D) 1-(2-Cyclopropyl-3-methylimidazo[1,2-a]pyridin-6-yl)-4-((4-fluorobenzyl)oxy)pyridin-2(1H)-one To a stirred degassed mixture of 4-((4-fluorobenzyl)oxy)pyridin-2(1H)-one (200 mg), 2-cyclopropyl-6-iodo-3-methylimidazo[1,2-a]pyridine (285 mg) and potassium carbonate (378 mg) in DMF (6 ml) were added copper iodide (34.7 mg) and trans-N,N'-dimethylcyclohexane-1,2-diamine (26 mg). The reaction vessel was sealed and heated at 130° C. for 16 h. DMF was removed in vacuo and then the residue was partitioned between EtOAc (100 ml) and water (20 ml). The organic layer was washed with brine, dried over Na$_2$SO$_4$ and concentrated in vacuo. Two batches were combined and purified by preparative HPLC to give the title compound (80 mg) as an off-white solid.

MS (ESI+): [M+H]+ 389.8.

$^1$H NMR (400 MHz, CD$_3$OD): δ 0.95-0.99 (4H, m), 2.06 (1H, m), 2.51 (3H, s), 5.14 (2H, s), 6.11 (1H, d, J=2.6 Hz), 6.28 (1H, dd, J=2.6, 7.6 Hz), 7.14 (2H, t, J=8.7 Hz), 7.21 (1H, dd, J=1.9, 9.4 Hz), 7.46-7.51 (3H, m), 7.60 (1H, d, J=7.6 Hz), 8.33 (1H, d, J=1.3 Hz).

Example 2

1-(2-Cyclopropyl-1-methyl-1H-benzimidazol-6-yl)-4-((4-fluorobenzyl)oxy)pyridin-2(1H)-one A) 5-Bromo-N-methyl-2-nitroaniline To a solution of 4-bromo-2-fluoro-1-nitrobenzene (25 g) in EtOH (100 ml) was added methylamine (40% in MeOH, 34.8 ml) at room temperature. The mixture was stirred at room temperature for 1 h. After being stirred, the reaction mixture was cooled to 0° C., and the precipitate was collected by filtration and washed with EtOH (0° C.) and IPE. The solid was dried to give the title compound (24.8 g) as a yellow solid.

$^1$H NMR (300 MHz, DMSO-d$_6$): δ 2.95 (3H, d, J=4.9 Hz), 6.83 (1H, dd, J=1.9, 9.1 Hz), 7.17 (1H, d, J=1.9 Hz), 7.98 (1H, d, J=9.1 Hz), 8.23 (1H, brs).

B) 6-Bromo-2-cyclopropyl-1-methyl-1H-benzimidazole

A mixture of 5-bromo-N-methyl-2-nitroaniline (4.2 g), zinc (5.9 g), NH$_4$Cl (9.7 g), MeOH (50 ml) and water (25 ml) was stirred at room temperature for 3 h. After removing MeOH, the mixture was neutralized with saturated NaHCO$_3$ solution and extracted with EtOAc. The organic layer was separated, washed with water and brine, dried over MgSO$_4$ and concentrated in vacuo. To a solution of the residue in POCl$_3$ (1.68 ml) was added cyclopropanecarboxylic acid (2.86 ml) at room temperature. The mixture was stirred at 120° C. for 3 h. After cooling to 0° C., ice water and saturated NaHCO$_3$ solution were carefully added, and the mixture was extracted with EtOAc. The extract was washed with brine, dried over MgSO$_4$, concentrated to give a brown solid. This solid was dissolved in 1 M HCl and washed with EtOAc. The aqueous layer was basified with 4 M NaOH, and extracted with EtOAc. The organic layer was washed with brine, dried over MgSO$_4$, and concentrated to give the title compound (3.3 g) as a brown solid.

$^1$H NMR (300 MHz, DMSO-d$_6$): δ 0.95-1.14 (4H, m), 2.23 (1H, tt, J=5.1, 7.9 Hz), 3.83 (3H, s), 7.24 (1H, dd, J=2.1, 8.5 Hz), 7.41 (1H, d, J=8.7 Hz), 7.75 (1H, d, J=1.9 Hz).

C) 1-(2-Cyclopropyl-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (2.44 g), 6-bromo-2-cyclopropyl-1-methyl-1H-benzimidazole (2.8 g), potassium carbonate (4.62 g), N,N'-dimethylethylenediamine (1.20 ml), copper iodide (2.12 g) and DMSO (56 ml) was stirred at 150° C. under Ar atmosphere for 2 h. After cooling to 0° C., 28% NH$_3$ solution (56.0 ml) was added. The mixture was stirred at 0° C. for 1 h and then at room temperature for 1 h. The precipitate was collected by filtration and washed with water and IPE. The collected material was dissolved in THF (500 ml), passed through a short NH silica gel column (EtOAc 100%) and concentrated in vacuo. The resulting solid was collected, washed with IPE (50 ml) and then EtOAc (50 ml), and dissolved in MeOH. To the solution was added activated carbon (ca. 200 mg), and the mixture was stirred at room temperature for 10 min. The insoluble material was removed by filtration and the filtrate was concentrated in vacuo. The residue was purified by NH silica gel column chromatography (hexane/EtOAc), and recrystallized from EtOH/water to give the title compound (1.60 g) as an off-white solid.

MS (ESI+): [M+H]+ 390.2.

$^1$H NMR (400 MHz, DMSO-d$_6$): δ 0.99-1.15 (4H, m), 2.20-2.33 (1H, m), 3.85 (3H, s), 5.13 (2H, s), 5.98 (1H, d, J=2.3 Hz), 6.09 (1H, dd, J=2.4, 7.5 Hz), 7.04 (1H, d, J=8.6 Hz), 7.26 (2H, t, J=8.8 Hz), 7.43-7.67 (5H, m).

Example 3

4-((4-Chlorobenzyl)oxy)-1-(2-cyclopropyl-3-methylimidazo[1,2-a]pyridin-6-yl)pyridin-2(1H)-one A mixture of 4-((4-chlorobenzyl)oxy)pyridin-2(1H)-one (1.0 g), 2-cyclopropyl-6-iodo-3-methylimidazo[1,2-a]pyridine (1.27 g), N,N'-dimethylethylenediamine (0.48 ml), copper iodide (0.81 g), potassium carbonate (1.76 g) and DMSO (15 ml) was heated at 150° C. for 3 h. Another batch of the same reaction was conducted. Then these reaction mixtures were combined, and poured into 14% NH$_3$ solution. The mixture was extracted with 1:1 mixture of EtOAc and THF. The extract was washed with brine, dried over MgSO$_4$, concentrated, and purified by silica gel column chromatography (EtOAc/MeOH), followed by NH silica gel column chromatography (hexane/EtOAc) to give a white solid (350 mg).

Then a mixture of 4-((4-chlorobenzyl)oxy)pyridin-2(1H)-one (1.0 g), 2-cyclopropyl-6-iodo-3-methylimidazo[1,2-a]pyridine (1.27 g), N,N'-dimethylethylenediamine (0.48 ml), copper iodide (0.81 g), potassium carbonate (1.76 g) and DMSO (13 ml) was heated at 110° C. under microwave irradiation for 1 h. Other two batches using 200 mg and 1 g of 4-((4-chlorobenzyl)oxy)pyridin-2(1H)-one were conducted. Then these reaction mixtures were combined, and poured into 14% NH$_3$ solution. The mixture was extracted with 1:1 mixture of EtOAc and THF. The extract was washed with brine, dried over MgSO$_4$, concentrated, and purified by silica gel column chromatography (hexane/EtOAc then EtOAc/MeOH), followed by NH silica gel column chromatography (hexane/EtOAc) to give the title compound as a white solid (950 mg).

These two lots were combined, and recrystallized from EtOH/water to give the title compound as a white solid (1.25 g).

MS (ESI+): [M+H]+ 406.1.

$^1$H NMR (300 MHz, DMSO-d$_6$): δ 0.84-0.96 (4H, m), 2.01-2.13 (1H, m), 2.47 (3H, s), 5.16 (2H, s), 6.00 (1H, d, J=2.6 Hz), 6.14 (1H, dd, J=2.6, 7.6 Hz), 7.11 (1H, dd, J=1.9, 9.4 Hz), 7.43 (1H, d, J=9.4 Hz), 7.50 (4H, s), 7.66 (1H, d, J=7.6 Hz), 8.36 (1H, d, J=1.1 Hz).

Example 4

1-(2-Cyclopropyl-1,4-dimethyl-1H-benzimidazol-6-yl)-4-((4-fluorobenzyl)oxy)pyridin-2(1H)-one A) 5-Bromo-3-methylbenzene-1,2-diamine To a stirred solution of compound 4-bromo-2-methyl-6-nitroaniline (5.0 g) in EtOH (85 ml) and water (43 ml) were added iron powder (6.0 g) and CaCl$_2$ (4.8 g) at room temperature and the resulting reaction mixture was then heated at reflux for 4 h. The mixture was then cooled to room temperature, filtered through Celite, and washed with EtOH. The filtrate was concentrated and the resulting residue was diluted with DCM. The DCM layer was successively washed with water and brine, dried over Na$_2$SO$_4$ and concentrated in vacuo to give the title compound (4.0 g) as a dark brown solid.

MS (ESI+): [M+H]+ 201.2.

B) Ethyl(2-amino-5-bromo-3-methylphenyl)carbamate

To a stirred solution of 5-bromo-3-methylbenzene-1,2-diamine (4 g) in DMF (80 ml) was added NaH (40% oil dispersion, 800 mg) at 0° C., and the reaction mixture was stirred for another 30 min at the same temperature. A solution of ethyl chloroformate (1.9 g) in DMF (10 ml) was added dropwise thereto at 0° C. and then the resulting reaction mixture was stirred at room temperature for 1 h. The reaction mixture was poured into saturated NH$_4$Cl solution, and extracted with EtOAc. The extract was washed with brine, dried over Na$_2$SO$_4$ and concentrated in vacuo. The residue was purified by silica gel column chromatography (hexane/EtOAc) to give the title compound (2.5 g) as a yellow solid.

MS (ESI+): [M+H]+ 273.1.

C) 5-Bromo-N$^1$,3-dimethylbenzene-1,2-diamine

To a stirred suspension of lithium aluminum hydride (400 mg) in THF (25 ml) was added a solution of ethyl(2-amino-5-bromo-3-methylphenyl)carbamate (1 g) in THF (10 ml) at 0° C. The mixture was then warmed to room temperature, followed by heating at reflux for 1 h. The reaction mixture was cooled to 0° C., diluted with THF (45 ml) and a saturated Na$_2$SO$_4$ solution was added dropwise thereto. The mixture was further stirred for 30 min and solids were filtered over Celite. The filtrate was concentrated in vacuo. The residue was purified by silica gel column chromatography (hexane/EtOAc) to give the title compound (550 mg) as a brownish liquid.

MS (ESI+): [M+H]+ 215.2.

D) 6-Bromo-2-cyclopropyl-1,4-dimethyl-1H-benzimidazole

To a stirred mixture of cyclopropanecarboxylic acid (356 μl) and 5-bromo-N',3-dimethylbenzene-1,2-diamine (600 mg) was added POCl$_3$ (10 ml), and the mixture was heated at 120° C. After 3 h, the mixture was poured into saturated aqueous NaHCO$_3$ solution, and extracted with EtOAc. The extract was washed with brine, dried over Na$_2$SO$_4$ and concentrated in vacuo. The residue was purified by silica gel column chromatography (hexane/EtOAc) to give the title compound (450 mg) as brown solid.

MS (ESI+): [M+H]+ 265.0.

E) 1-(2-Cyclopropyl-1,4-dimethyl-1H-benzimidazol-6-yl)-4-((4-fluorobenzyl)oxy)pyridin-2(1H)-one To a stirred degassed mixture of 4-((4-fluorobenzyl)oxy)pyridin-2(1H)-one (66 mg), 6-bromo-2-cyclopropyl-1,4-dimethyl-1H-benzimidazole (100 mg), potassium carbonate (156 mg) and dioxane (2 ml) were added copper iodide (14 mg) and trans-N,N'-dimethylcyclohexane-1,2-diamine (10 mg). The reaction vessel was sealed and heated at 110° C. for 16 h. The mixture was then cooled, filtered through Celite, and washed with dioxane. The filtrate was concentrated under reduced pressure and the residue was purified by silica gel column chromatography (MeOH/DCM) followed by preparative HPLC to give the title compound (60 mg) as an off-white solid.

MS (ESI+): [M+H]+ 404.0.

Example 5

1-(2-Cyclopropyl-3-methylimidazo[1,2-a]pyridin-6-yl)-4-((4-(trifluoromethyl)benzyl)oxy)pyridin-2(1H)-one A) 4-((4-(Trifluoromethyl)benzyl)oxy)pyridine 1-oxide To an ice-cold solution of NaH (40% oil dispersion, 231 mg) in THF (10 ml) was added (4-(trifluoromethyl)phenyl)methanol (815 mg) at 0° C. The reaction mixture was stirred at the same temperature for 10 min followed by the addition of 4-chloropyridine 1-oxide (500 mg) at 0° C. The resulting reaction mixture was stirred for 1 h at 0° C. and then warmed to room temperature. After 2 h, the reaction mixture was poured into ice-water and extracted with DCM twice. The organic layer was washed with brine, dried over Na$_2$SO$_4$ and concentrated in vacuo to give the title compound (300 mg) as a yellow solid.

MS (ESI+): [M+H]+ 270.2.

B) 4-((4-(Trifluoromethyl)benzyl)oxy)pyridin-2(1H)-one

A solution of 4-((4-(trifluoromethyl)benzyl)oxy)pyridine 1-oxide (350 mg) in acetic anhydride (6 ml) was heated under reflux for 4 h. The reaction mixture was then cooled to room temperature and concentrated in vacuo. The residue was diluted with MeOH (10 ml) and 2 M NaOH (10 ml), and heated at reflux for 1 h. The reaction mixture was cooled to room temperature and concentrated in vacuo. The residue was diluted with water and extracted with DCM. The DCM layer was concentrated in vacuo and purified by silica gel column chromatography (MeOH/DCM) to give the title compound (110 mg) as an off-white solid.

MS (ESI+): [M+H]+ 270.0.

C) 1-(2-Cyclopropyl-3-methylimidazo[1,2-a]pyridin-6-yl)-4-((4-(trifluoromethyl)benzyl)oxy)pyridin-2(1H)-one To a stirred degassed mixture of 4-((4-(trifluoromethyl)benzyl)oxy)pyridin-2(1H)-one (110 mg), 2-cyclopropyl-6- iodo-3-methylimidazo[1,2-a]pyridine (121 mg), potassium carbonate (168 mg) and dioxane (10 ml) were added copper iodide (15 mg) and trans-N,N'-dimethylcyclohexane-1,2-diamine (11 mg). The reaction vessel was sealed and heated at 110° C. for 16 h. The mixture was filtered through a Celite pad, and the filtrate was concentrated in vacuo. The residue was diluted with water, and extracted with EtOAc. The organic layer was washed with brine, dried over $Na_2SO_4$ and concentrated. The residue was purified by silica gel column chromatography (MeOH/DCM) to give the title compound (40 mg) as an off-white solid.

MS (ESI+): [M+H]+ 440.2.

$^1$H NMR (400 MHz, $CD_3OD$): δ 0.95-1.01 (4H, m), 2.06 (1H, m), 2.51 (3H, s), 5.28 (2H, s), 6.10 (1H, d, J=2.4 Hz), 6.33 (1H, dd, J=2.4, 7.6 Hz), 7.21 (1H, dd, J=2.0, 9.2 Hz), 7.47 (1H, d, J=9.6 Hz), 7.62-7.67 (3H, m), 7.72 (2H, d, J=8.4 Hz), 8.33 (1H, s).

Example 6

1-(2-Cyclopropyl-3-methylimidazo[1,2-a]pyridin-6-yl)-4-((4-(trifluoromethoxy)benzyl)oxy)pyridin-2(1H)-one A) 4-((4-(Trifluoromethoxy)benzyl)oxy)pyridine 1-oxide The title compound was obtained in an analogous manner to step A in example 5 using (4-(trifluoromethoxy)phenyl)methanol.

MS (ESI+): [M+H]+ 286.0.

B) 4-((4-(Trifluoromethoxy)benzyl)oxy)pyridin-2(1H)-one

The title compound was obtained in an analogous manner to step B in example 5 using 4-((4-(trifluoromethoxy)benzyl)oxy)pyridine 1-oxide.

MS (ESI+): [M+H]+ 286.0.

C) 1-(2-Cyclopropyl-3-methylimidazo[1,2-a]pyridin-6-yl)-4-((4-(trifluoromethoxy)benzyl)oxy)pyridin-2(1H)-one The title compound was obtained in an analogous manner to step C in example 5 using 4-((4-(trifluoromethoxy)benzyl)oxy)pyridin-2(1H)-one and 2-cyclopropyl-6-iodo-3-methylimidazo[1,2-a]pyridine.

MS (ESI+): [M+H]+ 456.4.

Example 7

6-((4-Chlorobenzyl)oxy)-3-(2-cyclopropyl-3-methylimidazo[1,2-a]pyridin-6-yl)pyrimidin-4(3H)-one A) (2-Cyclopropyl-3-methylimidazo[1,2-a]pyridin-6-yl)boronic acid To a solution of 2-cyclopropyl-6-iodo-3-methylimidazo[1,2-a]pyridine (742 mg) in THF (25 ml) was added n-butyl-lithium (1.6 M in hexane, 6.2 ml) at −78° C. The mixture was stirred at −78° C. under $N_2$ atmosphere for 30 min. After being stirred, boric acid triisopropyl ester (0.86 ml) was added to the reaction mixture at −78° C. The mixture was stirred at −78° C. under $N_2$ atmosphere for 30 min and then at room temperature for 3 h. The mixture was poured into 1 M NaOH at 0° C. and washed with EtOAc. The aqueous layer was neutralized with 1 M HCl (to pH 7.0) and extracted with EtOAc/IPA. The organic layer was separated, washed with brine, dried over $MgSO_4$ and concentrated in vacuo. The resulting solid was washed with EtOAc/MeOH to give the title compound (176 mg) as a yellow solid.

MS (ESI+) [M+H]+ 217.2.

B) 6-((4-Chlorobenzyl)oxy)pyrimidin-4(3H)-one

To a stirred solution of pyrimidine-4,6-diol (2.5 g) in THF (25 ml) was added silver carbonate (15.3 g) at room temperature followed by dropwise addition of 4-chlorobenzyl bromide (4.58 g), and the resultant mixture was heated at reflux for 2 h. The reaction mixture was then cooled to room temperature, filtered through Celite, and the filtrate was concentrated in vacuo. The residue was purified by silica gel column chromatography (MeOH/DCM) to give the title compound (500 mg) as a white solid.

MS (ESI+): [M+H]+ 237.2.

C) 6-((4-Chlorobenzyl)oxy)-3-(2-cyclopropyl-3-methylimidazo[1,2-a]pyridin-6-yl)pyrimidin-4(3H)-one To a mixture of 6-((4-chlorobenzyl)oxy)pyrimidin-4(3H)-one (150 mg), (2-cyclopropyl-3-methylimidazo[1,2-a]pyridin-6-yl)boronic acid (275 mg), DCM (15 ml) and MeOH (15 ml) were added copper acetate (346 mg) and pyridine (0.5 ml), and the resulting reaction mixture was stirred at room temperature for 16 h. The solids were then filtered through Celite, and the filtrate was poured into 1 M HCl. The mixture was extracted with DCM, and the combined DCM layer was washed successively with saturated $NaHCO_3$ solution, brine, dried over $Na_2SO_4$ and concentrated in vacuo. The crude product was purified by preparative HPLC to give the title compound (15 mg) as an off-white solid.

MS (ESI+): [M+H]+ 407.0.

Example 8

1-(2-tert-Butyl-1-methyl-1H-benzimidazol-6-yl)-4-((4-fluorobenzyl)oxy)pyridin-2(1H)-one A) 6-Bromo-2-tert-butyl-1-methyl-1H-benzimidazole To a stirred solution of 2,2-dimethylpropionic acid (304 mg) and 4-bromo-$N^2$-methylbenzene-1,2-diamine (400 mg) was added $POCl_3$ (5 ml), and the mixture was heated at reflux for 4 h. The mixture was then cooled to room temperature, and poured into ice-cold saturated $NaHCO_3$ solution. The mixture was extracted with EtOAc, and the organic layer was washed with brine, dried over $Na_2SO_4$ and concentrated in vacuo. The residue was purified by silica gel column chromatography (hexane/EtOAc) to give the title compound (200 mg) as a light orange solid.

MS (ESI+): [M+H]+ 266.6.

B) 1-(2-tert-Butyl-1-methyl-1H-benzimidazol-6-yl)-4-((4-fluorobenzyl)oxy)pyridin-2(1H)-one The title compound was obtained in an analogous manner to step C in example 5 using 4-((4-fluorobenzyl)oxy)pyridin-2(1H)-one and 6-bromo-2-tert-butyl-1-methyl-1H-benzimidazole.

MS (ESI+): [M+H]+ 405.9.

Example 9

4-(Benzyloxy)-1-(2-cyclopropyl-1-methyl-1H-benzimidazol-6-yl)pyridin-2(1H)-one A mixture of 4-(benzyloxy)pyridin-2(1H)-one (1.60 g), 6-bromo-2-cyclopropyl-1-methyl-1H-benzimidazole (2 g), potassium carbonate (3.30 g), N,N'-dimethylethylenediamine (0.855 ml), copper iodide (1.52 g) and DMSO (40 ml) was stirred at 150° C. under Ar atmosphere for 1 h. The mixture was poured into 28% $NH_3$ solution. The precipitate was collected by filtration and washed with water and EtOAc. The solid was dissolved in THF, put on through silica gel pad and concentrated in vacuo. The residue was purified by silica gel column chromatography (EtOAc/MeOH). The resulting solid was dissolved in MeOH, and stirred with activated charcoal at room temperature for 10 min. The insoluble material was removed by filtration, and the filtrate was concentrated in vacuo to give the title compound (1.60 g) as an off-white solid.

MS (ESI+): [M+H]+ 372.2.
$^1$H NMR (300 MHz, DMSO-$d_6$) δ 0.95-1.19 (4H, m), 2.18-2.34 (1H, m), 3.85 (3H, s), 5.15 (2H, s), 5.98 (1H, d, J=3.0 Hz), 6.10 (1H, dd, J=2.6, 7.6 Hz), 6.96-7.11 (1H, m), 7.29-7.66 (8H, m).

Example 10

4-((4-Chlorobenzyl)oxy)-1-(2-cyclopropyl-1-methyl-1H-benzimidazol-6-yl)pyridin-2(1H)-one To a stirred degassed mixture of 4-((4-chlorobenzyl)oxy)pyridin-2(1H)-one (502 mg), 6-bromo-2-cyclopropyl-1-methyl-1H-benzimidazole (470 mg), potassium carbonate (552 mg) and dry dioxane (15 ml) were added copper iodide (76 mg) and trans-N,N'-dimethylcyclohexane-1,2-diamine (56 mg). The reaction vessel was sealed and heated at 110° C. for 16 h. The reaction mixture was then cooled to room temperature, and concentrated in vacuo. The crude residue was diluted with DCM, washed with brine, dried over $Na_2SO_4$ and concentrated in vacuo. The residue was purified by silica gel column chromatography (MeOH/DCM) to give the title compound (150 mg) as a white solid.

MS (ESI+): [M+H]+ 406.0.
$^1$H NMR (400 MHz, $CD_3OD$): δ 1.14-1.20 (4H, m), 2.24 (1H, m), 3.90 (3H, s), 5.16 (2H, s), 6.09 (1H, d, J=2.6 Hz), 6.27 (1H, dd, J=2.7, 7.6 Hz), 7.15 (1H, dd, J=2.0, 8.5 Hz), 7.41-7.50 (5H, m), 7.69 (2H, t, J=8.3 Hz).

Example 11

4-(Benzyloxy)-1-(2-cyclopropyl-3-methylimidazo[1,2-a]pyridin-6-yl)pyridin-2(1H)-one A mixture of 2-cyclopropyl-6-iodo-3-methylimidazo[1,2-a]pyridine (1482 mg), 4-(benzyloxy)pyridin-2(1H)-one (1000 mg), copper iodide (946 mg), N,N'-dimethylethylenediamine (0.534 ml), potassium carbonate (2061 mg) and DMSO (13 ml) was heated 110° C. for 1 h under microwave irradiation. The residue was quenched with 28% $NH_3$ solution, and extracted with EtOAc/THF. The organic layer was separated, washed with water and brine, dried over $MgSO_4$, passed through silica gel pad (EtOAc only) and concentrated in vacuo. The residue was purified by silica gel column chromatography (EtOAc/MeOH) and recrystallized from EtOH (80 ml) to give the title compound (1027 mg) as an off-white solid.

MS (ESI+): [M+H]+ 372.2.
$^1$H NMR (300 MHz, DMSO-$d_5$): δ 0.83-0.96 (4H, m), 2.02-2.12 (1H, m), 2.47 (3H, s), 5.16 (2H, s), 6.01 (1H, d, J=2.6 Hz), 6.09-6.18 (1H, m), 7.11 (1H, dd, J=1.9, 9.4 Hz), 7.32-7.53 (6H, m), 7.66 (1H, d, J=7.5 Hz), 8.37 (1H, d, J=1.1 Hz).

Example 12

1-(2-Cyclopropyl-1-methyl-1H-benzimidazol-6-yl)-4-((1-methyl-3-(trifluoromethyl)-1H-pyrazol-5-yl)methoxy)pyridin-2(1H)-one The title compound was obtained in an analogous manner to example 75 using (1-methyl-3-(trifluoromethyl)-1H-pyrazol-5-yl)methanol and 1-(2-cyclopropyl-1-methyl-1H-benzo[d]imidazol-6-yl)-4-hydroxypyridin-2(1H)-one.

MS (ESI+): [M+H]+ 444.1.

Example 13

4-((4-Fluorobenzyl)oxy)-1-(1-methyl-2-(tetrahydrofuran-3-yl)-1H-benzimidazol-6-yl)pyridin-2(1H)-one

A) 4-((4-Fluorobenzyl)oxy)-1-(3-(methylamino)-4-nitrophenyl)pyridin-2(1H)-one A mixture of 4-((4-fluorobenzyl)oxy)pyridin-2(1H)-one (2.06 g), 5-bromo-N-methyl-2-nitroaniline (2.17 g), N,N'-dimethylethylenediamine (1.00 ml), copper iodide (1.79 g), potassium carbonate (3.90 g) and DMSO (30 ml) was stirred at 150° C. for 2 h. The mixture was added to 28% $NH_3$ solution. The precipitate was collected and washed with water to give the title compound (2.63 g) as a yellow solid.

MS (ESI+): [M+H]+ 370.1.

B) 1-(4-Amino-3-(methylamino)phenyl)-4-((4-fluorobenzyl)oxy)pyridin-2(1H)-one To a suspension of 4-((4-fluorobenzyl)oxy)-1-(3-(methylamino)-4-nitrophenyl)pyridin-2(1H)-one (500 mg) in AcOH (30 ml) was added zinc (885 mg), and the mixture was stirred at room temperature for 1 h. The insoluble material was removed by filtration and washed with MeOH. The filtrate was concentrated, and partitioned between EtOAc, THF and saturated $NaHCO_3$ solution. The organic layer was then washed with brine, dried over $MgSO_4$, and concentrated. The resulting solid was collected, and washed with IPE to give the title compound (366 mg) as a brown solid.

MS (ESI+): [M+H]+ 340.3.

C) 4-((4-Fluorobenzyl)oxy)-1-(1-methyl-2-(tetrahydrofuran-3-yl)-1H-benzimidazol-6-yl)pyridin-2(1H)-one A mixture of 1-(4-amino-3-(methylamino)phenyl)-4-((4-fluorobenzyl)oxy)pyridin-2(1H)-one (56.1 mg), tetrahydro-3-furoic acid (0.016 ml), HATU (66.0 mg) and N,N-diisopropylethylamine (0.087 ml) in DMF (1.50 ml) was stirred at room temperature for 1 h. The mixture was poured into saturated $NaHCO_3$ solution and extracted with EtOAc. The organic layer was separated, washed with brine, dried over $MgSO_4$ and concentrated in vacuo. The residue was dissolved in AcOH (1.50 ml), and the mixture was stirred at 80° C. for 1 h. The mixture was concentrated in vacuo. The residue was purified by silica gel column chromatography (MeOH/

EtOAc). The solid was washed with EtOAc/hexane to give the title compound (34.3 mg) as an off-white solid.
MS (ESI+): [M+H]+ 420.1.

Example 14

4-((4-Fluorobenzyl)oxy)-1-(1-methyl-1H-benzimidazol-6-yl)pyridin-2(1H)-one

A) 6-Bromo-1-methyl-2-(trichloromethyl)-1H-benzimidazole

A mixture of 5-bromo-N-methyl-2-nitroaniline (0.65 g), iron (0.63 g), $CaCl_2$ (0.62 g), EtOH (14 ml) and water (14 ml) was heated at 70° C. for 3 h. The inorganic material was removed by filtration, and the filtrate was concentrated. The residue was basified with saturated $NaHCO_3$, and extracted with EtOAc. The extract was washed with brine, dried over $MgSO_4$, and concentrated to give the title compound (0.51 g) as a brown oil.
To the oil in AcOH (3 ml), methyl 2,2,2-trichloroacetimidate (0.42 ml) was added dropwise at 0° C. The mixture was stirred at room temperature for 2 h. After addition of water, the precipitate was collected by filtration and washed with water to give the title compound (0.78 g) as a gray solid.
$^1$H NMR (300 MHz, $CDCl_3$): δ 4.09 (3H, s), 7.46 (1H, dd, J=1.7, 8.5 Hz), 7.58 (1H, d, J=1.5 Hz), 7.74 (1H, d, J=8.7 Hz).

B) Methyl 6-bromo-1-methyl-1H-benzimidazole-2-carboxylate

A mixture of 6-bromo-1-methyl-2-(trichloromethyl)-1H-benzimidazole (0.781 g), sodium carbonate (0.298 g), MeOH (20 ml), and water (2 ml) was refluxed overnight. After evaporation of the solvent and addition of water, the mixture was extracted with EtOAc twice. The organic layer was separated, washed with brine, dried over $MgSO_4$ and concentrated in vacuo. The solid was washed with $Et_2O$ to give the title compound (0.315 g) as a pale brown solid.
$^1$H NMR (300 MHz, $CDCl_3$): δ 4.05 (3H, s), 4.14 (3H, s), 7.46 (1H, dd, J=1.9, 8.7 Hz), 7.63 (1H, d, J=1.5 Hz), 7.74 (1H, d, J=8.7 Hz).

C) 4-((4-Fluorobenzyl)oxy)-1-(1-methyl-1H-benzimidazol-6-yl)pyridin-2(1H)-one

The title compound was obtained in an analogous manner to step C in example 5 using 4-((4-fluorobenzyl)oxy)pyridin-2(1H)-one and methyl 6-bromo-1-methyl-1H-benzimidazole-2-carboxylate.
MS (ESI+): [M+H]+ 350.2.

Example 15

1-(2-(Cyclopropylmethyl)-1-methyl-1H-benzimidazol-6-yl)-4-((4-fluorobenzyl)oxy)pyridin-2(1H)-one A) 6-Bromo-2-(cyclopropylmethyl)-1-methyl-1H-benzimidazole Zinc (212 mg) was added to a mixture of 5-bromo-N-methyl-2-nitroaniline (150 mg), $NH_4Cl$ (347 mg), MeOH (2 ml) and water (1 ml) at room temperature. The mixture was stirred at room temperature for 1 h. After filtration and addition of saturated $NaHCO_3$ solution, the mixture was concentrated and extracted with AcOEt. The organic layer was separated, washed with brine, dried over $MgSO_4$ and concentrated in vacuo. To the resulting residue, DMF (2.0 ml), cyclopropylacetic acid (0.060 ml), N,N-diisopropylethylamine (0.339 ml) and HATU (259 mg) were added, and the mixture was stirred at room temperature for 1 h. The mixture was quenched with brine and extracted with EtOAc twice. The organic layer was separated, washed with brine, dried over $MgSO_4$, passed through NH silica pad and concentrated in vacuo. The resulting residue was dissolved in AcOH (2.0 ml), and stirred at 80° C. for 1 h. After evaporation of the solvent, the residue was purified by NH silica gel column chromatography (hexane/EtOAc) to give the title compound (165 mg) as a purple gum.
MS (ESI+): [M+H]+ 265.1.

B) 1-(2-(Cyclopropylmethyl)-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (91 mg), 6-bromo-2-(cyclopropylmethyl)-1-methyl-1H-benzimidazole (165 mg), N,N'-dimethylethylenediamine (0.045 ml)-, copper iodide (79 mg), potassium carbonate (229 mg) and DMSO (3 ml) was heated at 150° C. for 2 h under microwave irradiation. After cooling, the reaction mixture was purified by NH silica gel column chromatography (hexane/EtOAc to MeOH/EtOAc). The resulting solid was washed with EtOAc and dried to give the title compound (62 mg) as a pale yellow solid.
MS (ESI+): [M+H]+ 404.2.
$^1$H NMR (300 MHz, $CDCl_3$): δ 0.27-0.37 (2H, m), 0.57-0.68 (2H, m), 1.12-1.25 (1H, m), 2.87 (2H, d, J=6.4 Hz), 3.75 (3H, 5), 5.02 (2H, s), 5.96-6.13 (2H, m), 7.04-7.16 (3H, m), 7.31 (1H, d, J=7.2 Hz), 7.35-7.45 (3H, m), 7.79 (1H, d, J=8.3 Hz).

Example 16

3-(6-(4-((4-Fluorobenzyl)oxy)-2-oxopyridin-1(2H)-yl)-1-methyl-1H-benzimidazol-2-yl)-2,2-dimethylpropanenitrile A) 3-(6-Bromo-1-methyl-1H-benzimidazol-2-yl)-2,2-dimethylpropanenitrile Thionyl chloride (0.454 ml) was added to a solution of (6-bromo-1-methyl-1H-benzimidazol-2-yl)methanol (300 mg) in THF (6 ml) at room temperature. The mixture was stirred at room temperature for 1 h and poured into water. After addition of $NaHCO_3$ solution, the mixture was extracted with EtOAc twice. The organic layer was separated, washed with brine, dried over $MgSO_4$ and concentrated in vacuo to give the corresponding chloride derivative. Lithium diisopropylamide in THF/ethylbenzene/heptane (2.0 M, 1.24 ml) was added to a solution of isobutyronitrile (0.226 ml) in THF (6 ml) at −78° C. The mixture was stirred at −78° C. under Ar atmosphere for 1 h. To this mixture, a solution of the chloride derivative in THF (2 ml) was added dropwise. The mixture was stirred at −78° C. under Ar atmosphere for 1 h and warmed up to room temperature. The mixture was stirred at room temperature overnight. The mixture was quenched with brine and extracted with EtOAc three times. The organic layer was separated, washed with brine, dried over $MgSO_4$ and concentrated in vacuo. The residue was purified by silica gel column chromatography (hexane/EtOAc) to give the title compound (25.5 mg) as a light brown oil.
MS (ESI+): [M+H]+ 292.1.

B) 3-(6-(4-((4-Fluorobenzyl)oxy)-2-oxopyridin-1 (2H)-yl)-1-methyl-1H-benzimidazol-2-yl)-2,2-dimethylpropanenitrile The title compound was obtained in an analogous manner to step C in example 5 using 4-((4-fluorobenzyl)oxy)pyridin-2(1H)-one and 3-(6-bromo-1-methyl-1H-benzimidazol-2-yl)-2,2-dimethylpropanenitrile.
MS (ESI+): [M+H]+ 431.2.

Example 17

1-(2-(2,2-Dimethylpropyl)-1-methyl-1H-benzimidazol-6-yl)-4-((4-fluorobenzyl)oxy)pyridin-2(1H)-one A) N-(5-Bromo-2-nitrophenyl)-N,3,3-trimethylbutanamide To a mixture of 5-bromo-N-methyl-2-nitroaniline (300 mg), 3,3-dimethylbutanoyl chloride (0.450 ml) and DMF (5 ml) was added NaH (40% oil dispersion, 57.1 mg), and the mixture was heated at 70° C. overnight. The mixture was poured into water, and extracted with EtOAc. The extract was washed with brine, dried over MgSO$_4$ and concentrated in vacuo. The residue was purified by silica gel column chromatography (hexane/EtOAc) to give the title compound (214 mg) as a solid.
$^1$H NMR (300 MHz, DMSO-d$_6$): δ 0.86-1.06 (9H, m), 1.67-2.39 (2H, m), 3.02-3.45 (3H, m), 7.68-8.13 (3H, m).

B) 6-Bromo-2-(2,2-dimethylpropyl)-1-methyl-1H-benzimidazole

To a solution of N-(5-bromo-2-nitrophenyl)-N,3,3-trimethylbutanamide (300 mg) in AcOH (5 ml) was added zinc (596 mg) at room temperature. Then the mixture was heated at 90° C. for 2 h. The inorganic material was removed by filtration, and the filtrate was concentrated. The residue was poured into a mixture of EtOAc and saturated NaHCO$_3$ solution. The organic layer was washed with brine, dried over MgSO$_4$, concentrated, and purified by NH silica gel column chromatography (hexane/EtOAc) to give the title compound (200 mg) as a white solid.
MS (ESI+): [M+H]+ 281.0.

C) 1-(2-(2,2-Dimethylpropyl)-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (78 mg), 6-bromo-2-(2,2-dimethylpropyl)-1-methyl-1H-benzimidazole (100 mg), N,N'-dimethylethylenediamine (31 mg), copper iodide (68 mg), potassium carbonate (147 mg) and DMSO (2 ml) was heated under Ar atmosphere at 150° C. for 2 h. The mixture was partitioned between 14% aqueous NH$_3$ and EtOAc. The organic layer was washed with brine, dried over MgSO$_4$ and concentrated in vacuo. The residue was purified by NH silica gel column chromatography (hexane/EtOAc) to give the title compound (50 mg) as a white solid.
MS (ESI+): [M+H]+ 420.2.

Example 18

4-((4-Chlorobenzyl)oxy)-1-(2-(2,2-dimethylpropyl)-1-methyl-1H-benzimidazol-6-yl)pyridin-2(1H)-one The title compound was obtained in an analogous manner to step C in example 17 using 4-((4-chlorobenzyl)oxy)pyridin-2(1H)-one and 6-bromo-2-(2,2-dimethylpropyl)-1-methyl-1H-benzimidazole.
MS (ESI+): [M+H]+ 436.1.

Example 19

1-(2-Cyclopropyl-1-propyl-1H-benzimidazol-6-yl)-4-((4-fluorobenzyl)oxy)pyridin-2(1H)-one A) 5-Bromo-2-nitro-N-propylaniline The title compound was obtained in an analogous manner to step A in example 2 using n-propylamine.
$^1$H NMR (300 MHz, CDCl$_3$): δ 1.06 (3H, t, J=7.5 Hz), 1.77 (2H, m), 3.25 (2H, td, J=5.1, 7.1 Hz), 6.74 (1H, dd, J=1.9, 9.0 Hz), 7.01 (1H, d, J=1.9 Hz), 7.92-8.11 (2H, m).

B) 6-Bromo-2-cyclopropyl-1-propyl-1H-benzimidazole

The title compound was obtained in an analogous manner to step B in example 2 using 5-bromo-2-nitro-N-propylaniline.
MS (ESI+): [M+H]+ 281.0.

C) 1-(2-Cyclopropyl-1-propyl-1H-benzimidazol-6-yl)-4-((4-fluorobenzyl)oxy)pyridin-2(1H)-one The title compound was obtained in an analogous manner to step C in example 2 using 6-bromo-2-cyclopropyl-1-propyl-1H-benzimidazole and 4-((4-fluorobenzyl)oxy)pyridin-2(1H)-one.
MS (ESI+): [M+H]+ 418.1.
$^1$H NMR (300 MHz, CDCl$_3$): δ 1.00 (3H, t, J=7.5 Hz), 1.08-1.18 (2H, m), 1.21-1.30 (2H, m), 1.90 (2H, q, J=7.4 Hz), 1.95-2.05 (1H, m), 4.20 (2H, t, J=7.3 Hz), 5.02 (2H, s), 5.99-6.13 (2H, m), 7.05-7.16 (3H, m), 7.28-7.37 (2H, m), 7.41 (2H, s), 7.70 (1H, d, J=8.3 Hz).

Example 20

1-(2-Cyclopropyl-1-ethyl-1H-benzimidazol-6-yl)-4-((4-fluorobenzyl)oxy)pyridin-2(1H)-one A) 5-Bromo-N-ethyl-2-nitroaniline The mixture of 4-bromo-2-fluoro-1-nitrobenzene (5 g) and ethylamine (2 M in THF, 17.05 ml) was stirred at room temperature for 2 h and at 50° C. for 2 h. After concentration of the mixture, the residue was quenched with saturated NaHCO$_3$ solution at room temperature and extracted with EtOAc. The organic layer was separated, washed with water and brine, dried over MgSO$_4$ and concentrated in vacuo. The progress of the reaction was followed by NMR, but 4-bromo-2-fluoro-1-nitrobenzene was remained. The resulting residue was dissolved in EtOH (25 ml), and heated with potassium carbonate (6.28 g) and ethylamine (15.6 M in water, 1.47 ml) at 50° C. for 2 h. The resulting suspension was filtered. The precipitate was washed with EtOH and water and dried to give the title compound (4.45 g) as a pale yellow solid.

¹H NMR (300 MHz, CDCl₃): δ 1.06 (3H, t, J=7.5 Hz), 3.25 (2H, td, J=5.1, 7.1 Hz), 6.74 (1H, dd, J=1.9, 9.0 Hz), 7.01 (1H, d, J=1.9 Hz), 7.92-8.11 (2H, m).

B) 4-Bromo-$N^2$-ethylbenzene-1,2-diamine

Zinc (8.0 g) was added to a solution of 5-bromo-N-ethyl-2-nitroaniline (3.0 g) in AcOH (60 ml) at room temperature. The mixture was stirred at room temperature for 30 min. The insoluble material was removed by filtration, and the filtrate was concentrated in vacuo. The mixture was neutralized with saturated NaHCO₃ solution at room temperature and extracted with EtOAc. The organic layer was separated, washed with water and brine, dried over MgSO₄ and concentrated in vacuo to give the title compound (1.2 g) as a pale yellow solid.
MS (ESI+): [M+H]+ 217.1.

C) 6-Bromo-2-cyclopropyl-1-ethyl-1H-benzimidazole

HATU (4.89 g) was added to a solution of 4-bromo-$N^2$-ethylbenzene-1,2-diamine (2.63 g), N,N-diisopropylethylamine (6.40 ml) and cyclopropanecarboxylic acid (0.979 ml) in DMF (40 ml) at room temperature. The mixture was stirred at room temperature for 1 h. The mixture was quenched with water and extracted with EtOAc. The organic layer was separated, washed with water and brine, dried over MgSO₄ and concentrated in vacuo. The residue was dissolved into AcOH (40.0 ml), and the mixture was stirred at 80° C. for 1 h. After concentration of the mixture, the residue was neutralized with saturated NaHCO₃ solution and extracted with EtOAc. The organic layer was separated, washed with water and brine, dried over MgSO₄ and concentrated in vacuo. The residue was purified by silica gel column chromatography (hexane/EtOAc) to give the title compound (1.2 g) as a pale yellow solid.
MS (ESI+): [M+H]+ 265.1.

D) 1-(2-Cyclopropyl-1-ethyl-1H-benzimidazol-6-yl)-4-((4-fluorobenzyl)oxy)pyridin-2(1H)-one The mixture of 4-((4-fluorobenzyl)oxy)pyridin-2(1H)-one (100 mg), 6-bromo-2-cyclopropyl-1-ethyl-1H-benzimidazole (133 mg), copper iodide (87 mg), N,N'-dimethylethylenediamine (0.051 ml), potassium carbonate (158 mg) and DMSO (2.5 ml) was heated 120° C. for 1 h under microwave irradiation. The mixture was quenched with 28% NH₃ solution at room temperature and extracted with EtOAc and THF. The organic layer was separated, washed with water and brine, dried over MgSO₄ and concentrated in vacuo. The residue was purified by silica gel column chromatography (hexane/EtOAc). The solid was crystallized from IPA-hexane to give the title compound (113 mg) as an off-white solid.
MS (ESI+): [M+H]+ 404.2.
¹H NMR (300 MHz, CDCl₃): δ 1.09-1.18 (2H, m), 1.21-1.31 (2H, m), 1.47 (3H, t, J=7.3 Hz), 1.95-2.06 (1H, m), 4.30 (2H, q, J=7.2 Hz), 5.02 (2H, s), 6.00-6.10 (2H, m), 7.04-7.16 (3H, m), 7.30-7.38 (2H, m), 7.37-7.45 (2H, m), 7.70 (1H, d, J=8.7 Hz).

Example 21

4-((4-Chlorobenzyl)oxy)-1-(2-cyclopropyl-1-ethyl-1H-benzimidazol-6-yl)pyridin-2(1H)-one The mixture of 4-((4-chlorobenzyl)oxy)pyridin-2(1H)-one (100 mg), 6-bromo-2-cyclopropyl-1-ethyl-1H-benzimidazole (124 mg), copper iodide (81 mg), N,N'-dimethylethylenediamine (0.048 ml), potassium carbonate (147 mg) and DMSO (2.5 ml) was heated 120° C. for 1 h under microwave irradiation. The mixture was quenched with 28% NH₃ solution at room temperature and extracted with EtOAc. The organic layer was separated, washed with brine, dried over MgSO₄ and concentrated in vacuo. The residue was purified by NH silica gel column chromatography (hexane/EtOAc). The solid was recrystallized from IPA/hexane to give the title compound (85 mg) as a light pink solid.
MS (ESI+): [M+H]+ 420.1.
¹H NMR (300 MHz, CDCl₃): δ 1.08-1.19 (2H, m), 1.20-1.31 (2H, m), 1.46 (3H, t, J=7.4 Hz), 1.93-2.05 (1H, m), 4.29 (2H, q, J=7.2 Hz), 5.02 (2H, s), 6.01-6.08 (2H, m), 7.10 (1H, dd, J=1.9, 8.7 Hz), 7.28-7.42 (6H, m), 7.70 (1H, d, J=8.3 Hz).

Example 22

1-(2-Cyclopropyl-3-methylimidazo[1,2-a]pyridin-6-yl)-4-((2,4-difluorobenzyl)oxy)pyridin-2(1H)-one A) 1-(2-Cyclopropyl-3-methylimidazo[1,2-a]pyridin-6-yl)-4-hydroxypyridin-2(1H)-one To a stirred solution of 4-(benzyloxy)-1-(2-cyclopropyl-3-methylimidazo[1,2-a]pyridin-6-yl)pyridin-2(1H)-one (127 mg) in MeOH (8 ml) was added Pd/C (10%, 25 mg), and the mixture was stirred under H₂ atmosphere at room temperature for 4 h. The insoluble materials were then filtered through Celite, and the filtrate was concentrated in vacuo. The residue was purified by silica gel column chromatography (MeOH/DCM) to give the title compound (56 mg) as an off-white solid.
MS (ESI+): [M+H]+ 282.2.

B) 1-(2-Cyclopropyl-3-methylimidazo[1,2-a]pyridin-6-yl)-4-((2,4-difluorobenzyl)oxy)pyridin-2(1H)-one To a stirred suspension of NaH (40% oil dispersion, 19 mg) in THF (6 ml) was added a solution of 1-(2-cyclopropyl-3-methylimidazo[1,2-a]pyridin-6-yl)-4-hydroxypyridin-2(1H)-one (75 mg) in THF (1 ml) at 0° C., and then the mixture was stirred at room temperature for 30 min. 2,4-Difluorobenzyl bromide (67 mg) in THF (0.5 ml) was added, and the resulting mixture was stirred at room temperature for further 3 h followed by heating at reflux for 6 h. The reaction mixture was then cooled to room temperature and quenched with ice-water. The mixture was extracted with DCM, and the extract was washed with brine, dried over Na₂SO₄ and concentrated in vacuo. The crude product was purified by silica gel column chromatography (MeOH/DCM) to give the title compound (38 mg) as an off-white solid.
MS (ESI+): [M+H]+ 408.2.
¹H NMR (400 MHz, CDCl₃): δ 0.96-1.04 (4H, m), 1.96 (1H, m), 2.47 (3H, s), 5.05 (2H, s), 6.04-6.06 (2H, m), 6.85-6.95 (2H, m), 7.03 (1H, dd, J=2.0, 9.2 Hz), 7.40-7.46 (2H, m), 7.53 (1H, d, J=9.2 Hz), 7.90 (1H, s).

Example 23

1-(2-Cyclobutyl-1-methyl-1H-benzimidazol-6-yl)-4-((4-fluorobenzyl)oxy)pyridin-2(1H)-one A) 6-Bromo-2-cyclobutyl-1-methyl-1H-benzimidazole The title compound was obtained in an analogous manner to step A in example 8 using 4-bromo-$N^2$-methylbenzene-1,2-diamine and cyclobutanecarboxylic acid.
MS (ESI+): [M+H]+ 264.8.

B) 1-(2-Cyclobutyl-1-methyl-1H-benzimidazol-6-yl)-4-((4-fluorobenzyl)oxy)pyridin-2(1H)-one The title compound was obtained in an analogous manner to step C in example 5 using 4-((4-fluorobenzyl)oxy)pyridin-2(1H)-one and 6-bromo-2-cyclobutyl-1-methyl-1H-benzimidazole.
MS (ESI+): [M+H]+ 404.0.

Example 24

1-(2-(Difluoromethyl)-1-methyl-1H-benzimidazol-6-yl)-4-((4-fluorobenzyl)oxy)pyridin-2(1H)-one A) 6-Bromo-2-(difluoromethyl)-1-methyl-1H-benzimidazole The title compound was obtained in an analogous manner to step A in example 8 using 4-bromo-$N^2$-methylbenzene-1,2-diamine and difluoroacetic acid.
MS (ESI+): [M+H]+ 264.8.

B) 1-(2-(Difluoromethyl)-1-methyl-1H-benzimidazol-6-yl)-4-((4-fluorobenzyl)oxy)pyridin-2(1H)-one The title compound was obtained in an analogous manner to step C in example 5 using 4-((4-fluorobenzyl)oxy)pyridin-2(1H)-one and 6-bromo-2-(difluoromethyl)-1-methyl-1H-benzimidazole.
MS (ESI+): [M+H]+ 399.8.

Example 25

4-((4-Chlorobenzyl)oxy)-1-(2,3-dimethylimidazo[1,2-a]pyridin-6-yl)pyridin-2(1H)-one A) 6-Iodo-2,3-dimethylimidazo[1,2-a]pyridine To a mixture of 3-bromobutan-2-one (1.0 g) and 2-amino-5-iodopyridine (800 mg) was added EtOH (25 ml), and the mixture was heated at 70° C. for 30 h. The reaction mixture was cooled, diluted with water, and extracted with DCM. The DCM layer was washed with brine, dried over Na$_2$SO$_4$ and concentrated in vacuo. The residue was purified by silica gel column chromatography (hexane/EtOAc) to give the title compound (250 mg) as a yellow solid.
MS (ESI+): [M+H]+ 272.6.

B) 4-((4-Chlorobenzyl)oxy)-1-(2,3-dimethylimidazo[1,2-a]pyridin-6-yl)pyridin-2(1H)-one To a stirred degassed mixture of compound 6-iodo-2,3-dimethylimidazo[1,2-a]pyridine (190 mg), 4-((4-chlorobenzyl)oxy)pyridin-2(1H)-one (150 mg), potassium carbonate (263 mg) and dioxane (10 ml) were added copper iodide (24 mg) and trans-N,N'-dimethylcyclohexane-1,2-diamine (18 mg). The reaction vessel was sealed and heated at 110° C. for 16 h. The reaction mixture was then cooled to room temperature and concentrated in vacuo. The residue was diluted with DCM, and the DCM layer was washed with brine, dried over Na$_2$SO$_4$ and concentrated in vacuo. The residue was purified by silica gel column chromatography (MeOH/DCM) to give the title compound (120 mg) as an off-white solid.
MS (ESI+): [M+H]+ 379.8.
$^1$H NMR (400 MHz, DMSO-d$_6$): δ 2.33 (3H, s), 2.39 (3H, s), 5.17 (2H, s), 5.99 (1H, d, J=2.4 Hz), 6.14 (1H, dd, J=2.3, 7.6 Hz), 7.12-7.14 (1H, m), 7.45-7.49 (5H, m), 7.67 (1H, d, J=7.6 Hz), 8.38 (1H, s).

Example 26

1-(2-Cyclopropyl-1-methyl-1H-benzimidazol-6-yl)-4-(pyridin-2-ylmethoxy)pyridin-2(1H)-one The title compound was obtained in an analogous manner to example 75 using pyridine-2-ylmethanol and 1-(2-cyclopropyl-1-methyl-1H-benzo[d]imidazol-6-yl)-4-hydroxypyridin-2(1H)-one.
MS (ESI+): [M+H]+ 373.1.

Example 27

4-((4-Chlorobenzyl)oxy)-1-(2-cyclopropyl-1-propyl-1H-benzimidazol-6-yl)pyridin-2(1H)-one The mixture of 4-((4-chlorobenzyl)oxy)pyridin-2(1H)-one (50 mg, 0.21 mmol), 6-bromo-2-cyclopropyl-1-propyl-1H-benzimidazole (65.2 mg, 0.23 mmol), copper iodide (40.4 mg, 0.21 mmol), N,N'-dimethylethylenediamine (0.024 ml, 0.21 mmol), potassium carbonate (73.3 mg, 0.53 mmol) and DMSO (1.5 ml) was heated at 120° C. for 1 h under microwave irradiation. The mixture was quenched with 28% NH$_3$ solution at room temperature and extracted with EtOAc. The organic layer was separated, washed with brine, dried over MgSO$_4$ and concentrated in vacuo. The residue was purified by NH silica gel column chromatography (hexane/EtOAc). The solid was recrystallized from EtOAc/hexane to give the title compound (10 mg) as an off-white solid.
MS (ESI+): [M+H]+ 434.2.
$^1$H NMR (300 MHz, CDCl$_3$): δ 1.00 (3H, t, J=7.5 Hz), 1.08-1.20 (2H, m), 1.23-1.33 (2H, m), 1.85-1.96 (2H, m), 1.96-2.04 (1H, m), 4.20 (2H, t, J=7.3 Hz), 5.02 (2H, s), 6.00-6.13 (2H, m), 7.01-7.16 (3H, m), 7.28-7.36 (2H, m), 7.37-7.45 (2H, m), 7.70 (1H, d, J=8.3 Hz).

Example 28

1-(2-Cyclopropyl-3,8-dimethylimidazo[1,2-a]pyridin-6-yl)-4-((4-fluorobenzyl)oxy)pyridin-2(1H)-one A) 2-Cyclopropyl-6-iodo-3,8-dimethylimidazo[1,2-a]pyridine A mixture of 5-iodo-3-methylpyridin-2-amine (100 mg), 2-bromo-1-cyclopropylpropan-1-one (113 mg) and DMF (1 ml) was stirred at 80° C. under a dry atmosphere (CaCl$_2$ tube) overnight. The mixture was quenched with saturated NaHCO$_3$ solution and extracted with EtOAc. The organic layer was separated, washed with water and brine, dried over MgSO$_4$ and concentrated in vacuo. The residue was purified by NH silica gel column chromatography (hexane/EtOAc) to give the title compound (69.3 mg) as a pale yellow oil.
MS (ESI+): [M+H]+ 313.0.

B) 1-(2-Cyclopropyl-3,8-dimethylimidazo[1,2-a]pyridin-6-yl)-4-((4-fluorobenzyl)oxy)pyridin-2(1H)-one The title compound was obtained in an analogous manner to step C in example 5 using 4-((4-fluorobenzyl)oxy)pyridin-2(1H)-one and 2-cyclopropyl-6-iodo-3,8-dimethylimidazo[1,2-a]pyridine.
MS (ESI+): [M+H]+ 404.2.

Example 29

4-((4-Chlorobenzyl)oxy)-1-(2-(methoxymethyl)-1-methyl-1H-benzimidazol-6-yl)pyridin-2(1H)-one

A) N-(5-Bromo-2-nitrophenyl)-2-methoxy-N-methylacetamide

To a solution of 5-bromo-N-methyl-2-nitroaniline (500 mg) in THF (10 ml) was added NaH (40% oil dispersion, 104 mg) at 0° C. The mixture was stirred at 0° C. under a dry atmosphere (CaCl$_2$ tube) for 30 min. After being stirred, methoxyacetyl chloride (0.237 ml) was added to the reaction mixture. The mixture was stirred at 60° C. under a dry atmosphere (CaCl$_2$ tube) for 3 h and then at room temperature overnight. The mixture was quenched with water and extracted with EtOAc. The organic layer was separated, washed with water and brine, dried over MgSO$_4$ and concentrated in vacuo. The residue was purified by silica gel column chromatography (hexane/EtOAc). The resulting solid was washed with Et$_2$O to give the title compound (478 mg) as a pale yellow solid.
MS (ESI+): [M+H]+ 305.0.

B) 6-Bromo-2-(methoxymethyl)-1-methyl-1H-benzimidazole

To a solution of N-(5-bromo-2-nitrophenyl)-2-methoxy-N-methylacetamide (477 mg) in AcOH (8 ml) was added zinc (400 mg) at 0° C. The mixture was stirred at 80° C. under a dry atmosphere (CaCl$_2$ tube) for 3 h and then at room temperature overnight. The mixture was neutralized with saturated NaHCO$_3$ solution and extracted with EtOAc. The organic layer was separated, washed with water and brine, dried over MgSO$_4$ and concentrated in vacuo. The residue was purified by NH silica gel column chromatography (hexane/EtOAc) to give the title compound (306 mg) as a pale yellow oil.
MS (ESI+): [M+H]+ 257.0.

C) 4-((4-Chlorobenzyl)oxy)-1-(2-(methoxymethyl)-1-methyl-1H-benzimidazol-6-yl)pyridin-2(1H)-one The title compound was obtained in an analogous manner to step C in example 5 using 4-((4-chlorobenzyl)oxy)pyridin-2(1H)-one and 6-bromo-2-(methoxymethyl)-1-methyl-1H-benzimidazole.
MS (ESI+): [M+H]+ 410.1.

Example 30

4-((4-Chlorobenzyl)oxy)-1-(2-isopropyl-1-methyl-1H-benzimidazol-6-yl)pyridin-2(1H)-one

A) 6-Bromo-2-isopropyl-1-methyl-1H-benzimidazole

To a solution of 5-bromo-N$^1$-methylbenzene-1,2-diamine (122 mg) and isobutyric acid (0.056 ml) in DMF (2 ml) was added HATU (242 mg) at room temperature. The mixture was stirred at room temperature under a dry atmosphere (CaCl$_2$ tube) for 1 h. After being stirred, N,N-diisopropylethylamine (0.311 ml) was added to the reaction mixture. The mixture was stirred at room temperature for 1 h. The mixture was quenched with water and extracted with EtOAc. The organic layer was separated, washed with water and brine, dried over MgSO$_4$ and concentrated in vacuo. The resulting residue was stirred in AcOH (2.00 ml) at 90° C. for 1 h and at room temperature overnight. The mixture was quenched with saturated NaHCO$_3$ solution at room temperature and extracted with EtOAc. The organic layer was separated, washed with water and brine, dried over MgSO$_4$ and concentrated in vacuo. The residue was purified by NH silica gel column chromatography (hexane/EtOAc) to give the title compound (119 mg) as a pale yellow solid.
MS (ESI+): [M+H]+ 255.0.

B) 4-((4-Chlorobenzyl)oxy)-1-(2-isopropyl-1-methyl-1H-benzimidazol-6-yl)pyridin-2(1H)-one The title compound was obtained in an analogous manner to step C in example 5 using 4-((4-chlorobenzyl)oxy)pyridin-2(1H)-one and 6-bromo-2-isopropyl-1-methyl-1H-benzimidazole.
MS (ESI+): [M+H]+ 408.2.

Example 31

1-(2-(Cyclopropylcarbonyl)-1-methyl-1H-benzimidazol-6-yl)-4-((4-fluorobenzyl)oxy)pyridin-2(1H)-one

A) 6-Bromo-N-methoxy-N,1-dimethyl-1H-benzimidazole-2-carboxamide

NaHCO$_3$ (717 mg) was added to a mixture of 6-bromo-1-methyl-2-(trichloromethyl)-1H-benzimidazole (400 mg), N,O-dimethylhydroxylamine hydrochloride (357 mg), NaHCO$_3$ (512 mg), CH$_3$CN (6 ml) and water (2 ml) at room temperature. The mixture was stirred at 60° C. overnight. The mixture was quenched with brine and extracted with EtOAc. The organic layer was separated, washed with brine, dried over MgSO$_4$ and concentrated in vacuo. The residue was purified by silica gel column chromatography (hexane/EtOAc) to give the title compound (134 mg) as an orange gum.
MS (ESI+): [M+H]+ 298.0.

B) (6-Bromo-1-methyl-1H-benzimidazol-2-yl)(cyclopropyl)methanone

Cyclopropylmagnesium bromide (0.70 M in THF, 7.19 ml) was added dropwise to a solution of 6-bromo-N-methoxy-N,1-dimethyl-1H-benzimidazole-2-carboxamide (1.00 g) in THF (3 ml) at 0° C. The mixture was stirred at 0° C. under Ar atmosphere for 30 min. The mixture was quenched with saturated NH$_4$Cl solution and extracted with EtOAc twice. The organic layer was separated, washed with brine, dried over MgSO$_4$ and concentrated in vacuo. The residue was purified by silica gel column chromatography (hexane/EtOAc), and the resulting solid was washed with hexane to give the title compound (0.625 g) as a white solid.
MS (ESI+): [M+H]+ 279.1.

C) 1-(2-(Cyclopropylcarbonyl)-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (236 mg), (6-bromo-1-methyl-1H-benzimidazol-2-yl)(cyclopropyl)methanone (300 mg), N,N'-dimethylethylenediamine (0.115 ml), copper iodide (205 mg) and potassium carbonate (594 mg) in DMSO (3 ml) was stirred at 150° C. for 1 h. The mixture was purified by NH silica gel column chromatography (hexane/EtOAc). The obtained solid was washed with water and IPE to give the title compound (76 mg) as a yellow solid.

MS (ESI+): [M+H]+ 418.1.

$^1$H NMR (300 MHz, CDCl$_3$): δ 1.15-1.38 (4H, m), 3.44-3.57 (1H, m), 4.13 (3H, s), 5.03 (2H, s), 6.03-6.12 (2H, m), 7.11 (2H, t, J=8.7 Hz), 7.28-7.34 (2H, m), 7.41 (2H, dd, J=5.3, 8.7 Hz), 7.51 (1H, d, J=1.9 Hz), 7.98 (1H, d, J=8.7 Hz).

Example 32

4-((5-Chloropyridin-2-yl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (100 mg), (5-chloropyridin-2-yl)methanol (102 mg) and tributylphosphine (266 μl) in THF (15 ml) was added 1,1'-(azodicarbonyl)dipiperidine (269 mg) at 60° C., and the mixture was stirred at the same temperature for 3 h. The mixture was diluted with EtOAc, and washed with water and brine. The organic layer was concentrated, and purified by NH silica gel column chromatography (hexane/EtOAc) to give the title compound (76.8 mg) as a white solid.

MS (ESI+): [M+H]+ 407.1.

$^1$H NMR (400 MHz, DMSO-d$_6$): δ 0.84-0.96 (4H, m), 2.01-2.12 (1H, m), 2.47 (3H, s), 5.24 (2H, s), 5.99 (1H, d, J=2.6 Hz), 6.18 (1H, dd, J=2.7, 7.6 Hz), 7.11 (1H, dd, J=1.8, 9.5 Hz), 7.43 (1H, d, J=9.5 Hz), 7.61 (1H, d, J=8.3 Hz), 7.68 (1H, d, J=7.7 Hz), 8.03 (1H, dd, J=2.4, 8.3 Hz), 8.37 (1H, s), 8.67 (1H, d, J=2.4 Hz).

Example 33

1-(2-(Cyclopropyl(methoxy)methyl)-1-methyl-1H-benzimidazol-6-yl)-4-((4-fluorobenzyl)oxy)pyridin-2(1H)-one A) 1-(2-(Cyclopropyl(hydroxy)methyl)-1-methyl-1H-benzimidazol-6-yl)-4-((4-fluorobenzyl)oxy)pyridin-2(1H)-one Sodium borohydride (10.9 mg) was added to a solution of 1-(2-(cyclopropylcarbonyl)-1-methyl-1H-benzimidazol-6-yl)-4-((4-fluorobenzyl)oxy)pyridin-2(1H)-one (60.0 mg) in THF (2 ml)-MeOH (0.2 ml) at room temperature. The mixture was stirred at room temperature for 30 min. The mixture was quenched with water and extracted with EtOAc/THF twice. The organic layer was separated, washed with brine, dried over MgSO$_4$ and concentrated in vacuo. The solid was washed with Et$_2$O to give the title compound (47.9 mg) as a white solid.

MS (ESI+): [M+H]+ 420.2.

B) 1-(2-(Cyclopropyl(methoxy)methyl)-1-methyl-1H-benzimidazol-6-yl)-4-((4-fluorobenzyl)oxy)pyridin-2(1H)-one NaH (40% oil dispersion, 5.2 mg) was added to a solution of 1-(2-(cyclopropyl(hydroxy)methyl)-1-methyl-1H-benzimidazol-6-yl)-4-((4-fluorobenzyl)oxy)pyridin-2(1H)-one (30 mg) and iodomethane (0.013 ml) in THF (2 ml)-DMF (1 ml) at room temperature. The mixture was stirred at room temperature for 30 min. The mixture was quenched with water and extracted with EtOAc twice. The organic layer was separated, washed with brine, dried over MgSO$_4$ and concentrated in vacuo. The resulting solid was washed with Et$_2$O to give the title compound (23.6 mg) as a white solid.

MS (ESI+): [M+H]+ 434.2.

Example 34

1-(6-(4-((4-Fluorobenzyl)oxy)-2-oxopyridin-1(2H)-yl)-1-methyl-1H-benzimidazol-2-yl)cyclopropanecarbonitrile To a solution of 1-(4-amino-3-(methylamino)phenyl)-4-((4-fluorobenzyl)oxy)pyridin-2(1H)-one (73 mg), 1-cyanocyclopropanecarboxylic acid (25.1 mg) and N,N-diisopropylethylamine (0.11 ml) in DMF (2 ml) was added HATU (86 mg), and the mixture was stirred at room temperature overnight. The mixture was poured into a mixture of EtOAc and water, and the organic layer was washed with brine, dried over MgSO$_4$, and concentrated. Then the resulting residue was heated in AcOH (1 ml) at 90° C. for 1 h. The mixture was concentrated, and poured into saturated NaHCO$_3$. The mixture was extracted with EtOAc, and the organic layer was washed with brine, dried over MgSO$_4$, concentrated, and purified by NH silica gel column chromatography (hexane/EtOAc) to give the title compound (8 mg) as a white solid.

MS (ESI+): [M+H]+ 415.1.

Example 35

4-((4-Fluorobenzyl)oxy)-1-(1-methyl-2-(tetrahydrofuran-2-yl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and tetrahydrofuran-2-carboxylic acid.

MS (ESI+): [M+H]+ 420.2.

Example 36

1-(2-Cyclopropyl-1-methyl-1H-benzimidazol-6-yl)-4-(1-phenylethoxy)pyridin-2(1H)-one The title compound was obtained in an analogous manner to example 75 using 1-phenylethanol and 1-(2-cyclopropyl-1-methyl-1H-benzimidazol-6-yl)-4-hydroxypyridin-2(1H)-one.

MS (ESI+): [M+H]+ 386.2.

Example 37

4-((4-Chlorobenzyl)oxy)-1-(2-isobutyl-1-methyl-1H-benzimidazol-6-yl)pyridin-2(1H)-one A) 6-Bromo-2-isobutyl-1-methyl-1H-benzimidazole To a solution of 5-bromo-N$^1$-methylbenzene-1,2-diamine (159 mg), isovaleric acid (0.087 ml) and N,N-diisopropylethylamine (0.41 ml) in DMF (2 ml) was added HATU (316 mg) at room temperature. The mixture was stirred at room temperature under a dry atmosphere (CaCl$_2$ tube) for 3 h. After evaporation of the mixture, the residue was purified by NH silica gel column chromatography (hexane/EtOAc). The resulting residue was stirred in AcOH (2.0 ml) at 80° C. for 1 h. After evaporation, the residue was purified by NH silica gel column chromatography (hexane/EtOAc) to give the title compound (156 mg) as a pale yellow solid.

MS (ESI+): [M+H]+ 268.0.

B) 4-((4-Chlorobenzyl)oxy)-1-(2-isobutyl-1-methyl-1H-benzimidazol-6-yl)pyridin-2(1H)-one A mixture of 4-((4-chlorobenzyl)oxy)pyridin-2(1H)-one (115 mg), 6-bromo-2-isobutyl-1-methyl-1H-benzimidazole (130 mg), potassium carbonate (202 mg), copper iodide (93 mg), N,N'-dimethylethylenediamine (0.052 ml) and DMSO (3 ml) was heated at 120° C. for 3 h under microwave irradiation. The mixture was poured into water and extracted with EtOAc. The organic layer was separated, washed with water and brine, dried over MgSO$_4$ and concentrated in vacuo. The precipitate was collected by filtration, and washed with IPE and EtOAc to give the title compound (23 mg) as an off-white solid.

MS (ESI+): [M+H]+ 422.2.
$^1$H NMR (300 MHz, DMSO-d$_6$): δ 0.98 (6H, d, J=6.8 Hz), 2.21 (1H, dt, J=6.8, 13.6 Hz), 2.77 (2H, d, J=7.2 Hz), 3.75 (3H, s), 5.16 (2H, s), 5.98 (1H, d, J=2.6 Hz), 6.06-6.14 (1H, m), 7.07 (1H, dd, J=1.9, 8.7 Hz), 7.50 (4H, s), 7.53 (1H, d, J=1.9 Hz), 7.60 (2H, dd, J=1.7, 8.1 Hz).

Example 38

1-(2-(2,2-Difluorocyclopropyl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 2,2-difluorocyclopropanecarboxylic acid.
MS (ESI+): [M+H]+ 426.1.

Example 39

1-(2-Cyclopentyl-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and cyclopentanecarboxylic acid.
MS (ESI+): [M+H]+ 418.1.

Example 40

1-(2-Cyclopropyl-1-methyl-1H-benzimidazol-6-yl)-4-(2,3-dihydro-1H-inden-1-yloxy)pyridin-2(1H)-one The title compound was obtained in an analogous manner to example 75 using 2,3-dihydro-1H-inden-1-ol and 1-(2-cyclopropyl-1-methyl-1H-benzo[d]imidazol-6-yl)-4-hydroxypyridin-2(1H)-one.
MS (ESI+): [M+H]+ 398.2.

Example 41

4-((4-Fluorobenzyl)oxy)-1-(2-(methoxymethyl)-3-methylimidazo[1,2-a]pyridin-6-yl)pyridin-2(1H)-one A) (6-Iodo-3-methylimidazo[1,2-a]pyridin-2-yl)methanol To a stirred solution of ethyl 6-iodo-3-methylimidazo[1,2-a]pyridine-2-carboxylate (2.0 g) in DCM (20 ml) was added diisobutylaluminum hydride (1.76 M solution in toluene, 7.72 ml) at −19° C. The resultant mixture was stirred at the same temperature for 3 h and then at room temperature for 4 h. The reaction mixture was then quenched with MeOH and water at −40° C. The reaction mixture was acidified with few drops of 5 M HCl and poured into saturated NaHCO$_3$. The mixture was extracted with EtOAc, and the extract was washed with brine, dried over Na$_2$SO$_4$ and concentrated in vacuo. The crude residue was purified by silica gel column chromatography (MeOH/DCM) to give the title compound (1.1 g) as a yellow solid.
MS (ESI+): [M+H]+ 288.9.

B) 2-(Chloromethyl)-6-iodo-3-methylimidazo[1,2-a]pyridine

To a stirred solution of (6-iodo-3-methylimidazo[1,2-a]pyridin-2-yl)methanol (200 mg) in DCM (2 ml) was added thionyl chloride (56 µl) at room temperature, and the mixture was stirred for 4 h. Additional thionyl chloride (125 µl) was added to the reaction mixture, and the mixture was stirred for further 3 h. The reaction mixture was diluted with DCM, and washed with saturated NaHCO$_3$ solution. The DCM layer was separated, dried over Na$_2$SO$_4$ and concentrated in vacuo to give the title compound (150 mg) as a yellow solid.
MS (ESI+): [M+H]+ 306.6.

C) 6-Iodo-2-(methoxymethyl)-3-methylimidazo[1,2-a]pyridine

To a stirred solution of 2-(chloromethyl)-6-iodo-3-methylimidazo[1,2-a]pyridine (150 mg) in MeOH (2.5 ml) was added sodium methoxide (65 mg), and the resulting mixture was heated at reflux for 3 h. The reaction mixture was then cooled to room temperature and concentrated in vacuo. The mixture was diluted with water, and extracted with EtOAc. The extract was washed with brine, dried over Na$_2$SO$_4$ and concentrated in vacuo. The crude product was purified by silica gel column chromatography (MeOH/DCM) to give the title compound (100 mg) as an off-white solid.
MS (ESI+): [M+H]+ 303.0.

D) 4-((4-Fluorobenzyl)oxy)-1-(2-(methoxymethyl)-3-methylimidazo[1,2-a]pyridin-6-yl)pyridin-2(1H)-one The title compound was obtained in an analogous manner to step C in example 5 using 4-((4-fluorobenzyl)oxy)pyridin-2(1H)-one and 6-iodo-2-(methoxymethyl)-3-methylimidazo[1,2-a]pyridine.
MS (ESI+): [M+H]+ 394.0.

Example 42

4-((4-Fluorobenzyl)oxy)-1-(3-methyl-2-(tetrahydrofuran-3-yl)imidazo[1,2-a]pyridin-6-yl)pyridin-2(1H)-one A) 1-(Tetrahydrofuran-3-yl)propan-1-one To a stirred solution of N-methoxy-N-methyltetrahydrofuran-3-carboxamide (4.1 g) in THF (40 ml) was added ethylmagnesium bromide (3 M in ether, 13.0 ml) at 0° C. The reaction mixture was then slowly warmed to room temperature and stirred for 4 h. The reaction mixture was quenched with saturated 1 M HCl (10 ml), and extracted with EtOAc. The extract was washed with brine, dried over Na$_2$SO$_4$ and concentrated in vacuo. The mixture was purified by silica gel column chromatography (hexane/EtOAc) to give the title compound (3.0 g) as a pale yellow liquid.

$^1$H NMR (400 MHz, CDCl$_3$): δ 1.06 (3H, t, J=7.3 Hz), 2.01-2.12 (2H, m), 2.42-2.54 (2H, m), 3.16-3.24 (1H, m), 3.69-3.95 (4H, m).

B) 6-Iodo-3-methyl-2-(tetrahydrofuran-3-yl)imidazo[1,2-a]pyridine

To a stirred solution of 1-(tetrahydrofuran-3-yl)propan-1-one (2.8 g) in MeOH (25 ml) was added a solution of bromine (1.12 ml) in MeOH (25 ml) over a period of 2 h, and the mixture was stirred at room temperature for further 4 h. The reaction mixture was then quenched with 0.1 M sodium thiosulfate under ice-cooled condition under stirring. The mixture was extracted with ether, and the extract was washed successively with water and brine, dried over Na$_2$SO$_4$, and concentrated in vacuo to give the intermediate bromide (1.8 g) as a black oil. A mixture of the intermediate bromide (4.0 g), 2-amino-5-iodopyridine (2.1 g) and EtOH (20 ml) was heated at reflux for 16 h. The reaction mixture was then cooled to room temperature and concentrated in vacuo. The resulting residue was diluted with EtOAc, washed with water followed by brine. The EtOAc layer was dried over Na$_2$SO$_4$ and concentrated in vacuo. The crude product thus obtained was purified by silica gel column chromatography (MeOH/DCM) to give the title compound (350 mg) as a yellow solid.

MS (ESI+): [M+H]+ 329.0.

C) 4-((4-Fluorobenzyl)oxy)-1-(3-methyl-2-(tetrahydrofuran-3-yl)imidazo[1,2-a]pyridin-6-yl)pyridin-2(1H)-one The title compound was obtained in an analogous manner to step C in example 5 using 4-((4-fluorobenzyl)oxy)pyridin-2(1H)-one and 6-iodo-3-methyl-2-(tetrahydrofuran-3-yl)imidazo[1,2-a]pyridine.

MS (ESI+): [M+H]+ 420.0.

Example 43

4-((4-Fluorobenzyl)oxy)-1-(1-methyl-2-(2-methylcyclopropyl)-1H-benzimidazol-6-yl)pyridin-2(1H)-one HATU (235 mg) was added to a solution of 1-(4-amino-3-(methylamino)phenyl)-4-((4-fluorobenzyl)oxy)pyridin-2(1H)-one (200 mg), N,N-diisopropylethylamine (0.308 ml) and 2-methylcyclopropanecarboxylic acid (0.057 ml) in DMF (3 ml) at room temperature. The mixture was stirred at room temperature for 1 h. The mixture was quenched with brine and extracted with EtOAc twice. The organic layer was separated, washed with brine, dried over MgSO$_4$, and concentrated in vacuo. The resulting residue in AcOH (1 ml) was stirred at 80° C. for 1 h. After evaporation of the solvent, the residue was passed through NH silica pad and concentrated in vacuo. The resulting solid was recrystallized from THF to give the title compound as a white solid.

MS (ESI+): [M+H]+ 404.2.

$^1$H NMR (300 MHz, CDCl$_3$): δ 0.87-0.99 (1H, m), 1.28 (3H, d, J=6.0 Hz), 1.41 (1H, dt, J=4.5, 8.8 Hz), 1.53-1.64 (1H, m), 1.64-1.74 (1H, m), 3.81 (3H, s), 5.02 (2H, s), 5.97-6.15 (2H, m), 7.00-7.17 (3H, m), 7.28-7.34 (2H, m), 7.41 (2H, dd, J=5.3, 8.7 Hz), 7.69 (1H, d, J=8.7 Hz).

Example 44

4-((4-Fluorobenzyl)oxy)-1-(1-methyl-2-(trichloromethyl)-1H-benzimidazol-6-yl)pyridin-2(1H)-one To a mixture of 1-(4-amino-3-(methylamino)phenyl)-4-((4-fluorobenzyl)oxy)pyridin-2(1H)-one (270 mg) in AcOH (3 ml) was added methyl 2,2,2-trichloroacetimidate (0.196 ml) dropwise at 0° C. The mixture was stirred at room temperature for 2 h. Water was added to the mixture. The resulting precipitate was collected by filtration and dried to give the title compound (220 mg) as an ivory solid.

MS (ESI+): [M+H]+ 466.0.

Example 45

4-((4-Chlorobenzyl)oxy)-1-(1-methyl-2-(trifluoromethyl)-1H-benzimidazol-6-yl)pyridin-2(1H)-one A) 6-Bromo-1-methyl-2-(trifluoromethyl)-1H-benzimidazole The mixture of 5-bromo-N$^1$-methylbenzene-1,2-diamine (300 mg) and TFA (10 ml) was stirred at 90° C. overnight. The mixture was quenched with saturated NaHCO$_3$ solution and extracted with EtOAc. The organic layer was separated, washed with water and brine, dried over MgSO$_4$, passed through NH silica gel pad and concentrated in vacuo. The precipitate was collected by filtration, washed with IPE/hexane and dried in vacuo to give the title compound (265 mg) as a purple solid.

MS (ESI+): [M+H]+ 280.9.

B) 4-((4-Chlorobenzyl)oxy)-1-(1-methyl-2-(trifluoromethyl)-1H-benzimidazol-6-yl)pyridin-2(1H)-one The title compound was obtained in an analogous manner to step C in example 5 using 4-((4-chlorobenzyl)oxy)pyridin-2(1H)-one and 6-bromo-1-methyl-2-(trifluoromethyl)-1H-benzimidazole.

MS (ESI+): [M+H]+ 434.1.

Example 46

4-((4-Chlorobenzyl)oxy)-1-(2-(2-methoxyethyl)-1-methyl-1H-benzimidazol-6-yl)pyridin-2(1H)-one A) N-(5-Bromo-2-nitrophenyl)-3-methoxy-N-methylpropanamide The title compound was obtained in an analogous manner to step A in example 29 using 5-bromo-N-methyl-2-nitroaniline and 3-methoxypropanoyl chloride.

MS (ESI+): [M+H]+ 319.0.

B) 6-Bromo-2-(2-methoxyethyl)-1-methyl-1H-benzimidazole

The title compound was obtained in an analogous manner to step B in example 29 using N-(5-bromo-2-nitrophenyl)-3-methoxy-N-methylpropanamide.

MS (ESI+): [M+H]+ 270.0.

C) 4-((4-Chlorobenzyl)oxy)-1-(2-(2-methoxyethyl)-1-methyl-1H-benzimidazol-6-yl)pyridin-2(1H)-one The title compound was obtained in an analogous manner to step C in example 5 using 4-((4-chlorobenzyl)oxy)pyridin-2(1H)-one and 6-bromo-2-(2-methoxyethyl)-1-methyl-1H-benzimidazole.

MS (ESI+): [M+H]+ 424.1.

Example 47

4-(Benzyloxy)-1-(2-ethyl-1-methyl-1H-benzimidazol-6-yl)pyridin-2(1H)-one

A) 6-Bromo-2-ethyl-1-methyl-1H-benzimidazole

A mixture of 5-bromo-N-methyl-2-nitroaniline (10 g), zinc (14.15 g), NH$_4$Cl (23.15 g), MeOH (70 ml), 1 M HCl (10 ml) and water (35 ml) was stirred at 50° C. overnight. The mixture was neutralized with saturated NaHCO$_3$ solution and passed through celite pad to remove the precipitate. After evaporation of the solvent, the mixture was extracted with EtOAc three times. The organic layer was separated, washed with water and brine, dried over MgSO$_4$, passed through NH silica pad, and concentrated in vacuo to give an intermediate diamine (8.36 g) as a dark brown oil.

The intermediate diamine was dissolved in DMF (0.160 ml), and N,N-diisopropylethylamine (15.12 ml), propanoic acid (3.53 ml) and HATU (18.1 g) were added. The mixture was stirred at room temperature for 2 h. The mixture was quenched with brine and extracted with EtOAc five times. The organic layer was separated, dried over MgSO$_4$ and concentrated in vacuo. The resulting residue was dissolved in AcOH (70.0 ml), and stirred at 80° C. for 1 h. After evaporation of the solvent, the residue was passed through NH silica pad and purified by NH silica gel column chromatography (hexane/EtOAc). The resulting solid was washed with IPE/hexane to give the title compound (5.92 g) as a red solid.

MS (ESI+): [M+H]+ 239.0.

B) 4-(Benzyloxy)-1-(2-ethyl-1-methyl-1H-benzimidazol-6-yl)pyridin-2(1H)-one A mixture of 4-benzyloxy-2(1H)-pyridone (1 g), 6-bromo-2-ethyl-1-methyl-1H-benzimidazole (1.19 g), N,N'-dimethylethylenediamine (0.530 ml), copper(I) iodide (0.946 g), potassium carbonate (2.06 g) and DMSO (20 ml) was stirred at 150° C. for 2 h. The mixture was added to 28% NH$_3$ solution, and the precipitate was collected. The solid was dissolved in THF, passed through NH silica pad and concentrated in vacuo to give the title compound (986 mg) as a pink solid. A part of the target compound was treated with activated carbon and recrystallized from THF to give 46.1 mg of the title compound as a white solid.

MS (ESI+): [M+H]+ 360.4.

$^1$H NMR (400 MHz, DMSO-d$_6$): δ 1.33 (3H, t, J=7.4 Hz), 2.90 (2H, q, J=7.5 Hz), 3.74 (3H, s), 5.16 (2H, s), 5.98 (1H, s), 6.10 (1H, d, J=5.4 Hz), 7.07 (1H, d, J=8.8 Hz), 7.34-7.51 (5H, m), 7.53 (1H, s), 7.55-7.62 (2H, m).

Example 48

4-((4-Fluorobenzyl)oxy)-1-(1-methyl-2-(2,2,2-trifluoroethyl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 3,3,3-trifluoropropanoic acid.

MS (ESI+): [M+H]+ 432.2.

Example 49

4-[(5-Chlorothiophen-2-yl)methoxy]-1-(2-ethyl-1-methyl-1H-benzimidazol-6-yl)pyridin-2(1H)-one

A) 1-(2-Ethyl-1-methyl-1H-benzimidazol-6-yl)-4-hydroxypyridin-2(1H)-one

A mixture of 4-(benzyloxy)-1-(2-ethyl-1-methyl-1H-benzimidazol-6-yl)pyridin-2(1H)-one (3.5 mg), Pd/C (10%, 700 mg) and MeOH (10 ml) was stirred under H$_2$ atmosphere at room temperature for 2 h. The insoluble material was removed by filtration, and the filtrate was concentrated to give the title compound (1.6 g) as a white solid.

MS (ESI+): [M+H]+ 270.2.

B) 4-[(5-Chlorothiophen-2-yl)methoxy]-1-(2-ethyl-1-methyl-1H-benzimidazol-6-yl)pyridin-2(1H)-one To a mixture of 1-(2-ethyl-1-methyl-1H-benzimidazol-6-yl)-4-hydroxypyridin-2(1H)-one (500 mg), (5-chloro-2-thienyl)methanol (552 mg) and tributylphosphine (1.38 ml) in THF (10 ml) was added 1,1'-(azodicarbonyl)dipiperidine (1.41 g), and the mixture was stirred at 60° C. for 2 h. The reaction mixture was partitioned between EtOAc and water, and the organic layer was washed with brine, dried over MgSO$_4$, and concentrated in vacuo. The residue was purified by NH silica gel column chromatography (hexane/EtOAc to MeOH/EtOAc). The resulting solid was recrystallized from EtOH to give the title compound (143 mg) as a white solid.

MS (ESI+): [M+H]+ 400.3.

$^1$H NMR (400 MHz, DMSO-d$_6$): δ 1.33 (3H, t, J=7.4 Hz), 2.90 (2H, q, J=7.5 Hz), 3.74 (3H, s), 5.30 (2H, s), 6.02-6.11 (2H, m), 7.03-7.12 (2H, m), 7.17 (1H, d, J=3.6 Hz), 7.54 (1H, s), 7.59 (2H, d, J=8.5 Hz).

Example 50

6-(4-((4-Fluorobenzyl)oxy)-2-oxopyridin-1(2H)-yl)-N-(2-hydroxyethyl)-1-methyl-1H-benzimidazole-2-carboxamide The title compound was obtained in an analogous manner to step A in example 31 using 2-aminoethanol and 4-((4-fluorobenzyl)oxy)-1-(1-methyl-2-(trichloromethyl)-1H-benzimidazol-6-yl)pyridin-2(1H)-one.

MS (ESI+): [M+H]+ 437.2.

Example 51

4-[(5-Chlorothiophen-3-yl)methoxy]-1-(2-ethyl-1-methyl-1H-benzimidazol-6-yl)pyridin-2(1H)-one To a mixture of 1-(2-ethyl-1-methyl-1H-benzimidazol-6-yl)-4-hydroxypyridin-2(1H)-one (126 mg), (5-chloro-3-thienyl)methanol (139 mg) and tributylphosphine (0.347 ml) in THF (8 ml) was added 1,1'-(azodicarbonyl)dipiperidine (354 mg), and the mixture was stirred at 60° C. for 2 h. The reaction mixture was partitioned between EtOAc and water, and the organic layer was washed with brine, dried MgSO$_4$, and concentrated in vacuo. The residue was purified by NH silica gel column chromatography (hexane/EtOAc to MeOH/EtOAc). The resulting solid was recrystallized from EtOH/hexane to give the title compound (90 mg) as a white solid.

MS (ESI+): [M+H]+ 400.3.

$^1$H NMR (400 MHz, DMSO-d$_6$): δ 1.33 (3H, t, J=7.5 Hz), 2.90 (2H, q, J=7.5 Hz), 3.74 (3H, s), 5.06 (2H, s), 5.99 (1H, d,

J=2.5 Hz), 6.07 (1H, dd, J=2.6, 7.5 Hz), 7.06 (1H, dd, J=1.8, 8.4 Hz), 7.21 (1H, s), 7.53 (1H, d, J=1.8 Hz), 7.55-7.63 (3H, m).

Example 52

4-((4-Fluorobenzyl)oxy)-1-(2-(2-fluoropropyl)-1-methyl-1H benzimidazol-6-yl)pyridin-2(1H)-one A) 4-((4-Fluorobenzyl)oxy)-1-(2-(2-hydroxypropyl)-1-methyl-1H-benzimidazol-6-yl)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 3-hydroxybutyric acid.
MS (ESI+): [M+H]+ 408.2.

B) 4-((4-Fluorobenzyl)oxy)-1-(2-(2-fluoropropyl)-1-methyl-1H-benzimidazol-6-yl)pyridin-2(1H)-one BAST (0.14 ml) was added dropwise to a mixture of 4-((4-fluorobenzyl)oxy)-1-(2-(2-hydroxypropyl)-1-methyl-1H-benzimidazol-6-yl)pyridin-2(1H)-one (78.6 mg) in toluene (1 ml) at room temperature. The mixture was stirred at 80° C. under Ar atmosphere for 5 min. The mixture was quenched with saturated NaHCO$_3$ solution at room temperature and extracted with EtOAc twice. The organic layer was separated, washed with brine, dried over MgSO$_4$ and concentrated in vacuo. The residue was purified by NH silica gel column chromatography (hexane/EtOAc to MeOH/EtOAc). The solid was recrystallized from IPA/hexane to give the title compound (24.6 mg) as a pink solid.
MS (ESI+): [M+H]+ 410.2.

Example 53

4-((4-Fluorobenzyl)oxy)-1-(1-methyl-2-(4-methyl-1,3-thiazol-5-yl)-1H-benzimidazol-6-yl)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 4-methyl-1,3-thiazole-5-carboxylic acid.
MS (ESI+): [M+H]+ 447.3.

Example 54

6-(4-((4-Fluorobenzyl)oxy)-2-oxopyridin-1(2H)-yl)-3-methylimidazo[1,2-a]pyridine-2-carbonitrile A) 6-Iodo-3-methylimidazo[1,2-a]pyridine-2-carboxylic acid To a stirred solution of ethyl 6-iodo-3-methylimidazo[1,2-a]pyridine-2-carboxylate (1.5 g) in a mixture of THF (10 ml) and water (10 ml) was added aqueous lithium hydroxide (381 mg), and the resulting mixture was stirred for 16 h at room temperature. The mixture was concentrated in vacuo, and partitioned between EtOAc and water. The organic layer was neutralized with 2 M HCl. The mixture was extracted with EtOAc, dried over Na$_2$SO$_4$, and concentrated in vacuo to give the title compound (1 g) as a yellow solid.
MS (ESI+): [M+H]+ 302.9.

B) 6-Iodo-3-methylimidazo[1,2-a]pyridine-2-carboxamide

To a stirred solution of 6-iodo-3-methylimidazo[1,2-a]pyridine-2-carboxylic acid (1.0 g) in DMF (15 ml) were added HATU (1.88 g) and triethylamine (1.38 ml) at 0° C. The mixture was allowed to warm to room temperature for 30 min, and then NH$_4$Cl (725 mg) was added thereto. The resultant mixture was stirred at the same temperature for 18 h. The mixture was then concentrated in vacuo and diluted with DCM (100 ml). The DCM layer was successively washed with saturated aqueous NH$_4$Cl solution, saturated aqueous NaHCO$_3$ solution, water and brine. The DCM layer was then dried over Na$_2$SO$_4$ and concentrated in vacuo to give the title compound (600 mg) as a yellow solid.
MS (ESI+): [M+H]+ 301.9.

C) 6-Iodo-3-methylimidazo[1,2-a]pyridine-2-carbonitrile

A mixture of 6-iodo-3-methylimidazo[1,2-a]pyridine-2-carboxamide (600 mg) and POCl$_3$ (40 ml) was heated at reflux for 3 h. The mixture was then cooled to room temperature, and the reaction mixture was concentrated in vacuo. The residue was poured into ice-cold saturated NaHCO$_3$ solution, and extracted with EtOAc. The extract was washed with water and brine, dried over Na$_2$SO$_4$ and concentrated in vacuo to give the title compound (500 mg) as a yellow solid.
MS (ESI+): [M+H]+ 283.9.

D) 6-(4-((4-Fluorobenzyl)oxy)-2-oxopyridin-1(2H)-yl)-3-methylimidazo[1,2-a]pyridine-2-carbonitrile The title compound was obtained in an analogous manner to step C in example 5 using 4-((4-fluorobenzyl)oxy)pyridin-2(1H)-one and 6-iodo-3-methylimidazo[1,2-a]pyridine-2-carbonitrile.
MS (ESI+): [M+H]+ 375.0.

Example 55

5-((4-Chlorobenzyl)oxy)-2-(2-cyclopropyl-3-methylimidazo[1,2-a]pyridin-6-yl)pyridazin-3(2H)-one A) 5-((4-Chlorobenzyl)oxy)-2-(tetrahydro-2H-pyran-2-yl)pyridazin-3(2H)-one To a mixture of 5-hydroxy-2-(tetrahydro-2H-pyran-2-yl) pyridazin-3(2H)-one (200 mg), 1-bromomethyl-4-chlorobenzene (209 mg), CH$_3$CN (8 ml) and DMF (1 ml) was added potassium carbonate (282 mg), and the resulting mixture was stirred at room temperature for 16 h. The reaction mixture was then concentrated in vacuo and diluted with water. The mixture was extracted with EtOAc, and extract was washed successively with water and brine, dried over Na$_2$SO$_4$ and concentrated in vacuo. The residue was triturated with n-hexane to give the title compound (210 mg) as a white solid.
MS (ESI+): [M+H]+ 321.2.

B) 5-((4-Chlorobenzyl)oxy)pyridazin-3(2H)-one

To a stirred suspension of 5-((4-chlorobenzyl)oxy)-2-(tetrahydro-2H-pyran-2-yl)pyridazin-3(2H)-one (210 mg) in MeOH (5 ml) was added conc. HCl (0.5 ml) at room temperature, and then the reaction mixture was heated at reflux for 3 h. The mixture was cooled to room temperature, concentrated in vacuo and neutralized with saturated NaHCO$_3$ (20 ml). The resulting precipitate was collected by filtration, washed with water and dried in vacuo to give the title compound (140 mg) as an off-white solid.

MS (ESI+): [M+H]+ 237.2.

C) 5-((4-Chlorobenzyl)oxy)-2-(2-cyclopropyl-3-methylimidazo[1,2-a]pyridin-6-yl)pyridazin-3(2H)-one To a stirred degassed mixture of 5-((4-chlorobenzyl)oxy) pyridazin-3(2H)-one (50 mg), 2-cyclopropyl-6-iodo-3-methylimidazo[1,2-a]pyridine (76 mg), potassium carbonate (88 mg) in dioxane (6 ml) were added copper iodide (8 mg) and trans-N,N'-dimethylcyclohexane-1,2-diamine (6 mg). The reaction vessel was sealed and heated at 110° C. for 16 h. The reaction mixture was then cooled to room temperature, and concentrated in vacuo. The crude residue was diluted with DCM (100 ml), washed with brine (30 ml), dried over Na$_2$SO$_4$ and concentrated in vacuo. The residue was purified by silica gel column chromatography (MeOH/DCM) to give the title compound (60 mg) as a white solid.

MS (ESI+): [M+H]+ 407.2.
$^1$H NMR (400 MHz, DMSO-d$_6$): δ 0.88-0.92 (4H, m), 2.06-2.09 (1H, m), 2.47 (3H, s), 5.23 (2H, s), 6.54 (1H, d, J=2.6 Hz), 7.23 (1H, dd, J=1.7, 9.3 Hz), 7.46 (1H, d, J=9.4 Hz), 7.50-7.55 (4H, m), 8.01 (1H, d, J=2.7 Hz), 8.46 (1H, s).

Example 56

1-(2-Cyclopropyl-1-methyl-1H-benzimidazol-6-yl)-4-((4-methyl-2-thienyl)methoxy)pyridin-2(1H)-one To a solution of 1-(2-cyclopropyl-1-methyl-1H-benzimidazol-6-yl)-4-hydroxypyridin-2(1H)-one (150 mg), (4-methyl-2-thienyl)methanol (138 mg) and tributylphosphine (322 mg) in THF (10 ml) was added 1,1'-(azodicarbonyl) dipiperidine (401 mg) in dry THF (5 ml). The mixture was stirred under sonication at 60° C. for 2 h. The reaction mixture was then cooled to room temperature and concentrated in vacuo. The residue was diluted with DCM, and the DCM layer was washed with water and brine, dried over Na$_2$SO$_4$ and concentrated in vacuo. The residue was purified by silica gel column chromatography (MeOH/DCM) to give the title compound (43 mg) as a white solid.

MS (ESI+): [M+H]+ 392.0.
$^1$H NMR (400 MHz, DMSO-d$_6$): δ 1.03-1.09 (4H, m), 2.21 (3H, s), 2.26-2.28 (1H, m), 3.85 (3H, s), 5.27 (2H, s), 6.02-6.06 (2H, m), 7.04 (1H, dd, J=1.8, 8.5 Hz), 7.08 (1H, s), 7.17 (1H, s), 7.50-7.52 (2H, m), 7.56 (1H, d, J=7.4 Hz).

Example 57

1-(2-Cyclopropyl-1-methyl-1H-benzimidazol-6-yl)-4-((5-methyl-2-thienyl)methoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (5-methyl-2-thienyl)methanol.

MS (ESI+): [M+H]+ 392.0.

Example 58

4-((4-Fluorobenzyl)oxy)-1-(1-methyl-2-(1-(trifluoromethyl)cyclopropyl)-1H-benzimidazol-6-yl)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 1-(trifluoromethyl)cyclopropanecarboxylic acid.

MS (ESI+): [M+H]+ 458.2.

Example 59

4-((4-Fluorobenzyl)oxy)-1-(1-methyl-2-(3,3,3-trifluoropropyl)-1H-benzimidazol-6-yl)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 4,4,4-trifluorobutanoic acid.

MS (ESI+): [M+H]+ 446.2.

Example 60

1-(2-(3,3-Difluorocyclobutyl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 3,3-difluorocyclobutanecarboxylic acid.

MS (ESI+): [M+H]+ 440.2.

Example 61

1-(2-sec-Butyl-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino) phenyl)-4-((4-fluorobenzyl)oxy)pyridin-2(1H)-one and 2-methylbutyric acid.

MS (ESI+): [M+H]+ 406.2.

Example 62

4-((4-Chlorobenzyl)oxy)-1-(2-(2,2-difluorocyclopropyl)-1-methyl-1H-benzimidazol-6-yl)pyridin-2(1H)-one A) 6-Bromo-2-(2,2-difluorocyclopropyl)-1-methyl-1H-benzimidazole A mixture of 5-bromo-N'-methylbenzene-1,2-diamine (300 mg), HATU (567 mg), N,N-diisopropylethylamine (0.255 ml), 2,2-difluorocyclopropanecarboxylic acid (182 mg) and DMF (10 ml) was stirred at room temperature for 1 h. The mixture was quenched with water and extracted with EtOAc. The organic layer was separated, washed with water and brine, dried over MgSO$_4$, passed through NH silica gel pad and concentrated in vacuo. The precipitate was washed with IPE/hexane, collected by filtration and dried in vacuo to give the title compound (255 mg) as a yellow solid.

MS (ESI+): [M+H]+ 288.9.

B) 4-((4-Chlorobenzyl)oxy)-1-(2-(2,2-difluorocyclopropyl)-1-methyl-1H-benzimidazol-6-yl)pyridin-2 (1H)-one A mixture of 4-((4-chlorobenzyl)oxy)pyridin-2(1H)-one (100 mg), 6-bromo-2-(2,2-difluorocyclopropyl)-1-methyl-1H-benzimidazole (122 mg), potassium carbonate (176 mg), N,N'-dimethylethylenediamine (0.046 ml), copper iodide (81 mg) and DMSO (3 ml) was stirred at 150° C. under Ar atmosphere for 1 h. The mixture was quenched with 28% $NH_3$ solution and the precipitate was collected by filtration. The solid was dissolved in THF, passed through NH silica gel pad and concentrated in vacuo. The precipitate was recrystallized from EtOAc/MeOH to give the title compound (2 mg) as a pale orange solid.

MS (ESI+): [M+H]+ 442.1.

$^1$H NMR (300 MHz, $CDCl_3$): δ 1.99-2.15 (1H, m), 2.43-2.57 (1H, m), 2.87 (1H, td, J=7.6, 11.0 Hz), 3.84 (3H, s), 5.03 (2H, s), 6.03-6.10 (2H, m), 7.16 (1H, dd, J=1.9, 8.7 Hz), 7.28-7.44 (6H, m), 7.79 (1H, d, J=8.7 Hz).

Example 63

1-(2-Ethyl-1-methyl-1H-benzimidazol-6-yl)-4-((4-fluorobenzyl)oxy)pyridin-2(1H)-one A mixture of 1-(4-amino-3-(methylamino)phenyl)-4-((4-fluorobenzyl)oxy)pyridin-2(1H)-one (90 mg), HATU (106 mg), propionic acid (0.040 ml), N,N-diisopropylethylamine (0.136 ml) and DMF (2 ml) was stirred at room temperature under a dry atmosphere ($CaCl_2$ tube) for 1 h. The mixture was quenched with water and extracted with EtOAc. The organic layer was separated, washed with water and brine, dried over $MgSO_4$ and concentrated in vacuo. The resulting residue was dissolved in AcOH (2 ml), and the mixture was stirred at 90° C. for 1 h. After evaporation of the solvent, the residue was purified by NH silica gel column chromatography (hexane/EtOAc). The resulting solid was recrystallized from EtOAc/MeOH to give the title compound (44.9 mg) as an off-white solid.

MS (ESI+): [M+H]+ 378.2.

$^1$H NMR (300 MHz, $CDCl_3$): δ 1.33 (3H, t, J=7.4 Hz), 2.90 (2H, q, J=7.6 Hz), 3.74 (3H, s), 5.13 (2H, s), 5.99 (1H, d, J=2.6 Hz), 6.09 (1H, dd, J=2.8, 7.7 Hz), 7.06 (1H, dd, J=1.9, 8.3 Hz), 7.21-7.31 (2H, m), 7.49-7.56 (3H, m), 7.59 (2H, dd, J=2.1, 8.1 Hz).

Example 63-1

1-(2-Ethyl-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (5 g), 6-bromo-2-ethyl-1-methyl-1H-benzimidazole (6.54 g), potassium carbonate (9.46 g), N,N'-dimethylethylenediamine (2.91 ml), copper iodide (1.3 g) and DMSO (100 ml) was stirred at 150° C. for 4 h. After cooling, the mixture was poured into 28% $NH_3$ solution at 0° C. The precipitate was collected by filtration and dissolved in EtOAc/THF. The resulting solution was washed with brine, dried over $MgSO_4$ and concentrated in vacuo. The residue was treated with activated carbon in MeOH, and recrystallized from MeOH/water to give the title compound (3.44 g) as a white solid.

MS (ESI+): [M+H]+ 378.2.

$^1$H NMR (400 MHz, DMSO-$d_6$): δ 1.33 (3H, t, J=7.5 Hz), 2.90 (2H, q, J=7.4 Hz), 3.74 (3H, s), 5.13 (2H, s), 5.99 (1H, d, J=2.5 Hz), 6.09 (1H, dd, J=2.6, 7.6 Hz), 7.06 (1H, dd, J=1.6, 8.3 Hz), 7.26 (2H, t, J=8.8 Hz), 7.48-7.56 (3H, m), 7.59 (2H, dd, J=3.0, 8.0 Hz).

Example 64

4-((4-Fluorobenzyl)oxy)-1-(1-methyl-2-propyl-1H-benzimidazol-6-yl)pyridin-2(1H)-one A mixture of 1-(4-amino-3-(methylamino)phenyl)-4-((4-fluorobenzyl)oxy)pyridin-2(1H)-one (90 mg), HATU (106 mg), n-butyric acid (0.024 ml), N,N-diisopropylethylamine (0.136 ml) and DMF (2 ml) was stirred at room temperature under a dry atmosphere ($CaCl_2$ tube) for 1 h. The mixture was quenched with water and extracted with EtOAc. The organic layer was separated, washed with water and brine, dried over $MgSO_4$ and concentrated in vacuo. The resulting residue was dissolved in AcOH (2.0 ml) and stirred at 90° C. for 1 h. After evaporation, the residue was purified by NH silica gel column chromatography (hexane/EtOAc). The resulting solid was recrystallized from EtOAc/MeOH to give the title compound (48.7 mg) as an off-white solid.

MS (ESI+): [M+H]+ 392.2.

$^1$H NMR (300 MHz, $CDCl_3$): δ 1.00 (3H, t, J=7.4 Hz), 1.74-1.88 (2H, m), 2.86 (2H, t, J=7.6 Hz), 3.74 (3H, s), 5.13 (2H, s), 5.98 (1H, s), 6.09 (1H, dd, J=3.0, 7.6 Hz), 7.06 (1H, dd, =2.1, 8.5 Hz), 7.21-7.31 (2H, m), 7.50-7.56 (3H, m), 7.56-7.61 (2H, m).

Example 65

1-(2-(4,5-Dihydro-1,3-oxazol-2-yl)-1-methyl-1H-benzimidazol-6-yl)-4-((4-fluorobenzyl)oxy)pyridin-2(1H)-one Thionyl chloride (0.078 ml) was added to a mixture of 6-(4-((4-fluorobenzyl)oxy)-2-oxopyridin-1(2H)-yl)-N-(2-hydroxyethyl)-1-methyl-1H-benzimidazole-2-carboxamide (50.0 mg) in THF (2 ml) at room temperature. The mixture was stirred at room temperature for 3 h, and at 50° C. under Ar atmosphere for 2 h. After evaporation of the solvent, THF (2 ml) was added to the residue. NaH (40% oil dispersion, 34.3 mg) was added to the mixture at 0° C. The mixture was stirred at room temperature for 1 h, and at 50° C. under Ar atmosphere for 2 h. After addition of water (0.5 ml), the mixture was stirred at room temperature over weekend. The mixture was quenched with brine and extracted with EtOAc/THF. The organic layer was separated, washed with brine, dried over $MgSO_4$ and concentrated in vacuo. The solid was washed with EtOAc to give the title compound (17.9 mg) as a white solid.

MS (ESI+): [M+H]+ 419.2.

Example 66

1-(2-Acetyl-1-methyl-1H-benzimidazol-6-yl)-4-((4-fluorobenzyl)oxy)pyridin-2(1H)-one A) 1-(6-Bromo-1-methyl-1H-benzimidazol-2-yl)ethanone Methylmagnesium chloride (1.0 M in THF, 4.70 ml) was added dropwise to a solution of 6-bromo-N-methoxy-N,1-dimethyl-1H-benzimidazole-2-carboxamide (700 mg) in THF (10 ml) at 0° C. The mixture was stirred at 0° C. under Ar atmosphere for 30 min. The mixture was quenched with saturated $NH_4Cl$ solution and extracted with EtOAc twice. The organic layer was separated, washed with brine, dried over $MgSO_4$ and concentrated ao in vacuo. The residue was purified by silica gel column chromatography (hexane/EtOAc), and the resulting solid was washed with IPE to give the title compound (360 mg) as a white solid.

MS (ESI+): [M+H]+ 253.0.

B) 1-(2-Acetyl-1-methyl-1H-benzimidazol-6-yl)-4-((4-fluorobenzyl)oxy)pyridin-2(1H)-one A mixture of 4-((4-fluorobenzyl)oxy)pyridin-2(1H)-one (312 mg), 1-(6-bromo-1-methyl-1H-benzimidazol-2-yl)

ethanone (360 mg), N,N'-dimethylethylenediamine (0.141 ml), copper iodide (250 mg) and potassium carbonate (393 mg) in DMSO (3 ml) was stirred at 150° C. for 1 h. The mixture was purified by NH silica gel column chromatography (hexane/EtOAc). The resulting solid was recrystallized from EtOH/IPA to give the title compound (54.6 mg) as a pale orange solid.

MS (ESI+): [M+H]+ 392.2.

$^1$H NMR (300 MHz, CDCl$_3$): δ 2.85 (3H, s), 4.13 (3H, s), 5.03 (2H, s), 6.04-6.21 (2H, m), 7.11 (2H, t, J=8.7 Hz), 7.22-7.34 (2H, m), 7.41 (2H, dd, J=5.3, 8.7 Hz), 7.51 (1H, d, J=1.9 Hz), 7.97 (1H, d, J=8.7 Hz).

Example 67

4-(Benzyloxy)-1-(2-cyclopropyl-3-methylimidazo[1,2-a]pyridin-6-yl)pyridin-2(1H)-one hydrochloride To a suspension of 4-(benzyloxy)-1-(2-cyclopropyl-3-methylimidazo[1,2-a]pyridin-6-yl)pyridin-2(1H)-one (50 mg) in EtOAc (3 ml) was added 4 M HCl (EtOAc solution) (0.067 ml), and the mixture was stirred at room temperature for 3 h. The resulting solid was collected, washed with EtOAc, and dried in vacuo to give the title compound (44.0 mg) as a white solid.

MS (ESI+): [M+H]+ 372.2.

$^1$H NMR (300 MHz, DMSO-d$_6$): δ 0.92-1.15 (4H, m), 2.16-2.30 (1H, m), 2.55 (3H, s), 5.18 (2H, s), 6.05 (1H, d, J=2.6 Hz), 6.22 (1H, dd, J=2.6, 7.6 Hz), 7.33-7.51 (5H, m), 7.64-7.79 (3H, m), 8.81 (1H, brs).

Example 68

4-((4-Fluorobenzyl)oxy)-1-(1-methyl-2-((2,2,2-trifluoroethoxy)methyl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and (2,2,2-trifluoroethoxy)acetic acid.

MS (ESI+): [M+H]+ 462.2.

Example 69

4-((4-Fluorobenzyl)oxy)-1-(1-methyl-2-(1,3-oxazol-5-yl)-1H-benzimidazol-6-yl)pyridin-2(1H)-one A mixture of 1-(4-amino-3-(methylamino)phenyl)-4-((4-fluorobenzyl)oxy)pyridin-2(1H)-one (100 mg), oxazole-5-carboxylic acid (33.3 mg), HATU (118 mg), N,N-diisopropylethylamine (0.154 ml) and DMF (2 ml) was stirred at room temperature for 2 h. The mixture was poured into saturated NaHCO$_3$ solution and extracted with EtOAc. The organic layer was separated, washed with brine, dried over MgSO$_4$ and concentrated in vacuo. The resulting residue was dissolved in AcOH (2 ml), and the mixture was stirred at 80° C. for 2 h. The mixture was concentrate in vacuo. The residue was purified by NH silica gel column chromatography (MeOH/EtOAc). The resulting solid was washed with EtOAc/hexane to give the title compound (40.7 mg) as an off-white solid.

MS (ESI+): [M+H]+ 417.2.

$^1$H NMR (300 MHz, DMSO-d$_6$): δ 4.03 (3H, s), 5.15 (2H, s), 6.01 (1H, d, J=2.6 Hz), 6.12 (1H, dd, J=2.6, 7.6 Hz), 7.18-7.32 (3H, m), 7.54 (2H, dd, J=5.3, 8.7 Hz), 7.64 (1H, d, J=7.6 Hz), 7.70-7.80 (2H, m), 8.02 (1H, s), 8.72 (1H, s).

Example 70

4-((4-Chlorobenzyl)oxy)-1-(2-cyclopropyl-3-methylimidazo[1,2-a]pyridin-6-yl)pyrimidin-2(1H)-one A) 2-Chloro-4-((4-chlorobenzyl)oxy)pyrimidine To a stirred solution of 2,4-dichloropyrimidine (10.4 g) and (4-chlorophenyl)methanol (10 g) in DMF (50 ml) was added potassium carbonate (14.5 g), and the resulting mixture was stirred at room temperature for 16 h. The reaction mixture was then diluted with water while the product was precipitated out from the reaction medium. The precipitate was collected by filtration and dried under vacuum to give the title compound (4.8 g) as an off-white solid.

MS (ESI+): [M+H]+ 255.2.

B) 4-((4-Chlorobenzyl)oxy)pyrimidin-2(1H)-one

To a stirred solution of 2-chloro-4-((4-chlorobenzyl)oxy)pyrimidine (2.8 g) in dioxane and water (1:4, 30 ml) was added NaOH (440 mg), and the mixture was heated at reflux for 3 h. The reaction mixture was then cooled to 0° C. and the product was precipitated out from the reaction medium. The precipitate was collected by filtration, washed with cold water, and dried under vacuum to give the title compound (130 mg) as an off-white solid.

MS (ESI+): [M+H]+ 237.2.

C) 4-((4-Chlorobenzyl)oxy)-1-(2-cyclopropyl-3-methylimidazo[1,2-a]pyridin-6-yl)pyrimidin-2(1H)-one To a stirred degassed mixture of 4-((4-chlorobenzyl)oxy)pyrimidin-2(1H)-one (130 mg), 2-cyclopropyl-6-iodo-3-methylimidazo[1,2-a]pyridine (180 mg), potassium carbonate (228 mg) and dry dioxane (8 ml) were added copper iodide (41.8 mg) and trans-N,N'-dimethylcyclohexane-1,2-diamine (32 mg). The reaction vessel was sealed and heated at 110° C. for 16 h. The reaction mixture was then cooled to room temperature, and concentrated in vacuo. The crude residue was diluted with DCM, and the DCM layer was washed with brine, dried over Na$_2$SO$_4$ and concentrated in vacuo. The residue was purified by silica gel column chromatography (MeOH/DCM) to give the title compound (40 mg) as an off-white solid.

MS (ESI+): [M+H]+ 407.2.

$^1$H NMR (400 MHz, DMSO-d$_6$): δ 0.85-0.92 (4H, m), 2.05-2.09 (1H, m), 2.47 (3H, s), 5.40 (2H, s), 6.21 (1H, d, J=7.2 Hz), 7.19 (1H, dd, J=1.6, 9.5 Hz), 7.44-7.52 (5H, m), 8.11 (1H, d, J=7.2 Hz), 8.47 (1H, s).

Example 71

1-(2-Cyclopropyl-1-methyl-1H-benzimidazol-6-yl)-4-((2-fluorobenzyl)oxy)pyridin-2(1H)-one A) 1-(2-Cyclopropyl-1-methyl-1H-benzimidazol-6-yl)-4-hydroxypyridin-2(1H)-one To a stirred solution of 4-(benzyloxy)-1-(2-cyclopropyl-1-methyl-1H-benzimidazol-6-yl)pyridin-2(1H)-one (840 mg) in TFA (21 ml) was added anisole (7 ml), and the reaction mixture was heated at 130° C. for 4 h. The mixture was cooled and concentrated in vacuo. The residue was triturated with Et$_2$O to give the title compound (778 mg) as a white solid.

MS (ESI+): [M+H]+ 282.0.

B) 1-(2-Cyclopropyl-1-methyl-1H-benzimidazol-6-yl)-4-((2-fluorobenzyl)oxy)pyridin-2(1H)-one To a stirred suspension of NaH (40% oil dispersion, 50 mg) in THF (9 ml) was added a solution of 1-(2-cyclopropyl-1-methyl-1H-benzimidazol-6-yl)-4-hydroxypyridin-2(1H)-one (150 mg) in THF (1 ml) at 0° C., and then the mixture was stirred at room temperature for 30 min. 1-Bromomethyl-2-fluorobenzene (150 mg) in THF (0.5 ml) was added, and the resulting mixture was stirred at room temperature for 12 h. The reaction mixture was quenched with ice-water and extracted with DCM. The extract was washed with brine, dried over $Na_2SO_4$ and concentrated in vacuo. The crude product was purified by silica gel column chromatography (MeOH/DCM) followed by crystallization with DCM/hexane (19:1, 2 ml) to give the title compound (56 mg) as a white solid.

MS (ESI+): [M+H]+ 390.0.
$^1$H NMR (400 MHz, DMSO-$d_6$): δ 1.04-1.11 (4H, m), 2.24-2.28 (1H, m), 3.85 (3H, s), 5.18 (2H, s), 6.03-6.09 (2H, m), 7.04 (1H, dd, J=1.6, 8.5 Hz), 7.26-7.31 (2H, m), 7.44-7.52 (3H, m), 7.57-7.60 (2H, m).

Example 72

1-(2-Cyclopropyl-1-methyl-1H-benzimidazol-6-yl)-4-((3-fluorobenzyl)oxy)pyridin-2(1H)-one To a stirred suspension of NaH (40% oil dispersion, 50 mg) in THF (9 ml) was added a solution of 1-(2-cyclopropyl-1-methyl-1H-benzimidazol-6-yl)-4-hydroxypyridin-2(1H)-one (150 mg) in THF (1 ml) at 0° C., and then the mixture was stirred at room temperature for 30 min. 1-Bromomethyl-3-fluorobenzene (150 mg) in THF (0.5 ml) was added, and the resulting mixture was stirred at room temperature for 12 h. The reaction mixture was quenched with ice-water and extracted with DCM. The extract was washed with brine, dried over $Na_2SO_4$ and concentrated in vacuo. The crude product was purified by silica gel column chromatography (MeOH/DCM) followed by crystallization with DCM/hexane to give the title compound (49 mg) as a white solid.

MS (ESI+): [M+H]+ 390.0.
$^1$H NMR (400 MHz, DMSO-$d_6$): δ 1.02-1.11 (4H, m), 2.24-2.28 (1H, m), 3.85 (3H, s), 5.18 (2H, s), 5.96 (1H, d, J=2.5 Hz), 6.11 (1H, dd, J=2.5, 7.6 Hz), 7.05 (1H, dd, J=1.5, 8.6 Hz), 7.20 (1H, m), 7.31 (2H, d, J=7.7 Hz), 7.45-7.52 (3H, m), 7.58 (1H, d, J=7.6 Hz).

Example 73

(6-(4-((4-Fluorobenzyl)oxy)-2-oxopyridin-1(2H)-yl)-3-methylimidazo[1,2-a]pyridin-2-yl)acetonitrile A) 4-((4-Fluorobenzyl)oxy)-1-(2-(hydroxymethyl)-3-methylimidazo[1,2-a]pyridin-6-yl)pyridin-2(1H)-one The title compound was obtained in an analogous manner to step C in example 5 using 4-((4-fluorobenzyl)oxy)pyridin-2(1H)-one and (6-iodo-3-methylimidazo[1,2-a]pyridin-2-yl)methanol.

MS (ESI+): [M+H]+ 380.0.

B) 1-(2-(Chloromethyl)-3-methylimidazo[1,2-a]pyridin-6-yl)-4-((4-fluorobenzyl)oxy)pyridin-2(1H)-one To a stirred solution of 4-((4-fluorobenzyl)oxy)-1-(2-(hydroxymethyl)-3-methylimidazo[1,2-a]pyridin-6-yl)pyridin-2(1H)-one (120 mg) in DCM (1 ml) was added thionyl chloride (1 ml), and the mixture was stirred at room temperature for 18 h. The reaction mixture was concentrated in vacuo, diluted with DCM and quenched with aqueous $NaHCO_3$ under ice-cold condition. The organic layer was separated, washed successively with water and brine, dried over $Na_2SO_4$ and concentrated in vacuo to give the title compound (120 mg) as an off-white solid.

MS (ESI+): [M+H]+ 398.2.

C) (6-(4-((4-Fluorobenzyl)oxy)-2-oxopyridin-1(2H)-yl)-3-methylimidazo[1,2-a]pyridin-2-yl)acetonitrile To a stirred solution of 1-(2-(chloromethyl)-3-methylimidazo[1,2-a]pyridin-6-yl)-4-((4-fluorobenzyl)oxy)pyridin-2(1H)-one (150 mg) in THF (5 ml) were added trimethylsilyl cyanide (115 µl) and TBAF (1 M in THF, 1.13 ml) at room temperature, and the resulting mixture was stirred at room temperature for 4 h. The reaction mixture was then quenched with saturated $FeSO_4$, and the organic layer was extracted with DCM. The extract was washed with brine, dried over $Na_2SO_4$ and concentrated in vacuo. The crude product was purified by silica gel column chromatography (MeOH/DCM) to give the title compound (60 mg) as a white solid.

MS (ESI+): [M+H]+ 389.4.

Example 74

Methyl(1RS,2RS)-2-(6-(4-((4-chlorobenzyl)oxy)-2-oxopyridin-1(2H)-yl)-1-methyl-1H-benzimidazol-2-yl)cyclopropanecarboxylate A) 4-((4-Chlorobenzyl)oxy)-1-(3-(methylamino)-4-nitrophenyl)pyridin-2(1H)-one A mixture of 4-((4-chlorobenzyl)oxy)pyridin-2(1H)-one (10 g), 5-bromo-N-methyl-2-nitroaniline (9.80 g), N,N'-dimethylethylenediamine (4.76 ml), copper iodide (8.08 g), potassium carbonate (17.59 g) and DMSO (200 ml) was heated at 150° C. for 2 h. The mixture was poured into 28% $NH_3$ solution. The resulting precipitate was collected and washed with IPA. The solid was dissolved in DMSO (100 ml) at 80° C., and allowed to cool to room temperature to give a precipitate. After filtration, the precipitate was washed with IPA and dried to give the title compound (12 g) as a yellow solid.

MS (ESI+): [M+H]+ 386.0.

B) 1-(4-Amino-3-(methylamino)phenyl)-4-((4-chlorobenzyl)oxy)pyridin-2(1H)-one

Zinc (20.34 g) was added to a suspension of 4-((4-chlorobenzyl)oxy)-1-(3-(methylamino)-4-nitrophenyl)pyridin-2(1H)-one (12 g) in AcOH (200 ml) at room temperature. The mixture was stirred at room temperature for 1 h. The insoluble material was removed by filtration, and the filtrate was concentrated in vacuo. The residue was neutralized with saturated $NaHCO_3$ at 0° C. and extracted with EtOAc. The organic layer was separated, washed with water and brine, dried over $MgSO_4$ and concentrated in vacuo. The residue was purified by NH silica gel column chromatography (MeOH/EtOAc) to give the title compound (5.5 g) as a pale orange solid.

MS (ESI+): [M+H]+ 356.2.

C) Methyl(1RS,2RS)-2-(6-(4-((4-chlorobenzyl)oxy)-2-oxopyridin-1(2H)-yl)-1-methyl-1H-benzimidazol-2-yl)cyclopropanecarboxylate The title compound was obtained in an analogous manner to step C in example 13 using 1-(4-amino-3-(methylamino)phenyl)-4-((4-chlorobenzyl)oxy)pyridin-2(1H)-one and (1RS,2RS)-2-(methoxycarbonyl)cyclopropanecarboxylic acid.

MS (ESI+): [M+H]+ 464.2.

Example 75

1-(2-Cyclopropyl-1-methyl-1H-benzimidazol-6-yl)-4-(3-thienylmethoxy)pyridin-2(1H)-one To a solution of 1-(2-cyclopropyl-1-methyl-1H-benzimidazol-6-yl)-4-hydroxypyridin-2(1H)-one (100 mg), 3-thienylmethanol (67 μl) and tributylphosphine (258 μl) in THF (10 ml) was added 1,1'-(azodicarbonyl)dipiperidine (264 mg). The mixture was stirred under sonication at 50° C. for 1 h. The reaction mixture was then cooled to room temperature, and concentrated in vacuo. The crude residue was diluted with DCM (100 ml), and the DCM layer was washed with water (100 ml), brine (30 ml), dried over $Na_2SO_4$ and concentrated in vacuo. The residue was purified by silica gel column chromatography (MeOH/DCM) to give the title compound (50 mg) as an off-white solid.

MS (ESI+): [M+H]+ 378.2.
$^1$H NMR (400 MHz, DMSO-$d_6$): δ 1.02-1.09 (4H, m), 2.24-2.28 (1H, m), 3.85 (3H, s), 5.13 (2H, s), 5.99 (1H, d, J=2.6 Hz), 6.06 (1H, dd, J=2.6, 7.5 Hz), 7.04 (1H, dd, J=1.7, 8.4 Hz), 7.19 (1H, d, J=4.2 Hz), 7.50-7.52 (2H, m), 7.56-7.60 (2H, m), 7.64 (1H, m).

Example 76

6-(4-((4-Fluorobenzyl)oxy)-2-oxopyridin-1(2H)-yl)-N,N,3-trimethylimidazo[1,2-a]pyridine-2-carboxamide A) 6-Iodo-N,N,3-trimethylimidazo[1,2-a]pyridine-2-carboxamide To a stirred solution of 6-iodo-3-methylimidazo[1,2-a]pyridine-2-carboxylic acid (150 mg) in DMF (5 ml) were added HATU (283 mg) and N,N-diisopropylethylamine (0.17 ml) at 0° C. The mixture was allowed to warm to room temperature and stirred for 30 min. Dimethylamine (2 M in THF, 0.2 ml) was added, and the resultant mixture was stirred at the same temperature for 18 h. The mixture was then concentrated in vacuo and the residue was diluted with DCM (100 ml). The DCM layer was successively washed with saturated aqueous $NH_4Cl$ solution (40 ml), saturated aqueous $NaHCO_3$ solution (20 ml), water (30 ml) and brine (50 ml). The DCM layer was then dried m over $Na_2SO_4$, and concentrated in vacuo to give the title compound (150 mg) as a brown oil.

MS (ESI+): [M+H]+ 329.8.

B) 6-(4-((4-Fluorobenzyl)oxy)-2-oxopyridin-1(2H)-yl)-N,N,3-trimethylimidazo[1,2-a]pyridine-2-carboxamide The title compound was obtained in an analogous manner to step C in example 5 using 4-((4-fluorobenzyl)oxy)pyridin-2(1H)-one and 6-iodo-N,N,3-trimethylimidazo[1,2-a]pyridine-2-carboxamide.

MS (ESI+): [M+H]+ 421.4.

Example 77

1-(2-Cyclopropyl-1-methyl-1H-benzimidazol-6-yl)-4-((4-methoxybenzyl)oxy)pyridin-2(1H)-one To a solution of 1-(2-cyclopropyl-1-methyl-1H-benzimidazol-6-yl)-4-hydroxypyridin-2(1H)-one (100 mg), (4-methoxy-phenyl)-methanol (98 mg) and tributylphosphine (320 μl) in THF (10 ml) was added 1,1'-(azodicarbonyl)dipiperidine (269 mg). The mixture was stirred under sonication at 50° C. for 1 h. The reaction mixture was then cooled to room temperature, and concentrated in vacuo. The crude residue was diluted with DCM (100 ml), and the DCM layer was washed with water (50 ml) and brine (30 ml), dried over $Na_2SO_4$ and concentrated in vacuo. The residue was purified by silica gel column chromatography (MeOH/DCM) to give the title compound (45 mg) as an off-white solid.

MS (ESI+): [M+H]+ 402.2.
$^1$H NMR (400 MHz, DMSO-$d_5$): δ 1.03-1.09 (4H, m), 2.24-2.28 (1H, s), 3.77 (3H, s), 3.84 (3H, s), 5.05 (2H, s), 5.97 (1H, d, J=2.5 Hz), 6.06 (1H, dd, J=2.6, 7.5 Hz), 6.97 (2H, d, J=8.5 Hz), 7.03 (1H, dd, J=1.7, 8.4 Hz), 7.40 (2H, d, J=8.5 Hz), 7.51 (2H, m), 7.55 (1H, d, J=7.6 Hz).

Example 78

4-((4-Fluorobenzyl)oxy)-1-(2-(fluoromethyl)-3-methylimidazo[1,2-a]pyridin-6-yl)pyridin-2(1H)-one A) 2-(Fluoromethyl)-6-iodo-3-methylimidazo[1,2-a]pyridine To a stirred solution of (6-iodo-3-methylimidazo[1,2-a]pyridin-2-yl)methanol (600 mg) in DCM (2 ml) was added DAST (500 mg) at −78° C. The reaction mixture was then allowed slowly to warm up to room temperature, and stirred at the same temperature for 16 h. The reaction mixture was then diluted with DCM (100 ml), washed with saturated $NaHCO_3$ solution (100 ml), and concentrated in vacuo. The residue was purified by silica gel column chromatography (MeOH/DCM) to give the title compound (280 mg) as an off-white solid.

MS (ESI+): [M+H]+ 290.8.

B) 4-((4-Fluorobenzyl)oxy)-1-(2-(fluoromethyl)-3-methylimidazo[1,2-a]pyridin-6-yl)pyridin-2(1H)-one The title compound was obtained in an analogous manner to step C in example 5 using 4-((4-fluorobenzyl)oxy)pyridin-2(1H)-one and 2-(fluoromethyl)-6-iodo-3-methylimidazo[1,2-a]pyridine.

MS (ESI+): [M+H]+ 382.0.

Example 79

1-(2-Cyclopropyl-1-methyl-1H-benzimidazol-6-yl)-4-(1,3-thiazol-2-ylmethoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and thiazol-2-ylmethanol.

MS (ESI+): [M+H]+ 379.4.

Example 80

((4-Chlorobenzyl)oxy)-1-(2-((1RS,2SR)-2-(2-hydroxypropan-2-yl)cyclopropyl)-1-methyl-1H-benzimidazol-6-yl)pyridin-2(1H)-one A) Methyl(1RS,2SR)-2-(6-bromo-1-methyl-1H-benzimidazol-2-yl)cyclopropanecarboxylate HATU (554 mg) was added to a solution of 5-bromo-$N^1$-methylbenzene-1,2-diamine (279 mg), N,N-diisopropylethylamine (0.727 ml) and (1RS,2SR)-2-(methoxycarbonyl)cyclopropanecarboxylic acid (200 mg) in DMF (5 ml) at room temperature. The mixture was stirred at room temperature for 1 h. The mixture was quenched with water and extracted with EtOAc. The organic layer was separated, washed with water and brine, dried over MgSO$_4$ and concentrated in vacuo. The residue was dissolved in AcOH (5 ml), and the mixture was stirred at 80° C. for 1 h. After concentration of the mixture, the residue was neutralized with saturated NaHCO$_3$ solution and extracted with EtOAc. The organic layer was separated, washed with water and brine, dried over MgSO$_4$ and concentrated in vacuo. The residue was purified by silica gel column chromatography (MeOH/EtOAc) to give the title compound (80 mg) as an off-white solid.
MS (ESI+): [M+H]+ 309.1.

B) 2-((1RS,2SR)-2-(6-Bromo-1-methyl-1H-benzo[d]imidazol-2-yl)cyclopropyl)propan-2-ol Methylmagnesium chloride (0.69 ml) was added to a solution of methyl(1RS,2SR)-2-(6-bromo-1-methyl-1H-benzimidazol-2-yl)cyclopropanecarboxylate (80 mg) in THF (2 ml) at 0° C. The mixture was stirred at room temperature for 3 h. The mixture was quenched with 1 M HCl at room temperature and extracted with EtOAc. The organic layer was separated, washed with saturated NaHCO$_3$ solution and brine, dried over MgSO$_4$ and concentrated in vacuo. The residue was purified by silica gel column chromatography (hexane/EtOAc) to give the title compound (34 mg) as a white solid.
MS (ESI+): [M+H]+ 309.2.

C) 4-((4-Chlorobenzyl)oxy)-1-(2-((1RS,2SR)-2-(2-hydroxypropan-2-yl)cyclopropyl)-1-methyl-1H-benzimidazol-6-yl)pyridin-2(1H)-one A mixture of 4-((4-chlorobenzyl)oxy)pyridin-2(1H)-one (27 mg), 2-((1RS,2SR)-2-(6-bromo-1-methyl-1H-benzo[d]imidazol-2-yl)cyclopropyl)propan-2-ol (35 mg), copper iodide (21.8 mg), N,N'-dimethylethylenediamine (10.1 mg), potassium carbonate (31.7 mg) and DMSO (1 ml) was stirred at 150° C. overnight. The mixture was quenched with 28% NH$_3$ solution at room temperature and extracted with EtOAc. The organic layer was separated, washed with water and brine, dried over MgSO$_4$ and concentrated in vacuo. The residue was purified by NH silica gel column chromatography (MeOH/EtOAc) to give the title compound (10 mg) as a pale yellow solid.
MS (ESI+): [M+H]+ 464.2.
$^1$H NMR (300 MHz, CDCl$_3$): δ 1.28 (3H, s), 1.35 (3H, s), 1.49-1.75 (3H, m), 2.03 (1H, td, J=6.4, 8.7 Hz), 3.83 (3H, s), 5.03 (2H, s), 6.00-6.14 (2H, m), 7.11 (1H, dd, J=1.9, 8.3 Hz), 7.27-7.33 (1H, m), 7.34-7.46 (5H, m), 7.64 (1H, d, J=8.3 Hz).

Example 81

4-((4-Chlorobenzyl)oxy)-1-(2-((1RS,2RS)-2-(2-hydroxypropan-2-yl)cyclopropyl)-1-methyl-1H-benzimidazol-6-yl)pyridin-2(1H)-one Methylmagnesium chloride (0.575 ml) was added to a solution of methyl(1RS,2RS)-2-(6-(4-((4-chlorobenzyl)oxy)-2-oxopyridin-1(2H)-yl)-1-methyl-1H-benzimidazol-2-yl)cyclopropanecarboxylate in THF (2 ml) at 0° C. The mixture was stirred at room temperature for 3 h. The mixture was quenched with 1 M HCl at room temperature and extracted with EtOAc. The organic layer was separated, washed with saturated NaHCO$_3$ solution and brine, dried over MgSO$_4$ and concentrated in vacuo. The residue was purified by silica gel column chromatography (hexane/EtOAc) to give the title compound (55 mg) as a white solid.
MS (ESI+): [M+H]+ 464.2.

Example 82

(1RS,2RS)-2-(6-(4-((4-Chlorobenzyl)oxy)-2-oxopyridin-1(2H)-yl)-1-methyl-1H-benzimidazol-2-yl)cyclopropanecarboxylic acid Sodium hydroxide (1.811 ml) was added to a solution of methyl(1RS,2RS)-2-(6-(4-((4-chlorobenzyl)oxy)-2-oxopyridin-1 (2H)-yl)-1-methyl-1H-benzimidazol-2-yl)cyclopropanecarboxylate (280 mg) in THF (3 ml)-MeOH (3 ml) at room temperature. The mixture was neutralized with 1 M HCl at 0° C. and extracted with EtOAc and MeOH. The organic layer was separated, washed with water and brine, dried over MgSO$_4$ and concentrated in vacuo. The resulting solid was washed with IPE and dried to give the title compound (220 mg) as a white solid.
MS (ESI+): [M+H]+ 450.2.

Example 83

(1RS,2RS)-2-(6-(4-((4-Chlorobenzyl)oxy)-2-oxopyridin-1(2H)-yl)-1-methyl-1H-benzimidazol-2-yl)cyclopropanecarboxamide To a solution of (1RS,2RS)-2-(6-(4-((4-chlorobenzyl)oxy)-2-oxopyridin-1(2H)-yl)-1-methyl-1H-benzimidazol-2-yl)cyclopropanecarboxylic acid (150 mg) and triethylamine (0.139 ml) in acetone (2 ml) was added ethyl chloroformate (0.096 ml) at 0° C. The mixture was stirred at 0° C. for 1 h and then NH$_3$ solution (0.101 ml) was added dropwise. The reaction mixture was stirred at room temperature for 3 h and then concentrated in vacuo. The residue was purified by silica gel chromatography (MeOH/EtOAc) to give the title compound (125 mg) as a white solid.
MS (ESI+): [M+H]+ 449.2.

Example 84

4-((4-Chlorobenzyl)oxy)-1-(2-cyclopropyl-4-fluoro-1-methyl-1H-benzimidazol-6-yl)pyridin-2(1H)-one A) N-(4-Bromo-2,6-difluorophenyl)cyclopropanecarboxamide Cyclopropanecarbonyl chloride (1.05 ml) was added to a solution of 4-bromo-2,6-difluoroaniline (1.00 g) and triethylamine (1.61 ml) in THF (10 ml) at room temperature. The mixture was stirred at room temperature for 2 h. The mixture was quenched with brine and extracted with EtOAc. The organic layer was separated, washed with brine, dried over MgSO$_4$, passed through NH silica gel pad and concentrated in vacuo. The solid was washed with IPE/hexane to give the title compound (1.08 g) as a white solid.

$^1$H NMR (300 MHz, CDCl$_3$): δ 0.76-0.97 (2H, m), 1.07-1.20 (2H, m), 1.45-1.68 (1H, m), 6.82 (1H, br. s.), 7.06-7.19 (2H, m).

B) 6-Bromo-2-cyclopropyl-4-fluoro-1-methyl-1H-benzimidazole

Thionyl chloride (3.17 ml) was added to a solution of N-(4-bromo-2,6-difluorophenyl)cyclopropanecarboxamide (600 mg) at room temperature. The mixture was stirred at 80° C. for 2 h. After evaporation of thionyl chloride, methylamine (36% in MeOH, 4.93 ml) was added. The mixture was stirred at room temperature for 30 min. After evaporation of the solvent and addition of water, the mixture was extracted with EtOAc. The organic layer was separated, washed with brine, dried over MgSO$_4$ and concentrated in vacuo. To the resulting residue in DMF (2 ml), potassium tert-butoxide (488 mg) was added. The mixture was stirred at 100° C. for 2 h. The mixture was quenched with brine and extracted with EtOAc twice. The organic layer was separated, washed with brine, dried over MgSO$_4$ and concentrated in vacuo. The residue was purified by silica gel column chromatography (hexane/EtOAc) to give the title compound (66.8 mg) as a yellow solid.

MS (ESI+): [M+H]+ 269.0.

6-Bromo-4-tert-butoxy-2-cyclopropyl-1-methyl-1H-benzimidazole (103 mg) was also obtained as a byproduct.

MS (ESI+): [M+H]+ 323.2.

C) 4-((4-Chlorobenzyl)oxy)-1-(2-cyclopropyl-4-fluoro-1-methyl-1H-benzimidazol-6-yl)pyridin-2(1H)-one The title compound was obtained in an analogous manner to step C in example 5 using 4-((4-chlorobenzyl)oxy)pyridin-2(1H)-one and 6-bromo-2-cyclopropyl-4-fluoro-1-methyl-1H-benzimidazole.

MS (ESI+): [M+H]+ 424.1.

Example 85

1-(4-tert-Butoxy-2-cyclopropyl-1-methyl-1H-benzimidazol-6-yl)-4-((4-chlorobenzyl)oxy)pyridin-2(1H)-one The title compound was obtained in an analogous manner to step C in example 5 using 4-((4-chlorobenzyl)oxy)pyridin-2(1H)-one and 6-bromo-4-tert-butoxy-2-cyclopropyl-1-methyl-1H-benzimidazole.

MS (ESI+): [M+H]+ 478.1.

Example 86

(1RS,2RS)-2-(6-(4-((4-Chlorobenzyl)oxy)-2-oxopyridin-1(2H)-yl)-1-methyl-1H-benzimidazol-2-yl)cyclopropanecarbonitrile Trifluoroacetic anhydride (0.109 ml) was added to a solution of (1RS,2RS)-2-(6-(4-((4-chlorobenzyl)oxy)-2-oxopyridin-1(2H)-yl)-1-methyl-1H-benzimidazol-2-yl)cyclopropanecarboxamide (117 mg) and pyridine (0.063 ml) in THF (3 ml) at 0° C. The mixture was stirred at 0° C. under Ar atmosphere for 1 h. The mixture was quenched with saturated NaHCO$_3$ solution at 0° C. and extracted with EtOAc. The organic layer was separated, washed with water and brine, dried over MgSO$_4$ and concentrated in vacuo. The resulting solid was crystallized from THF/hexane to give the title compound (15 mg) as an off-white solid.

MS (ESI+): [M+H]+ 431.2.

Example 87

4-((4-Fluorobenzyl)oxy)-1-(1-methyl-2-(3-methyl-1,2-oxazol-5-yl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 3-methyl-1,2-oxazole-5-carboxylic acid.

MS (ESI+): [M+H]+ 431.2.

Example 88

1-(2-(1,5-Dimethyl-1H-pyrazol-3-yl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 1,5-dimethyl-1H-pyrazole-3-carboxylic acid.

MS (ESI+): [M+H]+ 444.2.

Example 89

4-((4-Fluorobenzyl)oxy)-1-(1-methyl-2-(4-methyl-1,3-oxazol-5-yl)-1H-benzimidazol-6-yl)pyridin-2(1H)-one A mixture of 1-(4-amino-3-(methylamino)phenyl)-4-((4-fluorobenzyl)oxy)pyridin-2(1H)-one (100 mg), 4-methyl-1,3-oxazole-5-carboxylic acid (37.5 mg), HATU (118 mg) and N,N-diisopropylethylamine (0.154 ml) in DMF (2 ml) was stirred at room temperature for 2 h. The mixture was poured into saturated NaHCO$_3$ solution and extracted with EtOAc. The organic layer was separated, washed with brine, dried over MgSO$_4$ and concentrated in vacuo. The resulting residue was dissolved in AcOH (2 ml), and the mixture was stirred at 80° C. for 2 h. The mixture was concentrate in vacuo, and purified by NH silica gel column chromatography (MeOH/EtOAc). The resulting solid was washed with EtOAc/hexane to give the title compound (63.4 mg) as a white solid.

MS (ESI+): [M+H]+ 431.2.

$^1$H NMR (300 MHz, DMSO-d$_6$): δ 2.54 (3H, s), 4.01 (3H, s), 5.15 (2H, s), 6.01 (1H, d, J=2.6 Hz), 6.08-6.17 (1H, m), 7.21 (1H, dd, J=2.1, 8.5 Hz), 7.26 (2H, t, J=8.9 Hz), 7.54 (2H, dd, J=5.7, 8.7 Hz), 7.63 (1H, d, J=7.6 Hz), 7.71-7.79 (2H, m), 8.60 (1H, s).

Example 90

4-((4-Chlorobenzyl)oxy)-1-(1-methyl-2-(2-methylcyclopropyl)-1H-benzimidazol-6-yl)pyridin-2(1H)-one A mixture of HATU (101 mg), 1-(4-amino-3-(methylamino)phenyl)-4-((4-chlorobenzyl)oxy)pyridin-2(1H)-one (90 mg), N,N-diisopropylethylamine (0.130 ml), 2-methylcyclopropanecarboxylic acid (0.049 ml) and DMF (2 ml) was stirred at room temperature for 1 h. The mixture was quenched with water and extracted with EtOAc. The organic layer was separated, washed with water and brine, dried over MgSO$_4$ and concentrated in vacuo. The residue was dissolved in AcOH (2.00 ml), and the mixture was stirred at 90° C. for 2 h. After evaporation, the residue was purified by NH silica gel column chromatography (hexane/EtOAc). The resulting solid was recrystallized from EtOH to give the title compound (3 mg) as a diastereomeric mixture. The filtrate was concentrated in vacuo and the precipitate was recrystallized from THF to give the title compound (17 mg) as a diastereomeric mixture.

MS (ESI+): [M+H]+ 420.2.

$^1$H NMR (300 MHz, CDCl$_3$): δ 0.78-0.97 (1H, m), 1.18-1.29 (4H, m), 1.35-1.48 (1H, m), 1.99 (1H, dt, J=4.4, 8.2 Hz), 3.79-3.87 (3H, m), 5.16 (2H, s), 5.97 (1H, d, J=2.6 Hz), 6.06-6.13 (1H, m), 6.99-7.07 (1H, m), 7.45-7.54 (6H, m), 7.58 (1H, d, J=7.6 Hz).

Example 91

4-((4-Chlorobenzyl)oxy)-1-(2-(cyclopropylmethyl)-1-methyl-1H-benzimidazol-6-yl)pyridin-2(1H)-one A mixture of 1-(4-amino-3-(methylamino)phenyl)-4-((4-chlorobenzyl)oxy)pyridin-2(1H)-one (90 mg), HATU (101 mg), N,N-diisopropylethylamine (0.130 ml), cyclopropylacetic acid (0.024 ml) and DMF (2 ml) was stirred at room temperature for 1 h. The mixture was quenched with water and extracted with EtOAc. The organic layer was separated, washed with water and brine, dried over MgSO$_4$ and concentrated in vacuo. The residue was dissolved in AcOH (2.00 ml), and the mixture was stirred at 90° C. for 2 h. After evaporation, the residue was purified by NH silica gel column chromatography (hexane/EtOAc). The resulting solid was recrystallized from EtOH to give the title compound (56.3 mg) as an off-white solid.

MS (ESI+): [M+H]+ 420.2.

$^1$H NMR (300 MHz, CDCl$_3$): δ 0.22-0.31 (2H, m), 0.48-0.57 (2H, m), 1.12-1.27 (1H, m), 2.85 (2H, d, J=6.8 Hz), 3.76 (3H, s), 5.16 (2H, s), 5.97 (1H, d, J=2.6 Hz), 6.10 (1H, dd, J=2.8, 7.7 Hz), 7.04-7.11 (1H, m), 7.50 (4H, s), 7.53 (1H, d, J=1.9 Hz), 7.60 (2H, dd, J=2.6, 7.9 Hz).

Example 92

1-(2-(2,2-Dimethylcyclopropyl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 2,2-dimethylcyclopropanecarboxylic acid.

MS (ESI+): [M+H]+ 418.2.

Example 93

4-(6-(4-((4-Chlorobenzyl)oxy)-2-oxopyridin-1(2H)-yl)-1-methyl-1H-benzimidazol-2-yl)-2-methylbutanenitrile A) Methyl 4-(6-bromo-1-methyl-1H-benzimidazol-2-yl)butanoate The title compound was obtained in an analogous manner to step C in example 13 using 5-bromo-N'-methylbenzene-1,2-diamine and 5-methoxy-5-oxopentanoic acid.

$^1$H NMR (300 MHz, CDCl$_3$): δ 2.11-2.27 (2H, m), 2.46-2.56 (2H, m), 2.89-2.98 (2H, m), 3.66 (3H, s), 3.72 (3H, s), 7.33 (1H, dd, J=1.5, 8.3 Hz), 7.45 (1H, d, J=1.5 Hz), 7.56 (1H, d, J=8.3 Hz).

B) Methyl 4-(6-bromo-1-methyl-1H-benzimidazol-2-yl)-2-methylbutanoate

Lithium bis(trimethylsilyl)amide (1.6 M in THF, 6.15 ml) was added to a solution of methyl 4-(6-bromo-1-methyl-1H-benzimidazol-2-yl)butanoate (1.02 g) in THF (20 ml) at −78° C. After being stirred at −78° C. for 30 min, iodomethane (0.612 ml) was added to the reaction mixture. The mixture was stirred at room temperature under Ar atmosphere for 2 h. The mixture was quenched with saturated NH$_4$Cl solution at room temperature and extracted with EtOAc. The organic layer was separated, washed with saturated NaHCO$_3$ solution and brine, dried over MgSO$_4$, and concentrated in vacuo. The residue was purified by silica gel column chromatography (hexane/EtOAc) to give the title compound (440 mg) as a pale yellow solid.

MS (ESI+): [M+H]+ 325.1.

C) 4-(6-Bromo-1-methyl-1H-benzimidazol-2-yl)-2-methylbutanoic acid

The title compound was obtained in an analogous manner to example 82 using methyl 4-(6-bromo-1-methyl-1H-benzimidazol-2-yl)-2-methylbutanoate.

MS (ESI+): [M+H]+ 312.0.

D) 4-(6-Bromo-1-methyl-1H-benzimidazol-2-yl)-2-methylbutanamide

The title compound was obtained in an analogous manner to example 83 using 4-(6-bromo-1-methyl-1H-benzimidazol-2-yl)-2-methylbutanoic acid.

MS (ESI+): [M+H]+ 311.0.

E) 4-(6-Bromo-1-methyl-1H-benzimidazol-2-yl)-2-methylbutanenitrile

The title compound was obtained in an analogous manner to example 86 using 4-(6-bromo-1-methyl-1H-benzimidazol-2-yl)-2-methylbutanamide.

$^1$H NMR (300 MHz, CDCl$_3$): δ 1.37-1.46 (3H, m), 2.08-2.25 (1H, m), 2.26-2.42 (1H, m), 2.86-2.99 (1H, m), 3.00-3.16 (2H, m), 3.73 (3H, s), 7.35 (1H, dd, J=1.9, 8.7 Hz), 7.47 (1H, d, J=1.7 Hz), 7.56 (1H, d, J=8.7 Hz).

F) 4-(6-(4-((4-Chlorobenzyl)oxy)-2-oxopyridin-1(2H)-yl)-1-methyl-1H-benzimidazol-2-yl)-2-methylbutanenitrile The title compound was obtained in an analogous manner to step C in example 5 using 4-(6-bromo-1-methyl-1H-benzimidazol-2-yl)-2-methylbutanenitrile and 4-((4-chlorobenzyl)oxy)pyridin-2(1H)-one.

MS (ESI+): [M+H]+ 447.1.

Example 94

6-(4-((4-Fluorobenzyl)oxy)-2-oxopyridin-1(2H)-yl)-N,3-dimethylimidazo[1,2-a]pyridine-2-carboxamide

A) 6-Iodo-N,3-dimethylimidazo[1,2-a]pyridine-2-carboxamide

The title compound was obtained in an analogous manner to step A in example 76 using 6-iodo-3-methylimidazo[1,2-a]pyridine-2-carboxylic acid and methylamine.
MS (ESI+): [M+H]+ 316.2.

B) 6-(4-((4-Fluorobenzyl)oxy)-2-oxopyridin-1(2H)-yl)-N,3-dimethylimidazo[1,2-a]pyridine-2-carboxamide The title compound was obtained in an analogous manner to step C in example 5 using 4-((4-fluorobenzyl)oxy)pyridin-2(1H)-one and 6-iodo-N,3-dimethylimidazo[1,2-a]pyridine-2-carboxamide.
MS (ESI+): [M+H]+ 407.4.

Example 95

1-(2-Acetyl-3-methylimidazo[1,2-a]pyridin-6-yl)-4-((4-fluorobenzyl)oxy)pyridin-2(1H)-one

A) 6-Iodo-N-methoxy-N,3-dimethylimidazo[1,2-a]pyridine-2-carboxamide

The title compound was obtained in an analogous manner to step A in example 76 using 6-iodo-3-methylimidazo[1,2-a]pyridine-2-carboxylic acid and N,O-dimethylhydroxylamine hydrochloride.
MS (ESI+): [M+H]+ 345.6.

B) 6-(4-((4-Fluorobenzyl)oxy)-2-oxopyridin-1(2H)-yl)-N-methoxy-N,3-dimethylimidazo[1,2-a]pyridine-2-carboxamide The title compound was obtained in an analogous manner to step C in example 5 using 4-((4-fluorobenzyl)oxy)pyridine-2(1H)-one and 6-iodo-N-methoxy-N,3-dimethylimidazo[1,2-a]pyridine-2-carboxamide.
MS (ESI+): [M+H]+ 437.4.

C) 1-(2-Acetyl-3-methylimidazo[1,2-a]pyridin-6-yl)-4-((4-fluorobenzyl)oxy)pyridin-2(1H)-one To a stirred solution of 6-(4-((4-fluorobenzyl)oxy)-2-oxopyridin-1(2H)-yl)-N-methoxy-N,3-dimethylimidazo[1,2-a]pyridine-2-carboxamide (150 mg) in THF (10 ml) was added methylmagnesium bromide (3 M ether solution, 344 µl) at −78° C., and the resulting mixture was stirred at the same temperature for 2 h. The reaction mixture was then quenched with saturated aqueous NH₄Cl (40 ml) at −78° C., and slowly warmed to room temperature. The reaction mixture was concentrated in vacuo and diluted with EtOAc (100 ml). The EtOAc layer was washed with brine (40 ml), dried over Na₂SO₄ and concentrated in vacuo. The crude product was purified by silica gel column chromatography (MeOH/DCM) to give the title compound (55 mg) as a white solid.
MS (ESI+): [M+H]+ 392.0.

Example 96

1-(2-Cyclopropyl-1-methyl-1H-benzimidazol-6-yl)-4-(1,3-thiazol-5-ylmethoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and thiazol-5-yl-methanol.
MS (ESI+): [M+H]+ 379.0.

Example 97

1-(2-(Cyclopropylcarbonyl)-3-methylimidazo[1,2-a]pyridin-6-yl)-4-((4-fluorobenzyl)oxy)pyridin-2(1H)-one The title compound was obtained in an analogous manner to step C in example 95 using 6-(4-((4-fluorobenzyl)oxy)-2-oxopyridin-1(2H)-yl)-N-methoxy-N,3-dimethylimidazo[1,2-a]pyridine-2-carboxamide and cyclopropylmagnesium bromide.
MS (ESI+): [M+H]+ 418.0.

Example 98

1-(2-(Difluoromethyl)-3-methylimidazo[1,2-a]pyridin-6-yl)-4-((4-fluorobenzyl)oxy)pyridin-2(1H)-one

A) 6-Iodo-3-methylimidazo[1,2-a]pyridine-2-carbaldehyde

To a stirred solution of ethyl 6-iodo-3-methylimidazo[1,2-a]pyridine-2-carboxylate (1.0 g) in DCM (20 ml) was added a solution of diisobutylaluminum hydride (1.0 M toluene solution, 3.7 ml) at −78° C. The resultant mixture was stirred at the same temperature for 2 h. The reaction mixture was then quenched with a mixture of MeOH (2 ml) and water (2 ml) at −78° C. This reaction mixture was then acidified with a few drops of 5 M HCl, and washed with saturated NaHCO₃ solution (20 ml). The mixture was extracted with EtOAc (3×150 ml), and the extract was washed with brine (100 ml), dried over Na₂SO₄ and concentrated in vacuo. The crude residue was purified by silica gel column chromatography (MeOH/DCM) to give the title compound (600 mg) as an off-white solid.
MS (ESI+): [M+H]+ 286.8.

B) 2-(Difluoromethyl)-6-iodo-3-methylimidazo[1,2-a]pyridine

To a stirred solution of 6-iodo-3-methylimidazo[1,2-a]pyridine-2-carbaldehyde (600 mg) in DCM (2 ml) was added DAST (845 mg) at −78° C. The reaction mixture then slowly warm up to room temperature, and stirred at the same temperature for 16 h. The reaction mixture was then diluted with DCM (100 ml) and washed with saturated NaHCO₃ solution (100 ml). The DCM layer was concentrated in vacuo. The residue was purified by silica gel column chromatography (MeOH/DCM) to give the title compound (110 mg) as an off-white solid.
MS (ESI+): [M+H]+ 309.0.

C) 1-(2-(Difluoromethyl)-3-methylimidazo[1,2-a]pyridin-6-yl)-4-((4-fluorobenzyl)oxy)pyridin-2(1H)-one The title compound was obtained in an analogous manner to step C in example 5 using 4-((4-(trifluoromethyl)benzyl)

oxy)pyridin-2(1H)-one and 2-(difluoromethyl)-6-iodo-3-methylimidazo[1,2-a]pyridine.
MS (ESI+): [M+H]+ 400.0.

Example 99

1-(2-Cyclopropyl-1-methyl-1H-benzimidazol-6-yl)-4-((5-fluoropyridin-2-yl)methoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (5-fluoropyridin-2-yl)-methanol.
MS (ESI+): [M+H]+ 391.0.

Example 100

4-((4-Chlorobenzyl)oxy)-1-(2-((2,2-dimethylpropoxy)methyl)-1-methyl-1H-benzimidazol-6-yl)pyridin-2(1H)-one A) (2,2-Dimethylpropoxy)acetic acid NaH (40% oil dispersion, 432 mg) was added to a solution of 2,2-dimethylpropan-1-ol (0.319 ml) in THF (15 ml) at 0° C. After stirring for 5 min, 2-bromoacetic acid (500 mg) was added. The mixture was refluxed under Ar atmosphere for 2 h. The mixture was quenched with water, washed with EtOAc, acidified with 1 M HCl (11 ml) and extracted with EtOAc. The organic layer was separated, dried over MgSO$_4$ and concentrated in vacuo to give the title compound (490 mg) as a pale pink oil.
$^1$H NMR (300 MHz, CDCl$_3$): δ 0.95 (9H, s), 3.24 (2H, s), 4.12 (2H, s).

B) 4-((4-Chlorobenzyl)oxy)-1-(2-((2,2-dimethylpropoxy)methyl)-1-methyl-1H-benzimidazol-6-yl)pyridin-2(1H)-one The title compound was obtained in an analogous manner to step C in example 13 using 1-(4-amino-3-(methylamino)phenyl)-4-((4-chlorobenzyl)oxy)pyridin-2(1H)-one and (2,2-dimethylpropoxy)acetic acid.
MS (ESI+): [M+H]+ 466.1.

Example 101

4-((4-Chlorobenzyl)oxy)-1-(2-((3,3-dimethylbutoxy)methyl)-1-methyl-1H-benzimidazol-6-yl)pyridin-2(1H)-one A) (3,3-Dimethylbutoxy)acetic acid The title compound was obtained in an analogous manner to step A in example 100 using 3,3-dimethylbutan-1-ol and 2-bromoacetic acid.
$^1$H NMR (300 MHz, CDCl$_3$): δ 0.93 (9H, s), 1.58 (2H, t, J=7.4 Hz), 3.62 (2H, t, J=7.6 Hz), 4.10 (2H, s).

B) 4-((4-Chlorobenzyl)oxy)-1-(2-((3,3-dimethylbutoxy)methyl)-1-methyl-1H-benzimidazol-6-yl)pyridin-2(1H)-one The title compound was obtained in an analogous manner to step C in example 13 using 1-(4-amino-3-(methylamino)phenyl)-4-((4-chlorobenzyl)oxy)pyridin-2(1H)-one and (3,3-dimethylbutoxy)acetic acid.
MS (ESI+): [M+H]+ 480.1.

Example 102

4-((4-Chlorobenzyl)oxy)-1-(2-ethyl-1-methyl-1H-benzimidazol-6-yl)pyridin-2(1H)-one HATU (321 mg) was added to a solution of 1-(4-amino-3-(methylamino)phenyl)-4-((4-chlorobenzyl)oxy)pyridin-2(1H)-one (250 mg), N,N-diisopropylethylamine (0.367 ml) and propionic acid (57.3 mg) in DMF (3 ml) at room temperature. The mixture was stirred at room temperature for 1 h. The mixture was quenched with brine and extracted with EtOAc. The organic layer was separated, washed with brine, dried over MgSO$_4$, and concentrated in vacuo. The resulting residue in AcOH (1 ml) was stirred at 80° C. for 1 h. After evaporation of the solvent, the residue was purified by NH silica gel column chromatography (hexane/EtOAc to MeOH/EtOAc). The resulting solid was recrystallized twice from EtOH followed by THF to give the title compound (114 mg) as a white solid.
MS (ESI+): [M+H]+ 394.1.
$^1$H NMR (300 MHz, CDCl$_3$): δ 1.46 (3H, t, J=7.5 Hz), 2.93 (2H, q, J=7.5 Hz), 3.73 (3H, s), 5.03 (2H, s), 5.98-6.13 (2H, m), 7.12 (1H, dd, J=2.1, 8.5 Hz), 7.29-7.45 (6H, m), 7.77 (1H, d, J=8.7 Hz).

Example 103

4-((4-Chlorobenzyl)oxy)-1-(1-methyl-2-propyl-1H-benzimidazol-6-yl)pyridin-2(1H)-one HATU (321 mg) was added to a solution of 1-(4-amino-3-(methylamino)phenyl)-4-((4-chlorobenzyl)oxy)pyridin-2(1H)-one (250 mg), N,N-diisopropylethylamine (0.367 ml) and butyric acid (68.1 mg) in DMF (3 ml) at room temperature. The mixture was stirred at room temperature for 1 h. The mixture was quenched with brine and extracted with EtOAc. The organic layer was separated, washed with brine, dried over MgSO$_4$, and concentrated in vacuo. The resulting residue in AcOH (1 ml) was stirred at 80° C. for 1 h. After evaporation of the solvent, the residue was purified by NH silica gel column chromatography (hexane/EtOAc to MeOH/EtOAc). The resulting solid was recrystallized twice from EtOH followed by THF to give the title compound (126 mg) as a white solid.
MS (ESI+): [M+H]+ 408.1.
$^1$H NMR (300 MHz, CDCl$_3$): δ 1.07 (3H, t, J=7.5 Hz), 1.90 (2H, sxt, J=7.5 Hz), 2.81-2.95 (2H, m), 3.73 (3H, s), 5.03 (2H, s), 6.00-6.13 (2H, m), 7.12 (1H, dd, J=1.9, 8.3 Hz), 7.28-7.43 (6H, m), 7.76 (1H, d, J=8.3 Hz).

Example 104

1-(2-Acetyl-1-methyl-1H-benzimidazol-6-yl)-4-((4-chlorobenzyl)oxy)pyridin-2(1H)-one A mixture of 4-((4-chlorobenzyl)oxy)pyridin-2(1H)-one (596 mg), 1-(6-bromo-1-methyl-1H-benzimidazol-2-yl)ethanone (640 mg), N,N'-dimethylethylenediamine (0.272 ml), copper iodide (482 mg) and potassium carbonate (699 mg) in DMSO (10 ml) was stirred at 150° C. for 1 h. The mixture was quenched with NH$_3$ solution and extracted with EtOAc twice. The organic layer was separated, washed with brine, dried over MgSO$_4$ and concentrated in vacuo. The residue was purified by NH silica gel column chromatography (hexane/EtOAc). The resulting solid was recrystallized from EtOH to give the title compound (16.8 mg) as a white solid.

MS (ESI+): [M+H]+ 408.1.

$^1$H NMR (300 MHz, CDCl$_3$): δ 2.85 (3H, s), 4.13 (3H, s), 5.03 (2H, s), 6.03-6.13 (2H, m), 7.27-7.43 (6H, m), 7.51 (1H, d, J=1.9 Hz), 7.97 (1H, d, J=8.7 Hz).

Example 105

4-((4-Chlorobenzyl)oxy)-1-(2-(cyclopropylcarbonyl)-1-methyl-1H-benzimidazol-6-yl)pyridin-2(1H)-one The title compound was obtained in an analogous manner to step C in example 5 using 4-((4-chlorobenzyl)oxy)pyridin-2(1H)-one and (6-bromo-1-methyl-1H-benzimidazol-2-yl)(cyclopropyl)methanone.

MS (ESI+): [M+H]+ 434.0.

Example 106

1-(2-(5-Cyclopropyl-1,2-oxazol-3-yl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 5-cyclopropyl-1,2-oxazole-3-carboxylic acid.

MS (ESI+): [M+H]+ 457.2.

Example 107

4-((4-Chlorobenzyl)oxy)-1-(1,2-dimethyl-1H-benzimidazol-6-yl)pyridin-2(1H)-one

HATU (321 mg) was added to a solution of 1-(4-amino-3-(methylamino)phenyl)-4-((4-chlorobenzyl)oxy)pyridin-2(1H)-one (250 mg), N,N-diisopropylethylamine (0.367 ml) and AcOH (0.044 ml) in DMF (3 ml) at room temperature. The mixture was stirred at room temperature for 2 h. Water (6 ml) was added to the mixture. The precipitate was collected by filtration and dissolved to AcOH (3 ml). The mixture was stirred at 80° C. for 1 h. After evaporation of the solvent, the residue was purified by NH silica gel column chromatography (hexane/EtOAc). The resulting solid was recrystallized from EtOH to give the title compound (140 mg) as a pale pink solid.

MS (ESI+): [M+H]+ 380.0.

$^1$H NMR (300 MHz, CDCl$_3$): δ 2.63 (3H, s), 3.73 (3H, s), 5.03 (2H, s), 5.99-6.13 (2H, m), 7.12 (1H, dd, J=2.1, 8.5 Hz), 7.29-7.46 (6H, m), 7.73 (1H, d, J=8.3 Hz).

Example 108

4-((4-Chlorobenzyl)oxy)-1-(1-methyl-2-(oxetan-3-yl)-1H-benzimidazol-6-yl)pyridin-2(1H)-one The title compound was obtained in an analogous manner to step C in example 13 using 1-(4-amino-3-(methylamino)phenyl)-4-((4-chlorobenzyl)oxy)pyridin-2(1H)-one and 3-oxetanecarboxylic acid.

MS (ESI+): [M+H]+ 422.1.

Example 109

4-((4-Chlorobenzyl)oxy)-1-(2-cyclobutyl-1-methyl-1H-benzimidazol-6-yl)pyridin-2(1H)-one A mixture of 1-(4-amino-3-(methylamino)phenyl)-4-((4-chlorobenzyl)oxy)pyridin-2(1H)-one (90 mg), HATU (101 mg), N,N-diisopropylethylamine (0.130 ml), cyclobutanecarboxylic acid (0.024 ml) and DMF (2 ml) was stirred at room temperature for 2 h. The mixture was quenched with water and extracted with EtOAc. The organic layer was separated, washed with water and brine, dried over MgSO$_4$ and concentrated in vacuo. The residue was dissolved in AcOH (2 ml), and the mixture was stirred at 90° C. for 1 h. After evaporation, the residue was purified by NH silica gel column chromatography (hexane/EtOAc). The resulting solid was recrystallized from EtOH to give the title compound (22.72 mg) as an off-white solid.

MS (ESI+): [M+H]+ 420.2.

$^1$H NMR (300 MHz, DMSO-d$_6$): δ 1.87-2.19 (2H, m), 2.35-2.46 (4H, m), 3.66 (3H, s), 3.78-3.97 (1H, m), 5.16 (2H, s), 5.97 (1H, d, J=2.6 Hz), 6.09 (1H, s), 7.07 (1H, dd, J=1.9, 8.3 Hz), 7.44-7.54 (5H, m), 7.60 (2H, dd, J=7.9, 10.2 Hz).

Example 110

4-((4-Chlorobenzyl)oxy)-1-(2-(2-fluoropropyl)-1-methyl-1H-benzimidazol-6-yl)pyridin-2(1H)-one A) 4-((4-Chlorobenzyl)oxy)-1-(2-(2-hydroxypropyl)-1-methyl-1H-benzimidazol-6-yl)pyridin-2(1H)-one The title compound was obtained in an analogous manner to step C in example 13 using 1-(4-amino-3-(methylamino)phenyl)-4-((4-chlorobenzyl)oxy)pyridin-2(1H)-one and 3-hydroxybutanoic acid.

MS (ESI+): [M+H]+ 424.2.

B) 4-((4-Chlorobenzyl)oxy)-1-(2-(2-fluoropropyl)-1-methyl-1H-benzimidazol-6-yl)pyridin-2(1H)-one The title compound was obtained in an analogous manner to step B in example 52 using 4-((4-chlorobenzyl)oxy)-1-(2-(2-hydroxypropyl)-1-methyl-1H-benzimidazol-6-yl)pyridin-2(1H)-one.

MS (ESI+): [M+H]+ 426.2.

Example 111

4-((4-Fluorobenzyl)oxy)-1-(2-(3-methoxycyclobutyl)-1-methyl-1H-benzimidazol-6-yl)pyridin-2(1H)-one A) 6-Bromo-2-(3-methoxycyclobutyl)-1-methyl-1H-benzimidazole The title compound was obtained as a diastereomeric mixture in an analogous manner to step A in example 8 using 4-bromo-N$^2$-methylbenzene-1,2-diamine and 3-methoxycyclobutanecarboxylic acid.

MS (ESI+): [M+H]+ 294.8.

B) 4-((4-Fluorobenzyl)oxy)-1-(2-(3-methoxycyclobutyl)-1-methyl-1H-benzimidazol-6-yl)pyridin-2(1H)-one The title compound was obtained as a diastereomeric mixture in an analogous manner to step C in example 5 using 4-((4-fluorobenzyl)oxy)pyridin-2(1H)-one and 6-bromo-2-(3-methoxycyclobutyl)-1-methyl-1H-benzimidazole.

MS (ESI+): [M+H]+ 434.2.

Example 112

4-((5-Chloropyridin-2-yl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (200 mg), (5-chloropyridin-2-yl)-methanol (152 mg) and tributylphosphine (437 mg) in THF (10 ml) was added 1,1'-(azodicarbonyl)dipiperidine (536 mg). The mixture was stirred under sonication at 50° C. for 3 h. The reaction mixture was then cooled to room temperature, and concentrated in vacuo. The residue was diluted with DCM (100 ml), washed with water and brine (30 ml), dried over $Na_2SO_4$ and concentrated in vacuo. The residue was purified by silica gel column chromatography (MeOH/DCM) followed by preparative HPLC to give the title compound (40 mg) as a white solid.

MS (ESI+): [M+H]+ 407.4.

$^1$H NMR (400 MHz, DMSO-$d_6$): δ 1.04-1.09 (4H, m), 2.26-2.32 (1H, m), 3.84 (3H, s), 5.23 (2H, s), 5.96 (1H, s), 6.12 (1H, dd, J=2.6, 7.7 Hz), 7.04 (1H, m), 7.50-7.52 (2H, m), 7.59-7.61 (2H, m), 8.02-8.04 (1H, m), 8.67 (1H, s).

Example 113

4-((4-Fluorobenzyl)oxy)-1-(1-methyl-2-(3-oxocyclobutyl)-1H-benzimidazol-6-yl)pyridin-2(1H)-one A) N-(4-Bromo-2-(methylamino)phenyl)-3-oxocyclobutanecarboxamide To a stirred solution of 3-oxocyclobutanecarboxylic acid (1.1 g) in DMF (50 ml) were added HATU (5.7 g) and N,N-diisopropylethylamine (4.2 ml) at 0° C. The mixture was allowed to warm to room temperature and stirred for 30 min. A solution of 4-bromo-$N^2$-methylbenzene-1,2-diamine (2.0 g) in DMF (2 ml) was added, and the resultant mixture was stirred at the same temperature for 18 h. The mixture was then concentrated in vacuo, and the residue was diluted with DCM (200 ml) and washed with saturated $NH_4Cl$ (100 ml), saturated $NaHCO_3$ (60 ml), water (100 ml) and brine (100 ml). The DCM layer was then dried over $Na_2SO_4$ and concentrated in vacuo. The residue was purified by silica gel column chromatography (hexane/EtOAc) to give the title compound (2.7 g) as an off-white solid.

MS (ESI+): [M+H]+ 297.2.

B) 3-(6-Bromo-1-methyl-1H-benzimidazol-2-yl)cyclobutanone

To a stirred solution of N-(4-bromo-2-(methylamino)phenyl)-3-oxocyclobutanecarboxamide (2.7 g) in $CH_3CN$ (20 ml) was added glacial AcOH (2 ml) at room temperature, and then mixture was heated at reflux for 3 h. The mixture was then cooled to room temperature, concentrated in vacuo, and poured into ice-cold saturated $NaHCO_3$ (100 ml). The mixture was extracted with EtOAc, and the extract was washed with water (100 ml) and brine (100 ml), dried over $Na_2SO_4$ and concentrated in vacuo. The residue was purified by silica gel column chromatography (hexane/EtOAc) to give the title compound (2.0 g) as an off-white solid.

MS (ESI+): [M+H]+ 281.2.

C) 4-((4-Fluorobenzyl)oxy)-1-(1-methyl-2-(3-oxocyclobutyl)-1H-benzimidazol-6-yl)pyridin-2(1H)-one The title compound was obtained in an analogous manner to step C in example 5 using 4-((4-fluorobenzyl)oxy)pyridin-2(1H)-one and 3-(6-bromo-1-methyl-1H-benzimidazol-2-yl)cyclobutanone.

MS (ESI+): [M+H]+ 418.0.

Example 114

1-(2-Cyclopropyl-1-methyl-1H-benzimidazol-6-yl)-4-((5-(trifluoromethyl)pyridin-2-yl)methoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (5-(trifluoromethyl)pyridin-2-yl)methanol.

MS (ESI+): [M+H]+ 441.2.

Example 115

1-(2-Cyclopropyl-1-methyl-1H-benzimidazol-6-yl)-4-((3,4-difluorobenzyl)oxy)pyridin-2(1H)-one To a solution of 1-(2-cyclopropyl-1-methyl-1H-benzimidazol-6-yl)-4-hydroxypyridin-2(1H)-one (150 mg), (3,4-difluorophenyl)methanol (153 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM (60 ml), washed with water and brine (30 ml), dried over $Na_2SO_4$ and concentrated in vacuo. The residue was purified by silica gel column chromatography (MeOH/DCM) to give the title compound (85 mg) as a white solid.

MS (ESI+): [M+H]+ 408.0.

$^1$H NMR (400 MHz, DMSO-$d_6$): δ 1.02-1.11 (4H, m), 2.24-2.29 (1H, m), 3.85 (3H, s), 5.14 (2H, s), 5.97 (1H, d, J=2.6 Hz), 6.10 (1H, dd, J=2.7, 7.7 Hz), 7.04 (1H, dd, J=1.8, 8.4 Hz), 7.31-7.37 (1H, m), 7.46-7.60 (5H, m).

Example 116

4-((4-Fluorobenzyl)oxy)-1-(2-(3-hydroxycyclobutyl)-1-methyl-1H-benzimidazol-6-yl)pyridin-2(1H)-one To a stirred solution of 4-((4-fluorobenzyl)oxy)-1-(1-methyl-2-(3-oxocyclobutyl)-1H-benzimidazol-6-yl)pyridin-2(1H)-one (80 mg) in a mixture of THF (10 ml) and MeOH (3 ml) was added $NaBH_4$ (15 mg) at 0° C. The mixture was then allowed to warm to room temperature, and stirred for 3 h. The reaction mixture was then quenched with saturated $NH_4Cl$ (5 ml), and concentrated in vacuo. The residue was purified by silica gel column chromatography (MeOH/DCM) to give the title compound (50 mg) as an off-white solid.

MS (ESI+): [M+H]+ 420.4.

Example 117

1-(2-Cyclopropyl-3-(hydroxymethyl)imidazo[1,2-a]pyridin-6-yl)-4-((4-fluorobenzyl)oxy)pyridin-2(1H)-one

A) 2-Cyclopropyl-6-iodoimidazo[1,2-a]pyridine

A mixture of 2-bromo-1-cyclopropylethanone (18.0 g), 5-iodopyridin-2-amine (5.2 g) and EtOH (100 ml) was heated at reflux for 16 h. The reaction mixture was then cooled to room temperature, and concentrated in vacuo. The resulting residue was diluted with DCM (200 ml), and washed with water (100 ml) and brine (100 ml). The DCM layer was dried over $Na_2SO_4$ and concentrated in vacuo. The crude product thus obtained was purified by silica gel column chromatography (hexane/EtOAc) to give the title compound (1.53 g) as a yellow solid.
MS (ESI+): [M+H]+ 285.0.

B) (2-Cyclopropyl-6-iodoimidazo[1,2-a]pyridin-3-yl)methanol

To a solution of 2-cyclopropyl-6-iodoimidazo[1,2-a]pyridine (1.5 g) in AcOH (20 ml) were added sodium acetate (2.39 g) and 40% aqueous formaldehyde solution (4 ml), and the mixture was heated at 50° C. for 6 h. The reaction mixture was then cooled to room temperature, and concentrated in vacuo.

The resulting residue was diluted with DCM (200 ml), and the DCM layer was washed successively with saturated $NaHCO_3$ (100 ml), water (100 ml) and brine (100 ml). The DCM layer was dried over $Na_2SO_4$ and concentrated in vacuo. The crude product thus obtained was purified by silica gel column chromatography (hexane/EtOAc) to give the title compound (600 mg) as a yellow solid.
MS (ESI+): [M+H]+ 315.2.

C) 1-(2-Cyclopropyl-3-(hydroxymethyl)imidazo[1,2-a]pyridin-6-yl)-4-((4-fluorobenzyl)oxy)pyridin-2(1H)-one The title compound was obtained in an analogous manner to step C in example 5 using 4-((4-fluorobenzyl)oxy)pyridin-2(1H)-one and (2-cyclopropyl-6-iodoimidazo[1,2-a]pyridin-3-yl)methanol.
MS (ESI+): [M+H]+ 406.0.

Example 118

1-(2-Cyclopropyl-3-methylimidazo[1,2-a]pyridin-6-yl)-4-(pyridin-3-ylmethoxy)pyridin-2(1H)-one

A) 1-(2-Cyclopropyl-3-methylimidazo[1,2-a]pyridin-6-yl)-4-hydroxypyridin-2(1H)-one To a stirred solution of 4-(benzyloxy)-1-(2-cyclopropyl-3-methylimidazo[1,2-a]pyridin-6-yl)pyridin-2(1H)-one (127 mg) in MeOH (8 ml) was added Pd/C (10%, 25 mg), and the mixture was stirred under $H_2$ atmosphere at room temperature for 4 h. The solid was then filtered through Celite, and the filtrate was concentrated in vacuo. The residue was purified by silica gel column chromatography (MeOH/DCM) to give the title compound (56 mg) as an off-white solid.
MS (ESI+): [M+H]+ 282.2.

B) 1-(2-Cyclopropyl-3-methylimidazo[1,2-a]pyridin-6-yl)-4-(pyridin-3-ylmethoxy)pyridin-2(1H)-one The title compound was obtained in an analogous manner to example 75 using 1-(2-cyclopropyl-3-methylimidazo[1,2-a]pyridin-6-yl)-4-hydroxypyridin-2(1H)-one and pyridin-3-ylmethanol.
MS (ESI+): [M+H]+ 373.4.

Example 119

1-(2-Cyclopropyl-1-methyl-1H-benzimidazol-6-yl)-4-((3,5-difluorobenzyl)oxy)pyridin-2(1H)-one To a solution of 1-(2-cyclopropyl-1-methyl-1H-benzimidazol-6-yl)-4-hydroxypyridin-2(1H)-one (150 mg), (3,5-difluorophenyl)methanol (153 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (56 mg) as an off-white solid.
MS (ESI+): [M+H]+ 408.6.
$^1$H NMR (400 MHz, DMSO-$d_6$): δ 1.04-1.09 (4H, m), 2.26 (1H, m), 3.85 (3H, s), 5.19 (2H, s), 5.95 (1H, d, J=2.6 Hz), 6.13 (1H, dd, J=2.6, 7.6 Hz), 7.04 (1H, dd, J=1.7, 8.5 Hz), 7.21-7.25 (3H, m), 7.50-7.52 (2H, m), 7.60 (1H, d, J=7.6 Hz).

Example 120

4-(((1-(2-Cyclopropyl-1-methyl-1H-benzimidazol-6-yl)-2-oxo-1,2-dihydropyridin-4-yl)oxy)methyl)benzonitrile The title compound was obtained in an analogous manner to example 75 using 1-(2-cyclopropyl-1-methyl-1H-benzimidazol-6-yl)-4-hydroxypyridin-2(1H)-one and 4-(hydroxymethyl)benzonitrile
MS (ESI+): [M+H]+ 397.2.

Example 121

4-((5-Chloro-2-thienyl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (150 mg), (5-chloro-2-thienyl)methanol (158 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, and washed with water and brine, dried over $Na_2SO_4$ and concentrated in vacuo. The residue was purified by silica gel column chromatography (MeOH/DCM) to give the title compound (72 mg) as a white solid.
MS (ESI+): [M+H]+ 412.3.
$^1$H NMR (400 MHz, DMSO-$d_6$): δ 1.02-1.11 (4H, m), 2.23-2.28 (1H, m), 3.85 (3H, s), 5.29 (2H, s), 6.03-6.07 (2H, m), 7.02 (1H, dd, J=1.8, 8.5 Hz), 7.08 (1H, d, J=3.7 Hz), 7.16 (1H, d, J 3.8, Hz), 7.51 (2H, dd, J=3.5, 5.4 Hz), 7.57 (1H, d, J=7.4 Hz).

Example 122

1-(2-Cyclopropyl-3-methylimidazo[1,2-a]pyridin-6-yl)-4-(pyridin-4-ylmethoxy)pyridin-2(1H)-one The title compound was obtained in an analogous manner to example 75 using 1-(2-cyclopropyl-3-methylimidazo[1,2-a]pyridin-6-yl)-4-hydroxypyridin-2(1H)-one and pyridin-4-ylmethanol.
MS (ESI+): [M+H]+ 373.3.

Example 123

1-(2-Cyclopropyl-3-(methoxymethyl)imidazo[1,2-a]pyridin-6-yl)-4-((4-fluorobenzyl)oxy)pyridin-2(1H)-one To a stirred suspension of NaH (40% oil dispersion, 22 mg) in THF (9 ml) was added a solution of 1-(2-cyclopropyl-3-(hydroxymethyl)imidazo[1,2-a]pyridin-6-yl)-4-((4-fluorobenzyl)oxy)pyridin-2(1H)-one (100 mg) in THF (1 ml) at 0° C., and then the mixture was allowed to warm to room temperature and stirred for 30 min. Iodomethane (22 pa) in THF (0.5 ml) was added, and the resulting mixture was stirred at room temperature for 16 h. The reaction mixture was quenched with ice-water and extracted with DCM. The combined DCM layer was washed with brine, dried over $Na_2SO_4$ and concentrated in vacuo. The crude product was purified by silica gel column chromatography (MeOH/DCM) followed by recrystallization from DCM/hexane to give the title compound (40 mg) as a white solid.
MS (ESI+): [M+H]+ 420.3.

Example 124

1-(2-Cyclopropyl-1-methyl-1H-benzimidazol-6-yl)-4-(2-thienylmethoxy)pyridin-2(1H)-one To a solution of 1-(2-cyclopropyl-1-methyl-1H-benzimidazol-6-yl)-4-hydroxypyridin-2(1H)-one (150 mg), 2-thienylmethanol (100 μL) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, and the DCM layer was washed with water and brine, dried over $Na_2SO_4$ and concentrated in vacuo. The residue was purified by silica gel column chromatography (MeOH/DCM) to give the title compound (60 mg) as a white solid.
MS (ESI+): [M+H]+ 377.8.
$^1$H NMR (400 MHz, DMSO-$d_6$): δ 1.04-1.11 (4H, m), 2.24-2.28 (1H, m), 3.85 (3H, s), 5.34 (2H, s), 6.05-6.07 (2H, m), 7.03-7.08 (2H, m), 7.27 (1H, d, J=2.8 Hz), 7.50-7.52 (2H, m), 7.57 (1H, d, J=7.2 Hz), 7.61 (1H, d, J=4.9 Hz).

Example 125

4-((4-Fluorobenzyl)oxy)-1-(3-methyl-2-(5-methyl-1,3,4-oxadiazol-2-yl)imidazo[1,2-a]pyridin-6-yl)pyridin-2(1H)-one A) 6-Iodo-3-methylimidazo[1,2-a]pyridine-2-carbohydrazide To a stirred solution of ethyl 6-iodo-3-methylimidazo[1,2-a]pyridine-2-carboxylate (250 mg) in EtOH (5 ml) was added hydrazine hydrate (0.14 ml) at room temperature. The reaction vessel was sealed and heated at 80° C. for 16 h. The mixture was then cooled to room temperature, and the reaction mixture was concentrated in vacuo. The residue was washed with EtOAc to give the title compound (200 mg) as a light yellow solid.
MS (ESI+): [M+H]+ 317.0.

B) 6-Iodo-3-methyl-2-(5-methyl-1,3,4-oxadiazol-2-yl)imidazo[1,2-a]pyridine

To a stirred solution of 6-iodo-3-methylimidazo[1,2-a]pyridine-2-carbohydrazide (200 mg) in AcOH (0.5 ml) was added triethyl orthoacetate (2 ml) at room temperature, and the reaction mixture was heated at reflux for 4 h. The mixture was then cooled to room temperature, and the reaction mixture was concentrated in vacuo. The residue was diluted with EtOAc, and the EtOAc layer was washed with water and brine, dried over $Na_2SO_4$ and concentrated in vacuo. The residue was purified by silica gel column chromatography (MeOH/DCM) to give the title compound (100 mg) as a light yellow solid.
MS (ESI+): [M+H]+ 340.8.

C) 4-((4-Fluorobenzyl)oxy)-1-(3-methyl-2-(5-methyl-1,3,4-oxadiazol-2-yl)imidazo[1,2-a]pyridin-6-yl)pyridin-2(1H)-one The title compound was obtained in an analogous manner to step C in example 5 using 6-iodo-3-methyl-2-(5-methyl-1,3,4-oxadiazol-2-yl)imidazo[1,2-a]pyridine and 4-((4-fluorobenzyl)oxy)pyridin-2(1H)-one.
MS (ESI+): [M+H]+ 432.2.

Example 126

4-(Benzyloxy)-1-(1-methyl-2-propyl-1H-benzimidazol-6-yl)pyridin-2(1H)-one

A) 6-Bromo-1-methyl-2-propyl-1H-benzimidazole

To a stirred mixture of butyric acid (986 mg) and 4-bromo-$N^2$-methylbenzene-1,2-diamine (1.5 g) was added $POCl_3$ (10 ml), and the mixture was heated at reflux for 1 h. The mixture was then cooled to room temperature, and concentrated in vacuo. The residue was poured into ice-cold saturated $NaHCO_3$. The mixture was extracted with EtOAc, washed with brine, dried over $Na_2SO_4$ and concentrated in vacuo. The crude product thus obtained was purified by silica gel column chromatography (hexane/EtOAc) to give the title compound (1.4 g) as an off-white solid.
MS (ESI+): [M+H]+ 252.8.

B) 4-(Benzyloxy)-1-(1-methyl-2-propyl-1H-benzimidazol-6-yl)pyridin-2(1H)-one

To a stirred degassed mixture of 6-bromo-1-methyl-2-propyl-1H-benzimidazole (680 mg), 4-(benzyloxy)pyridin-2(1H)-one (450 mg), potassium carbonate (927 mg) and dioxane (15 ml) were added copper iodide (170 mg) and trans-N,N'-dimethylcyclohexane-1,2-diamine (128 mg). The reaction vessel was sealed and heated at 110° C. for 16 h. The reaction mixture was then cooled to room temperature, and concentrated in vacuo. The residue was diluted with DCM, washed with brine, dried over $Na_2SO_4$ and concentrated in vacuo. The residue was purified by silica gel column chromatography (MeOH/DCM) to give the title compound (320 mg) as an off-white solid.

MS (ESI+): [M+H]+ 374.0.

$^1$H NMR (400 MHz, DMSO-d$_6$): δ 0.99 (3H, t, J=7.4 Hz), 1.78-1.83 (2H, m), 2.86 (2H, t, =7.5 Hz), 3.74 (3H, s), 5.15 (2H, s), 5.98 (1H, d, J=2.6 Hz), 6.09 (1H, dd, J=2.6, 7.5 Hz), 7.06 (1H, dd, J=1.9, 8.4 Hz), 7.37-7.48 (5H, m), 7.53 (1H, d, J=1.7 Hz), 7.58 (2H, d, J=7.8 Hz).

Example 127

4-((3-Chlorobenzyl)oxy)-1-(2-cyclopropyl-1-methyl-1H-benzimidazol-6-yl)pyridin-2(1H)-one A) 4-((3-Chlorobenzyl)oxy)pyridine 1-oxide To an ice-cold suspension of NaH (40% oil dispersion, 1.51 g) in THF (60 ml) was added (3-chlorophenyl)methanol (3.0 g) at 0° C. The reaction mixture was stirred at the same temperature for 30 min followed by the portionwise addition of 4-chloropyridine 1-oxide (2.73 g) at 0° C. The resulting reaction mixture was stirred for 1 h at 0° C. and then warmed to room temperature. After 2 h, the reaction mixture was poured into ice-water (100 g) and extracted with DCM. The DCM layer was washed with brine, dried over Na$_2$SO$_4$ and concentrated in vacuo. The residue was triturated with Et$_2$O to give the title compound (2.2 g) as a brown solid.

MS (ESI+): [M+H]+ 236.0.

B) 4-((3-Chlorobenzyl)oxy)pyridin-2(1H)-one

To 4-((3-chlorobenzyl)oxy)pyridine 1-oxide (2.0 g) was added acetic anhydride (20 ml), and the solution was heated at reflux for 4 h. The reaction mixture was then cooled to room temperature and concentrated in vacuo. The residue was diluted with MeOH/NaOH (1:1, 150 ml) and heated at reflux for 1 h. The reaction mixture was cooled to room temperature and concentrated in vacuo. The residue was diluted with water and extracted with DCM. The combined DCM layer was concentrated in vacuo and the crude residue was purified by silica gel column chromatography (MeOH/DCM) to give the title compound (984 mg) as an off-white solid.

MS (ESI+): [M+H]+ 236.0.

C) 4-((3-Chlorobenzyl)oxy)-1-(2-cyclopropyl-1-methyl-1H-benzimidazol-6-yl)pyridin-2(1H)-one To a stirred degassed mixture of 6-bromo-2-cyclopropyl-1-methyl-1H-benzimidazole (694 mg), 4-((3-chlorobenzyl)oxy)pyridin-2(1H)-one (500 mg) and potassium carbonate (588 mg) in dioxane (30 ml) were added copper iodide (80 mg) and trans-N,N'-dimethylcyclohexane-1,2-diamine (60 mg). The reaction vessel was sealed and heated at 110° C. for 16 h. The reaction mixture was then cooled to room temperature, and the volatile matters were removed in vacuo. The residue was diluted with DCM, washed with brine, dried over Na$_2$SO$_4$ and concentrated in vacuo. The residue was purified by silica gel column chromatography (MeOH/DCM) followed by recrystallization from dioxane/water to give the title compound (252 mg) as a white solid.

MS (ESI+): [M+H]+ 405.8.

$^1$H NMR (400 MHz, DMSO-d$_6$): δ 1.02-1.11 (4H, m), 2.25-2.29 (1H, m), 3.85 (3H, s), 5.18 (2H, s), 5.97 (1H, d, J=2.4 Hz), 6.12 (1H, dd, J=2.5, 8.5 Hz), 7.04 (1H, dd, J=1.6, 8.5 Hz), 7.43-7.48 (3H, m), 7.49-7.55 (3H, m), 7.59 (1H, d, J=7.6 Hz).

Example 128

1-(2-Cyclopropyl-3-methylimidazo[1,2-a]pyridin-6-yl)-4-(pyrimidin-5-ylmethoxy)pyridin-2(1H)-one The title compound was obtained in an analogous manner to example 75 using 1-(2-cyclopropyl-3-methylimidazo[1,2-a]pyridin-6-yl)-4-hydroxypyridin-2(1H)-one and pyrimidin-5-ylmethanol.

MS (ESI+): [M+H]+ 374.2.

Example 129

1-(2-Cyclopropyl-1-methyl-1H-benzimidazol-6-yl)-4-((2-methyl-1,3-thiazol-5-yl)methoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (2-methyl-1,3-thiazol-5-yl)methanol.

MS (ESI+): [M+H]+ 393.0.

Example 130

1-(2-Cyclopropyl-3-methylimidazo[1,2-a]pyridin-6-yl)-4-((3-fluorobenzyl)oxy)pyridin-2(1H)-one To a solution of 1-(2-cyclopropyl-3-methylimidazo[1,2-a]pyridin-6-yl)-4-hydroxypyridin-2(1H)-one (150 mg), (3-fluorophenyl)-methanol (134 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature and concentrated in vacuo. The residue was diluted with DCM (100 ml), and the DCM layer was washed with water and brine, dried over Na$_2$SO$_4$ and concentrated in vacuo. The residue was purified by silica gel column chromatography (MeOH/DCM) to give the title compound (45 mg) as a white solid.

MS (ESI+): [M+H]+ 389.8.

$^1$H NMR (400 MHz, DMSO-d$_6$): δ 0.88-0.94 (4H, m), 2.04-2.10 (1H, m), 2.47 (3H, m), 5.19 (2H, s), 5.99 (1H, d, J=2.7 Hz), 6.16 (1H, dd, J=2.8, 7.7 Hz), 7.11 (1H, dd, J=1.9, 9.5 Hz), 7.19-7.23 (1H, m), 7.31 (2H, d, J=7.4 Hz), 7.42-7.51 (2H, m), 7.66 (1H, d, J=7.6 Hz), 8.37 (1H, d, J=1.4 Hz).

Example 131

4-((4-Chloro-3-fluorobenzyl)oxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (100 mg), (4-chloro-3-fluorophenyl)methanol (114 mg) and tributylphosphine (258 μl) in THF (15 ml) was added 1,1'-(azodicarbonyl)dipiperidine (265 mg). The mixture was stirred under sonication at 60° C. for 2 h. The reaction mixture was then cooled to room temperature, and concentrated in vacuo. The residue was diluted with DCM, washed with water and brine, dried over Na$_2$SO$_4$ and concentrated in vacuo. The residue was purified by silica gel column chromatography (MeOH/DCM) to give the title compound (25 mg) as an off-white solid.

MS (ESI+): [M+H]+ 397.2.

$^1$H NMR (400 MHz, DMSO-d$_6$): δ 1.03-1.09 (4H, m), 2.25-2.28 (1H, m), 3.85 (3H, s), 5.18 (2H, s), 5.96 (1H, d,

J=2.6 Hz), 6.11 (1H, dd, J=2.6, 7.6 Hz), 7.04 (1H, dd, J=1.8, 8.4 Hz), 7.35 (1H, d, J=9.4 Hz), 7.51-7.55 (3H, m), 7.59 (1H, d, J 7.6 Hz), 7.66 (1H, t, J=8.0 Hz).

Example 132

1-(2-Cyclopropyl-3-methylimidazo[1,2-a]pyridin-6-yl)-4-(2-thienylmethoxy)pyridin-2(1H)-one To a solution of 1-(2-cyclopropyl-3-methylimidazo[1,2-a]pyridin-6-yl)-4-hydroxypyridin-2(1H)-one (150 mg), 2-thienylmethanol (121 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (45 mg) as an off-white solid.
MS (ESI+): [M+H]+ 378.3.
$^1$H NMR (400 MHz, DMSO-$d_6$): δ 0.88-0.92 (4H, m), 2.06-2.08 (1H, m), 2.47 (3H, s), 5.35 (2H, s), 6.07-6.12 (2H, m), 7.07 (1H, dd, J=3.5, 4.9 Hz), 7.09-7.13 (1H, m), 7.27 (1H, d, J=3.1 Hz), 7.43 (1H, d, J=9.4 Hz), 7.61 (1H, d, J=5.0 Hz), 7.64 (1H, d, J=7.5 Hz), 8.37 (1H, s).

Example 133

1-(2-Cyclopropyl-3-methylimidazo[1,2-a]pyridin-6-yl)-4-(3-thienylmethoxy)pyridin-2(1H)-one To a solution of 1-(2-cyclopropyl-3-methylimidazo[1,2-a]pyridin-6-yl)-4-hydroxypyridin-2(1H)-one (150 mg), 3-thienylmethanol (121 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (80 mg) as a white solid.
MS (ESI+): [M+H]+ 378.3.
$^1$H NMR (400 MHz, DMSO-$d_6$): δ 0.88-0.94 (4H, m), 2.04-2.10 (1H, m), 2.47 (3H, s), 5.15 (2H, s), 6.02 (1H, d, J=2.6 Hz), 6.10 (1H, dd, J=2.6, 7.6 Hz), 7.07 (1H, dd, J=1.8, 9.5 Hz), 7.19 (1H, d, J=4.9 Hz), 7.43 (1H, d, J=9.4 Hz), 7.59 (1H, dd, J=2.9, 4.8 Hz), 7.64-7.66 (2H, m), 8.37 (1H, s).

Example 134

4-((4-Fluorobenzyl)oxy)-1-(2-(3-hydroxy-3-methylcyclobutyl)-1-methyl-1H-benzimidazol-6-yl)pyridin-2(1H)-one To a stirred suspension of cerium chloride (532 mg) in THF (30 ml) was added methyllithium (3 M in diethoxymethane, 719 μl) at −78° C. A cold solution of 4-((4-fluorobenzyl)oxy)-1-(1-methyl-2-(3-oxocyclobutyl)-1H-benzimidazol-6-yl)pyridin-2(1H)-one (150 mg) in dry THF (3 ml) was slowly added to the reaction mixture at −78° C. and stirred for 1 h at the same temperature. The reaction mixture was quenched with saturated $NH_4Cl$ at −78° C. and then warmed up to room temperature. The mixture was extracted with DCM, washed with brine, dried over $Na_2SO_4$ and concentrated in vacuo. The residue was purified by silica gel column chromatography (MeOH/DCM) followed by purification by preparative HPLC to give the title compound (33 mg) as a white solid.
MS (ESI+): [M+H]+ 434.3.

Example 135

1-(2-Cyclopropyl-1-methyl-1H-benzimidazol-6-yl)-4-(furan-2-ylmethoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and furan-2-ylmethanol.
MS (ESI+): [M+H]+ 361.8.

Example 136

4-((4-Chlorobenzyl)oxy)-1-(2-((1RS,2RS)-2-fluorocyclopropyl)-1-methyl-1H-benzimidazol-6-yl)pyridin-2(1H)-one A mixture of 1-(4-amino-3-(methylamino)phenyl)-4-((4-chlorobenzyl)oxy)pyridin-2(1H)-one (200 mg), HATU (224 mg), cis-2-fluoro-cyclopropanecarboxylic acid (100 mg), N,N-diisopropylethylamine (288 μl) and DMF (4 ml) was stirred at room temperature under a dry atmosphere ($CaCl_2$ tube) for 1 h. The mixture was quenched with water and extracted with EtOAc. The organic layer was separated, washed with water and brine, dried over $MgSO_4$ and concentrated in vacuo. The residue was dissolved in AcOH (4.0 ml) and stirred at 90° C. for 1 h. After AcOH was evaporated, the residue was purified by NH silica gel column chromatography (hexane/EtOAc). The resulting solid was recrystallized from EtOH to give the title compound (37.6 mg) as an off-white solid.
MS (ESI+): [M+H]+ 424.1.
$^1$H NMR (400 MHz, DMSO-$d_6$): δ 1.32-1.48 (1H, m), 1.85-2.01 (1H, m), 3.85 (3H, s), 5.00-5.25 (3H, m), 5.98 (1H, d, J=2.8 Hz), 6.11 (1H, dd, J=2.8, 7.7 Hz), 7.09 (1H, dd, J=1.9, 8.4 Hz), 7.50 (4H, s), 7.56 (1H, d, J=1.8 Hz), 7.61 (2H, d, J 8.0 Hz). 1H was overlapped with DMSO peak, and not detected.

Example 137

4-((4-Chlorobenzyl)oxy)-1-(2-((1RS,2SR)-2-fluorocyclopropyl)-1-methyl-1H-benzimidazol-6-yl)pyridin-2(1H)-one A mixture of 1-(4-amino-3-(methylamino)phenyl)-4-((4-chlorobenzyl)oxy)pyridin-2(1H)-one (200 mg), HATU (224 mg), trans-2-fluoro-cyclopropanecarboxylic acid (100 mg), N,N-diisopropylethylamine (288 μl) and DMF (4 ml) was stirred at room temperature under a dry atmosphere ($CaCl_2$ tube) for 1 h. The mixture was quenched with water and extracted with EtOAc. The organic layer was separated, washed with water and brine, dried over $MgSO_4$ and concentrated in vacuo. The residue was dissolved in AcOH (4.0 ml) and stirred at 90° C. for 1 h. After AcOH was evaporated, the residue was purified by NH silica gel column chromatography (hexane/EtOAc). The resulting solid was recrystallized from EtOH to give the title compound (25.8 mg) as a pale yellow solid.
MS (ESI+): [M+H]+424.1.
$^1$H NMR (400 MHz, DMSO-$d_6$): δ 1.39-1.50 (1H, m), 1.64-1.82 (1H, m), 2.85-3.00 (1H, m), 3.88 (3H, s), 4.96-5.20

(3H, m), 5.97 (1H, d, J=2.8 Hz), 6.10 (1H, dd, J=2.7, 7.6 Hz), 7.07 (1H, dd, J=2.0, 8.4 Hz), 7.50 (4H, s), 7.52-7.56 (2H, m), 7.58 (1H, d, J=7.5 Hz).

Example 138

Methyl(1RS,2SR)-2-(6-(4-((4-Chlorobenzyl)oxy)-2-oxopyridin-1(2H)-yl)-1-methyl-1H-benzimidazol-2-yl)cyclopropanecarboxylate Iodomethane (0.111 ml) was added to a solution of (1RS, 2SR)-2-(6-(4-((4-chlorobenzyl)oxy)-2-oxopyridin-1(2H)-yl)-1-methyl-1H-benzimidazol-2-yl)cyclopropanecarboxylic acid (400 mg) and potassium carbonate (246 mg) in DMF (5 ml) at room temperature. The mixture was stirred at room temperature for 1 h. The mixture was quenched with water at room temperature and extracted with EtOAc. The organic layer was separated, washed with water and brine, dried over $MgSO_4$ and concentrated in vacuo. The residue was purified by NH silica gel column chromatography (MeOH/EtOAc) to give the title compound (205 mg) as a pink solid.
MS (ESI+): [M+H]+ 464.1.

Example 139

4-((5-Chloro-2-thienyl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (150 mg), (5-chloro-2-thienyl)methanol (158 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (7 mg) as a white solid.
MS (ESI+): [M+H]+ 412.4.
$^1$H NMR (400 MHz, DMSO-$d_6$): δ 0.88-0.91 (4H, m), 2.05-2.08 (1H, m), 2.47 (3H, s), 5.30 (2H, s), 6.06 (1H, d, J=2.5 Hz), 6.09 (1H, dd, J=2.5, 7.5 Hz), 7.08-7.12 (2H, m), 7.17 (1H, d, J=3.7 Hz), 7.43 (1H, d, J=9.4 Hz), 7.65 (1H, d, J=7.6 Hz), 8.36 (1H, s).

Example 140

1-(2-Cyclopropyl-1-methyl-1H-benzimidazol-6-yl)-4-((5-methoxypyridin-2-yl)methoxy)pyridin-2(1H)-one The title compound was obtained in an analogous manner to example 75 using (5-methoxypyridin-2-yl)methanol and 1-(2-cyclopropyl-1-methyl-1H-benzimidazol-6-yl)-4-hydroxypyridin-2(1H)-one.
MS (ESI+): [M+H]+ 403.0.

Example 141

1-(2-Cyclopropyl-1-methyl-1H-benzimidazol-6-yl)-4-((5-methylpyridin-2-yl)methoxy)pyridin-2(1H)-one The title compound was obtained in an analogous manner to example 75 using (5-methylpyridin-2-yl)methanol and 1-(2-cyclopropyl-1-methyl-1H-benzimidazol-6-yl)-4-hydroxypyridin-2(1H)-one.
MS (ESI+): [M+H]+ 387.2.

Example 142

1-(2-Cyclopropyl-1-methyl-1H-benzimidazol-6-yl)-4-((4-methylbenzyl)oxy)pyridin-2(1H)-one To a solution of 1-(2-cyclopropyl-1-methyl-1H-benzimidazol-6-yl)-4-hydroxypyridin-2(1H)-one (170 mg), (4-methylphenyl)methanol (148 mg) and tributylphosphine (454 µl) in THF (15 ml) was added 1,1'-(azodicarbonyl)dipiperidine (458 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (50 mg) as an off-white solid.
MS (ESI+): [M+H]+ 386.2.
$^1$H NMR (400 MHz, DMSO-$d_6$): δ 1.02-1.09 (4H, m), 2.24-2.28 (1H, m), 2.32 (3H, s), 3.84 (3H, s), 5.09 (2H, s), 5.95 (1H, d, J=2.5 Hz), 6.07 (1H, dd, J=2.7, 7.6 Hz), 7.03 (1H, dd, J=1.8, 8.5 Hz), 7.23 (2H, d, J=7.9 Hz), 7.35 (2H, d, J=7.8 Hz), 7.50-7.52 (2H, m), 7.56 (1H, d, J=7.6 Hz).

Example 143

4-((5-Chloro-3-thienyl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (150 mg), (5-chloro-3-thienyl)methanol (158 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) followed by preparative HPLC to give the title compound (20 mg) as a white solid.
MS (ESI+): [M+H]+ 412.0.
$^1$H NMR (400 MHz, DMSO-$d_6$): δ 1.02-1.11 (4H, m), 2.24-2.32 (1H, m), 3.85 (3H, s), 5.05 (2H, s), 5.98 (1H, d, J=2.6 Hz), 6.06 (1H, dd, J=2.7, 7.6 Hz), 7.03 (1H, dd, J=1.8, 8.5 Hz), 7.20 (1H, d, J=1.5 Hz), 7.51 (2H, dd, J=3.5, 5.4 Hz), 7.56-7.58 (2H, m).

Example 144

4-((4-Fluorobenzyl)oxy)-1-(1-methyl-2-(1,2-oxazol-5-yl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 1,2-oxazole-5-carboxylic acid.
MS (ESI+): [M+H]+ 417.1

Example 145

4-((4-Fluorobenzyl)oxy)-1-(1-methyl-2-(5-methyl-1,3-oxazol-4-yl)-1H-benzimidazol-6-yl)pyridin-2(1H)-one The title compound was obtained in an analogous manner to step C in example 13 using 1-(4-amino-3-(methylamino)

phenyl)-4-((4-fluorobenzyl)oxy)pyridin-2(1H)-one and 5-methyl-1,3-oxazole-4-carboxylic acid.
MS (ESI+): [M+H]+ 431.1.

Example 146

1-(2-Cyclopropyl-3-methylimidazo[1,2-a]pyridin-6-yl)-4-((3,4-difluorobenzyl)oxy)pyridin-2(1H)-one To a solution of 1-(2-cyclopropyl-3-methylimidazo[1,2-a]pyridin-6-yl)-4-hydroxypyridin-2(1H)-one (150 mg), (3,4-difluorophenyl)methanol (153 mg) and tributylphosphine (322 mg) in THF (15 ml) was added 1,1'-(azodicarbonyl)dipiperidine (401 mg). The mixture was stirred under sonication at 60° C. for 4 h. The reaction mixture was then cooled to room temperature, and concentrated in vacuo. The residue was diluted with DCM, washed with water and brine, dried over $Na_2SO_4$ and concentrated in vacuo. The residue was purified by silica gel column chromatography (MeOH/DCM) to give the title compound (40 mg) as a white solid.
MS (ESI+): [M+H]+ 408.0.
$^1$H NMR (400 MHz, DMSO-$d_6$): δ 0.88-0.92 (4H, m), 2.06-2.08 (1H, m), 5.14 (2H, s), 6.00 (1H, d, J=2.4 Hz), 6.15 (1H, dd, J=2.5, 7.6 Hz), 7.11 (1H, d, J=9.4 Hz), 7.34 (1H, m), 7.43 (1H, d, J=9.4 Hz), 7.48-7.51 (1H, m), 7.55-7.60 (1H, m), 7.66 (1H, d, J=7.64 Hz), 8.37 (1H, s). 3H was overlapped with DMSO peak, and not detected.

Example 147

4-((4-Chlorobenzyl)oxy)-1-(2-ethyl-3-methylimidazo[1,2-a]pyridin-6-yl)pyridin-2(1H)-one A) 2-Bromopentan-3-one To a stirred solution of pentan-3-one (5.0 g) in $Et_2O$ (50 ml) was added a solution of bromine (2.5 ml) in $Et_2O$ (50 ml) over a period of 2 h at 0° C., and then the mixture was stirred at room temperature for 4 h. The reaction mixture was then quenched with aqueous sodium thiosulfate (0.1 M, 100 ml) at 0° C. The reaction mixture was then extracted with ether, washed with water and brine, dried over $Na_2SO_4$ and concentrated in vacuo to give the title compound (6.0 g) as a brown liquid.
$^1$H NMR (400 MHz, DMSO-$d_6$): δ 0.98 (3H, t, J=6.3 Hz), 1.63 (3H, d, J=6.6 Hz), 2.56-2.66 (1H, m), 2.74-2.83 (1H, m), 4.79 (1H, q, J=6.8 Hz).

B) 2-Ethyl-6-iodo-3-methylimidazo[1,2-a]pyridine

To a stirred mixture of 2-bromopentan-3-one (2.0 g), 2-amino-5-iodopyridine (1.0 g) and EtOH (50 ml) was heated at reflux for 16 h. The reaction mixture was cooled and concentrated in vacuo. The residue was diluted with water (100 ml), and extracted with DCM. The DCM layer was washed with brine, dried over $Na_2SO_4$ and concentrated in vacuo. The residue was purified by silica gel column chromatography (hexane/EtOAc) to give the title compound (400 mg) as a yellow solid.
MS (ESI+): [M+H]+ 286.8.

C) 4-((4-Chlorobenzyl)oxy)-1-(2-ethyl-3-methylimidazo[1,2-a]pyridin-6-yl)pyridin-2(1H)-one To a stirred degassed mixture of 2-ethyl-6-iodo-3-methylimidazo[1,2-a]pyridine (400 mg), 4-((4-chlorobenzyl)oxy)pyridin-2(1H)-one (263 mg), potassium carbonate (462 mg) and dioxane (5 ml) were added copper iodide (42 mg) and trans-N,N'-dimethylcyclohexane-1,2-diamine (31 mg). The reaction vessel was sealed and heated at 110° C. for 16 h. The reaction mixture was then cooled to room temperature and concentrated in vacuo. The residue was diluted with DCM, and the DCM layer was washed with brine, dried over $Na_2SO_4$ and concentrated in vacuo. The residue was purified by silica gel column chromatography (MeOH/DCM) to give the title compound (110 mg) as an off-white solid.
MS (ESI+): [M+H]+ 394.0.

Example 148

(1RS,2SR)-2-(6-(4-((4-Chlorobenzyl)oxy)-2-oxopyridin-1(2H)-yl)-1-methyl-1H-benzimidazol-2-yl)cyclopropanecarbonitrile A) (1RS,2SR)-2-(6-(4-((4-Chlorobenzyl)oxy)-2-oxopyridin-1(2H)-yl)-1-methyl-1H-benzimidazol-2-yl)cyclopropanecarboxylic acid A mixture of 1-(4-amino-3-(methylamino)phenyl)-4-((4-chlorobenzyl)oxy)pyridin-2(1H)-one (2.0 g), 3-oxabicyclo[3.1.0]hexane-2,4-dione (0.662 g) and triethylamine (1.175 ml) in THF (80 ml) was stirred at room temperature overnight. After concentration of the mixture in vacuo, AcOH (80 ml) was added to the residue. The mixture was stirred at 80° C. for 1 h. After concentration of the mixture in vacuo, the mixture was neutralized with saturated $NaHCO_3$ solution at 0° C. and extracted with EtOAc. The organic layer was separated, washed with water and brine, dried over $MgSO_4$ and concentrated in vacuo. The resulting solid was washed with IPE and dried to give the title compound (1.67 g) as a brown solid.
MS (ESI+): [M+H]+ 450.1.

B) (1RS,2SR)-2-(6-(4-((4-Chlorobenzyl)oxy)-2-oxopyridin-1(2H)-yl)-1-methyl-1H-benzimidazol-2-yl)cyclopropanecarboxamide To a solution of (1RS,2SR)-2-(6-(4-((4-chlorobenzyl)μ)oxy)-2-oxopyridin-1(2H)-yl)-1-methyl-1H-benzimidazol-2-yl)cyclopropanecarboxylic acid (500 mg, 1.11 mmol) and triethylamine (0.465 ml, 3.33 mmol) in THF (10 ml) was added ethyl carbonochloridate (0.319 ml, 3.33 mmol) dropwise at 0° C. Stirring was continued at 0° C. for 1.5 h and then 28% $NH_3$ solution (0.34 ml, 5.57 mmol) was added dropwise. The reaction mixture was stirred at room temperature for 3 h and then concentrated in vacuo. The resulting solid was washed with IPE to give the title compound (195 mg) as a white solid.
MS (ESI+): [M+H]+ 449.1.

C) (1RS,2SR)-2-(6-(4-((4-Chlorobenzyl)oxy)-2-oxopyridin-1(2H)-yl)-1-methyl-1H-benzimidazol-2-yl)cyclopropanecarbonitrile Trifluoroacetic anhydride (0.181 ml) was added to a solution of (1RS,2SR)-2-(6-(4-((4-chlorobenzyl)oxy)-2-oxopyridin-1(2H)-yl)-1-methyl-1H-benzimidazol-2-yl)cyclopropanecarboxamide (195 mg) and pyridine (0.105 ml) in THF (5 ml) at 0° C. The mixture was stirred at 0° C. for 2 h. The mixture was quenched with saturated $NaHCO_3$ solution at 0° C. and extracted with EtOAc. The organic layer was separated, washed with water and brine, dried over $MgSO_4$ and concentrated in vacuo. The residue was purified by silica gel column chromatography (MeOH/EtOAc). The residue was recrystallized from EtOH/hexane to give the title compound (35 mg) as a white solid.

MS (ESI+): [M+H]+ 431.1.

$^1$H NMR (400 MHz, DMSO-$d_6$): δ 1.62-1.77 (1H, m), 1.96-2.07 (1H, m), 2.37-2.46 (1H, m), 2.91-3.05 (1H, m), 3.90 (3H, s), 5.16 (2H, s), 5.99 (1H, d, J=2.3 Hz), 6.11 (1H, dd, J=2.5, 7.8 Hz), 7.12 (1H, d, J=8.3 Hz), 7.50 (4H, s), 7.60-7.68 (3H, m).

Example 149

4-((4-Chlorobenzyl)oxy)-1-(2-((1RS,2SR)-2-(hydroxymethyl)cyclopropyl)-1-methyl-1H-benzimidazol-6-yl)pyridin-2(1H)-one A suspension of methyl(1RS,2SR)-2-(6-(4-((4-chlorobenzyl)oxy)-2-oxopyridin-1(2H)-yl)-1-methyl-1H-benzimidazol-2-yl)cyclopropanecarboxylate (200 mg) in THF (1.5 ml) and MeOH (0.750 ml) was added dropwise to a solution of NaBH$_4$ (32.6 mg) and CaCl$_2$ (71.8 mg) in THF (3 ml) and MeOH (2 ml) at 0° C. The mixture was stirred at room temperature under Ar atmosphere overnight. NaBH$_4$ (300 mg) was added to the m resulting mixture at 50° C., and the mixture was stirred at 50° C. overnight. The mixture was neutralized with 1 M HCl at 0° C. and extracted with EtOAc. The organic layer was separated, washed with saturated NaHCO$_3$ solution and brine, dried over MgSO$_4$ and concentrated in vacuo. The residue was purified by NH silica gel column chromatography (hexane/EtOAc) to give the title compound (156 mg) as a white solid.

MS (ESI+): [M+H]+ 436.1.

$^1$H NMR (400 MHz, CDCl$_3$): δ 0.88-0.95 (1H, m), 1.30-1.37 (1H, m), 1.79-1.90 (1H, m), 2.07-2.15 (1H, m), 3.30 (1H, t, J=10.8 Hz), 3.84 (3H, s), 4.05-4.16 (1H, m), 5.03 (2H, s), 5.52 (1H, brs), 6.03-6.09 (2H, m), 7.13 (1H, dd, J=1.9, 8.4 Hz), 7.29-7.33 (1H, m), 7.34-7.42 (5H, m), 7.70 (1H, d, J=8.5 Hz).

Example 150

Methyl(1RS,2SR)-2-(6-(4-(benzyloxy)-2-oxopyridin-1(2H)-yl)-1-methyl-1H-benzimidazol-2-yl)cyclopropanecarboxylate A) 4-(Benzyloxy)-1-(3-(methylamino)-4-nitrophenyl)pyridin-2(1H)-one The mixture of 4-(benzyloxy)pyridin-2(1H)-one (5.0 g), 5-bromo-N-methyl-2-nitroaniline (5.74 g), copper iodide (4.73 g), N,N'-dimethylethylenediamine (2.8 ml) and potassium carbonate (10.30 g) in DMSO (250 ml) was stirred at 150° C. under N$_2$ for 1 h. After cooling to room temperature, 28% NH$_3$solution was added to the resulting mixture. The resulting suspension was filtered. The precipitate was washed with water and IPA and dried to give the title compound (5.1 g) as a yellow solid.

MS (ESI+): [M+H]+ 352.1.

B) 1-(4-Amino-3-(methylamino)phenyl)-4-(benzyloxy)pyridin-2(1H)-one

Zinc (9.49 g) was added to a solution of 4-(benzyloxy)-1-(3-(methylamino)-4-nitrophenyl)pyridin-2(1H)-one (5.1 g) in AcOH (120 ml) at room temperature. The mixture was stirred at room temperature for 2 h. The insoluble material was removed by filtration, and the filtrate was concentrated in vacuo. The mixture was neutralized with saturated NaHCO$_3$ solution at 0° C. and extracted with EtOAc. The organic layer was separated, washed with water and brine, dried over MgSO$_4$ and concentrated in vacuo. The residue was washed with IPE and dried to give the title compound (3.5 g) as a brown solid.

MS (ESI+): [M+H]+ 322.1.

C) Methyl(1RS,2SR)-2-(6-(4-(benzyloxy)-2-oxopyridin-1(2H)-yl)-1-methyl-1H-benzimidazol-2-yl)cyclopropanecarboxylate HATU (4.97, g) was added to a solution of 1-(4-amino-3-(methylamino)phenyl)-4-(benzyloxy)pyridin-2(1H)-one (3.5 g), (1RS,2SR)-2-(methoxycarbonyl)cyclopropanecarboxylic acid (1.884 g) and N,N-diisopropylethylamine (3.80 ml) in DMF (70 ml) at room temperature. The mixture was stirred at room temperature for 1 h. To the resulting mixture was added water, and the resulting precipitate was collected by filtration and washed with water and IPA. The obtained solid was dissolved in AcOH (35 ml). The mixture was stirred at 80° C. for 1 h. After evaporation of the mixture, the residue was diluted with saturated NaHCO$_3$ solution and EtOAc. The organic layer was washed with brine, dried over MgSO$_4$ and concentrated in vacuo. The residue was washed with IPE to give the title compound (2.9 g) as a pink solid.

MS (ESI+): [M+H]+ 430.1.

Example 151

4-((4-Chloro-3-fluorobenzyl)oxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (150 mg), (4-chloro-3-fluorophenyl)methanol (170 mg) and tributylphosphine (322 mg) in THF (10 ml) was added 1,1'-(azodicarbonyl)dipiperidine (401 mg) in THF (5 ml). The mixture was stirred under sonication at 60° C. for 4 h. The reaction mixture was then cooled to room temperature and concentrated in vacuo. The residue was diluted with DCM, and the DCM layer was washed with water and brine, dried over Na$_2$SO$_4$ and concentrated in vacuo. The residue was purified by silica gel column chromatography (MeOH/DCM) to give the title compound (50 mg) as a white solid.

MS (ESI+): [M+H]+ 424.0.

$^1$H NMR (400 MHz, DMSO-$d_6$): δ 0.88-0.92 (4H, m), 2.04-2.08 (1H, m), 5.19 (2H, s), 5.99 (1H, d, J=2.5 Hz), 6.16 (1H, dd, J=2.6, 7.7 Hz), 7.11 (1H, dd, J=1.7, 9.4 Hz), 7.34 (1H, d, J=7.7 Hz), 7.43 (1H, d, J=9.5 Hz), 7.54 (1H, d, J=9.3 Hz), 7.64-7.68 (2H, m), 8.37 (1H, s). 3H was overlapped with DMSO peak, and not detected.

Example 152

4-(Benzyloxy)-1-(2-((1RS,2SR)-2-(2-hydroxypropan-2-yl)cyclopropyl)-1-methyl-1H-benzimidazol-6-yl)pyridin-2(1H)-one Methylmagnesium bromide (1 M in THF, 27.0 ml) was added to a solution of methyl(1RS,2SR)-2-(6-(4-(benzyloxy)-2-oxopyridin-1(2H)-yl)-1-methyl-1H-benzimidazol-2-yl)cyclopropanecarboxylate (2.9 g) in THF (130 ml) at 0° C. The mixture was stirred at room temperature under N$_2$ atmosphere for 3 h. The mixture was quenched with saturated NH$_4$Cl solution at room temperature and extracted with EtOAc. The organic layer was separated, washed with water and brine, dried over MgSO$_4$ and concentrated in vacuo. The residue was purified by NH silica gel column chromatography (MeOH/EtOAc). The resulting solid was recrystallized from EtOH/IPE to give the title compound (1.6 g) as a white solid.

MS (ESI+): [M+H]+ 430.4.

$^1$H NMR (400 MHz, CDCl$_3$): δ 1.28 (3H, s), 1.33-1.40 (4H, m), 1.52-1.70 (2H, m), 1.97-2.08 (1H, m), 3.82 (3H, s), 5.06 (2H, s), 6.02-6.13 (2H, m), 6.88 (1H, s), 7.11 (1H, d, J=8.8 Hz), 7.29 (1H, d, J=7.5 Hz), 7.34-7.46 (6H, m), 7.64 (1H, d, J=8.3 Hz).

Example 153

4-((4-Chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR1)

(1RS,2SR)-4-((4-Chlorobenzyl)oxy)-1-(2-(2-(2-hydroxypropan-2-yl)cyclopropyl)-1-methyl-1H-benzimidazol-6-yl)pyridin-2(1H)-one (0.830 g) was resolved by a preparative SFC (CHIRALPAK AYH, CO$_2$/EtOH/CH$_3$CN=600/200/200) to give a white solid (355 mg, >99% ee). This solid was recrystallized from IPA to give the title compound (270 mg) as a white solid.

MS (ESI+): [M+H]+ 464.1.

$^1$H NMR (400 MHz, CDCl$_3$): δ 1.28 (3H, s), 1.32-1.42 (4H, m), 1.52-1.59 (1H, m), 1.61-1.68 (1H, m), 1.93-2.10 (1H, m), 3.82 (3H, s), 5.02 (2H, s), 6.00-6.12 (2H, m), 6.86 (1H, s), 7.11 (1H, dd, J=1.6, 8.4 Hz), 7.28-7.46 (6H, m), 7.64 (1H, d, J=8.4 Hz).

Analysis of enentiomeric excess
Column: CHIRALPAK AYH (2.0×150 mm)
Mobile phase: CO$_2$/EtOH/CH$_3$CN=600/200/200 (v/v/v)
Flow rate: 1.5 ml/min
Temperature: 35° C.
Detection: UV: 220 nm
Retention time: 1.52 min Example 154

4-((4-Chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR2)

(1RS,2SR)-4-((4-Chlorobenzyl)oxy)-1-(2-(2-(2-hydroxypropan-2-yl)cyclopropyl)-1-methyl-1H-benzimidazol-6-yl)pyridin-2(1H)-one (0.830 g) was resolved by a preparative SFC (CHIRALPAK AYH, CO$_2$/EtOH/CH$_3$CN=600/200/200) to give a white solid (351 mg, >99% ee). This solid was recrystallized from IPA to give the title compound (279 mg) as a white solid.

MS (ESI+): [M+H]+ 464.2.

$^1$H NMR (400 MHz, CDCl$_3$): δ 1.28 (3H, s), 1.33-1.40 (4H, m), 1.49-1.67 (2H, m), 1.95-2.06 (1H, m), 3.82 (3H, s), 5.02 (2H, s), 6.05 (2H, d, J=2.6 Hz), 6.86 (1H, s), 7.11 (1H, d, J=8.4 Hz), 7.28-7.32 (1H, m), 7.34-7.46 (5H, m), 7.64 (1H, d, J=8.4 Hz).

Analysis of enentiomeric excess
Column: CHIRALPAK AYH (2.0×150 mm)
Mobile phase: CO$_2$/EtOH/CH$_3$CN=600/200/200 (v/v/v)
Flow rate: 1.5 ml/min
Temperature: 35° C.
Detection: UV: 220 nm
Retention time: 2.88 min Example 155

4-(Benzyloxy)-1-(2-((1RS,2SR)-2-(2-fluoropropan-2-yl)cyclopropyl)-1-methyl-1H-benzimidazol-6-yl)pyridin-2(1H)-one BAST (0.172 ml) was added to a solution of 4-(benzyloxy)-1-(2-((1RS,2SR)-2-(2-hydroxypropan-2-yl)cyclopropyl)-1-methyl-1H-benzimidazol-6-yl)pyridin-2(1H)-one (100 mg) in toluene (2 ml) at 0° C. The mixture was stirred at 0° C. under a dry atmosphere for 30 min. The mixture was quenched with saturated NaHCO$_3$ solution at 0° C. and extracted with EtOAc. The organic layer was separated, washed with water and brine, dried over MgSO$_4$ and concentrated in vacuo. The residue was purified by silica gel column chromatography (MeOH/EtOAc) to give the title compound (25 mg) as an off-white solid.

MS (ESI+): [M+H]+ 432.4.

$^1$H NMR (400 MHz, DMSO-d$_6$): δ 1.00 (3H, d, J=20.8 Hz), 1.13-1.34 (4H, m), 1.57-1.67 (1H, m), 1.67-1.81 (1H, m), 2.31-2.44 (1H, m), 3.83 (3H, s), 5.16 (2H, s), 5.99 (1H, d, J=2.3 Hz), 6.09 (1H, dd, J=2.4, 7.7 Hz), 7.07 (1H, d, J=8.5 Hz), 7.33-7.50 (5H, m), 7.54 (1H, s), 7.60 (2H, dd, J=8.0, 16.3 Hz).

Example 156

1-(2-Cyclopropyl-3-methylimidazo[1,2-a]pyridin-6-yl)-4-((5-fluorothiophen-2-yl)methoxy)pyridin-2(1H)-one A mixture of 4-bromo-1-(2-cyclopropyl-3-methylimidazo[1,2-a]pyridin-6-yl)pyridin-2(1H)-one (285 mg), (5-fluorothiophen-2-yl)methanol (109 mg), potassium tert-butoxide (93 mg) and DME (5 ml) was heated at 120° C. for 30 min under microwave irradiation. Additional potassium tert-butoxide (93 mg) and (5-fluorothiophen-2-yl)methanol (109 mg) in DME (0.5 ml) were added to the reaction mixture, and the resulting mixture was heated at 120° C. for further 30 min under microwave irradiation. The mixture was quenched with water and extracted with EtOAc/MeOH. The organic layer was separated, washed with brine, dried over MgSO$_4$ and concentrated in vacuo. The resulting solid was crystallized from EtOH-IPA to give the title compound (120 mg) as an off-white solid.

MS (ESI+): [M+H]+ 396.1.

$^1$H NMR (400 MHz, DMSO-d$_6$): δ 0.85-0.94 (4H, m), 2.02-2.12 (1H, m), 2.48 (3H, s), 5.25 (2H, d, J=2.3 Hz), 6.05-6.13 (2H, m), 6.65-6.71 (1H, m), 7.01 (1H, t, J=3.6 Hz), 7.12 (1H, d, J=9.5 Hz), 7.44 (1H, d, J=9.5 Hz), 7.66 (1H, d, J=7.8 Hz), 8.37 (1H, s).

Example 157

1-(2-Cyclopropyl-1-methyl-1H-benzimidazol-6-yl)-4-((5-fluorothiophen-2-yl)methoxy)pyridin-2(1H)-one A mixture of 1-(2-cyclopropyl-1-methyl-1H-benzo[d]imidazol-6-yl)-4-hydroxypyridin-2(1H)-one (400 mg), (5-fluorothiophen-2-yl)methanol (376 mg), tributylphosphine (1.07 ml), 1,1'-(azodicarbonyl)dipiperidine (1.08 g) and THF (40 ml) was stirred at 60° C. under a dry atmosphere (CaCl$_2$ tube) for 3 h. After solvent was evaporated, the residue was purified by silica gel column chromatography (hexane/EtOAc then EtOAc/MeOH), followed by preparative HPLC (C18, mobile phase: H$_2$O/CH$_3$CN (0.1% TFA included)). The desired fraction was neutralized with saturated NaHCO$_3$ solution, and extracted with EtOAc. The organic layer was separated, dried over MgSO$_4$ and concentrated in vacuo to give the title compound (130 mg) as an off-white solid.

MS (ESI+): [M+H]+ 396.1.

$^1$H NMR (400 MHz, DMSO-d$_6$): δ 1.01-1.14 (4H, m), 2.23-2.31 (1H, m), 3.85 (3H, s), 5.17-5.28 (2H, m), 6.00-6.12 (2H, m), 6.64-6.73 (1H, m), 6.95-7.11 (2H, m), 7.49-7.54 (2H, m), 7.58 (1H, d, J=7.3 Hz).

Example 158

1-(2-Cyclopropyl-3-methylimidazo[1,2-a]pyridin-6-yl)-4-((5-(trifluoromethyl)thiophen-2-yl)methoxy)pyridin-2(1H)-one To a solution of 1-(2-cyclopropyl-3-methylimidazo[1,2-a]pyridin-6-yl)-4-hydroxypyridin-2(1H)-one (100 mg), (5-(trifluoromethyl)thiophen-2-yl)methanol (130 mg) and tributylphosphine (0.27 ml) in THF (10 ml) was added 1,1'-(azodicarbonyl)dipiperidine (269 mg) at 60° C., and the mixture was heated at the same temperature for 2 h. The mixture was poured into water, and extracted with EtOAc. The extract was washed with brine, dried over MgSO$_4$, concentrated, and purified by NH silica gel column chromatography (hexane/EtOAc), followed by silica gel column chromatography (EtOAc/MeOH). The resulting solid was purified by preparative HPLC (C18, mobile phase: H$_2$O/CH$_3$CN (0.1% TFA included)). The desired fraction was neutralized with saturated NaHCO$_3$ solution, and extracted with EtOAc. The organic layer was separated, dried over MgSO$_4$ and concentrated in vacuo to give the title compound (32.0 mg) as a white solid.

MS (ESI+): [M+H]+ 446.1.

$^1$H NMR (400 MHz, DMSO-d$_6$): δ 0.84-0.98 (4H, m), 2.02-2.12 (1H, m), 2.48 (3H, s), 5.46 (2H, s), 6.09 (1H, d, J=2.5 Hz), 6.14 (1H, dd, J=2.6, 7.5 Hz), 7.12 (1H, dd, J=1.7, 9.5 Hz), 7.39 (1H, d, J=2.8 Hz), 7.44 (1H, d, J=9.4 Hz), 7.65-7.71 (2H, m), 8.38 (1H, s).

Example 159

1-(2-Cyclopropyl-1-methyl-1H-benzimidazol-6-yl)-4-((5-(trifluoromethyl)thiophen-2-yl)methoxy)pyridin-2(1H)-one To a mixture of 1-(2-cyclopropyl-1-methyl-1H-benzo[d]imidazol-6-yl)-4-hydroxypyridin-2(1H)-one (100 mg), (5-(trifluoromethyl)thiophen-2-yl)methanol (130 mg) and tributylphosphine (0.26 ml) in THF (10 ml) was added 1,1'-(azodicarbonyl)dipiperidine (269 mg), and the mixture was stirred at 60° C. overnight. The solvent was evaporated and the residue was purified by silica gel column chromatography (hexane/EtOAc then EtOAc/MeOH), followed by NH silica gel column chromatography (hexane/EtOAc). The resulting solid was recrystallized from EtOAc-EtOH to give the title compound (55.7 mg) as an off-white solid.

MS (ESI+): [M+H]+ 446.1.

$^1$H NMR (400 MHz, DMSO-d$_6$): δ 0.99-1.14 (4H, m), 2.22-2.31 (1H, m), 3.85 (3H, s), 5.45 (2H, s), 6.06 (1H, d, J=2.5 Hz), 6.10 (1H, dd, J=2.7, 7.5 Hz), 7.05 (1H, dd, J=1.8, 8.5 Hz), 7.38 (1H, d, J=2.8 Hz), 7.49-7.54 (2H, m), 7.60 (1H, d, J=7.5 Hz), 7.69 (1H, d, J=2.8 Hz).

Example 160

1-(2-Cyclopropyl-3-methylimidazo[1,2-a]pyridin-6-yl)-4-((5-(trifluoromethyl)thiophen-2-yl)methoxy)pyridin-2(1H)-one hydrochloride 4 M HCl in EtOAc (0.714 ml) was added to a solution of 1-(2-cyclopropyl-3-methylimidazo[1,2-a]pyridin-6-yl)-4-((5-(trifluoromethyl)thiophen-2-yl)methoxy)pyridin-2(1H)-one (1.27 g) in EtOAc (25 ml) at room temperature. The mixture was stirred at room temperature for 2 h. The resulting suspension was filtered and the precipitate was washed with EtOAc. The precipitate was crystallized from EtOH-IPE to give the title compound (0.39 g) as a white solid.

MS (ESI+): [M+H]+ 446.3.

$^1$H NMR (400 MHz, DMSO-d$_6$): δ 0.88-1.02 (2H, m), 1.05-1.24 (2H, m), 2.23 (1H, brs), 2.55 (3H, s), 5.48 (2H, s), 6.14 (1H, d, J=2.5 Hz), 6.23 (1H, d, J=5.5 Hz), 7.40 (1H, brs), 7.67-7.74 (2H, m), 7.73-7.87 (2H, m), 8.86 (1H, brs).

Example 161

4-((5-Chloro-3-fluoropyridin-2-yl)methoxy)-1-(2-cyclopropyl-3-methylimidazo[1,2-a]pyridin-6-yl)pyridin-2(1H)-one The title compound was obtained in an analogous manner to example 75 using 1-(2-cyclopropyl-3-methylimidazo[1,2-a]pyridin-6-yl)-4-hydroxypyridin-2(1H)-one and (5-chloro-3-fluoropyridin-2-yl)methanol.

MS (ESI+): [M+H]+ 425.3.

Example 162

1-(2,3-Dimethylimidazo[1,2-a]pyridin-6-yl)-4-((4-fluorobenzyl)oxy)pyridin-2(1H)-one To a mixture of 6-iodo-2,3-dimethylimidazo[1,2-a]pyridine (204 mg), 4-((4-fluorobenzyl)oxy)pyridin-2(1H)-one (150 mg), potassium carbonate (283 mg) and dioxane (15 ml) were added CuI (51 mg) and trans-N,N'-dimethyl-cyclohexane-1,2-diamine (38 mg), and the mixture was heated at 110° C. in a sealed tube for 16 h. The reaction mixture was then cooled to room temperature, and concentrated in vacuo. The residue was diluted with DCM, washed with brine, dried over Na$_2$SO$_4$ and concentrated in vacuo. The crude product was purified by silica gel column chromatography (MeOH/DCM) to afford the title compound (75 mg) as an off-white solid.

MS (ESI+): [M+H]+ 363.8.

$^1$H NMR (400 MHz, DMSO-d$_6$): δ 2.33 (3H, s), 2.39 (3H, s), 5.14 (2H, s), 6.01 (1H, d, J=2.6 Hz), 6.13 (1H, dd, J=2.7, 7.6 Hz), 7.13 (1H, dd, J=1.9, 9.5 Hz), 7.26 (2H, t, J=8.8 Hz), 7.46 (1H, d, J=9.4 Hz), 7.52 (2H, dd, J=5.6, 8.5 Hz), 7.66 (1H, d, J=7.6 Hz), 8.38 (1H, d, J=1.3 Hz).

Example 163

4-(Benzyloxy)-1-(2,3-dimethylimidazo[1,2-a]pyridin-6-yl)pyridin-2(1H)-one

To a stirred degassed mixture of 6-iodo-2,3-dimethylimidazo[1,2-a]pyridine (149 mg), 4-(benzyloxy)pyridin-2(1H)-one (100 mg), potassium carbonate (206 mg) and dioxane (10 ml) were added CuI (19 mg) and trans-N,N'-dimethyl-cyclohexane-1,2-diamine (14 mg), and the mixture was heated at 110° C. in a sealed tube for 16 h. The reaction mixture was then cooled to room temperature, and concentrated in vacuo.

The residue was diluted with DCM, washed with brine, dried over Na$_2$SO$_4$ and concentrated in vacuo. The crude product was purified by silica gel column chromatography (MeOH/DCM) to afford the title compound (59 mg) as an off-white solid.

MS (ESI+): [M+H]+ 345.8.

$^1$H NMR (400 MHz, DMSO-d$_6$): δ 2.33 (3H, s), 2.39 (3H, s), 5.16 (2H, s), 6.01 (1H, d, J=2.6 Hz), 6.14 (1H, dd, J=2.6, 7.5 Hz), 7.13 (1H, dd, J=1.9, 9.4 Hz), 7.34-7.48 (6H, m), 7.66 (1H, d, J=7.6 Hz), 8.39 (1H, s).

Example 164

4-((5-Chlorothiophen-3-yl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (150 mg), (5-chlorothiophen-3-yl)methanol (158 mg) and tributylphosphine (322 mg) in THF (15 ml) was added 1,1'-(azodicarbonyl)dipiperidine (401 mg), and the mixture was stirred at 60° C. for 4 h. The reaction mixture was then cooled to room temperature and concentrated in vacuo. The residue was diluted with DCM (100 ml), washed with water and brine successively, dried over Na$_2$SO$_4$, and concentrated in vacuo. The crude product was purified by silica gel column chromatography (MeOH/DCM) to afford the title compound (90 mg) as a white solid.

MS (ESI+): [M+H]+ 412.0.

$^1$H NMR (400 MHz, DMSO-d$_6$): δ 0.88-0.92 (4H, m), 2.05-2.09 (1H, m), 2.47 (3H, s), 5.06 (2H, s), 6.01 (1H, d, J=2.6 Hz), 6.10 (1H, dd, J=2.7, 7.6 Hz), 7.11 (1H, dd, J=1.9, 9.5 Hz), 7.20 (1H, d, J=1.7 Hz), 7.43 (1H, d, J=9.4 Hz), 7.56 (1H, d, J=1.2 Hz), 7.65 (1H, d, J=7.7 Hz), 8.36 (1H, d, J=1.3 Hz).

Example 165

4-((5-Chlorothiophen-3-yl)methoxy)-1-(2,3-dimethylimidazo[1,2-a]pyridin-6-yl)pyridin-2(1H)-one A) 1-(2,3-Dimethylimidazo[1,2-a]pyridin-6-yl)-4-hydroxypyridin-2(1H)-one To a stirred solution of 4-(benzyloxy)-1-(2,3-dimethylimidazo[1,2-a]pyridin-6-yl)pyridin-2(1H)-one (500 mg) in TFA (21 ml) was added anisole (7 ml), and the reaction mixture was heated at 130° C. for 4 h. The mixture was concentrated in vacuo to afford the title compound (310 mg) as a white solid.

MS (ESI+): [M+H]+ 256.2.

B) 4-((5-Chlorothiophen-3-yl)methoxy)-1-(2,3-dimethylimidazo[1,2-a]pyridin-6-yl)pyridin-2(1H)-one To a solution of 1-(2,3-dimethylimidazo[1,2-a]pyridin-6-yl)-4-hydroxypyridin-2(1H)-one (150 mg), (5-chlorothiophen-3-yl)methanol (174 mg) and tributylphosphine (358 mg) in THF (15 ml) was added 1,1'-(azodicarbonyl)dipiperidine (447 mg), and the mixture was stirred at 60° C. for 4 h. The reaction mixture was then cooled to room temperature, and concentrated in vacuo. The residue was diluted with DCM (100 ml), washed with water and brine successively, dried over Na$_2$SO$_4$, and concentrated in vacuo. The crude product was purified by silica gel column chromatography (MeOH/DCM) to afford the title compound (90 mg) as a white solid.

MS (ESI+): [M+H]+ 385.8.

$^1$H NMR (400 MHz, DMSO-d$_6$): δ 2.32 (3H, s), 2.39 (3H, s), 5.06 (2H, s), 6.01 (1H, d, J=2.4 Hz), 6.11 (1H, dd, J=2.4, 7.5 Hz), 7.12 (1H, dd, J=1.6, 9.6 Hz), 7.20 (1H, s), 7.46 (1H, d, J=9.4 Hz), 7.56 (1H, s), 7.66 (1H, d, J=7.5 Hz), 8.38 (1H, s).

Example 166

4-((5-Chlorothiophen-2-yl)methoxy)-1-(2,3-dimethylimidazo[1,2-a]pyridin-6-yl)pyridin-2(1H)-one To a solution of 1-(2,3-dimethylimidazo[1,2-a]pyridin-6-yl)-4-hydroxypyridin-2(1H)-one (150 mg), (5-chlorothiophen-2-yl)methanol (174 mg) and tributylphosphine (358 mg) in THF (15 ml) was added 1,1'-(azodicarbonyl)dipiperidine (447 mg), and the mixture was stirred at 60° C. for 4 h. The reaction mixture was then cooled to room temperature, and concentrated in vacuo. The residue was diluted with DCM (100 ml), washed with water and brine successively, dried over Na$_2$SO$_4$, and concentrated in vacuo. The crude product was purified by silica gel column chromatography (MeOH/DCM) to afford the title compound (56 mg) as a white solid.

MS (ESI+): [M+H]+ 386.0.

$^1$H NMR (400 MHz, DMSO-d$_6$): δ 2.32 (3H, s), 2.39 (3H, s), 5.30 (2H, s), 6.06 (1H, d, J=2.6 Hz), 6.10 (1H, dd, J=2.6, 7.5 Hz), 7.08 (1H, d, J=3.8 Hz), 7.13 (1H, dd, J=1.9, 9.8 Hz), 7.17 (1H, d, J=3.8 Hz), 7.46 (1H, d, J=9.6 Hz), 7.67 (1H, d, J=7.5 Hz), 8.38 (1H, d, J=1.4 Hz).

Example 167

4-(Benzyloxy)-1-(2-ethyl-3-methylimidazo[1,2-a]pyridin-6-yl)pyridin-2(1H)-one

A) N-(5-Iodo-1-(3-oxopentan-2-yl)pyridin-2(1H)-ylidene)-4-methylbenzenesulfonamide To a stirred solution of N-(5-iodopyridin-2-yl)-4-methylbenzenesulfonamide (3 g) and 2-bromopentan-3-one (3.3 g) in THF (50 ml) was added N,N-diisopropylethylamine (5.6 ml) at 0° C., and the resulting mixture was stirred at room temperature for 16 h. The reaction mixture was concentrated in vacuo, poured into saturated NaHCO$_3$ solution and extracted with EtOAc. The extract was washed with brine, dried over Na$_2$SO$_4$, concentrated in vacuo and purified by silica gel column chromatography (hexane/EtOAc) to afford the title compound (1.6 g) as a yellow solid.

MS (ESI+): [M+H]+ 459.0.

B) 2-Ethyl-6-iodo-3-methylimidazo[1,2-a]pyridine

To a stirred solution of N-(5-iodo-1-(3-oxopentan-2-yl)pyridin-2(1H)-ylidene)-4-methylbenzenesulfonamide (4 g) in THF (50 ml) was added trifluoroacetic anhydride (10 ml) at 0° C., and the resulting mixture was stirred at room temperature for 16 h. The reaction mixture was concentrated in vacuo, poured into saturated aqueous NaHCO$_3$ solution and extracted with DCM. The extract was washed with brine, dried over Na$_2$SO$_4$, concentrated in vacuo, and purified by silica gel column chromatography (hexane/EtOAc) to afford the title compound (1.3 g) as a yellow solid.

MS (ESI+): [M+H]+ 286.6.

C) 4-(Benzyloxy)-1-(2-ethyl-3-methylimidazo[1,2-a]
pyridin-6-yl)pyridin-2(1H)-one The title compound was obtained in an analogous manner to example 163 using 4-(benzyloxy)pyridin-2(1H)-one and 2-ethyl-6-iodo-3-methylimidazo[1,2-a]pyridine.
MS (ESI+): [M+H]+ 359.8.

Example 168

4-((4-Chlorothiophen-2-yl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (150 mg), (4-chlorothiophen-2-yl)methanol (158 mg) and tributylphosphine (322 mg) in THF (15 ml) was added 1,1'-(azodicarbonyl)dipiperidine (400 mg), and the mixture was stirred at 60° C. for 4 h. The reaction mixture was then cooled to room temperature, and concentrated in vacuo. The residue was diluted with DCM (100 ml), washed with water and brine successively, dried over $Na_2SO_4$, and concentrated in vacuo. The crude product was purified by silica gel column chromatography (MeOH/DCM) to afford the title compound (12 mg) as a white solid.
MS (ESI+): [M+H]+ 412.2.
$^1$H NMR (400 MHz, DMSO-$d_6$): δ 0.87-0.92 (4H, m), 2.05-2.09 (1H, m), 2.47 (3H, s), 5.33 (2H, s), 6.06 (1H, d, J=2.7 Hz), 6.11 (1H, dd, J=2.8, 7.3 Hz), 7.11 (1H, dd, J=1.9, 9.4 Hz), 7.28 (1H, d, J=1.3 Hz), 7.43 (1H, d, J=9.3 Hz), 7.64-7.65 (1H, m), 7.67 (1H, s), 8.37 (1H, d, J=1.6 Hz).

Example 169

1-(2-Ethyl-3-methylimidazo[1,2-a]pyridin-6-yl)-4-((4-fluorobenzyl)oxy)pyridin-2(1H)-one The title compound was obtained in an analogous manner to example 163 using 4-((4-fluorobenzyl)oxy)pyridin-2(1H)-one and 2-ethyl-6-iodo-3-methylimidazo[1,2-a]pyridine.
MS (ESI+): [M+H]+ 378.2.

Example 170

1-(2-Cyclopropyl-3-methylimidazo[1,2-a]pyridin-6-yl)-4-((4-fluorophenoxy)methyl)pyridin-2(1H)-one A) Methyl 2-oxo-1,2-dihydropyridine-4-carboxylate To a stirred solution of 2-hydroxypyridine-4-carboxylic acid (5.0 g) in MeOH (50 ml) was added acetyl chloride (26 ml) dropwise at 0° C. over 15 min. The reaction mixture was slowly warmed to room temperature, and stirred for 20 h. The reaction mixture was concentrated in vacuo, and diluted with EtOAc and water. The organic layer was washed with saturated $NaHCO_3$ solution, concentrated in vacuo, and purified by column chromatography (MeOH/DCM) to afford the title compound (3.5 g) as an off-white solid.
MS (ESI+): [M+H]+ 154.0.

B) Methyl 1-(2-cyclopropyl-3-methylimidazo[1,2-a]
pyridin-6-yl)-2-oxo-1,2-dihydropyridine-4-carboxylate To a mixture of 2-cyclopropyl-6-iodo-3-methylimidazo[1,2-a]pyridine (1.9 g), methyl 2-oxo-1,2-dihydropyridine-4-carboxylate (1.0 g), potassium carbonate (901 mg) and dioxane (30 ml) were added CuI (248 mg) and trans-N,N'-dimethyl-cyclohexane-1,2-diamine (308 mg), and the mixture was heated at 110° C. in a sealed tube for 16 h. The reaction mixture was cooled to room temperature, concentrated in vacuo, and diluted with a mixture of DCM and MeOH. The insoluble material was removed by filtration, and the filtrate was concentrated in vacuo and purified by column chromatography (MeOH/DCM) to afford the title compound (550 mg) as a brown solid.
MS (ESI+): [M+H]+ 323.8.

C) 1-(2-Cyclopropyl-3-methylimidazo[1,2-a]pyridin-6-yl)-4-(hydroxymethyl)pyridin-2(1H)-one To a solution of methyl 1-(2-cyclopropyl-3-methylimidazo[1,2-a]pyridin-6-yl)-2-oxo-1,2-dihydropyridine-4-carboxylate (600 mg) in DCM (10 ml) was added diisobutylaluminum hydride (1.76 M in toluene, 2.1 ml) at 78° C. The mixture was stirred at same temperature for 3 h, and allowed to warm to room temperature for 4 h. The mixture was quenched with a mixture of MeOH and water, and filtered through celite. The filtrate was concentrated in vacuo and purified by column chromatography (MeOH/DCM) to afford the title compound (200 mg) as a brown solid.
MS (ESI+): [M+H]+ 296.0.

D) 1-(2-Cyclopropyl-3-methylimidazo[1,2-a]pyridin-6-yl)-4-((4-fluorophenoxy)methyl)pyridin-2(1H)-one To a solution of 1-(2-cyclopropyl-3-methylimidazo[1,2-a]pyridin-6-yl)-4-(hydroxymethyl)pyridin-2(1H)-one (150 mg), 4-fluorophenol (85 mg) and tributylphosphine (307 mg) in THF (20 ml) was added 1,1'-(azodicarbonyl)dipiperidine (386 mg), and the mixture was stirred at 60° C. for 5 h. The reaction mixture was cooled to room temperature, concentrated in vacuo, and diluted with DCM. The mixture was washed with water and brine successively, dried over $Na_2SO_4$, concentrated in vacuo and purified by column chromatography (MeOH/DCM) followed by preparative HPLC to afford the title compound (24 mg) as a white solid.
MS (ESI+): [M+H]+ 390.0.
$^1$H NMR (400 MHz, DMSO-$d_6$): δ 0.88-0.92 (4H, m), 2.07 (1H, m), 5.06 (2H, s), 6.36 (1H, d, J=7.0 Hz), 6.54 (1H, s), 7.04-7.07 (2H, m), 7.14-7.18 (3H, m), 7.45 (1H, d, J=9.4 Hz), 7.74 (1H, d, J=7.0 Hz), 8.43 (1H, s). 3H was overlapped with DMSO peak, and not detected.

Example 171

4-((5-Chlorothiophen-2-yl)methoxy)-1-(2-ethyl-3-methylimidazo[1,2-a]pyridin-6-yl)pyridin-2(1H)-one A) 1-(2-Ethyl-3-methylimidazo[1,2-a]pyridin-6-yl)-4-hydroxypyridin-2(1H)-one The title compound was obtained in an analogous manner to step A in example 165 using 4-(benzyloxy)-1-(2-ethyl-3-methylimidazo[1,2-a]pyridin-6-yl)pyridin-2(1H)-one.
MS (ESI+): [M+H]+ 270.0.

B) 4-((5-Chlorothiophen-2-yl)methoxy)-1-(2-ethyl-3-methylimidazo[1,2-a]pyridin-6-yl)pyridin-2(1H)-one The title compound was obtained in an analogous manner to example 75 using 1-(2-ethyl-3-methylimidazo[1,2-a]pyridin-6-yl)-4-hydroxypyridin-2(1H)-one and (5-chlorothiophen-2-yl)methanol.
MS (ESI+): [M+H]+ 270.0.

Example 172

4-((5-Chlorothiophen-3-yl)methoxy)-1-(2-ethyl-3-methylimidazo[1,2-a]pyridin-6-yl)pyridin-2(1H)-one To a solution of 1-(2-ethyl-3-methylimidazo[1,2-a]pyridin-6-yl)-4-hydroxypyridin-2(1H)-one (150 mg), (5-chlorothiophen-3-yl)methanol (165 mg) and tributylphosphine (340 mg) in THF (15 ml) was added 1,1'-(azodicarbonyl) dipiperidine (424 mg), and the mixture was stirred at 60° C. for 5 h. The reaction mixture was cooled to room temperature, concentrated in vacuo, and diluted with DCM. The mixture was washed with water and brine successively, dried over $Na_2SO_4$, concentrated in vacuo and purified by column chromatography (MeOH/DCM) to afford the title compound (60 mg) as a white solid.

MS (ESI+): [M+H]+ 270.0.

$^1$H NMR (400 MHz, DMSO-$d_6$): δ 1.22 (3H, t, J=7.5 Hz), 2.39 (3H, s), 2.69 (2H, q, J=7.5 Hz), 5.06 (2H, s), 6.01 (1H, d, J=2.6 Hz), 6.11 (1H, dd, J=2.7, 7.6 Hz), 7.13 (1H, dd, J=1.9, 9.5 Hz), 7.20 (1H, d, J=1.7 Hz), 7.48 (1H, d, J=9.4 Hz), 7.56 (1H, s), 7.66 (1H, d, J=7.6 Hz), 8.38 (1H, d, J=1.5 Hz).

Example 173

4-((4-Chlorobenzyl)oxy)-1-(2-(2-(2-hydroxypropan-2-yl)cyclopropyl)-3-methylimidazo[1,2-a]pyridin-6-yl)pyridin-2(1H)-one

A) 6-Iodo-3-methylimidazo[1,2-a]pyridine-2-carbaldehyde

To a stirred solution of ethyl 6-iodo-3-methylimidazo[1,2-a]pyridine-2-carboxylate (2.0 g) in DCM (40 ml) was added diisobutylaluminum hydride (1.0 M solution in toluene, 8 ml) at −78° C., and the resultant mixture was stirred at same temperature for 3 h. The reaction mixture was quenched with MeOH (10 ml) and 2 M HCl (15 ml), and basified with saturated aqueous $NaHCO_3$ solution (20 ml) at 0° C. The mixture was extracted with DCM, washed with brine, dried over $Na_2SO_4$, concentrated in vacuo and purified by column chromatography (MeOH/DCM) to afford the title compound (1.2 g) as a light yellow solid.

MS (ESI+): [M+H]+ 287.0.

B) 2-Ethenyl-6-iodo-3-methylimidazo[1,2-a]pyridine

To a stirred suspension of methyltriphenylphosphonium bromide (3.1 g) in THF (20 ml) was added NaH (60% in oil, 336 mg) at 0° C. The reaction mixture was then stirred at room temperature for 16 h. A solution of 6-iodo-3-methylimidazo[1,2-a]pyridine-2-carbaldehyde (500 mg) in THF (10 ml) was added to the reaction mixture at 0° C., and the resulting mixture was stirred at room temperature for 4 h. The reaction mixture was quenched with ice-water (20 ml) and extracted with EtOAc. The extract was washed with brine, dried over $Na_2SO_4$, concentrated in vacuo and purified by column chromatography (hexane/EtOAc) to afford the title compound (350 mg) as an off-white solid.

MS (ESI+): [M+H]+ 284.8.

C) Ethyl 2-(6-iodo-3-methylimidazo[1,2-a]pyridin-2-yl)cyclopropanecarboxylate To a stirred solution of 2-ethenyl-6-iodo-3-methylimidazo [1,2-a]pyridine (680 mg) in xylene (20 ml) was added ethyl diazoacetate (1.5 ml) at room temperature. The reaction mixture was heated at reflux for 5 h. The resulting reaction mixture was then cooled to room temperature, concentrated in vacuo, and purified by preparative HPLC to afford the title compound (200 mg) as a yellow solid.

MS (ESI+): [M+H]+ 371.0.

D) Ethyl 2-(6-(4-((4-chlorobenzyl)oxy)-2-oxopyridin-1(2H)-yl)-3-methylimidazo[1,2-a]pyridin-2-yl)cyclopropanecarboxylate To a mixture of ethyl 2-(6-iodo-3-methylimidazo[1,2-a] pyridin-2-yl)cyclopropanecarboxylate (280 mg), 4-((4-chlorobenzyl)oxy)pyridin-2(1H)-one (140 mg), potassium carbonate (243 mg) and dioxane (2 ml) were added CuI (57 mg) and trans-N,N'-dimethyl-cyclohexane-1,2-diamine (43 mg), and the mixture was heated at 110° C. for 12 h. The reaction mixture was then cooled to room temperature and concentrated in vacuo. The resulting residue was diluted with DCM, washed with brine, dried over $Na_2SO_4$, concentrated in vacuo and purified by column chromatography (MeOH/DCM) to afford the title compound (250 mg) as a white solid.

MS (ESI+): [M+H]+ 478.4.

E) 4-((4-Chlorobenzyl)oxy)-1-(2-(2-(2-hydroxypropan-2-yl)cyclopropyl)-3-methylimidazo[1,2-a]pyridin-6-yl)pyridin-2(1H)-one To a stirred solution of ethyl 2-(6-(4-((4-chlorobenzyl) oxy)-2-oxopyridin-1(2H)-yl)-3-methylimidazo[1,2-a]pyridin-2-yl)cyclopropanecarboxylate (250 mg) in THF (2 ml) was added methylmagnesium bromide (3.0 M solution in ether, 1.8 ml) at 0° C., and the resulting mixture was stirred at room temperature for 3 h. The reaction mixture was then quenched with saturated $NH_4Cl$ solution, and extracted with DCM. The extract was washed with brine, dried over $Na_2SO_4$, concentrated in vacuo and purified by column chromatography (MeOH/DCM) to afford the title compound (7 mg) as an off-white solid.

MS (ESI+): [M+H]+ 464.0.

Example 174

2-(6-(4-((4-Chlorobenzyl)oxy)-2-oxopyridin-1(2H)-yl)-3-methylimidazo[1,2-a]pyridin-2-yl)cyclopropanecarbonitrile

A) (2E)-3-(6-Iodo-3-methylimidazo[1,2-a]pyridin-2-yl)prop-2-enenitrile

To a stirred suspension of cyanomethylphosphonic acid diethyl ester (619 mg) in THF (2 ml) was added NaH (60% in oil, 144 mg) at 0° C., and the mixture was stirred at same temperature for 16 h. A solution of 6-iodo-3-methylimidazo [1,2-a]pyridine-2-carbaldehyde (250 mg) in THF (2 ml) was added, and the resulting mixture was stirred at room temperature for 4 h. The reaction mixture was quenched with saturated $NH_4Cl$ solution, and extracted with EtOAc. The extract was washed with brine, dried over $Na_2SO_4$, concentrate, and purified by column chromatography (hexane/EtOAc) to afford the title compound (120 mg) as a pale yellow solid.

MS (ESI+): [M+H]+ 464.0.

B) 2-(6-Iodo-3-methylimidazo[1,2-a]pyridin-2-yl)cyclopropanecarbonitrile

To a stirred suspension of NaH (60% in oil, 270 mg) in DMF (5 ml) was added trimethylsulfoxonium iodide (1.37 g)

at room temperature, and the mixture was stirred for 3 h. A solution of (2E)-3-(6-iodo-3-methylimidazo[1,2-a]pyridin-2-yl)prop-2-enenitrile (600 mg) in DMF (1 ml) was added, and the resulting mixture was stirred at room temperature for 24 h. The reaction mixture was quenched with saturated NH₄Cl solution and extracted with EtOAc. The extract was washed with brine, dried over Na₂SO₄, concentrated in vacuo, and purified by column chromatography (hexane/EtOAc) followed by preparative HPLC to afford the title compound (40 mg) as an off-white solid.

MS (ESI+): [M+H]+ 324.0.

C) 2-(6-(4-((4-Chlorobenzyl)oxy)-2-oxopyridin-1 (2H)-yl)-3-methylimidazo[1,2-a]pyridin-2-yl)cyclopropanecarbonitrile To a mixture of 2-(6-iodo-3-methylimidazo[1,2-a]pyridin-2-yl)cyclopropanecarbonitrile (26 mg), 4-((4-chlorobenzyl)oxy)pyridin-2(1H)-one (45 mg), potassium carbonate (58 mg) and dioxane (2 ml) were added CuI (7 mg) and trans-N,N'-dimethyl-cyclohexane-1,2-diamine (5 mg), and the mixture was heated at 110° C. for 16 h. The reaction mixture was then cooled to room temperature and concentrated in vacuo. The residue was diluted with DCM, washed with brine, dried over Na₂SO₄, concentrated in vacuo and purified by column chromatography (MeOH/DCM) to afford the title compound (15 mg) as an off-white solid.

MS (ESI+): [M+H]+ 431.2.
¹H NMR (400 MHz, DMSO-d₆): δ 1.23-1.65 (2H, m), 2.07-2.11 (1H, m), 2.94-2.99 (1H, m), 5.17 (2H, s), 6.00 (1H, d, J=2.4 Hz), 6.15 (1H, dd, J=2.4, 7.6 Hz), 7.19 (1H, d, J=9.5 Hz), 7.46-7.49 (5H, m), 7.66 (1H, d, J=7.6 Hz), 8.44 (1H, s). 3H was overlapped with DMSO peak, and not detected.

Example 175

1-(2-Cyclopropyl-3-methylimidazo[1,2-a]pyridin-6-yl)-4-((5-fluoro-2-thienyl)methoxy)pyridin-2(1H)-one A mixture of 4-bromo-1-(2-cyclopropyl-3-methylimidazo[1,2-a]pyridin-6-yl)pyridin-2(1H)-one (285 mg), (5-fluorothiophen-2-yl)methanol (109 mg), potassium tert-butoxide (93 mg) and DME (5 ml) was heated at 120° C. for 30 min under microwave irradiation. Additional potassium tert-butoxide (93 mg) and (5-fluorothiophen-2-yl)methanol (109 mg) in DME (0.5 ml) were added to the reaction mixture, and the resulting mixture was heated at 120° C. for further 30 min under microwave irradiation. The mixture was quenched with water and extracted with EtOAc/MeOH. The organic layer was separated, washed with brine, dried over MgSO₄ and concentrated in vacuo. The residue was crystallized from EtOH-IPA to give the title compound (120 mg) as an off-white solid.

MS (ESI+): [M+H]+ 396.1.
¹H NMR (400 MHz, DMSO-d₆): δ 0.85-0.94 (4H, m), 2.02-2.12 (1H, m), 2.48 (3H, s), 5.25 (2H, d, J=2.3 Hz), 6.05-6.13 (2H, m), 6.65-6.71 (1H, m), 7.01 (1H, t, J=3.6 Hz), 7.12 (1H, d, J=9.5 Hz), 7.44 (1H, d, J=9.5 Hz), 7.66 (1H, d, J=7.8 Hz), 8.37 (1H, s).

Example 176

1-(2-Cyclopropyl-1-methyl-1H-benzimidazol-6-yl)-4-((5-fluorothiophen-2-yl)methoxy)pyridin-2(1H)-one To a solution of 1-(2-cyclopropyl-1-methyl-1H-benzimidazol-6-yl)-4-hydroxypyridin-2(1H)-one (127 mg), (5-fluorothiophen-2-yl)methanol (40 mg) and tributylphosphine (182 mg) in THF (15 ml) was added 1,1'-(azodicarbonyl)dipiperidine (227 mg), and the mixture was stirred at 60° C. for 4 h. The reaction mixture was then cooled to room temperature, and concentrated in vacuo. The residue was diluted with DCM, washed with water and brine successively, dried over Na₂SO₄, concentrated in vacuo and purified by column chromatography (MeOH/DCM) followed by preparative HPLC to afford the title compound (6 mg) as a white solid.

MS (ESI+): [M+H]+ 396.0.
¹H NMR (400 MHz, CD₃OD): δ 1.14-1.17 (4H, m), 2.23 (1H, m), 3.90 (3H, s), 5.22 (2H, s), 6.14 (1H, s), 6.23 (1H, d, J=5.8 Hz), 6.49 (1H, s), 6.90 (1H, s), 7.15 (1H, d, J=7.7 Hz), 7.49 (1H, s), 7.59 (2H, t, J=8.4 Hz).

Example 177

4-((5-Bromo-3-thienyl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (87 mg), (5-bromo-3-thienyl)methanol (119 mg) and tributylphosphine (188 mg) in THF (4 ml) was added 1,1'-(azodicarbonyl)dipiperidine (234 mg), and the reaction mixture was stirred at 60° C. for 3 h. The reaction mixture was then cooled to room temperature, concentrated, and purified by silica gel column chromatography (hexane/EtOAc then MeOH/EtOAc). The resulting solid was recrystallized from EtOH/hexane to give the title compound (38 mg) as a white solid.

MS (ESI+): [M+H]+ 456.0.
¹H NMR (400 MHz, DMSO-d₆): δ 0.82-0.98 (4H, m), 2.07 (1H, t, J=5.3 Hz), 2.48 (3H, brs), 5.09 (2H, s), 6.01 (1H, d, J=2.5 Hz), 6.11 (1H, dd, J=2.6, 7.7 Hz), 7.11 (1H, d, J=9.3 Hz), 7.30 (1H, s), 7.43 (1H, d, J=9.4 Hz), 7.61-7.71 (2H, m), 8.37 (1H, s).

Example 178

1-(2-Cyclopropyl-3-methylimidazo[1,2-a]pyridin-6-yl)-4-((5-(difluoromethyl)-2-thienyl)methoxy)pyridin-2(1H)-one A) Methyl 5-(difluoromethyl)thiophene-2-carboxylate To a solution of methyl 5-formylthiophene-2-carboxylate (4.15 g) in toluene (100 ml) was added dropwise DAST (4.83 ml) at 0° C., and the reaction mixture was stirred at room temperature overnight. The reaction mixture was poured into saturated NaHCO₃ solution and extracted with EtOAc. The extract was washed with brine, dried over MgSO₄, concentrated and purified by silica gel column chromatography (hexane/EtOAc) to give the title compound (2.23 g) as a pale yellow solid.

¹H NMR (400 MHz, CDCl₃): δ 3.91 (3H, s), 6.83 (1H, t, J=55.8 Hz), 7.27 (1H, brs), 7.69-7.77 (1H, m).

B) (5-(Difluoromethyl)-2-thienyl)methanol

To a solution of methyl 5-(difluoromethyl)thiophene-2-carboxylate (2.23 g) in THF (60 ml)-MeOH (15 ml) was added NaBH₄ (2.20 g) at room temperature, and the reaction mixture was stirred at 60° C. for 1 h. The reaction mixture was quenched with saturated aqueous NH₄Cl solution, and extracted with EtOAc. The extract was washed with brine, dried over MgSO$_4$, concentrated and purified by silica gel column chromatography (hexane/EtOAc) to give the title compound (1.94 g) as a pale yellow oil.

$^1$H NMR (400 MHz, CDCl$_3$): δ 1.86 (1H, t, J=6.0 Hz), 4.85 (2H, d, J=5.5 Hz), 6.62-6.99 (2H, m), 7.16 (1H, brs).

C) 1-(2-Cyclopropyl-3-methylimidazo[1,2-a]pyridin-6-yl)-4-((5-(difluoromethyl)-2-thienyl)methoxy)pyridin-2(1H)-one To a solution of 1-(2-cyclopropyl-3-methylimidazo[1,2-a]pyridin-6-yl)-4-hydroxypyridin-2(1H)-one (350 mg), (5-(difluoromethyl)-2-thienyl)methanol (409 mg) and tributylphosphine (755 mg) in THF (12 ml) was added 1,1'-(azodicarbonyl)dipiperidine (942 mg), and the reaction mixture was stirred at 60° C. for 3 h. The reaction mixture was cooled to room temperature, concentrated and purified by silica gel column chromatography (hexane/EtOAc then MeOH/EtOAc). The resulting solid was recrystallized from EtOH-hexane to give the title compound (80 mg) as a white solid.

MS (ESI+): [M+H]+ 428.4.

$^1$H NMR (400 MHz, DMSO-d$_6$): δ 0.83-0.94 (4H, m), 2.07 (1H, brs), 5.42 (2H, s), 6.04-6.17 (2H, m), 7.12 (1H, d, J=9.3 Hz), 7.31 (1H, d, J=5.3 Hz), 7.43 (1H, d, J=9.5 Hz), 7.67 (1H, d, J=7.5 Hz), 8.01 (2H, s), 8.38 (1H, s).

Example 179

1-(2-Cyclopropyl-3-methylimidazo[1,2-a]pyridin-6-yl)-4-((2-(trifluoromethyl)-1,3-thiazol-4-yl)methoxy)pyridin-2(1H)-one A mixture of 4-bromo-1-(2-cyclopropyl-3-methylimidazo[1,2-a]pyridin-6-yl)pyridin-2(1H)-one (80 mg), (2-(trifluoromethyl)-1,3-thiazol-4-yl)methanol (51.1 mg), potassium tert-butoxide (78 mg) and toluene (2 ml) was heated at 100° C. for 1 h. The mixture was poured into water, and extracted with EtOAc. The extract was washed with brine, dried over MgSO$_4$, concentrated and purified by NH silica gel column chromatography (hexane/EtOAc) to give the title compound (16.2 mg) as a white solid.

MS (ESI+): [M+H]+ 447.4.

$^1$H NMR (400 MHz, DMSO-d$_6$): δ 0.85-0.96 (4H, m), 2.03-2.13 (1H, m), 2.48 (3H, brs), 5.33 (2H, s), 6.12 (1H, s), 6.16 (1H, d, J=7.7 Hz), 7.12 (1H, d, J=9.4 Hz), 7.44 (1H, d, J=9.4 Hz), 7.68 (1H, d, J=7.7 Hz), 8.36 (2H, d, J=16.8 Hz).

Example 180

1-(2-Cyclopropyl-3-methylimidazo[1,2-a]pyridin-6-yl)-4-((5-(trifluoromethyl)-2-furyl)methoxy)pyridin-2(1H)-one A) 4-Bromo-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (3.0 g) in DMF (25 ml) was added phosphorus oxybromide (2.17 ml) at room temperature, and the mixture was stirred at 110° C. for 1 h. The mixture was diluted with EtOAc and water, quenched with saturated NaHCO$_3$ solution, and extracted with EtOAc. The organic layer was separated, washed with water and brine successively, dried over MgSO$_4$ and concentrated in vacuo. The residue was purified by column chromatography (hexane/EtOAc) to give the title compound (0.70 g) as a pale yellow solid.

MS (ESI+): [M+H]+ 344.0.

B) 1-(2-Cyclopropyl-3-methylimidazo[1,2-a]pyridin-6-yl)-4-((5-(trifluoromethyl)-2-furyl)methoxy)pyridin-2(1H)-one To a suspension of 4-bromo-1-(2-cyclopropyl-3-methylimidazo[1,2-a]pyridin-6-yl)pyridin-2(1H)-one (120 mg) and (5-(trifluoromethyl)furan-2-yl)methanol (87 mg) in toluene (2 ml) was added potassium tert-butoxide (117 mg) at room temperature, and the mixture was stirred at 100° C. for 1 h. The mixture was quenched with water, and the precipitate was collected by filtration and washed with IPE to give the title compound (75 mg) as a yellow solid.

MS (ESI+): [M+H]+ 430.1

$^1$H NMR (400 MHz, DMSO-d$_6$): δ 0.84-0.95 (4H, m), 2.02-2.12 (1H, m), 2.48 (3H, brs), 5.24 (2H, s), 6.09-6.18 (2H, m), 6.92 (1H, d, J=2.6 Hz), 7.08-7.16 (1H, m), 7.28 (1H, brs), 7.44 (1H, d, J=9.4 Hz), 7.67 (1H, d, J=7.7 Hz), 8.38 (1H, s).

Example 181

4-(((5-Chloro-2-thienyl)methyl)amino)-1-(2-cyclopropyl-3-methylimidazo[1,2-a]pyridin-6-yl)pyridin-2(1H)-one A mixture of 4-bromo-1-(2-cyclopropyl-3-methylimidazo[1,2-a]pyridin-6-yl)pyridin-2(1H)-one (30 mg), 1-(5-chloro-2-thienyl)methanamine (20 mg), tris(dibenzylideneacetone)dipalladium(0) (2.0 mg), cesium carbonate (57 mg), 4,5-bis(diphenylphosphino)-9,9-dimethylxanthene (3 mg) and DMA (0.4 ml) was heated at 120° C. for 1 h under microwave irradiation. To this mixture was added water, and the precipitate was collected by filtration. The resulting solid was recrystallized from EtOAc-hexane-EtOH to give the title compound (8.6 mg) as a yellow solid.

MS (ESI+): [M+H]+ 411.1.

$^1$H NMR (400 MHz, DMSO-d$_6$): δ 0.83-0.94 (4H, m), 2.01-2.11 (1H, m), 2.46 (3H, s), 4.44 (2H, d, J=5.9 Hz), 5.33 (1H, s), 5.89 (1H, d, J=5.8 Hz), 6.95-7.02 (2H, m), 7.07 (1H, d, J=9.5 Hz), 7.32-7.46 (3H, m), 8.27 (1H, s).

Example 182

4-(((5-Chloro-2-thienyl)methyl)(methyl)amino)-1-(2-cyclopropyl-3-methylimidazo[1,2-a]pyridin-6-yl)pyridin-2(1H)-one To a suspension of 4-(((5-chloro-2-thienyl)methyl)amino)-1-(2-cyclopropyl-3-methylimidazo[1,2-a]pyridin-6-yl)pyridin-2(1H)-one (11.5 mg) in DMF (1 ml) was added NaH (60% in oil, 1.7 mg) at 0° C. After the reaction mixture was stirred at 0° C. for 10 min, iodomethane (2.61 μl) was added to the reaction mixture. The mixture was stirred at room temperature for 3 h. The mixture was quenched with water, and extracted with EtOAc. The organic layer was separated, washed with water and brine successively, dried over MgSO$_4$ and concentrated in vacuo. The residue was triturated with IPE, and the resulting solid was collected by filtration and washed with EtOAc-IPE to give the title compound (4.0 mg) as a pale yellow solid.

MS (ESI+): [M+H]+ 425.1.

¹H NMR (400 MHz, DMSO-d₆): δ 0.85-0.94 (4H, m), 2.02-2.10 (1H, m), 2.47 (3H, brs), 3.01 (3H, s), 4.75 (2H, s), 5.44 (1H, d, J=2.3 Hz), 6.18-6.26 (1H, m), 6.93 (1H, d, J=3.6 Hz), 7.02 (1H, d, J=3.6 Hz), 7.10 (1H, d, J=11.0 Hz), 7.40 (1H, d, J=9.4 Hz), 7.52 (1H, d, J=7.8 Hz), 8.31 (1H, s).

Example 183

1-(2-Cyclopropyl-3-methylimidazo[1,2-a]pyridin-6-yl)-4-((5-(trifluoromethyl)-3-thienyl)methoxy)pyridin-2(1H)-one A) Methyl 5-iodothiophene-3-carboxylate A mixture of 5-iodothiophene-3-carboxylic acid (3.48 g), iodomethane (2.92 g), potassium carbonate (2.84 g) and DMF (35 ml) was stirred at room temperature for 1 day. The reaction mixture was poured into water, and extracted with EtOAc. The extract was washed with brine, dried over MgSO₄, concentrated and purified by silica gel column chromatography (hexane/EtOAc) to give the title compound (3.62 g) as a white solid.

¹H NMR (400 MHz, CDCl₃): δ 3.86 (3H, s), 7.66 (1H, s), 8.08 (1H, s).

B) Methyl 5-(trifluoromethyl)thiophene-3-carboxylate

To a solution of methyl 5-iodothiophene-3-carboxylate (15.2 g), copper iodide (21.5 g) and hexamethylphosphoramide (50.6 g) in DMF (150 ml) was added methyl 2,2-difluoro-2-(fluorosulfonyl)acetate (54.3 g) at room temperature, and the reaction mixture was stirred at 80° C. under N₂ atmosphere for 5 h. The reaction mixture was then cooled to room temperature, neutralized with saturated NaHCO₃ solution and extracted with EtOAc. The extract was washed with brine, dried over MgSO₄, concentrated and purified by silica gel column chromatography (hexane/toluene) to give the title compound (9.39 g) as a colorless oil.

¹H NMR (400 MHz, CDCl₃): δ 3.89 (3H, s), 7.86 (1H, s), 8.23 (1H, d, J=1.0 Hz).

C) (5-(Trifluoromethyl)-3-thienyl)methanol

To a solution of methyl 5-(trifluoromethyl)thiophene-3-carboxylate (523 mg) in THF (1 ml)-MeOH (1 ml) was added NaBH₄ (2.2 g) at room temperature, and the reaction mixture was stirred at 60° C. for 3 h. The reaction mixture was quenched with water, and extracted with EtOAc. The extract was washed with brine, dried over MgSO₄, concentrated and purified by silica gel column chromatography (hexane/EtOAc) to give the title compound (449 mg) as a pale yellow oil.

¹H NMR (400 MHz, CDCl₃): δ 1.71 (1H, t, J=5.7 Hz), 4.70 (2H, d, J=5.6 Hz), 7.39 (1H, s), 7.43 (1H, s). D) 1-(2-Cyclopropyl-3-methylimidazo[1,2-a]pyridin-6-yl)-4-((5-(trifluoromethyl)-3-thienyl)methoxy)pyridin-2(1H)-one A mixture of 4-bromo-1-(2-cyclopropyl-3-methylimidazo[1,2-a]pyridin-6-yl)pyridin-2(1H)-one (111 mg), (5-(trifluoromethyl)-3-thienyl)methanol (88 mg), potassium tert-butoxide (109 mg) and toluene (3 ml) was heated at 100° C. for 1 h. The reaction mixture was cooled to room temperature, poured into water and extracted with EtOAc-THF. The extract was washed with brine, dried over MgSO₄, concentrated and purified by NH silica gel column chromatography (hexane/EtOAc). The resulting solid was recrystallized from IPA-IPE to give the title compound (47.5 mg) as a white solid.

MS (ESI+): [M+H]+ 446.4.

¹H NMR (400 MHz, DMSO-d₆): δ 0.83-0.99 (4H, m), 2.07 (1H, brs), 5.17 (2H, s), 6.05 (1H, s), 6.13 (1H, d, J=5.0 Hz), 7.12 (1H, d, J=9.9 Hz), 7.44 (1H, d, J=9.3 Hz), 7.67 (1H, d, J=7.5 Hz), 7.81 (1H, s), 8.07 (1H, s), 8.37 (1H, s).

Example 184

1-(2-Cyclopropyl-3-methylimidazo[1,2-a]pyridin-6-yl)-4-((5-(difluoromethyl)-3-thienyl)methoxy)pyridin-2 (1H)-one A) Methyl 5-(difluoromethyl)thiophene-3-carboxylate To a solution of methyl 5-formylthiophene-3-carboxylate (500 mg) in toluene (10 ml) was added dropwise DAST (947 mg), and the reaction mixture was stirred at room temperature overnight. The reaction mixture was poured into saturated NaHCO₃ solution and extracted with EtOAc. The extract was washed with brine, dried over MgSO₄, concentrated and purified by silica gel column chromatography (hexane/EtOAc) to give the title compound (213 mg) as a colorless oil.

¹H NMR (400 MHz, CDCl₃): δ 3.88 (3H, s), 6.82 (1H, t, J=55.8 Hz), 7.70 (1H, d, J=1.1 Hz), 8.20 (1H, s).

B) (5-(Difluoromethyl)-3-thienyl)methanol

To a solution of methyl 5-(difluoromethyl)thiophene-3-carboxylate (267 mg) in THF (5 ml)-MeOH (1 ml) was added NaBH₄ (263 mg) at room temperature, and the reaction mixture was stirred at 60° C. for 1 h. The reaction mixture was quenched with water, and extracted with EtOAc. The extract was washed with brine, dried over MgSO₄, concentrated and purified by silica gel column chromatography (hexane/EtOAc) to give the title compound (192 mg) as a colorless oil.

¹H NMR (400 MHz, CDCl₃): δ 1.66 (1H, t, J=5.8 Hz), 4.69 (2H, d, J=5.8, Hz), 6.81 (1H, t, J=56.1 Hz), 7.29 (1H, brs), 7.35 (1H, s).

C) 1-(2-Cyclopropyl-3-methylimidazo[1,2-a]pyridin-6-yl)-4-((5-(difluoromethyl)-3-thienyl)methoxy) pyridin-2(1H)-one A mixture of 4-bromo-1-(2-cyclopropyl-3-methylimidazo[1,2-a]pyridin-6-yl)pyridin-2(1H)-one (100 mg), (5-(difluoromethyl)-3-thienyl)methanol (88 mg), potassium tert-butoxide (109 mg) and toluene (3 ml) was heated at 100° C. for 1 h. The reaction mixture was then cooled to room temperature, poured into water and extracted with EtOAc-THF. The extract was washed with brine, dried over MgSO₄, concentrated and purified by NH silica gel column chromatography (hexane/EtOAc). The resulting solid was recrystallized from IPA-IPE to give the title compound (64.1 mg) as a white solid.

MS (ESI+): [M+H]+ 428.3.

¹H NMR (400 MHz, DMSO-d₆): δ 0.90 (4H, t, J=7.5 Hz), 2.00-2.13 (1H, m), 2.48 (3H, brs), 5.15 (2H, s), 6.04 (1H, d, J=2.4 Hz), 6.12 (1H, dd, J=7.8, 2.6 Hz), 7.12 (1H, d, J=9.5 Hz), 7.17-7.47 (2H, m), 7.55 (1H, s), 7.66 (1H, d, J=7.7 Hz), 7.91 (1H, s), 8.37 (1H, s).

Reference Example 185

4-((4-Chlorobenzyl)oxy)-1-(2-cyclopropyl-3-methylimidazo[1,2-a]pyrazin-6-yl)pyridin-2(1H)-one A) N-(5-Bromo-1-(1-cyclopropyl-1-oxopropan-2-yl) pyrazin-2(1H)-ylidene)-4-methylbenzenesulfonamide To a solution of N-(5-bromopyrazin-2-yl)-4-methylbenzenesulfonamide (1.73 g) in DMF (20 ml) was added NaH (60% in oil, 0.316 g) at 0° C., and the mixture was stirred at room temperature for 30 min. To the mixture was added 2-bromo-1-cyclopropylpropan-1-one (1.87 g) at room temperature, and the mixture was stirred overnight. The mixture was partitioned between EtOAc and water, and the organic layer was washed with brine, dried over MgSO$_4$, concentrated in vacuo, and purified by silica gel column chromatography (hexane/EtOAc) to give the title compound (1.02 g) as a solid.
$^1$H NMR (400 MHz, DMSO-d$_6$): δ 0.74-1.00 (4H, m), 1.71 (3H, d, J=7.3 Hz), 2.21-2.29 (1H, m), 2.36 (3H, s), 5.63 (1H, d, J=7.3 Hz), 7.34 (2H, d, J=8.0 Hz), 7.69 (2H, d, J=8.2 Hz), 8.31 (1H, s), 8.76 (1H, s).

B) 6-Bromo-2-cyclopropyl-3-methylimidazo[1,2-a] pyrazine

To a solution of N-(5-bromo-1-(1-cyclopropyl-1-oxopropan-2-yl)pyrazin-2(1H)-ylidene)-4-methylbenzenesulfonamide (1.24 g) in THF (10 ml) was added trifluoroacetic anhydride (1.23 g) at 0° C., and the mixture was heated at 60° C. for 3 h. The mixture was partitioned between EtOAc and saturated NaHCO$_3$ solution, and the organic layer was washed with 1 M NaOH and brine successively, dried over MgSO$_4$, concentrated in vacuo, and purified by silica gel column chromatography (hexane/EtOAc) to give the title compound (593 mg) as pale yellow crystals.
MS (ESI+): [M+H]+ 252.2.

C) 4-((4-Chlorobenzyl)oxy)-1-(2-cyclopropyl-3-methylimidazo[1,2-a]pyrazin-6-yl)pyridin-2(1H)-one A mixture of 4-((4-chlorobenzyl)oxy)pyridin-2(1H)-one (26.2 mg), 6-bromo-2-cyclopropyl-3-methylimidazo[1,2-a] pyrazine (42.1 mg), N,N'-dimethyl-1,2-ethanediamine (19.63 mg), CuI (21.2 mg), potassium carbonate (46.2 mg) and DMSO (1 ml) was heated at 150° C. for 1 h under microwave irradiation. The mixture was poured into 28% NH$_3$ solution at room temperature and extracted with EtOAc. The organic layer was separated, washed with water and brine successively, dried over MgSO$_4$, concentrated in vacuo, and purified by column chromatography (hexane/EtOAc) to give the title compound (19.1 mg) as pale yellow crystals.
MS (ESI+): [M+H]+ 407.4.
$^1$H NMR (400 MHz, DMSO-d$_6$): δ 0.92-1.04 (4H, m), 2.14-2.24 (1H, m), 2.54 (3H, s), 5.18 (2H, s), 6.01 (1H, d, J=2.4 Hz), 6.17 (1H, dd, J=2.6, 7.7 Hz), 7.50 (4H, s), 7.78 (1H, d, J=7.7 Hz), 8.68 (1H, s), 8.83 (1H, s).

Example 186

4-((4-Chlorobenzyl)amino)-1-(2-cyclopropyl-3-methylimidazo[1,2-a]pyridin-6-yl)pyridin-2(1H)-one A mixture of 4-bromo-1-(2-cyclopropyl-3-methylimidazo [1,2-a]pyridin-6-yl)pyridin-2(1H)-one (80 mg), 4-chlorobenzylamine (49.4 mg), xantphos (10.8 mg), tris(dibenzylideneacetone)dipalladium(0) (5.3 mg), cesium carbonate (151 mg) and DMA (2 ml) was heated at 120° C. for 30 min under microwave irradiation. The reaction mixture was cooled to room temperature, poured into water and extracted with EtOAc-THF. The extract was washed with brine, dried over MgSO$_4$, concentrated and purified by NH silica gel column chromatography (hexane/EtOAc then EtOAc/MeOH) to give the title compound (19.1 mg) as a white solid.
MS (ESI+): [M+H]+ 405.3.
$^1$H NMR (400 MHz, DMSO-d$_6$): δ 0.79-0.98 (4H, m), 1.98-2.13 (1H, m), 2.46 (3H, s), 4.30 (2H, d, J=5.9 Hz), 5.18 (1H, brs), 5.92 (1H, dd, J=2.2, 7.6 Hz), 7.06 (1H, dd, J=1.8, 9.6 Hz), 7.31-7.47 (7H, m), 8.25 (1H, s).

Reference Example 187

4-(Benzyloxy)-1-(2-cyclopropyl-3-methylimidazo[1, 2-a]pyrazin-6-yl)pyridin-2(1H)-one The title compound was obtained in an analogous manner to step C in reference example 185 using 4-(benzyloxy)pyridin-2(1H)-one and 6-bromo-2-cyclopropyl-3-methylimidazo[1,2-a]pyrazine:
MS (ESI+): [M+H]+ 373.3.
$^1$H NMR (400 MHz, DMSO-d$_6$): δ 0.89-1.06 (4H, m), 2.13-2.25 (1H, m), 2.54 (3H, s), 5.18 (2H, s), 6.01 (1H, d, J=2.5 Hz), 6.17 (1H, dd, J=2.6, 7.7 Hz), 7.30-7.51 (5H, m), 7.77 (1H, d, J=7.8 Hz), 8.69 (1H, s), 8.83 (1H, s).

Reference Example 188

4-((E)-2-(4-Chlorophenyl)ethenyl)-1-(2-cyclopropyl-3-methylimidazo[1,2-a]pyridin-6-yl)pyridin-2(1H)-one A mixture of 4-bromo-1-(2-cyclopropyl-3-methylimidazo [1,2-a]pyridin-6-yl)pyridin-2(1H)-one (178 mg), (E)-(4-chlorostyryl)boronic acid (189 mg), potassium carbonate (214 mg), PdCl$_2$(dppf) (18.9 mg), THF (3 ml) and water (1 ml) was heated at 70° C. under N$_2$ atmosphere overnight. The mixture was partitioned between EtOAc and water, and the organic layer was washed with brine, dried over MgSO$_4$, concentrated in vacuo, and purified by silica gel column chromatography (hexane/EtOAc) to give the title compound (80 mg) as a solid.
MS (ESI+): [M+H]+ 402.1.
$^1$H NMR (400 MHz, DMSO-d$_6$): δ 0.86-0.98 (4H, m), 2.02-2.16 (1H, m), 3.28 (3H, brs), 6.60 (1H, s), 6.74 (1H, d, J=7.4 Hz), 7.14-7.28 (2H, m), 7.42-7.57 (4H, m), 7.66-7.78 (3H, m), 8.45 (1H, s).

Example 189

4-((2-Bromo-1,3-thiazol-4-yl)methoxy)-1-(2-cyclopropyl-3-methylimidazo[1,2-a]pyridin-6-yl)pyridin-2 (1H)-one To a solution of 1-(2-cyclopropyl-3-methylimidazo[1,2-a] pyridin-6-yl)-4-hydroxypyridin-2(1H)-one (239 mg), (2-bromothiazol-4-yl)methanol (330 mg) and triphenylphosphine (669 mg) in THF (5 ml) was added bis(2-methoxyethyl) azodicarboxylate (597 mg), and the mixture was stirred at room temperature for 3 h. The mixture was diluted with EtOAc, washed with water and brine successively, concentrated in vacuo, and purified by silica gel column chromatography (EtOAc/MeOH) to give the title compound (185 mg) as a white solid.
MS (ESI+): [M+H]+ 457.3.

¹H NMR (400 MHz, DMSO-d₆): δ 0.85-0.96 (4H, m), 2.02-2.12 (1H, m), 2.48 (3H, brs), 5.19 (2H, s), 6.08 (1H, d, J=2.5 Hz), 6.13 (1H, dd, J=2.5, 7.5 Hz), 7.12 (1H, dd, J=1.6, 9.4 Hz), 7.44 (1H, d, J=9.4 Hz), 7.67 (1H, d, J=7.7 Hz), 7.91 (1H, s), 8.38 (1H, s).

Example 190

4-((4-tert-Butylbenzyl)oxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (200 mg) in DMF (3 ml) were added 1-(bromomethyl)-4-(tert-butyl)benzene (178 mg) and potassium carbonate (197 mg) at room temperature, and the mixture was stirred for 17 h. The mixture was poured into water, and the resultant solid was collected by filtration. The solid was recrystallized from acetone to give the title compound (143 mg) as white crystals.
MS (ESI+): [M+H]+ 428.4.

Example 191

1-(2-Cyclopropyl-3-methylimidazo[1,2-a]pyridin-6-yl)-4-((4-isopropylbenzyl)oxy)pyridin-2(1H)-one The title compound was obtained in an analogous manner to example 190 using 1-(bromomethyl)-4-isopropylbenzene and 1-(2-cyclopropyl-3-methylimidazo[1,2-a]pyridin-6-ya)-4-hydroxypyridin-2(1H)-one.
MS (ESI+): [M+H]+ 414.4.

Example 192

4-((4-Bromobenzyl)oxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (500 mg) in THF (5 ml) were added p-bromobenzyl alcohol (332 mg), (E)-bis(2-methoxyethyl)diazene-1,2-dicarboxylate (541 mg) and triphenylphosphine (606 mg), and the mixture was stirred at room temperature for 16 h. The mixture was partitioned between EtOAc and water, and the organic layer was washed with brine, dried over MgSO₄, concentrated in vacuo, and purified by silica gel column chromatography (EtOAc/MeOH), followed by crystallization from hot EtOAc to give the title compound (502 mg) as white crystals.
MS (ESI+): [M+H]+ 450.3.
¹H NMR (400 MHz, DMSO-d₆): δ 0.82-0.96 (4H, m), 2.07 (1H, brs), 2.47 (3H, brs), 5.15 (2H, s), 5.99 (1H, d, J=2.4 Hz), 6.14 (1H, dd, J=2.5, 7.9 Hz), 7.06-7.15 (1H, m), 7.43 (3H, d, J=8.8 Hz), 7.59-7.69 (3H, m), 8.37 (1H, s).

Example 193

1-(2-Cyclopropyl-3-methylimidazo[1,2-a]pyridin-6-yl)-4-((4-(trifluoromethyl)-1,3-thiazol-2-yl)methoxy)pyridin-2(1H)-one To a solution of 1-(2-cyclopropyl-3-methylimidazo[1,2-a]pyridin-6-yl)-4-hydroxypyridin-2(1H)-one (49 mg), (4-(trifluoromethyl)-1,3-thiazol-2-yl)methanol (68.3 mg) and triphenylphosphine (137 mg) in THF (5 ml) was added bis(2-methoxyethyl) azodicarboxylate (122 mg), and the mixture was stirred at room temperature for 3 h. The reaction mixture was poured into water and extracted with EtOAc. The extract was washed with brine, dried over MgSO₄, concentrated and purified by silica gel column chromatography (hexane/EtOAc then EtOAc/MeOH). The resulting solid was recrystallized from EtOH-hexane to give the title compound (21.5 mg) as a white solid.
MS (ESI+): [M+H]+ 447.4.
¹H NMR (400 MHz, DMSO-d₆): δ 0.85-0.95 (4H, m), 2.07 (1H, brs), 2.48 (3H, brs), 5.57 (2H, s), 6.11 (1H, d, J=2.5 Hz), 6.21 (1H, dd, J=2.3, 7.5 Hz), 7.12 (1H, d, J=7.5 Hz), 7.44 (1H, d, J=9.4 Hz), 7.72 (1H, d, J=7.7 Hz), 8.40 (1H, s), 8.62 (1H, s).

Example 194

4-((4-Bromo-1,3-thiazol-2-yl)methoxy)-1-(2-cyclopropyl-3-methylimidazo[1,2-a]pyridin-6-yl)pyridin-2(1H)-one To a solution of 1-(2-cyclopropyl-3-methylimidazo[1,2-a]pyridin-6-yl)-4-hydroxypyridin-2(1H)-one (50 mg), (4-bromo-1,3-thiazol-2-yl)methanol (69 mg) and triphenylphosphine (140 mg) in THF (6 ml) was added bis(2-methoxyethyl) azodicarboxylate (125 mg), and the mixture was stirred at room temperature for 3 h. The reaction mixture was poured into water and extracted with EtOAc. The extract was washed with brine, dried over MgSO₄, concentrated and purified by silica gel column chromatography (hexane/EtOAc then EtOAc/MeOH). The resulting solid was recrystallized from EtOH-hexane to give the title compound (37.9 mg) as a white solid.
MS (ESI+): [M+H]+ 457.3.
¹H NMR (400 MHz, DMSO-d₆): δ 0.77-1.01 (4H, m), 2.07 (1H, brs), 5.51 (2H, s), 6.08 (1H, brs), 6.19 (1H, d, J=7.8 Hz), 7.12 (1H, d, J=9.4 Hz), 7.44 (1H, d, J=8.8 Hz), 7.70 (1H, d, J=7.9 Hz), 7.96 (1H, s), 8.39 (1H, s).

Reference Example 195

1-(2-Cyclopropyl-3-methylimidazo[1,2-a]pyrazin-6-yl)-4-((4-(trifluoromethyl)-1,3-thiazol-2-yl)methoxy)pyridin-2(1H)-one A mixture of 4-(benzyloxy)-1-(2-cyclopropyl-3-methylimidazo[1,2-a]pyrazin-6-yl)pyridin-2(1H)-one (113 mg), 10% Pd/C (32.3 mg) and MeOH (5 ml) was stirred under H₂ atmosphere at room temperature for 2 h. The catalyst was removed by filtration, and the filtrate was concentrated in vacuo. The resulting residue was dissolved in THF (2 ml), to which (4-(trifluoromethyl)-1,3-thiazol-2-yl)methanol (67.0 mg), bis(2-methoxyethyl) azodicarboxylate (93 mg) and triphenylphosphine (104 mg) were added, and the resulting mixture was stirred at room temperature for 3 h. The mixture was partitioned between EtOAc and water, and the organic layer was washed with brine, dried over MgSO₄, concentrated in vacuo, and purified by silica gel column chromatography (EtOAc/MeOH), followed by crystallization from hot EtOAc-hexane to give the title compound (35.3 mg) as white crystals.
MS (ESI+): [M+H]+ 448.3.
¹H NMR (400 MHz, DMSO-d₆): δ 0.91-1.05 (4H, m), 2.19 (1H, d, J=4.6 Hz), 2.55 (3H, s), 5.58 (2H, s), 6.12 (1H, brs), 6.24 (1H, d, J=6.9 Hz), 7.83 (1H, d, J=7.7 Hz), 8.62 (1H, s), 8.71 (1H, s), 8.83 (1H, s).

Example 196

4-((5-Chloro-1,2,4-thiadiazol-3-yl)methoxy)-1-(2-cyclopropyl-3-methylimidazo[1,2-a]pyridin-6-yl)pyridin-2(1H)-one The title compound was obtained in an analogous manner to example 190 using 5-chloro-3-(chloromethyl)-1,2,4-thiadiazole and 1-(2-cyclopropyl-3-methylimidazo[1,2-a]pyridin-6-yl)-4-hydroxypyridin-2(1H)-one.
MS (ESI+): [M+H]+ 414.3.

Reference Example 197

4-((4-Chlorobenzyl)oxy)-1-(2-cyclopropyl-3-methylimidazo[1,2-b]pyridazin-6-yl)pyridin-2(1H)-one A) 6-Bromo-2-cyclopropyl-3-methylimidazo[1,2-b]pyridazine To a solution of 6-bromopyridazin-3-amine (1.0 g) in DMA (10 ml) were added 2-bromo-1-cyclopropylpropan-1-one (2.04 g) and NaHCO$_3$ (0.966 g) at room temperature, and the mixture was stirred at 80° C. for 16 h. The mixture was partitioned between EtOAc and water, and the organic layer was washed with brine, dried over MgSO$_4$, concentrated in vacuo, and purified by silica gel column chromatography (hexane/EtOAc) to give the title compound (1.10 g) as yellow crystals.
MS (ESI+): [M+H]+ 252.0.

B) 4-((4-Chlorobenzyl)oxy)-1-(2-cyclopropyl-3-methylimidazo[1,2-b]pyridazin-6-yl)pyridin-2(1H)-one A mixture of 4-((4-chlorobenzyl)oxy)pyridin-2(1H)-one (108 mg), 6-bromo-2-cyclopropyl-3-methylimidazo[1,2-b]pyridazine (150 mg), N,N'-dimethyl-1,2-ethanediamine (81 mg), CuI (87 mg), potassium carbonate (190 mg) and DMSO (3 ml) was heated at 150° C. for 1 h under microwave irradiation. The mixture was poured into 28% NH$_3$ solution, and extracted with EtOAc. The organic layer was separated, washed with water and brine successively, dried over MgSO$_4$, concentrated in vacuo, and purified by column chromatography (hexane/EtOAc), followed by crystalization from EtOAc-hexane to give the title compound (52.3 mg) as pale yellow crystals.
MS (ESI+): [M+H]+ 407.3.

Reference Example 198

1-(2-Cyclopropyl-3-methylimidazo[1,2-b]pyridazin-6-yl)-4-((4-fluorobenzyl)oxy)pyridin-2(1H)-one The title compound was obtained in an analogous manner to step B in reference example 197 using 4-((4-fluorobenzyl)oxy)pyridin-2(1H)-one and 6-bromo-2-cyclopropyl-3-methylimidazo[1,2-b]pyridazine.
MS (ESI+): [M+H]+ 391.3.

Reference Example 199

4-((4-Chlorobenzyl)oxy)-1-(2-cyclopropyl-3-methylimidazo[1,2-a]pyrimidin-6-yl)pyridin-2(1H)-one A) 6-Bromo-2-cyclopropyl-3-methylimidazo[1,2-a]pyrimidine To a solution of 5-bromopyrimidin-2-amine (500 mg) in DMF (10 ml) was added 2-bromo-1-cyclopropylpropan-1-one (1.02 g) at room temperature, and the mixture was stirred at 100° C. for 24 h. The mixture was partitioned between EtOAc and 1 M NaOH, and the organic layer was washed with 1 M NaOH and brine successively, dried over MgSO$_4$, concentrated in vacuo, and purified by NH silica gel column chromatography (hexane/EtOAc) to give the title compound (89 mg) as yellow crystals.
$^1$H NMR (400 MHz, DMSO-d$_6$): δ 0.84-1.02 (4H, m), 2.04-2.15 (1H, m), 2.50 (3H, brs), 8.41 (1H, s), 8.98 (1H, s).

B) 4-((4-Chlorobenzyl)oxy)-1-(2-cyclopropyl-3-methylimidazo[1,2-a]pyrimidin-6-yl)pyridin-2(1H)-one The title compound was obtained in an analogous manner to step B in reference example 197 using 4-((4-chlorobenzyl)oxy)pyridin-2(1H)-one and 6-bromo-2-cyclopropyl-3-methylimidazo[1,2-a]pyrimidine.
MS (ESI+): [M+H]+ 407.4.

Example 200

1-(2-(2,4-Dimethyl-1,3-oxazol-5-yl)-1-methyl-1H-benzimidazol-6-yl)-4-((4-fluorobenzyl)oxy)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 2,4-dimethyl-1,3-oxazole-5-carboxylic acid.
MS (ESI+): [M+H]+ 445.4.

Example 201

1-(2-(4-Ethyl-1,3-oxazol-5-yl)-1-methyl-1H-benzimidazol-6-yl)-4-((4-fluorobenzyl)oxy)pyridin-2(1H)-one A mixture of 1-(4-amino-3-(methylamino)phenyl)-4-((4-fluorobenzyl)oxy)pyridin-2(1H)-one (67.9 mg), 4-ethyl-1,3-oxazole-5-carboxylic acid (28.2 mg), HATU (80.0 mg), N,N-diisopropylethylamine (0.105 ml) and DMF (2.0 ml) was stirred at room temperature for 2 h. The mixture was poured into saturated NaHCO$_3$ solution and extracted with EtOAc. The extract was washed with brine, dried over MgSO$_4$, concentrated in vacuo. The residue was dissolved in AcOH (1.5 ml), and the mixture was stirred at 80° C. for 1 h. The mixture was concentrated in vacuo. The residue was purified by NH silica gel column chromatography (hexane/EtOAc then EtOAc/MeOH). The resulting solid was recrystallized from EtOAc-hexane to give the title compound (15.7 mg) as a white solid.
MS (ESI+): [M+H]+ 445.4.
$^1$H NMR (400 MHz, DMSO-d$_6$): δ 1.25 (3H, t, J=7.3 Hz), 2.95-3.03 (2H, m), 4.00 (3H, s), 5.15 (2H, s), 6.02 (1H, s), 6.12 (1H, d, J=9.7 Hz), 7.21 (1H, d, J=8.5 Hz), 7.26 (2H, t, J=8.7 Hz), 7.49-7.59 (2H, m), 7.63 (1H, d, J=7.5 Hz), 7.70-7.80 (2H, m), 8.60 (1H, s).

Example 202

4-((5-Chloro-2-furyl)methoxy)-1-(2-cyclopropyl-1-methyl-1H-benzimidazol-6-yl)pyridin-2(1H)-one To a mixture of 1-(2-cyclopropyl-1-methyl-1H-benzimidazol-6-yl)-4-hydroxypyridin-2(1H)-one (100 mg), (5-chloro-2-furyl)methanol (94 mg), tributylphosphine (0.264 ml) and THF (10 ml) was added 1,1'-(azodicarbonyl)dipiperidine (269 mg), and the mixture was stirred at 60° C. for 2 h. The reaction mixture was diluted with EtOAc, washed with water and brine successively, dried over MgSO$_4$, and concentrated in vacuo. The residue was purified by NH silica gel column chromatography (hexane/EtOAc), followed by silica gel column chromatography (hexane/EtOAc then EtOAc/MeOH) to give the title compound (3.8 mg) as an off-white solid.

MS (ESI+): [M+H]+396.1.

$^1$H NMR (400 MHz, DMSO-d$_6$): δ 1.01-1.13 (4H, m), 2.23-2.30 (1H, m), 3.85 (3H, s), 5.10 (2H, s), 6.04-6.10 (2H, m), 6.53 (1H, d, J=3.3 Hz), 6.78 (1H, d, J=3.0 Hz), 7.05 (1H, d, J=9.0 Hz), 7.49-7.55 (2H, m), 7.58 (1H, d, J=8.3 Hz).

Example 203

4-((5-Chloro-2-thienyl)methoxy)-1-(2-((1RS,2SR)-2-(2-hydroxypropan-2-yl)cyclopropyl)-1-methyl-1H-benzimidazol-6-yl)pyridin-2(1H)-one A) 4-Hydroxy-1-(2-((1RS,2SR)-2-(2-hydroxypropan-2-yl)cyclopropyl)-1-methyl-1H-benzimidazol-6-yl)pyridin-2(1H)-one A mixture of 4-(benzyloxy)-1-(2-((1RS,2SR)-2-(2-hydroxypropan-2-yl)cyclopropyl)-1-methyl-1H-benzimidazol-6-yl)pyridin-2(1H)-one (1.35 g), 10% Pd/C (0.6 g) and MeOH (30 ml) was stirred under H$_2$ atmosphere at room temperature for 3 h. The catalyst was removed by filtration, and the filtrate was concentrated in vacuo to give the title compound (950 mg) as an off-white solid.

MS (ESI+): [M+H]+ 340.3.

B) 4-((5-Chloro-2-thienyl)methoxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (5-chloro-2-thienyl)methanol (88 mg), tributylphosphine (0.219 ml) and THF (10 ml) was added 1,1'-(azodicarbonyl)dipiperidine (223 mg), and the mixture was stirred at 60° C. for 2 h. The reaction mixture was partitioned between EtOAc and water, and the organic layer was washed with brine, dried over MgSO$_4$, and concentrated in vacuo. The residue was purified by NH silica gel column chromatography (EtOAc/MeOH), followed by silica gel column chromatography (hexane/EtOAc then EtOAc/MeOH). The resulting solid was recrystallized from IPE-IPA to give the title compound (29.1 mg) as an off-white solid.

MS (ESI+): [M+H]+ 470.1.

$^1$H NMR (300 MHz, DMSO-d$_6$): δ 1.06-1.13 (6H, m), 1.27 (1H, td, J=4.1, 8.9 Hz), 1.36-1.44 (1H, m), 1.56-1.66 (1H, m), 2.27 (1H, td, J=6.3, 8.8 Hz), 3.87 (3H, s), 5.30 (2H, s), 5.86 (1H, s), 6.03-6.09 (2H, m), 7.05-7.13 (2H, m), 7.17 (1H, d, J=3.8 Hz), 7.51-7.65 (3H, m).

Example 204

4-((5-Chloropyridin-2-yl)methoxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (5-chloropyridin-2-yl)methanol (85 mg), tributylphosphine (0.219 ml) and THF (10 ml) was added 1,1'-(azodicarbonyl)dipiperidine (223 mg), and the mixture was stirred at 60° C. for 2 h. The reaction mixture was diluted with EtOAc, quenched with water, and extracted with EtOAc. The organic layer was separated, washed with water and brine successively, dried over MgSO$_4$, filtered through silica pad, and concentrated in vacuo. The residue was purified by column chromatography (hexane/EtOAc then EtOAc/MeOH), followed by recrystallization from IPA-IPE to give the title compound (68.4 mg) as an off-white solid.

MS (ESI+): [M+H]+ 465.4.

$^1$H NMR (400 MHz, DMSO-d$_6$): δ 1.09 (6H, s), 1.27 (1H, td, J=4.0, 8.8 Hz), 1.36-1.44 (1H, m), 1.61 (1H, q, J=8.2 Hz), 2.23-2.31 (1H, m), 3.86 (3H, s), 5.24 (2H, s), 5.86 (1H, s), 5.97 (1H, s), 6.14 (1H, d, J=7.5 Hz), 7.09 (1H, d, J=8.4 Hz), 7.54 (1H, d, J=8.5 Hz), 7.58 (1H, s), 7.59-7.65 (2H, m), 8.03 (1H, d, J=8.3 Hz), 8.67 (1H, s).

Example 205

4-((4-Fluorobenzyl)oxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (4-fluorophenyl)methanol (74.3 mg), tributylphosphine (0.219 ml) and THF (10 ml) was added 1,1'-(azodicarbonyl)dipiperidine (223 mg), and the mixture was stirred at 60° C. for 2 h. The reaction mixture was diluted with EtOAc, washed with water and brine successively, dried over MgSO$_4$, filtered through NH silica gel pad, and concentrated in vacuo. The residue was purified by column chromatography (hexane/EtOAc then EtOAc/MeOH). The resulting solid was washed with toluene, and recrystallized from IPA-IPE to give the title compound (49.6 mg) as an off-white solid.

MS (ESI+): [M+H]+ 448.2.

$^1$H NMR (400 MHz, DMSO-d$_6$): δ 1.09 (6H, s), 1.23-1.32 (1H, m), 1.36-1.44 (1H, m), 1.56-1.65 (1H, m), 2.23-2.31 (1H, m), 3.87 (3H, s), 5.14 (2H, s), 5.86 (1H, s), 5.99 (1H, d, J=2.1 Hz), 6.09 (1H, dd, J=1.8, 7.6 Hz), 7.09 (1H, d, J=8.4 Hz), 7.21-7.31 (2H, m), 7.49-7.58 (4H, m), 7.61 (1H, d, J=7.7 Hz).

Example 206

4-((4-Chlorobenzyl)oxy)-1-(2-((1RS,2SR)-2-(3-hydroxypentan-3-yl)cyclopropyl)-1-methyl-1H-benzimidazol-6-yl)pyridin-2(1H)-one Ethylmagnesium bromide (1.0 M solution in THF, 1.29 ml) was added to a solution of methyl(1RS,2RS)-2-(6-(4-((4-chlorobenzyl)oxy)-2-oxopyridin-1(2H)-yl)-1-methyl-1H-benzimidazol-2-yl)cyclopropanecarboxylate (150 mg) in THF (5 ml) at 0° C., and the mixture was stirred at room temperature for 3 h. The mixture was quenched with saturated NH$_4$Cl solution, and extracted with EtOAc. The organic layer was separated, washed with water and brine successively, dried over MgSO$_4$, and concentrated in vacuo. The residue was purified by NH silica gel column chromatography (EtOAc/MeOH), and the resulting solid was crystallized from EtOH to give the title compound (48 mg) as a white solid.

MS (ESI+): [M+H]+ 493.5.

$^1$H NMR (400 MHz, CDCl$_3$): δ 0.85 (3H, t, J=7.4 Hz), 1.01 (3H, t, J=7.4 Hz), 1.31-1.45 (2H, m), 1.46-1.54 (1H, m), 1.60-1.75 (4H, m), 1.92-2.06 (1H, m), 3.82 (3H, s), 5.03 (2H, s), 5.99-6.07 (2H, m), 6.64 (1H, s), 7.10 (1H, d, J=8.5 Hz), 7.27-7.33 (1H, m), 7.33-7.42 (5H, m), 7.62 (1H, d, J=8.5 Hz).

Example 207

4-((4-Chlorobenzyl)oxy)-1-(2-((1R*,2S*)-2-(2-fluoropropan-2-yl)cyclopropyl)-1-methyl-1H-benzimidazol-6-yl)pyridin-2(1H)-one (optically active, IA tR2)

BAST (0.294 ml) was added to a solution of 4-((4-chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR2, 185 mg) obtained in Example 154 in toluene (3 ml) at 0° C., and the mixture was stirred for 30 min. The resulting mixture was quenched with saturated NaHCO$_3$ solution and extracted with EtOAc. The organic layer was separated, washed with water and brine successively, dried over MgSO$_4$, and concentrated in vacuo. The residue was purified by silica gel column chromatography (EtOAc/MeOH) to give the title compound (87 mg) as a white solid.

MS (ESI+): [M+H]+ 466.4.

$^1$H NMR (400 MHz, CDCl$_3$): δ 0.92 (3H, d, J=21.3 Hz), 1.35-1.49 (4H, m), 1.68-1.82 (2H, m), 2.12-2.22 (1H, m), 3.84 (3H, s), 5.03 (2H, s), 6.01-6.10 (2H, m), 7.13 (1H, d, J=8.3 Hz), 7.31 (1H, d, J=7.3 Hz), 7.33-7.42 (5H, m), 7.75 (1H, d, J=8.5 Hz).

Analysis of enantiomeric excess
Column: CHIRALPAK IA (4.6×250 mm)
Mobile phase: Hexane/EtOH=3/7 (v/v/v)
Flow rate: 0.5 ml/min
Temperature: 30° C.
Detection: UV: 220 nm
Retention time: 23.75 min

Example 208

4-((4-Chlorobenzyl)oxy)-1-(1-methyl-2-propanoyl-1H-benzimidazol-6-yl)pyridin-2(1H)-one A) 1-(6-Bromo-1-methyl-1H-benzimidazol-2-yl)propan-1-one Ethylmagnesium bromide (1 M in THF, 11.0 ml) was added to a solution of 6-bromo-N-methoxy-N,1-dimethyl-1H-benzo[d]imidazole-2-carboxamide (1.09 g) in THF (15 ml) at 0° C. The mixture was stirred at 0° C. under N$_2$ atmosphere for 2 h. The mixture was quenched with saturated NH$_4$Cl solution, and extracted with EtOAc. The organic layer was separated, washed with brine, dried over MgSO$_4$ and concentrated in vacuo. The residue was purified by column chromatography (hexane/EtOAc) to give the title compound (0.86 g) as a white solid.

MS (ESI+): [M+H]+ 267.0.

B) 4-((4-Chlorobenzyl)oxy)-1-(1-methyl-2-propanoyl-1H-benzimidazol-6-yl)pyridin-2(1H)-one A mixture of 4-((4-chlorobenzyl)oxy)pyridin-2(1H)-one (100 mg), 1-(6-bromo-1-methyl-1H-benzo[d]imidazol-2-yl)propan-1-one (170 mg), N,N'-dimethylethylenediamine (0.046 ml), CuI (81 mg) and potassium carbonate (176 mg) in DMSO (3 ml) was stirred at 150° C. for 30 min under N$_2$ atmosphere. The mixture was purified by NH silica gel column chromatography (hexane/EtOAc), followed by recrystallization from IPA to give the title compound (6.1 mg) as a pale yellow solid.

MS (ESI+): [M+H]+ 422.1.

$^1$H NMR (400 MHz, CDCl$_3$): δ 1.27 (3 H, t, J=7.3 Hz), 3.35 (2 H, q, J=7.2 Hz), 4.13 (3 H, s), 5.03 (2 H, s), 6.03-6.12 (2 H, m), 7.30 (2 H, t, J=7.6 Hz), 7.34-7.42 (4 H, m), 7.50 (1 H, s), 7.96 (1 H, d, J=8.5 Hz).

Example 209

4-((4-Chlorobenzyl)oxy)-1-(2-((1R*,2S*)-2-(2-fluoropropan-2-yl)cyclopropyl)-1-methyl-1H-benzimidazol-6-yl)pyridin-2(1H)-one (optically active, IA tR1)

BAST (0.296 ml) was added to a solution of 4-((4-chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR1, 186 mg) obtained in Example 153 in toluene (3 ml) at 0° C., and the mixture was stirred for 30 min. The mixture was quenched with saturated NaHCO$_3$ solution at 0° C. and extracted with EtOAc. The organic layer was separated, washed with water and brine successively, dried over MgSO$_4$ and concentrated in vacuo. The residue was purified by silica gel column chromatography (EtOAc/MeOH) to give the title compound (15 mg) as an off-white solid.

MS (ESI+): [M+H]+ 466.4.

$^1$H NMR (400 MHz, CDCl$_3$): δ 0.92 (3H, d, J=21.8 Hz), 1.35-1.44 (4H, m), 1.67-1.82 (2H, m), 2.13-2.23 (1H, m), 3.84 (3H, s), 5.03 (2H, s), 6.02-6.09 (2H, m), 7.13 (1H, d, J=8.5 Hz), 7.31 (1H, d, J=7.3 Hz), 7.33-7.42 (5H, m), 7.75 (1H, d, J=8.5 Hz).

Analysis of enantiomeric excess
Column: CHIRALPAK IA (4.6×250 mm)
Mobile phase: Hexane/EtOH=3/7 (v/v)
Flow rate: 0.5 ml/min
Temperature: 30° C.
Detection: UV: 220 nm
Retention time: 18.89 min

Example 210

4-(Benzyloxy)-1-(2-ethyl-1-methyl-1H-benzimidazol-6-yl)pyridin-2(1H)-one

A mixture of 4-(benzyloxy)pyridin-2(1H)-one (1.0 g), 6-bromo-2-ethyl-1-methyl-1H-benzimidazole (1.19 g), potassium carbonate (2.06 g), N,N'-dimethylethylenediamine (0.53 ml), CuI (0.95 g) and DMSO (20 ml) was stirred at 150° C. for 2 h. After cooling to 0° C., 28% NH$_3$ solution (56.0 ml) was added. The precipitate was collected by filtration. The collected material was dissolved in THF, passed through a plug of NH silica gel (EtOAc) and concentrated in vacuo. The resulting solid was collected to give the title compound (1.03 g) as a pink solid.

MS (ESI+): [M+H]+ 360.3.

$^1$H NMR (400 MHz, DMSO-d$_6$): δ 1.33 (3H, t, J=7.4 Hz), 2.90 (2H, q, J=7.5 Hz), 3.74 (3H, s), 5.16 (2H, s), 5.98 (1H, s), 6.10 (1H, d, J=5.4 Hz), 7.07 (1H, d, J=8.8 Hz), 7.34-7.51 (5H, m), 7.53 (1H, s), 7.55-7.62 (2H, m).

Example 211

4-((5-Chlorothiophen-2-yl)methoxy)-1-(2-ethyl-1-methyl-1H-benzimidazol-6-yl)pyridin-2(1H)-one To a solution of 1-(2-ethyl-1-methyl-1H-benzimidazol-6-yl)-4-hydroxypyridin-2(1H)-one (150 mg), (5-chloro-2-thienyl) methanol (166 mg) and tributylphosphine (388 mg) in THF (10 ml) was added 1,1'-(azodicarbonyl)dipiperidine (422 mg), and the reaction mixture was stirred at 60° C. for 2 h. The reaction mixture was cooled to room temperature. The mixture was poured into water and extracted with EtOAc. The extract was washed with brine, dried over $MgSO_4$, concentrated and purified by NH silica gel column chromatography (hexane/EtOAc then EtOAc/MeOH). The resulting solid was recrystallized from EtOH-hexane to give the title compound (16.1 mg) as a white solid.

MS (ESI+): [M+H]+ 400.3.

$^1$H NMR (400 MHz, DMSO-$d_6$): δ 1.33 (3H, t, J=7.5 Hz), 2.90 (2H, q, J=7.7 Hz), 3.74 (3H, s), 5.30 (2H, s), 6.00-6.11 (2H, m), 7.09 (2H, d, J=4.0 Hz), 7.17 (1H, d, J=3.5 Hz), 7.53 (1H, s), 7.58 (1H, s), 7.60 (1H, d, J=2.8 Hz).

Example 212

4-((3,4-Difluorobenzyl)oxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (3,4-difluorophenyl)methanol (0.066 ml), tributylphosphine (0.219 ml) and THF (10 ml) was added 1,1'-(azodicarbonyl)dipiperidine (223 mg), and the mixture was stirred at 60° C. for 2 h. The reaction mixture was diluted with EtOAc, and quenched with water. The organic layer was separated, washed with water and brine successively, dried over $MgSO_4$, filtered through NH silica gel pad, and concentrated in vacuo. The residue was purified by silica gel column chromatography (hexane/EtOAc then EtOAc/MeOH), followed by NH silica gel column chromatography (hexane/EtOAc). The resulting solid was recrystallized from IPA-IPE to give the title compound (51.4 mg) as an off-white solid.

MS (ESI+): [M+H]+ 466.4.

$^1$H NMR (400 MHz, DMSO-$d_6$): δ 1.09 (6H, s), 1.23-1.32 (1H, m), 1.36-1.44 (1H, m), 1.57-1.66 (1H, m), 2.23-2.31 (1H, m), 3.87 (3H, s), 5.14 (2H, s), 5.86 (1H, s), 5.99 (1H, d, J=2.1 Hz), 6.11 (1H, dd, J=2.3, 7.7 Hz), 7.09 (1H, d, J=7.5 Hz), 7.31-7.38 (1H, m), 7.44-7.67 (5H, m).

Example 213

1-(2-Cyclopropyl-1-methyl-1H-benzimidazol-6-yl)-4-((5-methyl-3-thienyl)methoxy)pyridin-2(1H)-one A) tert-Butyl(dimethyl)(3-thienylmethoxy)silane A mixture of tert-butyldimethylchlorosilane (1.58 g), triethylamine (2.44 ml), 3-thiophenemethanol (0.822 ml) and DMF (20 ml) was stirred at 60° C. for 1 h. Additional DMF (20 ml) was added to the reaction mixture, and the mixture was stirred at 60° C. for 2 h. The mixture was quenched with saturated $NaHCO_3$ solution, and extracted with EtOAc. The organic layer was separated, washed with water and brine successively, dried over $MgSO_4$, and concentrated in vacuo. The residue was purified by silica gel column chromatography (hexane) to give the title compound (1.6 g) as a colorless oil.

$^1$H NMR (400 MHz, DMSO-$d_6$): δ 0.00 (6H, s), 0.83 (9H, s), 4.62 (2H, s), 6.95-7.00 (1H, m), 7.22-7.28 (1H, m), 7.41-7.46 (1H, m).

B) (5-Methyl-3-thienyl)methanol

To a solution of tert-butyl(dimethyl)(3-thieylmethoxy)silane (150 mg) in THF (1 ml) was added sec-butyllithium (1 M in cyclohexane/n-hexane, 0.79 ml) at −78° C., and the mixture was stirred for 30 min. Iodomethane (0.049 ml) was added, and the mixture was stirred at the same temperature for 1 h, and then raised to room temperature slowly. The mixture was quenched with water and extracted with EtOAc. The organic layer was separated, washed with water and brine successively, dried over $MgSO_4$, and concentrated in vacuo. The resulting residue was dissolved in THF (1 ml), and TBAF (1 M in THF, 0.79 ml) was added to the solution. The mixture was quenched with water and extracted with EtOAc. The organic layer was separated, washed with water and brine successively, dried over $MgSO_4$, filtered through NH silica gel pad and concentrated in vacuo. The residue was purified by silica gel column chromatography (hexane/EtOAc) to give the title compound (72 mg) as a mixture with (2-methyl-3-thienyl) ethanol.

$^1$H NMR (400 MHz, $CDCl_3$): δ 1.59 (1H, brs), 2.47 (3H, s), 4.59 (2H, brs), 6.75 (1H, s), 6.96 (1H, s).

C) 1-(2-Cyclopropyl-1-methyl-1H-benzimidazol-6-yl)-4-((5-methyl-3-thienyl)methoxy)pyridin-2(1H)-one A mixture of (5-methyl-3-thienyl)methanol (72 mg), 1-(2-cyclopropyl-1-methyl-1H-benzimidazol-6-yl)-4-hydroxypyridin-2(1H)-one (100 mg), tributylphosphine (0.264 ml), 1,1'-(azodicarbonyl)dipiperidine (269 mg) and THF (10 ml) was stirred at 60° C. for 3 h. The reaction mixture was partitioned between EtOAc and water, and the organic layer was washed with brine, dried with $MgSO_4$, and concentrated in vacuo. The residue was purified by silica gel column chromatography (hexane/EtOAc then EtOAc/MeOH), followed by NH silica gel column chromatography (hexane/EtOAc) to give the title compound as a mixture with 1-(2-cyclopropyl-1-methyl-1H-benzimidazol-6-yl)-4-((2-methyl-3-thienyl)methoxy)pyridin-2(1H)-one. This mixture was subjected to HPLC separation (C18, mobile phase: $H_2O$/$CH_3CN$ (0.1% TFA included)). The solution was neutralized with saturated $Na_2CO_3$ solution and extracted with EtOAc. The organic layer was separated, washed with water and brine successively, dried over $MgSO_4$, filtered through a plug of silica gel and concentrated in vacuo. The resulting solid was recrystallized from EtOH to give the title compound (15.8 mg) as an off-white solid.

MS (ESI+): [M+H]+ 392.1.

$^1$H NMR (400 MHz, DMSO-$d_6$): δ 1.00-1.14 (4H, m), 2.22-2.31 (1H, m), 2.45 (3H, s), 3.85 (3H, s), 5.04 (2H, s), 5.98 (1H, d, J=2.6 Hz), 6.05 (1H, dd, J=2.3, 7.5 Hz), 6.88 (1H, s), 7.02-7.07 (1H, m), 7.36 (1H, s), 7.48-7.59 (3H, m).

Example 214

1-(2-Cyclopropyl-1-methyl-1H-benzimidazol-6-yl)-4-((2-methyl-3-thienyl)methoxy)pyridin-2(1H)-one A) (2-Methyl-3-thienyl)methanol The title compound was obtained in step B in example 213 as a mixture with (5-methyl-3-thienyl)methanol.

$^1$H NMR (400 MHz, $CDCl_3$): δ 1.67 (1H, brs), 2.46 (3H, s), 4.60 (2H, brs), 6.97-7.01 (1H, m), 7.03-7.06 (1H, m).

B) 1-(2-Cyclopropyl-1-methyl-1H-benzimidazol-6-yl)-4-((2-methyl-3-thienyl)methoxy)pyridin-2(1H)-one A mixture of the title compound and 1-(2-cyclopropyl-1-methyl-1H-benzimidazol-6-yl)-4-((5-methyl-3-thienyl)methoxy)pyridin-2(1H)-one obtained in step C in example 213 was subjected to HPLC separation (C18, mobile phase: H₂O/CH₃CN (0.1% TFA included)). The solution was neutralized with saturated Na₂CO₃ and extracted with EtOAc. The organic layer was separated, washed with water and brine successively, dried over MgSO₄, filtered through a plug of silica gel, and concentrated in vacuo. The residue was recrystallized from EtOH to give the title compound (4.3 mg) as an off-white solid.
MS (ESI+): [M+H]+ 392.1.
¹H NMR (400 MHz, DMSO-d₆): δ 1.00-1.13 (4H, m), 2.22-2.31 (1H, m), 2.45 (3H, s), 3.85 (3H, s), 5.05 (2H, s), 6.02 (1H, d, J=2.3 Hz), 6.05 (1H, dd, J=2.4, 7.5 Hz), 7.01-7.09 (2H, m), 7.30 (1H, d, J=5.1 Hz), 7.49-7.59 (3H, m).

Example 215

4-((5-Chloro-3-thienyl)methoxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (5-chloro-3-thienyl)methanol (77 mg), tributylphosphine (0.219 ml) and THF (10 ml) was added 1,1'-(azodicarbonyl)dipiperidine (223 mg), and the mixture was stirred at 60° C. for 2 h. The solvent was evaporated, and the residue was purified by column chromatography (hexane/EtOAc then EtOAc/MeOH). The resulting solid was suspended in toluene, and the insoluble material was collected by filtration to give the title compound (12 mg) as an off-white solid.
MS (ESI+): [M+H]+ 470.1.
¹H NMR (400 MHz, DMSO-d₆): δ 1.06-1.12 (6H, m), 1.23-1.31 (1H, m), 1.37-1.44 (1H, m), 1.57-1.66 (1H, m), 2.23-2.31 (1H, m), 3.87 (3H, s), 5.06 (2H, s), 5.86 (1H, s), 5.99 (1H, d, J=2.3 Hz), 6.08 (1H, dd, J=2.4, 7.5 Hz), 7.09 (1H, d, J=8.5 Hz), 7.21 (1H, s), 7.50-7.66 (4H, m).

Example 216

1-(2-Cyclopropyl-1-methyl-1H-benzimidazol-6-yl)-4-((5-fluoro-3-thienyl)methoxy)pyridin-2(1H)-one A) (5-Fluoro-3-thienyl)methanol To a solution of tert-butyl(dimethyl) (3-thienylmethoxy)silane (300 mg) in THF (3 ml) was added sec-butyllithium (1 M in cyclohexane/n-hexane, 1.58 ml) at −78° C., and the mixture was stirred for 30 min. NFSI (497 mg) was added to the mixture, and the resulting mixture was stirred at the same temperature for 1 h and allowed to warm to room temperature for 1 h. The mixture was quenched with water and extracted with EtOAc. The organic layer was separated, washed with water and brine successively, dried over MgSO₄, and concentrated in vacuo. The residue was dissolved with THF (3 ml), and TBAF (1 M in THF, 1.58 ml) was added to the solution. The mixture was stirred at room temperature for 3 h. The mixture was quenched with water and extracted with EtOAc. The organic layer was separated, washed with water and brine successively, dried over MgSO₄ and concentrated in vacuo. The residue was purified by silica gel column chromatography (hexane/EtOAc) to give the title compound (130 mg) as a mixture with (2-fluoro-3-thienyl)methanol.
¹H NMR (400 MHz, CDCl₃): δ 4.55 (2H, s), 6.48 (1H, s), 6.55 (1H, brs).

B) 1-(2-Cyclopropyl-1-methyl-1H-benzimidazol-6-yl)-4-((5-fluoro-3-thienyl)methoxy)pyridin-2(1H)-one A mixture of (5-fluoro-3-thienyl)methanol (130 mg), 1-(2-cyclopropyl-1-methyl-1H-benzimidazol-6-yl)-4-hydroxypyridin-2(1H)-one (100 mg), tributylphosphine (0.264 ml), 1,1'-(azodicarbonyl)dipiperidine (269 mg) and THF (10 ml) was stirred at 60° C. for 3 h. The reaction mixture was partitioned between EtOAc and water, and the organic layer was washed with brine, dried with MgSO₄, filtered and concentrated in vacuo. The residue was purified by NH silica gel column chromatography (EOAc/MeOH), followed by silica gel column chromatography (hexane/EtOAc then EtOAc/MeOH) to give the title compound as a mixture with 1-(2-cyclopropyl-1-methyl-1H-benzimidazol-6-yl)-4-((2-fluoro-3-thienyl)methoxy)pyridin-2(1H)-one. This mixture was subjected to HPLC separation (C18, mobile phase: H₂O/CH₃CN (0.1% TFA included)). The solution was neutralized with saturated Na₂CO₃ solution and extracted with EtOAc. The organic layer was separated, washed with water and brine successively, dried over MgSO₄, filtered through a plug of silica gel and concentrated in vacuo. The resulting solid was recrystallized from EtOH to give the title compound (18.1 mg) as an off-white solid.
MS (ESI+): [M+H]+ 396.1.
¹H NMR (400 MHz, DMSO-d₆): δ 1.00-1.13 (4H, m), 2.22-2.30 (1H, m), 3.85 (3H, s), 5.01 (2H, s), 5.95-6.02 (1H, m), 6.07 (1H, dd, J=7.7, 2.3 Hz), 6.82 (1H, s), 7.04 (1H, d, J=9.0 Hz), 7.11 (1H, brs), 7.48-7.63 (3H, m).

Example 217

1-(2-Cyclopropyl-1-methyl-1H-benzimidazol-6-yl)-4-((2-fluoro-3-thienyl)methoxy)pyridin-2(1H)-one A) (2-Fluoro-3-thienyl)methanol The title compound was obtained in step A in example 216 as a mixture with (5-fluoro-3-thienyl)methanol.
¹H NMR (400 MHz, CDCl₃): δ 4.61 (2H, s), 6.60-6.67 (1H, m), 6.80 (1H, dd, J=3.7, 6.0 Hz).

B) 1-(2-Cyclopropyl-1-methyl-1H-benzimidazol-6-yl)-4-((2-fluoro-3-thienyl)methoxy)pyridin-2(1H)-one A mixture of the title compound and 1-(2-cyclopropyl-1-methyl-1H-benzimidazol-6-yl)-4-((5-fluoro-3-thienyl)methoxy)pyridin-2(1H)-one obtained in step B in example 216 was subjected to HPLC separation (C18, mobile phase: H₂O/CH₃CN (0.1% TFA included)). The solution was neutralized with saturated Na₂CO₃ solution and extracted with EtOAc. The organic layer was separated, washed with water and brine successively, dried over MgSO₄, filtered through a plug of silica gel, and concentrated in vacuo. The residue was recrystallized from EtOH to give the title compound (12.8 mg) as an off-white solid.
MS (ESI+): [M+H]+ 396.1.
¹H NMR (400 MHz, DMSO-d₆): δ 1.01-1.13 (4H, m), 2.23-2.31 (1H, m), 3.85 (3H, s), 5.04 (2H, s), 6.02 (1H, d, J=1.9 Hz), 6.05 (1H, dd, J=2.2, 7.2 Hz), 6.96 (1H, dd, J=3.4, 5.9 Hz), 7.02-7.08 (2H, m), 7.48-7.61 (3H, m).

Example 218

3-(6-(4-((4-Fluorobenzyl)oxy)-2-oxopyridin-1(2H)-yl)-1-methyl-1H-benzimidazol-2-yl)cyclobutanecarbonitrile (Retention time: short)

A) N-(2-Amino-4-bromophenyl)-3-oxocyclobutanecarboxamide

To a stirred solution of 3-oxocyclobutanecarboxylic acid (1.1 g) in DMF (50 ml) were added HATU (5.7 g) and N,N-diisopropylethylamine (4.2 ml) at 0° C., and the mixture was allowed to warm to room temperature for 30 min. A solution of 4-bromo-$N^2$-methylbenzene-1,2-diamine (2.0 g) in DMF (2 ml) was added, and the resulting mixture was stirred at room temperature for 18 h. The mixture was concentrated in vacuo and diluted with DCM. The mixture was washed with saturated $NH_4Cl$ solution, saturated $NaHCO_3$ solution and brine successively, dried over $Na_2SO_4$, concentrated in vacuo and purified by column chromatography (hexane/EtOAc) to afford the title compound (2.7 g) as an off-white solid.
MS (ESI+): [M+H]+ 297.2.

B) 3-(6-Bromo-1-methyl-1H-benzimidazol-2-yl)cyclobutanone

To a stirred solution of N-(2-amino-4-bromophenyl)-3-oxocyclobutanecarboxamide (2.7 g) in $CH_3CN$ (20 ml) was added AcOH (2 ml), and the mixture was heated under reflux for 3 h. The mixture was concentrated in vacuo, and poured into saturated $NaHCO_3$ solution. The mixture was extracted with EtOAc, washed with water and brine successively, dried over $Na_2SO_4$, concentrated in vacuo, and purified by column chromatography (hexane/EtOAc) to afford the title compound (2.0 g) as an off-white solid.
MS (ESI+): [M+H]+ 281.2.

C) 6-Bromo-2-(3-(methoxymethylidene)cyclobutyl)-1H-benzimidazole

To a stirred solution of (methoxymethyl)triphenylphosphonium chloride (4.98 g) in THF (20 ml) was added lithium hexamethyldisilazide (1.0 M solution in hexane, 29 ml) at −15° C., and the resulting mixture was stirred at the same temperature for 30 min. A solution of 3-(6-bromo-1-methyl-1H-benzimidazol-2-yl)cyclobutanone (2.7 g) in THF (5 ml) was added to the reaction mixture, and the resulting mixture was stirred at room temperature for 16 h. The reaction mixture was quenched with saturated $NH_4Cl$ solution, concentrated in vacuo and diluted with EtOAc. The organic layer was washed with brine, dried over $Na_2SO_4$, concentrated in vacuo and purified by column chromatography (hexane/EtOAc) to afford the title compound (850 mg) as a yellow solid.
MS (ESI+): [M+H]+ 307.0.

D) 3-(6-Bromo-1-methyl-1H-benzimidazol-2-yl)cyclobutanecarbaldehyde

To a solution of 6-bromo-2-(3-(methoxymethylidene)cyclobutyl)-1H-benzimidazole (850 mg) in $CH_3CN$ (20 ml) was added 2 M HCl (4.2 ml), and the resulting mixture was stirred at same temperature for 16 h. The reaction mixture was then quenched with saturated $NaHCO_3$ solution, and extracted with DCM. The extract was washed with brine, dried over $Na_2SO_4$, concentrated in vacuo and purified by column chromatography (hexane/EtOAc) to afford two isomers of the title compound (Less polar isomer: 200 mg, polar isomer: 300 mg) as yellow sticky solids.
Data for less polar isomer: $^1$H NMR (400 MHz, DMSO-$d_6$): δ 2.31-2.48 (2H, m), 2.57-2.71 (3H, m), 3.62-3.63 (3H, m), 3.77-3.81(1H, m), 7.29 (1H, dd, J=1.5, 8.2 Hz), 7.54 (1H, d, J=8.4Hz), 7.79 (1H, d, J=1.6 Hz), 9.84 (1H, s).
Data for polar isomer: $^1$H NMR (400 MHz, DMSO-$d_6$): δ 2.31-2.34(1H, m), 2.56-2.60 (4H, m), 3.62-3.63 (4H, m), 7.27 (1H, dd, J=1.5, 8.3 Hz), 7.52 (1H, d, J=8.4 Hz), 7.76 (1H, d, J=1.1 Hz), 9.66 (1H, d, J=1.2 Hz).

E) 1-(3-(6-Bromo-1-methyl-1H-benzimidazol-2-yl)cyclobutyl)-N-hydroxymethanimine (Retention time: short)

To a stirred solution of 3-(6-bromo-1-methyl-1H-benzimidazol-2-yl)cyclobutanecarbaldehyde (less polar isomer, 200 mg) in EtOH (10 ml) was added hydroxylamine hydrochloride (50 mg), and the resulting mixture was heated under reflux for 2 h. The reaction mixture was concentrated in vacuo to afford the title compound (200 mg) as an off-white solid.
LC/MS Analysis
Column: Zorbax Extend C18 (4.6×50 mm)
Mobile Phase:
10 mM $NH_4OAc$ in $H_2O$/$CH_3CN$=9/1 to 7/3 (v/v) from 0 to 1.5 min
10 mM $NH_4OAc$ in $H_2O$/$CH_3CN$=7/3 to 1/9 (v/v) from 1.5 to 3.0 min
10 mM $NH_4OAc$ in $H_2O$/$CH_3CN$=1/9 (v/v) from 3.0 to 4.0 min
Detection: UV: 220 nm
Retention time: 2.82 min
MS (ESI+): [M+H]+ 308.0.

F) 3-(6-Bromo-1-methyl-1H-benzimidazol-2-yl)cyclobutanecarbonitrile (Retention time: short)

To a stirred solution of 1-(3-(6-bromo-1-methyl-1H-benzimidazol-2-yl)cyclobutyl)-N-hydroxymethanimine (100 mg) in $CH_3CN$ (10 ml) was added phosphorous oxychloride (1 ml), and the mixture was stirred at room temperature for 16 h. The mixture was then concentrated in vacuo and poured into saturated $NaHCO_3$ solution. The mixture was extracted with DCM, and the organic layer was washed with brine, dried over $Na_2SO_4$ and purified by column chromatography (MeOH/DCM) to afford the title compound (50 mg) as a yellow solid.
LC/MS Analysis
Column: Zorbax Extend C18 (4.6×50 mm)
Mobile Phase:
10 mM $NH_4OAc$ in $H_2O$/$CH_3CN$=9/1 to 7/3 (v/v) from 0 to 1.5 min
10 mM $NH_4OAc$ in $H_2O$/$CH_3CN$=7/3 to 1/9 (v/v) from 1.5 to 3.0 min
10 mM $NH_4OAc$ in $H_2O$/$CH_3CN$=1/9 (v/v) from 3.0 to 4.0 min
Detection: UV: 220 nm
Retention time: 2.94 min
MS (ESI+): [M+H]+ 290.0.

G) 3-(6-(4-((4-Fluorobenzyl)oxy)-2-oxopyridin-1 (2H)-yl)-1-methyl-1H-benzimidazol-2-yl)cyclobutanecarbonitrile (Retention time: short)

The title compound was obtained in an analogous manner to step C in example 5 using 3-(6-bromo-1-methyl-1H-benzimidazol-2-yl)cyclobutanecarbonitrile and 4-((4-fluorobenzyl)oxy)pyridin-2(1H)-one.
MS (ESI+): [M+H]+ 429.2.

HPLC analysis (C18, mobile phase: H₂O/CH₃CN (0.05% TFA included))
Column: Zorbax SB C18 (4.6×50 mm)
Mobile Phase:
0.05% TFA in H₂O/CH₃CN=98/2 to 75/25 (v/v) from 0 to 0.5 min
0.05% TFA in H₂O/CH₃CN=75/25 to 65/35 (v/v) from 0.5 to 6.5 min
0.05% TFA in H₂O/CH₃CN=65/35 to 10/90 (v/v) from 6.5 to 8.0 min
0.05% TFA in H₂O/CH₃CN=10/90 (v/v) from 8.0 to 13.0 min
Detection: UV: 220 nm
Flow rate: 1 mL/min
Retention time: 5.488 min Example 219

4-((4-Fluorobenzyl)oxy)-1-(1-methyl-2-(1-methyl-1H-pyrazol-5-yl)-1H-benzimidazol-6-yl)pyridin-2(1H)-one The title compound was obtained in an analogous manner to step C in example 13 using 1-(4-amino-3-(methylamino)phenyl)-4-((4-fluorobenzyl)oxy)pyridin-2(1H)-one and 1-methyl-1H-pyrazole-5-carboxylic acid.
MS (ESI+): [M+H]+ 430.4.

Example 220

4-((4-Chloro-3-fluorobenzyl)oxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (4-chloro-3-fluorophenyl)methanol (0.073 ml), tributylphosphine (0.219 ml) and THF (10 ml) was added 1,1'-(azodicarbonyl)dipiperidine (223 mg), and the mixture was stirred at 60° C. overnight. The solvent was evaporated, and the residue was purified by column chromatography (hexane/EtOAc then EtOAc/MeOH), followed by NH silica gel column chromatography (hexane/EtOAc). The resulting solid was recrystallized from IPA-EtOAc to give the title compound (59.7 mg) as an off-white solid.
MS (ESI+): [M+H]+ 482.2.
¹H NMR (400 MHz, DMSO-d₆): δ 1.09 (6H, s), 1.23-1.32 (1H, m), 1.36-1.44 (1H, m), 1.56-1.66 (1H, m), 1.64-1.64 (1H, m), 2.22-2.31 (1H, m), 3.86 (3H, s), 5.18 (2H, s), 5.86 (1H, s), 5.98 (1H, d, J=2.3 Hz), 6.13 (1H, dd, J=2.3 7.8 Hz), 7.09 (1H, d, J=8.4 Hz), 7.35 (1H, d, J=7.9 Hz), 7.51-7.59 (3H, m), 7.60-7.70 (2H, m).

Example 221

4-((2-Chloro-3-thienyl)methoxy)-1-(2-cyclopropyl-1-methyl-1H-benzimidazol-6-yl)pyridin-2(1H)-one A) (2-Chloro-3-thienyl)methanol To a solution of methyl 2-chlorothiophene-3-carboxylate (530 mg) in MeOH (10 ml) was added NaBH₄ (113 mg) at room temperature, and the mixture was stirred at 60° C. for 1 day. After MeOH was evaporated, the mixture was quenched with saturated NaHCO₃ solution, and extracted with EtOAc. The organic layer was separated, washed with water and brine successively, dried over MgSO₄, filtered through a plug of silica gel, and concentrated in vacuo. The resulting residue was dissolved with THF (9 ml), where NaBH₄ (113 mg) and MeOH (1 ml) were added, and the mixture was stirred at 60° C. for 3 h. Additional NaBH₄ (113 mg) and MeOH (1 ml) were added, and the mixture was stirred at 60° C. for further 3 h. The mixture was quenched with saturated NH₄Cl solution, and extracted with EtOAc. The organic layer was separated, washed with water and brine successively, dried over MgSO₄, filtered through a plug of silica gel, and concentrated in vacuo to give the title compound (400 mg) as a pale yellow oil.
¹H NMR (400 MHz, DMSO-d₆): δ 4.40 (2H, d, J=5.5 Hz), 5.21 (1H, t, J=5.6 Hz), 7.05 (1H, d, J=5.6 Hz), 7.40 (1H, d, J=5.6 Hz).

B) 4-((2-Chloro-3-thienyl)methoxy)-1-(2-cyclopropyl-1-methyl-1H-benzimidazol-6-yl)pyridin-2(1H)-one To a mixture of 1-(2-cyclopropyl-1-methyl-1H-benzimidazol-6-yl)-4-hydroxypyridin-2(1H)-one (100 mg), (2-chloro-3-thienyl)methanol (106 mg) and tributylphosphine (0.264 ml) in THF (10 ml) was added 1,1'-(azodicarbonyl)dipiperidine (269 mg), and the mixture was stirred at 60° C. for 2 h. The reaction mixture was diluted with EtOAc, washed with water and brine successively, dried over MgSO₄, and concentrated in vacuo. The residue was purified by NH silica gel column chromatography (hexane/EtOAc), followed by silica gel column chromatography (hexane/EtOAc then EtOAc/MeOH) to give the title compound (42.4 mg) as an off-white solid.
MS (ESI+): [M+H]+ 412.1.
¹H NMR (400 MHz, DMSO-d₆): δ 1.01-1.13 (4H, m), 2.22-2.31 (1B, m), 3.85 (3H, s), 5.06 (2H, s), 6.02 (1H, d, J=2.3 Hz), 6.07 (1H, dd, J=2.5, 7.5 Hz), 7.05 (1H, dd, J=1.6, 8.5 Hz), 7.19 (1H, d, J=5.8 Hz), 7.49-7.55 (3H, m), 7.58 (1H, d, J=7.5 Hz).

Example 222

4-((3-Chloro-4-fluorobenzyl)oxy)-1-(2-((1RS,2SR)-2-(2-hydroxypropan-2-yl)cyclopropyl)-1-methyl-1H-benzimidazol-6-yl)pyridin-2(1H)-one To a mixture of 4-hydroxy-1-(2-((1RS,2SR)-2-(2-hydroxypropan-2-yl)cyclopropyl)-1-methyl-1H-benzimidazol-6-yl)pyridin-2(1H)-one (100 mg), (3-chloro-4-fluorophenyl)methanol (95 mg), tributylphosphine (0.219 ml) and THF (10 ml) was added 1,1'-(azodicarbonyl)dipiperidine (223 mg), and the mixture was stirred at 60° C. for 2 h. The reaction mixture was diluted with EtOAc, washed with water and brine successively, dried over MgSO₄, filtered through a plug of NH silica gel, and concentrated in vacuo. The residue was purified by silica gel column chromatography (hexane/EtOAc then EtOAc/MeOH), followed by NH silica gel column chromatography (hexane/EtOAc). Then the resulting solid was recrystallized from IPA-EtOAc to give the title compound (58.4 mg) as an off-white solid.
MS (ESI+): [M+H]+ 482.2.
¹H NMR (400 MHz, DMSO-d₆): δ 1.09 (6H, s), 1.23-1.32 (1H, m), 1.36-1.44 (1H, m), 1.56-1.66 (1H, m), 2.22-2.31 (1H, m), 3.86 (3H, s), 5.18 (2H, s), 5.86 (1H, s), 5.98 (1H, d, J=2.3 Hz), 6.13 (1H, dd, J=2.3, 7.8 Hz), 7.09 (1H, d, J=8.4 Hz), 7.35 (1H, d, J=7.9 Hz), 7.51-7.59 (3H, m), 7.60-7.70 (2H, m).

Example 223

4-((4-Chlorobenzyl)oxy)-1-(2-((1RS,2SR)-2-(2-hydroxypropan-2-yl)cyclobutyl)-1-methyl-1H-benzimidazol-6-yl)pyridin-2(1H)-one

A) (1RS,2SR)-2-(Methoxycarbonyl)cyclobutanecarboxylic acid

A mixture of 3-oxabicyclo[3.2.0]heptane-2,4-dione (1 g), triethylamine (1.36 ml) and MeOH (20 ml) was stirred at room temperature over weekend. The mixture was quenched with 1 M HCl, and extracted with EtOAc. The organic layer was separated, washed with water and brine successively, dried over $MgSO_4$, and concentrated in vacuo to give the title compound (1.18 g) as a colorless oil.

$^1$H NMR (400 MHz, $CDCl_3$): δ 2.17-2.31 (2H, m), 2.31-2.46 (2H, m), 3.44 (2H, t, J=7.3 Hz), 3.64-3.73 (3H, m).

B) Methyl(1RS,2SR)-2-(6-(4-((4-chlorobenzyl)oxy)-2-oxopyridin-1(2H)-yl)-1-methyl-1H-benzimidazol-2-yl)cyclobutanecarboxylate A mixture of 1-(4-amino-3-(methylamino)phenyl)-4-((4-chlorobenzyl)oxy)pyridin-2(1H)-one (830 mg), (1RS, 2SR)-2-(methoxycarbonyl)cyclobutanecarboxylic acid (406 mg), HATU (1.33 g), N,N-diisopropylethylamine (0.611 ml) and DMF (20 ml) was stirred at room temperature for 2 h. The mixture was quenched with water, and extracted with EtOAc. The organic layer was separated, washed with water and brine successively, dried over $MgSO_4$ and concentrated in vacuo. Then a mixture of the obtained residue and AcOH (20 ml) was stirred at 80° C. for 30 min. After concentration of the mixture, the residue was poured into saturated $NaHCO_3$ solution, and extracted with EtOAc. The organic layer was separated, washed with water and brine successively, dried over $MgSO_4$, and concentrated in vacuo. The residual solid was washed with IPE to give the title compound (172 mg) as a brown solid.

MS (ESI+): [M+H]+ 478.4.

C) 4-((4-Chlorobenzyl)oxy)-1-(2-((1RS,2SR)-2-(2-hydroxypropan-2-yl)cyclobutyl)-1-methyl-1H-benzimidazol-6-yl)pyridin-2(1H)-one Methylmagnesium bromide (1.0 M in THF, 1.42 ml) was added to a solution of methyl(1RS,2SR)-2-(6-(4-((4-chlorobenzyl)oxy)-2-oxopyridin-1(2H)-yl)-1-methyl-1H-benzimidazol-2-yl)cyclobutanecarboxylate (170 mg) in THF (5 ml) at 0° C. The mixture was stirred at room temperature for 3 h. The mixture was quenched with saturated $NH_4Cl$ solution, and extracted with EtOAc. The organic layer was separated, washed with water and brine successively, dried over $MgSO_4$ and concentrated in vacuo. The residue was purified by silica gel column chromatography (EtOAc/MeOH) to give the title compound (45 mg) as a white solid.

MS (ESI+): [M+H]+ 478.4.

$^1$H NMR (400 MHz, $CDCl_3$): δ 0.98 (3H, s), 1.14 (3H, s), 1.26 (1H, s), 2.10-2.24 (1H, m), 2.40-2.59 (2H, m), 2.80-2.93 (1H, m), 3.67 (3H, s), 3.88-3.97 (1H, m), 5.03 (2H, s), 6.01-6.09 (2H, m), 7.14 (1H, d, J=8.5 Hz), 7.27-7.33 (1H, m), 7.33-7.42 (5H, m), 7.75 (1H, d, J=8.5 Hz).

Example 224

(1RS,2SR)-2-(6-(4-((4-Chlorobenzyl)oxy)-2-oxopyridin-1(2H)-yl)-1-methyl-1H-benzimidazol-2-yl)cyclobutanecarbonitrile

A) (1RS,2SR)-2-(6-(4-((4-Chlorobenzyl)oxy)-2-oxopyridin-1(2H)-yl)-1-methyl-1H-benzimidazol-2-yl)cyclobutanecarboxylic acid The title compound was obtained in an analogous manner to step A in example 148 using 1-(4-amino-3-(methylamino)phenyl)-4-((4-chlorobenzyl)oxy)pyridin-2(1H)-one and 3-oxabicyclo[3.2.0]heptane-2,4-dione.

MS (ESI+): [M+H]+ 464.2.

B) (1RS,2SR)-2-(6-(4-((4-Chlorobenzyl)oxy)-2-oxopyridin-1(2H)-yl)-1-methyl-1H-benzimidazol-2-yl)cyclobutanecarboxamide The title compound was obtained in an analogous manner to example 83 using (1RS,2SR)-2-(6-(4-((4-chlorobenzyl)oxy)-2-oxopyridin-1(2H)-yl)-1-methyl-1H-benzimidazol-2-yl)cyclobutanecarboxylic acid.

MS (ESI+): [M+H]+ 463.4.

C) (1RS,2SR)-2-(6-(4-((4-Chlorobenzyl)oxy)-2-oxopyridin-1(2H)-yl)-1-methyl-1H-benzimidazol-2-yl)cyclobutanecarbonitrile The title compound was obtained in an analogous manner to example 86 using (1RS,2SR)-2-(6-(4-((4-chlorobenzyl)oxy)-2-oxopyridin-1(2H)-yl)-1-methyl-1H-benzimidazol-2-yl)cyclobutanecarboxamide.

MS (ESI+): [M+H]+ 445.4.

Example 225

3-(6-(4-((4-Fluorobenzyl)oxy)-2-oxopyridin-1(2H)-yl)-1-methyl-1H-benzimidazol-2-yl)cyclobutanecarbonitrile (Retention time: long)

A) 1-(3-(6-Bromo-1-methyl-1H-benzimidazol-2-yl)cyclobutyl)-N-hydroxymethanimine (Retention time: long)

The title compound was obtained in an analogous manner to step E in example 218 using 3-(6-bromo-1-methyl-1H-benzimidazol-2-yl)cyclobutanecarbaldehyde (polar isomer).

LC/MS Analysis
Column: Zorbax Extend C18 (4.6×50 mm)
Mobile phase:
10 mM $NH_4OAc$ in $H_2O/CH_3CN$=9/1 to 7/3 (v/v) from 0 to 1.5 min
10 mM $NH_4OAc$ in $H_2O/CH_3CN$=7/3 to 1/9 (v/v) from 1.5 to 3.0 min
10 mM $NH_4OAc$ in $H_2O/CH_3CN$=1/9 (v/v) from 3.0 to 4.0 min
Detection: UV: 220 nm
Retention time: 3.02 min
MS (ESI+): [M+H]+ 308.0.

B) 3-(6-Bromo-1-methyl-1H-benzimidazol-2-yl)cyclobutanecarbonitrile (Retention time: long)

The title compound was obtained in an analogous manner to step F in example 218 using 1-(3-(6-bromo-1-methyl-1H-benzimidazol-2-yl)cyclobutyl)-N-hydroxymethanimine.

LC/MS Analysis
Column: Zorbax Extend C18 (4.6×50 mm)
Mobile Phase:
10 mM NH$_4$OAc in H$_2$O/CH$_3$CN=9/1 to 7/3 (v/v) from 0 to 1.5 min
10 mM NH$_4$OAc in H$_2$O/CH$_3$CN=7/3 to 1/9 (v/v) from 1.5 to 3.0 min
10 mM NH$_4$OAc in H$_2$O/CH$_3$CN=1/9 (v/v) from 3.0 to 4.0 min
Detection: UV: 220 nm
Retention time: 3.18 min
MS (ESI+): [M+H]+ 290.0.

C) 3-(6-(4-((4-Fluorobenzyl)oxy)-2-oxopyridin-1 (2H)-yl)-1-methyl-1H-benzimidazol-2-yl)cyclobutanecarbonitrile (Retention time: long)

The title compound was obtained in an analogous manner to step C in example 5 using 3-(6-bromo-1-methyl-1H-benzimidazol-2-yl)cyclobutanecarbonitrile and 4-((4-fluorobenzyl)oxy)pyridin-2(1H)-one.
MS (ESI+): [M+H]+ 429.2.
HPLC analysis (C18, mobile phase: H$_2$O/CH$_3$CN (0.05% TFA included))
Column: Zorbax SB C18 (4.6×50 mm)
Mobile Phase:
0.05% TFA in H$_2$O/CH$_3$CN=90/10 (v/v) from 0 to 0.5 min
0.05% TFA in H$_2$O/CH$_3$CN=90/10 to 70/30 (v/v) from 0.5 to 3.0 min
0.05% TFA in H$_2$O/CH$_3$CN=70/30 to 50/50 (v/v) from 3.0 to 6.0 min
0.05% TFA in H$_2$O/CH$_3$CN=50/50 to 10/90 (v/v) from 6.0 to 10.0 min
0.05% TFA in H$_2$O/CH$_3$CN=10/90 (v/v) from 10.0 to 14.0 min
Detection: UV: 220 nm
Flow rate: 1 mL/min
Retention time: 5.634 min Example 226

4-((5-Chloro-3-thienyl)methoxy)-1-(2-ethyl-1-methyl-1H-benzimidazol-6-yl)pyridin-2(1H)-one To a solution of 1-(2-ethyl-1-methyl-1H-benzimidazol-6-yl)-4-hydroxypyridin-2(1H)-one (2.5 g), (5-chloro-3-thienyl)methanol (2.48 g) and tributylphosphine (5.63 g) in THF (150 ml) was added 1,1'-(azodicarbonyl)dipiperidine (7.03 g), and the reaction mixture was stirred at 60° C. for 2 h. The reaction mixture was cooled to room temperature. The mixture was poured into water and extracted with EtOAc. The extract was washed With brine, dried over MgSO$_4$, concentrated and purified by NH silica gel column chromatography (hexane/EtOAc then ETOAc/MeOH). The resulting solid was recrystallized from EtOH-hexane to give the title compound (1.15 g) as a white solid.
MS (ESI+): [M+H]+ 400.3.
$^1$H NMR (400 MHz, DMSO-d$_6$): δ 1.33 (3H, t, J=7.5 Hz), 2.90 (2H, q, J=7.1 Hz), 3.74 (3H, s), 5.06 (2H, s), 5.99 (1H, s), 6.07 (1H, d, J=7.4 Hz), 7.06 (1H, d, J=10.5 Hz), 7.21 (1H, s), 7.53 (1H, s), 7.55-7.63 (3H, m).

Example 227

1-(2-Cyclopropyl-1-methyl-1H-benzimidazol-6-yl)-4-((2,5-dichloro-3-thienyl)methoxy)pyridin-2(1H)-one To a mixture of 1-(2-cyclopropyl-1-methyl-1H-benzimidazol-6-yl)-4-hydroxypyridin-2(1H)-one (100 mg), (2,5-dichloro-3-thienyl)methanol (130 mg), tributylphosphine (0.264 ml) and THF (10 ml) was added 1,1'-(azodicarbonyl)dipiperidine (269 mg), and the mixture was stirred at 60° C. for 2 h. The reaction mixture was diluted with EtOAc, washed with water and brine successively, dried over MgSO$_4$, and concentrated in vacuo. The residue was purified by NH silica gel column chromatography (hexane/EtOAc), followed by silica gel column chromatography (hexane/EtOAc then EtOAc/MeOH) to give the title compound (39.9 mg) as an off-white solid.
MS (ESI+): [M+H]+ 447.1.
$^1$H NMR (400 MHz, DMSO-d$_6$): δ 1.00-1.13 (4H, m), 2.22-2.32 (1H, m), 3.85 (3H, s), 5.02 (2H, s), 6.02 (1H, d, J=2.5 Hz), 6.07 (1H, dd, J=2.6, 7.5 Hz), 7.05 (1H, dd, J=1.9, 8.5 Hz), 7.30 (1H, s), 7.52 (2H, dd, J=3.2, 5.1 Hz), 7.59 (1H, d, J=7.7 Hz).

Example 228

4-((4-Chlorothiophen-2-yl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (150 mg), 4-chlorothiophen-2-methanol (158 mg) and tributylphosphine (322 mg) in THF (15 ml) was added 1,1'-(azodicarbonyl)dipiperidine (401 mg). The mixture was stirred at 60° C. for 4 h. The reaction mixture was concentrated in vacuo, and diluted with DCM. The organic layer was washed with water and brine successively, dried over Na$_2$SO$_4$, concentrated in vacuo and purified by column chromatography, (MeOH/DCM) to afford the title compound (53 mg) as an off-white solid.
MS (ESI+): [M+H]+ 412.2.
$^1$HNMR (400 MHz, DMSO-d$_6$): δ 1.04-1.09 (4H, m), 2.26 (1H, m), 3.85 (3H, s), 5.32 (2H, s), 6.03-6.08 (2H, m), 7.04 (1H, dd, J=1.8, 8.5 Hz), 7.28 (1H, s), 7.50-7.52 (2H, m), 7.58 (1H, d, J=7.5 Hz), 7.64 (1H, s).

Example 229

4-((4-Chloro-3-fluorobenzyl)oxy)-1-(2-ethyl-1-methyl-1H-benzimidazol-6-yl)pyridin-2(1H)-one To a solution of 1-(2-ethyl-1-methyl-1H-benzimidazol-6-yl)-4-hydroxypyridin-2(1H)-one (500 mg), (4-chloro-3-fluorophenyl)methanol (596 mg) and tributylphosphine (1.13 g) in THF (20 ml) was added 1,1'-(azodicarbonyl)dipiperidine (1.41 g), and the reaction mixture was stirred at 60° C. for 2 h. The reaction mixture was cooled to room temperature. The mixture was poured into water and extracted with EtOAc. The extract was washed with brine, dried over MgSO$_4$, concentrated and purified by NH silica gel column chromatography (hexane/EtOAc then EtOAc/MeOH). The resulting solid was recrystallized from EtOH-water to give the title compound (265 mg) as a white solid.
MS (ESI+): [M+H]+ 412.3.
$^1$H NMR (400 MHz, DMSO-d$_6$): δ 1.33 (3H, t, J=7.5 Hz), 2.90 (2H, q, J=7.5 Hz), 3.74 (3H, s), 5.18 (2H, s), 5.97 (1H, d, J=2.6 Hz), 6.12 (1H, dd, J=2.4, 7.5 Hz), 7.07 (1H, d, J=8.4 Hz), 7.35 (1H, d, J=8.5 Hz), 7.52-7.57 (2H, m), 7.60 (2H, dd, J=4.8, 7.8 Hz), 7.66 (1H, t, J=8.2 Hz).

Example 230

(1RS,2SR)-2-(6-(4-(Benzyloxy)-2-oxopyridin-1(2H)-yl)-1-methyl-1H-benzimidazol-2-yl)cyclopropanecarbonitrile A) (1RS,2SR)-2-(6-(4-(Benzyloxy)-2-oxopyridin-1(2H)-yl)-1-methyl-1H-benzimidazol-2-yl)cyclopropanecarboxylic acid The title compound was obtained in an analogous manner to step A in example 148 using 1-(4-amino-3-(methylamino)phenyl)-4-(benzyloxy)pyridin-2(1H)-one and 3-oxabicyclo[3.1.0]hexane-2,4-dione.
MS (ESI+): [M+H]+ 416.2.

B) (1RS,2SR)-2-(6-(4-(Benzyloxy)-2-oxopyridin-1(2H)-yl)-1-methyl-1H-benzimidazol-2-yl)cyclopropanecarboxamide The title compound was obtained in an analogous manner to example 83 using (1RS,2SR)-2-(6-(4-(benzyloxy)-2-oxopyridin-1(2H)-yl)-1-methyl-1H-benzimidazol-2-yl)cyclopropanecarboxylic acid.
MS (ESI+): [M+H]+ 415.4.

C) (1RS,2SR)-2-(6-(4-(Benzyloxy)-2-oxopyridin-1(2H)-yl)-1-methyl-1H-benzimidazol-2-yl)cyclopropanecarbonitrile The title compound was obtained in an analogous manner to example 86 using (1RS,2SR)-2-(6-(4-(benzyloxy)-2-oxopyridin-1(2H)-yl)-1-methyl-1H-benzimidazol-2-yl)cyclopropanecarboxamide.
MS (ESI+): [M+H]+ 397.4.

Example 231

1-(2-Ethyl-1-methyl-1H-benzimidazol-6-yl)-4-((5-fluoro-3-thienyl)methoxy)pyridin-2(1H)-one A) (5-Fluoro-3-thienyl)methanol To a solution of tert-butyl(dimethyl)(3-thienylmethoxy)silane (1.0 g) in THF (10 ml) was added sec-butyllithium (1 M in cyclohexane/n-hexane, 5.25 ml) at −78° C., and the reaction mixture was stirred under $N_2$ atmosphere for 30 min. NFSI (1.66 g) was added to the reaction mixture at −78° C., and the reaction mixture was stirred for 1 h. Then, the reaction mixture was warmed to room temperature slowly and stirred for 1 h. The mixture was quenched with water and extracted with EtOAc. The extract was washed with brine, dried over $MgSO_4$, and concentrated. The residue was dissolved in THF (10 ml), and TBAF (1 M in THF, 5.25 ml) was added to the solution. The mixture was stirred at room temperature for 3 h. The mixture was quenched with water and extracted with EtOAc. The extract was washed with brine, dried over $MgSO_4$, concentrated and purified by silica gel column chromatography (hexane/EtOAc) to give the title compound (460 mg) as a mixture with (2-fluoro-3-thienyl)methanol and 3-thienylmethanol.
$^1$H NMR (400 MHz, $CDCl_3$): δ 4.55 (2H, s), 6.49 (1H, s), 6.55 (1H, brs).

B) 1-(2-Ethyl-1-methyl-1H-benzimidazol-6-yl)-4-((5-fluoro-3-thienyl)methoxy)pyridin-2(1H)-one A mixture of 1-(2-ethyl-1-methyl-1H-benzimidazol-6-yl)-4-hydroxypyridin-2(1H)-one (250 mg), (5-fluoro-3-thienyl)methanol (245 mg), tributylphosphine (563 mg), 1,1'-(azodicarbonyl)dipiperidine (703 mg) and THF (10 ml) was stirred at 60° C. for 3 h. The mixture was poured into water and extracted with EtOAc. The extract was washed with brine, dried over $MgSO_4$, concentrated and purified by silica gel column chromatography (hexane/EtOAc then EtOAc/MeOH) to give the title compound as a mixture with 1-(2-ethyl-1-methyl-1H-benzimidazol-6-yl)-4-((2-fluoro-3-thienyl)methoxy)pyridin-2(1H)-one and 1-(2-ethyl-1-methyl-1H-benzimidazol-6-yl)-4-(3-thienylmethoxy)pyridin-2(1H)-one. This mixture was subjected to HPLC separation (C18, mobile phase: $H_2O/CH_3CN$ (0.1% TFA included)). The desired fraction was neutralized with saturated $NaHCO_3$ solution and extracted with EtOAc. The organic layer was separated, dried over $MgSO_4$ and concentrated in vacuo to give the title compound (16.4 mg) as a white solid.
MS (ESI+): [M+H]+ 384.3.
$^1$H NMR (400 MHz, DMSO-$d_6$): δ 1.33 (3H, t, J=7.5 Hz), 2.90 (2H, q, J=7.7 Hz), 3.74 (3H, s), 5.01 (2H, s), 5.99 (1H, s), 6.07 (1H, d, J=7.7 Hz), 6.82 (1H, s), 7.07 (1H, d, J=9.3 Hz), 7.11 (1H, brs), 7.53 (1H, s), 7.56-7.63 (2H, m).

Example 232

4-((4-Bromo-5-chloro-2-thienyl)methoxy)-1-(2-cyclopropyl-1-methyl-1H-benzimidazol-6-yl)pyridin-2(1H)-one A) (4-Bromo-5-chloro-2-thienyl)methanol Sulfuryl chloride (0.6 ml) was added to a solution of ((4-bromothiophen-2-yl)methoxy)(tert-butyl)diphenylsilane (2.0 g) in $CH_3CN$ (20 ml) at room temperature. The mixture was stirred at room temperature overnight. The mixture was quenched with saturated sodium thiosulfate solution (40 ml) at room temperature and extracted with EtOAc. The organic layer was separated, washed with water and brine successively, dried over $MgSO_4$ and concentrated in vacuo. The residue was purified by silica gel column chromatography (hexane/EtOAc) to give the title compound (182 mg) as a brown oil.
$^1$H NMR (400 MHz, DMSO-$d_6$): δ 4.58 (2H, s), 5.74 (1H, brs), 6.97 (1H, s).

B) 4-((4-Bromo-5-chloro-2-thienyl)methoxy)-1-(2-cyclopropyl-1-methyl-1H-benzimidazol-6-yl)pyridin-2(1H)-one 1,1-(Azodicarbonyl)dipiperidine (269 mg) was added to a solution of 1-(2-cyclopropyl-1-methyl-1H-benzo[d]imidazol-6-yl)-4-hydroxypyridin-2(1H)-one (100 mg), (4-bromo-5-chloro-2-thienyl)methanol (162 mg) and tributylphosphine (0.26 ml) in THF (5 ml) at room temperature. The mixture was stirred at 60° C. for 2 h. The mixture was quenched with water at room temperature and extracted with EtOAc. The organic layer was separated, washed with water and brine successively, dried over $MgSO_4$ and concentrated in vacuo. The residue was purified by silica gel column chromatography (hexane/EtOAc) and preparative HPLC (L-Column 2 ODS, eluted with $H_2O$ in acetonitrile containing 0.1% TFA). The desired fraction was neutralized with saturated $NaHCO_3$ solution and extracted with EtOAc. The organic layer was separated, dried over $MgSO_4$ and concentrated in vacuo to give the title compound (12 mg) as a white solid.
MS (ESI+): [M+H]+ 491.3.
$^1$H NMR (400 MHz, $CDCl_3$): δ 1.13-1.21 (2H, m), 1.23-1.30 (2H, m), 1.99-2.12 (1H, m), 3.86 (3H, s), 5.11 (2H, s), 6.02-6.06 (1H, m), 6.06-6.08 (1H, m), 7.00 (1H, s), 7.08-7.14 (1H, m), 7.32-7.37 (2H, m), 7.73 (1H, d, J=8.5 Hz).

Example 233

1-(2-Ethyl-1-methyl-1H-benzimidazol-6-yl)-4-((5-(trifluoromethyl)-2-thienyl)methoxy)pyridin-2(1H)-one To a solution of 1-(2-ethyl-1-methyl-1H-benzimidazol-6-yl)-4-hydroxypyridin-2(1H)-one (120 mg), (5-(trifluoromethyl)-2-thienyl)methanol (162 mg) and tributylphosphine (270 mg) in THF (8 ml) was added 1,1'-(azodicarbonyl)dipiperidine (337 mg), and the reaction mixture was stirred at 60° C., for 2 h. The reaction mixture was cooled to room temperature. The mixture was poured into water and extracted with EtOAc. The extract was washed with brine, dried over MgSO$_4$, concentrated and purified by NH silica gel column chromatography (hexane/EtOAc then EtOAc/MeOH). The resulting solid was recrystallized from EtOH to give the title compound (33.9 mg) as a white solid.
MS (ESI+): [M+H]+ 434.3.
$^1$H NMR (400 MHz, DMSO-d$_6$): δ 1.33 (3H, t, J, =7.5 Hz), 2.90 (2H, q, J=7.5 Hz), 3.74 (3H, s), 5.45 (2H, s), 6.07 (1H, s), 6.08-6.13 (1H, m), 7.07 (1H, d, J=8.5 Hz), 7.38 (1H, d, J=2.9 Hz), 7.54 (1H, s), 7.60 (2H, dd, J=6.1, 7.8 Hz), 7.69 (1H, d, J=3.0 Hz).

Example 234

1-(2-Ethyl-1-methyl-1H-benzimidazol-6-yl)-4-((2-fluoro-3-thienyl)methoxy)pyridin-2(1H)-one A) (2-Fluoro-3-thienyl)methanol The title compound was obtained in step A in example 231 as a mixture with (5-fluoro-3-thienyl)methanol and 3-thienylmethanol.
$^1$H NMR (400 MHz, CDCl$_3$): δ 4.61 (2H, s), 6.64 (1H, dd, J=3.8, 6.0 Hz), 6.80 (1H, dd, J=3.5, 6.0 Hz).

B) 1-(2-Ethyl-1-methyl-1H-benzimidazol-6-yl)-4-((2-fluoro-3-thienyl)methoxy)pyridin-2(1H)-one A mixture of the title compound, 1-(2-ethyl-1-methyl-1H-benzimidazol-6-yl)-4-((5-fluoro-3-thienyl)methoxy)pyridin-2(1H)-one and 1-(2-ethyl-1-methyl-1H-benzimidazol-6-yl)-4-(3-thienylmethoxy)pyridin-2(1H)-one obtained in step B in example 231 was subjected to HPLC separation (C18, mobile phase: H$_2$O/CH$_3$CN (0.1% TFA included)). The desired fraction was neutralized with saturated NaHCO$_3$ solution and extracted with EtOAc. The organic layer was separated, dried over MgSO$_4$ and concentrated in vacuo to give the title compound (1.8 mg) as a white solid.
MS (ESI+): [M+H]+ 384.3.
$^1$H NMR (400 MHz, DMSO-d$_6$): δ 1.33 (3H, t, J=7.5 Hz), 2.91 (2H, q, J=7.4 Hz), 3.74 (3H, s), 5.04 (2H, s), 6.02 (1H, s), 6.06 (1H, d, J=7.5 Hz), 6.91-6.99 (1H, m), 7.01-7.13 (2H, m), 7.54 (1H, s), 7.59 (2H, t, J=7.2 Hz).

Example 235

1-(2-Ethyl-1-methyl-1H-benzimidazol-6-yl)-4-(3-thienylmethoxy)pyridin-2(1H)-one

A) 3-Thienylmethanol

The title compound was obtained in step A in example 231 as a mixture with (5-fluoro-3-thienyl)methanol and (2-fluoro-3-thienyl)methanol.
$^1$H NMR (400 MHz, CDCl$_3$): δ 4.71 (2H, s), 7.10 (1H, d, J=4.8 Hz), 7.24 (1H, brs), 7.32 (1H, dd, J=3.0, 4.8 Hz).

B) 1-(2-Ethyl-1-methyl-1H-benzimidazol-6-yl)-4-(3-thienylmethoxy)pyridin-2(1H)-one A mixture of the title compound, 1-(2-ethyl-1-methyl-1H-benzimidazol-6-yl)-4-((5-fluoro-3-thienyl)methoxy)pyridin-2(1H)-one and 1-(2-ethyl-1-methyl-1H-benzimidazol-6-yl)-4-((2-fluoro-3-thienyl)methoxy)pyridin-2(1H)-one obtained in step B in example 231 was subjected to HPLC separation (C18, mobile phase: H$_2$O/CH$_3$CN (0.1% TFA included)). The desired fraction was neutralized with saturated NaHCO$_3$ solution and extracted with EtOAc. The organic layer was separated, dried over MgSO$_4$ and concentrated in vacuo to give the title compound (26.8 mg) as a white solid.
MS (ESI+): [M+H]+ 366.3.
$^1$H NMR (400 MHz, DMSO-d$_6$): δ 1.33 (3H, t, J=7.5 Hz), 2.90 (2H, q, J=7.7 Hz), 3.74 (3H, s), 5.14 (2H, s), 6.01 (1H, s), 6.07 (1H, dd, J=2.8, 7.7 Hz), 7.07 (1H, d, J=8.9 Hz), 7.21 (1H, d, J=4.6 Hz), 7.53 (1H, s), 7.55-7.62 (3H, m), 7.65 (1H, s).

Example 236

4-((4-Chlorothiophen-2-yl)methoxy)-1-(2-ethyl-1-methyl-1H-benzimidazol-6-yl)pyridin-2(1H)-one To a solution of 1-(2-ethyl-1-methyl-1H-benzimidazol-6-yl)-4-hydroxypyridin-2(1H)-one (150 mg), (4-chlorothiophen-2-yl)methanol (167 mg) and tributylphosphine (338 mg) in THF (15 ml) was added 1,1'-(azodicarbonyl)dipiperidine (422 mg), and the mixture was stirred under at 60° C. for 4 h. The reaction mixture was then cooled to room temperature, and concentrated in vacuo. The residue was diluted with DCM, washed with water and brine successively, dried over Na$_2$SO$_4$, concentrated in vacuo, and purified by silica gel column chromatography (MeOH/DCM) to afford the title compound as a white solid.
MS (ESI+): [M+H]+ 400.0.
$^1$H NMR (400 MHz, DMSO-d$_6$): δ 1.33 (3H, t, J=7.4 Hz), 2.90 (2H, d, J=7.6 Hz), 3.73 (3H, s), 5.32 (2H, s), 6.03 (1H, d, J=2.5 Hz), 6.07 (1H, d, J=7.3 Hz), 7.06 (1H, d, J=8.6 Hz), 7.28 (1H, s), 7.53 (1H, m), 7.58-7.60 (2H, m), 7.64 (1H, s).

Example 237

(1R*,2S*)-2-(6-(4-((4-Chlorobenzyl)oxy)-2-oxopyridin-1(2H)-yl)-1-methyl-1H-benzimidazol-2-yl)cyclopropanecarbonitrile hydrochloride (optically active, IC tR1)

(1RS,2SR)-4-((4-Chlorobenzyl)oxy)-1-(2-(2-(2-hydroxypropan-2-yl)cyclopropyl)-1-methyl-1H-benzimidazol-6-yl)pyridin-2(1H)-one (460 mg) was resolved by a preparative HPLC (CHIRALPAK IC, EtOH) to give a white solid (171 mg, >99% ee). To the solution of this solid in MeOH (5 ml) was added 4M HCl in EtOAc (0.12 ml). The mixture was stirred at room temperature for 30 min. After evaporation of the solvent, the residue was crystallized from IPA-IPE to give the title compound (153 mg) as an off-white solid.
MS (ESI+): [M+H]+ 431.4.
$^1$H NMR (400 MHz, DMSO-d$_6$): δ 1.88 (1H, td, J=5.6, 8.5 Hz), 2.33 (1H, q, J=5.9 Hz), 2.60-2.71 (1H, m), 3.12-3.27 (1H, m), 4.04 (3H, s), 5.18 (2H, s), 6.02 (1H, d, J=2.5 Hz), 6.17 (1H, dd, J=2.5, 7.5 Hz), 7.42 (1H, d, J=8.8 Hz), 7.51 (4H, s), 7.68 (1H, d, J=7.5 Hz), 7.82 (1H, d, J=8.8 Hz), 7.96 (1H, s).

Analysis of enantiomeric excess
Column: CHIRALPAK IC (4.6×250 mm)
Mobile phase: EtOH 100%
Flow rate: 0.5 ml/min
Temperature: 30° C.
Detection: UV: 220 nm
Retention time: 13.49 min Example 238

(1R*,2S*)-2-(6-(4-((4-Chlorobenzyl)oxy)-2-oxopyridin-1(2H)-yl)-1-methyl-1H-benzimidazol-2-yl) cyclopropanecarbonitrile hydrochloride (optically active, IC tR2)

(1RS,2SR)-4-((4-Chlorobenzyl)oxy)-1-(2-(2-(2-hydroxypropan-2-yl)cyclopropyl)-1-methyl-1H-benzimidazol-6-yl)pyridin-2(1H)-one (460 mg) was resolved by a preparative HPLC (CHIRALPAK IC, EtOH) to give a white solid (177 mg, >99% ee). To the solution of this solid in MeOH (5 ml) was added 4 M HCl in EtOAc (0.10 ml). The mixture was stirred at room temperature for 30 min. After evaporation of the solvent, the residue was crystallized from IPA-IPE to give the title compound (73 mg) as an off-white solid.

MS (ESI+): [M+H]+ 431.4.

$^1$H NMR (400 MHz, DMSO-$d_6$): δ 1.88 (1H, td, J=5.6, 8.5 Hz), 2.33 (1H, q, J=5.9 Hz), 2.60-2.71 (1H, m), 3.12-3.27 (1H, m), 4.04 (3H, s), 5.18 (2H, s), 6.02 (1H, d, J=2.5 Hz), 6.17 (1H, dd, J=2.5, 7.5 Hz), 7.42 (1H, d, J=8.8 Hz), 7.51 (4H, s), 7.68 (1H, d, J=7.5 Hz), 7.82 (1H, d, J=8.8 Hz), 7.96 (1H, s).

Analysis of Enantiomeric Excess
Column: CHIRALPAK IC (4.6×250 mm)
Mobile phase: EtOH 100%
Flow rate: 0.5 ml/min
Temperature: 30° C.
Detection: UV: 220 nm
Retention time: 16.14 min Example 239

1-(2-Cyclopropyl-1-methyl-1H-benzimidazol-6-yl)-4-((4,5-difluoro-2-thienyl)methoxy)pyridin-2(1H)-one A) 2-(4-Bromo-5-fluoro-2-thienyl)-1,3-dioxolane To a solution of 2-(4,5-dibromo-2-thienyl)-1,3-dioxolane (2 g) in THF (60 ml) was added n-butyllithium (1.6 M in n-hexane, 5.18 ml) dropwise at −78° C. under $N_2$ atmosphere, and the mixture was stirred for 1 h. A solution of NFSI (2.61 g) in THF (20.0 ml) was added dropwise at −78° C., and the mixture was stirred at the same temperature for 1 h, and then warmed to −60° C. slowly. The mixture was quenched with saturated $NH_4Cl$ solution and extracted with EtOAc. The organic layer was separated, washed with water and brine successively, dried over $MgSO_4$ and concentrated in vacuo. The residue was purified by silica gel column chromatography (hexane/EtOAc) to give the title compound (1.11 g) as a mixture with 2-(4-bromo-2-thienyl)-1,3-dioxolane.

$^1$H NMR (400 MHz, $CDCl_3$): δ 3.94-4.16 (4H, m), 5.95 (1H, d, J=2.6 Hz), 6.79 (1H, d, J=3.4 Hz).

B) 2-(4,5-Difluoro-2-thienyl)-1,3-dioxolane

To a solution of 2-(4-bromo-5-fluoro-2-thienyl)-1,3-dioxolane (1.14 g) in THF (10 ml) was added n-butyllithium (1.6 M in hexane, 3.66 ml) dropwise at −78° C. under $N_2$ atmosphere, and the mixture was stirred for 1 h. A solution of NFSI (1.85 g) in THF (15 ml) was added dropwise at −78° C., and the mixture was stirred at the same temperature for 1 h, and then warmed to −60° C. slowly. The mixture was quenched with saturated $NH_4Cl$ solution and extracted with EtOAc. The organic layer was separated, washed with water and brine successively, dried over $MgSO_4$ and concentrated in vacuo. The residue was purified by silica gel column chromatography (hexane/EtOAc) to give the title compound (586 mg) as a mixture with 2-(4-bromo-2-thienyl)-1,3-dioxolane and 2-(4-bromo-5-fluoro-2-thienyl)-1,3-dioxolane.

$^1$H NMR (400 MHz, $CDCl_3$): δ 3.95-4.14 (4H, m), 5.93 (1H, d, J=2.9 Hz), 6.75 (1H, d, J=3.4 Hz).

C) (4,5-Difluoro-2-thienyl)methanol

A mixture of 2-(4,5-difluoro-2-thienyl)-1,3-dioxolane (586 mg), THF (10 ml) and 6 M HCl (1 ml) was stirred at ambient temperature for 1 h. The mixture was quenched with saturated $NaHCO_3$ solution and extracted with EtOAc. The organic layer was separated, washed with water and brine successively, dried over $MgSO_4$ and concentrated in vacuo. The residue was purified by silica gel column chromatography (hexane/EtOAc). The resulting oil was dissolved in THF (10 ml), and $NaBH_4$ (48.5 mg) and MeOH (0.1 ml) were added to the solution at room temperature. After the mixture was stirred at room temperature for 15 min, the mixture was poured into saturated $NH_4Cl$ solution and extracted with EtOAc. The organic layer was separated, washed with water and brine successively, dried over $MgSO_4$ and concentrated in vacuo. The residue was purified by silica gel column chromatography (hexane/EtOAc) to give the title compound (190 mg) as a mixture with (4-bromo-2-thienyl)methanol and (4-bromo-5-fluoro-2-thienyl)methanol.

$^1$H NMR (400 MHz, $CDCl_3$): δ 4.64 (2H, dd, J=2.1, 5.8 Hz), 6.59 (1H, d, J=3.3 Hz).

D) 1-(2-Cyclopropyl-1-methyl-1H-benzimidazol-6-yl)-4-((4,5-difluoro-2-thienyl)methoxy)pyridin-2 (1H)-one A mixture of (4,5-difluoro-2-thienyl)methanol (190 mg), 1-(2-cyclopropyl-1-methyl-1H-benzimidazol-6-yl)-4-hydroxypyridin-2(1H)-one (237 mg), 1,1'-(azodicarbonyl)dipiperidine (639 mg), tributylphosphine (0.632 ml) and THF (10 ml) was stirred at 60° C. for 3 h. After the solvent was removed, the residue was purified by silica gel column chromatography (hexane/EtOAc then EtOAc/MeOH) to give the title compound as a mixture with 4-((4-bromo-2-thienyl) methoxy)-1-(2-cyclopropyl-1-methyl-1H-benzimidazol-6-yl)pyridin-2(1H)-one and 4-((4-bromo-5-fluoro-2-thienyl) methoxy)-1-(2-cyclopropyl-1-methyl-1H-benzimidazol-6-yl)pyridin-2(1H)-one. This mixture was subjected to HPLC separation (C18, mobile phase: $H_2O/CH_3CN$ (0.1% TFA included)). The solution was neutralized with saturated $NaHCO_3$ solution and extracted with EtOAc. The organic layer was separated, washed with water and brine successively, dried over $MgSO_4$, filtered through a plug of silica gel and concentrated in vacuo. The resulting solid was recrystallized from EtOH to give the title compound (15 mg) as an off-white solid.

MS (ESI+): [M+H]+ 414.1.

¹H NMR (400 MHz, DMSO-d₆): δ 1.00-1.16 (4H, m), 2.23-2.31 (1H, m), 3.85 (3H, s), 5.23 (2H, s), 6.01-6.10 (2H, m), 7.04 (1H, d, J=8.7 Hz), 7.23 (1H, d, J=3.4 Hz), 7.48-7.54 (2H, m), 7.59 (1H, d, J=7.7 Hz).

Example 240

4-((4-Bromo-2-thienyl)methoxy)-1-(2-cyclopropyl-1-methyl-1H-benzimidazol-6-yl)pyridin-2(1H)-one A) (4-Bromo-2-thienyl)methanol The title compound was obtained in step C in example 239 as a mixture with (4,5-difluoro-2-thienyl)methanol and (4-bromo-5-fluoro-2-thienyl)methanol.

¹H NMR (400 MHz, CDCl₃): δ 1.82-1.88 (1H, m), 4.80 (2H, d, J=6.0 Hz), 6.93 (1H, s), 7.17 (1H, s).

B) 4-((4-Bromo-2-thienyl)methoxy)-1-(2-cyclopropyl-1-methyl-1H-benzimidazol-6-yl)pyridin-2(1H)-one A mixture of the title compound, 1-(2-cyclopropyl-1-methyl-1H-benzimidazol-6-yl)-4-((4,5-difluoro-2-thienyl)methoxy)pyridin-2(1H)-one and 4-((4-bromo-5-fluoro-2-thienyl)methoxy)-1-(2-cyclopropyl-1-methyl-1H-benzimidazol-6-yl)pyridin-2(1H)-one obtained in step D in example 219 was subjected to HPLC separation (C18, mobile phase: H₂O/CH₃CN (0.1% TFA included)). The solution was neutralized with saturated Na₂CO₃ solution and extracted with EtOAc. The organic layer was separated, washed with water and brine successively, dried over MgSO₄, filtered through a plug of silica gel, and concentrated in vacuo. The residual solid was recrystallized from EtOH to give the title compound (30.0 mg) as an off-white solid.

MS (ESI+): [M+H]+ 457.1.

¹H NMR (300 MHz, DMSO-d₆): δ 0.98-1.15 (4H, m), 2.22-2.30 (1H, m), 3.85 (3H, s), 5.34 (2H, s), 6.02-6.10 (2H, m), 7.01-7.07 (1H, m), 7.31 (1H, d, J=1.5 Hz), 7.48-7.54 (2H, m), 7.58 (1H, d, J=7.5 Hz), 7.74 (1H, d, J=1.5 Hz).

Example 241

1-(2-Cyclopropyl-1-methyl-1H-benzimidazol-6-yl)-4-((5-(trifluoromethyl)-2-furyl)methoxy)pyridin-2(1H)-one To a suspension of 1-(2-cyclopropyl-1-methyl-1H-benzimidazol-6-yl)-4-hydroxypyridin-2(1H)-one (400 mg) and (5-(trifluoromethyl)-2-furyl)methanol (462 mg) in THF (40 ml) were added tributylphosphine (1.06 ml) and 1,1'-(azodicarbonyl)dipiperidine (1.08 g) at 60° C., and the mixture was stirred for 3 h. After the solvent was evaporated, the residue was purified by silica gel column chromatography (hexane/EtOAc then EtOAc/MeOH), followed by NH silica gel column chromatography (hexane/EtOAc then EtOAc/MeOH). Then the resulting solid was recrystallized from EtOH-hexane to give the title compound (313 mg) as an off-white solid.

MS (ESI+): [M+H]+ 430.1.

¹H NMR (400 MHz, DMSO-d₆): δ 1.00-1.15 (4H, m), 2.22-2.31 (1H, m), 3.86 (3H, s), 5.23 (2H, s), 6.05-6.13 (2H, m), 6.92 (1H, d, J=3.1 Hz), 7.05 (1H, d, J=8.3 Hz), 7.29 (1H, d, J=2.5 Hz), 7.49-7.56 (2H, m), 7.59 (1H, d, J=7.3 Hz).

Example 242

1-(2-Cyclopropyl-1-methyl-1H-benzimidazol-6-yl)-4-((5-(trifluoromethyl)-2-thienyl)methoxy)pyridin-2(1H)-one hydrochloride HCl (4 M in EtOAc, 0.146 ml) was added to a solution of 1-(2-cyclopropyl-1-methyl-1H-benzimidazol-6-yl)-4-((5-(trifluoromethyl)-2-thienyl)methoxy)pyridin-2(1H)-one (260 mg) in EtOAc (5 ml), and the mixture was stirred at room temperature for 2 h. The resulting precipitate was collected by filtration and washed with EtOAc. The solid was recrystallized from EtOH-IPE to give the title compound (210 mg) as a white solid.

MS (ESI+): [M+H]+ 446.4.

¹H NMR (400 MHz, DMSO-d₆): δ 1.31-1.46 (4H, m), 2.53-2.61 (1H, m), 4.02 (3H, s), 5.47 (2H, s), 6.11 (1H, s), 6.17 (1H, dd, J=1.4, 7.7 Hz), 7.36-7.44 (1H, m), 7.48 (1H, d, J=8.0 Hz), 7.64 (1H, d, J=7.8 Hz), 7.68-7.73 (1H, m), 7.77 (1H, d, J=8.5 Hz), 8.02 (1H, s).

Example 243

1-(2-Cyclopropyl-1-methyl-1H-benzimidazol-6-yl)-4-((4-fluorophenoxy)methyl)pyridin-2(1H)-one A) Methyl 1-(2-cyclopropyl-1-methyl-1H-benzimidazol-6-yl)-2-oxo-1,2-dihydropyridine-4-carboxylate To a mixture of 6-bromo-2-cyclopropyl-1-methyl-1H-benzimidazole (984 mg), methyl 2-oxo-1,2-dihydropyridine-4-carboxylate (600 mg), potassium carbonate (1.08 g) and dioxane (25 ml) were added CuI (298 mg) and trans-N,N'-dimethylcyclohexane-1,2-diamine (223 mg), and the mixture was heated at 80° C. for 12 h. The mixture was concentrated in vacuo, and diluted with DCM. The mixture was washed with brine, dried over Na₂SO₄, concentrated in vacuo, and purified by column chromatography (MeOH/DCM) to give the title compound (800 mg) as a white solid.

MS (ESI+): [M+H]+ 324.0.

B) 1-(2-Cyclopropyl-1-methyl-1H-benzimidazol-6-yl)-4-(hydroxymethyl)pyridin-2(1H)-one To a stirred solution of methyl 1-(2-cyclopropyl-1-methyl-1H-benzimidazol-6-yl)-2-oxo-1,2-dihydropyridine-4-carboxylate (800 mg) in DCM (20 ml) was added diisobutylaluminum hydride (1.0 M in toluene, 1.04 ml) at −78° C., and the mixture was stirred at same temperature for 2 h. The reaction mixture was then quenched with a mixture of MeOH (2 ml) and water (2 ml), filtered through celite and the resulting filtrate was concentrated in vacuo. The residue was purified by column chromatography (MeOH/DCM) to give the title compound (350 mg) as a yellow solid.

MS (ESI+): [M+H]+ 296.0.

C) 1-(2-Cyclopropyl-1-methyl-1H-benzimidazol-6-yl)-4-((4-fluorophenoxy)methyl)pyridin-2(1H)-one To a solution of 1-(2-cyclopropyl-1-methyl-1H-benzimidazol-6-yl)-4-(hydroxymethyl)pyridin-2(1H)-one (150 mg), 4-fluorophenol (114 mg) and tributylphosphine (307 mg) in THF (5 ml) was added 1,1'-(azodicarbonyl)dipiperidine (385 mg), and the mixture was stirred at 60° C. for 4 h. The mixture was concentrated in vacuo, and diluted with DCM. The mixture was washed with water and brine successively, dried over Na₂SO₄, concentrated in vacuo and purified by column chromatography (MeOH/DCM) to afford the title compound (40 mg) as a white solid.

MS (ESI+): [M+H]+ 390.2.

¹H NMR (400 MHz, DMSO-d₆): δ 1.05-1.10 (4H, m), 2.27-2.28 (1H, m), 3.85 (3H, s), 5.06 (2H, s), 6.33 (1H, d, J=7.0 Hz), 6.51 (1H, s), 7.04-7.09 (3H, m), 7.17 (2H, t, J=8.7 Hz), 7.53 (1H, d, J=8.4 Hz), 7.57 (1H, s), 7.67 (1H, d, J=7.0 Hz).

Example 244

4-((4-Bromo-5-fluoro-2-thienyl)methoxy)-1-(2-cyclopropyl-1-methyl-1H-benzimidazol-6-yl)pyridin-2(1H)-one A) (4-Bromo-5-fluoro-2-thienyl)methanol The title compound was obtained in step C in example 239 as a mixture with (4,5-difluoro-2-thienyl)methanol and (4-bromo-2-thienyl)methanol.

¹H NMR (400 MHz, CDCl₃): δ 4.68 (2H, dd, J=5.8, 2.0 Hz), 6.62 (1H, d, J=3.1 Hz).

B) 4-((4-Bromo-5-fluoro-2-thienyl)methoxy)-1-(2-cyclopropyl-1-methyl-1H-benzimidazol-6-yl)pyridin-2(1H)-one A mixture of the title compound, 1-(2-cyclopropyl-1-methyl-1H-benzimidazol-6-yl)-4-((4,5-difluoro-2-thienyl)methoxy)pyridin-2(1H)-one and 4-((4-bromo-2-thienyl)methoxy)-1-(2-cyclopropyl-1-methyl-1H-benzimidazol-6-yl)pyridin-2(1H)-one obtained in step D in example 219 was subjected to HPLC separation (C18, mobile phase: H₂O/CH₃CN (0.1% TFA included)). The solution was neutralized with saturated Na₂CO₃ solution and extracted with EtOAc. The organic layer was separated, washed with water and brine successively, dried over MgSO₄, filtered through a plug of silica gel, and concentrated in vacuo. The residual solid was recrystallized from EtOH to give the title compound (10.0 mg) as an off-white solid.

MS (ESI+): [M+H]+ 475.0.

¹H NMR (400 MHz, DMSO-d₆): δ 1.01-1.14 (4H, m), 2.23-2.31 (1H, m), 3.85 (3H, s), 5.26 (2H, s), 6.00-6.12 (2H, m), 7.04 (1H, d, J=8.5 Hz), 7.18 (1H, d, J=2.8 Hz), 7.52 (2H, d, J=3.6 Hz), 7.60 (1H, s).

Example 245

4-((4-Chlorophenoxy)methyl)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-(hydroxymethyl)pyridin-2(1H)-one (150 mg), 4-chlorophenol (130 mg) and tributylphosphine (514 mg) in THF (15 ml) was added 1,1'-(azodicarbonyl)dipiperidine (641 mg), and the mixture was stirred at 60° C. for 4 h. The mixture was concentrated in vacuo, and diluted with DCM. The mixture was washed with water and brine successively, dried over Na₂SO₄, concentrated in vacuo and purified by column chromatography (MeOH/DCM) to afford the title compound (45 mg) as a white solid.

MS (ESI+): [M+H]+ 406.0.

¹H NMR (400 MHz, DMSO-d₆): δ 1.05-1.10 (4H, m), 2.27 (1H, m), 3.85 (3H, s), 5.08 (2H, s), 6.32 (1H, d, J=6.9 Hz), 6.51 (1H, s), 7.06-7.08 (3H, m), 7.38 (2H, d, J=8.8 Hz), 7.53 (1H, d, J=8.5 Hz), 7.57 (1H, s), 7.68 (1H, d, J=7.0 Hz).

Example 246

1-(2-Ethyl-1-methyl-1H-benzimidazol-6-yl)-4-((5-fluorothiophen-2-yl)methoxy)pyridin-2(1H)-one To a solution of 1-(2-ethyl-1-methyl-1H-benzimidazol-6-yl)-4-hydroxypyridin-2(1H)-one (224 mg), (5-fluorothiophen-2-yl)methanol (100 mg) and tributylphosphine (750 mg) in THF (15 ml) was added 1,1'-(azodicarbonyl)dipiperidine (956 mg), and the mixture was stirred at 60° C. for 4 h. The reaction mixture was concentrated in vacuo, and diluted with DCM. The mixture was washed with water and brine successively, dried over Na₂SO₄, concentrated in vacuo and purified by silica gel column chromatography (MeOH/DCM) followed by preparative HPLC to afford the title compound (20 mg) as a white solid.

MS (ESI+): [M+H]+ 384.0.

¹H NMR (400 MHz, DMSO-d₆): δ 1.33 (3H, t, J=7.5 Hz), 2.90 (2H, q, J=7.4 Hz), 3.74 (3H, s), 5.23 (2H, d, J=2.4 Hz), 6.04-6.06 (2H, m), 6.68 (1H, dd, J=2.1, 3.9 Hz), 7.01 (1H, t, J=3.7 Hz), 7.06 (1H, dd, J=1.9, 8.4 Hz), 7.53 (1H, d, J=1.8 Hz), 7.57-7.60 (2H, m).

Example 247

1-(2-Cyclopropyl-1-methyl-1H-benzimidazol-6-yl)-4-((4-(trifluoromethyl)phenoxy)methyl)pyridin-2(1H)-one The title compound was obtained in an analogous manner to step C in example 243 using 1-(2-cyclopropyl-1-methyl-1H-benzimidazol-6-yl)-4-(hydroxymethyl)pyridin-2(1H)-one and 4-trifluoromethylphenol.

MS (ESI+): [M+H]+ 440.2.

Example 248

1-(2-Cyclopropyl-1-methyl-1H-benzimidazol-6-yl)-4-((5-(difluoromethyl)-2-thienyl)methoxy)pyridin-2(1H)-one To a solution of 1-(2-cyclopropyl-1-methyl-1H-benzimidazol-6-yl)-4-hydroxypyridin-2(1H)-one (78 mg), (5-(trifluoromethyl)-2-thienyl)methanol (77 mg) and tributylphosphine (168 mg) in THF (3 ml) was added 1,1'-(azodicarbonyl)dipiperidine (210 mg), and the reaction mixture was stirred at 60° C. for 3 h. The reaction mixture was concentrated in vacuo. The residue was purified by NH silica gel column chromatography (hexane/EtOAc then EtOAc/MeOH). The resulting solid was recrystallized from EtOH-hexane to give the title compound (48.5 mg) as a white solid.

MS (ESI+): [M+H]+ 428.3.

¹H NMR (400 MHz, DMSO-d₆): δ 0.95-1.16 (4H, m), 2.22-2.31 (1H, m), 3.85 (3H, s), 5.41 (2H, s), 6.02-6.12 (2H, m), 7.05 (1H, d, J=8.3 Hz), 7.31 (1H, t, J=56.0 Hz), 7.29 (1H, brs), 7.43 (1H, brs), 7.48-7.55 (2H, m), 7.59 (1H, d, J=7.7 Hz).

Example 249

4-(((5-Chloropyridin-2-yl)oxy)methyl)-1-(2-cyclopropyl-1-methyl-1H-benzimidazol-6-yl)pyridin-2(1H)-one The title compound was obtained in an analogous manner to step C in example 243 using 1-(2-cyclopropyl-1-methyl-1H-benzimidazol-6-yl)-4-(hydroxymethyl)pyridin-2(1H)-one and 5-chloropyridin-2-ol.

MS (ESI+): [M+H]+ 407.2.

Example 250

4-((5-Bromo-3-thienyl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (98 mg), (5-bromo-3-thienyl)methanol (135 mg) and tributylphosphine (211 mg) in THF (3 ml) was added 1,1'-(azodicarbonyl) dipiperidine (264 mg), and the reaction mixture was stirred at 60° C. for 3 h. The reaction mixture was concentrated in vacuo. The residue was purified by silica gel column chromatography (hexane/EtOAc then EtOAc/MeOH). The resulting solid was recrystallized from EtOH-water to give the title compound (48.8 mg) as a white solid.
MS (ESI+): [M+H]+ 456.0.
$^1$H NMR (400 MHz, DMSO-d$_6$): δ 0.97-1.17 (4H, m), 2.15-2.34 (1H, m), 3.85 (3H, s), 5.08 (2H, s), 5.99 (1H, s), 6.07 (1H, d, J=5.5 Hz), 7.04 (1H, d, J=8.8 Hz), 7.30 (1H, s), 7.52 (2H, d, J=3.8 Hz), 7.58 (1H, d, J=7.4 Hz), 7.67 (1H, s).

Example 251

1-(2-Cyclopropyl-1-methyl-1H-benzimidazol-6-yl)-4-(((5-(trifluoromethyl)pyridin-2-yl)oxy)methyl)pyridin-2(1H)-one The title compound was obtained in an analogous manner to step C in example 243 using 1-(2-cyclopropyl-1-methyl-1H-benzimidazol-6-yl)-4-(hydroxymethyl)pyridin-2(1H)-one and 2-fluoro-5-trifluoromethyl-pyridine.
MS (ESI+): [M+H]+ 441.2.

Example 252

1-(2-Cyclopropyl-1-methyl-1H-benzimidazol-6-yl)-4-((5-(trifluoromethyl)-3-thienyl)methoxy)pyridin-2(1H)-one A mixture of 4-chloro-1-(2-cyclopropyl-1-methyl-1H-benzimidazol-6-yl)pyridin-2(1H)-one (800 mg), (5-(trifluoromethyl)-3-thienyl)methanol (972 mg), cesium carbonate (2.61 g) and DMF (8 ml) was stirred at 80° C. overnight. The mixture was poured into water and extracted with EtOAc-THF. The extract was washed with brine, dried over MgSO$_4$, concentrated and purified by NH silica gel column chromatography (hexane/EtOAc). The resulting solid was recrystallized from EtOH-water to give the title compound (258 mg) as a white solid.
MS (ESI+): [M+H]+ 446.3.
$^1$H NMR (300 MHz, DMSO-d$_6$): δ 1.00-1.15 (4H, m), 2.18-2.33 (1H, m), 3.85 (3H, s), 5.16 (2H, s), 6.01 (1H, d, J=2.7 Hz), 6.09 (1H, dd, J=2.7, 7.6 Hz), 7.04 (1H, dd, J=2.0, 8.5 Hz), 7.48-7.55 (2H, m), 7.59 (1H, d, J=7.6 Hz), 7.81 (1H, d, J=1.3 Hz), 8.06 (1H, d, J=1.5 Hz).

Example 253

4-((1RS,2RS)-2-(4-chlorophenyl)cyclopropyl)-1-(2-cyclopropyl-1-methyl-1H-benzimidazol-6-yl)pyridin-2(1H)-one

A) 4-Bromo-1-(2-cyclopropyl-1-methyl-1H-benzimidazol-6-yl)pyridin-2(1H)-one To a suspension of 1-(2-cyclopropyl-1-methyl-1H-benzimidazol-6-yl)-4-hydroxypyridin-2(1H)-one (2 g) in DMF (35 ml) was added phosphoryltribromide (2.45 g) at room temperature, and the mixture was stirred at 50° C. overnight. The mixture was poured into saturated NaHCO$_3$ solution, and extracted with EtOAc. The organic layer was washed with water and brine successively, dried over MgSO$_4$ and concentrated in vacuo. The resulting residual solid was recrystallized from EtOH-hexane to give the title compound (1.70 g) as a brown solid.
MS (ESI+): [M+H]+ 345.1.

B) ((2RS,3SR)-2-(4-chlorophenyl)-3-(4,4,5,5-tetramethyl-1,3,2-dioxaborolan-2-yl)cyclopropyl)(trimethyl)silane To a solution of 2-((E)-2-(4-chlorophenyl)ethenyl)-4,4,5,5-tetramethyl-1,3,2-dioxaborolane (300 mg) and Pd(OAc)$_2$ (127 mg) in Et$_2$O (10 ml) was added trimethylsilyldiazomethane (2.83 ml), and the mixture was stirred at room temperature for 3 h. The mixture was purified by silica gel column chromatography (hexane/EtOAc) to give the title compound (260 mg) as an oil.
$^1$H NMR (400 MHz, DMSO-d$_6$): δ −0.36 (9H, s), 0.14 (1H, t, J=9.0 Hz), 0.35-0.43 (1H, m), 1.11 (12H, s), 2.32-2.39 (1H, m), 7.12-7.27 (4H, m).

C) 4-((1RS,2RS)-2-(4-chlorophenyl)-3-(trimethylsilyl)cyclopropyl)-1-(2-cyclopropyl-1-methyl-1H-benzimidazol-6-yl)pyridin-2(1H)-one A mixture of 4-bromo-1-(2-cyclopropyl-1-methyl-1H-benzimidazol-6-yl)pyridin-2(1H)-one (108 mg), ((2RS,3SR)-2-(4-chlorophenyl)-3-(4,4,5,5-tetramethyl-1,3,2-dioxaborolan-2-yl)cyclopropyl)(trimethyl)silane (110 mg), potassium carbonate (130 mg), PdCl$_2$(dppf) (11.5 mg), THF (6 ml) and water (2.0 ml) was heated at 70° C. overnight. The mixture was partitioned between water and EtOAc. The organic layer was washed with brine, dried over MgSO$_4$, concentrated in vacuo, and purified by silica gel column chromatography (hexane/EtOAc) to give the title compound (26.0 mg) as a white solid.
MS (ESI+): [M+H]+ 488.2.

D) 4-((1RS,2RS)-2-(4-chlorophenyl)cyclopropyl)-1-(2-cyclopropyl-1-methyl-1H-benzimidazol-6-yl)pyridin-2(1H)-one A mixture of 4-((1RS,2RS)-2-(4-chlorophenyl)-3-(trimethylsilyl)cyclopropyl)-1-(2-cyclopropyl-1-methyl-1H-benzimidazol-6-yl)pyridin-2(1H)-one (26 mg), TBAF (1.0 M in THF, 0.533 ml) and THF (1 ml) was heated at 100° C. under microwave irradiation for 1 h. The mixture was purified by NH silica gel column chromatography (hexane/EtOAc) to give the title compound (9.2 mg) as a white solid.
MS (ESI+): [M+H]+ 416.1.
$^1$H NMR (400 MHz, DMSO-d$_6$): δ 1.00-1.14 (4H, m), 1.51-1.61 (2H, m), 2.10-2.18 (1H, m), 2.22-2.30 (1H, m), 2.36-2.44 (1H, m), 3.85 (3H, s), 6.14 (1H, d, J=6.5 Hz), 6.31 (1H, s), 7.06 (1H, d, J=8.5 Hz), 7.24 (2H, d, J=8.2 Hz), 7.35 (2H, d, J=8.0 Hz), 7.48-7.60 (3H, m

Example 254

1-(1,2-Dimethyl-1H-benzimidazol-6-yl)-4-((4-fluorobenzyl)oxy)pyridin-2(1H)-one A mixture of 6-bromo-1,2-dimethyl-1H-benzimidazole (500 mg), 4-((4-fluorobenzyl)oxy)pyridin-2(1H)-one (487 mg), CuI (423 mg), N,N'-dimethyl-1,2-ethanediamine (0.236 ml), potassium carbonate (921 mg) and DMSO (10 ml) was stirred at 150° C. for 1 h. 28% NH$_3$ solution was added to the resulting mixture, and the solid was washed with water. The solid was purified by NH silica gel column chromatography (hexane/EtOAc), followed by recrystallization from EtOAc-hexane to give the title compound (200 mg) as a white solid.

MS (ESI+): [M+H]+ 364.3.

$^1$H NMR (400 MHz, DMSO-d$_6$): δ 2.55 (3H, s), 3.73 (3H, s), 5.14 (2H, s), 5.99 (1H, s), 6.09 (1H, d, J=6.8 Hz), 7.06 (1H, d, J=8.5 Hz), 7.26 (2H, t, J=8.7 Hz), 7.45-7.64 (5H, m).

Example 255

4-(1-Benzothiophen-5-ylmethoxy)-1-(2-cyclopropyl-1-methyl-1H-benzimidazol-6-yl)pyridin-2(1H)-one A mixture of 4-chloro-1-(2-cyclopropyl-1-methyl-1H-benzimidazol-6-yl)pyridin-2(1H)-one (100 mg), benzo[b]thiophen-5-ylmethanol (110 mg), cesium carbonate (326 mg) and DMF (3 ml) was heated at 100° C. overnight. The mixture was poured into water, and extracted with EtOAc. The organic layer was washed with brine, dried over MgSO$_4$, concentrated in vacuo, and purified by NH silica gel column chromatography (hexane/EtOAc) to give the title compound (15 mg) as a white solid.

MS (ESI+): [M+H]+ 428.3.

$^1$H NMR (400 MHz, DMSO-d$_6$): δ 1.00-1.15 (4H, m), 2.22-2.31 (1H, m), 3.85 (3H, s), 5.28 (2H, s), 6.02 (1H, s), 6.11 (1H, d, J=7.4 Hz), 7.04 (1H, d, J=8.4 Hz), 7.43-7.54 (4H, m), 7.58 (1H, d, J=7.5 Hz), 7.82 (1H, d, J=5.3 Hz), 8.00 (1H, s), 8.06 (1H, d, J=8.3 Hz).

Example 256

1-(2-Cyclopropyl-1-methyl-1H-benzimidazol-6-yl)-4-((4-(trifluoromethyl)-1,3-thiazol-2-yl)methoxy)pyridin-2($^1$H)-one To a solution of 1-(2-cyclopropyl-1-methyl-1H-benzimidazol-6-yl)-4-hydroxypyridin-2(1H)-one (50 mg), (4-(trifluoromethyl)-1,3-thiazol-2-yl)methanol (65.1 mg) and triphenylphosphine (140 mg) in THF (5 ml) was added bis(2-methoxyethyl) azodicarboxylate (125 mg), and the mixture was stirred at room temperature for 3 h. The mixture was poured into water and extracted with EtOAc. The extract was washed with brine, dried over MgSO$_4$, concentrated and purified by silica gel column chromatography (hexane/EtOAc then EtOAc/MeOH). The resulting solid was recrystallized from EtOH-hexane to give the title compound (26.5 mg) as a white solid.

MS (ESI+): [M+H]+ 447.3.

$^1$H NMR (400 MHz, DMSO-d$_6$): δ 0.97-1.16 (4H, m), 2.27 (1H, brs), 3.85 (3H, s), 5.56 (2H, s), 6.08 (1H, brs), 6.17 (1H, d, J=7.2 Hz), 7.05 (1H, d, J=9.3 Hz), 7.47-7.57 (2H, m), 7.64 (1H, d, J=8.0 Hz), 8.61 (1H, s).

Example 257

1-(2-Cyclopropyl-1-methyl-1H-benzimidazol-6-yl)-4-(2,3-dihydro-1-benzofuran-5-ylmethoxy)pyridin-2(1H)-one A mixture of 4-chloro-1-(2-cyclopropyl-1-methyl-1H-benzimidazol-6-yl)pyridin-2(1H)-one (100 mg), (2,3-dihydrobenzofuran-5-yl)methanol (100 mg), cesium carbonate (326 mg) and DMF (3 ml) was heated at 100° C. overnight. The mixture was poured into water, and extracted with EtOAc. The organic layer was washed with brine, dried over MgSO$_4$, concentrated in vacuo, and purified by NH silica gel column chromatography (hexane/EtOAc) to give the title compound (40 mg) as a white solid.

MS (ESI+): [M+H]+ 414.4.

$^1$H NMR (400 MHz, DMSO-d$_6$): δ 1.00-1.13 (4H, m), 2.22-2.32 (1H, m), 3.20 (2H, t, J=8.5 Hz), 3.85 (3H, s), 4.55 (2H, t, J=8.5 Hz), 5.02 (2H, s), 5.98 (1H, brs), 6.05 (1H, d, J=7.3 Hz), 6.78 (1H, d, J=8.3 Hz), 7.04 (1H, d, J=8.9 Hz), 7.19 (1H, d, J=8.2 Hz), 7.33 (1H, s), 7.48-7.61 (3H, m).

Example 258

4-((5-Chloro-1,2,4-thiadiazol-3-yl)methoxy)-1-(2-cyclopropyl-1-methyl-1H-benzimidazol-6-yl)pyridin-2(1H)-one The title compound was obtained in an analogous manner to example 190 using 5-chloro-3-(chloromethyl)-1,2,4-thiadiazole and 1-(2-cyclopropyl-1-methyl-1H-benzimidazol-6-ya)-4-hydroxypyridin-2(1H)-one.

MS (ESI+): [M+H]+ 414.3.

Example 259

4-((5-Bromo-2-furyl)methoxy)-1-(2-cyclopropyl-1-methyl-1H-benzimidazol-6-yl)pyridin-2(1H)-one A) 4-Chloro-1-(2-cyclopropyl-1-methyl-1H-benzimidazol-6-yl)pyridin-2(1H)-one To a suspension of 1-(2-cyclopropyl-1-methyl-1H-benzimidazol-6-yl)-4-hydroxypyridin-2(1H)-one (75 g) in DMF (1.3 L) was added phosphorus oxychloride (29.8 ml) at room temperature, and the mixture was stirred at 45-50° C. under Ar atmosphere for 26 h. The mixture was poured into EtOAc (1.5 L), and washed with saturated NaHCO$_3$ solution (1.5 L). The organic layer was separated, and aqueous layer was extracted with EtOAc (2.0 L) two times. The combined organic layer was washed with brine (1.0 L), dried over Na$_2$SO$_4$ and concentrated in vacuo. The residue was dissolved in EtOAc/THF (1/1, 700 ml), and NH silica gel (100 g) was added to the solution. The mixture was filtered through a plug of NH silica gel (500 g) with EtOAc as an eluent to give the title compound (47.0 g) as a pale yellow solid.

MS (ESI+): [M+H]+ 300.2.

B) 4-((5-Bromo-2-furyl)methoxy)-1-(2-cyclopropyl-1-methyl-1H-benzimidazol-6-yl)pyridin-2(1H)-one To a solution of 4-chloro-1-(2-cyclopropyl-1-methyl-1H-benzimidazol-6-yl)pyridin-2(1H)-one (150 mg) and (5-bromo-2-furyl)methanol (177 mg) in toluene (2.0 ml) was added potassium tert-butoxide (112 mg) at 100° C., and the mixture was stirred for 30 min. The mixture was quenched with water (2 ml), and the precipitate was collected. The resulting solid was recrystallized from EtOH—H$_2$O to give the title compound (158 mg) as an off-white solid.

MS (ESI+): [M+H]+ 441.1.

$^1$H NMR (400 MHz, DMSO-d$_5$): δ 0.99-1.14 (4H, m), 2.22-2.31 (1H, m), 3.85 (3H, s), 5.11 (2H, s), 6.03-6.10 (2H, m), 6.63 (1H, d, J=3.0 Hz), 6.74 (1H, d, J=2.8 Hz), 7.05 (1H, d, J=8.5 Hz), 7.51 (2H, d, J=4.9 Hz), 7.58 (1H, d, J=7.9 Hz).

Example 260

4-((5-Bromopyridin-2-yl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (50 mg), (5-bromopyridin-2-yl)methanol (66.8 mg) and triphenylphosphine (140 mg) in THF (6 ml) was added bis(2-methoxyethyl) azodicarboxylate (125 mg), and the mixture was stirred at room temperature for 3 h. The mixture was poured into water and extracted with EtOAc. The extract was washed with brine, dried over $MgSO_4$, concentrated and purified by silica gel column chromatography (hexane/EtOAc to EtOAc/MeOH). The resulting solid was recrystallized from EtOH-water to give the title compound (25.2 mg) as a white solid.

MS (ESI+): [M+H]+ 452.3.

$^1$H NMR (400 MHz, DMSO-$d_5$): δ 0.98-1.15 (4H, m), 2.26 (1H, brs), 3.85 (3H, s), 5.21 (2H, s), 5.96 (1H, brs), 6.13 (1H, d, J=7.5 Hz), 7.04 (1H, d, J=8.4 Hz), 7.47-7.57 (3H, m), 7.60 (1H, d, J=8.0 Hz), 8.15 (1H, d, J=7.5 Hz), 8.75 (1H, s).

Example 261

1-(2-Ethyl-1-methyl-1H-benzimidazol-6-yl)-4-((4-(trifluoromethyl)-1,3-thiazol-2-yl)methoxy)pyridin-2(1H)-one To a solution of 1-(2-ethyl-1-methyl-1H-benzo[d]imidazol-6-yl)-4-hydroxypyridin-2(1H)-one (400 mg), (4-(trifluoromethyl)-1,3-thiazol-2-yl)methanol (544 mg) and triphenylphosphine (1.17 g) in THF (35 ml) was added bis(2-methoxyethyl) azodicarboxylate (1.04 g) at room temperature. After 3 h, the mixture was poured into water and extracted with EtOAc. The extract was washed with brine, dried over $MgSO_4$ and concentrated in vacuo. The residue was purified by silica gel column chromatography (EtOAc/MeOH), followed by recrystallization from IPA-IPE to give the title compound (175 mg) as a white solid.

MS (ESI+): [M+H]+ 435.1.

$^1$H NMR (400 MHz, DMSO-$d_6$): δ 1.34 (3H, t, J=7.4 Hz), 2.91 (2H, q, J=7.5 Hz), 3.74 (3H, s), 5.57 (2H, s), 6.08 (1H, s), 6.13-6.22 (1H, m), 7.08 (1H, d, J=8.4 Hz), 7.55 (1H, s), 7.58-7.68 (2H, m), 8.61 (1H, s).

Example 262

4-((5-Bromo-3-furyl)methoxy)-1-(2-cyclopropyl-1-methyl-1H-benzimidazol-6-yl)pyridin-2(1H)-one To a solution of 5-bromo-3-furoic acid (215 mg) in THF (2 ml) were added triethylamine (0.314 ml) and isobutyl chloroformate (0.175 ml) at 0° C., and the mixture was stirred at the same temperature for 1 h. To this mixture was added $LiBH_4$ (54 mg) at 0° C., and the mixture was stirred at room temperature for 1 h. Additional $LiBH_4$ (10 mg) was added, and the mixture was stirred at room temperature for further 2 h. The reaction mixture was quenched with saturated $NaHCO_3$ solution at 0° C., and extracted with EtOAc. The organic layer was separated, washed with saturated $NaHCO_3$ solution and brine successively, dried over $MgSO_4$ and concentrated in vacuo. The resulting residue was dissolved in toluene (2.0 ml). 4-Chloro-1-(2-cyclopropyl-1-methyl-1H-benzimidazol-6-yl)pyridin-2(1H)-one (150 mg) and potassium tert-butoxide (112 mg) were added to the solution, and the mixture was stirred at 100° C. for 30 min. The mixture was quenched with water (2 ml)/IPE (2 ml), and the resulting solid was recrystallized from EtOH—$H_2O$ to give the title compound (57.0 mg) as a pale yellow solid.

MS (ESI+): [M+H]+ 441.1.

$^1$H NMR (400 MHz, DMSO-$d_6$): δ 0.98-1.15 (4H, m), 2.21-2.32 (1H, m), 3.85 (3H, s), 4.99 (2H, s), 5.96-6.09 (2H, m), 6.72 (1H, s), 7.04 (1H, d, J=8.2 Hz), 7.47-7.61 (3H, m), 7.95 (1H, s).

Example 263

1-(2-Cyclopropyl-3-methylimidazo[1,2-a]pyridin-6-yl)-4-(pyridin-2-ylmethoxy)pyridin-2(1H)-one hydrochloride To a solution of 1-(2-cyclopropyl-3-methylimidazo[1,2-a]pyridin-6-yl)-4-hydroxypyridin-2(1H)-one (500 mg) in DMF (5 ml) were added 2-(bromomethyl)pyridine hydrobromide (450 mg) and potassium carbonate (491 mg) at room temperature, and the mixture was stirred for 3 hour. The mixture was poured into water and extracted with EtOAc. The organic layer was separated, washed with saturated $NaHCO_3$ solution and brine successively, dried over $MgSO_4$, concentrated in vacuo, and purified by NH silica gel column chromatography (EtOAc/hexane). The resulting solid was treated with HCl (4 M in EtOAc, 0.444 ml) to give the title compound (232 mg) as white crystals.

MS (ESI+): [M+H]+ 373.2.

$^1$H NMR (400 MHz, DMSO-$d_6$): δ 1.05 (2H, d, J=3.8 Hz), 1.16 (2H, d, J=8.3 Hz), 2.23-2.32 (1H, m), 2.58 (3H, s), 5.29 (2H, s), 6.07 (1H, d, J=2.3 Hz), 6.30 (1H, dd, J=2.4, 7.7 Hz), 7.41-7.53 (1H, m), 7.62 (1H, d, J=7.9 Hz), 7.72 (1H, d, J=7.8 Hz), 7.85-7.92 (1H, m), 7.93-8.01 (2H, m), 8.65 (1H, d, J=4.5 Hz), 9.00 (1H, s).

Example 264

4-((5-Chloropyrimidin-2-yl)methoxy)-1-(2-cyclopropyl-1-methyl-1H-benzimidazol-6-yl)pyridin-2(1H)-one A) ((1-(2-Cyclopropyl-1-methyl-1H-benzimidazol-6-yl)-2-oxo-1,2-dihydropyridin-4-yl)oxy)acetonitrile A mixture of 1-(2-cyclopropyl-1-methyl-1H-benzimidazol-6-yl)-4-hydroxypyridin-2(1H)-one (3.0 g), bromoacetonitrile (0.82 ml), potassium carbonate (4.42 g) and DMF (10 ml) was stirred at 80° C. for 2 h. The mixture was poured into water and extracted with EtOAc. The extract was washed with brine, dried over $MgSO_4$, concentrated and purified by silica gel column chromatography (hexane/EtOAc). The resulting solid was washed with IPE to give the title compound (2.39 g) as a pale yellow solid.

MS (ESI+): [M+H]+ 321.1.

B) 2-((1-(2-Cyclopropyl-1-methyl-1H-benzimidazol-6-yl)-2-oxo-1,2-dihydropyridin-4-yl)oxy)ethanimidamide hydrochloride To a solution of ((1-(2-cyclopropyl-1-methyl-1H-benzimidazol-6-yl)-2-oxo-1,2-dihydropyridin-4-yl)oxy)acetonitrile (300 mg) in MeOH (4 ml) was added sodium methoxide (2.5 mg), and the mixture was stirred at room temperature for 4 h. $NH_4Cl$ (52.6 mg) was added to the mixture, and the mixture was stirred at room temperature overnight. The solvent was evaporated, and the residual solid was washed with IPA-IPE to give the title compound (368 mg) as a light brown solid.

MS (ESI+): [M+H]+ 338.1.

C) 4-((5-Chloropyrimidin-2-yl)methoxy)-1-(2-cyclopropyl-1-methyl-1H-benzimidazol-6-yl)pyridin-2(1H)-one A mixture of 2-((1-(2-cyclopropyl-1-methyl-1H-benzimidazol-6-yl)-2-oxo-1,2-dihydropyridin-4-yl)oxy)ethanimidamide hydrochloride (100 mg), 2-chloro-3-(dimethylamino)-N,N-dimethylprop-2-en-1-iminium hexafluorophosphate (0.82 ml), sodium methoxide (43.3 mg) and MeOH (10 ml) was stirred at room temperature for 1 h. The mixture was concentrated, and the residue was partitioned between EtOAc and water. The extract was washed with brine, dried over MgSO$_4$, concentrated and purified by NH silica gel column chromatography (hexane/EtOAc) to give the title compound (56 mg) as a white solid.

MS (ESI+): [M+H]+ 408.3.

Example 265

1-(2-Ethyl-1-methyl-1H-benzimidazol-6-yl)-4-((5-(trifluoromethyl)-3-thienyl)methoxy)pyridin-2(1H)-one To a solution of 1-(2-ethyl-1-methyl-1H-benzimidazol-6-yl)-4-hydroxypyridin-2(1H)-one (300 mg), (5-(trifluoromethyl)-3-thienyl)methanol (352 mg) and triphenylphosphine (877 mg) in THF (10 ml) was added bis(2-methoxyethyl) azodicarboxylate (783 mg), and the mixture was stirred at room temperature for 3 h. The mixture was poured into water and extracted with EtOAc. The extract was washed with brine, dried over MgSO$_4$, concentrated and purified by silica gel column chromatography (hexane/EtOAc then EtOAc/MeOH). The resulting solid was recrystallized from IPA-IPE to give the title compound (70.0 mg) as a white solid.

MS (ESI+): [M+H]+ 434.3.

$^1$H NMR (400 MHz, DMSO-d$_6$): δ 1.33 (3H, t, J=7.6 Hz), 2.91 (2H, d, J=7.4 Hz), 3.74 (3H, s), 5.17 (2H, s), 6.02 (1H, s), 6.10 (1H, d, J=10.0 Hz), 7.07 (1H, d, J=9.2 Hz), 7.53 (1H, s), 7.59 (2H, d, J=8.3 Hz), 7.81 (1H, s), 8.06 (1H, s).

Example 266

1-(2-Cyclopropyl-1-methyl-1H-benzimidazol-6-yl)-4-((2-(trifluoromethyl)-1,3-thiazol-4-yl)methoxy)pyridin-2(1H)-one To a mixture of 4-bromo-1-(2-cyclopropyl-1-methyl-1H-benzimidazol-6-yl)pyridin-2(1H)-one (100 mg), (2-(trifluoromethyl)thiazol-4-yl)methanol (80 mg) and toluene (5 ml) was added potassium tert-butoxide (98 mg) at 100° C., and the mixture was stirred at the same temperature overnight. The mixture was poured into water, and extracted with EtOAc. The extract was washed with brine, dried over MgSO$_4$, concentrated in vacuo, and purified by NH silica gel column chromatography (hexane/EtOAc) to give the title compound (29.0 mg) as a white solid.

MS (ESI+): [M+H]+ 447.3.

$^1$H NMR (400 MHz, DMSO-d$_6$): δ 1.00-1.14 (4H, m), 2.27 (1H, brs), 3.85 (3H, s), 5.32 (2H, s), 6.05-6.15 (2H, m), 7.05 (1H, d, J=8.7 Hz), 7.52 (2H, d, J=4.9 Hz), 7.60 (1H, d, J=7.7 Hz), 8.33 (1H, s).

Example 267

1-(2-Cyclopropyl-1-methyl-1H-benzimidazol-6-yl)-4-((5-(trifluoromethyl)pyrazin-2-yl)methoxy)pyridin-2(1H)-one

A) 2-(Bromomethyl)-5-(trifluoromethyl)pyrazine

To a solution of 2-methyl-5-(trifluoromethyl)pyrazine (1 g) in trifluoromethylbenzene (10 ml) was added N-bromosuccinimide (1.21 g) at room temperature, and the mixture was heated at 90° C. for 30 min. To the mixture was then added azobisisobutyronitrile (0.051 g), and the mixture was stirred for 7 h. The mixture was cooled, and the solvent was evaporated. The residue was purified by column chromatography (hexane/EtOAc) to give the title compound (404 mg) as a pale yellow oil.

$^1$H NMR (400 MHz, DMSO-d$_6$): δ 4.88 (2H, s), 9.03 (1H, s), 9.20 (1H, s).

B) 1-(2-Cyclopropyl-1-methyl-1H-benzimidazol-6-yl)-4-((5-(trifluoromethyl)pyrazin-2-yl)methoxy)pyridin-2(1H)-one The title compound was obtained in an analogous manner to example 190 using 1-(2-cyclopropyl-1-methyl-1H-benzimidazol-6-yl)-4-hydroxypyridin-2(1H)-one and 2-(bromomethyl)-5-(trifluoromethyl)pyrazine.

MS (ESI+): [M+H]+ 442.1.

Example 268

1-(2-Cyclopropyl-1-methyl-1H-benzimidazol-6-yl)-4-((4-methyl-1,3-thiazol-2-yl)methoxy)pyridin-2(1H)-one To a solution of 1-(2-cyclopropyl-1-methyl-1H-benzimidazol-6-yl)-4-hydroxypyridin-2(1H)-one (50 mg), (4-methyl-1,3-thiazol-2-yl)methanol (45.9 mg) and triphenylphosphine (140 mg) in THF (5 ml) was added bis(2-methoxyethyl) azodicarboxylate (125 mg), and the mixture was stirred at room temperature for 3 h. The mixture was poured into water and extracted with EtOAc. The extract was washed with brine, dried over MgSO$_4$, concentrated and purified by silica gel column chromatography (hexane/EtOAc then EtOAc/MeOH). The resulting solid was recrystallized from EtOH-water to give the title compound (11.3 mg) as a white solid.

MS (ESI+): [M+H]+ 393.1.

$^1$H NMR (400 MHz, DMSO-d$_6$): δ 0.94-1.18 (4H, m), 2.27 (1H, brs), 2.40 (3H, s), 3.85 (3H, s), 5.42 (2H, s), 6.04 (1H, brs), 6.12 (1H, d, J=7.4 Hz), 7.05 (1H, d, J=8.8 Hz), 7.37 (1H, s), 7.48-7.55 (2H, m), 7.61 (1H, d, J=7.4 Hz).

Example 269

2-(((1-(2-Cyclopropyl-1-methyl-1H-benzimidazol-6-yl)-2-oxo-1,2-dihydropyridin-4-yl)oxy)methyl)-1,3-thiazole-4-carbonitrile

A) 2-(Ethoxycarbonyl)-1,3-thiazole-4-carboxylic acid

A mixture of ethyl 2-amino-2-thioxoacetate (10.1 g), 3-bromo-2-oxopropanoic acid (12.7 g) and THF (200 ml) was stirred at 50° C. overnight. The mixture was concentrated in vacuo, and the resulting solid was suspended in EtOAc. The precipitate was collected by filtration to give the title compound (7.4 g) as a white solid.
MS (ESI+): [M+H]+ 447.3.

B) Ethyl 4-cyano-1,3-thiazole-2-carboxylate

A mixture of 2-(ethoxycarbonyl)-1,3-thiazole-4-carboxylic acid (1 g), triethylamine (2.77 ml), i-hydroxybenzotriazole-ammonia complex (2.27 g), 1-ethyl-3-(3-dimethylaminopropyl)carbodiimide hydrochloride (2.86 g) and DMF (10 ml) was stirred at room temperature overnight. The mixture was poured into water, and extracted with EtOAc. The extract was washed with brine, dried over $MgSO_4$, and concentrated in vacuo to give an intermediate amide. The intermediate amide was dissolved in THF (10 ml). Pyridine (0.92 ml) and trifluoroacetic acid anhydride (1.58 ml) were successively added to the solution at 0° C., and the mixture was stirred at room temperature for 2 h. The mixture was poured into saturated $NaHCO_3$ solution, and extracted with EtOAc. The extract was washed with brine, dried over $MgSO_4$, and concentrated in vacuo to give the title compound (0.34 g) as a white solid.
$^1$H NMR (400 MHz, DMSO-$d_6$): δ 1.34 (3H, t, J=7.1 Hz), 4.42 (2H, q, J=7.0 Hz), 9.17 (1H, s).

C) 2-(Hydroxymethyl)-1,3-thiazole-4-carbonitrile

To a solution of ethyl 4-cyano-1,3-thiazole-2-carboxylate (336 mg) in MeOH (10 ml) was added $NaBH_4$ (140 mg), and the mixture was stirred at room temperature for 3 h. The mixture was poured into saturated $NH_4Cl$ solution, concentrated in vacuo, and extracted with EtOAc. The extract was washed with brine, dried over $MgSO_4$, and concentrated in vacuo to give the title compound (253 mg) as a yellow oil.
$^1$H NMR (400 MHz, DMSO-$d_6$): δ 4.76 (2H, d, J=5.8 Hz), 6.34 (1H, t, J=5.8 Hz), 8.78 (1H, s).

D) 2-(((1-(2-Cyclopropyl-1-methyl-1H-benzimidazol-6-yl)-2-oxo-1,2-dihydropyridin-4-yl)oxy)methyl)-1,3-thiazole-4-carbonitrile The title compound was obtained in an analogous manner to example 189 using 1-(2-cyclopropyl-1-methyl-1H-benzimidazol-6-yl)-4-hydroxypyridin-2(1H)-one and 2-(hydroxymethyl)-1,3-thiazole-4-carbonitrile.
MS (ESI+): [M+H]+ 404.3.

Example 270

1-(2-Cyclopropyl-1-methyl-1H-benzimidazol-6-yl)-4-((4-(fluoromethyl)-1,3-thiazol-2-yl)methoxy)pyridin-2(1H)-one A) Ethyl 4-(hydroxymethyl)-1,3-thiazole-2-carboxylate A mixture of 2-(ethoxycarbonyl)-1,3-thiazole-4-carboxylic acid (2 g), boran-THF complex (1.0 M in THF, 45.2 ml) and THF (50 ml) was heated under reflux overnight. After MeOH (2.0 ml) was added to the mixture at the same temperature, the mixture was concentrated in vacuo to dryness. The residue was purified by NH silica gel column chromatography (hexane/EtOAc) to give the title compound (0.96 g) as a white solid.
MS (ESI+): [M+H]+ 188.0.

B) Ethyl 4-(fluoromethyl)-1,3-thiazole-2-carboxylate

To a solution of ethyl 4-(hydroxymethyl)-1,3-thiazole-2-carboxylate (960 mg) in toluene (20 ml) was added BAST (1.04 ml) at 0° C. After stirring for 1 h, additional BAST (0.38 ml) was added, and the mixture was stirred at room temperature for 1 h. The mixture was poured into saturated $NaHCO_3$ solution, and extracted with EtOAc. The extract was washed with brine, dried over $MgSO_4$, concentrated in vacuo, and purified by silica gel column chromatography (hexane/EtOAc) to give the title compound (175 mg) as a white solid.
MS (ESI+): [M+H]+ 190.0.

C) (4-(Fluoromethyl)-1,3-thiazol-2-yl)methanol

To a solution of ethyl 4-(fluoromethyl)-1,3-thiazole-2-carboxylate (170 mg) in MeOH (5 ml) was added $NaBH_4$ (68 mg), and the mixture was stirred at room temperature for 3 h. The mixture was poured into saturated $NH_4Cl$ solution, and extracted with EtOAc. The extract was washed with brine, dried over $MgSO_4$, and concentrated in vacuo to give the title compound (114 mg) as a colorless oil.
$^1$H NMR (400 MHz, DMSO-$d_6$): δ 4.72 (1H, d, J=5.8 Hz), 5.29-5.50 (1H, m), 6.08 (1H, t, J=5.8 Hz), 7.76 (1H, d, J=3.5 Hz).

D) 1-(2-Cyclopropyl-1-methyl-1H-benzimidazol-6-yl)-4-((4-(fluoromethyl)-1,3-thiazol-2-yl)methoxy)pyridin-2(1H)-one To a suspension of 1-(2-cyclopropyl-1-methyl-1H-benzo[d]imidazol-6-yl)-4-hydroxypyridin-2(1H)-one (100 mg), (4-(fluoromethyl)thiazol-2-yl)methanol (105 mg), triphenylphosphine (280 mg) and THF (5 ml) was added bis(2-methoxyethyl) azodicarboxylate (250 mg), and the mixture was stirred at room temperature for 2 h, then at 70° C. for 2 h. The mixture was poured into water, and extracted with EtOAc. The extract was washed with brine, dried over $MgSO_4$, concentrated in vacuo, and purified by silica gel column chromatography (EtOAc/MeOH) to give the title compound (4.0 mg) as a white solid.
MS (ESI+): [M+H]+ 411.1.
$^1$H NMR (400 MHz, DMSO-$d_6$): δ 1.02-1.14 (4H, m), 2.23-2.31 (1H, m), 3.85 (3H, s), 5.39-5.55 (4H, m), 6.04-6.10 (1H, m), 6.14 (1H, d, J=7.5 Hz), 7.05 (1H, d, J=7.7 Hz), 7.49-7.54 (2H, m), 7.62 (1H, d, J=7.8 Hz), 7.97 (1H, s).

Example 271

4-((5-Chloro-1,3-thiazol-2-yl)methoxy)-1-(2-cyclopropyl-1-methyl-1H-benzimidazol-6-yl)pyridin-2(1H)-one The title compound was obtained in an analogous manner to example 259 using 4-chloro-1-(2-cyclopropyl-1-methyl-1H-benzimidazol-6-yl)pyridin-2(1H)-one and (5-chloro-1,3-thiazol-2-yl)methanol.
MS (ESI+): [M+H]+ 413.1.

Example 272

4-((5-Chloro-1,3-thiazol-2-yl)methoxy)-1-(2-ethyl-1-methyl-1H-benzimidazol-6-yl)pyridin-2(1H)-one The title compound was obtained in an analogous manner to example 189 using 1-(2-ethyl-1-methyl-1H-benzo[d]imidazol-6-yl)-4-hydroxypyridin-2(1H)-one and (5-chlorothiazol-2-yl)methanol.
MS (ESI+): [M+H]+ 401.2.

Example 273

1-(2-Cyclopropyl-1-methyl-1H-benzimidazol-6-yl)-4-((2-(trifluoromethyl)-1,3-thiazol-5-yl)methoxy)pyridin-2(1H)-one The title compound was obtained in an analogous manner to example 266 using 4-bromo-1-(2-cyclopropyl-1-methyl-1H-benzimidazol-6-yl)pyridin-2(1H)-one and (2-(trifluoromethyl)-1,3-thiazol-5-yl)methanol.

MS (ESI+): [M+H]+ 447.3.

Example 274

1-(2-Cyclopropyl-1-methyl-1H-benzimidazol-6-yl)-4-((4-(methylsulfonyl)benzyl)oxy)pyridin-2(1H)-one The title compound was obtained in an analogous manner to example 189 using 1-(2-cyclopropyl-1-methyl-1H-benzimidazol-6-yl)-4-hydroxypyridin-2(1H)-one and (4-(methylsulfonyl)phenyl)methanol.

MS (ESI+): [M+H]+ 450.1.

Example 275

1-(2-Cyclopropyl-1-methyl-1H-benzimidazol-6-yl)-4-((4-(trifluoromethyl)-2-thienyl)methoxy)pyridin-2(1H)-one A) 3-(Trifluoromethyl)thiophene To a solution of 3-iodothiophene (20 g) in DMA (300 ml) were added methyl difluoro(fluorosulfonyl)acetate (73.2 g), hexamethylphosphoramide (68.3 g) and CuI (20.0 g) at room temperature, and the mixture was stirred at 80° C. overnight. After cooling to 0° C., the mixture was slowly added to 28% $NH_3$ solution, and the mixture was extracted with $Et_2O$. The organic layer was separated, washed with water and brine successively, dried over $MgSO_4$ and concentrated in vacuo. The crude material was distilled to give the title compound (6.99 g, 130° C. at 760 mmHg) as a colorless oil.

$^1$H NMR (400 MHz, DMSO-$d_6$): δ 7.41 (1H, d, J=5.0 Hz), 7.77-7.84 (1H, m), 8.21-8.30 (1H, m).

B) (4-(Trifluoromethyl)-2-thienyl)methanol

To a solution of 2,2,6,6-tetramethylpiperidine (7.79 g) in THF (150 ml) was added n-butyllithium (1.6 M in hexane, 34.5 ml) at −78° C., and the mixture was stirred at 0° C. for 10 min. The solution was cooled to −78° C., and stirred for 30 min. To the solution was added 3-(trifluoromethyl)thiophene (6.99 g) in THF over 30 min, and the mixture was stirred for 1 h at same temperature. Then DMF (10.1 g) was added to the mixture, and the mixture was stirred overnight at room temperature. The mixture was quenched with 1 M HCl and extracted with EtOAc. The organic layer was separated, washed with 1 M HCl and brine successively, dried over $MgSO_4$, concentrated in vacuo, and purified by column chromatography (hexane/EtOAc). The resulting residue was dissolved in MeOH (100 ml), and $NaBH_4$ (0.865 g) was added to the mixture at 0° C. After stirred at room temperature for 30 min, the mixture was quenched with saturated $NH_4Cl$ solution and extracted with EtOAc. The organic layer was separated, washed with saturated $NH_4Cl$ solution and brine successively, dried over $MgSO_4$ and concentrated in vacuo. The residue was purified by column chromatography (hexane/EtOAc) to give the title compound (1.79 g) as a colorless oil.

$^1$H NMR (400 MHz, DMSO-$d_6$): δ 4.65 (2H, d, J=5.6 Hz), 5.65 (1H, t, J=5.6 Hz), 7.21 (1H, s), 8.12 (1H, s).

C) 1-(2-Cyclopropyl-1-methyl-1H-benzimidazol-6-yl)-4-((4-(trifluoromethyl)-2-thienyl)methoxy)pyridin-2(1H)-one To a solution of (4-(trifluoromethyl)thiophen-2-yl)methanol (50 mg) in DMA (2 ml) was added NaH (60% in oil, 18.3 mg) at room temperature, and the mixture was stirred for 30 min. 4-Bromo-1-(2-cyclopropyl-1-methyl-1H-benzimidazol-6-yl)pyridin-2(1H)-one (79 mg) was added to the mixture, and the mixture was heated at 120° C. for 30 min under microwave irradiation. The mixture was poured into water and extracted with EtOAc. The organic layer was separated, washed with saturated $NaHCO_3$ solution and brine successively, dried over $MgSO_4$ and concentrated in vacuo. The residue was purified by column chromatography (EtOAc/MeOH), followed by crystallized from hot EtOAc to give the title compound (15.3 mg) as pale yellow crystals.

MS (ESI+): [M+H]+ 446.3.

$^1$H NMR (300 MHz, DMSO-$d_6$): δ 1.00-1.13 (4H, m), 2.19-2.32 (1H, m), 3.85 (3H, s), 5.39 (2H, s), 6.03-6.12 (2H, m), 7.05 (1H, dd, J=2.0, 8.5 Hz), 7.52 (2H, dd, J=2.9, 5.2 Hz), 7.56-7.62 (2H, m), 8.30-8.35 (1H, m).

Example 276

1-(2-Ethyl-1-methyl-1H-benzimidazol-6-yl)-4-((4-(trifluoromethyl)-2-thienyl)methoxy)pyridin-2(1H)-one To a solution of (4-(trifluoromethyl)thiophen-2-yl)methanol (50 mg) in THF (3 ml) were added 1-(2-ethyl-1-methyl-1H-benzo[d]imidazol-6-yl)-4-hydroxypyridin-2(1H)-one (73.9 mg), bis(2-methoxyethyl) azodicarboxylate (129 mg) and $PPh_3$ (144 mg) at room temperature, and the mixture was stirred for 3 h. The mixture was poured into water and extracted with EtOAc. The organic layer was separated, washed with saturated $NaHCO_3$ solution and brine successively, dried over $MgSO_4$ and concentrated in vacuo. The residue was purified by column chromatography (EtOAc/MeOH) to give the title compound (10.2 mg) as white crystals.

MS (ESI+): [M+H]+ 434.3.

$^1$H NMR (300 MHz, DMSO-$d_6$): δ 1.33 (3H, t, J=7.5 Hz), 2.90 (2H, q, J=7.6 Hz), 3.74 (3H, s), 5.39 (2H, s), 6.04-6.12 (2H, m), 7.07 (1H, dd, J=2.0, 8.5 Hz), 7.51-7.63 (4H, m), 8.33 (1H, t, J=1.4 Hz).

Example 277

1-(2-Cyclopropyl-1-methyl-1H-benzimidazol-6-yl)-4-((4-cyclopropyl-1,3-thiazol-2-yl)methoxy)pyridin-2(1H)-one A) 4-((4-Bromo-1,3-thiazol-2-yl)methoxy)-1-(2-cyclopropyl-1-methyl-1H-benzimidazol-6-yl)pyridin-2(1H)-one To a solution of 1-(2-cyclopropyl-1-methyl-1H-benzimidazol-6-yl)-4-hydroxypyridin-2(1H)-one (289 mg), (4-bromo-1,3-thiazol-2-yl)methanol (399 mg) and triphenylphosphine (808 mg) in THF (8 ml) was added bis(2-methoxyethyl) azodicarboxylate (722 mg), and the mixture was stirred at room temperature for 3 h. The mixture was poured into water and extracted with EtOAc. The extract was washed with brine, dried over MgSO₄, concentrated and purified by silica gel column chromatography (hexane/EtOAc then EtOAc/MeOH) to give the title compound (128 mg) as a white solid.

MS (ESI+): [M+H]+ 457.2.

B) 1-(2-Cyclopropyl-1-methyl-1H-benzimidazol-6-yl)-4-((4-cyclopropyl-1,3-thiazol-2-yl)methoxy)pyridin-2(1H)-one A mixture of 4-((4-bromo-1,3-thiazol-2-yl)methoxy)-1-(2-cyclopropyl-1-methyl-1H-benzimidazol-6-yl)pyridin-2(1H)-one (50 mg), cyclopropylboronic acid (10.3 mg), tetrakis(triphenylphosphine)palladium (6.3 mg), potassium carbonate (60.4 mg), DME (1 ml) and water (0.3 ml) was heated at 150° C. for 15 min under microwave irradiation. Additional cyclopropylboronic acid (14.1 mg) was added to the mixture, and the mixture was heated 150° C. for further 15 min under microwave irradiation. The reaction mixture was poured into water and extracted with EtOAc. The extract was washed with brine, dried over MgSO₄, concentrated and purified by silica gel column chromatography (hexane/EtOAc then EtOAc/MeOH). The resulting solid was recrystallized from EtOH-water to give the title compound (14.1 mg) as a white solid.

MS (ESI+): [M+H]+ 419.1.

$^1$H NMR (400 MHz, DMSO-d₆): δ 0.81 (2H, dd, J=1.8, 4.5 Hz), 0.88-0.96 (2H, m), 1.01-1.13 (4H, m), 2.06-2.16 (1H, m), 2.21-2.32 (1H, m), 3.85 (3H, s), 5.39 (2H, s), 6.03 (1H, d, J=2.5 Hz), 6.11 (1H, dd, J=2.6, 7.8 Hz), 7.05 (1H, d, J=10.2 Hz), 7.36 (1H, s), 7.49-7.55 (2H, m), 7.60 (1H, d, J=7.8 Hz).

Example 278

1-(2-Cyclopropyl-1-methyl-1H-benzimidazol-6-yl)-4-((2-(pentafluoroethyl)-1,3-thiazol-4-yl)methoxy)pyridin-2(1H)-one A) Ethyl 2-(perfluoroethyl)thiazole-4-carboxylate A mixture of 2,2,3,3,3-pentafluoropropanamide (2 g), Lawesson's reagent (2.98 g) and THF (30 ml) was heated under reflux overnight. Then ethyl 3-bromo-2-oxopropanoate (2.99 g) was added, and the mixture was heated at the same temperature overnight. The mixture was poured into water, and extracted with EtOAc. The extract was washed with brine, dried over MgSO₄, concentrated in vacuo, and purified by silica gel column chromatography (hexane/EtOAc) to give the title compound (0.91 g) as a yellow solid.

MS (ESI+): [M+H]+ 276.0.

B) 2-(Perfluoroethyl)thiazol-4-yl)methanol

To a solution of ethyl 2-(perfluoroethyl)thiazole-4-carboxylate (900 mg) in THF (30 ml) was added LiBH₄ (107 mg) portionwise at 0° C., and the mixture was stirred at 0° C. for 1 h. To the solution was added MeOH (0.198 ml), and the mixture was stirred at 0° C. for 30 min. The mixture was poured into 1 M HCl and extracted with EtOAc. The organic layer was washed with brine, dried over MgSO₄ and concentrated in vacuo. The residue was purified by silica gel column chromatography (hexane/EtOAc) to give the title compound (570 mg) as a colorless oil.

MS (ESI+): [M+H]+ 234.0.

C) 1-(2-Cyclopropyl-1-methyl-1H-benzimidazol-6-yl)-4-((2-(pentafluoroethyl)-1,3-thiazol-4-yl)methoxy)pyridin-2(1H)-one NaH (60% in oil, 51.5 mg) was added to a solution of (2-(perfluoroethyl)thiazol-4-yl)methanol (300 mg) in DMA (5 ml) at 0° C. After being stirred at 0° C. for 30 min, 4-bromo-1-(2-cyclopropyl-1-methyl-1H-benzo[d]imidazol-6-yl)pyridin-2(1H)-one (295 mg) was added to the reaction mixture. The mixture was stirred at 120° C. under N₂ atmosphere for 1 h. The mixture was quenched with water and extracted with EtOAc. The organic layer was separated, washed with water and brine successively, dried over MgSO₄ and concentrated in vacuo. The residue was purified by NH silica gel column chromatography (hexane/EtOAc), followed by crystallization from EtOH-water to give the title compound (25 mg) as a white solid.

MS (ESI+): [M+H]+ 497.1.

Example 279

1-(2-Ethyl-1-methyl-1H-benzimidazol-6-yl)-4-((2-(pentafluoroethyl)-1,3-thiazol-4-yl)methoxy)pyridin-2(1H)-one The title compound was obtained in an analogous manner to example 189 using 1-(2-ethyl-1-methyl-1H-benzo[d]imidazol-6-yl)-4-hydroxypyridin-2(1H)-one and (2-(perfluoroethyl)thiazol-4-yl)methanol.

MS (ESI+): [M+H]+ 485.1.

Example 280

4-((2-Chlorobenzyl)oxy)-1-(2-cyclopropyl-1-methyl-1H-benzimidazol-6-yl)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (2-chlorophenyl)methanol.

MS (ESI+): [M+H]+ 406.1.

Example 281

1-(2-Cyclopropyl-1-methyl-1H-benzimidazol-6-yl)-4-((2,2-difluoro-1,3-benzodioxol-5-yl)methoxy)pyridin-2(1H)-one The title compound was obtained in an analogous manner to example 75 using 1-(2-cyclopropyl-1-methyl-1H-benzimidazol-6-yl)-4-hydroxypyridin-2(1H)-one and (2,2-difluoro-1,3-benzodioxol-5-yl)methanol.

MS (ESI+): [M+H]+ 452.1.

Example 282

2-(((1-(2-cyclopropyl-3-methylimidazo[1,2-a]pyridin-6-yl)-2-oxo-1,2-dihydropyridin-4-yl)oxy)methyl)-5-fluorobenzonitrile The title compound was obtained in an analogous manner to example 190 using 2-(bromomethyl)-5-fluorobenzonitrile and 1-(2-cyclopropyl-3-methylimidazo[1,2-a]pyridin-6-yl)-4-hydroxypyridin-2(1H)-one.

MS (ESI+): [M+H]+ 415.3.

Example 283

1-(2-Cyclopropyl-1-methyl-1H-benzimidazol-6-yl)-4-((4-(difluoromethyl)-1,3-thiazol-2-yl)methoxy)pyridin-2(1H)-one

A) Ethyl 4-formyl-1,3-thiazole-2-carboxylate

A mixture of ethyl 4-(hydroxymethyl)-1,3-thiazole-2-carboxylate (1.23 g), manganese dioxide (5.71 g) and THF (25 ml) was heated at 50° C. overnight. The inorganic material was removed by filtration, and the filtrate was concentrated in vacuo to give the title compound (1.11 g) as a yellow solid.
MS (ESI+): [M+H]+ 186.0.

B) Ethyl 4-(difluoromethyl)-1,3-thiazole-2-carboxylate

To a solution of ethyl 4-formyl-1,3-thiazole-2-carboxylate (1.11 g) in toluene (15 ml) was added a solution of BAST (2.21 ml) in toluene (5.0 ml) at 0° C., and the mixture was stirred at room temperature for 3 h. The mixture was partitioned between EtOAc and water, and the organic layer was washed with brine, dried over $MgSO_4$, concentrated in vacuo, and purified by silica gel column chromatography (hexane/EtOAc) to give the title compound (0.90 g) as a colorless oil.
$^1$H NMR (400 MHz, DMSO-$d_6$): δ 1.35 (3H, t, J=7.1 Hz), 4.41 (2H, q, J=7.1 Hz), 7.02-7.36 (1H, m), 8.52 (1H, s).

C) (4-(Difluoromethyl)-1,3-thiazol-2-yl)methanol

To a solution of ethyl 4-(difluoromethyl)-1,3-thiazole-2-carboxylate (900 mg) in MeOH (15 ml) was added $NaBH_4$ (329 mg), and the mixture was stirred at room temperature for 2 h. The mixture was partitioned between saturated $NH_4Cl$ solution and EtOAc. The organic layer was washed with brine, dried over $MgSO_4$, and concentrated in vacuo to give the title compound (703 mg) as a colorless oil.
$^1$H NMR (400 MHz, DMSO-$d_6$): δ 4.74 (1H, s), 6.17 (1H, brs), 6.84-7.24 (1H, m), 8.04 (1H, s).

D) 1-(2-Cyclopropyl-1-methyl-1H-benzimidazol-6-yl)-4-((4-(difluoromethyl)-1,3-thiazol-2-yl)methoxy)pyridin-2(1H)-one A mixture of (4-(difluoromethyl)-1,3-thiazol-2-yl)methanol (50 mg), 4-bromo-1-(2-cyclopropyl-1-methyl-1H-benzo[d]imidazol-6-yl)pyridin-2(1H)-one (69.5 mg), NaH (60% in oil, 12.1 mg) and DMA (1 ml) was heated at 120° C. under microwave irradiation for 2 h. The mixture was poured into water and extracted with EtOAc. The extract was washed with brine, dried over $MgSO_4$, concentrated in vacuo, and purified by NH silica gel column chromatography (hexane/EtOAc) to give the title compound (17 mg) as a white solid.
MS (ESI+): [M+H]+ 429.1.
$^1$H NMR (400 MHz, DMSO-$d_6$): δ 0.99-1.15 (4H, m), 2.23-2.31 (1H, m), 3.85 (3H, s), 5.53 (2H, s), 6.07 (1H, d, J=2.6 Hz), 6.15 (1H, dd, J=2.7, 7.6 Hz), 6.98-7.31 (2H, m), 7.50-7.56 (2H, m), 7.63 (1H, d, J=7.5 Hz), 8.24 (1H, s).

Example 284

4-((4-(Difluoromethyl)-1,3-thiazol-2-yl)methoxy)-1-(2-ethyl-1-methyl-1H-benzimidazol-6-yl)pyridin-2(1H)-one A mixture of (4-(difluoromethyl)-1,3-thiazol-2-yl)methanol (61.3 mg), 1-(2-ethyl-1-methyl-1H-benzo[d]imidazol-6-yl)-4-hydroxypyridin-2(1H)-one (50 mg), triphenylphosphine (146 mg), bis(2-methoxyethyl) azodicarboxylate (130 mg) and THF (3 ml) was stirred at room temperature for 3 h. The mixture was diluted with water, and extracted with EtOAc. The extract was washed with brine, dried over $MgSO_4$, concentrated in vacuo and purified by NH silica gel column chromatography (hexane/EtOAc) to give the title compound (10.1 mg) as a white solid.
MS (ESI+): [M+H]+ 417.1.
$^1$H NMR (400 MHz, DMSO-$d_6$): δ 1.33 (3H, t, J=7.3 Hz), 2.91 (2H, q, J=7.5 Hz), 3.74 (3H, s), 5.53 (2H, s), 6.07 (1H, d, J=2.5 Hz), 6.16 (1H, dd, J=2.4, 7.5 Hz), 6.98-7.29 (2H, m), 7.55 (1H, d, J=1.8 Hz), 7.62 (2H, dd, J=7.9, 15.1 Hz), 8.24 (1H, s).

Example 285

1-(2-Cyclopropyl-1-methyl-1H-benzimidazol-6-yl)-4-((2-cyclopropyl-1,3-thiazol-4-yl)methoxy)pyridin-2(1H)-one

A) 4-((2-Bromo-1,3-thiazol-4-yl)methoxy)-1-(2-cyclopropyl-1-methyl-1H-benzimidazol-6-yl)pyridin-2(1H)-one To a solution of (2-bromo-1,3-thiazol-4-yl)methanol (169 mg) in DMA (5 ml) was added NaH (60% in oil, 34.9 mg) at 0° C. After being stirred at 0° C. for 30 min, 4-bromo-1-(2-cyclopropyl-1-methyl-1H-benzimidazol-6-yl)pyridin-2(1H)-one was added to the reaction mixture, and the mixture was stirred at 120° C. under $N_2$ atmosphere for 30 min. The reaction mixture was quenched with water and extracted with EtOAc. The extract was washed with brine, dried over $MgSO_4$, concentrated and purified by NH silica gel column chromatography (hexane/EtOAc) to give the title compound (57.0 mg) as a white solid.
MS (ESI+): [M+H]+ 457.2.

B) 1-(2-Cyclopropyl-1-methyl-1H-benzimidazol-6-yl)-4-((2-cyclopropyl-1,3-thiazol-4-yl)methoxy)pyridin-2(1H)-one A mixture of 4-((2-bromo-1,3-thiazol-4-yl)methoxy)-1-(2-cyclopropyl-1-methyl-1H-benzimidazol-6-yl)pyridin-2(1H)-one (54 mg), cyclopropylboronic acid (30.4 mg), tetrakis(triphenylphosphine)palladium (6.8 mg), potassium carbonate (65.3 mg), DME (1.5 ml) and water (0.5 ml) was heated at 150° C. for 20 min under microwave irradiation. The reaction mixture was then cooled to room temperature, poured into water and extracted with EtOAc. The extract was washed with brine, dried over $MgSO_4$, concentrated and purified by silica gel column chromatography (hexane/EtOAc then EtOAc/MeOH). The resulting solid was recrystallized from EtOH-water to give the title compound (12.2 mg) as a white solid.
MS (ESI+): [M+H]+ 419.3.
$^1$H NMR (400 MHz, DMSO-$d_6$): δ 0.96 (2H, dd, J=2, 8, 4.6 Hz), 1.03-1.18 (6H, m), 2.27 (1H, s), 2.42 (1H, t, J=4.5 Hz), 3.85 (3H, s), 5.10 (2H, s), 6.03 (1H, d, J=2.6 Hz), 6.06-6.12 (1H, m), 7.04 (1H, d, J=6.8 Hz), 7.48-7.53 (2H, m), 7.54-7.60 (2H, m).

Example 286

1-(1,2-Dimethyl-1H-benzimidazol-6-yl)-4-((4-(trifluoromethyl)thiophen-2-yl)methoxy)pyridin-2(1H)-one

A) 1-(1,2-Dimethyl-1H-benzimidazol-6-yl)-4-hydroxypyridin-2(1H)-one

A mixture of 4-(benzyloxy)-1-(1,2-dimethyl-1H-benzimidazol-6-yl)pyridin-2(1H)-one (627 mg), 10% Pd/C (193 mg) and MeOH (10 ml) was stirred under $H_2$ atmosphere at room temperature for 1 h. The catalyst was removed by filtration, and the filtrate was concentrated in vacuo to give the title compound (421 mg) as white crystals.
MS (ESI+): [M+H]+ 256.2.

B) 1-(1,2-Dimethyl-1H-benzimidazol-6-yl)-4-((4-(trifluoromethyl)thiophen-2-yl)methoxy)pyridin-2(1H)-one To a suspension of 1-(1,2-dimethyl-1H-benzimidazol-6-yl)-4-hydroxypyridin-2(1H)-one (200 mg) in THF (5 ml) were added (4-(trifluoromethyl)thiophen-2-yl)methanol (157 mg), 1,1'-(azodicarbonyl)dipiperidine (257 mg) and tributylphosphine (0.25 ml) at room temperature, and the mixture was stirred at 50° C. overnight. After cooling, the mixture was purified by NH silica gel column chromatography (EtOAc/MeOH), followed by preparative HPLC (C18, mobile phase: $H_2O/CH_3CN$ (0.1% TFA included)). The desired fraction was neutralized with saturated $NaHCO_3$ solution, and extracted with EtOAc. The organic layer was separated, dried over $MgSO_4$ and concentrated in vacuo to give the title compound (129 mg) as white crystals.
MS (ESI+): [M+H]+ 420.2.
$^1$H NMR (400 MHz, DMSO-$d_6$): δ 2.55 (3H, s), 3.74 (3H, s), 5.39 (2H, s), 6.03-6.11 (2H, m), 7.06 (1H, dd, J=8.5, 1.6 Hz), 7.50-7.63 (4H, m), 8.33 (1H, s).

Example 287

1-(2-Cyclopropyl-1-methyl-1H-benzimidazol-6-yl)-4-((2-(difluoromethyl)-1,3-thiazol-4-yl)methoxy)pyridin-2($^1$H)-one

A) Ethyl 2-(diethoxymethyl)-1,3-thiazole-4-carboxylate

A mixture of 2,2-diethoxyethanethioamide (2 g), ethyl bromopyruvate (1.61 ml), MS-4A (2 g) and EtOH (15 ml) was heated under reflux for 1 h. The mixture was concentrated, and the residue was diluted with AcOEt. The mixture was washed with water and brine successively, dried with $MgSO_4$ and concentrated in vacuo. The residue was purified by NH silica gel column chromatography (hexane/EtOAc) to give the title compound (2.5 g) as an off-white solid.
$^1$H NMR (400 MHz, CDCl$_3$): δ 1.26 (6H, t, J=7.0 Hz), 1.40 (3H, t, J=7.1 Hz), 3.60-3.82 (4H, m), 4.43 (2H, q, J=7.1 Hz), 5.71 (1H, s), 8.19 (1H, s).

B) Ethyl 2-formyl-1,3-thiazole-4-carboxylate

A solution of ethyl 2-(diethoxymethyl)thiazole-4-carboxylate (1.6 g) and 1 M HCl (12.3 ml) in acetone (100 ml) was heated under reflux for 5 h. After the solvent was removed by evaporation, the residue was diluted with AcOEt, neutralized with saturated $NaHCO_3$ solution and extracted with EtOAc. The organic layer was separated, washed with water and brine successively, dried over $MgSO_4$ and concentrated in vacuo. The residue was purified by silica gel column chromatography (hexane/EtOAc) to give the title compound (1.0 g) as an off-white solid.
MS (ESI+): [M+H]+ 186.0.

C) Ethyl 2-(difluoromethyl)-1,3-thiazole-4-carboxylate

To a solution of ethyl 2-formylthiazole-4-carboxylate (1.0 g) in toluene (15 ml) was added a solution of BAST (2.99 ml) in toluene (5 ml) at 0° C. The mixture was stirred at room temperature under $N_2$ atmosphere overnight. The mixture was diluted with AcOEt, quenched with saturated $NaHCO_3$ solution, washed with water and brine successively, dried over $MgSO_4$ and concentrated in vacuo. The residue was purified by silica gel column chromatography (hexane/EtOAc) to give the title compound (0.81 g) as an off-white solid.
MS (ESI+): [M+H]+ 208.0.

D) (2-(Difluoromethyl)-1,3-thiazol-4-yl)methanol

To a solution of ethyl 2-(difluoromethyl)thiazole-4-carboxylate (100 mg) in MeOH (1 ml) was added NaBH$_4$ (36.5 mg) at 0° C., and the mixture was stirred at 0° C. for 3 h. The mixture was quenched with saturated NH$_4$Cl solution, and extracted with EtOAc. The organic layer was separated, washed with water and brine successively, dried over $MgSO_4$ and concentrated in vacuo. The residue was purified by NH silica gel column chromatography (hexane/EtOAc) to give the title compound (44.0 mg) as a pale yellow oil.
$^1$H NMR (400 MHz, CDCl$_3$): δ 2.11 (1 H, t, J=6.0 Hz), 4.84 (2 H, d, J=5.8 Hz), 6.67-6.98 (1 H, m), 7.41 (1 H, s).

E) 1-(2-Cyclopropyl-1-methyl-1H-benzimidazol-6-yl)-4-((2-(difluoromethyl)-1,3-thiazol-4-yl)methoxy)pyridin-2(1H)-one To a suspension of (2-(difluoromethyl)thiazol-4-yl)methanol (44 mg) and 4-chloro-1-(2-cyclopropyl-1-methyl-1H-benzo[d]imidazol-6-yl)pyridin-2(1H)-one (66.5 mg) in toluene (1 ml) was added potassium tert-butoxide (49.8 mg) at 100° C., and the mixture was stirred at 100° C. under dry atmosphere (CaCl$_2$ tube) for 30 min. The mixture was quenched with water and extracted with EtOAc. The organic layer was separated, washed with water and brine successively, dried over $MgSO_4$ and concentrated in vacuo. The residue was purified by silica gel column chromatography (hexane/EtOAc then EtOAc/MeOH), followed by recrystallization from EtOH-water to give the title compound (47.7 mg) as an off-white solid.
MS (ESI+): [M+H]+ 429.1.
$^1$H NMR (400 MHz, CDCl$_3$): δ 1.11-1.17 (2H, m), 1.21-1.27 (2H, m), 1.97-2.05 (1H, m), 3.84 (3H, s), 5.22 (2H, s), 6.04-6.12 (2H, m), 6.71-7.03 (1H, m), 7.10 (1H, dd, J=1.9, 8.4 Hz), 7.30-7.37 (2H, m), 7.59 (1H, s), 7.70 (1H, d, J=8.5 Hz).

Example 288

4-((2-(Difluoromethyl)-1,3-thiazol-4-yl)methoxy)-1-(2-ethyl-1-methyl-1H-benzimidazol-6-yl)pyridin-2(1H)-one To a suspension of (2-(difluoromethyl)thiazol-4-yl)methanol (39 mg) and 4-bromo-1-(2-ethyl-1-methyl-1H-benzo[d]

imidazol-6-yl)pyridin-2(1H)-one (52.3 mg) in toluene (1 ml) was added potassium tert-butoxide (35.3 mg) at 100° C. The mixture was stirred at 100° C. under dry atmosphere (CaCl$_2$ tube) for 30 min. The mixture was quenched with water and extracted with EtOAc. The organic layer was separated, washed with water and brine successively, dried over MgSO$_4$ and concentrated in vacuo. The residue was purified by silica gel column chromatography (hexane/EtOAc then EtOAc/MeOH), followed by recrystallization from EtOH-water to give the title compound (20.0 mg) as an off-white solid.

MS (ESI+): [M+H]+ 417.1.

$^1$H NMR (400 MHz, CDCl$_3$): δ 1.46 (3H, t, J=7.5 Hz), 2.93 (2H, q, J=7.6 Hz), 3.73 (3H, s), 5.22 (2H, s), 6.05-6.13 (2H, m), 6.72-7.02 (1H, m), 7.12 (1H, dd, J=1.9, 8.5 Hz), 7.31-7.38 (2H, m), 7.59 (1H, s), 7.78 (1H, d, J=8.5 Hz).

Example 289

4-(Benzyloxy)-1-(1,2-dimethyl-1H-benzimidazol-6-yl)pyridin-2(1H)-one

To a suspension of 4-benzyloxy-2(1H)-pyridone (21.5 g), 6-bromo-1,2-dimethyl-1H-benzo[d]imidazole (16 g), N,N'-dimethylethylenediamine (7.57 ml) and potassium carbonate (29.5 g) in DMSO (160 ml) was added CuI (13.5 g), and the mixture was stirred at 90° C. for 5 h under Ar atmosphere. After the mixture was cooled, 28% NH$_3$ solution (160 ml) and water (160 ml) were added. The precipitate was collected by filtration, washed with water and diisopropyl ether successively, and dried to give a solid. The residue was purified by silica gel column chromatography (hexane/EtOAc then EtOAc/MeOH) to give the title compound (14.5 g) as an off-white solid.

MS (ESI+): [M+H]+ 346.1.

$^1$H NMR (400 MHz, CDCl$_3$): δ 2.62 (3H, s), 3.72 (3H, s), 5.06 (2H, s), 6.03-6.12 (2H, m), 7.13 (1H, dd, J=1.9, 8.4 Hz), 7.30 (1H, d, J=7.5 Hz), 7.33-7.47 (6H, m), 7.73 (1H, d, J=8.4 Hz).

Example 290

1-(1,2-Dimethyl-1H-benzimidazol-6-yl)-4-((5-(trifluoromethyl)thiophen-3-yl)methoxy)pyridin-2(1H)-one To a suspension of 1-(1,2-dimethyl-1H-benzo[d]imidazol-6-yl)-4-hydroxypyridin-2(1H)-one (100 mg) in THF (5 ml) were added (5-(trifluoromethyl)thiophen-3-yl)methanol (78 mg), 1,1'-(azodicarbonyl)dipiperidine (128 mg) and tributylphosphine (0.13 ml) at room temperature, and the mixture was stirred at 50° C. overnight. After cooling, the mixture was purified by NH silica gel column chromatography (EtOAc/MeOH). The same reaction was conducted, and the combined products were purified by preparative HPLC (C18, mobile phase: H$_2$O/CH$_3$CN (0.1% TFA included)). The desired fraction was neutralized with saturated NaHCO$_3$ solution, and extracted with EtOAc. The organic layer was separated, dried over MgSO$_4$ and concentrated in vacuo to give the title compound (129 mg) as a white solid.

MS (ESI+): [M+H]+ 420.1.

$^1$H NMR (400 MHz, DMSO-d$_6$): δ 2.55 (3 H, s), 3.74 (3 H, s), 5.16 (2 H, s), 6.01 (1 H, d, J=2.5 Hz), 6.09 (1 H, dd, J=2.5, 7.6 Hz), 7.06 (1 H, d, J=6.5 Hz), 7.52 (1 H, s), 7.58 (2 H, dd, J=8.0, 14.7 Hz), 7.81 (1 H, s), 8.06 (1 H, s).

Example 291

1-(2-Cyclopropyl-3-methylimidazo[1,2-a]pyridin-6-yl)-4-((5-fluoropyridin-2-yl)methoxy)pyridin-2(1H)-one hydrochloride A mixture of 1-(2-cyclopropyl-3-methylimidazo[1,2-a]pyridin-6-yl)-4-hydroxypyridin-2(1H)-one (300 mg), (5-fluoropyridin-2-yl)methanol (271 mg), 1,1'-(azodicarbonyl)dipiperidine (807 mg), tributylphosphine (0.752 ml) and THF (20 ml) was heated at 60° C. for 3 h. The mixture was diluted with EtOAc, washed with water and brine successively, dried over MgSO$_4$, and concentrated. The residue was purified by silica gel column chromatography (EtOAc/MeOH), followed by preparative HPLC (C18, mobile phase: H$_2$O/CH$_3$CN (0.1% TFA included)). The desired fraction was neutralized with saturated NaHCO$_3$ solution, and extracted with EtOAc. The resulting solid was dissolved in EtOAc (1 ml) and THF (1 ml), and HCl (4 M in EtOAc, 0.144 ml) was added. Then the mixture was stirred at room temperature for 1 h. The resulting precipitate was collected by filtration, and washed with EtOAc to give the title compound (88 mg) as a white solid.

MS (ESI+): [M+H]+ 390.1.

$^1$H NMR (400 MHz, DMSO-d$_6$): δ 0.96-1.05 (2H, m), 1.09-1.18 (2H, m), 2.20-2.31 (1H, m), 2.57 (3H, s), 5.25 (2H, s), 6.07 (1H, d, J=2.5 Hz), 6.28 (1H, dd, J=2.7, 7.6 Hz), 7.62-7.73 (2H, m), 7.78-7.90 (3H, m), 8.63 (1H, d, J=2.9 Hz), 8.93 (1H, brs).

TABLE 1

| Example | IUPAC Name | Structure | MS |
|---|---|---|---|
| 1 | 1-(2-cyclopropyl-3-methylimidazo[1,2-a]pyridin-6-yl)-4-((4-fluorobenzyl)oxy)pyridin-2(1H)-one | 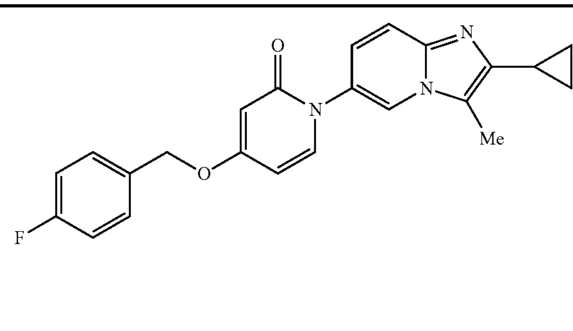 | 389.8 |

TABLE 1-continued

| Example | IUPAC Name | Structure | MS |
|---|---|---|---|
| 2 | 1-(2-cyclopropyl-1-methyl-1H-benzimidazol-6-yl)-4-((4-fluorobenzyl)oxy)pyridin-2(1H)-one | 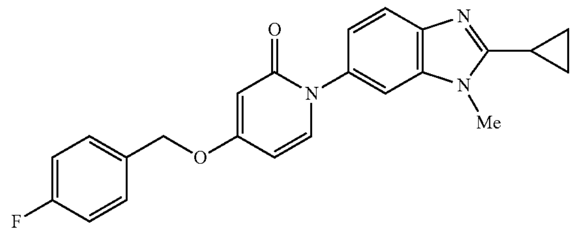 [SMILES: Cn1c(C2CC2)nc2ccc(-n3ccc(OCc4ccc(F)cc4)cc3=O)cc21] | 390.2 |
| 3 | 4-((4-chlorobenzyl)oxy)-1-(2-cyclopropyl-3-methylimidazo[1,2-a]pyridin-6-yl)pyridin-2(1H)-one | 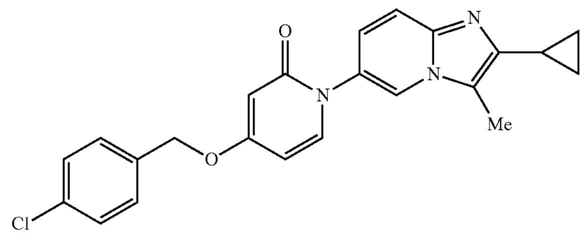 | 406.1 |
| 4 | 1-(2-cyclopropyl-1,4-dimethyl-1H-benzimidazol-6-yl)-4-((4-fluorobenzyl)oxy)pyridin-2(1H)-one | 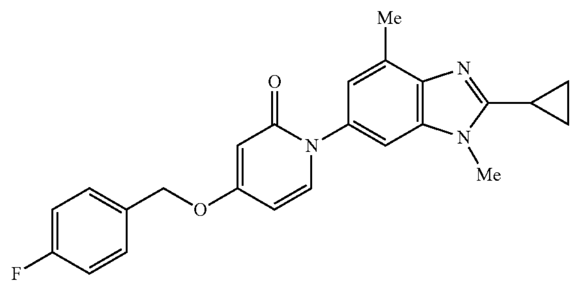 [SMILES: Cc1cc(-n2ccc(OCc3ccc(F)cc3)cc2=O)cc2c1nc(C1CC1)n2C] | 404.0 |
| 5 | 1-(2-cyclopropyl-3-methylimidazo[1,2-a]pyridin-6-yl)-4-((4-(trifluoromethyl)benzyl)oxy)pyridin-2(1H)-one | 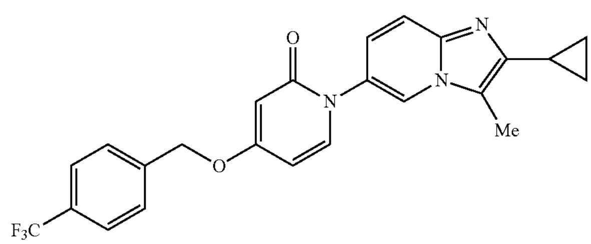 [SMILES: Cc1c(C2CC2)nc2ccc(-n3ccc(OCc4ccc(C(F)(F)F)cc4)cc3=O)cn12] | 440.2 |
| 6 | 1-(2-cyclopropyl-3-methylimidazo[1,2-a]pyridin-6-yl)-4-((4-(trifluoromethoxy)benzyl)oxy)pyridin-2(1H)-one | 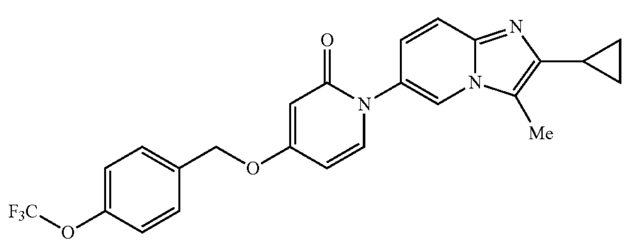 [SMILES: Cc1c(C2CC2)nc2ccc(-n3ccc(OCc4ccc(OC(F)(F)F)cc4)cc3=O)cn12] | 456.4 |
| 7 | 6-((4-chlorobenzyl)oxy)-3-(2-cyclopropyl-3-methylimidazo[1,2-a]pyridin-6-yl)pyrimidine-4(3H)-one | 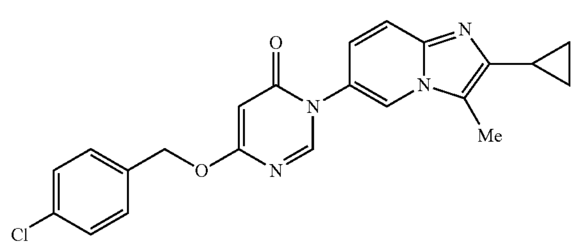 [SMILES: Cc1c(C2CC2)nc2ccc(-n3cnc(OCc4ccc(Cl)cc4)cc3=O)cn12] | 407.0 |

TABLE 1-continued

| Example | IUPAC Name | Structure | MS |
|---|---|---|---|
| 8 | 1-(2-tert-butyl-1-methyl-1H-benzimidazol-6-yl)-4-((4-fluorobenzyl)oxy)pyridin-2(1H)-one | 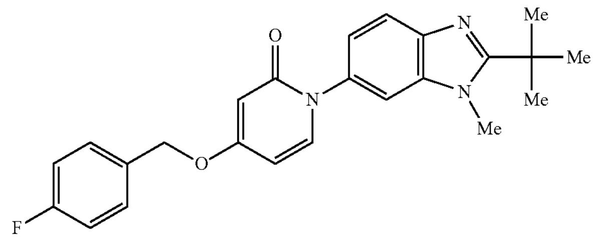 [SMILES: Cn1c(C(C)(C)C)nc2ccc(-n3ccc(OCc4ccc(F)cc4)cc3=O)cc21] | 405.9 |
| 9 | 4-(benzyloxy)-1-(2-cyclopropyl-1-methyl-1H-benzimidazol-6-yl)pyridin-2(1H)-one | 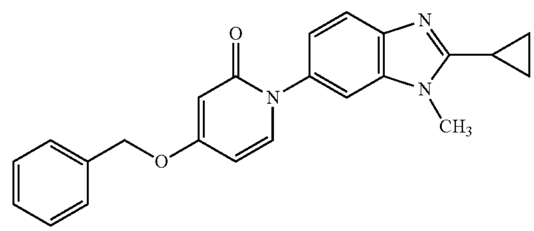 [SMILES: Cn1c(C2CC2)nc2ccc(-n3ccc(OCc4ccccc4)cc3=O)cc21] | 372.2 |
| 10 | 4-((4-chlorobenzyl)oxy)-1-(2-cyclopropyl-1-methyl-1H-benzimidazol-6-yl)pyridin-2(1H)-one | 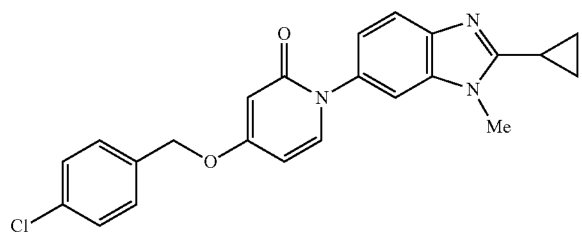 | 406.0 |
| 11 | 4-(benzyloxy)-1-(2-cyclopropyl-3-methylimidazo[1,2-a]pyridin-6-yl)pyridin-2(1H)-one | 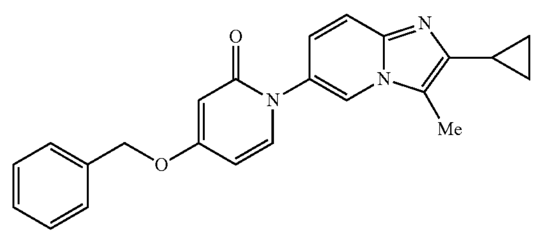 [SMILES: Cc1c(C2CC2)nc2ccc(-n3ccc(OCc4ccccc4)cc3=O)cn12] | 372.2 |
| 12 | 1-(2-cyclopropyl-1-methyl-1H-benzimidazol-6-yl)-4-((1-methyl-3-(trifluoromethyl)-1H-pyrazol-5-yl)methoxy)pyridin-2(1H)-one | 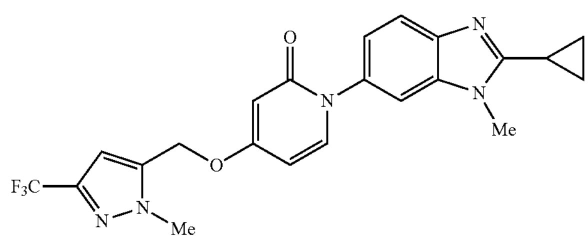 [SMILES: Cn1nc(C(F)(F)F)cc1COc1ccn(-c2ccc3nc(C4CC4)n(C)c3c2)c(=O)c1] | 444.1 |
| 13 | 4-((4-fluorobenzyl)oxy)-1-(1-methyl-2-(tetrahydrofuran-3-yl)-1H-benzimidazol-6-yl)pyridin-2(1H)-one | 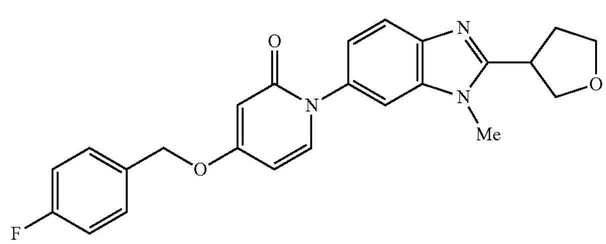 [SMILES: Cn1c(C2CCOC2)nc2ccc(-n3ccc(OCc4ccc(F)cc4)cc3=O)cc21] | 420.1 |

TABLE 1-continued

| Example | IUPAC Name | Structure | MS |
|---|---|---|---|
| 14 | 4-((4-fluorobenzyl)oxy)-1-(1-methyl-1H-benzimidazol-6-yl)pyridin-2(1H)-one | 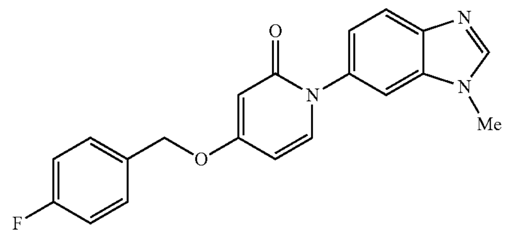 [SMILES: Cn1cnc2ccc(-n3ccc(OCc4ccc(F)cc4)cc3=O)cc21] | 350.2 |
| 15 | 1-(2-(cyclopropylmethyl)-1-methyl-1H-benzimidazol-6-yl)-4-((4-fluorobenzyl)oxy)pyridin-2(1H)-one | 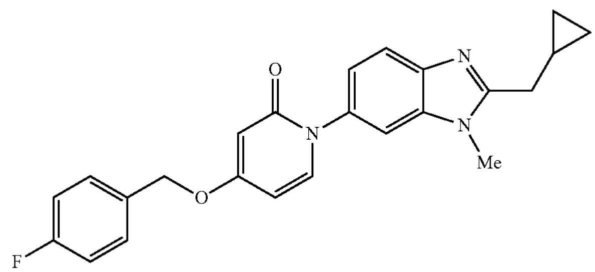 [SMILES: Cn1c(CC2CC2)nc2ccc(-n3ccc(OCc4ccc(F)cc4)cc3=O)cc21] | 404.2 |
| 16 | 3-(6-(4-((4-fluorobenzyl)oxy)-2-oxopyridin-1(2H)-yl)-1-methyl-1H-benzimidazol-2-yl)-2,2-dimethylpropanenitrile | 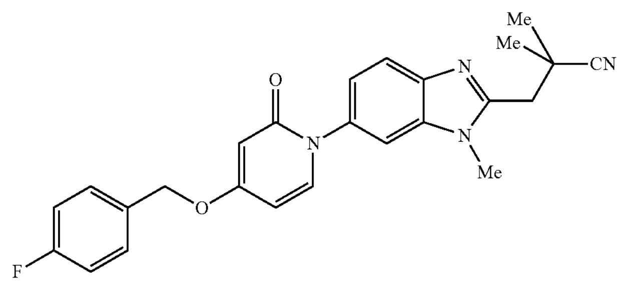 [SMILES: Cn1c(CC(C)(C)C#N)nc2ccc(-n3ccc(OCc4ccc(F)cc4)cc3=O)cc21] | 431.2 |
| 17 | 1-(2-(2,2-dimethylpropyl)-1-methyl-1H-benzimidazol-6-yl)-4-((4-fluorobenzyl)oxy)pyridin-2(1H)-one | 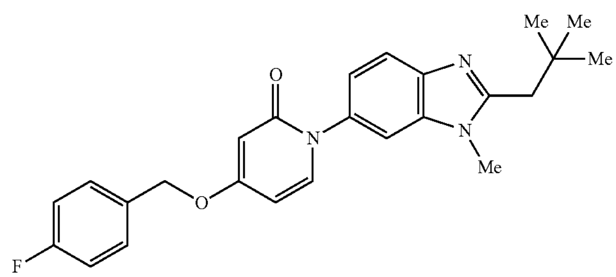 [SMILES: Cn1c(CC(C)(C)C)nc2ccc(-n3ccc(OCc4ccc(F)cc4)cc3=O)cc21] | 420.2 |
| 18 | 4-((4-chlorobenzyl)oxy)-1-(2-(2,2-dimethylpropyl)-1-methyl-1H-benzimidazol-6-yl)pyridin-2(1H)-one | 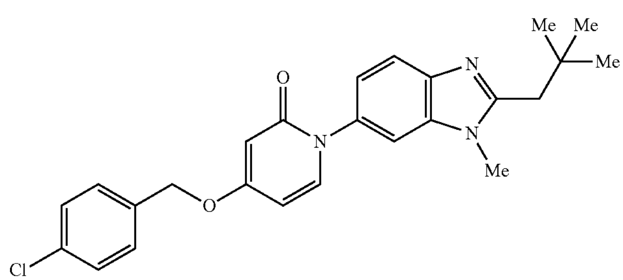 [SMILES: Cn1c(CC(C)(C)C)nc2ccc(-n3ccc(OCc4ccc(Cl)cc4)cc3=O)cc21] | 436.1 |
| 19 | 1-(2-cyclopropyl-1-propyl-1H-benzimidazol-6-yl)-4-((4-fluorobenzyl)oxy)pyridin-2(1H)-one | 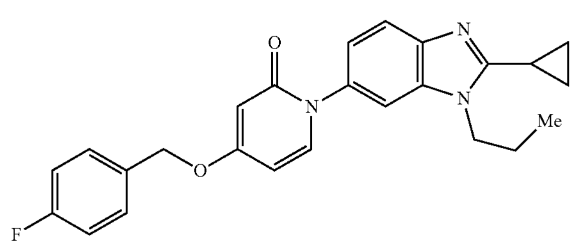 [SMILES: CCCn1c(C2CC2)nc2ccc(-n3ccc(OCc4ccc(F)cc4)cc3=O)cc21] | 418.1 |

TABLE 1-continued

| Example | IUPAC Name | Structure | MS |
|---|---|---|---|
| 20 | 1-(2-cyclopropyl-1-ethyl-1H-benzimidazol-6-yl)-4-((4-fluorobenzyl)oxy)pyridin-2(1H)-one | 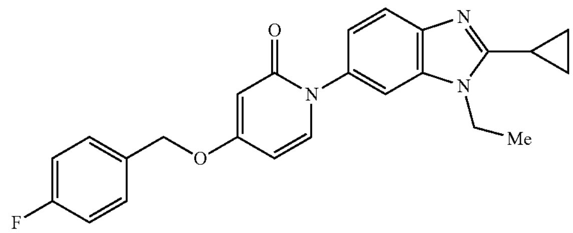 [SMILES: CCn1c(C2CC2)nc2ccc(-n3ccc(OCc4ccc(F)cc4)cc3=O)cc21] | 404.2 |
| 21 | 4-((4-chlorobenzyl)oxy)-1-(2-cyclopropyl-1-ethyl-1H-benzimidazol-6-yl)pyridin-2(1H)-one | 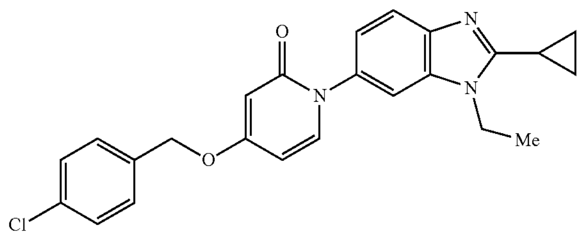 [SMILES: CCn1c(C2CC2)nc2ccc(-n3ccc(OCc4ccc(Cl)cc4)cc3=O)cc21] | 420.1 |
| 22 | 1-(2-cyclopropyl-3-methylimidazo[1,2-a]pyridin-6-yl)-4-((2,4-difluorobenzyl)oxy)pyridin-2(1H)-one | 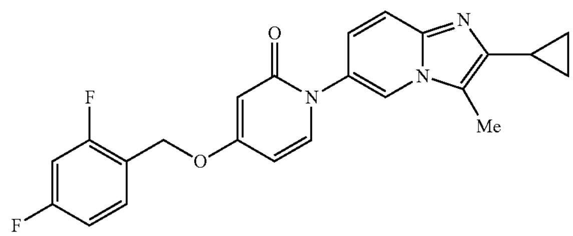 [SMILES: Cc1c(C2CC2)nc2ccc(-n3ccc(OCc4ccc(F)cc4F)cc3=O)cn12] | 408.2 |
| 23 | 1-(2-cyclobutyl-1-methyl-1H-benzimidazol-6-yl)-4-((4-fluorobenzyl)oxy)pyridin-2(1H)-one | 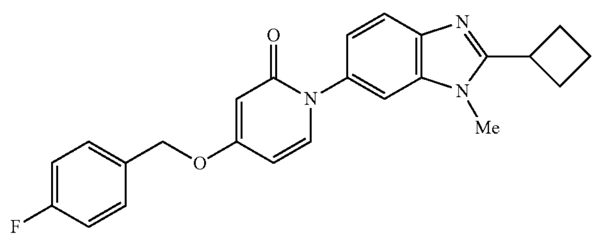 [SMILES: Cn1c(C2CCC2)nc2ccc(-n3ccc(OCc4ccc(F)cc4)cc3=O)cc21] | 404.0 |
| 24 | 1-(2-(difluoromethyl)-1-methyl-1H-benzimidazol-6-yl)-4-((4-fluorobenzyl)oxy)pyridin-2(1H)-one | 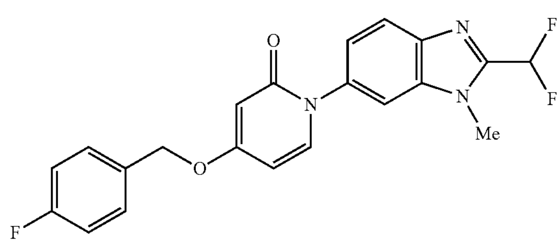 [SMILES: Cn1c(C(F)F)nc2ccc(-n3ccc(OCc4ccc(F)cc4)cc3=O)cc21] | 399.8 |
| 25 | 4-((4-chlorobenzyl)oxy)-1-(2,3-dimethylimidazo[1,2-a]pyridin-6-yl)pyridin-2(1H)-one | 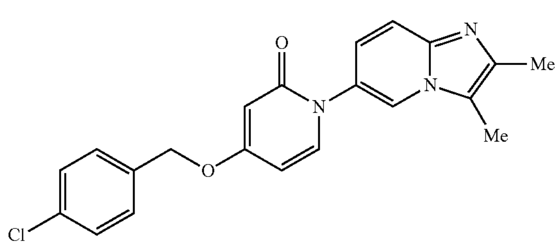 [SMILES: Cc1nc2ccc(-n3ccc(OCc4ccc(Cl)cc4)cc3=O)cn2c1C] | 379.8 |

TABLE 1-continued

| Example | IUPAC Name | Structure | MS |
|---|---|---|---|
| 26 | 1-(2-cyclopropyl-1-methyl-1H-benzimidazol-6-yl)-4-(pyridin-2-ylmethoxy)pyridin-2(1H)-one | 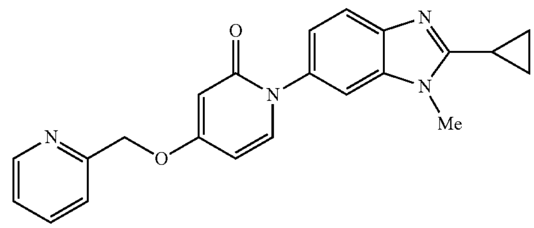 [SMILES: Cn1c(C2CC2)nc2ccc(-n3ccc(OCc4ccccn4)cc3=O)cc21] | 373.1 |
| 27 | 4-((4-chlorobenzyl)oxy)-1-(2-cyclopropyl-1-propyl-1H-benzimidazol-6-yl)pyridin-2(1H)-one | 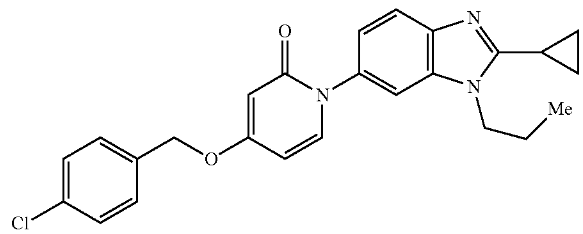 [SMILES: CCCn1c(C2CC2)nc2ccc(-n3ccc(OCc4ccc(Cl)cc4)cc3=O)cc21] | 434.2 |
| 28 | 1-(2-cyclopropyl-3,8-dimethylimidazo[1,2-a]pyridin-6-yl)-4-((4-fluorobenzyl)oxy)pyridin-2(1H)-one | 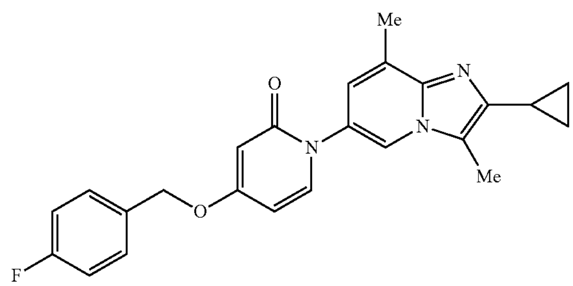 [SMILES: Cc1cc(-n2ccc(OCc3ccc(F)cc3)cc2=O)cn2c(C)c(C3CC3)nc12] | 404.2 |
| 29 | 4-((4-chlorobenzyl)oxy)-1-(2-(methoxymethyl)-1-methyl-1H-benzimidazol-6-yl)pyridin-2(1H)-one | 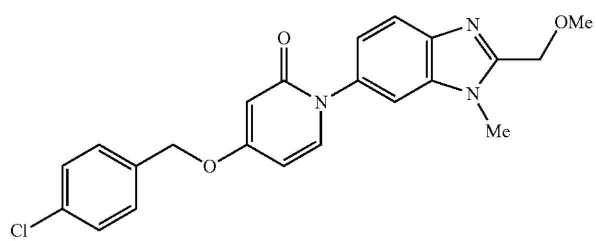 [SMILES: COCc1nc2ccc(-n3ccc(OCc4ccc(Cl)cc4)cc3=O)cc2n1C] | 410.1 |
| 30 | 4-((4-chlorobenzyl)oxy)-1-(2-isopropyl-1-methyl-1H-benzimidazol-6-yl)pyridin-2(1H)-one | 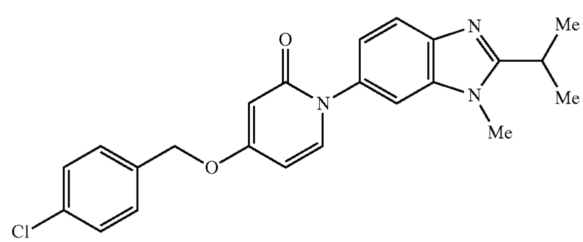 [SMILES: CC(C)c1nc2ccc(-n3ccc(OCc4ccc(Cl)cc4)cc3=O)cc2n1C] | 408.2 |
| 31 | 1-(2-(cyclopropylcarbonyl)-1-methyl-1H-benzimidazol-6-yl)-4-((4-fluorobenzyl)oxy)pyridin-2(1H)-one | 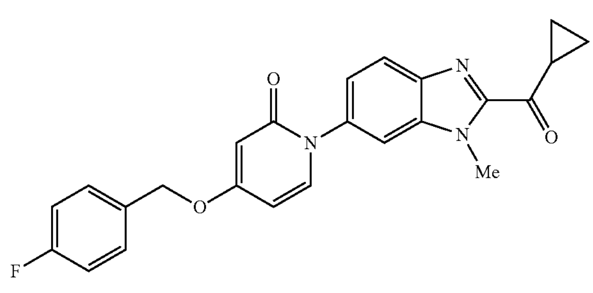 [SMILES: Cn1c(C(=O)C2CC2)nc2ccc(-n3ccc(OCc4ccc(F)cc4)cc3=O)cc21] | 418.1 |

TABLE 1-continued

| Example | IUPAC Name | Structure | MS |
|---|---|---|---|
| 32 | 4-((5-chloropyridin-2-yl)methoxy)-1-(2-cyclopropyl-3-methylimidazo[1,2-a]pyridin-6-yl)pyridin-2(1H)-one | 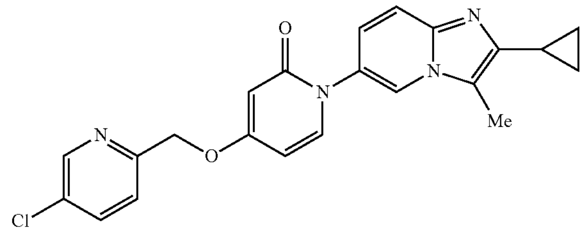 [SMILES: Cc1c(C2CC2)nc2ccc(-n3ccc(OCc4ccc(Cl)cn4)cc3=O)cn12] | 407.1 |
| 33 | 1-(2-(cyclopropyl(methoxy)methyl)-1-methyl-1H-benzimidazol-6-yl)-4-((4-fluorobenzyl)oxy)pyridin-2(1H)-one | 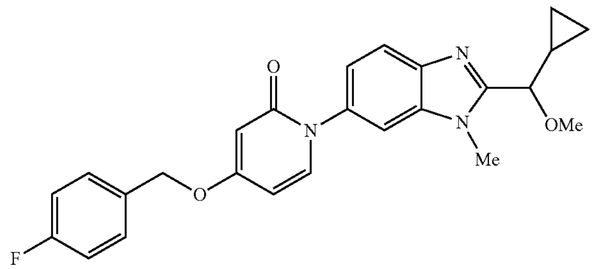 [SMILES: COC(c1nc2ccc(-n3ccc(OCc4ccc(F)cc4)cc3=O)cc2n1C)C1CC1] | 434.2 |
| 34 | 1-(6-(4-((4-fluorobenzyl)oxy)-2-oxopyridin-1(2H)-yl)-1-methyl-1H-benzimidazol-2-yl)cyclopropanecarbonitrile | 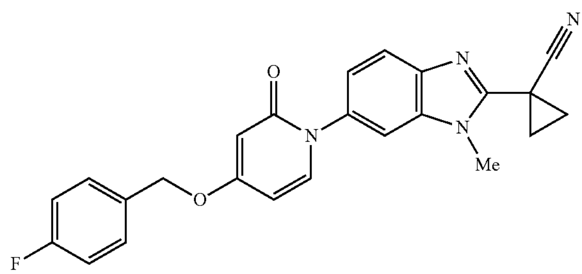 [SMILES: Cn1c(C2(C#N)CC2)nc2ccc(-n3ccc(OCc4ccc(F)cc4)cc3=O)cc21] | 415.1 |
| 35 | 4-((4-fluorobenzyl)oxy)-1-(1-methyl-2-(tetrahydrofuran-2-yl)-1H-benzimidazol-6-yl)pyridin-2(1H)-one | 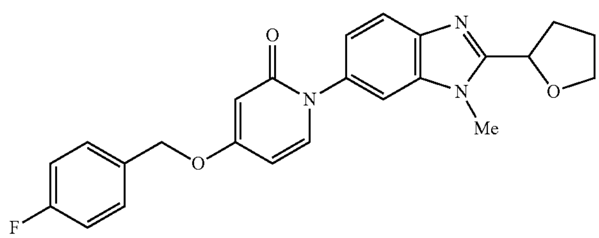 | 420.2 |
| 36 | 1-(2-cyclopropyl-1-methyl-1H-benzimidazol-6-yl)-4-(1-phenylethoxy)pyridin-2(1H)-one | 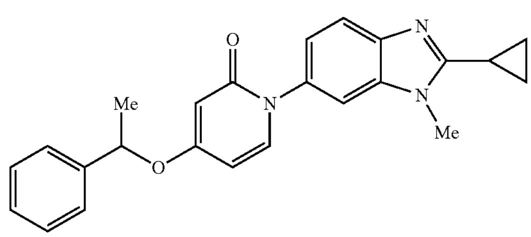 [SMILES: CC(Oc1ccn(-c2ccc3nc(C4CC4)n(C)c3c2)c(=O)c1)c1ccccc1] | 386.2 |
| 37 | 4-((4-chlorobenzyl)oxy)-1-(2-isobutyl-1-methyl-1H-benzimidazol-6-yl)pyridin-2(1H)-one | 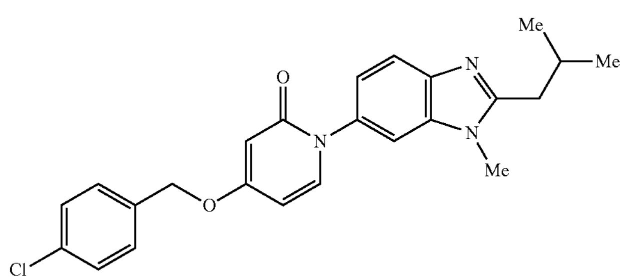 [SMILES: CC(C)Cc1nc2ccc(-n3ccc(OCc4ccc(Cl)cc4)cc3=O)cc2n1C] | 422.2 |

TABLE 1-continued

| Example | IUPAC Name | Structure | MS |
|---|---|---|---|
| 38 | 1-(2-(2,2-difluorocyclopropyl)-1-methyl-1H-benzimidazol-6-yl)-4-((4-fluorobenzyl)oxy)pyridin-2(1H)-one | 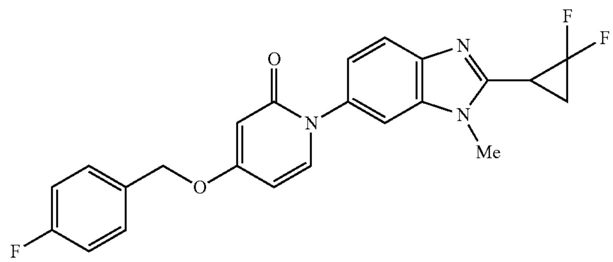 [SMILES: Cn1c(C2CC2(F)F)nc2ccc(-n3ccc(OCc4ccc(F)cc4)cc3=O)cc21] | 426.1 |
| 39 | 1-(2-cyclopentyl-1-methyl-1H-benzimidazol-6-yl)-4-((4-fluorobenzyl)oxy)pyridin-2(1H)-one | 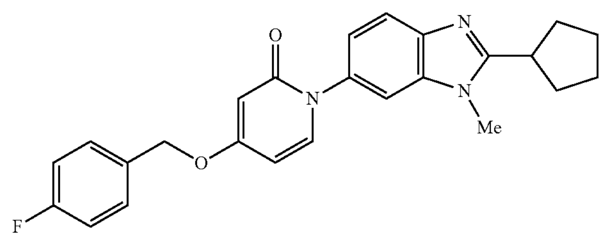 [SMILES: Cn1c(C2CCCC2)nc2ccc(-n3ccc(OCc4ccc(F)cc4)cc3=O)cc21] | 418.1 |
| 40 | 1-(2-cyclopropyl-1-methyl-1H-benzimidazol-6-yl)-4-(2,3-dihydro-1H-inden-1-yloxy)pyridin-2(1H)-one | 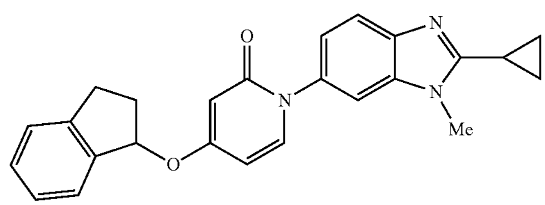 [SMILES: Cn1c(C2CC2)nc2ccc(-n3ccc(OC4CCc5ccccc54)cc3=O)cc21] | 398.2 |
| 41 | 4-((4-fluorobenzyl)oxy)-1-(2-(methoxymethyl)-3-methylimidazo[1,2-a]pyridin-6-yl)pyridin-2(1H)-one | 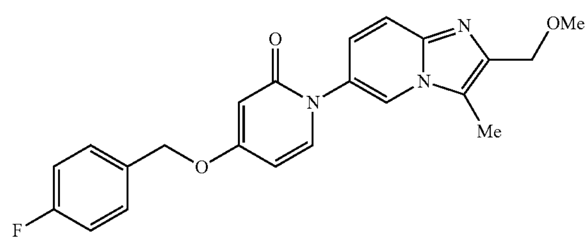 [SMILES: COCc1nc2ccc(-n3ccc(OCc4ccc(F)cc4)cc3=O)cn2c1C] | 394.0 |
| 42 | 4-((4-fluorobenzyl)oxy)-1-(3-methyl-2-(tetrahydrofuran-3-yl)imidazo[1,2-a]pyridin-6-yl)pyridin-2(1H)-one | 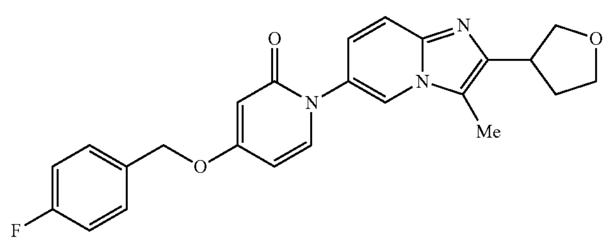 [SMILES: Cc1c(C2CCOC2)nc2ccc(-n3ccc(OCc4ccc(F)cc4)cc3=O)cn12] | 420.0 |
| 43 | 4-((4-fluorobenzyl)oxy)-1-(1-methyl-2-(2-methylcyclopropyl)-1H-benzimidazol-6-yl)pyridin-2(1H)-one | 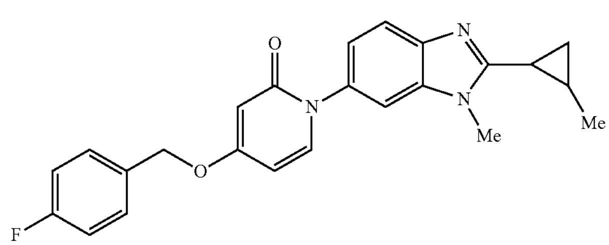 [SMILES: CC1CC1c1nc2ccc(-n3ccc(OCc4ccc(F)cc4)cc3=O)cc2n1C] | 404.2 |

TABLE 1-continued

| Example | IUPAC Name | Structure | MS |
|---|---|---|---|
| 44 | 4-((4-fluorobenzyl)oxy)-1-(1-methyl-2-(trichloromethyl)-1H-benzimidazol-6-yl)pyridin-2(1H)-one | 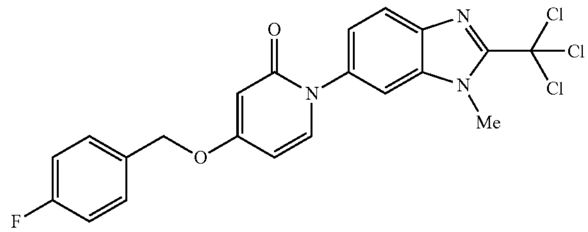 [SMILES: Cn1c(C(Cl)(Cl)Cl)nc2ccc(-n3ccc(OCc4ccc(F)cc4)cc3=O)cc21] | 466.0 |
| 45 | 4-((4-chlorobenzyl)oxy)-1-(1-methyl-2-(trifluoromethyl)-1H-benzimidazol-6-yl)pyridin-2(1H)-one | 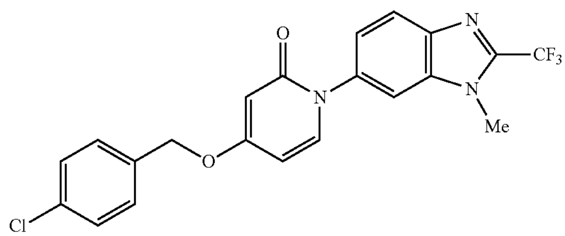 [SMILES: Cn1c(C(F)(F)F)nc2ccc(-n3ccc(OCc4ccc(Cl)cc4)cc3=O)cc21] | 434.1 |
| 46 | 4-((4-chlorobenzyl)oxy)-1-(2-(2-methoxyethyl)-1-methyl-1H-benzimidazol-6-yl)pyridin-2(1H)-one | 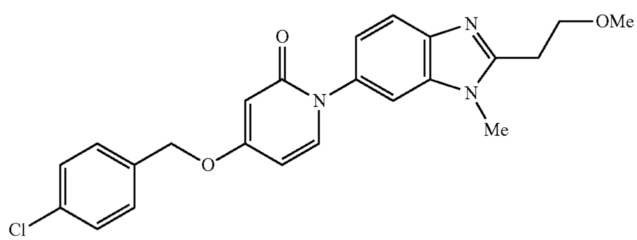 [SMILES: COCCc1nc2ccc(-n3ccc(OCc4ccc(Cl)cc4)cc3=O)cc2n1C] | 424.1 |
| 47 | 4-(benzyloxy)-1-(2-ethyl-1-methyl-1H-benzimidazol-6-yl)pyridin-2(1H)-one | 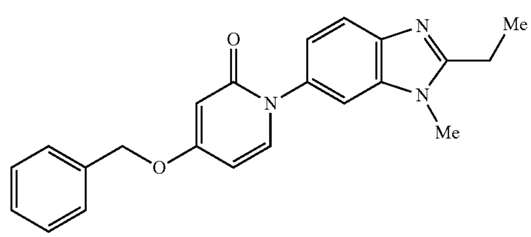 [SMILES: CCc1nc2ccc(-n3ccc(OCc4ccccc4)cc3=O)cc2n1C] | 360.4 |
| 48 | 4-((4-fluorobenzyl)oxy)-1-(1-methyl-2-(2,2,2-trifluoroethyl)-1H-benzimidazol-6-yl)pyridin-2(1H)-one | 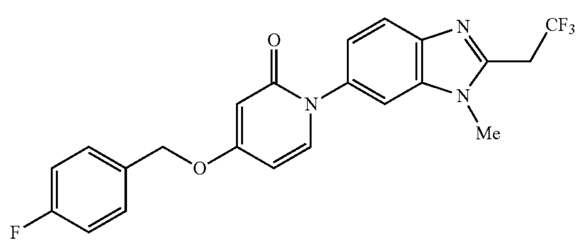 [SMILES: Cn1c(CC(F)(F)F)nc2ccc(-n3ccc(OCc4ccc(F)cc4)cc3=O)cc21] | 432.2 |
| 49 | 4-[(5-chlorothiophen-2-yl)methoxy]-1-(2-ethyl-1-methyl-1H-benzimidazol-6-yl)pyridin-2(1H)-one | 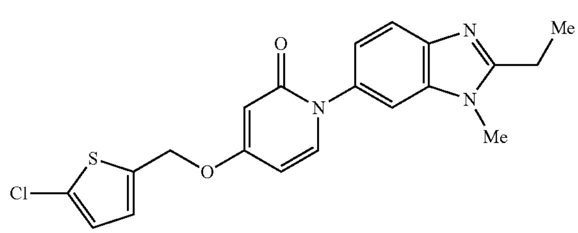 [SMILES: CCc1nc2ccc(-n3ccc(OCc4ccc(Cl)s4)cc3=O)cc2n1C] | 400.3 |

TABLE 1-continued

| Example | IUPAC Name | Structure | MS |
|---|---|---|---|
| 50 | 6-(4-((4-fluorobenzyl)oxy)-2-oxopyridin-1(2H)-yl)-N-(2-hydroxyethyl)-1-methyl-1H-benzoimidazole-2-carboxamide | 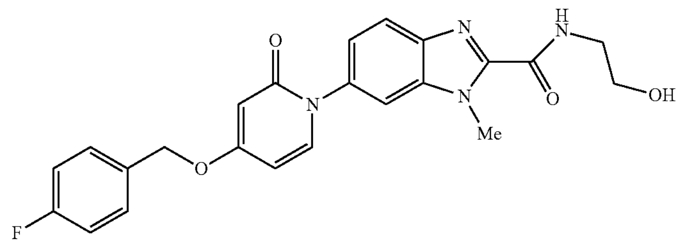 [SMILES: Cn1c(C(=O)NCCO)nc2ccc(-n3ccc(OCc4ccc(F)cc4)cc3=O)cc21] | 437.2 |
| 51 | 4-[(5-chlorothiophen-3-yl)methoxy]-1-(2-ethyl-1-methyl-1H-benzimidazol-6-yl)pyridin-2(1H)-one | 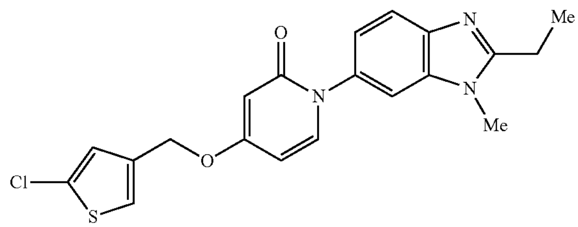 [SMILES: CCc1nc2ccc(-n3ccc(OCc4csc(Cl)c4)cc3=O)cc2n1C] | 400.3 |
| 52 | 4-((4-fluorobenzyl)oxy)-1-(2-(2-fluoropropyl)-1-methyl-1H-benzimidazol-6-yl)pyridin-2(1H)-one | 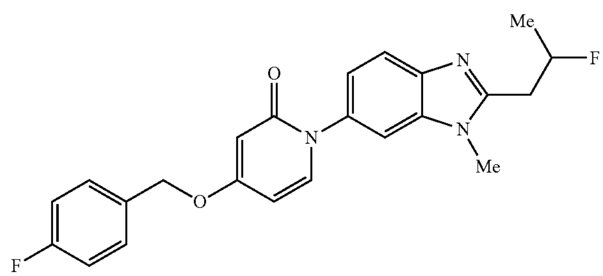 [SMILES: CC(F)Cc1nc2ccc(-n3ccc(OCc4ccc(F)cc4)cc3=O)cc2n1C] | 410.2 |
| 53 | 4-((4-fluorobenzyl)oxy)-1-(1-methyl-2-(4-methyl-1,3-thiazol-5-yl)-1H-benzimidazol-6-yl)pyridin-2(1H)-one | 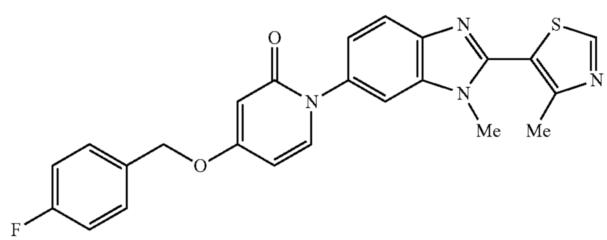 [SMILES: Cc1ncsc1-c1nc2ccc(-n3ccc(OCc4ccc(F)cc4)cc3=O)cc2n1C] | 447.3 |
| 54 | 6-(4-((4-fluorobenzyl)oxy)-2-oxopyridin-1(2H)-yl)-3-methylimidazo[1,2-a]pyridine-2-carbonitrile | 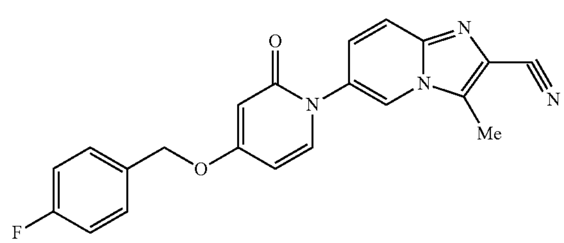 [SMILES: Cc1c(C#N)nc2ccc(-n3ccc(OCc4ccc(F)cc4)cc3=O)cn12] | 420.0 |
| 55 | 5-((4-chlorobenzyl)oxy)-2-(2-cyclopropyl-3-methylimidazo[1,2-a]pyridin-6-yl)pyridazine-3(2H)-one | 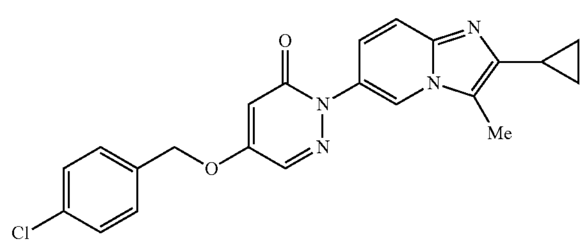 [SMILES: Cc1c(C2CC2)nc2ccc(-n3ncc(OCc4ccc(Cl)cc4)cc3=O)cn12] | 407.2 |

TABLE 1-continued

| Example | IUPAC Name | Structure | MS |
|---------|------------|-----------|-----|
| 56 | 1-(2-cyclopropyl-1-methyl-1H-benzimidazol-6-yl)-4-((4-methyl-2-thienyl)methoxy)pyridin-2(1H)-one | 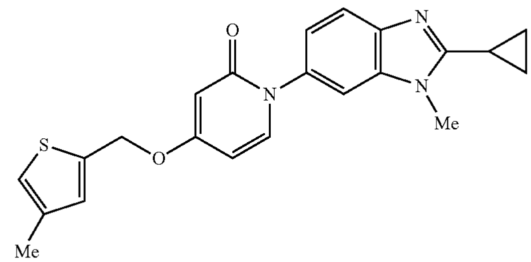 [SMILES: Cc1csc(COc2ccn(-c3ccc4nc(C5CC5)n(C)c4c3)c(=O)c2)c1] | 392.0 |
| 57 | 1-(2-cyclopropyl-1-methyl-1H-benzimidazol-6-yl)-4-((5-methyl-2-thienyl)methoxy)pyridin-2(1H)-one | 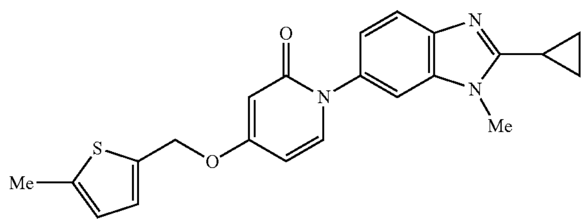 [SMILES: Cc1ccc(COc2ccn(-c3ccc4nc(C5CC5)n(C)c4c3)c(=O)c2)s1] | 392.0 |
| 58 | 4-((4-fluorobenzyl)oxy)-1-(1-methyl-2-(1-(trifluoromethyl)cyclopropyl)-1H-benzimidazol-6-yl)pyridin-2(1H)-one | 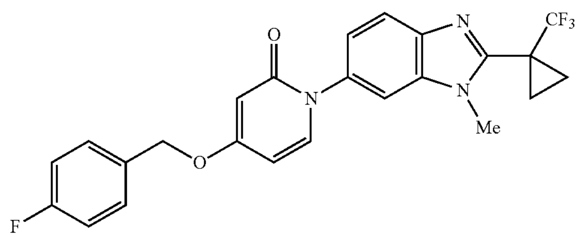 [SMILES: Cn1c(C2(C(F)(F)F)CC2)nc2ccc(-n3ccc(OCc4ccc(F)cc4)cc3=O)cc21] | 458.2 |
| 59 | 4-((4-fluorobenzyl)oxy)-1-(1-methyl-2-(3,3,3-trifluoropropyl)-1H-benzimidazol-6-yl)pyridin-2(1H)-one | 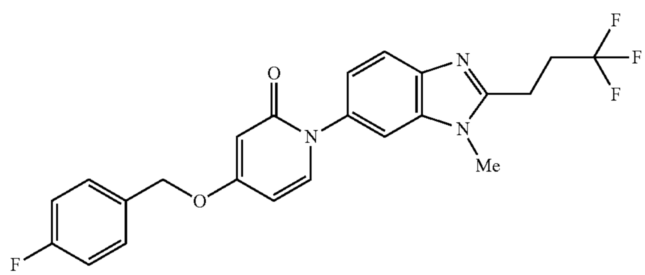 [SMILES: Cn1c(CCC(F)(F)F)nc2ccc(-n3ccc(OCc4ccc(F)cc4)cc3=O)cc21] | 446.2 |
| 60 | 1-(2-(3,3-difluorocyclobutyl)-1-methyl-1H-benzimidazol-6-yl)-4-((4-fluorobenzyl)oxy)pyridin-2(1H)-one | 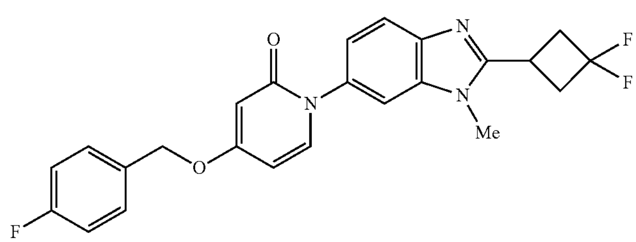 [SMILES: Cn1c(C2CC(F)(F)C2)nc2ccc(-n3ccc(OCc4ccc(F)cc4)cc3=O)cc21] | 440.2 |
| 61 | 1-(2-sec-butyl-1-methyl-1H-benzimidazol-6-yl)-4-((4-((4 fluorobenzyl)oxy)pyridin-2(1H)-one | 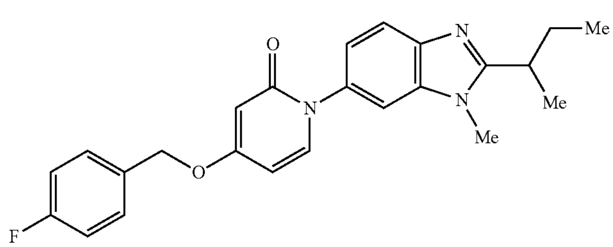 [SMILES: CCC(C)c1nc2ccc(-n3ccc(OCc4ccc(F)cc4)cc3=O)cc2n1C] | 406.2 |

TABLE 1-continued

| Example | IUPAC Name | Structure | MS |
|---|---|---|---|
| 62 | 4-((4-chlorobenzyl)oxy)-1-(2-(2,2-difluorocyclopropyl)-1-methyl-1H-benzimidazol-6-yl)pyridin-2(1H)-one | 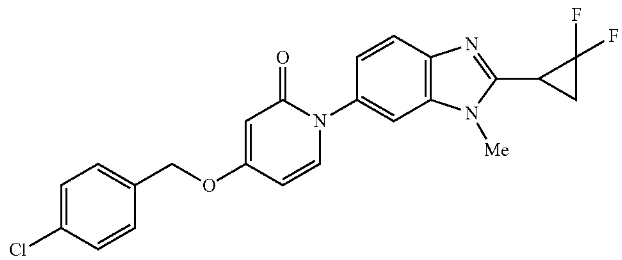 [SMILES: Cn1c(C2CC2(F)F)nc2ccc(-n3ccc(OCc4ccc(Cl)cc4)cc3=O)cc21] | 442.1 |
| 63 | 1-(2-ethyl-1-methyl-1H-benzimidazol-6-yl)-4-((4-fluorobenzyl)oxy)pyridin-2(1H)-one | 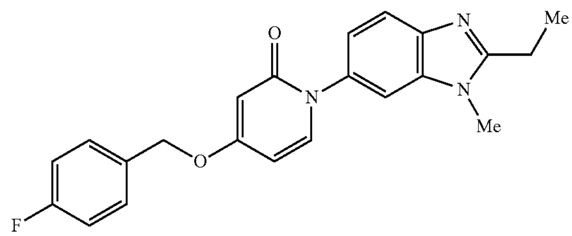 [SMILES: CCc1nc2ccc(-n3ccc(OCc4ccc(F)cc4)cc3=O)cc2n1C] | 378.2 |
| 64 | 4-((4-fluorobenzyl)oxy)-1-(1-methyl-2-propyl-1H-benzimidazol-6-yl)pyridin-2(1H)-one | 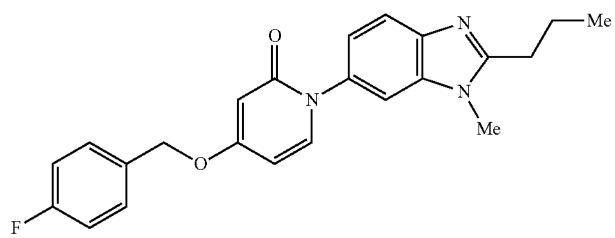 [SMILES: CCCc1nc2ccc(-n3ccc(OCc4ccc(F)cc4)cc3=O)cc2n1C] | 392.2 |
| 65 | 1-(2-(4,5-dihydro-1,3-oxazol-2-yl)-1-methyl-1H-benzimidazol-6-yl)-4-((4-fluorobenzyl)oxy)pyridin-2(1H)-one | 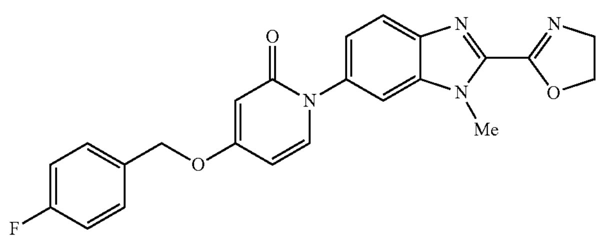 [SMILES: Cn1c(C2=NCCO2)nc2ccc(-n3ccc(OCc4ccc(F)cc4)cc3=O)cc21] | 419.2 |
| 66 | 1-(2-acetyl-1-methyl-1H-benzimidazol-6-yl)-4-((4-fluorobenzyl)oxy)pyridin-2(1H)-one | 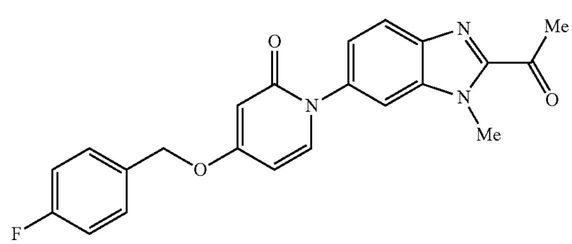 [SMILES: CC(=O)c1nc2ccc(-n3ccc(OCc4ccc(F)cc4)cc3=O)cc2n1C] | 392.2 |
| 67 | 4-(benzyloxy)-1-(2-cyclopropyl-3-methylimidazo[1,2-a]pyridin-6-yl)pyridin-2(1H)-one hydrochloride | 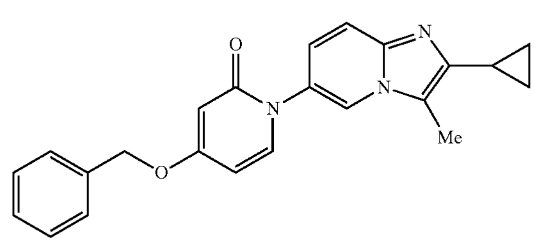 [SMILES: Cc1c(C2CC2)nc2ccc(-n3ccc(OCc4ccccc4)cc3=O)cn12] | 372.2 |

TABLE 1-continued

| Example | IUPAC Name | Structure | MS |
|---|---|---|---|
| 68 | 4-((4-fluorobenzyl)oxy)-1-(1-methyl-2-((2,2,2-trifluoroethoxy)methyl)-1H-benzimidazol-6-yl)pyridin-2(1H)-one | 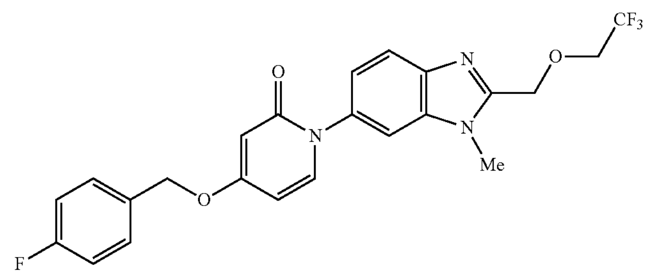 [SMILES: Cn1c(COCC(F)(F)F)nc2ccc(-n3ccc(OCc4ccc(F)cc4)cc3=O)cc21] | 462.2 |
| 69 | 4-((4-fluorobenzyl)oxy)-1-(1-methyl-2-(1,3-oxazol-5-yl)-1H-benzimidazol-6-yl)pyridin-2(1H)-one | 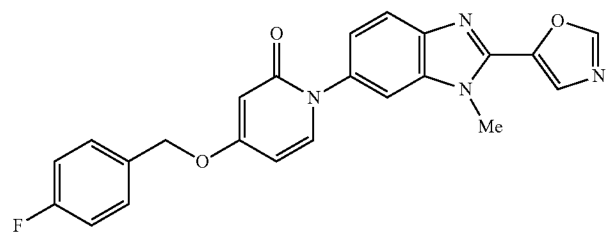 [SMILES: Cn1c(-c2cnco2)nc2ccc(-n3ccc(OCc4ccc(F)cc4)cc3=O)cc21] | 417.2 |
| 70 | 4-((4-chlorobenzyl)oxy)-1-(2-cyclopropyl-3-methylimidazo[1,2-a]pyridin-6-yl)pyrimidin-2(1H)-one | 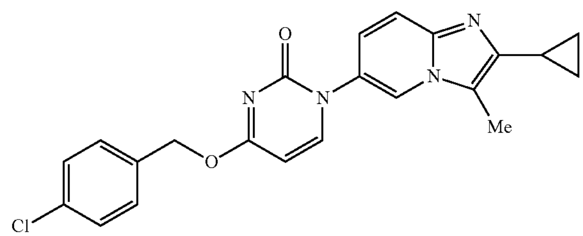 [SMILES: Cc1c(C2CC2)nc2ccc(-n3ccc(OCc4ccc(Cl)cc4)nc3=O)cn12] | 407.2 |
| 71 | 1-(2-cyclopropyl-1-methyl-1H-benzimidazol-6-yl)-4-((2-fluorobenzyl)oxy)pyridin-2(1H)-one | 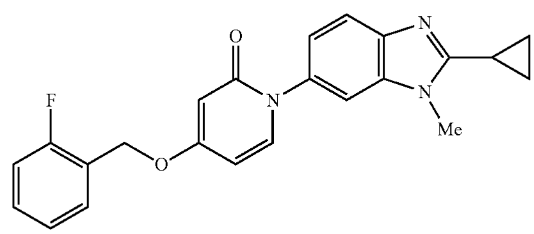 [SMILES: Cn1c(C2CC2)nc2ccc(-n3ccc(OCc4ccccc4F)cc3=O)cc21] | 390.0 |
| 72 | 1-(2-cyclopropyl-1-methyl-1H-benzimidazol-6-yl)-4-((3-fluorobenzyl)oxy)pyridin-2(1H)-one | 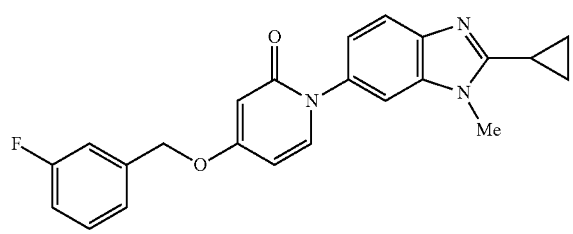 [SMILES: Cn1c(C2CC2)nc2ccc(-n3ccc(OCc4cccc(F)c4)cc3=O)cc21] | 390.0 |
| 73 | (6-(4-((4-fluorobenzyl)oxy)-2-oxopyridin-1(2H)-yl)-3-methylimidazo[1,2-a]pyridin-2-yl)acetonitrile | 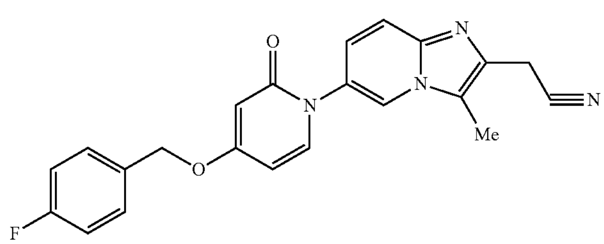 [SMILES: Cc1c(CC#N)nc2ccc(-n3ccc(OCc4ccc(F)cc4)cc3=O)cn12] | 389.4 |

TABLE 1-continued

| Example | IUPAC Name | Structure | MS |
|---------|------------|-----------|-----|
| 74 | methyl (1RS,2RS)-2-(6-(4-((4-chlorobenzyl)oxy)-2-oxopyridin-1(2H)-yl)-1-methyl-1H-benzimidazol-2-yl)cyclopropanecarboxylate | 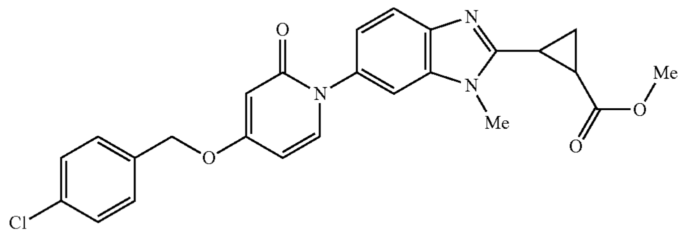 [SMILES: COC(=O)C1CC1c1nc2ccc(-n3ccc(OCc4ccc(Cl)cc4)cc3=O)cc2n1C] | 464.2 |
| 75 | 1-(2-cyclopropyl-1-methyl-1H-benzimidazol-6-yl)-4-(3-thienylmethoxy)pyridin-2(1H)-one | 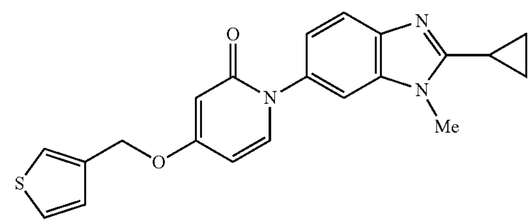 [SMILES: Cn1c(C2CC2)nc2ccc(-n3ccc(OCc4ccsc4)cc3=O)cc21] | 378.2 |
| 76 | 6-(4-((4-fluorobenzyl)oxy)-2-oxopyridin-1(2H)-yl)-N,N,3-trimethylimidazo[1,2-a]pyridine-2-carboxamide | 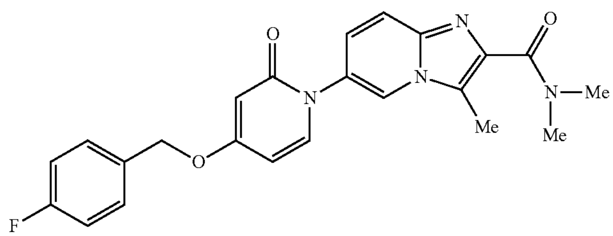 [SMILES: Cc1c(C(=O)N(C)C)nc2ccc(-n3ccc(OCc4ccc(F)cc4)cc3=O)cn12] | 421.4 |
| 77 | 1-(2-cyclopropyl-1-methyl-1H-benzimidazol-6-yl)-4-((4-methoxybenzyl)oxy)pyridin-2(1H)-one | 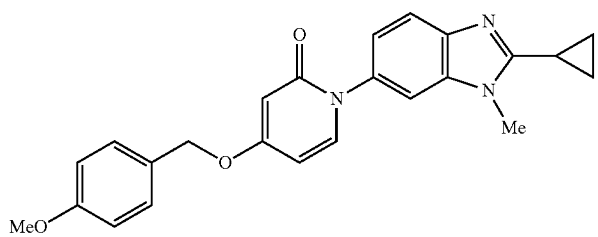 [SMILES: COc1ccc(COc2ccn(-c3ccc4nc(C5CC5)n(C)c4c3)c(=O)c2)cc1] | 402.2 |
| 78 | 4-((4-fluorobenzyl)oxy)-1-(2-(fluoromethyl)-3-methylimidazo[1,2-a]pyridin-6-yl)pyridin-2(1H)-one | 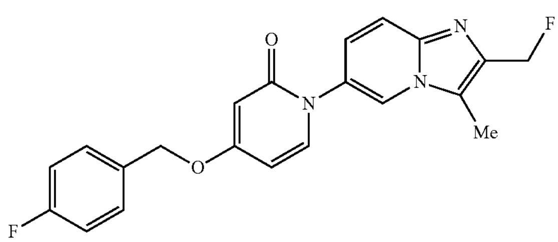 [SMILES: Cc1c(CF)nc2ccc(-n3ccc(OCc4ccc(F)cc4)cc3=O)cn12] | 382.0 |
| 79 | 1-(2-cyclopropyl-1-methyl-1H-benzimidazol-6-yl)-4-(1,3-thiazol-2-ylmethoxy)pyridin-2(1H)-one | 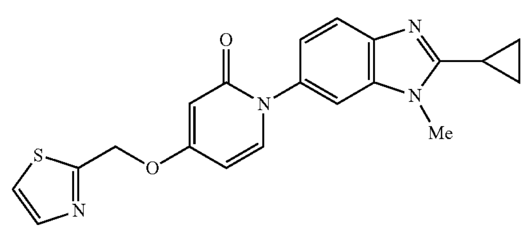 [SMILES: Cn1c(C2CC2)nc2ccc(-n3ccc(OCc4nccs4)cc3=O)cc21] | 379.4 |

TABLE 1-continued

| Example | IUPAC Name | Structure | MS |
|---------|-----------|-----------|-----|
| 80 | 4-((4-chlorobenzyl)oxy)-1-(2-((1RS,2SR)-2-(2-hydroxypropan-2-yl)cyclopropyl)-1-methyl-1H-benzimidazol-6-yl)pyridin-2(1H)-one | 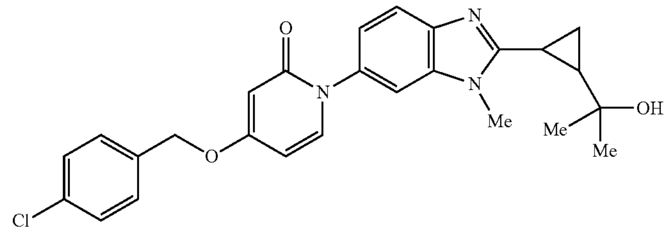 [SMILES: Cn1c(C2CC2C(C)(C)O)nc2ccc(-n3ccc(OCc4ccc(Cl)cc4)cc3=O)cc21] | 464.2 |
| 81 | 4-((4-chlorobenzyl)oxy)-1-(2-((1RS,2RS)-2-(2-hydroxypropan-2-yl)cyclopropyl)-1-methyl-1H-benzimidazol-6-yl)pyridin-2(1H)-one | 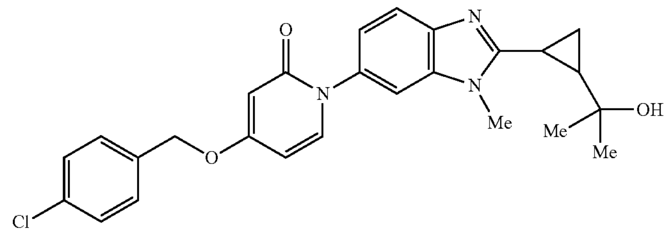 [SMILES: Cn1c(C2CC2C(C)(C)O)nc2ccc(-n3ccc(OCc4ccc(Cl)cc4)cc3=O)cc21] | 464.2 |
| 82 | (1RS,2RS)-2-(6-(4-((4-chlorobenzyl)oxy)-2-oxopyridin-1(2H)-yl)-1-methyl-1H-benzimidazol-2-yl)cyclopropanecarboxylic acid | 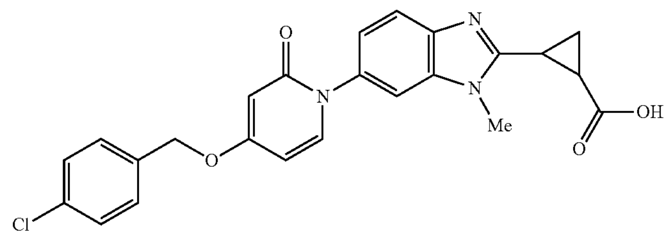 [SMILES: Cn1c(C2CC2C(=O)O)nc2ccc(-n3ccc(OCc4ccc(Cl)cc4)cc3=O)cc21] | 450.2 |
| 83 | (1RS,2RS)-2-(6-(4-((4-chlorobenzyl)oxy)-2-oxopyridin-1(2H)-yl)-1-methyl-1H-benzimidazol-2-yl)cyclopropanecarboxamide | 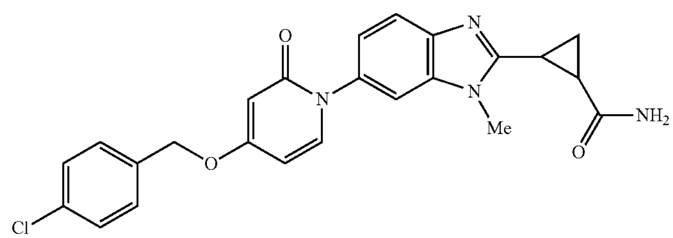 [SMILES: Cn1c(C2CC2C(N)=O)nc2ccc(-n3ccc(OCc4ccc(Cl)cc4)cc3=O)cc21] | 449.2 |
| 84 | 4-((4-chlorobenzyl)oxy)-1-(2-cyclopropyl-4-fluoro-1-methyl-1H-benzimidazol-6-yl)pyridin-2(1H)-one | 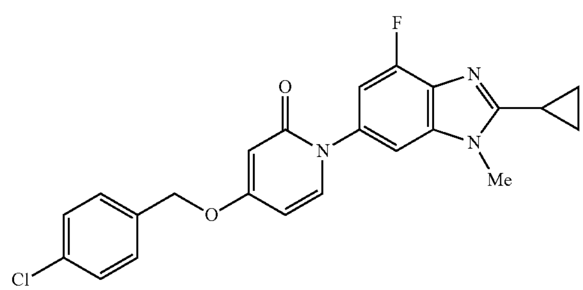 [SMILES: Cn1c(C2CC2)nc2c(F)cc(-n3ccc(OCc4ccc(Cl)cc4)cc3=O)cc21] | 424.1 |
| 85 | 1-(4-tert-butoxy-2-cyclopropyl-1-methyl-1H-benzimidazol-6-yl)-4-((4-chlorobenzyl)oxy)pyridin-2(1H)-one | 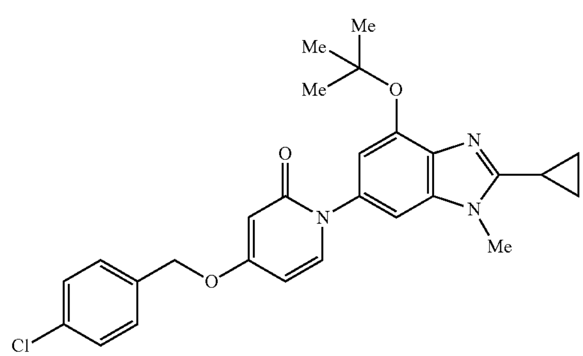 [SMILES: Cn1c(C2CC2)nc2c(OC(C)(C)C)cc(-n3ccc(OCc4ccc(Cl)cc4)cc3=O)cc21] | 478.1 |

TABLE 1-continued

| Example | IUPAC Name | Structure | MS |
|---------|-----------|-----------|-----|
| 86 | (1RS,2RS)-2-(6-(4-((4-chlorobenzyl)oxy)-2-oxopyridin-1(2H)-yl)-1-methyl-1H-benzimidazol-2-yl)cyclopropanecarbonitrile | 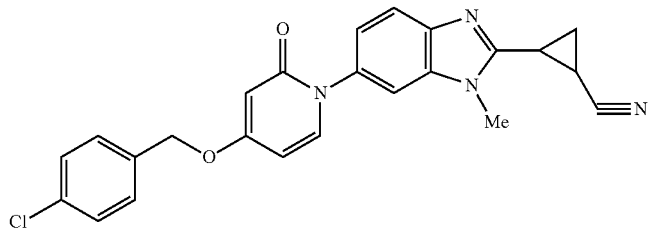 [SMILES: Cn1c(C2CC2C#N)nc2ccc(-n3ccc(OCc4ccc(Cl)cc4)cc3=O)cc21] | 478.1 |
| 87 | 4-((4-fluorobenzyl)oxy)-1-(1-methyl-2-(3-methyl-1,2-oxazol-5-yl)-1H-benzimidazol-6-yl)pyridin-2(1H)-one | 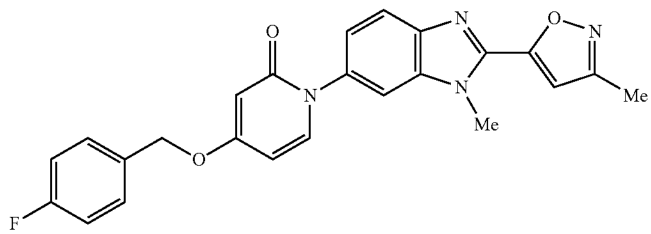 [SMILES: Cc1cc(-c2nc3ccc(-n4ccc(OCc5ccc(F)cc5)cc4=O)cc3n2C)on1] | 431.2 |
| 88 | 1-(2-(1,5-dimethyl-1H-pyrazol-3-yl)-1-methyl-1H-benzimidazol-6-yl)-4-((4-fluorobenzyl)oxy)pyridin-2(1H)-one | 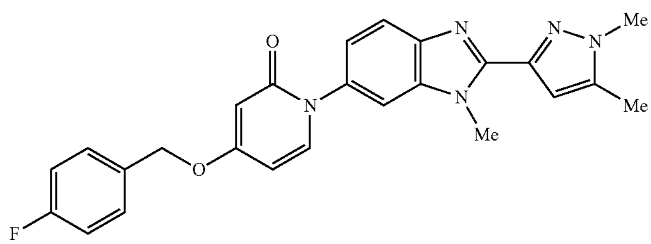 [SMILES: Cc1cc(-c2nc3ccc(-n4ccc(OCc5ccc(F)cc5)cc4=O)cc3n2C)nn1C] | 444.2 |
| 89 | 4-((4-fluorobenzyl)oxy)-1-(1-methyl-2-(4-methyl-1,3-oxazol-5-yl)-1H-benzimidazol-6-yl)pyridin-2(1H)-one | 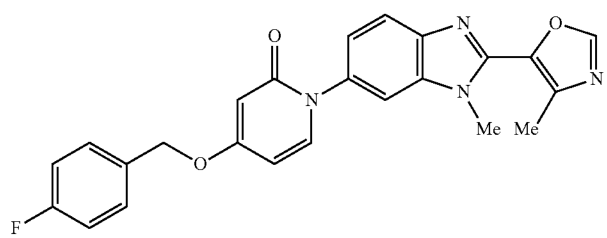 [SMILES: Cc1ncoc1-c1nc2ccc(-n3ccc(OCc4ccc(F)cc4)cc3=O)cc2n1C] | 431.2 |
| 90 | 4-((4-chlorobenzyl)oxy)-1-(1-methyl-2-(2-methylcyclopropyl)-1H-benzimidazol-6-yl)pyridin-2(1H)-one | 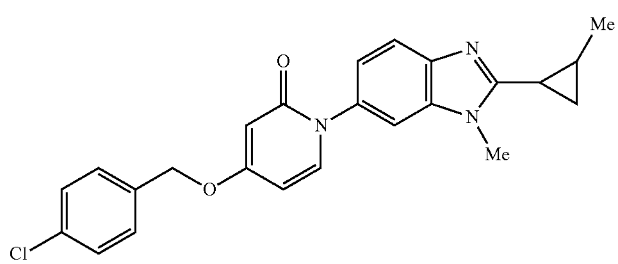 [SMILES: CC1CC1c1nc2ccc(-n3ccc(OCc4ccc(Cl)cc4)cc3=O)cc2n1C] | 420.2 |
| 91 | 4-((4-chlorobenzyl)oxy)-1-(2-(cyclopropylmethyl)-1-methyl-1H-benzimidazol-6-yl)pyridin-2(1H)-one | 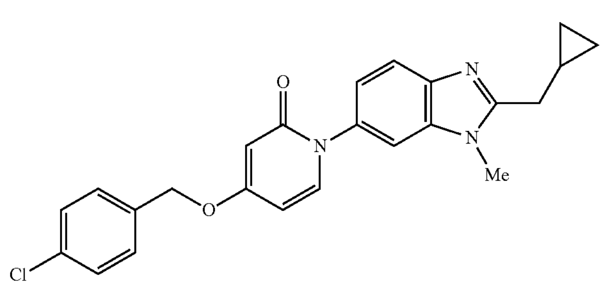 [SMILES: Cn1c(CC2CC2)nc2ccc(-n3ccc(OCc4ccc(Cl)cc4)cc3=O)cc21] | 420.2 |

TABLE 1-continued

| Example | IUPAC Name | Structure | MS |
|---|---|---|---|
| 92 | 1-(2-(2,2-dimethylcyclopropyl)-1-methyl-1H-benzimidazol-6-yl)-4-((4-fluorobenzyl)oxy)pyridin-2(1H)-one | 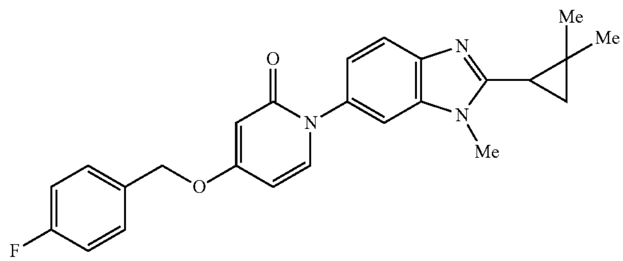 [SMILES: Cn1c(C2CC2(C)C)nc2ccc(-n3ccc(OCc4ccc(F)cc4)cc3=O)cc21] | 418.2 |
| 93 | 4-(6-(4-((4-chlorobenzyl)oxy)-2-oxopyridin-1(2H)-yl)-1-methyl-1H-benzimidazol-2-yl)-2-methylbutanenitrile | 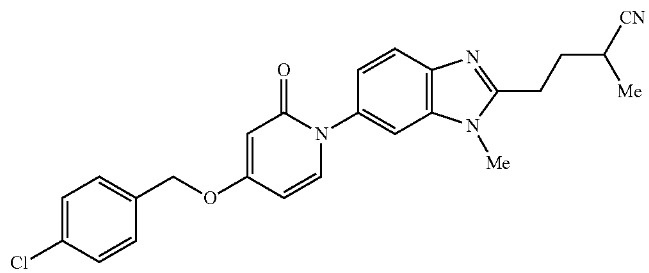 [SMILES: CC(C#N)CCc1nc2ccc(-n3ccc(OCc4ccc(Cl)cc4)cc3=O)cc2n1C] | 447.1 |
| 94 | 6-(4-((4-fluorobenzyl)oxy)-2-oxopyridin-1(2H)-yl)-N,3-dimethylimidazo[1,2-a]pyridine-2-carboxamide | 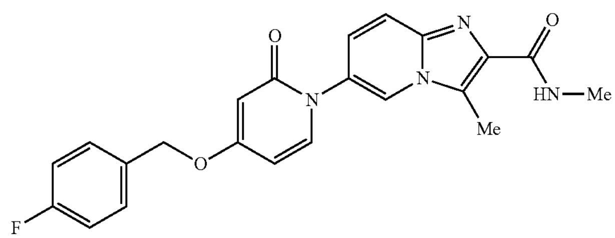 [SMILES: CNC(=O)c1nc2ccc(-n3ccc(OCc4ccc(F)cc4)cc3=O)cn2c1C] | 407.4 |
| 95 | 1-(2-acetyl-3-methylimidazo[1,2-a]pyridin-6-yl)-4-((4-fluorobenzyl)oxy)pyridin-2(1H)-one | 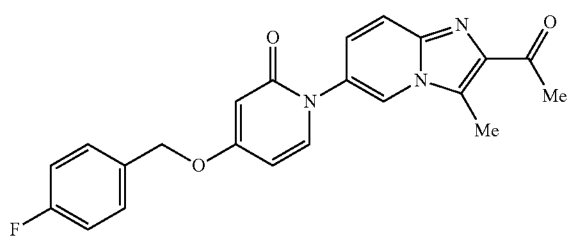 [SMILES: CC(=O)c1nc2ccc(-n3ccc(OCc4ccc(F)cc4)cc3=O)cn2c1C] | 392.0 |
| 96 | 1-(2-cyclopropyl-1-methyl-1H-benzimidazol-6-yl)-4-(1,3-thiazol-5-ylmethoxy)pyridin-2(1H)-one | 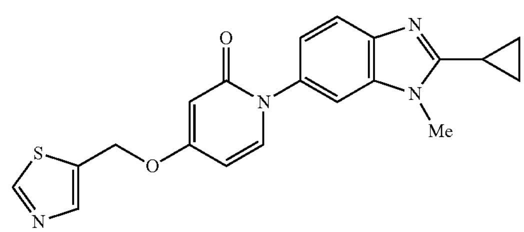 [SMILES: Cn1c(C2CC2)nc2ccc(-n3ccc(OCc4cncs4)cc3=O)cc21] | 379.0 |
| 97 | 1-(2-(cyclopropylcarbonyl)-3-methylimidazo[1,2-a]pyridin-6-yl)-4-((4-fluorobenzyl)oxy)pyridin-2(1H)-one | 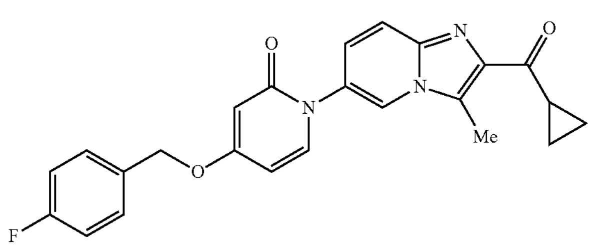 [SMILES: Cc1c(C(=O)C2CC2)nc2ccc(-n3ccc(OCc4ccc(F)cc4)cc3=O)cn12] | 418.0 |

TABLE 1-continued

| Example | IUPAC Name | Structure | MS |
|---|---|---|---|
| 98 | 1-(2-(difluoromethyl)-3-methylimidazo[1,2-a]pyridin-6-yl)-4-((4-fluorobenzyl)oxy)pyridin-2(1H)-one | 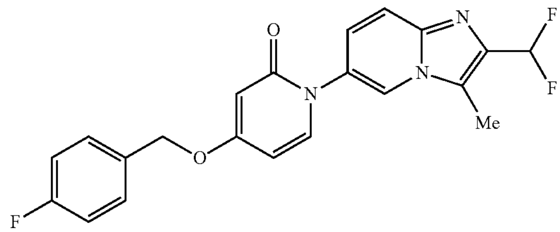 | 400.0 |
| 99 | 1-(2-cyclopropyl-1-methyl-1H-benzimidazol-6-yl)-4-((5-fluoropyridin-2-yl)methoxy)pyridin-2(1H)-one | 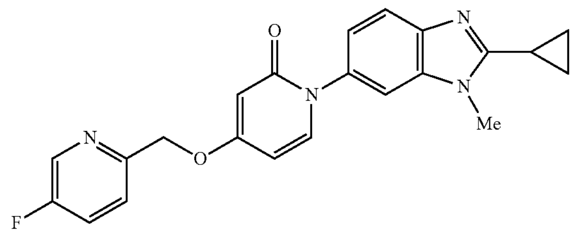 | 391.0 |
| 100 | 4-((4-chlorobenzyl)oxy)-1-(2-((2,2-dimethylpropoxy)methyl)-1-methyl-1H-benzimidazol-6-yl)pyridin-2(1H)-one | 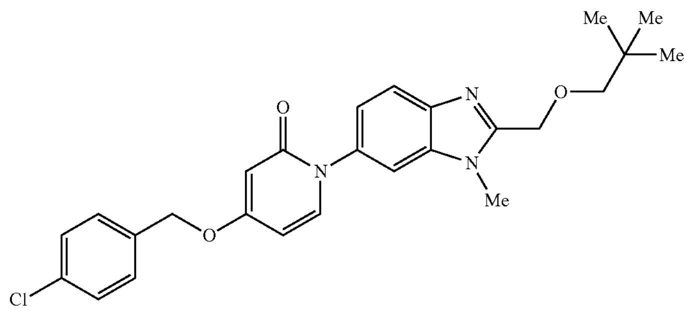 [SMILES: Cn1c(COCC(C)(C)C)nc2ccc(-n3ccc(OCc4ccc(Cl)cc4)cc3=O)cc21] | 466.1 |
| 101 | 4-((4-chlorobenzyl)oxy)-1-(2-((3,3-dimethylbutoxy)rnethyl)-1-methyl-1H-benzimidazol-6-yl)pyridin-2(1H)-one | 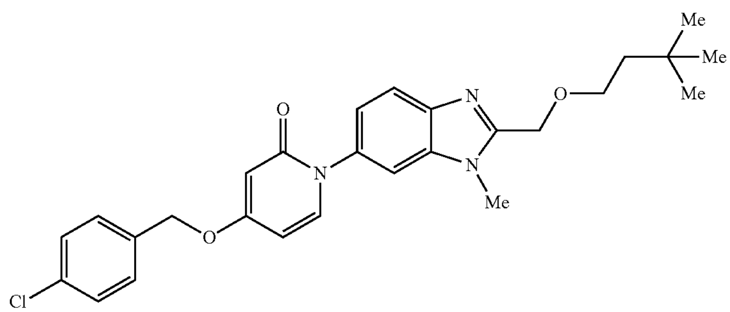 [SMILES: Cn1c(COCCC(C)(C)C)nc2ccc(-n3ccc(OCc4ccc(Cl)cc4)cc3=O)cc21] | 480.1 |
| 102 | 4-((4-chlorobenzyl)oxy)-1-(2-ethyl-1-methyl-1H-benzimidazol-6-yl)pyridin-2(1H)-one | 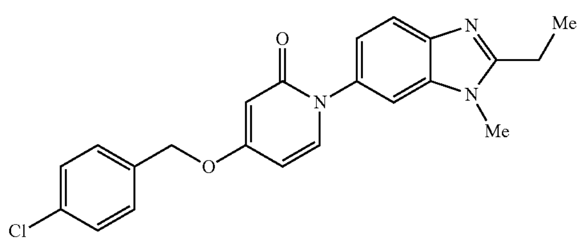 [SMILES: CCc1nc2ccc(-n3ccc(OCc4ccc(Cl)cc4)cc3=O)cc2n1C] | 394.1 |
| 103 | 4-((4-chlorobenzyl)oxy)-1-(1-methyl-2-propyl)1-1H-benzimidazol-6-yl)pyridin-2(1H)-one | 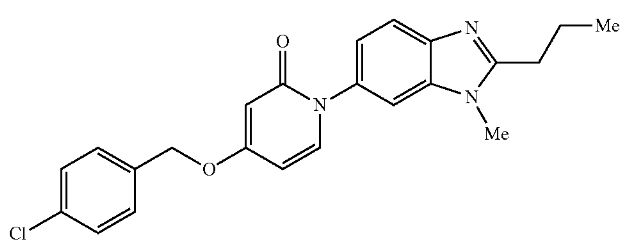 [SMILES: CCCc1nc2ccc(-n3ccc(OCc4ccc(Cl)cc4)cc3=O)cc2n1C] | 408.1 |

TABLE 1-continued

| Example | IUPAC Name | Structure | MS |
|---|---|---|---|
| 104 | 1-(2-acetyl-1-methyl-1H-benzimidazol-6-yl)-4-((4-chlorobenzyl)oxy)pyridin-2(1H)-one | 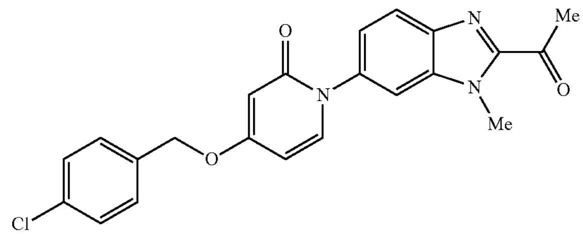 [SMILES: CC(=O)c1nc2ccc(-n3ccc(OCc4ccc(Cl)cc4)cc3=O)cc2n1C] | 408.1 |
| 105 | 4-((4-chlorobenzyl)oxy)-1-(2-(cyclopropylcarbonyl)-1-methyl-1H-benzimidazol-6-yl)pyridin-2(1H)-one | 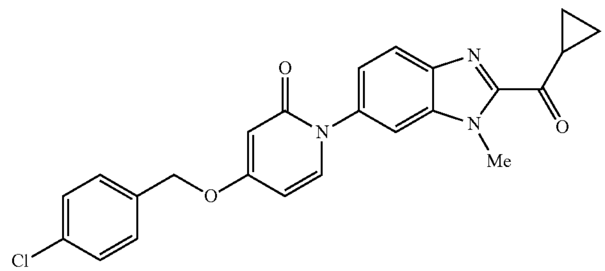 [SMILES: Cn1c(C(=O)C2CC2)nc2ccc(-n3ccc(OCc4ccc(Cl)cc4)cc3=O)cc21] | 434.0 |
| 106 | 1-(2-(5-cyclopropyl-1,2-oxazol-3-yl)-1-methyl-1H-benzimidazol-6-yl)-4-((4-fluorobenzyl)oxy)pyridin-2(1H)-one | 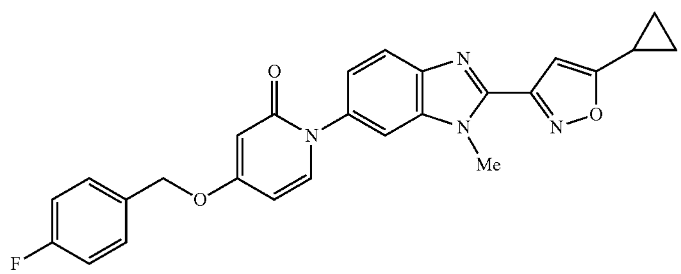 [SMILES: Cn1c(-c2cc(C3CC3)on2)nc2ccc(-n3ccc(OCc4ccc(F)cc4)cc3=O)cc21] | 457.2 |
| 107 | 4-((4-chlorobenzyl)oxy)-1-(1,2-dimethyl-1H-benzimidazol-6-yl)pyridin-2(1H)-one | 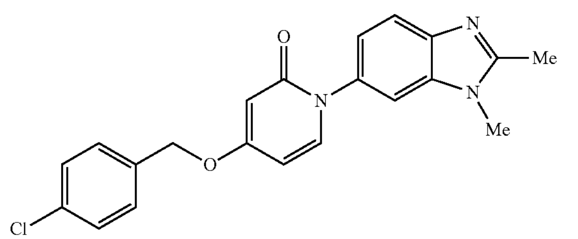 [SMILES: Cc1nc2ccc(-n3ccc(OCc4ccc(Cl)cc4)cc3=O)cc2n1C] | 380.0 |
| 108 | 4-((4-chlorobenzyl)oxy)-1-(1-methyl-2-(oxetan-3-yl)-1H-benzimidazol-6-yl)pyridin-2(1H)-one | 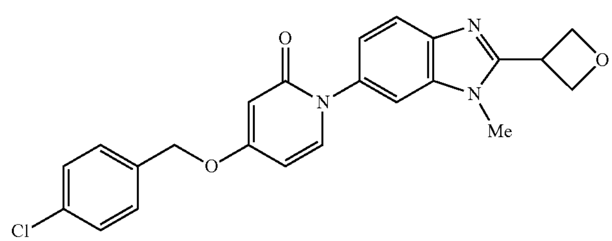 [SMILES: Cn1c(C2COC2)nc2ccc(-n3ccc(OCc4ccc(Cl)cc4)cc3=O)cc21] | 422.2 |
| 109 | 4-((4-chlorobenzyl)oxy)-1-(2-cyclobutyl-1-methyl-1H-benzimidazol-6-yl)pyridin-2(1H)-one | 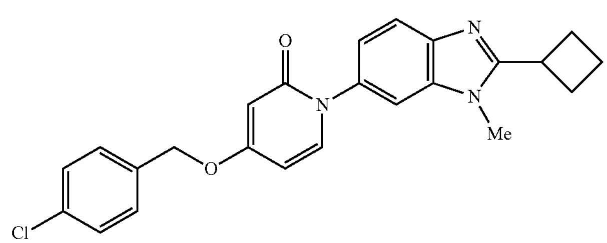 [SMILES: Cn1c(C2CCC2)nc2ccc(-n3ccc(OCc4ccc(Cl)cc4)cc3=O)cc21] | 420.2 |

TABLE 1-continued

| Example | IUPAC Name | Structure | MS |
|---|---|---|---|
| 110 | 4-((4-chlorobenzyl)oxy)-1-(2-(2-fluoropropyl)-1-methyl-1H-benzimidazol-6-yl)pyridin-2(1H)-one | 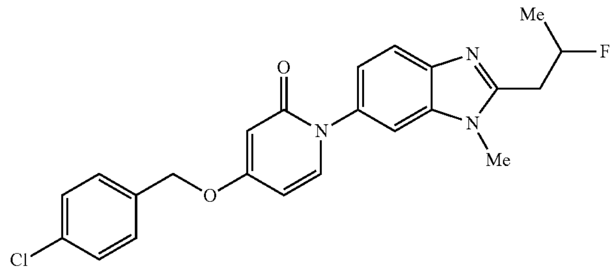 [SMILES: CC(F)Cc1nc2ccc(-n3ccc(OCc4ccc(Cl)cc4)cc3=O)cc2n1C] | 424.2 |
| 111 | 4-((4-fluorobenzyl)oxy)-1-(2-(3-methoxycyclobutyl)-1-methyl-1H-benzimidazol-6-yl)pyridin-2(1H)-one | 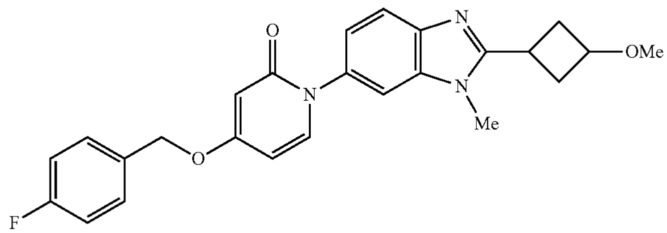 [SMILES: COC1CC(c2nc3ccc(-n4ccc(OCc5ccc(F)cc5)cc4=O)cc3n2C)C1] | 434.2 |
| 112 | 4-((5-chloropyridin-2-yl)methoxy)-1-(2-cyclopropyl-1-methyl-1H-benzimidazol-6-yl)pyridin-2(1H)-one | 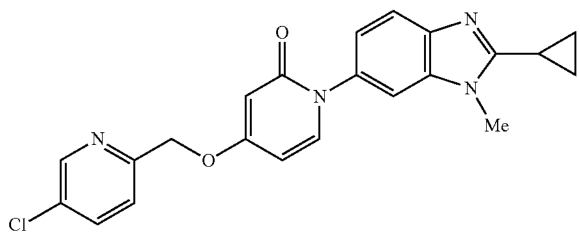 [SMILES: Cn1c(C2CC2)nc2ccc(-n3ccc(OCc4ccc(Cl)cn4)cc3=O)cc21] | 407.4 |
| 113 | 4-((4-fluorobenzyl)oxy)-1-(1-methyl-2-(3-oxocyclobutyl)-1H-benzimidazol-6-yl)pyridin-2(1H)-one | 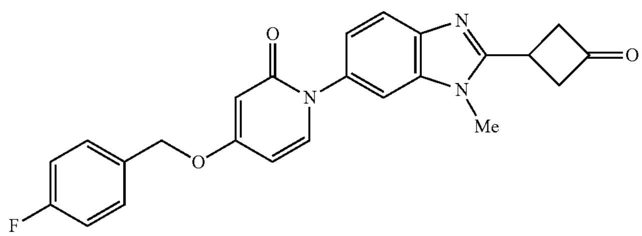 [SMILES: Cn1c(C2CC(=O)C2)nc2ccc(-n3ccc(OCc4ccc(F)cc4)cc3=O)cc21] | 418.0 |
| 114 | 1-(2-cyclopropyl-1-methyl-1H-benzimidazol-6-yl)-4-((5-(trifluoromethyl)pyridin-2-yl)methoxy)pyridin-2(1H)-one | 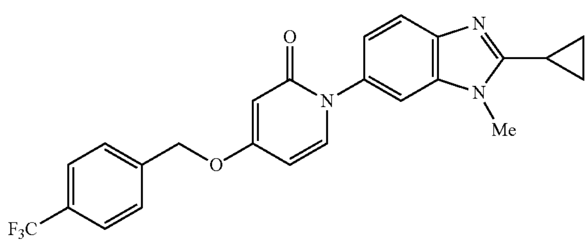 [SMILES: Cn1c(C2CC2)nc2ccc(-n3ccc(OCc4ccc(C(F)(F)F)cc4)cc3=O)cc21] | 441.2 |
| 115 | 1-(2-cyclopropyl-1-methyl-1H-benzimidazol-6-yl)-4-((3,4-difluorobenzyl)oxy)pyridin-2(1H)-one | 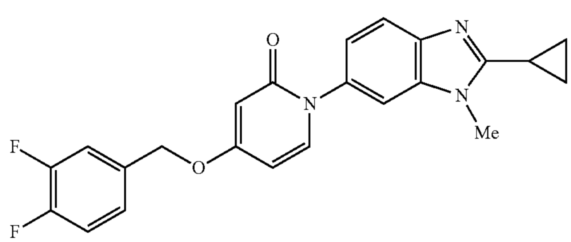 [SMILES: Cn1c(C2CC2)nc2ccc(-n3ccc(OCc4ccc(F)c(F)c4)cc3=O)cc21] | 408.0 |

TABLE 1-continued

| Example | IUPAC Name | Structure | MS |
|---|---|---|---|
| 116 | 4-((4-fluorobenzyl)oxy)-1-(2-(3-hydroxycyclobutyl)-1-methyl-1H-benzimidazol-6-yl)pyridin-2(1H)-one | 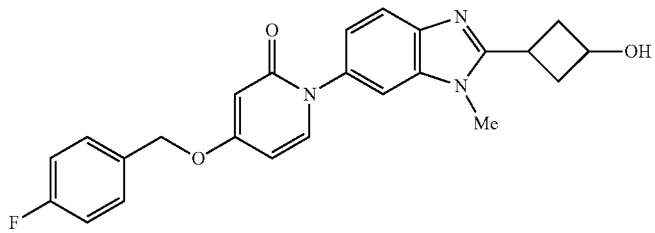 [SMILES: Cn1c(C2CC(O)C2)nc2ccc(-n3ccc(OCc4ccc(F)cc4)cc3=O)cc21] | 420.4 |
| 117 | 1-(2-cyclopropyl-3-(hydroxymethyl)imidazo[1,2-a]pyridin-6-yl)-4-((4-fluorobenzyl)oxy)pyridin-2(1H)-one | 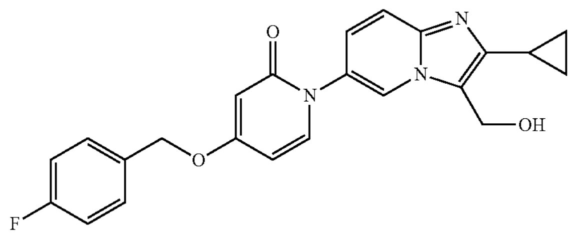 [SMILES: O=c1cc(OCc2ccc(F)cc2)ccn1-c1ccc2nc(C3CC3)c(CO)n2c1] | 406.0 |
| 118 | 1-(2-cyclopropyl-3-methylimidazo[1,2-a]pyridin-6-yl)-4-(pyridin-3-ylmethoxy)pyridin-2(1H)-one | 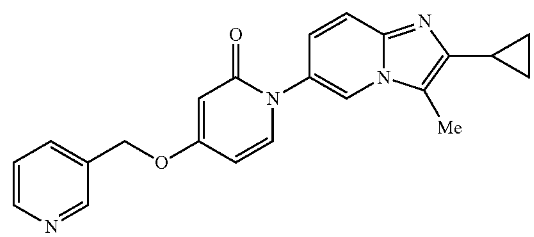 [SMILES: Cc1c(C2CC2)nc2ccc(-n3ccc(OCc4cccnc4)cc3=O)cn12] | 373.4 |
| 119 | 1-(2-cyclopropyl-1-methyl-1H-benzimidazol-6-yl)-4-((3,5-difluorobenzyl)oxy)pyridin-2(1H)-one | 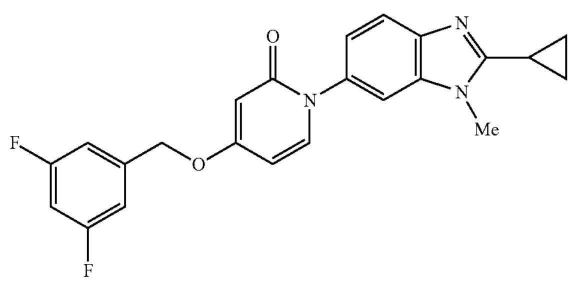 [SMILES: Cn1c(C2CC2)nc2ccc(-n3ccc(OCc4cc(F)cc(F)c4)cc3=O)cc21] | 408.6 |
| 120 | 4-(((1-(2-cyclopropyl-1-methyl-1H-benzimidazol-6-yl)-2-oxo-1,2-dihydropyridin-4-yl)oxy)methyl)benzonitrile | 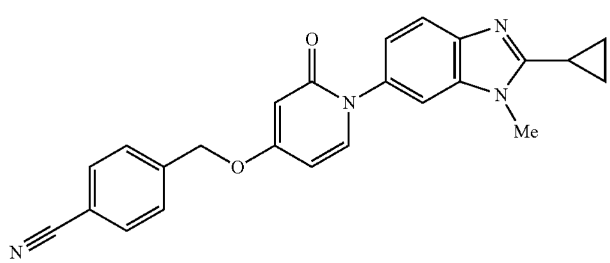 [SMILES: Cn1c(C2CC2)nc2ccc(-n3ccc(OCc4ccc(C#N)cc4)cc3=O)cc21] | 397.2 |
| 121 | 4-((5-chloro-2-thienyl)methoxy)-1-(2-cyclopropyl-1-methyl-1H-benzimidazol-6-yl)pyridin-2(1H)-one | 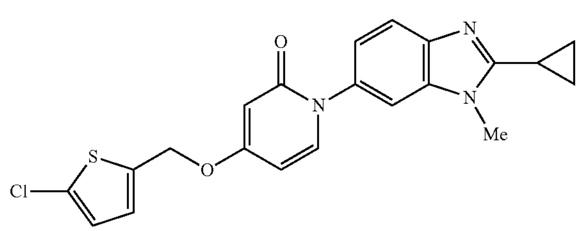 | 412.3 |

TABLE 1-continued

| Example | IUPAC Name | Structure | MS |
|---|---|---|---|
| 122 | 1-(2-cyclopropyl-3-methylimidazo[1,2-a]pyridin-6-yl)-4-(pyridin-4-ylmethoxy)pyridin-2(1H)-one | 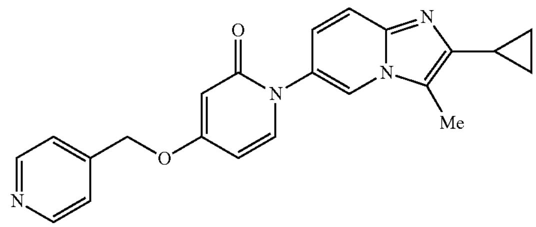 [SMILES: Cc1c(C2CC2)nc2ccc(-n3ccc(OCc4ccncc4)cc3=O)cn12] | 373.3 |
| 123 | 1-(2-cyclopropyl-3-(methoxymethyl)imidazo[1,2-a]pyridin-6-yl)-4-((4-fluorobenzyl)oxy)pyridin-2(1H)-one | 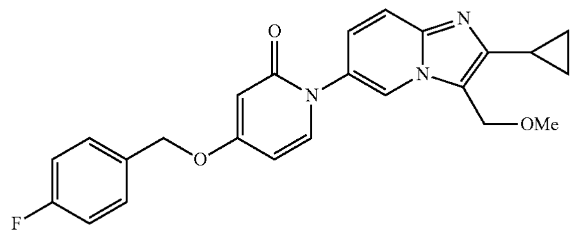 [SMILES: COCc1c(C2CC2)nc2ccc(-n3ccc(OCc4ccc(F)cc4)cc3=O)cn12] | 420.3 |
| 124 | 1-(2-cyclopropyl-1-methyl-1H-benzimidazol-6-yl)-4-(2-thienylmethoxy)pyridin-2(1H)-one | 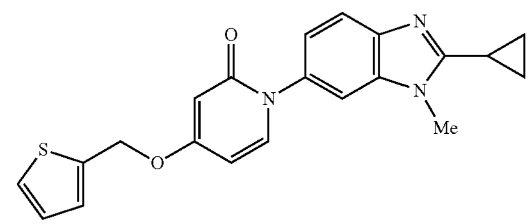 | 377.8 |
| 125 | 4-((4-fluorobenzyl)oxy)-1-(3-methyl-2-(5-methyl-1,3,4-oxadiazol-2-yl)imidazo[1,2-a]pyridin-6-yl)pyridin-2(1H)-one | 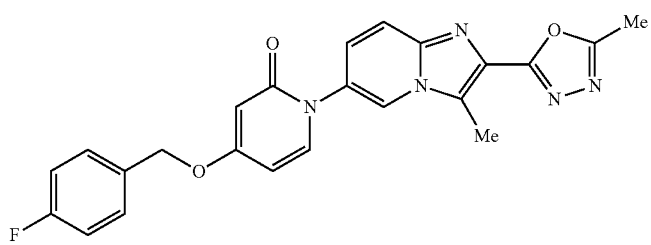 [SMILES: Cc1nnc(-c2nc3ccc(-n4ccc(OCc5ccc(F)cc5)cc4=O)cn3c2C)o1] | 432.2 |
| 126 | 4-(benzyloxy)-1-(1-methyl-2-propyl-1H-benzimidazol-6-yl)pyridin-2(1H)-one | 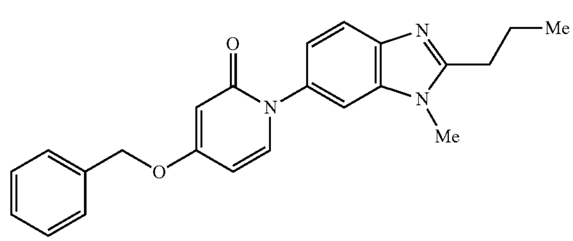 [SMILES: CCCc1nc2ccc(-n3ccc(OCc4ccccc4)cc3=O)cc2n1C] | 374.0 |
| 127 | 4-((3-chlorobenzyl)oxy)-1-(2-cyclopropyl-1-methyl-1H-benzimidazol-6-yl)pyridin-2(1H)-one | 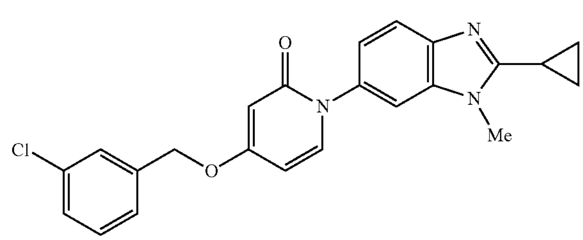 [SMILES: Cn1c(C2CC2)nc2ccc(-n3ccc(OCc4cccc(Cl)c4)cc3=O)cc21] | 405.8 |

TABLE 1-continued

| Example | IUPAC Name | Structure | MS |
|---|---|---|---|
| 128 | 1-(2-cyclopropyl-3-methylimidazo[1,2-a]pyridin-6-yl)-4-(pyrimidin-5-ylmethoxy)pyridin-2(1H)-one | 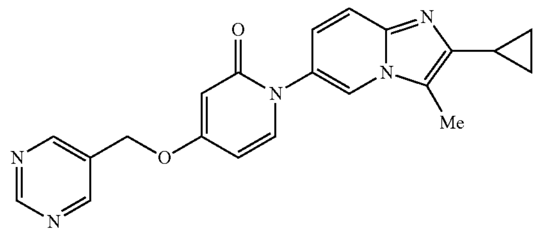 [SMILES: Cc1c(C2CC2)nc2ccc(-n3ccc(OCc4cncnc4)cc3=O)cn12] | 374.2 |
| 129 | 1-(2-cyclopropyl-1-methyl-1H-benzimidazol-6-yl)-4-((2-methyl-1,3-thiazol-5-yl)methoxy)pyridin-2(1H)-one | 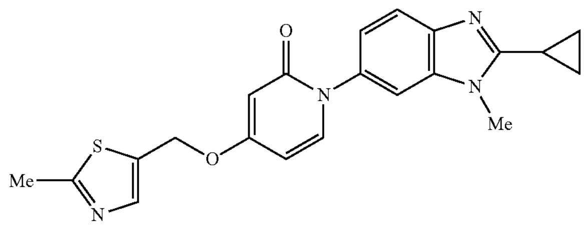 [SMILES: Cc1ncc(COc2ccn(-c3ccc4nc(C5CC5)n(C)c4c3)c(=O)c2)s1] | 393.0 |
| 130 | 1-(2-cyclopropyl-3-methylimidazo[1,2-a]pyridin-6-yl)-4((3-fluorobenzyl)oxy)pyridin-2(1H)-one | 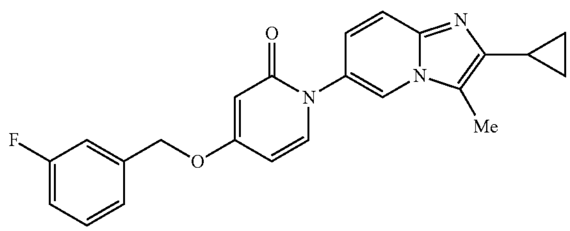 [SMILES: Cc1c(C2CC2)nc2ccc(-n3ccc(OCc4cccc(F)c4)cc3=O)cn12] | 389.8 |
| 131 | 4-((4-chloro-3-fluorobenzyl)oxy)-1-(2-cyclopropyl-1-methyl-1H-benzimidazol-6-yl)pyridin-2(1H)-one | 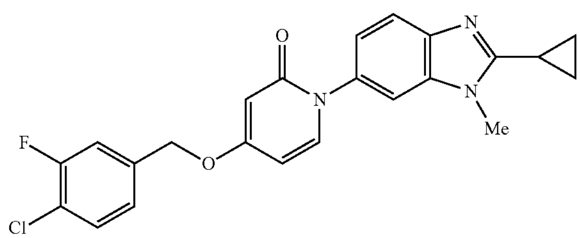 [SMILES: Cn1c(C2CC2)nc2ccc(-n3ccc(OCc4ccc(Cl)c(F)c4)cc3=O)cc21] | 397.2 |
| 132 | 1-(2-cyclopropyl-3-methylimidazo[1,2-a]pyridin-6-yl)-4-(2-thienylmethoxy)pyridin-2(1H)-one | 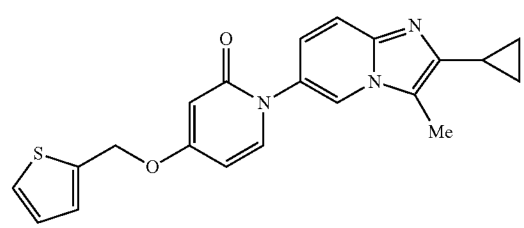 [SMILES: Cc1c(C2CC2)nc2ccc(-n3ccc(OCc4cccs4)cc3=O)cn12] | 378.3 |
| 133 | 1-(2-cyclopropyl-3-methylimidazo[1,2-a]pyridin-6-yl)-4-(3-thienylmethoxy)pyridin-2(1H)-one | 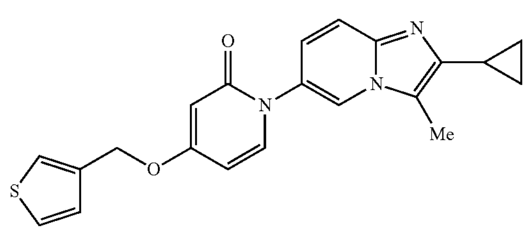 [SMILES: Cc1c(C2CC2)nc2ccc(-n3ccc(OCc4ccsc4)cc3=O)cn12] | 378.3 |

TABLE 1-continued

| Example | IUPAC Name | Structure | MS |
|---------|------------|-----------|-----|
| 134 | 4-((4-fluorobenzyl)oxy)-1-(2-(3-hydroxy-3-methylcyclobutyl)-1-methyl-1H-benzimidazol-6-yl)pyridin-2(1H)-one | 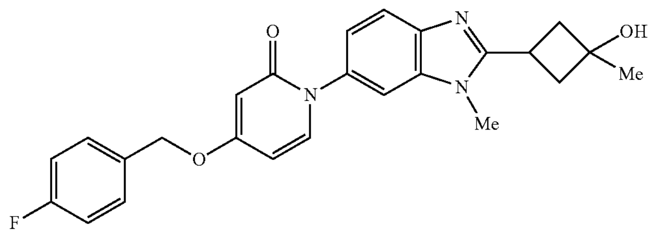 [SMILES: Cn1c(C2CC(C)(O)C2)nc2ccc(-n3ccc(OCc4ccc(F)cc4)cc3=O)cc21] | 434.3 |
| 135 | 1-(2-cyclopropyl-1-methyl-1H-benzimidazol-6-yl)-4-(furan-2-ylmethoxy)pyridin-2(1H)-one | 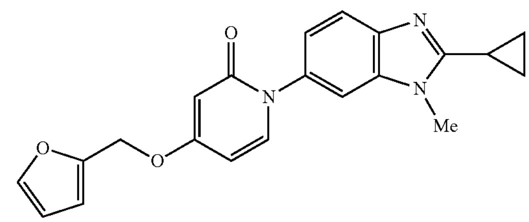 [SMILES: Cn1c(C2CC2)nc2ccc(-n3ccc(OCc4ccco4)cc3=O)cc21] | 361.8 |
| 136 | 4-((4-chlorobenzyl)oxy)-1-(2-((1RS,2RS)-2-fluorocyclopropyl)-1-methyl-1H-benzimidazol-6-yl)pyridin-2(1H)-one | 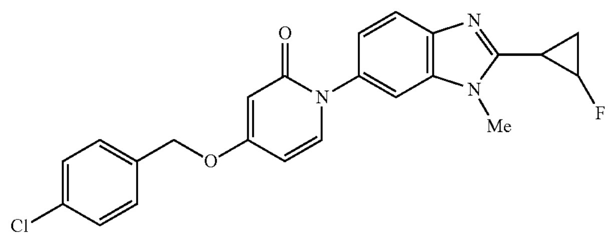 [SMILES: Cn1c(C2CC2F)nc2ccc(-n3ccc(OCc4ccc(Cl)cc4)cc3=O)cc21] | 424.1 |
| 137 | 4-((4-chlorobenzyl)oxy)-1-(2-((1RS,2SR)-2-fluorocyclopropyl)-1-methyl-1H-benzimidazol-6-yl)pyridin-2(1H)-one | 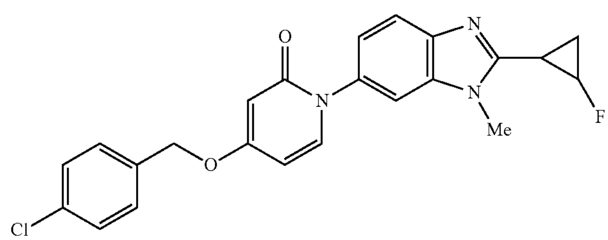 [SMILES: Cn1c(C2CC2F)nc2ccc(-n3ccc(OCc4ccc(Cl)cc4)cc3=O)cc21] | 424.1 |
| 138 | methyl (1RS,2SR)-2-(6-(4-((4-chlorobenzyl)oxy)-2-oxopyridin-1(2H)-yl)-1-methyl-1H-benzimidazol-2-yl)cyclopropanecarboxylate | 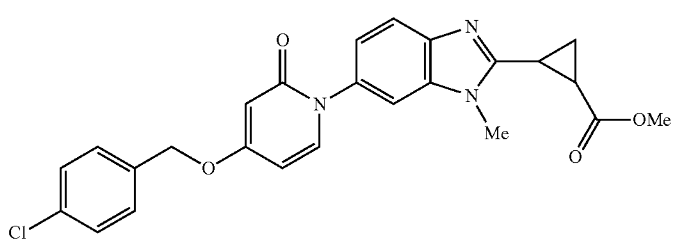 [SMILES: COC(=O)C1CC1c1nc2ccc(-n3ccc(OCc4ccc(Cl)cc4)cc3=O)cc2n1C] | 464.1 |
| 139 | 4-((5-chloro-2-thienyl)methoxy)-1-(2-cyclopropyl-3-methylimidazo[1,2-a]pyridin-6-yl)pyridin-2(1H)-one | 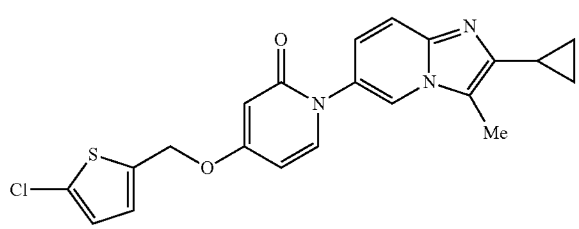 [SMILES: Cc1c(C2CC2)nc2ccc(-n3ccc(OCc4ccc(Cl)s4)cc3=O)cn12] | 412.4 |

TABLE 1-continued

| Example | IUPAC Name | Structure | MS |
|---|---|---|---|
| 140 | 1-(2-cyclopropyl-1-methyl-1H-benzimidazol-6-yl)-4-((5-methoxypyridin-2-yl)methoxy)pyridin-2(1H)-one | 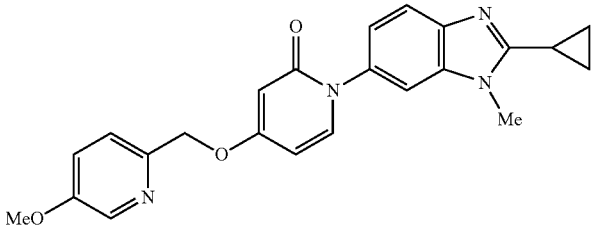 | 403.0 |
| 141 | 1-(2-cyclopropyl-1-methyl-1H-benzimidazol-6-yl)-4-((5-methylpyridin-2-yl)methoxy)pyridin-2(1H)-one | 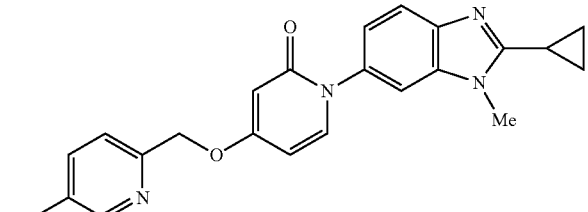 | 387.2 |
| 142 | 1-(2-cyclopropyl-1-methyl-1H-benzimidazol-6-yl)-4-((4-methylbenzyl)oxy)pyridin-2(1H)-one | 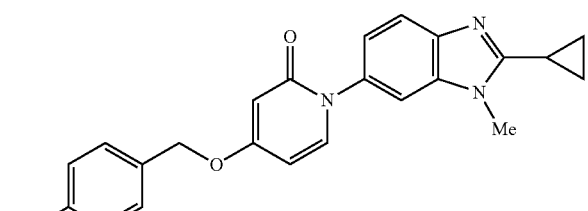 | 386.2 |
| 143 | 4-((5-chloro-3-thienyl)methoxy)-1-(2-cyclopropyl-1-methyl-1H-benzimidazol-6-yl)pyridin-2(1H)-one | 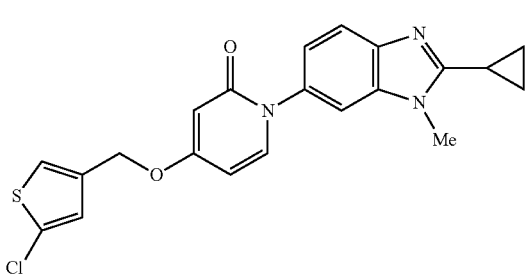 [SMILES: Cn1c(C2CC2)nc2ccc(-n3ccc(OCc4csc(Cl)c4)cc3=O)cc21] | 412.0 |
| 144 | 4-((4-fluorobenzyl)oxy)-1-(1-methyl-2-(1,2-oxazol-5-yl)-1H-benzimidazol-6-yl)pyridin-2(1H)-one | 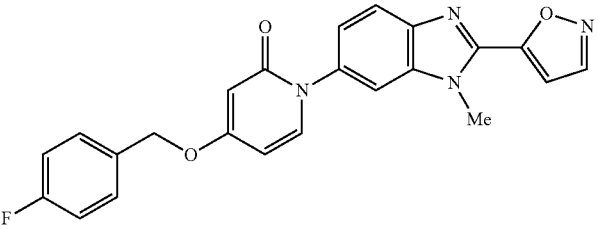 [SMILES: Cn1c(-c2ccno2)nc2ccc(-n3ccc(OCc4ccc(F)cc4)cc3=O)cc21] | 417.1 |
| 145 | 4-((4-fluorobenzyl)oxy)-1-(1-methyl-2-(5-methyl-1,3-oxazol-4-yl)-1H-benzimidazol-6-yl)pyridin-2(1H)-one | 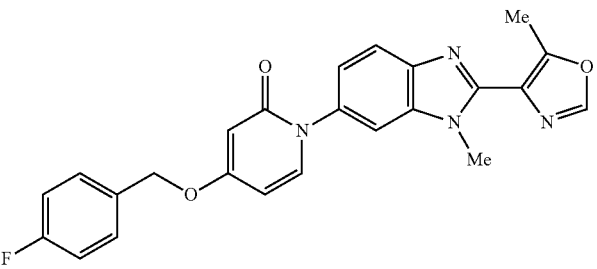 [SMILES: Cc1ocnc1-c1nc2ccc(-n3ccc(OCc4ccc(F)cc4)cc3=O)cc2n1C] | 431.1 |

TABLE 1-continued

| Example | IUPAC Name | Structure | MS |
|---|---|---|---|
| 146 | 1-(2-cyclopropyl-3-methylimidazo[1,2-a]pyridin-6-yl)-4-((3,4-difluorobenzyl)oxy)pyridin-2(1H)-one | 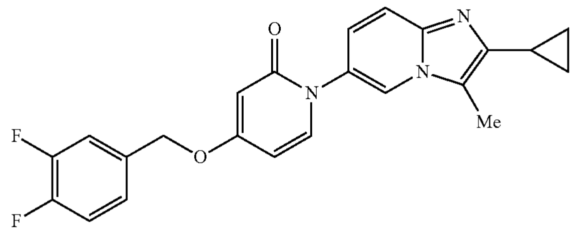 [SMILES: Cc1c(C2CC2)nc2ccc(-n3ccc(OCc4ccc(F)c(F)c4)cc3=O)cn12] | 408.0 |
| 147 | 4-((4-chlorobenzyl)oxy)-1-(2-ethyl-3-methylimidazo[1,2-a]pyridin-6-yl)pyridin-2(1H)-one | 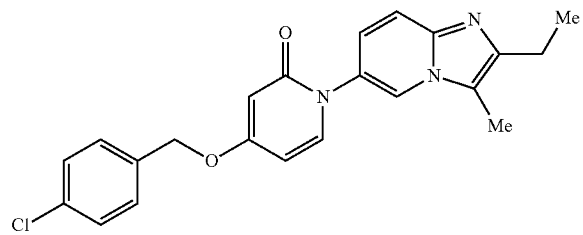 [SMILES: CCc1nc2ccc(-n3ccc(OCc4ccc(Cl)cc4)cc3=O)cn2c1C] | 394.0 |
| 148 | (1RS,2SR)-2-(6-(4-((4-chlorobenzyl)oxy)-2-oxopyridin-1(2H)-yl)-1-methyl-1H-benzimidazol-2-yl)cyclopropanecarbonitrile | 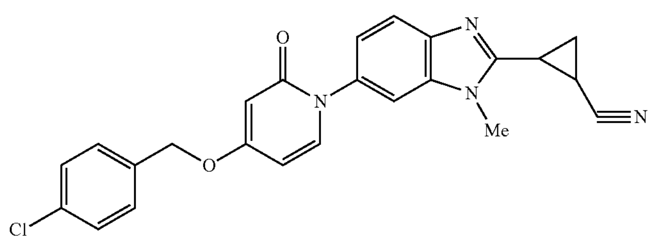 [SMILES: Cn1c(C2CC2C#N)nc2ccc(-n3ccc(OCc4ccc(Cl)cc4)cc3=O)cc21] | 431.1 |
| 149 | 4-((4-chlorobenzyl)oxy)-1-(2-((1RS,2SR)-2-(hydroxymethyl)cyclopropyl)-1-methyl-1H-benzimidazol-6-yl)pyridin-2(1H)-one | 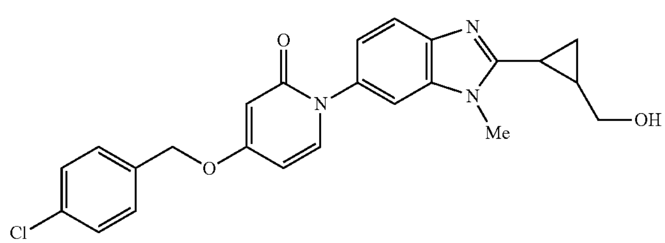 [SMILES: Cn1c(C2CC2CO)nc2ccc(-n3ccc(OCc4ccc(Cl)cc4)cc3=O)cc21] | 436.1 |
| 150 | methyl (1RS,2SR)-2-(6-(4-(benzyloxy)-2-oxopyridin-1(2H)-yl)-1-methyl-1H-benzimidazol-2-yl)cyclopropanecarboxylate | 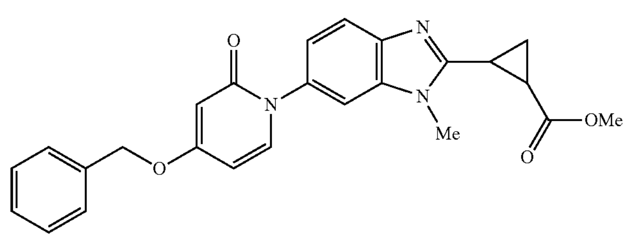 [SMILES: COC(=O)C1CC1c1nc2ccc(-n3ccc(OCc4ccccc4)cc3=O)cc2n1C] | 430.1 |
| 151 | 4-((4-chloro-3-fluorobenzyl)oxy)-1-(2-cyclopropyl-3-methylimidazo[1,2-a]pyridin-6-yl)pyridin-2(1H)-one | 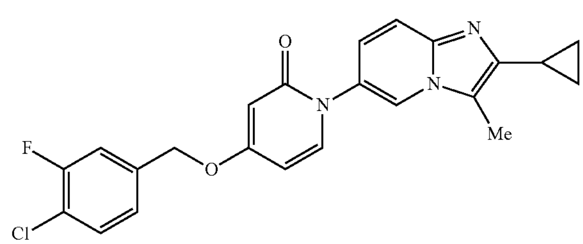 [SMILES: Cc1c(C2CC2)nc2ccc(-n3ccc(OCc4ccc(Cl)c(F)c4)cc3=O)cn12] | 424.0 |

TABLE 1-continued

| Example | IUPAC Name | Structure | MS |
|---|---|---|---|
| 152 | 4-(benzyloxy)-1-(2-((1RS,2SR)-2-(2-hydroxypropan-2-yl)cyclopropyl)-1-methyl-1H-benzimidazol-6-yl)pyridin-2(1H)-one | 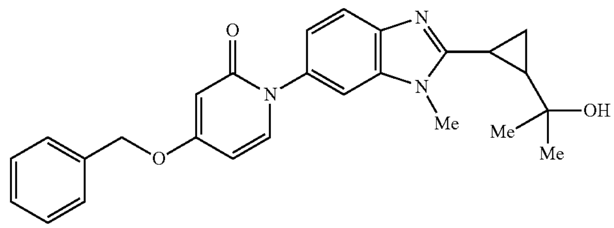 [SMILES: Cn1c(C2CC2C(C)(C)O)nc2ccc(-n3ccc(OCc4ccccc4)cc3=O)cc21] | 430.4 |
| 153 | 4-((4-chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR1) | 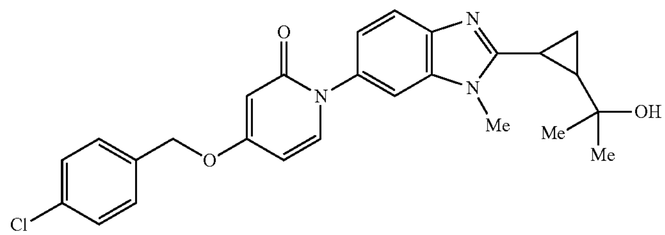 [SMILES: Cn1c(C2CC2C(C)(C)O)nc2ccc(-n3ccc(OCc4ccc(Cl)cc4)cc3=O)cc21] | 464.1 |
| 154 | 4-((4-chlorobenzyl)oxy)-1-(2-((1R*,2S*)-2-(2-hydroxypropan-2-yl)cyclopropyl)-1-methyl-1H-benzimidazol-6-yl)pyridin-2(1H)-one (optically active, AYH tR2) | 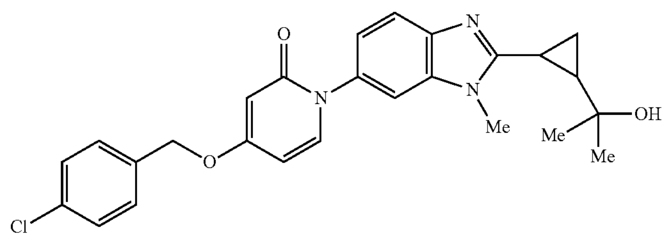 [SMILES: Cn1c(C2CC2C(C)(C)O)nc2ccc(-n3ccc(OCc4ccc(Cl)cc4)cc3=O)cc21] | 464.2 |
| 155 | 4-(benzyloxy)-1-(2-((1RS,2SR)-2-(2-fluoropropan-2-yl)cyclopropyl)-1-methyl-1H-benzimidazol-6-yl)pyridin-2(1H)-one | 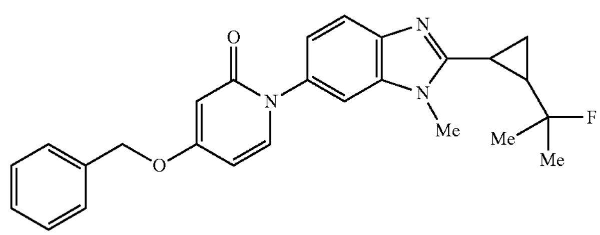 [SMILES: Cn1c(C2CC2C(C)(C)F)nc2ccc(-n3ccc(OCc4ccccc4)cc3=O)cc21] | 432.4 |
| 156 | 1-(2-cyclopropyl-3-methylimidazo[1,2-a]pyridin-6-yl)-4-((5-fluorothiophen-2-yl)methoxy)pyridin-2(1H)-one | 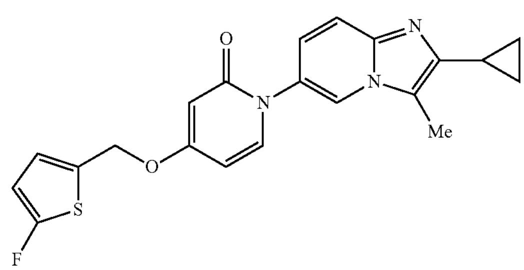 [SMILES: Cc1c(C2CC2)nc2ccc(-n3ccc(OCc4ccc(F)s4)cc3=O)cn12] | 395.4 |
| 157 | 1-(2-cyclopropyl-1-methyl-1H-benzimidazol-6-yl)-4-((5-fluorothiophen-2-yl)methoxy)pyridin-2(1H)-one | 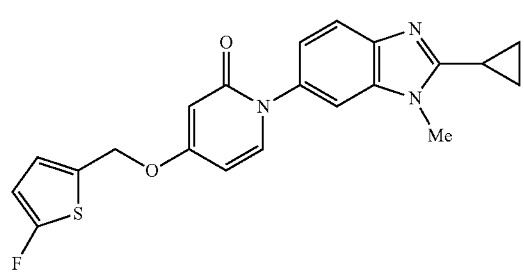 [SMILES: Cn1c(C2CC2)nc2ccc(-n3ccc(OCc4ccc(F)s4)cc3=O)cc21] | 395.4 |

TABLE 1-continued

| Example | IUPAC Name | Structure | MS |
|---|---|---|---|
| 158 | 1-(2-cyclopropyl-3-methylimidazo[1,2-a]pyridin-6-yl)-4-((5-(trifluoromethyl)thiophen-2-yl)methoxy)pyridin-2(1H)-one | 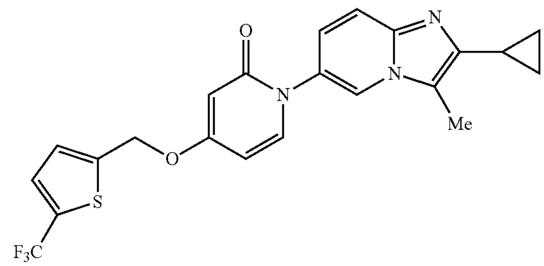 [SMILES: Cc1c(C2CC2)nc2ccc(-n3ccc(OCc4ccc(C(F)(F)F)s4)cc3=O)cn12] | 445.5 |
| 159 | 1-(2-cyclopropyl-1-methyl-1H-benzimidazol-6-yl)-4-((5-(trifluoromethyl)thiophen-2-yl)methoxy)pyridin-2(1H)-one | 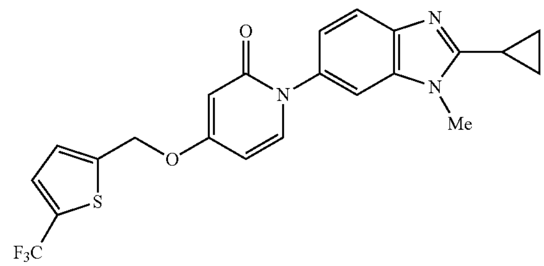 [SMILES: Cn1c(C2CC2)nc2ccc(-n3ccc(OCc4ccc(C(F)(F)F)s4)cc3=O)cc21] | 445.5 |
| 160 | 1-(2-cyclopropyl-3-methylimidazo[1,2-a]pyridin-6-yl)-4-((5-(trifluoromethyl)thiophen-2-yl)methoxy)pyridin-2(1H)-one hydrochloride | 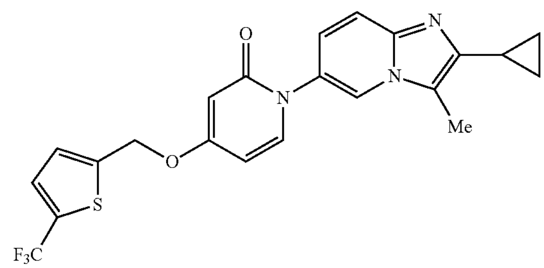 [SMILES: Cc1c(C2CC2)nc2ccc(-n3ccc(OCc4ccc(C(F)(F)F)s4)cc3=O)cn12] | 445.5 |
| 161 | 4-((5-chloro-3-fluoropyridin-2-yl)methoxy)-1-(2-cyclopropyl-3-methylimidazo[1,2-a]pyridin-6-yl)pyridin-2(1H)-one | 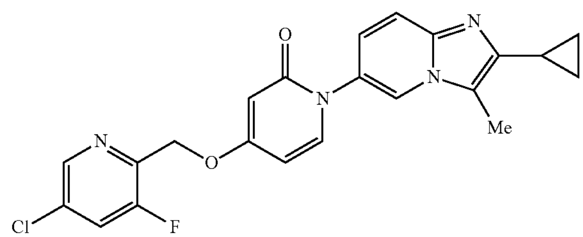 [SMILES: Cc1c(C2CC2)nc2ccc(-n3ccc(OCc4ncc(Cl)cc4F)cc3=O)cn12] | 425.3 |
| 162 | 1-(2,3-dimethylimidazo[1,2-a]pyridin-6-yl)-4-((4-fluorobenzyl)oxy)pyridin-2(1H)-one | 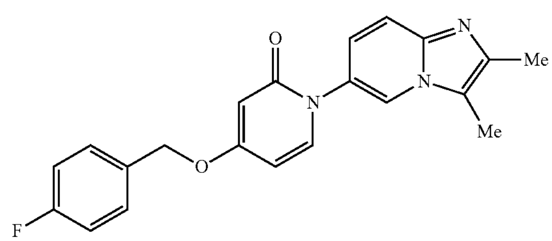 [SMILES: Cc1nc2ccc(-n3ccc(OCc4ccc(F)cc4)cc3=O)cn2c1C] | 363.8 |
| 163 | 4-(benzyloxy)-1-(2,3-dimethylimidazo[1,2-a]pyridin-6-yl)pyridin-2(1H)-one | 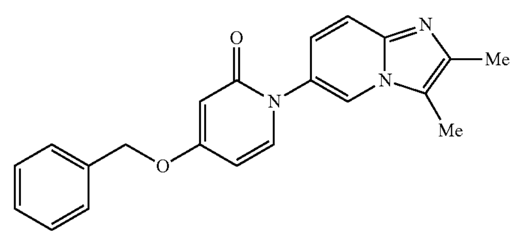 [SMILES: Cc1nc2ccc(-n3ccc(OCc4ccccc4)cc3=O)cn2c1C] | 345.8 |

TABLE 1-continued

| Example | IUPAC Name | Structure | MS |
|---|---|---|---|
| 164 | 4-((5-chlorothiophen-3-yl)methoxy)-1-(2-cyclopropyl-3-methylimidazo[1,2-a]pyridin-6-yl)pyridin-2(1H)-one | 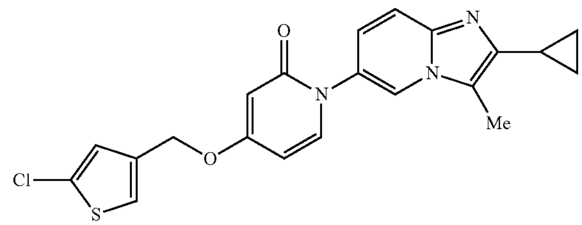 [SMILES: Cc1c(C2CC2)nc2ccc(-n3ccc(OCc4csc(Cl)c4)cc3=O)cn12] | 412.0 |
| 165 | 4-((5-chlorothiophen-3-yl)methoxy)-1-(2,3-dimethylimidazo[1,2-a]pyridin-6-yl)pyridin-2(1H)-one | 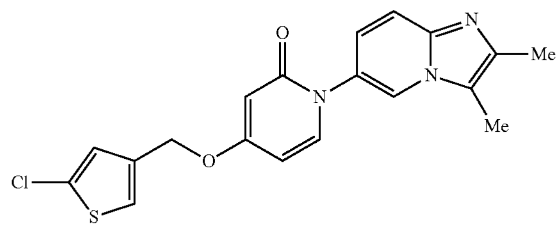 [SMILES: Cc1nc2ccc(-n3ccc(OCc4csc(Cl)c4)cc3=O)cn2c1C] | 385.8 |
| 166 | 4-((5-chlorothiophen-2-yl)methoxy)-1-(2,3-dimethylimidazo[1,2-a]pyridin-6-yl)pyridin-2(1H)-one | 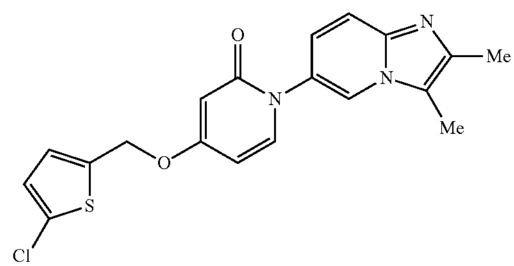 [SMILES: Cc1nc2ccc(-n3ccc(OCc4ccc(Cl)s4)cc3=O)cn2c1C] | 386.0 |
| 167 | 4-(benzyloxy)-1-(2-ethyl-3-methylimidazo[1,2-a]pyridin-6-yl)pyridin-2(1H)-one | 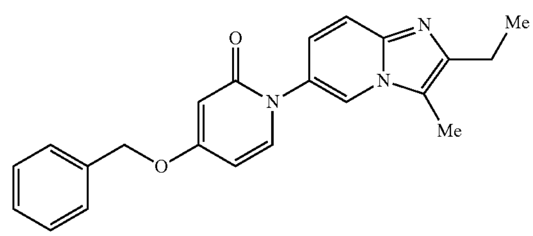 [SMILES: CCc1nc2ccc(-n3ccc(OCc4ccccc4)cc3=O)cn2c1C] | 359.8 |
| 168 | 4-((4-chlorothiophen-2-yl)methoxy)-1-(2-cyclopropyl-3-methylimidazo[1,2-a]pyridin-6-yl)pyridin-2(1H)-one | 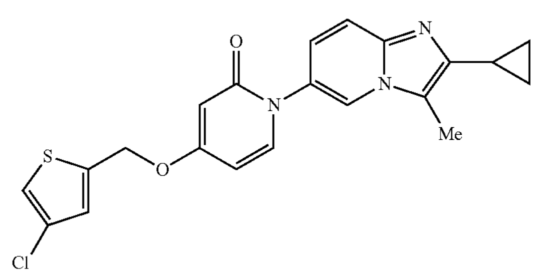 [SMILES: Cc1c(C2CC2)nc2ccc(-n3ccc(OCc4cc(Cl)cs4)cc3=O)cn12] | 412.2 |
| 169 | 1-(2-ethyl-3-methylimidazo[1,2-a]pyridin-6-yl)-4-((4-fluorobenzyl)oxy)pyridin-2(1H)-one | 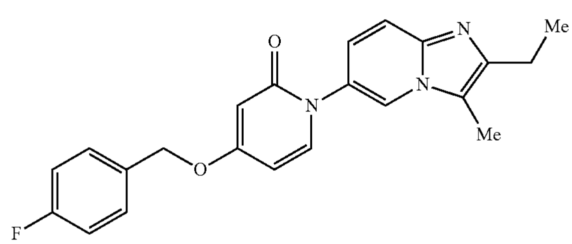 [SMILES: CCc1nc2ccc(-n3ccc(OCc4ccc(F)cc4)cc3=O)cn2c1C] | 378.2 |

TABLE 1-continued

| Example | IUPAC Name | Structure | MS |
|---|---|---|---|
| 170 | 1-(2-cyclopropyl-3-methylimidazo[1,2-a]pyridin-6-yl)-4-((4-fluorophenoxy)methyl)pyridin-in-2(1H)-one | 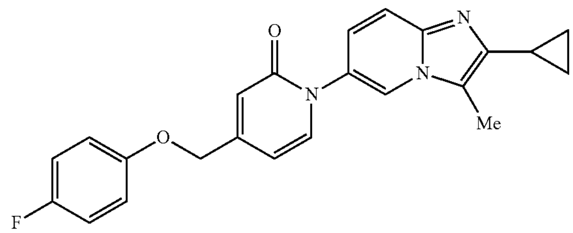 [SMILES: Cc1c(C2CC2)nc2ccc(-n3ccc(COc4ccc(F)cc4)cc3=O)cn12] | 390.0 |
| 171 | 4-((5-chlorothiophen-2-yl)methoxy)-1-(2-ethyl-3-methylimidazo[1,2-a]pyridin-6-yl)pyridin-2(1H)-one | 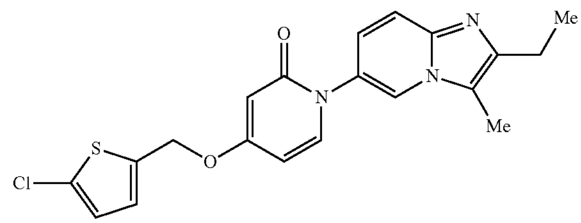 [SMILES: CCc1nc2ccc(-n3ccc(OCc4ccc(Cl)s4)cc3=O)cn2c1C] | 400.0 |
| 172 | 4-((5-chlorothiophen-3-yl)methoxy)-1-(2-ethyl-3-methylimidazo[1,2-a]pyridin-6-yl)pyridin-2(1H)-one | 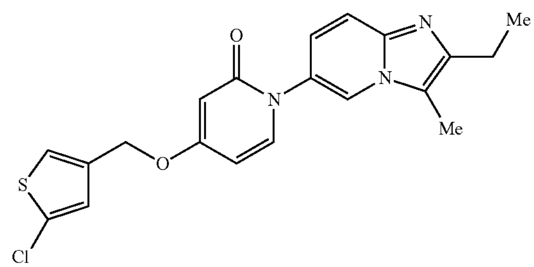 [SMILES: CCc1nc2ccc(-n3ccc(OCc4csc(Cl)c4)cc3=O)cn2c1C] | 400.2 |
| 173 | 4-((4-chlorobenzyl)oxy)-1-(2-(2-(2-hydroxypropan-2-yl)cyclopropyl)-3-methylimidazo[1,2-a]pyridin-6-yl)pyridin-2(1H)-one | 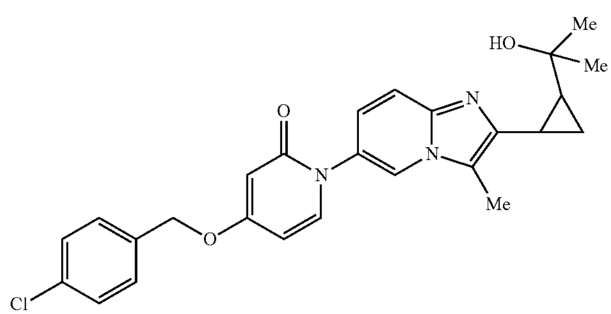 [SMILES: Cc1c(C2CC2C(C)(C)O)nc2ccc(-n3ccc(OCc4ccc(Cl)cc4)cc3=O)cn12] | 464.0 |
| 174 | 2-(6-(4-((4-chlorobenzyl)oxy)-2-oxopyridin-1(2H)-yl)-3-methylimidazo[1,2-a]pyridin-2-yl)cyclopropanecarbonitrile | 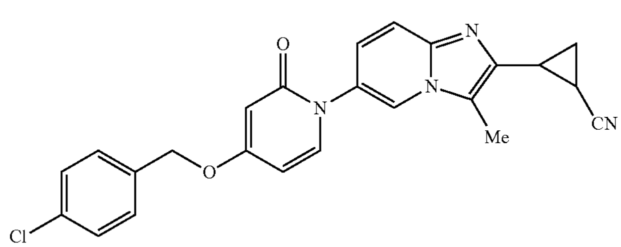 [SMILES: Cc1c(C2CC2C#N)nc2ccc(-n3ccc(OCc4ccc(Cl)cc4)cc3=O)cn12] | 431.2 |
| 175 | 1-(2-cyclopropyl-3-methylimidazo[1,2-a]pyridin-6-yl)-4-((5-fluoro-2-thienyl)methoxy)pyridin-2(1H)-one | 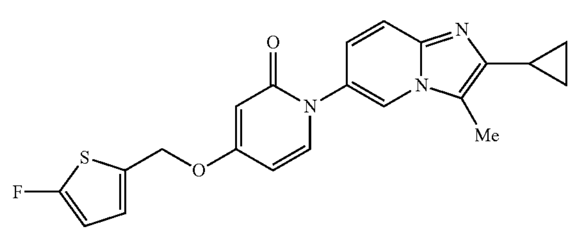 [SMILES: Cc1c(C2CC2)nc2ccc(-n3ccc(OCc4ccc(F)s4)cc3=O)cn12] | 396.1 |

TABLE 1-continued

| Example | IUPAC Name | Structure | MS |
|---|---|---|---|
| 176 | 1-(2-cyclopropyl-1-methyl-1H-benzimidazol-6-yl)-4-((5-fluorothiophen-2-yl)methoxy)pyridin-2(1H)-one | 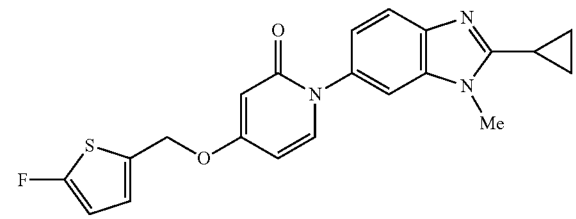 [SMILES: Cn1c(C2CC2)nc2ccc(-n3ccc(OCc4ccc(F)s4)cc3=O)cc21] | 396.0 |
| 177 | 4-((5-bromo-3-thienyl)methoxy)-1-(2-cyclopropyl-3-methylimidazo[1,2-a]pyridin-6-yl)pyridin-2(1H)-one | 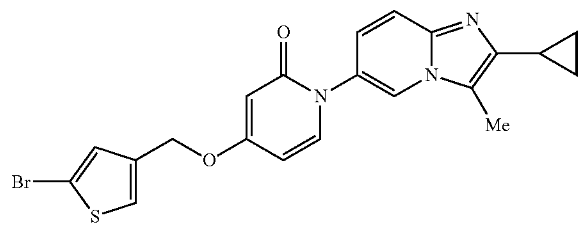 | 456.0 |
| 178 | 1-(2-cyclopropyl-3-methylimidazo[1,2-a]pyridin-6-yl)-4-((5-(difluoromethyl)-2-thienyl)methoxy)pyridin-2(1H)-one | 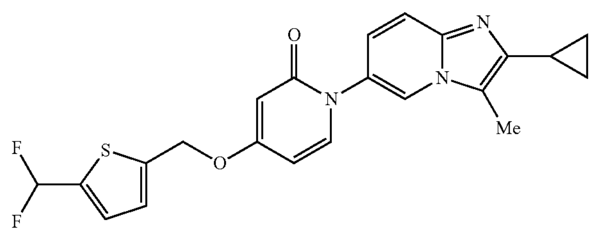 [SMILES: Cc1c(C2CC2)nc2ccc(-n3ccc(OCc4ccc(C(F)F)s4)cc3=O)cn12] | 428.4 |
| 179 | 1-(2-cyclopropyl-3-methylimidazo[1,2-a]pyridin-6-yl)-4-((2-(trifluoromethyl)-1,3-thiazol-4-yl)methoxy)pyridin-2(1H)-one | 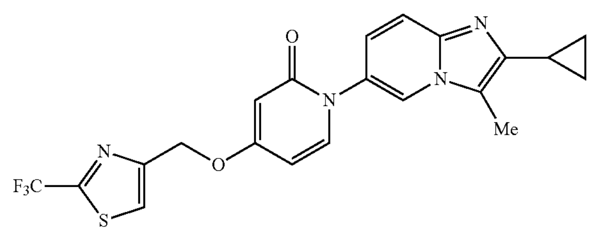 [SMILES: Cc1c(C2CC2)nc2ccc(-n3ccc(OCc4csc(C(F)(F)F)n4)cc3=O)cn12] | 447.4 |
| 180 | 1-(2-cyclopropyl-3-methylimidazo[1,2-a]pyridin-6-yl)-4((5-(trifluoromethyl)-2-furyl)methoxy)pyridin-2(1H)-one | 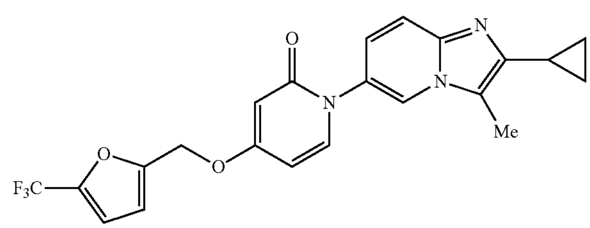 [SMILES: Cc1c(C2CC2)nc2ccc(-n3ccc(OCc4ccc(C(F)(F)F)o4)cc3=O)cn12] | 430.1 |
| 181 | 4-(((5-chloro-2-thienyl)methyl)amino)-1-(2-cyclopropyl-3-methylimidazo[1,2-a]pyridin-6-yl)pyridin-2(1H)-one | 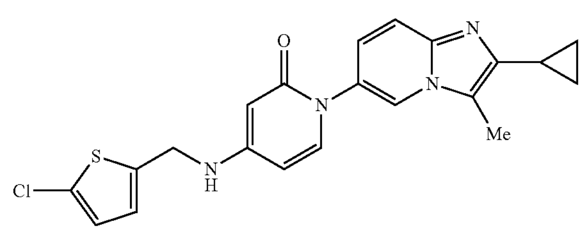 [SMILES: Cc1c(C2CC2)nc2ccc(-n3ccc(NCc4ccc(Cl)s4)cc3=O)cn12] | 411.1 |
| 182 | 4-(((5-chloro-2-thienyl)methyl)(methyl)amino)-1-(2-cyclopropyl-3-methylimidazo[1,2-a]pyridin-6-yl)pyridin-2(1H)-one | 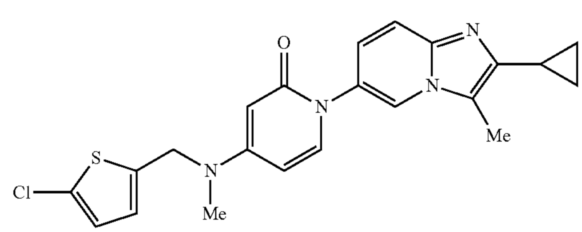 [SMILES: Cc1c(C2CC2)nc2ccc(-n3ccc(N(C)Cc4ccc(Cl)s4)cc3=O)cn12] | 425.1 |

TABLE 1-continued

| Example | IUPAC Name | Structure | MS |
|---|---|---|---|
| 183 | 1-(2-cyclopropyl-3-methylimidazo[1,2-a]pyridin-6-yl)-4-((5-(trifluoromethyl)-3-thienyl)methoxy)pyridin-2(1H)-one | 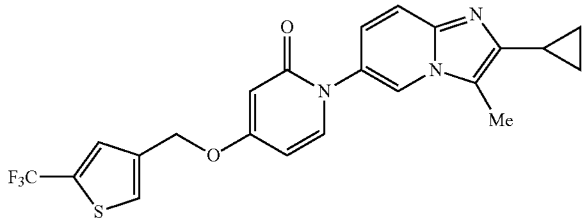 [SMILES: Cc1c(C2CC2)nc2ccc(-n3ccc(OCc4csc(C(F)(F)F)c4)cc3=O)cn12] | 446.4 |
| 184 | 1-(2-cyclopropyl-3-methylimidazo[1,2-a]pyridin-6-yl)-4-((5-(difluoromethyl)-3-thienyl)methoxy)pyridin-2(1H)-one | 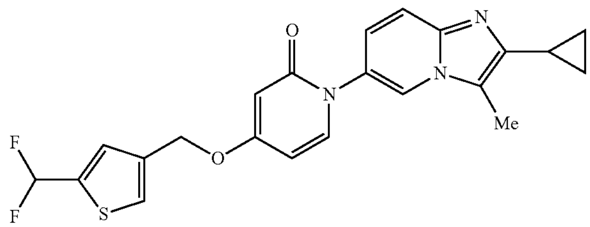 [SMILES: Cc1c(C2CC2)nc2ccc(-n3ccc(OCc4csc(C(F)F)c4)cc3=O)cn12] | 428.3 |
| 186 | 4-((4-chlorobenzyl)amino)-1-(2-cyclopropyl-3-methylimidazo[1,2-a]pyridin-6-yl)pyridin-2(1H)-one | 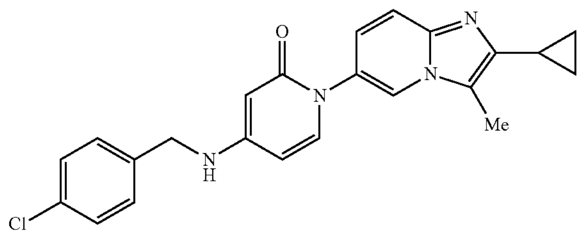 [SMILES: Cc1c(C2CC2)nc2ccc(-n3ccc(NCc4ccc(Cl)cc4)cc3=O)cn12] | 405.3 |
| 189 | 4-((2-bromo-1,3-thiazol-4-yl)methoxy)-1-(2-cyclopropyl-3-methylimidazo[1,2-a]pyridin-6-yl)pyridin-2(1H)-one | 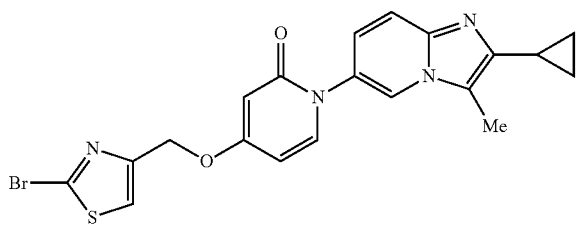 [SMILES: Cc1c(C2CC2)nc2ccc(-n3ccc(OCc4csc(Br)n4)cc3=O)cn12] | 457.3 |
| 190 | 4-((4-tert-butylbenzyl)oxy)-1-(2-cyclopropyl-3-methylimidazo[1,2-a]pyridin-6-yl)pyridin-2(1H)-one | 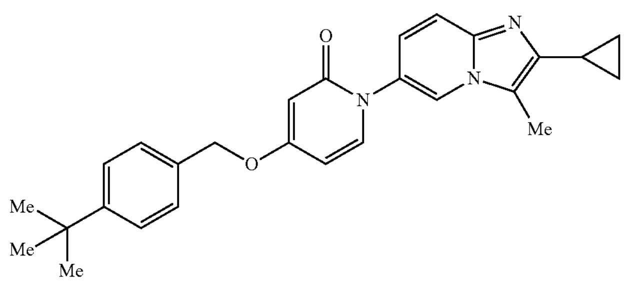 [SMILES: Cc1c(C2CC2)nc2ccc(-n3ccc(OCc4ccc(C(C)(C)C)cc4)cc3=O)cn12] | 428.4 |
| 191 | 1-(2-cyclopropyl-3-methylimidazo[1,2-a]pyridin-6-yl)-4-((4-isopropylbenzyl)oxy)pyridin-2(1H)-one | 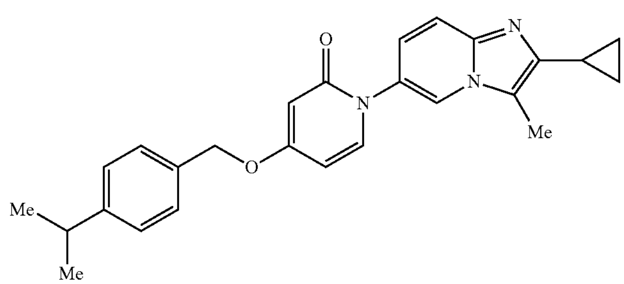 [SMILES: Cc1c(C2CC2)nc2ccc(-n3ccc(OCc4ccc(C(C)C)cc4)cc3=O)cn12] | 414.4 |

TABLE 1-continued

| Example | IUPAC Name | Structure | MS |
|---|---|---|---|
| 192 | 4-((4-bromobenzyl)oxy)-1-(2-cyclopropyl-3-methylimidazo[1,2-a]pyridin-6-yl)pyridin-2(1H)-one | 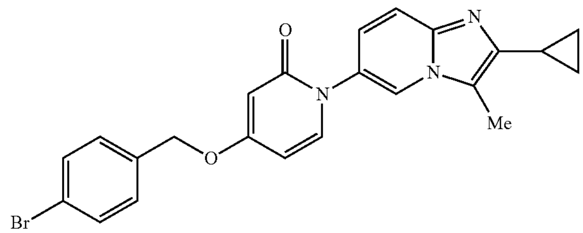 [SMILES: Cc1c(C2CC2)nc2ccc(-n3ccc(OCc4ccc(Br)cc4)cc3=O)cn12] | 450.3 |
| 193 | 1-(2-cyclopropyl-3-methylimidazo[1,2-a]pyridin-6-yl)-4-((4-(trifluoromethyl)-1,3-thiazol-2-yl)methoxy)pyridin-2(1H)-one | 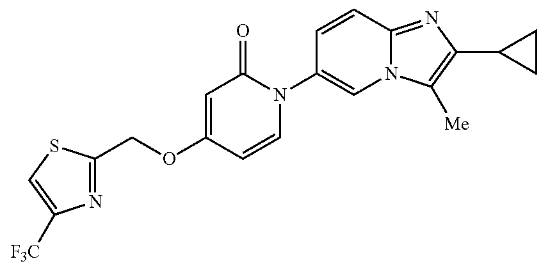 [SMILES: Cc1c(C2CC2)nc2ccc(-n3ccc(OCc4nc(C(F)(F)F)cs4)cc3=O)cn12] | 447.4 |
| 194 | 4-((4-bromo-1,3-thiazol-2-yl)methoxy)-1-(2-cyclopropyl-3-methylimidazo[1,2-a]pyridin-6-yl)pyridin-2(1H)-one | 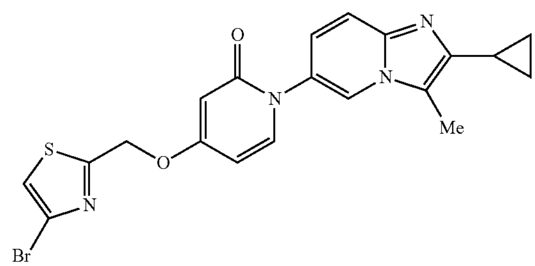 | 457.3 |
| 196 | 4-((5-chloro-1,2,4-thiadiazol-3-yl)methoxy)-1-(2-cyclopropyl-3-methylimidazo[1,2-a]pyridin-6-yl)pyridin-2(1H)-one | 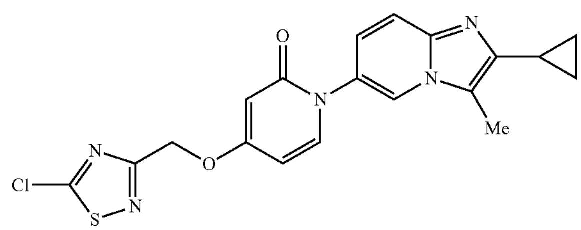 [SMILES: Cc1c(C2CC2)nc2ccc(-n3ccc(OCc4nsc(Cl)n4)cc3=O)cn12] | 414.3 |
| 200 | 1-(2-(2,4-dimethyl-1,3-oxazol-5-yl)-1-methyl-1H-benzimidazol-6-yl)-4-((4-fluorobenzyl)oxy)pyridin-2(1H)-one | 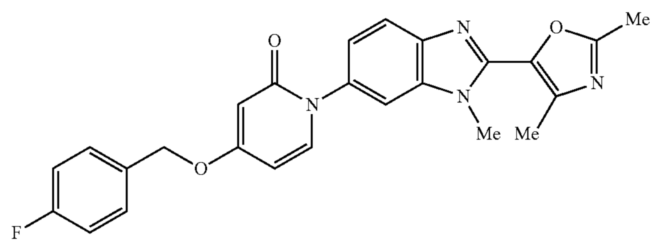 [SMILES: Cc1nc(C)c(-c2nc3ccc(-n4ccc(OCc5ccc(F)cc5)cc4=O)cc3n2C)o1] | 445.4 |
| 201 | 1-(2-(4-ethyl-1,3-oxazol-5-yl)-1-methyl-1H-benzimidazol-6-yl)-4-((4-fluorobenzyl)oxy)pyridin-2(1H)-one | 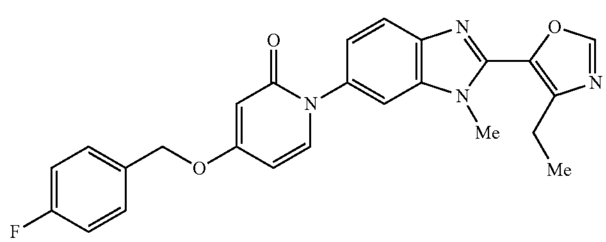 [SMILES: CCc1ncoc1-c1nc2ccc(-n3ccc(OCc4ccc(F)cc4)cc3=O)cc2n1C] | 445.4 |

TABLE 1-continued

| Example | IUPAC Name | Structure | MS |
|---|---|---|---|
| 202 | 4-((5-chloro-2-furyl)methoxy)-1-(2-cyclopropyl-1-methyl-1H-benzimidazol-6-yl)pyridin-2(1H)-one | 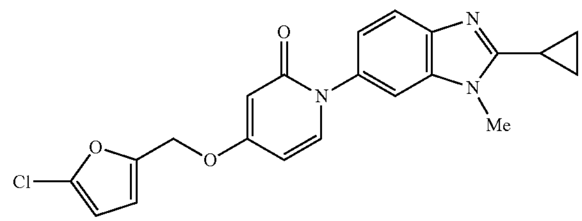 | 396.1 |
| 203 | 4-((5-chloro-2-thienyl)methoxy)-1-(2-((1RS,2SR)-2-(2-hydroxypropan-2-yl)cyclopropyl)-1-methyl-1H-benzimidazol-6-yl)pyridin-2(1H)-one | 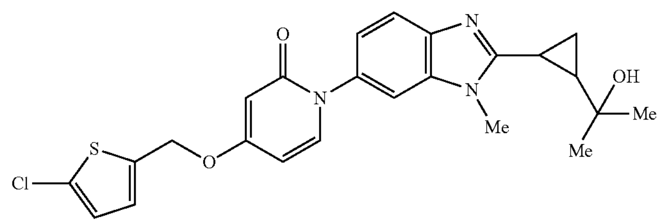 [SMILES: Cn1c(C2CC2C(C)(C)O)nc2ccc(-n3ccc(OCc4ccc(Cl)s4)cc3=O)cc21] | 470.1 |
| 204 | 4-((5-chloropyridin-2-yl)methoxy)-1-(2-((1RS,2SR)-2-(2-hydroxypropan-2-yl)cyclopropyl)-1-methyl-1H-benzimidazol-6-yl)pyridin-2(1H)-one | 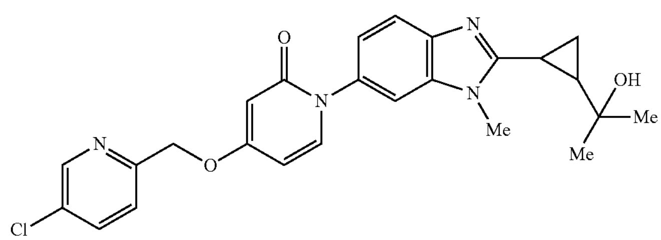 [SMILES: Cn1c(C2CC2C(C)(C)O)nc2ccc(-n3ccc(OCc4ccc(Cl)cn4)cc3=O)cc21] | 465.4 |
| 205 | 4-((4-fluorobenzyl)oxy)-1-(2-((1RS,2SR)-2-(2-hydroxypropan-2-yl)cyclopropyl)-1-methyl-1H-benzimidazol-6-yl)pyridin-2(1H)-one | 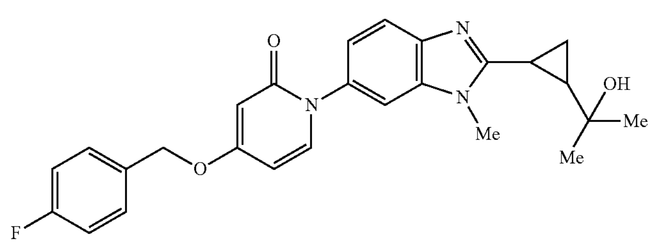 [SMILES: Cn1c(C2CC2C(C)(C)O)nc2ccc(-n3ccc(OCc4ccc(F)cc4)cc3=O)cc21] | 448.2 |
| 206 | 4-((4-chlorobenzyl)oxy)-1-(2-((1RS,2SR)-2-(3-hydroxypentan-3-yl)cyclopropyl)-1-methyl-1H-benzimidazol-6-yl)pyridin-2(1H)-one | 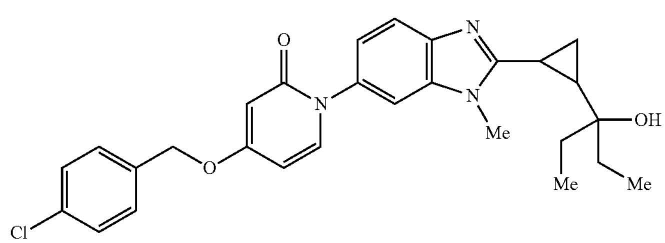 [SMILES: CCC(O)(CC)C1CC1c1nc2ccc(-n3ccc(OCc4ccc(Cl)cc4)cc3=O)cc2n1C] | 493.5 |
| 207 | 4-((4-chlorobenzyl)oxy)-1-(2-((1R*,2S*)-2-(2-fluoropropan-2-yl)cyclopropyl)-1-methyl-1H-benzimidazol-6-yl)pyridin-2(1H)-one (optically active, IA tR2) | 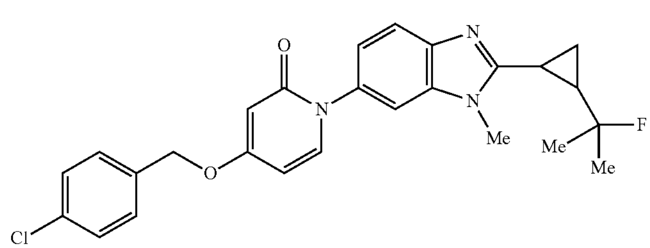 [SMILES: Cn1c(C2CC2C(C)(C)F)nc2ccc(-n3ccc(OCc4ccc(Cl)cc4)cc3=O)cc21] | 466.4 |

TABLE 1-continued

| Example | IUPAC Name | Structure | MS |
|---|---|---|---|
| 208 | 4-((4-chlorobenzyl)oxy)-1-(1-methyl-2-propanoyl-1H-benzimidazol-6-yl)pyridin-2(1H)-one | 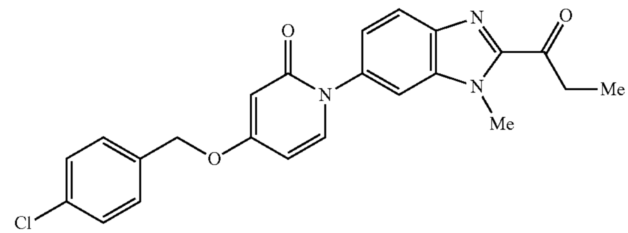 [SMILES: CCC(=O)c1nc2ccc(-n3ccc(OCc4ccc(Cl)cc4)cc3=O)cc2n1C] | 422.1 |
| 209 | 4-((4-chlorobenzyl)oxy)-1-(2-((1R*,2S*)-2-(2-fluoropropan-2-yl)cyclopropyl)-1-methyl-1H-benzimidazol-6-yl)pyridin-2(1H)-one (optically active, IA tR1) | 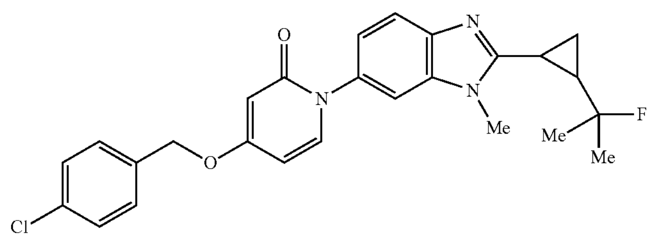 [SMILES: Cn1c(C2CC2C(C)(C)F)nc2ccc(-n3ccc(OCc4ccc(Cl)cc4)cc3=O)cc21] | 466.4 |
| 210 | 4-(benzyloxy)-1-(2-ethyl-1-methyl-1H-benzimidazol-6-yl)pyridin-2(1H)-one | 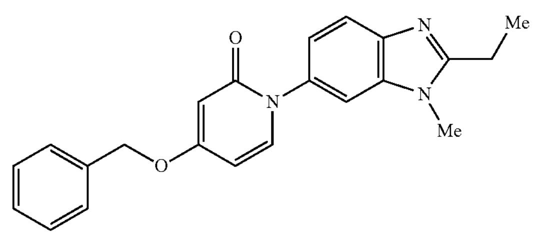 [SMILES: CCc1nc2ccc(-n3ccc(OCc4ccccc4)cc3=O)cc2n1C] | 360.3 |
| 211 | 4-((5-chlorothiophen-2-yl)methoxy)-1-(2-ethyl-1-methyl-1H-benzimidazol-6-yl)pyridin-2(1H)-one | 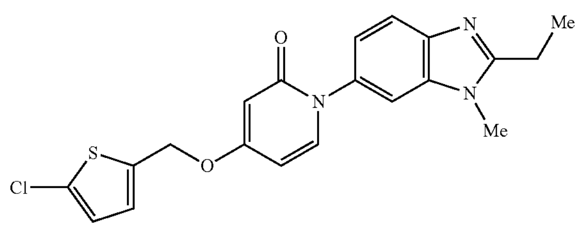 [SMILES: CCc1nc2ccc(-n3ccc(OCc4ccc(Cl)s4)cc3=O)cc2n1C] | 400.3 |
| 212 | 4-((3,4-difluorobenzyl)oxy)-1-(2-((1RS,2SR)-2-(2-hydroxypropan-2-yl)cyclopropyl)-1-methyl-1H-benzimidazol-6-yl)pyridin-2(1H)-one | 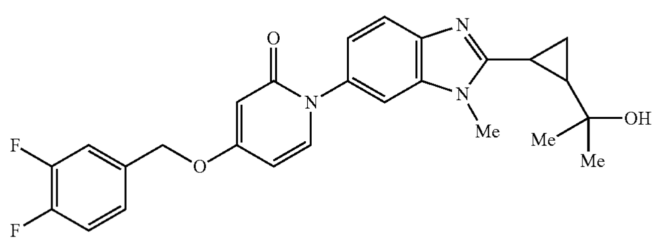 [SMILES: Cn1c(C2CC2C(C)(C)O)nc2ccc(-n3ccc(OCc4ccc(F)c(F)c4)cc3=O)cc21] | 466.4 |
| 213 | 1-(2-cyclopropyl-1-methyl-1H-benzimidazol-6-yl)-4-((5-methyl-3-thienyl)methoxy)pyridin-2(1H)-one | 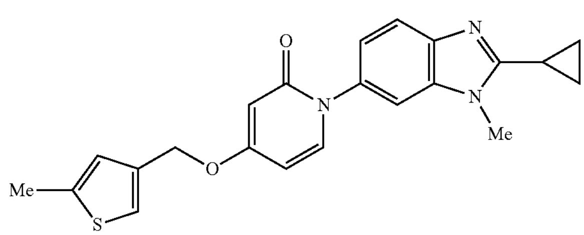 [SMILES: Cc1cc(COc2ccn(-c3ccc4nc(C5CC5)n(C)c4c3)c(=O)c2)cs1] | 392.1 |

TABLE 1-continued

| Example | IUPAC Name | Structure | MS |
|---|---|---|---|
| 214 | 1-(2-cyclopropyl-1-methyl-1H-benzimidazol-6-yl)-4-((2-methyl-3-thienyl)methoxy)pyridin-2(1H)-one | 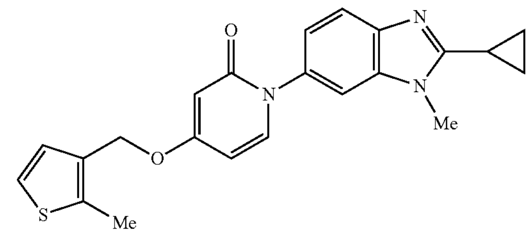 [SMILES: Cc1sccc1COc1ccn(-c2ccc3nc(C4CC4)n(C)c3c2)c(=O)c1] | 392.1 |
| 215 | 4-((5-chloro-3-thienyl)methoxy)-1-(2-((1RS,2SR)-2-(2-hydroxypropan-2-yl)cyclopropyl)-1-methyl-1H-benzimidazol-6-yl)pyridin-2(1H)-one | 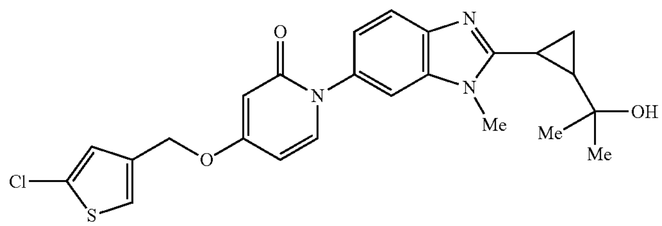 [SMILES: Cn1c(C2CC2C(C)(C)O)nc2ccc(-n3ccc(OCc4csc(Cl)c4)cc3=O)cc21] | 470.1 |
| 216 | 1-(2-cyclopropyl-1-methyl-1H-benzimidazol-6-yl)-4-((5-fluoro-3-thienyl)methoxy)pyridin-2(1H)-one | 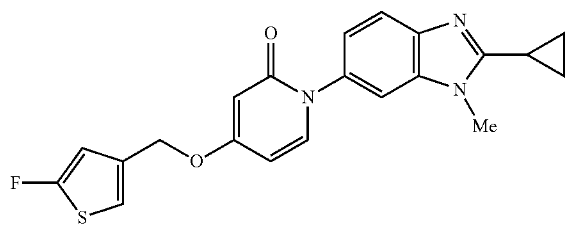 [SMILES: Cn1c(C2CC2)nc2ccc(-n3ccc(OCc4csc(F)c4)cc3=O)cc21] | 396.1 |
| 217 | 1-(2-cyclopropyl-1-methyl-1H-benzimidazol-6-yl)-4-((2-fluoro-3-thienyl)methoxy)pyridin-2(1H)-one | 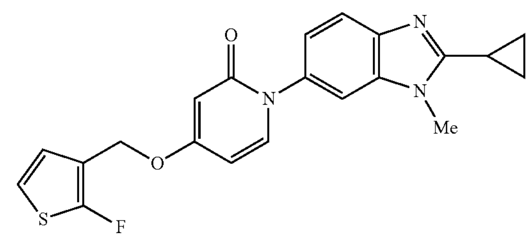 [SMILES: Cn1c(C2CC2)nc2ccc(-n3ccc(OCc4ccsc4F)cc3=O)cc21] | 396.1 |
| 218 | 3-(6-(4-((4-fluorobenzyl)oxy)-2-oxopyridin-1(2H)-yl)-1-methyl-1H-benzimidazol-2-yl)cyclobutanecarbonitrile (Retention time: short) | 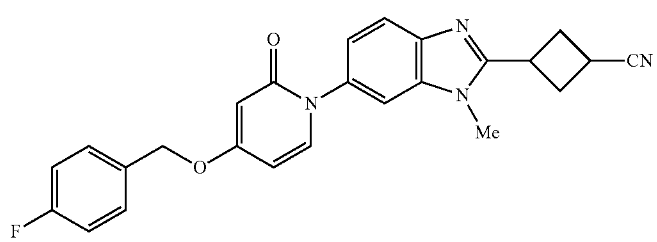 [SMILES: Cn1c(C2CC(C#N)C2)nc2ccc(-n3ccc(OCc4ccc(F)cc4)cc3=O)cc21] | 429.2 |
| 219 | 4((4-fluorobenzyl)oxy)-1-(1-methyl-2-(1-methyl-1H-pyrazol-5-yl)-1H-benzimidazol-6-yl)pyridin-2(1H)-one | 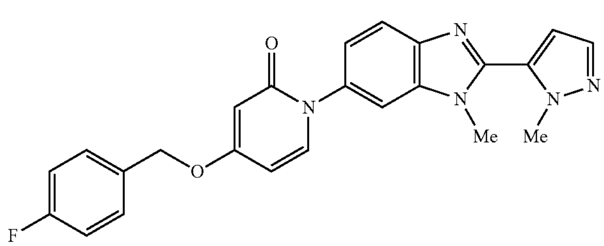 [SMILES: Cn1nccc1-c1nc2ccc(-n3ccc(OCc4ccc(F)cc4)cc3=O)cc2n1C] | 430.4 |

TABLE 1-continued

| Example | IUPAC Name | Structure | MS |
|---|---|---|---|
| 220 | 4-((4-chloro-3-fluorobenzyl)oxy)-1-(2-((1RS,2SR)-2-(2-hydroxypropan-2-yl)cyclopropyl)-1-methyl-1H-benzimidazol-6-yl)pyridin-2(1H)-one | 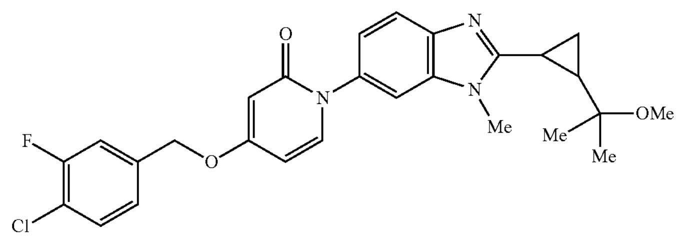 [SMILES: COC(C)(C)C1CC1c1nc2ccc(-n3ccc(OCc4ccc(Cl)c(F)c4)cc3=O)cc2n1C] | 482.2 |
| 221 | 4-((2-chloro-3-thienyl)methoxy)-1-(2-cyclopropyl-1-methyl-1H-benzimidazol-6-yl)pyridin-2(1H)-one | 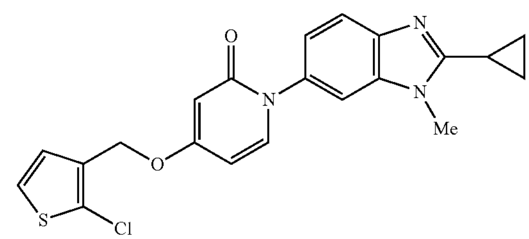 [SMILES: Cn1c(C2CC2)nc2ccc(-n3ccc(OCc4ccsc4Cl)cc3=O)cc21] | 412.1 |
| 222 | 4-((3-chloro-4-fluorobenzyl)oxy)-1-(2-((1RS,2SR)-2-(2-hydroxypropan-2-yl)cyclopropyl)-1-methyl-1H-benzimidazol-6-yl)pyridin-2(1H)-one | 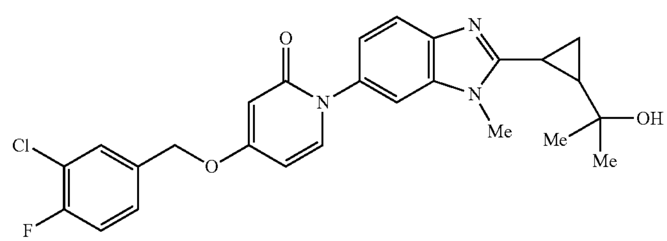 [SMILES: Cn1c(C2CC2C(C)(C)O)nc2ccc(-n3ccc(OCc4ccc(F)c(Cl)c4)cc3=O)cc21] | 482.2 |
| 223 | 4-((4-chlorobenzyl)oxy)-1-(2-((1RS,2SR)-2-(2-hydroxypropan-2-yl)cyclobutyl)-1-methyl-1H-benzimidazol-6-yl)pyridin-2(1H)-one | 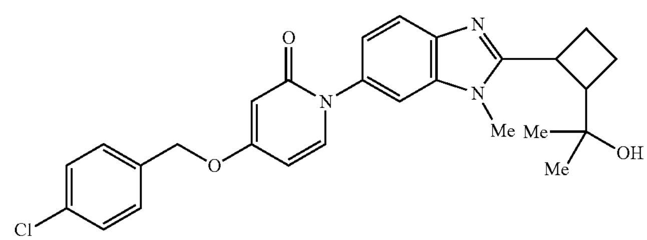 [SMILES: Cn1c(C2CCC2C(C)(C)O)nc2ccc(-n3ccc(OCc4ccc(Cl)cc4)cc3=O)cc21] | 478.4 |
| 224 | (1RS,2SR)-2-(6-(4-((4-chlorobenzyl)oxy)-2-oxopyridin-1(2H)-yl)-1-methyl-1H-benzimidazol-2-yl)cyclobutanecarbonitrile | 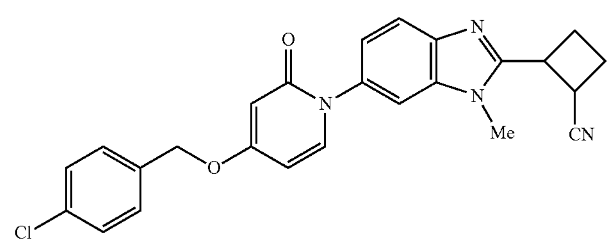 [SMILES: Cn1c(C2CCC2C#N)nc2ccc(-n3ccc(OCc4ccc(Cl)cc4)cc3=O)cc21] | 445.4 |
| 225 | 3-(6-(4-((4-fluorobenzyl)oxy)-2-oxopyridin-1(2H)-yl)-1-methyl-1H-benzimidazol-2-yl)cyclobutanecarbonitrile (Retention time: long) | 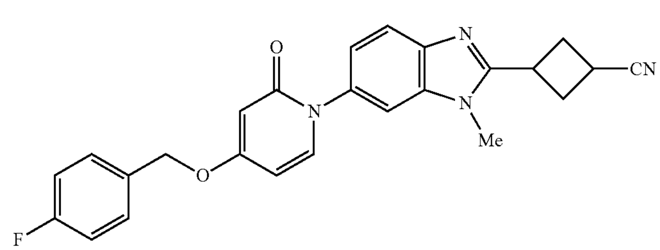 [SMILES: Cn1c(C2CC(C#N)C2)nc2ccc(-n3ccc(OCc4ccc(F)cc4)cc3=O)cc21] | 429.2 |

TABLE 1-continued

| Example | IUPAC Name | Structure | MS |
|---|---|---|---|
| 226 | 4-((5-chloro-3-thienyl)methoxy)-1-(2-ethyl-1-methyl-1H-benzimidazol-6-yl)pyridin-2(1H)-one | 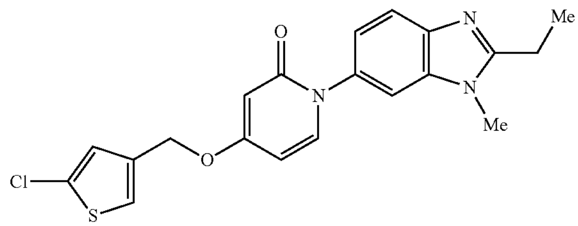 [SMILES: CCc1nc2ccc(-n3ccc(OCc4csc(Cl)c4)cc3=O)cc2n1C] | 400.3 |
| 227 | 1-(2-cyclopropyl-1-methyl-1H-benzimidazol-6-yl)-4-((2,5-dichloro-3-thienyl)methoxy)pyridin-2(1H)-one | 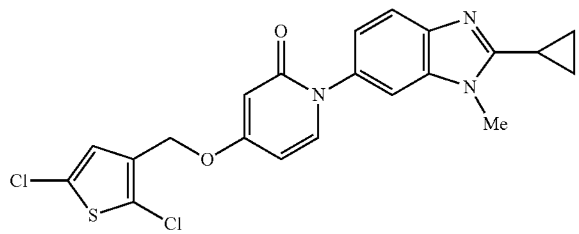 [SMILES: Cn1c(C2CC2)nc2ccc(-n3ccc(OCc4cc(Cl)sc4Cl)cc3=O)cc21] | 447.1 |
| 228 | 4-((4-chlorothiophen-2-yl)methoxy)-1-(2-cyclopropyl-1-methyl-1H-benzimidazol-6-yl)pyridin-2(1H)-one | 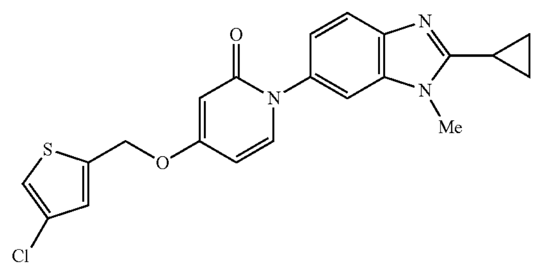 [SMILES: Cn1c(C2CC2)nc2ccc(-n3ccc(OCc4cc(Cl)cs4)cc3=O)cc21] | 412.2 |
| 229 | 4-((4-chloro-3-fluorobenzyl)oxy)-1-(2-ethyl-1-methyl-1H-benzimidazol-6-yl)pyridin-2(1H)-one | 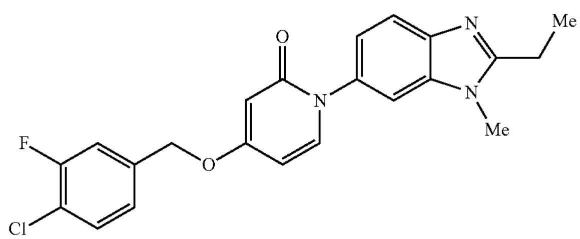 [SMILES: CCc1nc2ccc(-n3ccc(OCc4ccc(Cl)c(F)c4)cc3=O)cc2n1C] | 412.3 |
| 230 | (1RS,2SR)-2-(6-(4-(benzyloxy)-2-oxopyridin-1(2H)-yl)-1-methyl-1H-benzimidazol-2-yl)cyclopropanecarbonitrile | 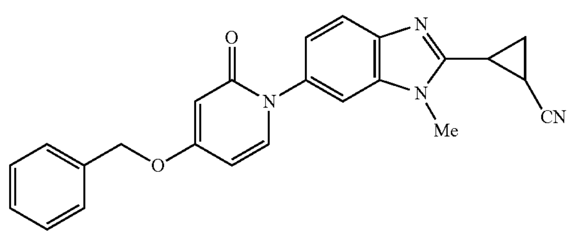 [SMILES: Cn1c(C2CC2C#N)nc2ccc(-n3ccc(OCc4ccccc4)cc3=O)cc21] | 397.4 |
| 231 | 1-(2-ethyl-1-methyl-1H-benzimidazol-6-yl)-4-((5-fluoro-3-thienyl)methoxy)pyridin-2(1H)-one | 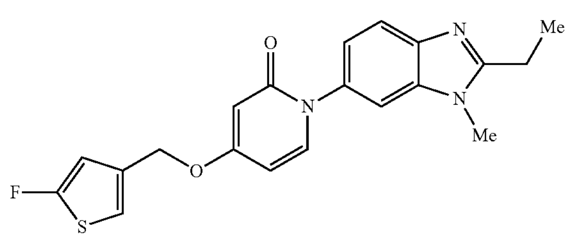 [SMILES: CCc1nc2ccc(-n3ccc(OCc4csc(F)c4)cc3=O)cc2n1C] | 384.3 |

TABLE 1-continued

| Example | IUPAC Name | Structure | MS |
|---|---|---|---|
| 232 | 4-((4-bromo-5-chloro-2-thienyl)methoxy)-1-(2-cyclopropyl-1-methyl-1H-benzimidazol-6-yl)pyridin-2(1H)-one | 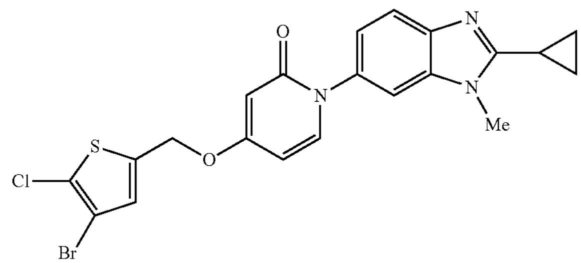 [SMILES: Cn1c(C2CC2)nc2ccc(-n3ccc(OCc4cc(Br)c(Cl)s4)cc3=O)cc21] | 491.3 |
| 233 | 1-(2-ethyl-1-methyl-1H-benzimidazol-6-yl)-4-((5-(trifluoromethyl)-2-thienyl)methoxy)pyridin-2(1H)-one | 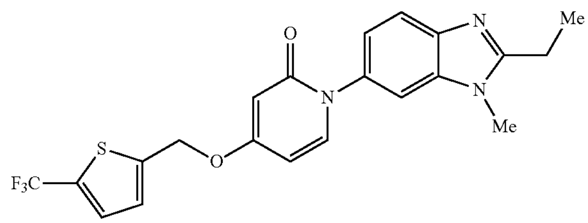 [SMILES: CCc1nc2ccc(-n3ccc(OCc4ccc(C(F)(F)F)s4)cc3=O)cc2n1C] | 434.3 |
| 234 | 1-(2-ethyl-1-methyl-1H-benzimidazol-6-yl)-4-((2-fluoro-3-thienyl)methoxy)pyridin-2(1H)-one | 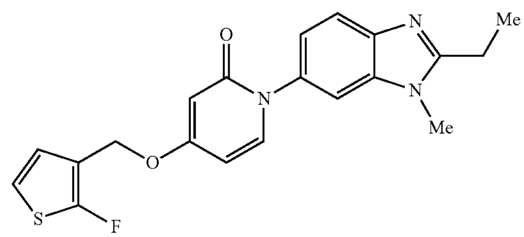 [SMILES: CCc1nc2ccc(-n3ccc(OCc4ccsc4F)cc3=O)cc2n1C] | 384.3 |
| 235 | 1-(2-ethyl-1-methyl-1H-benzimidazol-6-yl)-4-(3-thienylmethoxy)pyridin-2(1H)-one | 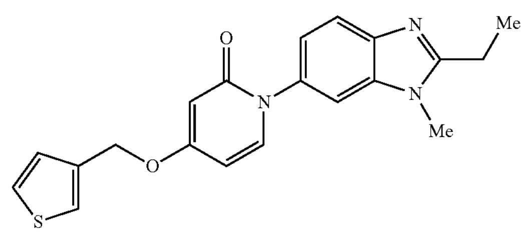 [SMILES: CCc1nc2ccc(-n3ccc(OCc4ccsc4)cc3=O)cc2n1C] | 366.3 |
| 236 | 4-((4-chlorothiophen-2-yl)methoxy)-1-(2-ethyl-1-methyl-1H-benzimidazol-6-yl)pyridin-2(1H)-one | 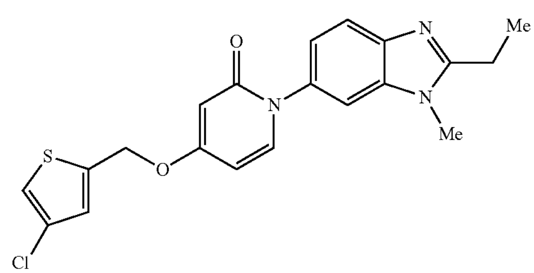 [SMILES: CCc1nc2ccc(-n3ccc(OCc4cc(Cl)cs4)cc3=O)cc2n1C] | 400.0 |
| 237 | (1R*,2S*)-2-(6-(4-((4-chlorobenzyl)oxy)-2-oxopyridin-1(2H)-yl)-1-methyl-1H-benzimidazol-2-yl)cyclopropanecarbonitrile hydrochloride (optically active, IC tR1) | 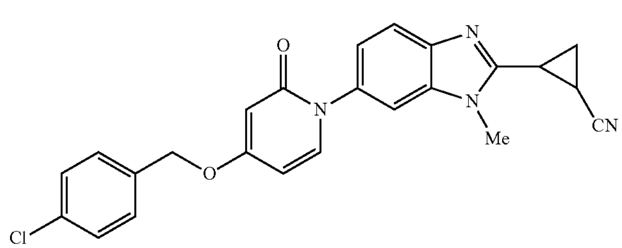 [SMILES: Cn1c(C2CC2C#N)nc2ccc(-n3ccc(OCc4ccc(Cl)cc4)cc3=O)cc21] | 431.4 |

TABLE 1-continued

| Example | IUPAC Name | Structure | MS |
|---|---|---|---|
| 238 | (1R*,2S*)-2-(6-(4-((4-chlorobenzyl)oxy)-2-oxopyridin-1(2H)-yl)-1-methyl-1H-benzimidazol-2-yl)cyclopropanecarbonitrile hydrochloride (optically active, IC tR2) | 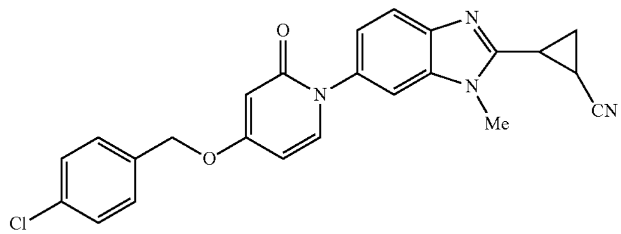 [SMILES: Cn1c(C2CC2C#N)nc2ccc(-n3ccc(OCc4ccc(Cl)cc4)cc3=O)cc21] | 431.4 |
| 239 | 1-(2-cyclopropyl-1-methyl-1H-benzimidazol-6-yl)-4-((4,5-difluoro-2-thienyl)methoxy)pyridin-2(1H)-one | 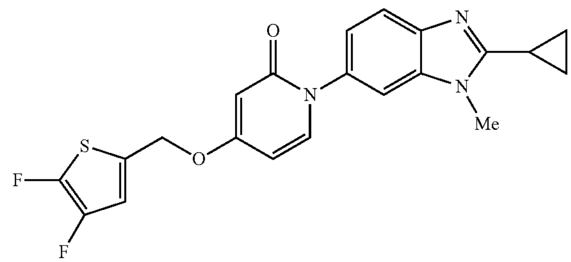 [SMILES: Cn1c(C2CC2)nc2ccc(-n3ccc(OCc4cc(F)c(F)s4)cc3=O)cc21] | 414.1 |
| 240 | 4-((4-bromo-2-thienyl)methoxy)-1-(2-cyclopropyl-1-methyl-1H-benzimidazol-6-yl)pyridin-2(1H)-one | 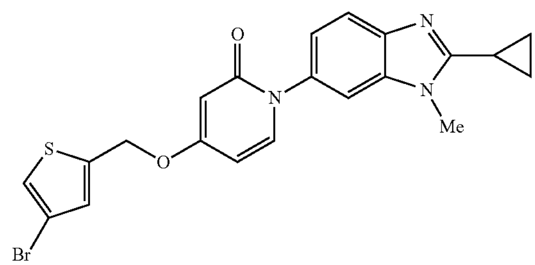 [SMILES: Cn1c(C2CC2)nc2ccc(-n3ccc(OCc4cc(Br)cs4)cc3=O)cc21] | 457.1 |
| 241 | 1-(2-cyclopropyl-1-methyl-1H-benzimidazol-6-yl)-4-((5-(trifluoromethyl)-2-furyl)methoxy)pyridin-2(1H)-one | 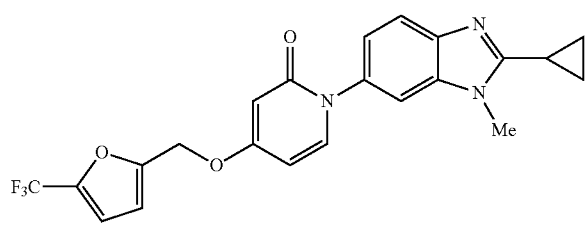 [SMILES: Cn1c(C2CC2)nc2ccc(-n3ccc(OCc4ccc(C(F)(F)F)o4)cc3=O)cc21] | 430.1 |
| 242 | 1-(2-cyclopropyl-1-methyl-1H-benzimidazol-6-yl)-4-((5-(trifluoromethyl)-2-thienyl)methoxy)pyridin-2(1H)-one hydrochloride | 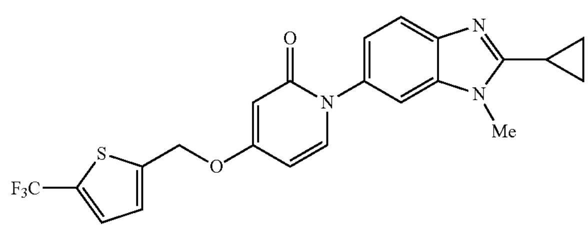 | 446.4 |
| 243 | 1-(2-cyclopropyl-1-methyl-1H-benzimidazol-6-yl)-4-((4-fluorophenoxy)methyl)pyridin-2(1H)-one | 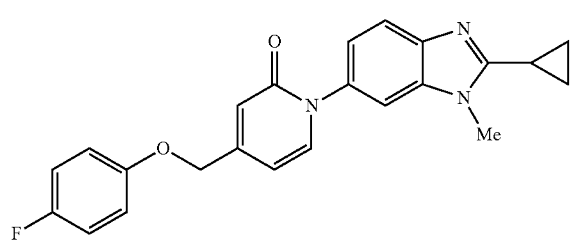 [SMILES: Cn1c(C2CC2)nc2ccc(-n3ccc(COc4ccc(F)cc4)cc3=O)cc21] | 390.2 |

TABLE 1-continued

| Example | IUPAC Name | Structure | MS |
|---|---|---|---|
| 244 | 4-((4-bromo-5-fluoro-2-thienyl)methoxy)-1-(2-cyclopropyl-1-methyl-1H-benzimidazol-6-yl)pyridin-2(1H)-one | 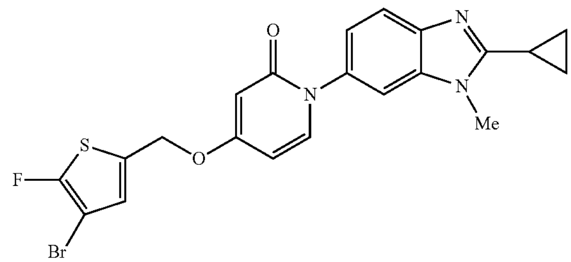 [SMILES: Cn1c(C2CC2)nc2ccc(-n3ccc(OCc4cc(Br)c(F)s4)cc3=O)cc21] | 475.0 |
| 245 | 4-((4-chlorophenoxy)methyl)-1-(2-cyclopropyl-1-methyl-1H-benzimidazol-6-yl)pyridin-2(1H)-one | 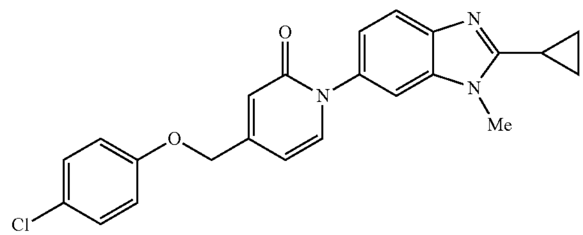 [SMILES: Cn1c(C2CC2)nc2ccc(-n3ccc(COc4ccc(Cl)cc4)cc3=O)cc21] | 406.0 |
| 246 | 1-(2-ethyl-1-methyl-1H-benzimidazol-6-yl)-4-((5-fluorothiophen-2-yl)methoxy)pyridin-2(1H)-one | 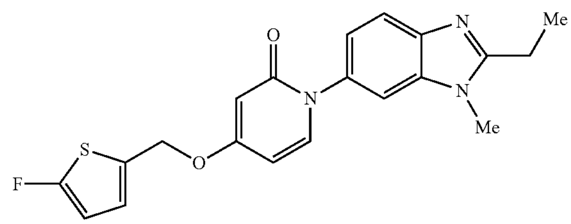 [SMILES: CCc1nc2ccc(-n3ccc(OCc4ccc(F)s4)cc3=O)cc2n1C] | 384.0 |
| 247 | 1-(2-cyclopropyl-1-methyl-1H-benzimidazol-6-yl)-4-((4-(trifluoromethyl)phenoxy)methyl)pyridin-2(1H)-one | 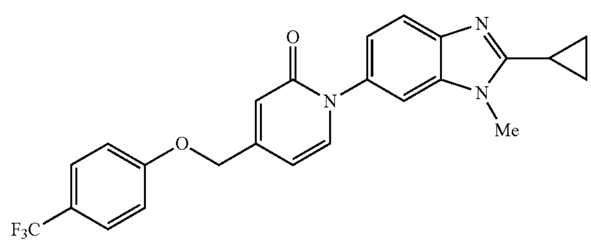 [SMILES: Cn1c(C2CC2)nc2ccc(-n3ccc(COc4ccc(C(F)(F)F)cc4)cc3=O)cc21] | 440.2 |
| 248 | 1-(2-cyclopropyl-1-methyl-1H-benzimidazol-6-yl)-4-((5-(difluoromethyl)-2-thienyl)methoxy)pyridin-2(1H)-one | 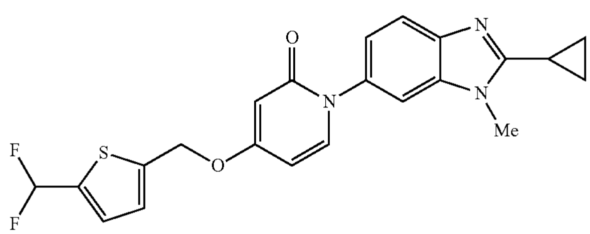 [SMILES: Cn1c(C2CC2)nc2ccc(-n3ccc(OCc4ccc(C(F)F)s4)cc3=O)cc21] | 428.3 |
| 249 | 4-(((5-chloropyridin-2-yl)oxy)methyl)-1-(2-cyclopropyl-1-methyl-1H-benzimidazol-6-yl)pyridin-2(1H)-one | 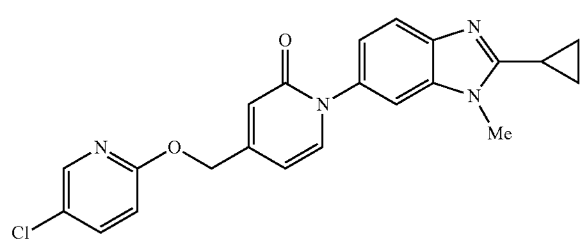 [SMILES: Cn1c(C2CC2)nc2ccc(-n3ccc(COc4ccc(Cl)cn4)cc3=O)cc21] | 407.2 |

TABLE 1-continued

| Example | IUPAC Name | MS |
|---|---|---|
| 250 | 4-((5-bromo-3-thienyl)methoxy)-1-(2-cyclopropyl-1-methyl-1H-benzimidazol-6-yl)pyridin-2(1H)-one | 456.0 |
| 251 | 1-(2-cyclopropyl-1-methyl-1H-benzimidazol-6-yl)-4-(((5-(trifluoromethyl)pyridin-2-yl)oxy)methyl)pyridin-2(1H)-one | 441.2 |
| 252 | 1-(2-cyclopropyl-1-methyl-1H-benzimidazol-6-yl)-4-((5-(trifluoromethyl)-3-thienyl)methoxy)pyridin-2(1H)-one | 446.3 |
| 253 | 4-((1RS,2RS)-2-(4-chlorophenyl)cyclopropyl)-1-(2-cyclopropyl-1-methyl-1H-benzimidazol-6-yl)pyridin-2(1H)-one | 416.1 |
| 254 | 1-(1,2-dimethyl-1H-benzimidazol-6-yl)-4-((4-fluorobenzyl)oxy)pyridin-2(1H)-one | 364.3 |
| 255 | 4-(1-benzothiophen-5-ylmethoxy)-1-(2-cyclopropyl-1-methyl-1H-benzimidazol-6-yl)pyridin-2(1H)-one | 428.3 |

TABLE 1-continued

| Example | IUPAC Name | Structure | MS |
|---|---|---|---|
| 256 | 1-(2-cyclopropyl-1-methyl-1H-benzimidazol-6-yl)-4-((4-(trifluoromethyl)-1,3-thiazol-2-yl)methoxy)pyridin-2(1H)-one | 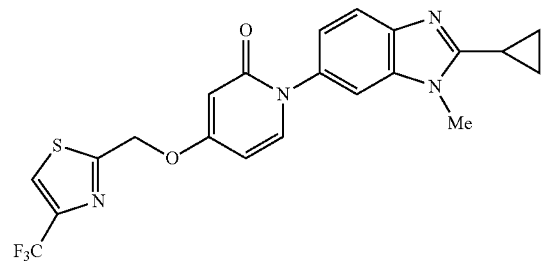 [SMILES: Cn1c(C2CC2)nc2ccc(-n3ccc(OCc4nc(C(F)(F)F)cs4)cc3=O)cc21] | 447.3 |
| 257 | 1-(2-cyclopropyl-1-methyl-1H-benzimidazol-6-yl)-4-(2,3-dihydro-1-benzofuran-5-ylmethoxy)pyridin-2(1H)-one | 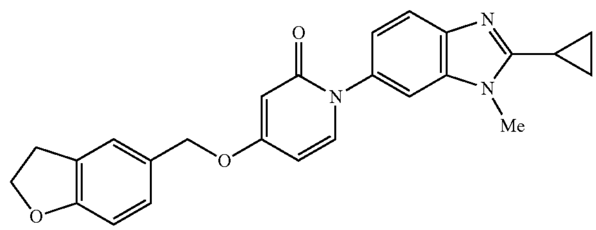 [SMILES: Cn1c(C2CC2)nc2ccc(-n3ccc(OCc4ccc5c(c4)CCO5)cc3=O)cc21] | 414.4 |
| 258 | 4-((5-chloro-1,2,4-thiadiazol-3-yl)methoxy)-1-(2-cyclopropyl-1-methyl-1H-benzimidazol-6-yl)pyridin-2(1H)-one | 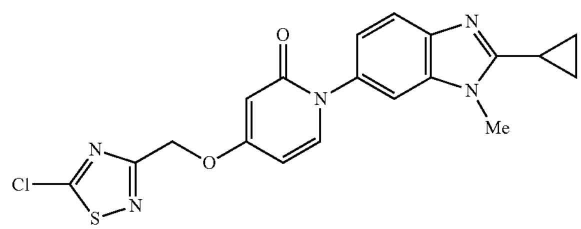 [SMILES: Cn1c(C2CC2)nc2ccc(-n3ccc(OCc4nsc(Cl)n4)cc3=O)cc21] | 414.3 |
| 259 | 4-((5-bromo-2-furyl)methoxy)-1-(2-cyclopropyl-1-methyl-1H-benzimidazol-6-yl)pyridin-2(1H)-one | 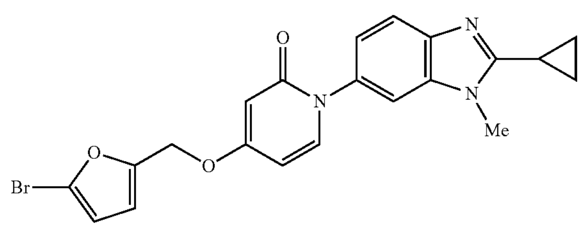 | 441.1 |
| 260 | 4-((5-bromopyridin-2-yl)methoxy)-1-(2-cyclopropyl-1-methyl-1H-benzimidazol-6-yl)pyridin-2(1H)-one | 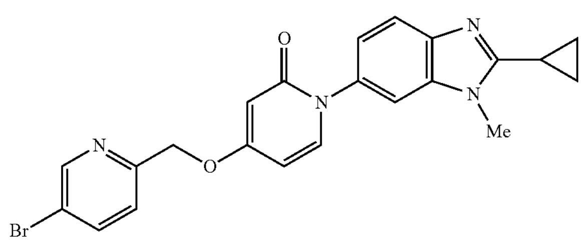 | 452.3 |
| 261 | 1-(2-ethyl-1-methyl-1H-benzimidazol-6-yl)-4-((4-(trifluoromethyl)-1,3-thiazol-2-yl)methoxy)pyridin-2(1H)-one | 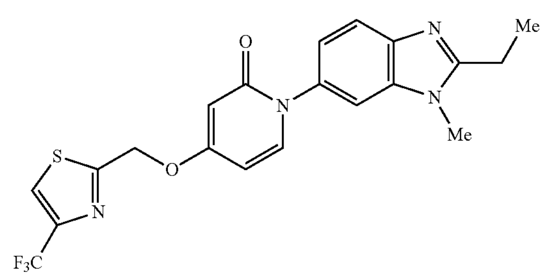 [SMILES: CCc1nc2ccc(-n3ccc(OCc4nc(C(F)(F)F)cs4)cc3=O)cc2n1C] | 435.1 |

TABLE 1-continued

| Example | IUPAC Name | Structure | MS |
|---------|------------|-----------|-----|
| 262 | 4-((5-bromo-3-furyl)methoxy)-1-(2-cyclopropyl-1-methyl-1H-benzimidazol-6-yl)pyridin-2(1H)-one | 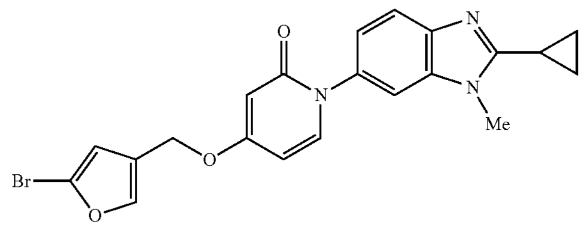 [SMILES: Cn1c(C2CC2)nc2ccc(-n3ccc(OCc4coc(Br)c4)cc3=O)cc21] | 441.1 |
| 263 | 1-(2-cyclopropyl-3-methylimidazo[1,2-a]pyridin-6-yl)-4-(pyridin-2-ylmethoxy)pyridin-2(1H)-one hydrochloride | 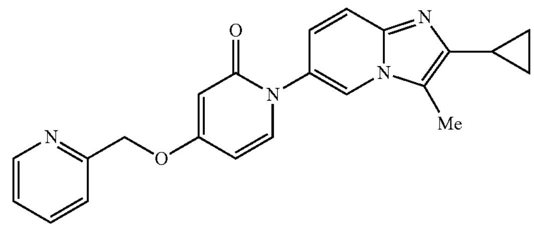 [SMILES: Cc1c(C2CC2)nc2ccc(-n3ccc(OCc4ccccn4)cc3=O)cn12] | 373.2 |
| 264 | 4-((5-chloropyrimidin-2-yl)methoxy)-1-(2-cyclopropyl-1-methyl-1H-benzimidazol-6-yl)pyridin-2(1H)-one | 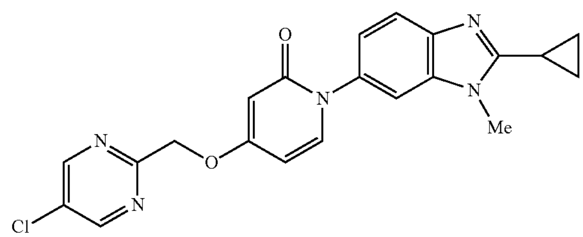 [SMILES: Cn1c(C2CC2)nc2ccc(-n3ccc(OCc4ncc(Cl)cn4)cc3=O)cc21] | 408.3 |
| 265 | 1-(2-ethyl-1-methyl-1H-benzimidazol-6-yl)-4-((5-(trifluoromethyl)-3-thienyl)methoxy)pyridin-2(1H)-one | 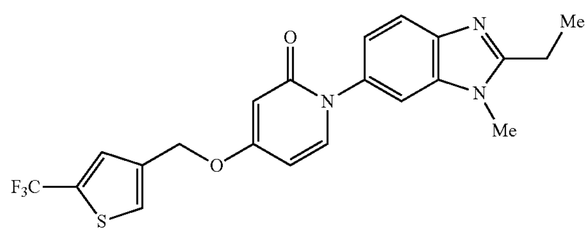 [SMILES: CCc1nc2ccc(-n3ccc(OCc4csc(C(F)(F)F)c4)cc3=O)cc2n1C] | 434.3 |
| 266 | 1-(2-cyclopropyl-1-methyl-1H-benzimidazol-6-yl)-4-((2-(trifluoromethyl)-1,3-thiazol-4-yl)methoxy)pyridin-2(1H)-one | 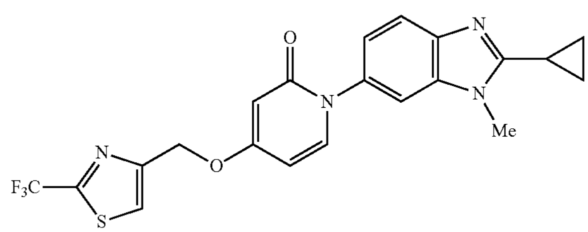 [SMILES: Cn1c(C2CC2)nc2ccc(-n3ccc(OCc4csc(C(F)(F)F)n4)cc3=O)cc21] | 447.3 |
| 267 | 1-(2-cyclopropyl-1-methyl-1H-benzimidazol-6-yl)-4-((5-(trifluoromethyl)pyrazin-2-yl)methoxy)pyridin-2(1H)-one | 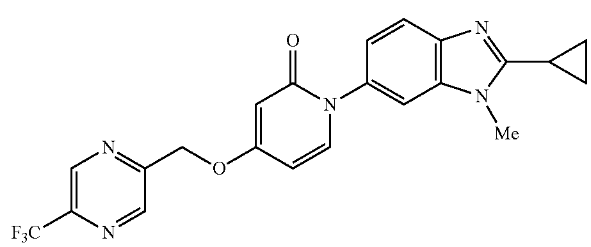 [SMILES: Cn1c(C2CC2)nc2ccc(-n3ccc(OCc4cnc(C(F)(F)F)cn4)cc3=O)cc21] | 442.1 |

TABLE 1-continued

| Example | IUPAC Name | Structure | MS |
|---|---|---|---|
| 268 | 1-(2-cyclopropyl-1-methyl-1H-benzimidazol-6-yl)-4-((4-methyl-1,3-thiazol-2-yl)methoxy)pyridin-2(1H)-one | 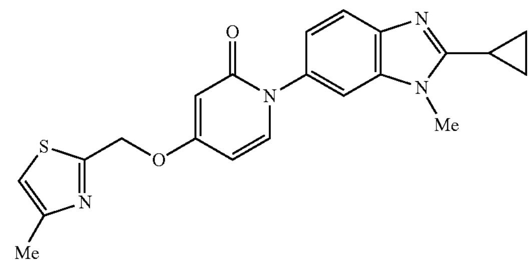 [SMILES: Cc1csc(COc2ccn(-c3ccc4nc(C5CC5)n(C)c4c3)c(=O)c2)n1] | 393.1 |
| 269 | 2-(((1-(2-cyclopropyl-1-methyl-1H-benzimidazol-6-yl)-2-oxo-1,2-dihydropyridin-4-yl)oxy)methyl)-1,3-thiazole-4-carbonitrile | 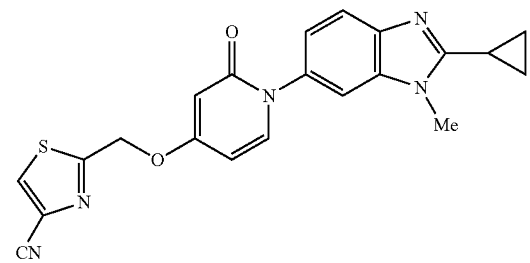 [SMILES: Cn1c(C2CC2)nc2ccc(-n3ccc(OCc4nc(C#N)cs4)cc3=O)cc21] | 404.3 |
| 270 | 1-(2-cyclopropyl-1-methyl-1H-benzimidazol-6-yl)-4-((4-(fluoromethyl)-1,3-thiazol-2-yl)methoxy)pyridin-2(1H)-one | 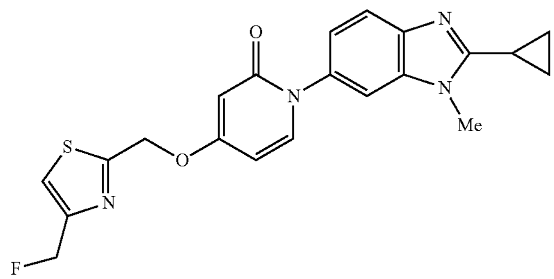 [SMILES: Cn1c(C2CC2)nc2ccc(-n3ccc(OCc4nc(CF)cs4)cc3=O)cc21] | 411.1 |
| 271 | 4-((5-chloro-1,3-thiazol-2-yl)methoxy)-1-(2-cyclopropyl-1-methyl-1H-benzimidazol-6-yl)pyridin-2(1H)-one | 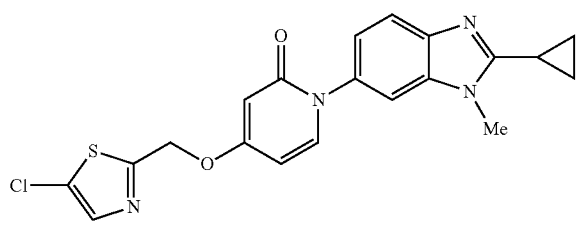 [SMILES: Cn1c(C2CC2)nc2ccc(-n3ccc(OCc4ncc(Cl)s4)cc3=O)cc21] | 413.1 |
| 272 | 4-((5-chloro-1,3-thiazol-2-yl)methoxy)-1-(2-ethyl-1-methyl-1H-benzimidazol-6-yl)pyridin-2(1H)-one | 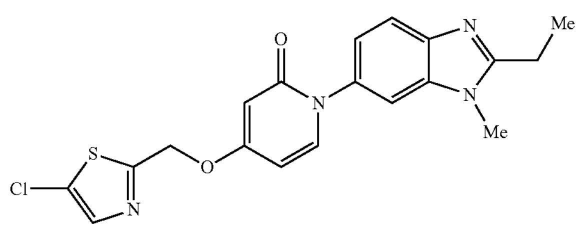 [SMILES: CCc1nc2ccc(-n3ccc(OCc4ncc(Cl)s4)cc3=O)cc2n1C] | 401.2 |
| 273 | 1-(2-cyclopropyl-1-methyl-1H-benzimidazol-6-yl)-4-((2-(trifluoromethyl)-1,3-thiazol-5-yl)methoxy)pyridin-2(1H)-one | 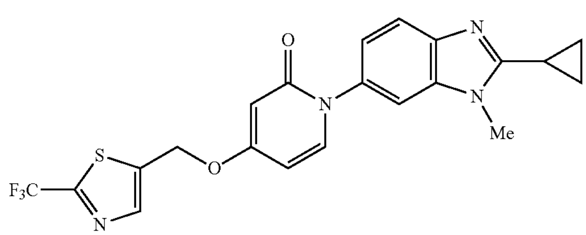 [SMILES: Cn1c(C2CC2)nc2ccc(-n3ccc(OCc4cnc(C(F)(F)F)s4)cc3=O)cc21] | 447.3 |

TABLE 1-continued

| Example | IUPAC Name | Structure | MS |
|---------|-----------|-----------|-----|
| 274 | 1-(2-cyclopropyl-1-methyl-1H-benzimidazol-6-yl)-4-((4-(methylsulfonyl)benzyl)oxy)pyridin-2(1H)-one | 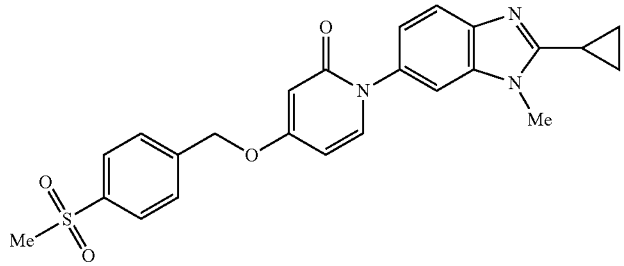 [SMILES: Cn1c(C2CC2)nc2ccc(-n3ccc(OCc4ccc(S(C)(=O)=O)cc4)cc3=O)cc21] | 450.1 |
| 275 | 1-(2-cyclopropyl-1-methyl-1H-benzimidazol-6-yl)-4-((4-(trifluoromethyl)-2-thienyl)methoxy)pyridin-2(1H)-one | 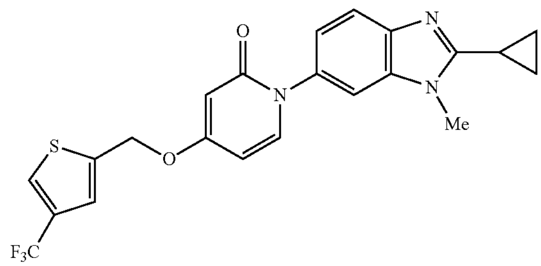 [SMILES: Cn1c(C2CC2)nc2ccc(-n3ccc(OCc4cc(C(F)(F)F)cs4)cc3=O)cc21] | 446.3 |
| 276 | 1-(2-ethyl-1-methyl-1H-benzimidazol-6-yl)-4((4-(trifluoromethyl)-2-thienyl)methoxy)pyridin-2(1H)-one | 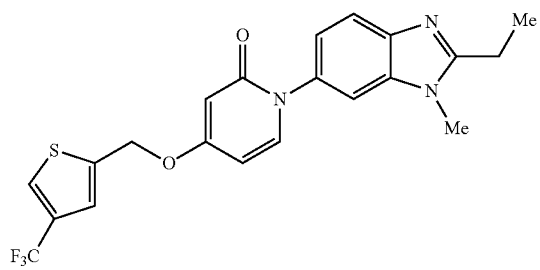 [SMILES: CCc1nc2ccc(-n3ccc(OCc4cc(C(F)(F)F)cs4)cc3=O)cc2n1C] | 434.3 |
| 277 | 1-(2-cyclopropyl-1-methyl-1H-benzimidazol-6-yl)-4-((4-cyclopropyl-1,3-thiazol-2-yl)methoxy)pyridin-2(1H)-one | 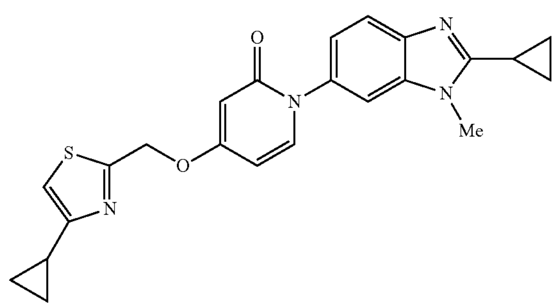 [SMILES: Cn1c(C2CC2)nc2ccc(-n3ccc(OCc4nc(C5CC5)cs4)cc3=O)cc21] | 419.1 |
| 278 | 1-(2-cyclopropyl-1-methyl-1H-benzimidazol-6-yl)-4-((2-(pentafluoroethyl)-1,3-thiazol-4-yl)methoxy)pyridin-2(1H)-one | 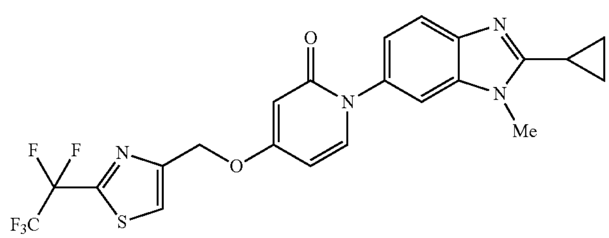 [SMILES: Cn1c(C2CC2)nc2ccc(-n3ccc(OCc4csc(C(F)(F)C(F)(F)F)n4)cc3=O)cc21] | 497.1 |
| 279 | 1-(2-ethyl-1-methyl-1H-benzimidazol-6-yl)-4-((2-(pentafluoroethyl)-1,3-thiazol-4-yl)methoxy)pyridin-2(1H)-one | 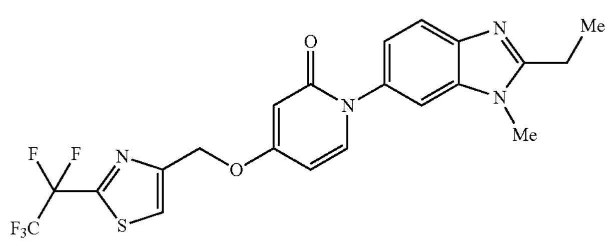 [SMILES: CCc1nc2ccc(-n3ccc(OCc4csc(C(F)(F)C(F)(F)F)n4)cc3=O)cc2n1C] | 485.1 |

TABLE 1-continued

| Example | IUPAC Name | Structure | MS |
|---|---|---|---|
| 280 | 4-((2-chlorobenzyl)oxy)-1-(2-cyclopropyl-1-methyl-1H-benzimidazol-6-yl)pyridin-2(1H)-one | 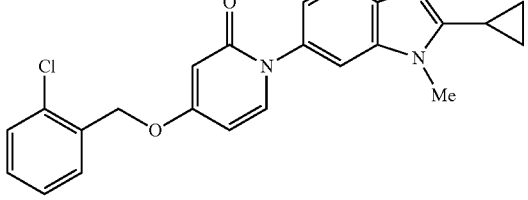 | 406.1 |
| 281 | 1-(2-cyclopropyl-1-methyl-1H-benzimidazol-6-yl)-4-((2,2-difluoro-1,3-benzodioxol-5-yl)methoxy)pyridin-2(1H)-one | 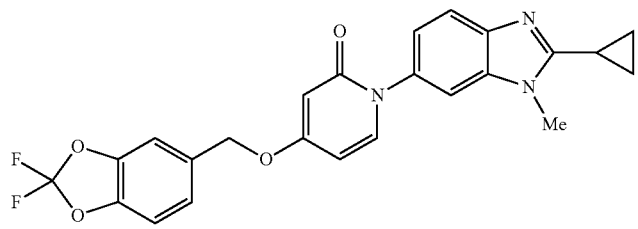 [SMILES: Cn1c(C2CC2)nc2ccc(-n3ccc(OCc4ccc5c(c4)OC(F)(F)O5)cc3=O)cc21] | 452.1 |
| 282 | 2-(((1-(2-cyclopropyl-3-methylimidazo[1,2-a]pyridin-6-yl)-2-oxo-1,2-dihydropyridin-4-yl)oxy)methyl)-5-fluorobenzonitrile | 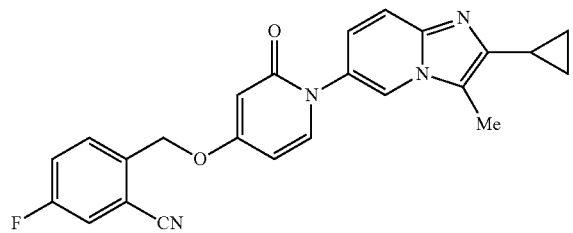 [SMILES: Cc1c(C2CC2)nc2ccc(-n3ccc(OCc4ccc(F)cc4C#N)cc3=O)cn12] | 415.3 |
| 283 | 1-(2-cyclopropyl-1-methyl-1H-benzimidazol-6-yl)-4-((4-(difluoromethyl)-1,3-thiazol-2-yl)methoxy)pyridin-2(1H)-one | 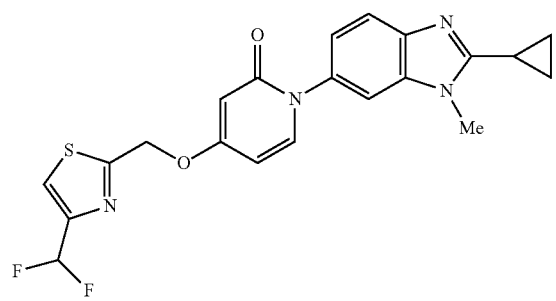 [SMILES: Cn1c(C2CC2)nc2ccc(-n3ccc(OCc4nc(C(F)F)cs4)cc3=O)cc21] | 429.1 |
| 284 | 4-((4-(difluoromethyl)-1,3-thiazol-2-yl)methoxy)-1-(2-ethyl-1-methyl-1H-benzimidazol-6-yl)pyridin-2(1H)-one | 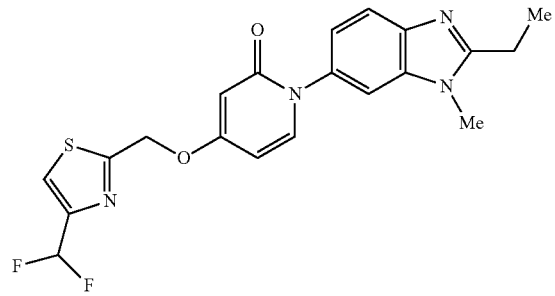 [SMILES: CCc1nc2ccc(-n3ccc(OCc4nc(C(F)F)cs4)cc3=O)cc2n1C] | 417.1 |
| 285 | 1-(2-cyclopropyl-1-methyl-1H-benzimidazol-6-yl)-4-((2-cyclopropyl-1,3-thiazol-4-yl)methoxy)pyridin-2(1H)-one | 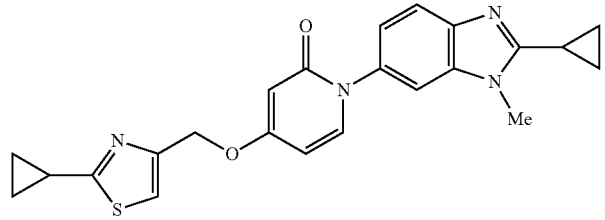 [SMILES: Cn1c(C2CC2)nc2ccc(-n3ccc(OCc4csc(C5CC5)n4)cc3=O)cc21] | 419.3 |

TABLE 1-continued

| Example | IUPAC Name | Structure | MS |
|---|---|---|---|
| 286 | 1-(1,2-dimethyl-1H-benzimidazol-6-yl)-4-((4-(trifluoromethy)thiophen-2-yl)methoxy)pyridin-2(1H)-one | 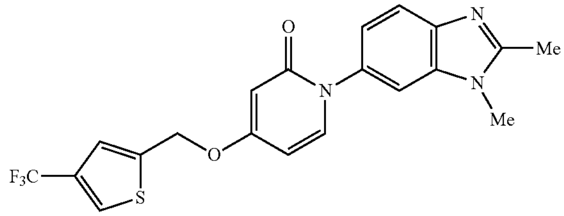 [SMILES: Cc1nc2ccc(-n3ccc(OCc4cc(C(F)(F)F)cs4)cc3=O)cc2n1C] | 420.2 |
| 287 | 1-(2-cyclopropyl-1-methyl-1H-benzimidazol-6-yl)-4-((2-(difluoromethyl)-1,3-thiazol-4-yl)methoxy)pyridin-2(1H)-one | 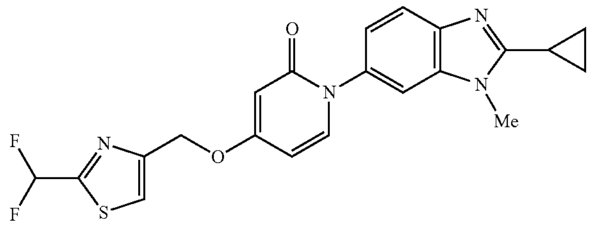 [SMILES: Cn1c(C2CC2)nc2ccc(-n3ccc(OCc4csc(C(F)F)n4)cc3=O)cc21] | 429.1 |
| 288 | 4-((2-(difluoromethyl)-1,3-thiazol-4-yl)methoxy)-1-(2-ethyl-1-methyl-1H-benzimidazol-6-yl)pyridin-2(1H)-one | 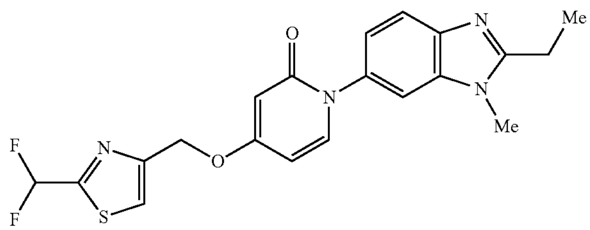 [SMILES: CCc1nc2ccc(-n3ccc(OCc4csc(C(F)F)n4)cc3=O)cc2n1C] | 417.1 |
| 289 | 4-(benzyloxy)-1-(1,2-dimethyl-1H-benzimidazol-6-yl)pyridin-2(1H)-one | 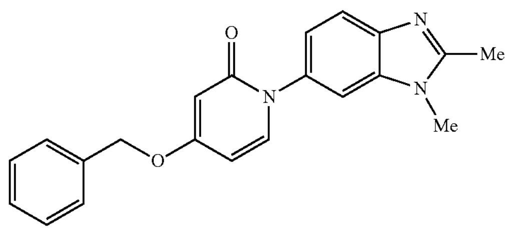 [SMILES: Cc1nc2ccc(-n3ccc(OCc4ccccc4)cc3=O)cc2n1C] | 346.1 |
| 290 | 1-(1,2-dimethyl-1H-benzimidazol-6-yl)-4((5-(trifluoromethyl)-3-thienyl)methoxy)pyridin-2(1H)-one | 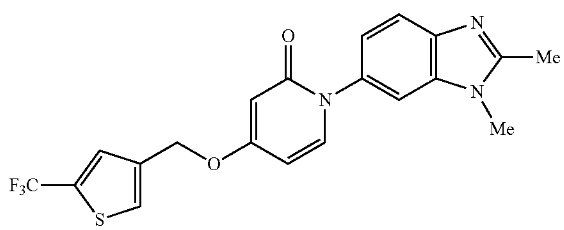 [SMILES: Cc1nc2ccc(-n3ccc(OCc4csc(C(F)(F)F)c4)cc3=O)cc2n1C] | 420.1 |
| 291 | 1-(2-cyclopropyl-3-methylimidazo[1,2-a]pyridin-6-yl)-4-((5-fluoropyridin-2-yl)methoxy)pyridin-2(1H)-one hydrochloride | 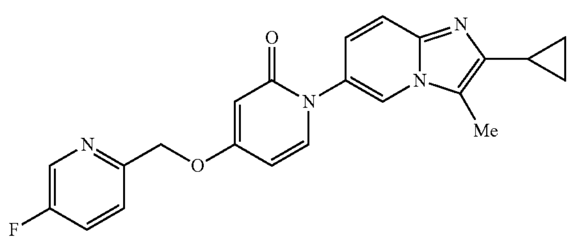 | 390.1 |

Preparation Example 1

| | |
|---|---|
| (1) Compound of Example 1 | 50 mg |
| (2) Lactose | 34 mg |
| (3) Cornstarch | 10.6 mg |
| (4) Cornstarch (paste) | 5 mg |

-continued

| | |
|---|---|
| (5) Magnesium stearate | 0.4 mg |
| (6) Calcium carboxymethylcellulose | 20 mg |
| Total | 120 mg |

The above-mentioned (1) to (6) are mixed according to a conventional method and the mixture is tableted by a tableting machine to give a tablet.

Preparation Example 2 (Production of Capsule)

| (1) Compound of Example 1 | 30 mg |
|---|---|
| (2) Crystalline cellulose | 10 mg |
| (3) Lactose | 19 mg |
| (4) Magnesium stearate | 1 mg |
| Total | 60 mg |

(1), (2), (3) and (4) are mixed and filled in a gelatin capsule.

Experimental Example 1

Determination of human MCH receptor 1 (MCHR1) competitive inhibitory activity of test compound using binding assay 1. Preparation of Membrane Fraction Using human MCHR1 (=SLC-1 receptor)-expressing CHO cell clone 57 described in WO01/82925, MCHR1-expressing CHO cell membrane fractions were prepared by the following method.

In phosphate buffered saline (pH 7.4) supplemented with 5 mM EDTA (ethylenediaminetetraacetic acid) were respectively suspended human MCHR1-expressing CHO cells ($1\times10^8$ cells) and centrifuged. Homogenate buffer (10 mL, 10 mM $NaHCO_3$, 5 mM EDTA, pH 7.5, 0.5 mM PMSF (phenylmethylsulfonyl fluoride), 20 mg/L leupeptin, 4 mg/L E-64, 1 mg/L pepstatin A) was added to the pellets of the cells and, using Polytron Homogenizer, the mixture was homogenated. The supernatant obtained after centrifugation at 400×g for 10 min was further centrifuged at 100,000×g for 1 hr to give precipitate of the membrane fraction. The precipitate were suspended in 2 mL of assay buffer [20 mM Tris-HCl (pH 7.5), 5 mM EDTA, 0.5 mM PMSF, 20 mg/L leupeptin, 4 mg/L E-64, 1 mg/L pepstatin A]. The membrane fractions were suspended in assay buffer to a protein concentration of 2 mg/mL, and after dispensing, preserved at −80° C. and used upon thawing each time when in use.

2. Binding Assay

The MCHR1 ligand binding inhibitory activity of the test compound was determined as follows.

An MCHR1-expressing CHO cell membrane fraction (173 µL) diluted with an assay buffer was dispensed to a 96 well polypropylene plate (3363, Corning). DMSO solution (2 µL), 33 µM cold MCH(1-19) diluted with DMSO solution (2 µL), or a test compound solution diluted with DMSO solution to various concentrations (2 µL) was added, and lastly, [$^{125}$I]-MCH (4-19) diluted with assay buffer (hereinafter, sometimes to be referred to as "hot MCH", 25 µL) was added to each well. The mixture was reacted with stirring at room temperature for 1 hr, and the plate was set on FilterMate Harvester (PerkinElmer). Using a treating glass filter plate (GF/C, PerkinElmer) with polyethyleneimine, which had been previously set, the plate was suction-filtered and washed three times with washing buffer (50 mM Tris-HCl buffer pH 7.5). The glass filter plate was dried, MicroScinti0 (PerkinElmer) was added at 25 µL/well, and the resulting radioactivity was measured by TopCount liquid scintillation counter (PerkinElmer). The binding inhibition rate of the test compound was calculated by the following formula.

Binding inhibition (%)=100−(radioactivity upon addition of test compound and hot MCH−radioactivity upon addition of cold MCH and hot MCH solution)/(radioactivity upon addition of DMSO solution and hot MCH−radioactivity upon addition of cold MCH and hot MCH solution)×100

The binding inhibition rates (%) of test compounds (0.1 µM) as measured using human MCHR1-expressing CHO cell are shown in Table 2.

TABLE 2

| Compound No. | Binding inhibition rate % (0.1 µM) |
|---|---|
| Example 1 | 91 |
| Example 2 | 80 |
| Example 3 | 88 |
| Example 5 | 58 |
| Example 9 | 72 |
| Example 10 | 89 |
| Example 11 | 81 |
| Example 15 | 53 |
| Example 20 | 59 |
| Example 21 | 76 |
| Example 22 | 81 |
| Example 25 | 58 |
| Example 27 | 55 |
| Example 31 | 52 |
| Example 32 | 83 |
| Example 37 | 59 |
| Example 43 | 69 |
| Example 47 | 62 |
| Example 49 | 76 |
| Example 51 | 89 |
| Example 55 | 53 |
| Example 56 | 61 |
| Example 62 | 63 |
| Example 63 | 74 |
| Example 64 | 76 |
| Example 66 | 57 |
| Example 69 | 65 |
| Example 70 | 79 |
| Example 71 | 72 |
| Example 72 | 80 |
| Example 75 | 84 |
| Example 77 | 71 |
| Example 80 | 91 |
| Example 89 | 73 |
| Example 90 | 80 |
| Example 91 | 67 |
| Example 102 | 75 |
| Example 103 | 78 |
| Example 104 | 60 |
| Example 107 | 60 |
| Example 109 | 50 |
| Example 112 | 70 |
| Example 115 | 82 |
| Example 119 | 56 |
| Example 121 | 95 |
| Example 124 | 58 |
| Example 126 | 65 |
| Example 127 | 80 |
| Example 130 | 79 |
| Example 131 | 78 |
| Example 132 | 51 |
| Example 133 | 79 |
| Example 136 | 69 |
| Example 137 | 68 |
| Example 139 | 88 |
| Example 142 | 69 |
| Example 143 | 91 |
| Example 145 | 52 |
| Example 146 | 77 |
| Example 148 | 69 |
| Example 149 | 55 |
| Example 151 | 73 |
| Example 152 | 75 |
| Example 153 | 94 |
| Example 154 | 91 |

TABLE 2-continued

| Compound No. | Binding inhibition rate % (0.1 μM) |
|---|---|
| Example 155 | 54 |
| Example 156 | 48 |
| Example 157 | 71 |
| Example 158 | 83 |
| Example 159 | 87 |
| Example 162 | 57 |
| Example 163 | 49 |
| Example 164 | 92 |
| Example 165 | 81 |
| Example 166 | 64 |
| Example 168 | 84 |
| Example 170 | 23 |
| Example 172 | 72 |
| Example 174 | 45 |
| Example 177 | 97 |
| Example 178 | 74 |
| Example 179 | 64 |
| Example 180 | 64 |
| Example 181 | 57 |
| Example 183 | 91 |
| Example 184 | 82 |
| Example 186 | 25 |
| Example 189 | 86 |
| Example 192 | 85 |
| Example 193 | 89 |
| Example 194 | 82 |
| Example 201 | 84 |
| Example 202 | 67 |
| Example 203 | 91 |
| Example 204 | 67 |
| Example 205 | 76 |
| Example 206 | 95 |
| Example 207 | 85 |
| Example 208 | 39 |
| Example 209 | 89 |
| Example 210 | 51 |
| Example 211 | 76 |
| Example 212 | 80 |
| Example 213 | 79 |
| Example 215 | 92 |
| Example 216 | 88 |
| Example 217 | 73 |
| Example 220 | 81 |
| Example 221 | 58 |
| Example 222 | 80 |
| Example 223 | 60 |
| Example 226 | 89 |
| Example 228 | 89 |
| Example 229 | 45 |
| Example 231 | 71 |
| Example 232 | 73 |
| Example 233 | 67 |
| Example 234 | 50 |
| Example 235 | 69 |
| Example 236 | 76 |
| Example 237 | 78 |
| Example 238 | 65 |
| Example 239 | 74 |
| Example 240 | 91 |
| Example 241 | 56 |
| Example 243 | 38 |
| Example 244 | 83 |
| Example 245 | 59 |
| Example 246 | 52 |
| Example 248 | 79 |
| Example 250 | 92 |
| Example 252 | 66 |
| Example 253 | 64 |
| Example 254 | 57 |
| Example 255 | 85 |
| Example 256 | 70 |
| Example 259 | 70 |
| Example 260 | 75 |
| Example 261 | 57 |
| Example 262 | 80 |
| Example 263 | 30 |
| Example 265 | 61 |
| Example 266 | 50 |
| Example 268 | 66 |
| Example 270 | 58 |
| Example 275 | 75 |
| Example 276 | 71 |
| Example 277 | 55 |
| Example 283 | 56 |
| Example 284 | 37 |
| Example 285 | 36 |
| Example 286 | 58 |
| Example 287 | 47 |
| Example 288 | 40 |
| Example 289 | 48 |
| Example 290 | 77 |
| Example 291 | 47 |

As is clear from Table 2, the compound of the present invention has a superior MCH receptor 1 competitive inhibitory activity.

Experimental Example 2

Measurement of MCH Receptor 1 Antagonistic Activity of Test Compound Using $Ca^{2+}$ Mobilization Assay Using an expression vector plasmid introduced with human MCHR1 gene for expression in animal cells, human MCHR1 gene was introduced into CHO cells (CHO dhfr⁻) by Lipofectamine LTX (Invitrogen). The cells were cultured in selection MEMα medium [445 mL of MEMα medium without nucleic acid and added with 5 mL of Penicillin-Streptomycin (Invitrogen) and 50 mL of dialyzed fetal bovine serum]. Colony 24 clones grown in the selection medium, which were human MCHR1 gene-expressing CHO cell candidates, were selected. From these clones, clone #4 which showed the highest response to the change of $Ca^{2+}$ concentration on stimulation by the addition of 25 nM ligand MCH (4-19) was selected by $Ca^{2+}$ mobilization assay. In the following test, this human MCHR1-expressing CHO cell (clone #4) was used. An integrated dispensing function fluorometer (CellLux, PerkinElmer) was used for $Ca^{2+}$ mobilization assay. The CHO cells were sown in a 96 well plate (type 3904, Corning) with a black wall and clear well bottom at a density of 20000 cells/well, and cultured in an incubator for about 24 hr at 5% $CO_2$, 37° C. The medium was removed, and the cells were washed with phosphate buffered saline (PBS). A $Ca^{2+}$ indicator dye reagent (DOJINDO LABORATORIES, Ca screening no-wash kit Fluo4) was added at 100 μL/well, and the dye was allowed to penetrate into the cell for 30 min in an incubator at 5% $CO_2$, 37° C. The plate was set on a plate reader. First, a test compound solution diluted with an assay buffer [10 mM HEPES (pH 7.4), 1× assay buffer containing 0.1% BSA (DOJINDO LABORATORIES, attached to Ca screening no-wash kit Fluo4)] or DMSO solution was added at 50 μL/well, and then ligand MCH (4-19) peptide (final concentration 2 nM) diluted with assay buffer or DMSO was added at 50 μL/well, during which changes in intracellular fluorescence were measured at 2 second intervals. The antagonistic activity of the test compound was calculated by the following formula and shown as an inhibition rate (%) wherein the intracellular fluorescence activity resulting from the stimulation by the addition of ligand MCH (4-19) peptide was 100% and that of the well added with DMSO solution alone was 0%.

inhibitory rate (%)=100−[fluorescence activity upon addition of test compound and MCH(4-19)peptide solution−fluorescence activity upon addition of DMSO solution only]/[fluorescence activity upon addition of DMSO solution and MCH(4-19)peptide solution−fluorescence activity upon addition of DMSO solution only]×100

The inhibition rates (%) of test compounds (0.1 μM) as antagonist activity measured using human MCHR1-expressing CHO cells (clone #4) are shown in the following Table 3.

TABLE 3

| Compound No. | Inhibitory rate % (0.1 μM) |
|---|---|
| Example 1 | 98 |
| Example 2 | 99 |
| Example 3 | 99 |
| Example 9 | 100 |
| Example 10 | 99 |
| Example 11 | 101 |
| Example 15 | 90 |
| Example 31 | 61 |
| Example 37 | 51 |
| Example 43 | 100 |
| Example 55 | 78 |
| Example 62 | 57 |
| Example 63 | 100 |
| Example 64 | 99 |
| Example 66 | 84 |
| Example 69 | 58 |
| Example 70 | 35 |
| Example 71 | 43 |
| Example 72 | 58 |
| Example 75 | 80 |
| Example 80 | 99 |
| Example 89 | 46 |
| Example 91 | 70 |
| Example 102 | 97 |
| Example 103 | 63 |
| Example 104 | 61 |
| Example 107 | 101 |
| Example 112 | 48 |
| Example 121 | 96 |
| Example 124 | 80 |
| Example 127 | 77 |
| Example 130 | 99 |
| Example 132 | 96 |
| Example 133 | 98 |
| Example 148 | 94 |
| Example 156 | 90 |
| Example 157 | 95 |
| Example 158 | 105 |
| Example 159 | 107 |
| Example 164 | 102 |
| Example 168 | 103 |
| Example 170 | 62 |
| Example 177 | 97 |
| Example 178 | 69 |
| Example 179 | 94 |
| Example 180 | 99 |
| Example 181 | 21 |
| Example 183 | 75 |
| Example 186 | 74 |
| Example 189 | 100 |
| Example 192 | 98 |
| Example 193 | 99 |
| Example 194 | 100 |
| Example 202 | 104 |
| Example 226 | 106 |
| Example 228 | 103 |
| Example 231 | 95 |
| Example 235 | 93 |
| Example 236 | 96 |
| Example 237 | 67 |
| Example 238 | 42 |
| Example 239 | 92 |
| Example 240 | 99 |
| Example 241 | 76 |
| Example 243 | 72 |

TABLE 3-continued

| Compound No. | Inhibitory rate % (0.1 μM) |
|---|---|
| Example 244 | 98 |
| Example 245 | 58 |
| Example 248 | 97 |
| Example 250 | 100 |
| Example 252 | 85 |
| Example 253 | 69 |
| Example 254 | 95 |
| Example 256 | 97 |
| Example 259 | 100 |
| Example 260 | 104 |
| Example 261 | 100 |
| Example 262 | 98 |
| Example 263 | 52 |
| Example 265 | 97 |
| Example 266 | 73 |
| Example 268 | 86 |
| Example 270 | 73 |
| Example 275 | 89 |
| Example 276 | 97 |
| Example 277 | 77 |
| Example 283 | 99 |
| Example 284 | 83 |
| Example 285 | 58 |
| Example 286 | 100 |
| Example 287 | 95 |
| Example 288 | 87 |
| Example 289 | 100 |
| Example 290 | 90 |
| Example 291 | 98 |

As is clear from Table 3, the compound of the present invention has a superior MCH receptor 1 antagonistic activity.

Experimental Example 3

Evaluation of Anorectic Effect Using Male Diet-Induced Obese F344/Jcl Rats

Male diet-induced obese F344/Jcl rats (44-50 weeks old) fed with a high-fat diet (D12451: Research Diets) from 5 weeks old were used. From before the start of experiment, the rats were singly housed, given a powder high-fat diet (D12451M: Research Diets), and habituated to oral administration with tap water. The food intake from the evening of the day before the start of experiment to the next morning was measured, and the rats were grouped based on both the food intake and the body weight of the previous day. In the evening of the day of the start of experiment and the next day, 0.5% methylcellulose solution was orally administered to the control group, and 0.5% methylcellulose suspension (5 mg/mL) of the test compound was orally administered to the compound administration group at 2 mL/kg (6 per group for both control group and compound administration group). The food intake for 2 days from the initial administration was measured. The food intake inhibition rate of each compound administration group to the control group was calculated. The results are shown in Table 4.

TABLE 4

| Compound No. | Food intake suppression rate (%) |
|---|---|
| Example 1 | 19.5 |
| Example 2 | 27.8 |
| Example 3 | 29.6 |
| Example 9 | 14.8 |
| Example 10 | 58.1 |
| Example 11 | 21.8 |

TABLE 4-continued

| Compound No. | Food intake suppression rate (%) |
|---|---|
| Example 15 | 45.4 |
| Example 49 | 29.3 |
| Example 51 | 50.0 |
| Example 63 | 45.5 |
| Example 112 | 25.5 |
| Example 115 | 32.0 |
| Example 121 | 36.5 |
| Example 131 | 44.3 |
| Example 143 | 39.4 |
| Example 158 | 20.3 |
| Example 160 | 22.7 |
| Example 242 | 17.4 |
| Example 252 | 30.8 |
| Example 254 | 38.7 |
| Example 266 | 20.0 |
| Example 275 | 50.1 |
| Example 276 | 57.9 |
| Example 290 | 43.5 |

As is clear from Table 4, the compound of the present invention has anorectic effect.

Experimental Example 4

Evaluation of HERG Inhibitory Activity

MEM medium, MEM nonessential amino acid solution, sodium pyruvate solution and G418 sulfate solution (Geneticin) were purchased from Invitrogen Corporation (Carlsbad, Calif.). Bovine serum albumin (BSA, Fatty Acid Free) was a product of Wako Pure Chemical Industries, Ltd. (Osaka, Japan). Fetal calf serum (FCS) was a product of Trau Scientific Ltd. (Melbourne, Australia).

As HERG-expressing cell HERG.T.HEK, the cell obtained from Wisconsin ALUMNI Research Foundation was used. HERG.T.HEK was maintained and passaged at 37° C. in the presence of 5% $CO_2$ using an MEM medium containing 10% FCS, 1 mM MEM nonessential amino acid, 1 mM sodium pyruvate and 500 µg/ml Geneticin.

80-90% confluent cells were collected by a trypsin treatment and plated on an IVF dish (Falcon, Franklin Lakes, N.J.). After 2-3 hr, cells were adhered to a glass electrode (resistance value 2-3 MΩ) filled with an electrode internal fluid (7 mM NaCl, 130 mM KCl, 1 mM $MgCl_2$, 5 mM HEPES, 5 mM. EGTA, 5 mM ATP-Na: pH 7.2) while perfusing with an extracellular fluid (137 mM NaCl, 4 mM KCl, 1 mM $MgCl_2$, 1.8 mM $CaCl_2$, 10 mM HEPES, 11 mM dextrose: pH 7.4), using a patch clamp amplifier AXOPATCH 200B (Axon instruments, Foster City, Calif.), whereby formation of whole-cell configuration and stimulation by voltage clamp protocol were performed (holding potential −75 mV, primary voltage 10 mV: 0.5 sec, secondary voltage −40 mV: 0.5 sec, stimulation frequency 10 sec). A preliminary stimulation was applied and the HERG electric current value (peak tail current) was measured when the electric current waveform was stabilized.

For measurement of the HERG electric current with addition of the test compound, the cells were first perfused with the extracellular fluid and, when the waveform was stabilized, the cells were perfused with an extracellular fluid containing 10 µM of a test compound. When the electric current waveform was stabilized under respective perfuse conditions, the HERG electric current was measured.

The HERG electric current inhibitory rate (%) of the test compound was calculated with the HERG electric current value without addition of the test compound as 100%. The results are shown in Table 5.

TABLE 5

| Compound No. | HERG inhibitory action (%) |
|---|---|
| Example 2 | 27.3 |
| Example 63 | 23.0 |
| Example 254 | 26.4 |

As is clear from Table 5, the compound of the present invention shows low HERG inhibitory activity, and was confirmed to be low toxic.

Experimental Example 5

Evaluation of PLsis Inducing Potential

DMEM medium, L-glutamine, penicillin-streptomycin, pyruvic acid, and N-(7-nitrobenz-2-oxa-1,3-diazol-4-yl)-1,2-hexadecanoyl-sn-glycero-3-phosphoethanolamine triethylammonium salt (NBD-PE) were purchased from Invitrogen Corporation. As bovine serum albumin (BSA), a product of Thermo Trace Ltd. (Melbourne, Australia) was used, and as Amiodarone, a product of ICN (Costa Mesa, Calif.) was used. A test compound was used in the form of a 10 mM DMSO solution.

FBS was added at a final concentration of 5 vol % to DMEM medium supplemented with L-glutamine, pyruvic acid and penicillin-streptomycin and subjected to the experiment. Culture was performed using 5% carbon dioxide gas-95% air as a gas phase in a $CO_2$ incubator at 37° C. HepG2 cells were suspended in a culture medium at $50 \times 10^4$ cells/mL, plated in a 96 well plate at 50 µL/well and precultured for 24 hr. After preculture, the culture medium was removed, a culture medium containing 60 µM NBD-PE was added at 50 µL/well, and a culture medium containing 0.6 µM or 20 µM test compounds were each added at 50 µL/well to HepG2 cells, and the cells were cultured for 24 hr. As a positive control, Amiodarone was used at a final concentration of 10 µM.

After exposure to the test compound for 24 hr, the fluorescence intensity (Ex. 485 nm, Em. 538 nm) of NBD-PE uptaken by the cells was measured by a fluorometer. The measurement value with addition of 0 µM test compound solution was subtracted as a blank, a relative value to the measurement 5 value with addition of 10 µM Amiodarone was calculated, and the maximum value per unit concentration of the test compound was obtained as a phospholipidosis (PLsis) inducing potential. The results are shown in Table 6.

TABLE 6

| Compound No. | PLsis inducing potential |
|---|---|
| Example 1 | 2.5 |
| Example 2 | 2.2 |
| Example 3 | 2.4 |
| Example 11 | 2.0 |
| Example 63 | 1.6 |
| Example 112 | 1.6 |
| Example 115 | 1.8 |
| Example 121 | 1.7 |
| Example 143 | 1.6 |
| Example 156 | 2.0 |
| Example 226 | 2.1 |
| Example 254 | 1.7 |

As is clear from Table 6, the compound of the present invention shows low PLsis inducing potential, and was confirmed to be low toxic.

INDUSTRIAL APPLICABILITY

Compound (I) has a melanin-concentrating hormone (MCH) receptor antagonistic action, and is low toxic. Therefore, the compound is highly useful as an anorexigenic agent and an agent for the prophylaxis or treatment of obesity and the like.

This application is based on U.S. provisional patent application No. 61/585,877, the contents of which are incorporated by reference in full herein.

The invention claimed is:
1. A compound of formula (I):

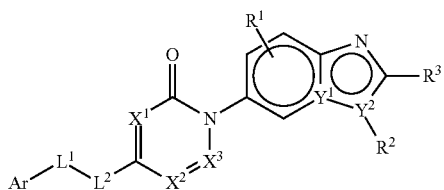

wherein
Ar is a thienyl group or a thiazolyl group, each of which is optionally substituted by 1 to 3 substituents selected from the group consisting of
  (1) a halogen atom,
  (2) a $C_{1-6}$ alkyl group optionally substituted by 1 to 3 halogen atoms, and
  (3) a $C_{1-6}$ alkoxy group optionally substituted by 1 to 3 halogen atoms;
$X^1$ is $CR^4$ or N;
$X^2$ and $X^3$ are each independently CH or N;
one of $Y^1$ and $Y^2$ is C, and the other is N;
$L^1$ is O, $S(O)_{m1}$, $NR^{5A}$ or $CR^{5B}R^{5C}$;
$L^2$ is O, $S(O)_{m2}$, $NR^{6A}$ or $CR^{6B}R^{6C}$;
wherein at least one of $L^1$ and $L^2$ is $CR^{5B}R^{5C}$ or $CR^{6B}R^{6C}$;
$R^1$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group;
$R^2$ is a halogen atom, an optionally substituted $C_{1-6}$ alkyl group or an optionally substituted cyclic group;
$R^3$ is (1) a hydrogen atom, (2) a halogen atom, (3) a cyano group, (4) a $C_{1-6}$ alkyl group optionally substituted by 1 to 3 substituents selected from the group consisting of a halogen atom, a cyano group, an optionally substituted $C_{1-6}$ alkoxy group, an optionally substituted $C_{3-10}$ cycloalkyl group, an optionally substituted aromatic ring group, —CO—$R^{7A}$ and —S(O)$_{n1}$—$R^{7B}$, (5) a $C_{1-6}$ alkoxy group optionally substituted by 1 to 3 substituents selected from the group consisting of a halogen atom, a cyano group, an optionally substituted $C_{1-6}$ alkoxy group, an optionally substituted $C_{3-10}$ cycloalkyl group, an optionally substituted aromatic ring group, —CO—$R^{8A}$ and —S(O)$_{n2}$—$R^{8B}$, (6) an optionally substituted $C_{2-6}$ alkenyl group, (7) an optionally substituted cyclic group, or (8) —CO—$R^9$;
$R^4$ is a hydrogen atom, a halogen atom, an optionally substituted $C_{1-6}$ alkyl group, an optionally substituted $C_{3-10}$ cycloalkyl group or an optionally substituted $C_{1-6}$ alkoxy group;
$R^{5A}$ and $R^{6A}$ are each independently a hydrogen atom or an optionally substituted hydrocarbon group;
$R^{5B}$, $R^{5C}$, $R^{6B}$ and $R^{6C}$ are each independently a hydrogen atom, a halogen atom, a cyano group, a nitro group, an optionally substituted hydrocarbon group, an optionally substituted heterocyclic group, an optionally substituted hydroxy group, an optionally substituted mercapto group, an optionally substituted amino group or an acyl group;
wherein $R^{5B}$ and $R^{6B}$ optionally form an optionally substituted ring together with the adjacent carbon atoms, or $R^{5B}$ and the substituent of Ar are optionally joined to form an optionally substituted ring;
$R^{7A}$, $R^{7B}$, $R^{8A}$, $R^{8B}$ and $R^9$ are each independently an optionally substituted $C_{1-6}$ alkyl group, an optionally substituted $C_{3-10}$ cycloalkyl group or an optionally substituted amino group; and
m1, m2, n1 and n2 are each independently an integer of 0 to 2,
wherein:
the substituents of the "optionally substituted $C_{1-6}$ alkyl group", the "optionally substituted $C_{1-6}$ alkoxy group", and the "optionally substituted $C_{2-6}$ alkenyl group" are selected from the group consisting of the following Substituent group A;
Substituent group A:
(1) a $C_{3-10}$ cycloalkyl group;
(2) a $C_{6-14}$ aryl group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(4) a nonaromatic heterocyclic group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;
(5) an amino group optionally mono- or di-substituted by substituent(s) selected from the group consisting of
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{1-6}$ alkoxy-carbonyl group optionally substituted by 1 to 3 halogen atoms,
  (d) a carbamoyl group optionally mono- or di-substituted by $C_{1-6}$ alkyl group(s) optionally substituted by 1 to 3 halogen atoms, and
  (e) a formyl group;
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from the group consisting of (a) a halogen atom, and
(b) a $C_{1-6}$ alkoxy group;
(8) a $C_{1-6}$ alkylsulfonyl group optionally substituted by 1 to 3 halogen atoms;
(9) a carbamoyl group optionally mono- or di-substituted by $C_{1-6}$ alkyl group(s) optionally substituted by 1 to 3 halogen atoms;
(10) a thiocarbamoyl group optionally mono- or di-substituted by $C_{1-6}$ alkyl group(s) optionally substituted by 1 to 3 halogen atoms;
(11) a sulfamoyl group optionally mono- or di-substituted by $C_{1-6}$ alkyl group(s) optionally substituted by 1 to 3 halogen atoms;
(12) a carboxy group;
(13) a hydroxy group;
(14) a $C_{1-6}$ alkoxy group optionally substituted by 1 to 3 substituents selected from the group consisting of
  (a) a halogen atom,
  (b) a carboxy group,
  (c) a $C_{1-6}$ alkoxy group,
  (d) a $C_{1-6}$ alkoxy-carbonyl group,
  (e) an amino group optionally mono- or di-substituted by substituent(s) selected from the group consisting of a $C_{1-6}$ alkyl group and a $C_{1-6}$ alkoxy-carbonyl group,
  (f) a $C_{6-14}$ aryl group,
  (g) a $C_{3-10}$ cycloalkyl group,
  (h) an aromatic heterocyclic group, and
  (i) a hydroxy group;
(15) a $C_{2-6}$ alkenyloxy group optionally substituted by 1 to 3 halogen atoms;
(16) a $C_{6-14}$ aryloxy group;
(17) a $C_{1-6}$ alkyl-carbonyloxy group;
(18) a $C_{6-14}$ aryl-carbonyl group optionally substituted by 1 to 3 substituents selected from the group consisting of
  (a) a halogen atom, and
  (b) a $C_{1-6}$ alkyl group optionally substituted by 1 to 3 halogen atoms;
(19) a nonaromatic heterocyclylcarbonyl group optionally substituted by 1 to 3 $C_{1-6}$ alkyl groups optionally substituted by 1 to 3 halogen atoms;
(20) a mercapto group;
(21) a $C_{1-6}$ alkylthio group optionally substituted by 1 to 3 halogen atoms;
(22) a $C_{7-13}$ aralkylthio group;
(23) a $C_{6-14}$ arylthio group;
(24) a cyano group;
(25) a nitro group;
(26) a halogen atom;
(27) a $C_{1-3}$ alkylenedioxy group optionally substituted by 1 to 3 halogen atoms;
(28) an aromatic heterocyclylcarbonyl group optionally substituted by 1 to 3 $C_{1-6}$ alkyl groups optionally substituted by 1 to 3 halogen atoms; and
(29) a hydroxyimino group optionally substituted by a $C_{1-6}$ alkyl group optionally substituted by 1 to 3 $C_{6-14}$ aryl groups;
  the substituents of the "optionally substituted $C_{3-10}$ cycloalkyl group", the "optionally substituted cyclic group", the "optionally substituted aromatic ring group", the "optionally substituted hydrocarbon group", and the "optionally substituted heterocyclic group" are selected from the group consisting of the following Substituent group B;

Substituent group B:
(1) Substituent group A;
(2) a $C_{1-6}$ alkyl group optionally substituted by 1 to 5 substituents selected from the group consisting of
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a $C_{3-10}$ cycloalkyloxy group;
(3) a $C_{2-6}$ alkenyl group optionally substituted by 1 to 3 substituents selected from the group consisting of
  (a) a halogen atom,
  (b) a carboxy group,
  (c) a hydroxy group,
  (d) a $C_{1-6}$ alkoxy-carbonyl group,
  (e) a $C_{1-6}$ alkoxy group,
  (f) an amino group optionally mono- or di-substituted by $C_{1-6}$ alkyl group(s), and
  (g) a $C_{3-10}$ cycloalkyl group;
(4) a $C_{2-6}$ alkenyl group optionally substituted by 1 to 3 $C_{3-10}$ cycloalkyl groups;
(5) a $C_{7-13}$ aralkyl group optionally substituted by 1 to 3 substituents selected from the group consisting of
  (a) a $C_{1-6}$ alkyl group optionally substituted by 1 to 3 halogen atoms,
  (b) a hydroxy group,
  (c) a $C_{1-6}$ alkoxy group, and
  (d) a halogen atom; and
(6) an oxo group;
  the substituent of the "optionally substituted hydroxy group" is selected from the group consisting of a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, and a heterocyclic group;
  the substituent of the "optionally substituted mercapto group" is selected from the group consisting of a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a $C_{1-6}$ alkyl-carbonyl group, and a heterocyclic group;
  the substituents of the "optionally substituted amino group" are selected from the group consisting of a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-13}$ aralkyl group, a $C_{8-13}$ arylalkenyl group, a heterocyclic group, and acyl group;
  the "optionally substituted ring" formed by $R^{5B}$ and $R^{6B}$ together with the adjacent carbon atoms is optionally substituted $C_{3-6}$ cycloalkane, and the substituents of the "optionally substituted $C_{3-6}$ cycloalkane" are selected from the group consisting of a halogen atom, a cyano group, a nitro group, a hydroxy group, and a $C_{1-6}$ alkyl group; and
  the "optionally substituted ring" formed by $R^{5B}$ and the substituent of Ar is optionally substituted $C_{5-7}$ cycloalkane, and the substituents of the "optionally substituted $C_{5-7}$ cycloalkane" are selected from the group consisting of a halogen atom, a cyano group, a nitro group, a hydroxy group, and a $C_{1-6}$ alkyl group;
or a salt thereof.

2. The compound according to claim 1, wherein $X^1$, $X^2$ and $X^3$ are CH, or a salt thereof.

3. The compound according to claim 1, wherein $L^1$ is $CH_2$; and
$L^2$ is O, or a salt thereof.

4. The compound according to claim 1, wherein $R^1$ is a hydrogen atom, or a salt thereof.

5. The compound according to claim 1, wherein $Y^1$ is C, and $Y^2$ is N, or a salt thereof.

6. The compound according to claim 1, wherein $R^2$ is a $C_{1-6}$ alkyl group, or a salt thereof.

7. The compound according to claim 1, wherein $R^3$ is
(1) a $C_{1-6}$ alkyl group optionally substituted by 1 to 3 substituents selected from the group consisting of
   (a) a halogen atom,
   (b) a cyano group, and
   (c) a $C_{1-6}$ alkoxy group optionally substituted by 1 to 3 halogen atoms, or
(2) a $C_{3-10}$ cycloalkyl group optionally substituted by 1 to 3 substituents selected from the group consisting of
   (a) a halogen atom,
   (b) a cyano group,
   (c) a $C_{1-6}$ alkyl group optionally substituted by 1 to 3 substituents selected from the group consisting of a halogen atom and a hydroxy group,
   (d) a carbamoyl group,
   (e) a $C_{1-6}$ alkoxy group,
   (f) an oxo group,
   (g) a hydroxy group,
   (h) a $C_{1-6}$ alkoxy-carbonyl group, and
   (i) a carboxy group,
or a salt thereof.

8. The compound according to claim 1, wherein $R^3$ is a $C_{1-6}$ alkyl group or a $C_{3-6}$ cycloalkyl, or a salt thereof.

9. A pharmaceutical composition comprising the compound according to claim 1 or a salt thereof and a pharmacologically acceptable carrier.

10. The pharmaceutical composition according to claim 9, which is a melanin-concentrating hormone receptor antagonist.

11. A method of treating obesity in a mammal, comprising administering an effective amount of the compound according to claim 1 or a salt thereof to the mammal.

12. A method of antagonizing a melanin-concentrating hormone receptor in a mammal, comprising administering an effective amount of the compound according to claim 1 or a salt thereof to the mammal.

13. A method of suppressing food intake in a mammal, comprising administering an effective amount of the compound according to claim 1 or a salt thereof to the mammal.

14. 4-((5-Chloro-2-thienyl)methoxy)-1-(2-cyclopropyl-1-methyl-1H-benzimidazol-6-yl)pyridin-2(1H)-one or a salt thereof.

* * * * *